(12) United States Patent
Cherry et al.

(10) Patent No.: US 6,876,932 B1
(45) Date of Patent: Apr. 5, 2005

(54) MALTOGENIC ALPHA-AMYLASE VARIANTS

(75) Inventors: Joel Cherry, Davis, CA (US); Allan Svendsen, Birkeroed (DK); Carsten Andersen, Vaerloese (DK); Lars Beier, Lyngby (DK); Torben Peter Frandsen, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 1 day.

(21) Appl. No.: 09/607,142

(22) Filed: Jun. 29, 2000

Related U.S. Application Data

(60) Division of application No. 09/386,607, filed on Aug. 31, 1999, now Pat. No. 6,162,628, which is a continuation-in-part of application No. PCT/DK99/00088, filed on Feb. 26, 1999.
(60) Provisional application No. 60/077,795, filed on Mar. 12, 1998.

(30) Foreign Application Priority Data

Feb. 27, 1998 (DK) ............................................. 98/00269

(51) Int. Cl.$^7$ ......................... G06F 17/00; G01N 33/48; C12P 21/06; C07K 1/00
(52) U.S. Cl. ......................... 702/27; 702/19; 435/69.1; 530/350
(58) Field of Search .................... 702/19, 27; 435/69.1, 435/202, 252.31, 471; 530/350

(56) References Cited

FOREIGN PATENT DOCUMENTS

| EP | 0 120 693 | 5/1989 |
|---|---|---|
| WO | WO 89/03421 | 4/1989 |
| WO | WO 96/23874 | 8/1996 |
| WO | WO96/23874 | * 8/1996 |
| WO | WO 96/33267 | 10/1996 |
| WO | WO 97/41213 | 11/1997 |
| WO | WO 97/43424 | 11/1997 |
| WO | PCT/DK99/00088 | 2/1999 |

OTHER PUBLICATIONS

Branden et al. Introduction to Protein Structure. New York and London: Garland Publishing, Inc. 1991, p. 271.*
Dauter Z. et al.: Biochemistry, vol. 38, pp. 8385–8392 (1999).
Kim et al., Biochemistry and Molecular Biology International, vol. 41, No. 2, pp. 227–234 (1997).
Sin et al., Journal of Biotechnology, vol. 32, pp. 283–288 (1994).
Penninga et al., Biochemistry, vol. 34, pp. 3368–3376 (1995).
Biochemical Journal, vol. 316, pp. 695–696 (1996).
Christophersen et al., Starch/Stärke, vol. 50, No. 1, pp. 39–45 (1998).
Bernard Henrissat, Biochem. J., vol. 280, pp. 309–316 (1991).
Tachibana et al., Journal of Fermentation and Bioengineering, vol. 83, No. 6, pp. 540–548 (1997).
Norman et al., Denpun Kagaku, vol. 39, No. 2., pp. 101–108 (1992).
Hofmann et al., J. Mol. Biol., vol. 209, pp. 793–800 (1989).
Lawson et al., J. Mol. Biol., vol. 236, pp. 590–600 (1994).
Strokopytov et al., Biochemistry, vol. 34, pp. 2234–2240 (1995).
Knegtel et al., J. Mol. Biol., vol. 256, pp. 611–622 (1996).
Boel et al., Biochemistry, vol. 29, pp. 6244–6249 (1990).
Machius et al., J. Mol. Biol., vol. 246, pp. 545–559 (1995).
Chang et al., J. Mol. Biol., vol. 229, pp. 235–238 (1993).
Kubota et al., J. Mol. Biol., vol. 38, No. 2, pp. 141–146 (1991).
Birte Svensson, Plant Molecular Biology, vol. 25, pp. 141–157 (1994).
Abstract (sequence listing) of Swiss application No. P19531.
Klein et al., J. Mol. Biol., vol. 217, pp. 737–750 (1991).
Diderichsen et al., FEMS Microbiology Letters, vol. 56, pp. 53–60 (1988).
Wind et al., Eur. J. Biochem., vol. 253, pp. 598–605 (1998).
Dalmia et al., Biotechnology and Bioengineering, vol. 47, pp. 575–584 (1995).
Jespersen et al., Biochem. J., vol. 280, pp. 51–55 (1991).
del–Rio et al., Febs Letters, vol. 416, pp. 221–224 (1997).
Holm et al., Protein Engineering, vol. 3, pp. 181–191 (1990).
Janecek et al., Febs 11085, vol. 304, pp. 1–3 (1992).

* cited by examiner

Primary Examiner—Marianne P. Allen
Assistant Examiner—Channing S. Mahatan
(74) Attorney, Agent, or Firm—Elias Lambiris; Jason Garbell

(57) ABSTRACT

The inventors have modified the amino acid sequence of a maltogenic alpha-amylase to obtain variants with improved properties, based on the three-dimensional structure of the maltogenic alpha-amylase Novamyl. The variants have altered physicochemical properties., e.g. an altered pH optimum, improved thermostability, increased specific activity, an altered cleavage pattern or an increased ability to reduce retrogradation of starch or staling of bread.

17 Claims, 1 Drawing Sheet

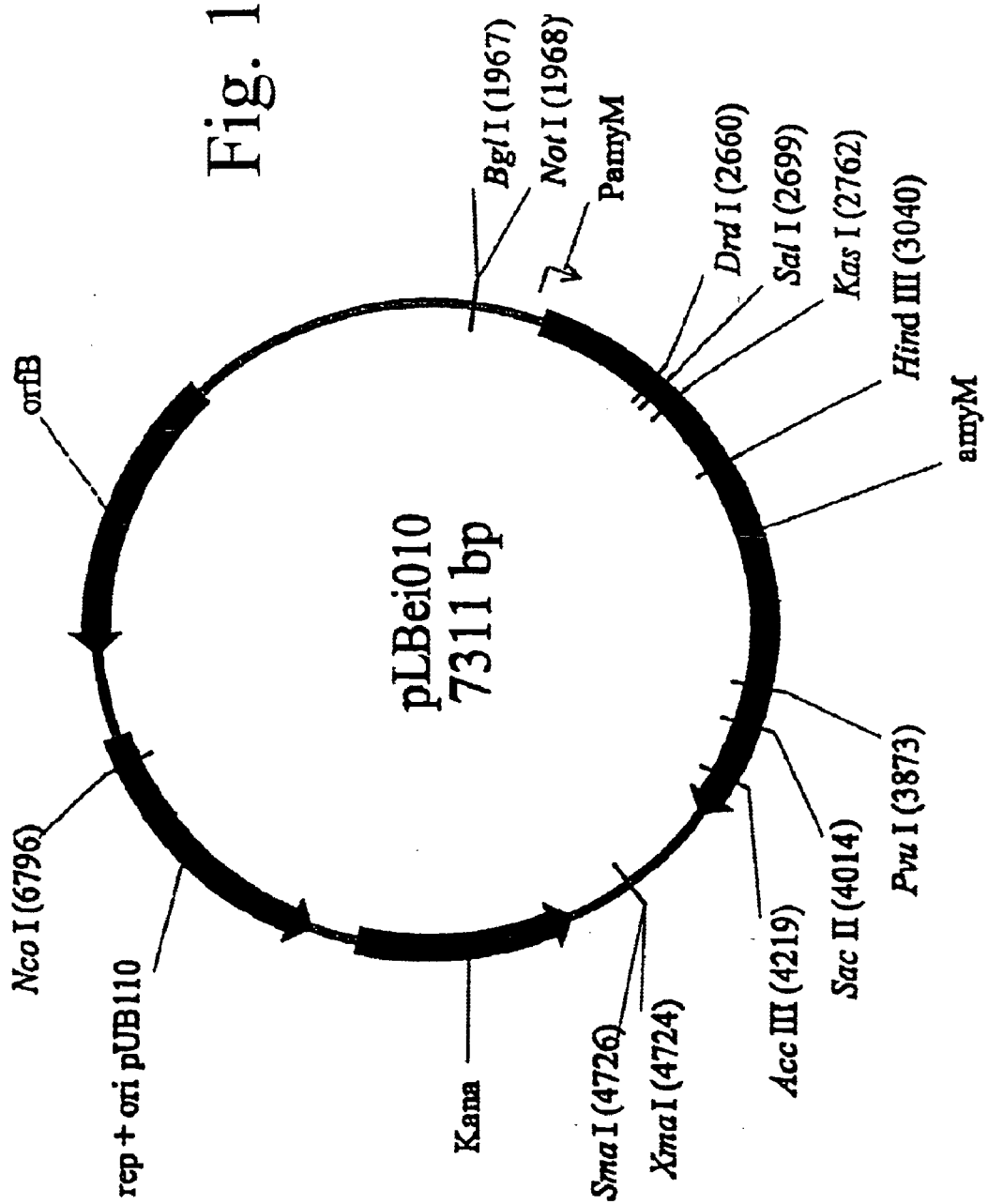

MALTOGENIC ALPHA-AMYLASE VARIANTS

CROSS-REFERENCE TO RELATED APPLICATIONS

This application is a divisional of U.S. application Ser. No. 09/386,607 filed on Aug. 31, 1999, U.S. Pat. No. 6,162,628, which is a continuation-in-part of PCT/DK99/00088 filed on Feb. 26, 1999, and claims priority under 35 U.S.C. 119 of Danish application no. 98/00269 filed on Feb. 27, 1998, and U.S. provisional application No. 60/077,795 filed on Mar. 12, 1998, the contents of which are fully incorporated herein by reference.

FIELD OF THE INVENTION

The present invention relates to variants of maltogenic amylase and to methods of constructing such variants.

BACKGROUND OF THE INVENTION

Malogenic alpha-amylase (glucan 1,4-α-maltohydrolase, E.C. 3.2.1.133) is able to hydrolyze amylose and amylopectin to maltose in the alpha-configuration, and is also able to hydrolyze maltotriose as well as cyclodextrin.

A maltogenic alpha-amylase from *Bacillus* (EP 120 693) is commercially available under the trade name Novamyl® (product of Novo Nordisk A/S, Denmark) and is widely used in the baking industry as an anti-staling agent due to its ability to reduce retrogradation of starch (WO 91/04669). Itis most active at 6070° C. (Christophersen, C., et al., 1997, Starch, vol. 50, No. 1, 39–45).

Novamyl® shares several characteristics with cyclodextrin glucanotransferases (CGTases), including sequence homology (Henrissat B., Bairoch A. 1996) and formation of transglycosylation products (Christophersen, C., et al., 1997, Starch, vol. 50, No. 1, 39–45). Cyclomaltodextrin glucanotransferase (E.C. 2.4.1.19), also designated cyclodextrin glucanotransferase or cyclodextrin glycosyltransferase, abbreviated herein as CGTase, catalyses the conversion of starch and similar substrates into cyclomaltodextrins via an intramolecular transglycosylation reaction, thereby forming cyclomaltodextrins (or CD) of various sizes.

CGTases are widely distributed and from several different bacterial sources, including *Bacillus, Brevibacterium, Clostridium, Corynebactedum, Klebsiella, Micrococcus, Thermoanaerobacter* and *Thermoanaerobacterium* have been extensively described in the literature. A CGTase produced by *Thermoanaerobacter* sp. has been reported in Norman B E, Jørgensen S T; *Dengun Kaaaku* 1992 39 99–106, and WO 89/03421, and the amino acid sequence has been disclosed in WO 96/33267. The sequence of CGTases from *Thermoanaembacterium thermosulfurigenes* and from *Bacillus circulansis* available on the Internet (SCOP or PDF home pages) as pdf file 1CIU, and the sequence of a CGTase from *B. circulans* is available as pdf file 1 CDG.

Tachibana, Y., Journal of Fermentation and Bioengineering, 83 (6), 540–548 (1997) describes the cloning and expression of a CGTase. Variants of CGTases have been described by Kim, Y. H., Biochemistry and Molecular Biology International, 41 (2), 227–234 (1997); Sin K-A, Journal of Biotechnology, 32 (3), 283–288 (1994); D Penninga, Biochemistry, 34 (10), 3368–3376 (1995); and WO 96/33267. Recently, the tertiary structure of several CGTases have been reported. Hofman et al. [Hofman B E, Bender H, Schultz G E; *J. Mol. Biol.* 1989 209 793800] and Klein & Schulz [Klein C, Schulz G E; *J. Mol. Biol.* 1991 217 737–750] report the tertiary structure of a CGTase derived from *Bacillus circulans* Strain 8, Kubota et al. [Kubota M, Matsuura Y, Sakai S and Katsube Y; *Denpun Kagaku* 1991 38 141–146] report the tertiary structure of a CGTase derived from *Bacillus stearothermophilus* TC-91, Lawson et al. [Lawson C L, van Montfort R, Strokopytov B, Rozeboom H J, Kalk K H, de Vries G E, Penninga D, Dijikhuizen L, and Dijkstra B W. *J. Mol. Biol.* 1994 236 590–600] report the tertiary structure of a CGTase derived from *Bacillus circulans* Strain 25.1, Strokopytov et al [Strokopytov B, Penninga D, Rozeboom H J; Kalk K H, Dijkhuizen: L and Dijkstra B W; *Biochemistry* 1995 34 2234–2240] report the tertiary structure of a CGTase derived from *Bacillus circulans* Strain 251, which CGTase has been complexed with acarbose, an effective CGTase inhibitor, and Knegtel et al. [Knegtel R M A, Wind R D, Rozeboom H J, Kalk K H, Buitelaar R M, Dijkuizen L and Dijkstra B W, *J. Mol. Biol.* 1996 256 611–622] report the tertiary structure of a CGTase derived from *Thermoanaerobacterium thermosulfurigenes*.

BRIEF DISCLOSURE OF THE INVENTION

The inventors have found that the anti-staling effect of a maltogenic amylase can be improved by using a variant having increased thermostability. Further, they found that such a variant improves the softness of baked products in the initial period after baking, particularly the first 24 hours after baking, so that the baked product has improved softness, both when eaten on the same day and when stored for several days after baking.

Accordingly, the invention provides a polypeptide which:
a) has maltogenic amylase activity;
b) has at least 70% identity to SEQ ID NO: 2,
c) has optimum maltogenic amylase activity in the range pH 3.5–7.0 (preferably 4–5.5), and
d) shows a residual maltogenic amylase activity of at least 25% after incubation with 1 mM $Ca^{++}$ at pH 4.3, 80° C. for 15 minutes.

The inventors found that thermostable variants can be prepared by random DNA mutagenesis followed by screening for thermostable variants. Thus, the invention also provides a method of preparing a maltogenic amylase variant having improved anti-staling properties, which method comprises
a) subjecting a DNA sequence encoding the maltogenic amylase to random mutagenesis,
b) expressing the mutated DNA sequence obtained in step (a) in a host cell, and
c) screening for host cells expressing a mutated maltogenic amylase which shows a higher thermostability, and
d) preparing the mutated maltogenic amylase expressed by the host cells.

Further, the inventors have modified the amino acid sequence of a malogenic alpha-amylase to obtain variants with improved properties, based on the three-dimensional structure of the maltogenic alpha-amylase Novamyl. The variants have altered physicochemical properties., e.g. an altered pH optimum, improved thermostability, increased specific activity, an altered cleavage pattern or an increased ability to reduce retrogradation of starch or staling of bread.

Accordingly, the present invention provides a method of constructing a variant of a parent maltogenic alpha-amylase, wherein the variant has at least one altered property as compared to said parent maltogenic alpha-amylase, which method comprises:
i) analyzing the structure of the maltogenic alpha-amylase to identify, on the basis of an evaluation of structural considerations, at least one amino acid residue or at least one structural region of the maltogenic alpha-amylase, which is of relevance for altering said property;

ii) constructing a variant of the maltogenic alpha-amylase, which as compared to the parent, has been modified in the amino acid residue or structural part identified in i) so as to alter said property; and iii) testing the resulting maltogenic alpha-amylase variant for said property.

The property which may be altered by the above methods of the present invention may be, e.g., stability, pH dependent activity, ability to reduce retrogradation of starch or staling of bread, specific activity, or substrate specificity. Thus, the variant may have, e.g., increased thermostability or higher activity at a lower pH an altered pH optimum, improved thermostability, increased specific activity or increased ability to reduce retrogradation of starch or staling of bread.

In still further aspects the invention relates to variants of a maltogenic alpha-amylase, the DNA encoding such variants and methods of preparing the variants. Finally, the invention relates to the use of the variants for various industrial purposes, in particular baking.

BRIEF DESCRIPTION OF THE FIGURE

FIG. 1 shows the plasmid pLBei010, which contains the *Bacillus stearothermophilus* maltogenic amylase gene

DETAILED DISCLOSURE OF THE INVENTION

Maltogenic Alpha-Amylase

The maltogenic alpha-amylase is an enzyme classified in EC 3.2.1.133. The enzymatic activity does not require a non-reducing end on the substrate and the primary enzymatic activity results in the degradation of amylopectin and amylose to maltose and longer maltodextrins. It is able to hydrolyze amylose and amylopectin to maltose in the alpha-configuration, and is also able to hydrolyze maltotriose as well as cyclodextrin.

A particularly preferred maltogenic alpha-amylase is the amylase cloned from *Bacillus* as described in EP 120 693 (hereinafter referred to as Novamyl). Novamyl has the amino acid sequence set forth in amino acids 1–686 of SEQ ID NO: 2. Novamyl is encoded in the gene harbored in the *Bacillus* strain NCIB 11837 which has the nucleic acid sequence set forth in SEQ ID NO:1. The three-dimensional structure of Novamyl is described below.

In general, a preferred maltogenic alpha-amylase should have one or more of the following properties:

i) a three dimensional structural homology to Novamyl, ii) an amino acid sequence having at least 70% identity to SEQ ID NO: 2, preferably at least 80% or 90%, e.g. 95% or 98%, iii) a DNA sequence which hybridizes to the DNA sequence set forth in SEQ ID NO:1 or to the DNA sequence encoding Novamyl harbored in the *Bacillus* strain NCIB 11837;

iv) a calcium binding site comprising a coordination equivalent to a backbone carbonyl atom from Asn77, sidechain atom OE2 and, OE1 from Glu102, a sidechain atom OD1 from Asp79, a sidechain atom OD1 from Asp76, and a sidechain atom OE1 from Glu101, and one water molecule WAT V21, atom OWO, wherein the positions are as shown in Appendix 1;

v) a sequence of five amino acids corresponding to Pro-Ala-Gly-Phe-Ser in a position equivalent to residues 191–195 in the amino acid sequence shown in SEQ ID NO: 2; and The structural homology referred to above in i) is based on other sequence homologies, hydrophobic cluster analysis or by reverse threading (Huber, T; Torda, AE, PROTEIN SCIENCE Vol. 7, No. 1 pp. 142–149 (1998)) and which by any of these methods is predicted to have the same tertiary structure as Novamyl, wherein the tertiary structure refers to the overall folding or the folding of Domains A, B, and C, more preferably including Domain D, and most preferably including Domain E. Alternatively, a structural alignment between Novamyl and a maltogenic alpha-amylase may be used to identify equivalent positions.

The calcium binding site referred to above in iv) is based on a calcium binding site identified in the three-dimensional structure of Novamyl, and is discussed below in the section "Calcium binding sites."

The "equivalent position" referred to above in v) is based on amino acid or DNA sequence alignment or structural homology using methods known in the art.

Three-Dimensional Structure of Maltogenic Alpha-Amylase

Novamyl was used to elucidate the three-dimensional structure forming the asis for the present invention.

The structure of Novamyl was solved in accordance with the principle for x-ray crystallographic methods, for example, as given in *X-Ray Structure Determination*, Stout, G. K. and Jensen, L. H., John Wiley & Sons, Inc. NY, 1989.

The structural coordinates for the solved crystal structure of Novamyl at 2.2 Å resolution using the isomorphous replacement method are given in standard PDB format (Protein Data Bank, Brookhaven National Laboratory, Brookhaven, Conn.) as set forth in Appendix 1. It is to be understood that Appendix 1 forms part of the present application. In the context of Appendix 1, the following abbreviations are used: CA refers to calcium ion or alpha-carbon atom of the polypeptide backbone, WAT refers to water or to calcium, MAL refers to maltose, HEX refers to a carbohydrate unit of a substrate analogue, and SUL refers to a sulfate ion.

Amino acid residues of the enzyme are identified herein by their respective one- or three-letter amino acid code.

The structure of said maltogenic alpha-amylase is made up of five globular domains, ordered A, B, C, D and E. The domains can be defined as being residues 1–132 and 204403 for Domain A, residues 133–203 for Domain B, residues 404–496 for Domain C, residues 497–579 for Domain D, and residues 580–686 for Domain E, wherein the numbering refers to the amino acid sequence in SEQ ID NO: 2. Features of Domains A, B, and C of particular interest are described below.

Domain A

Domain A is the largest domain and contains the active site which comprises a cluster of three amino acid residues, D329, D228 and E256, spatially arranged at the bottom of a cleft in the surface of the enzyme. The structure of Domain A shows an overall fold in common with the α-amylases for which the structure is known, viz. the (beta/alpha) 8 barrel with eight central beta strands (numbered 1–8) and eight flanking a-helices. The Parrel is defined by McGregor op. cit. The C-terminal end of the beta strand 1 is connected to helix 1 by a loop denoted loop 1 and an identical pattern is 1 found for the other loops, although the loops show some variation in size and some can be quite extensive.

The eight central beta-strands in the (beta/alpha) 8 barrel superimpose reasonably well with the known structures of CGTases. This part of the structure, including the close surroundings of the active site located at the C-terminal end of the beta-strands, shows a high degree of identity with CGTases.

In contrast, the loops connecting the beta-strands and alpha helices display a high degree of variation from the known structures of CGTases. These loops constitute the structural context of the active site, and the majority of the contacts to the substrate is found among residues located in these loops. Distinguishing characteristics such as substrate specificity, substrate binding, pH activity profile, substrate cleavage pattern, and the like, are determined by specific amino acids and the positions they occupy in these loops. In Novamyl Domain A contains two calcium binding sites, one of which is homologous to the calcium binding site in CGTases; the other is unique to Novamyl. The structure of the calcium binding site is discussed further below in the section "Calcium binding sites."

Domain B

Domain B, also referred to as loop 3 of the (beta/alpha) 8 barrel, in comprises amino acid residues 133–203 of the amino acid sequence shown in SEQ ID NO: 2. The structure is partially homologous to the structure of Domain B in CGTases, the most striking difference being the presence of a five amino acid insert corresponding to positions 191–195 in the amino acid sequence shown in SEQ ID NO: 2 which is not found in the CGTases. This insert is spatially positioned close to the active site residues and in close contact to the substrate.

Domain C

Domain C in Novamyl comprises amino acid residues 404–496 of the amino acid sequence shown in SEQ ID NO: 2. Domain C is composed entirely of β-strands which form a single 8-stranded sheet structure that folds back on itself, and thus may be described as a β-sandwich structure. One part of the β-sheet forms the interface to Domain A.

Calcium Binding Sites

The structure of the maltogenic alpha-amylase exhibits three calcium-binding sites; that is, three calcium ions are found to be present in the structure. In common with most of the known family 13 structures, one calcium ion, WAT 693 in Appendix 1, is located between the A and B domains. This calcium ion is coordinated by a backbone carbonyl atom from Gln184 and His232, sidechain atoms OD2 and OD1 from Asp198, a sidechain atom OD1 from Asn131, and three water molecules WAT V1, WAT V5 and WAT V8.

A second calcium ion is located in the A domain and is common to CGTases, but not found in α-amylases. The calcium ion WAT 694 is coordinated by a backbone carbonyl atom from Gly48 and Asp23, sidechain atom OD2 from Asp50, a sidechain atom OD1 from Asp21, a sidechain atom OD1 from Asn26, and a sidechain atom OD1 from Asn27, and one water molecule WAT V62.

The third calcium ion is located in the A Domain and is unique to Novamyl. The calcium ion is WAT 692 and the coordination comprises a backbone carbonyl atom from Asn77, sidechain atom OE2 and OE1 from Glu102, a sidechain atom OD1 from Asp79, a sidechain atom OD1 from Asp76, and a sidechain atom OE1 from Glu101, and one water molecule WAT V21.

Substrate Binding Site

Parts of the loop discussed above in the context of domains A and B are of particular interest for substrate interaction and active site reactivity. In particular, in domain A, residues 37–45 in loop 1, residues 261–266 in loop 5, residues 327–330 in loop 7 and residues 370–376 in loop 8; in domain B, residues 135–145 in loop 3, residues 173–180 and 188–196 in loop 3, wherein residue positions correspond to the amino acids in the amino acid sequence in SEQ ID NO: 2.

Without being limited to any theory, it is presently believed that binding between a substrate and an enzyme is supported by favorable interactions found within a sphere of 4 to 6 Å between the substrate molecule and the enzyme, such as hydrogen bonds and/or strong electrostatic interaction. The following residues of Novamyl (SEQ ID NO: 2) are within a distance of 6 Å of the substrate HEX and thus believed to be involved in interactions with said substrate:

44, 89, 90, 92, 93, 127, 129, 132, 135, 177, 178, 188, 191, 194, 196, 226, 228, 229, 230, 231, 232, 256, 258–261, 288, 328, 329, 371, 372, 373, 376, and 690.

The following residues of Novamyl are within a distance of 4 Å of the substrate HEX and thus believed to be involved in interactions with said substrate:

90, 92, 93, 129, 132, 177, 188, 189, 190, 191, 196, 226, 228, 229, 231, 232, 256, 258, 259, 260, 261, 328, 329, 372, 376, and 690.

Homology Building of Novamyl®

The structure of the Novamyl® was model built on the structure disclosed in Appendix 1 herein. The structure of other maltogenic alpha-amylases may be built analogously.

A model structure of a maltogenic alpha-amylase can be built using the Homology program or a comparable program, e.g., Modeller (both from Molecular Simulations, Inc., San Diego, Calif.). The principle is to align the sequence of the maltogenic alpha-amylase with the known structure with that of the maltogenic alpha-amylase for which a model structure is to be constructed. The structurally conserved regions can then be built on the basis of consensus sequences. In areas lacking homology, loop structures can be inserted, or sequences can be deleted with subsequent bonding of the necessary residues using, e.g., the program Homology. Subsequent relaxing and optimization of the structure should be done using either Homology or another molecular simulation program, e.g., CHARMm from Molecular Simulations.

Methods for Designing Novel Maltogenic Alpha-Amylase Variants

In a first aspect, the invention relates to a method of constructing a variant of a parent maltogenic alpha-amylase, wherein said variant has at least one altered property as compared to said parent α-amylase, which method comprises:

i) analyzing the structure of the maltogenic alpha-amylase to identify at least one amino acid or structural region of said α-amylase, which, on the basis of structural or functional considerations, is determined to be of relevance for altering said property of the parent maltogenic alpha-amylase;

ii) constructing a variant of the maltogenic alpha-amylase, which as compared to the parent, has been modified in the amino acid residue or structural region identified in i) has been modified so as to after said property; and iii) testing the resulting variant for said property.

The structural part which is identified in step i) of the method of the invention may be composed of one amino acid residue. However, normally the structural part comprises more than one amino acid residue, typically constituting one of the above parts of the maltogenic alpha-amylase structure such as one of the A, B, C, D or E domains, an interface between any of these domains, a calcium binding site, a loop structure, the substrate binding site, or the like.

The structural or functional considerations may involve an analysis of the relevant structure or structural part and its contemplated impact on the function of the enzyme. For example, an analysis of the functional differences between maltogenic alpha-amylase and the various CGTases may be used for assigning certain properties of Novamyl to certain parts of the Novamyl structure or to contemplate such relationship. For instance, differences in the pattern or structure of loops surrounding the active site may result in differences in access to the active site of the substrate and thus differences in substrate specificity and/or cleavage pattern.

Furthermore, parts of a maltogenic alpha-amylase involved in substrate binding, and thus, for example, substrate specificity and/or cleavage, calcium ion binding, important, for example, for the calcium dependency of the enzyme, and the like, have been identified (vide infra).

The modification of an amino acid residue or structural region is typically accomplished by suitable modifications of a DNA sequence encoding the parent enzyme in question. The modification may be substitution, deletion or insertion of an amino acid residue or a structural part.

The property to be modified may be stability (e.g. thermostability), pH dependent activity, substrate specificity, specific activity or ability to reduce retrogradation of starch or staling of bread. Thus, the altered property may be an altered specific activity at a given pH and/or an altered substrate specificity, such as an altered pattern of substrate cleavage or an altered pattern of substrate inhibition.

In step ii) of the method according to the invention the part of the structure to be identified is preferably one which in the folded enzyme is believed to be in contact with the substrate (cf, the disclosure above in the section entitled "Substrate Binding Site") or involved in substrate specificity and/or cleavage pattern, and/or one which is in contact with one of the calcium ions and/or one, which is contributing to the pH or temperature profile of the enzyme, or is otherwise responsible for the properties of the maltogenic alpha-amylase.

Described in the following are specific types of variants which have been designed by use of the method of the invention.

The variants of the invention may comprise additional modifications in addition to the modifications described herein. The variants preferably have an amino acid having more than 70% identity with SEQ ID NO: 2, preferably more than 80%, particularly more than 90%, especially more than 95%, e.g. more than 98%.

Maltogenic Alpha-Amylase Variants with Altered pH Dependent Activity Profile

The pH dependent activity profile can be changed by changing the pKa of residues within 10 Å of the active site residues of the maltogenic alpha-amylase. Changing the pKa of the active site residues is achieved, e.g., by changing the electrostatic interaction or hydrophobic interaction between functional groups of amino acid side chains of a given amino acid residue and its close surroundings. To obtain a higher activity at a higher pH, negatively charged residues are placed near a hydrogen donor acid, whereas positively charged residues placed near a nucleophilic acid will result in higher activity at low pH. Also, a decrease in the pKa can be obtained by reducing the accessibility of water or increasing hydrophobicity of the environment.

Thus, another aspect of the present invention relates to a variant of a parent maltogenic alpha-amylase, in which the variant has an altered pH dependent activity profile as compared to the parent, wherein the variant may be obtained by the following method:

i) identifying an amino acid residue within 15 Å from an active site residue of a maltogenic alpha-amylase in the three-dimensional structure of said parent maltogenic alpha-amylase, in particular 10 Å from an active site residue, wherein said amino acid residue is contemplated to be involved in electrostatic or hydrophobic interactions with an active site residue;

ii) substituting, in the structure, said amino acid residue with an amino acid residue which changes the electrostatic and/or hydrophobic surroundings of an active site residue, and evaluating the accommodation of the amino acid residue in the structure, iii) optionally repeating step i) and/or ii) recursively until an amino acid substitution has been identified which is accommodated into the structure, iv) constructing a maltogenic alpha-amylase variant resulting from steps i) and ii), and optionally iii), and testing the pH dependent enzymatic activity of said variant.

In a preferred embodiment, the variant of a maltogenic alpha-amylase having an altered pH dependent activity profile as compared to the parent maltogenic alpha-amylase comprises a modification of an amino acid residue corresponding to one or more of the following residues of the amino acid sequence set forth in SEQ ID NO: 2:

D127, V129, F188, A229, Y258, V281, F284, T288, N327, M330, G370, N371, and D372, L71, S72, V74, L75, L78, T80, L81, G83, T84, D85, N86, T87, G88, Y89, H90, G91, T94, R95, D96, F97, I174, S175, N176, D178, D179, R180, Y181, E182, A183, Q184, K186, N187, F188, T189, D190, A192, G193, F194, 8195, L196.

In more preferred embodiment, the variant comprises a modification corresponding to one or more of the following modifications in the amino acid sequence set forth in SEQ ID NO: 2:

D127N/L, V129S/TG/V, F188E/K/H, A229S/T/G/V, Y258E/D/K/R/F/N, V281L/T, F284K/H/D/E/Y, T288E/K/R, N327D, M330F/I/D/E/K, G370N, N371D/E/G/K, and D372N/V, L71I, S72C, V74I, L75N/D/Q/I/V, L78N/I, T80I/L/V/S/N/G, L81I/V/S/T/N/Q/K/H, G83A/S/T/N/Q/E/D/R/H/L, T84S/A/N/D/G, D85A/T/S/N/G, N86Q/E/D/Y/H/K, T87S/I, G88A/S/T, Y89F, H$_{90}$N/Q/K, G91A/S/T, T94N/D/A/V/I, R95K/Q, D96N/V/Q/I, F97Y, I174N/Q/L, S175T/A/N/D, N176S/T/H/Q/P, D178N/Q/E/K/H, D179Y/N/H, R180W, Y181R/F/CAL, E182D, A183S/C/G, Q184E, K186R, N187Q/E/L/F/H/K/V/L, F188Y/L/I/H/N, T189N/D/A/S/H/Y/G, D190E/Q/H/N/K, A192T/D/E/N/K, G193A/S/T, F194Y, S195N/D/E/R/K/G, L196I.

Similar modifications may be introduced in equivalent positions of other maltogenic alpha-amylases. Variants of particular interest have a combination of one or more of the above with any of the other modifications disclosed herein.

Maltogenic Alpha-Amylase Variants with Altered Stability

A variant with improved stability (typically increased stability) may be obtained by stabilization of calcium binding, substitution with proline, substitution of histidine with another amino acid, introduction of an interdomain disulfide bond, removal of a deamidation site, altering a hydrogen bond contact, filling in an internal structural cavity with one or more amino acids with bulkier side groups, introduction of interdomain interactions, altering charge distribution, helix capping, or introduction of a salt bridge.

Calcium Binding

The invention provides a variant of a parent maltogenic alpha-amylase, which has an altered stability due to an altered stabilization of calcium ($Ca^{2+}$) binding. The enzyme variant may have altered thermostability or pH dependent stability, or it may have maltogenic alpha-amylase activity in the presence of a lower concentration of calcium ion. It is presently believed that amino acid residues located within 10 Å from a calcium ion are involved in or are of importance for the $Ca^{2+}$ binding capability of the enzyme.

The amino acid residues found within a distance of 10 Å from the $Ca^{2+}$ binding sites of the maltogenic alpha-amylase with the amino acid sequence set forth in SEQ ID NO: 2 were determined as described in Example 2 and are as follows:

16, 17, 18, 19, 20, 21, 22, 23, 24, 25, 26, 27, 28, 29, 30, 31, 32, 33, 35, 36, 40, 46, 47, 48, 49, 50, 51, 52, 53, 54, 56, 73, 74, 75, 76, 77, 78, 79, 80, 81, 87, 88, 89, 91, 93, 94, 95, 96, 99, 100, 101, 102, 103, 104, 105, 109, 129, 130, 131, 132, 133, 134, 145, 150, 167, 168, 169, 170, 171, 172, 174, 177, 180, 181, 182, 183, 184, 185, 186, 187, 188, 189, 196, 197, 198, 199, 200, 201, 202, 206, 210, 228, 229, 230, 231, 232, 233, 234, 235, 237, 378, and 637.

In order to construct a variant according to this aspect of the invention it is desirable to substitute at least one of the above mentioned amino acid residues, which is determined to be involved in a non-optimal calcium binding, with any other amino acid residue which improves the $Ca^{2+}$ binding affinity of the variant enzyme. Accordingly, another aspect of the invention relates to a method of constructing a variant of a parent maltogenic alpha-amylase wherein said variant has a stabilised $Ca^{2+}$ binding as compared to said parent, which method comprises:

i) identifying an amino acid residue within 10 Å from a $Ca^{2+}$ binding site of a maltogenic alpha-amylase in a model of the three-dimensional structure of said α-amylase which, from structural or functional considerations, is determined to be responsible for a non-optimal calcium ion interaction;

ii) constructing a variant in which said amino acid residue is substituted with another amino acid residue which, from structural or functional considerations, is determined to be important for establishing an altered $Ca^{2+}$ binding affinity; and iii) testing the $Ca^{2+}$ binding of the resulting maltogenic alpha-amylase variant.

Substituting an amino acid residue responsible for non-optimal calcium ion interaction with another residue may alter a calcium ion binding interaction of the enzyme. For instance, the amino acid residue in question may be selected on the basis of one or more of the following objectives:

a) to obtain an improved interaction between a calcium ion and an amino acid residue as identified from the structure of the maltogenic alpha-amylase. For instance, if the amino acid residue in question is exposed to a surrounding solvent, it may be advantageous to increase the shielding of said amino acid residue from the solvent so as to stabilize the interaction between said amino acid residue and a calcium ion. This can be achieved by substituting said residue, or an amino acid residue in the vicinity of said residue contributing to the shielding, with an amino acid residue with a bulkier side group or which otherwise results in an improved shielding effect.

b) to stabilize a calcium binding site, for instance by stabilizing the structure of the maltogenic alpha-amylase, e.g. by stabilizing the contacts between two or more of the five domains or stabilizing one or more of the individual domains as such. This may, e.g., be achieved by providing for a better coordination to amino acid side chains, which may, e.g., be obtained by substituting an N residue with a D residue and/or a Q residue with an E residue, e.g. within 10 Å, and preferably within 3 or 4 Å, of a calcium binding site.

c) to improve the coordination between the calcium ion and the calcium binding residues, e.g., by improving the interaction between the ion and the coordinating residues or increasing the number of sidechain coordinations by substituting a coordinating water with an amino acid sidechain.

d) replace water by a coordinating calcium amino acid residue.

Preferably, the amino acid residue to be modified is located within 8 Å of a $Ca^{2+}$ ion, preferably within 5 Å of a $Ca^{2+}$ ion. The amino acid residues within 8 Å and 5 Å, respectively, may easily be identified by an analogous method used for identifying amino acid residues within 10 Å (cf. Example 2).

In a preferred embodiment, the variant of a maltogenic alpha-amylase having an altered $Ca^{2+}$ binding as compared to the parent maltogenic alpha-amylase comprises a substitution of an amino acid residue corresponding to one or more of the following residues of the amino acid sequence set forth in SEQ ID NO: 2:

D17, A30, S32, R95, H103, N131, Q201, I174, and/or H169,

V74, L75, L78, T80, L81, T87, G88, Y89, H90, G91, T94, R95, D96, F97, Y167, F168, H169, H170, N171, G172, D173, I174, S175, N176, D178, D179, R180, Y181, E182, A183, Q184, K186, N187, F188, T189.

In more preferred embodiment, the variant of a maltogenic alpha-amylase comprises a substitution corresponding to one or more of the following substitutions in the amino acid sequence set forth in SEQ ID NO: 2:

D17E/Q, A30M/L/A/V/I/E/Q, S32D/E/N/Q, R95M/L/A/V/I/E/Q, H103Y/N/Q/D/E, N131D, Q201E, I174E/Q, and H169N/D/E/Q V74I, L75N/D/Q/I/V, L78N/I, T80I/L/V/S/N/G, L81I/V/S/T/N/Q/K/H, T87S/I, G88A/S/T, Y89F, H90N/Q/K, G91A/S/T, T94N/D/A/M/V/I, R95K/Q, D96N/V/Q/I, F97Y, Y167F/R/C, F168Y, H169N/Q/K, H170N/Q/K, N171D/E/Q/H/R/K/G, G172A/T/S, D173N/S/T/Y/R/G, I174N/Q/L, S175T/A/N/D, N176S/T/H/Q/P, D178N/Q/E/K/H, D179Y/N/H, R180W, Y181R/F/C/L, E182D, A183S/C/G, Q184E, K186R, N187Q/E/L/F/H/K/N/L, F188Y/L/I/H/N, T/89N/D/A/S/H/Y/G.

In another preferred embodiment of the invention with respect to altering the $Ca^{2+}$ binding of a maltogenic alpha-amylase the partial sequence N28P29-A30-K31-S32-Y33-G34 as set forth in SEQ ID NO: 2 is modified.

Similar substitutions may be introduced in equivalent positions of other maltogenic alpha-amylases. Modifications of particular interest are any combination of one or more of the above with any of the other modifications disclosed herein.

Other Substitutions

Variants with improved stability of the enzyme can be achieved by improving existing or introducing new interdomain and intradomain contacts. Such improved stability can be achieved by the modifications listed below.

The maltogenic alpha-amylase having the amino acid sequence shown in SEQ ID NO: 2 may be stabilized by the introduction of one or more interdomain disulfide bonds. Accordingly, another preferred embodiment of the present invention relates to a variant of a parent maltogenic alpha-amylase which has improved stability and at least one more interdomain disulfide bridge as compared to said parent, wherein said variant comprises a modification in a position corresponding to at least one of the following pairs of positions in SEQ ID NO: 2:

G236+S583, G618+R272, T252+V433 and/or A348+V487.

In a more preferred embodiment, the substitution corresponds to at least one of the following pairs:

G236C+S583C, G618C+R272C, T252C+V433C and/or A348C+V487C.

Another preferred embodiment of the invention relates to a variant of a parent maltogenic alpha-amylase which has an improved stability and an altered interdomain interaction as compared to said parent, wherein said variant comprises a substitution in a position corresponding at least one of the following sets of positions in SEQ ID NO: 2:

i) F143, F194, L78;

ii) A341, A348, L398, I415, T439, L464, L465, iii) L557;

iv) S240, L268;

v) Q208, L628;

vi) F427, Q500, N507, M508, S573; and vii) I510, V620.

In a more preferred embodiment, the substitution corresponds to at least one of the following sets:

i) F143Y, F194Y, L78Y/F/W/E/Q;

ii) A341S/D/N, A348V/I/L, L398E/Q/N/D, I415E/Q, T439D/E/Q/N, L464D/E, L465D/E/N/Q/R/K;

iii) L557Q/E/N/D;

iv) S240D/E/N/Q, L268D/E/N/Q/R/K;

v) Q208D/E/Q, L628E/Q/N/D;

vi) F427E/Q/R/K/Y, Q500Y, N507Q/E/D, M508K/R/E/Q, S573D/E/N/Q; and/or vii) I510D/E/N/Q/S, V620D/E/N/Q.

Another preferred embodiment of the invention relates to a variant of a parent maltogenic alpha-amylase which has an improved stability and one or more salt bridges as compared to said parent, wherein said variant comprises a substitution in a position corresponding at least one of the following sets of positions in SEQ ID NO: 2:

N106, N320 and Q624.

In a more preferred embodiment, the variant of a maltogenic alpha-amylase comprises a substitution corresponding to the following substitutions in the amino acid sequence set forth in SEQ ID NO: 2:

N106R, N320E/D and/or Q624E.

Another preferred embodiment of the invention relates to a variant of a parent maltogenic alpha-amylase which has an improved stability and wherein said variant comprises a substitution in a position corresponding at least one of the following sets of positions in SEQ ID NO: 2:

K40, V74, S141, T142, F188, N234, K249, D261, D261, L268, V279, N342, G397, A403, K425, S442, S479, S493, T494, S495, A496, S497, A498, Q500, K520, A555 and N595.

In a more preferred embodiment, the variant of a maltogenic alpha-amylase comprises a substitution corresponding to one or more of the following substitutions with proline in the amino acid sequence set forth in SEQ ID NO: 2:

V74P, S141P, N234P, K249P, L268P, V279P, N342P, G397P, A403P! S442P, S479P, S493P, T494P, S495P, A496P, S497P, A498P, Q500P, and/or A555P.

Other preferred substitutions are K40R, T142A, F188/L, D261G, K425E, K520R, and/or N5951.

Analogously, it may be preferred that one or more histidine residues present in the parent maltogenic alpha-amylase is or are substituted with a non-histidine residues such as Y, V I, L, F, M, E, Q, N, or D. Accordingly, in another preferred embodiment, the variant of a maltogenic alpha-amylase comprises a substitution of an amino acid residue corresponding to one or more of the following residues of the amino acid sequence set forth in SEQ ID NO: 2:

H103, H220, and H344

In a more preferred embodiment, the variant of a maltogenic alpha-amylase comprises a substitution corresponding to one or more of the following substitutions in the amino acid sequence set forth in SEQ ID NO: 2:

H103Y/V/I/L/F/Y, H220Y/L/M, and H344E/Q/N/D/Y.

It may be preferred that one or more asparagine or glutamine residues present in the parent maltogenic alpha-amylase is or are substituted with a residue lacking the amide on the side chain. Accordingly, in another preferred embodiment, the variant of a Novamyl-like comprises a substitution of an amino acid residue corresponding to one or more of the following residues of the amino acid sequence set forth in SEQ ID NO: 2:

Q13, N26, N77, N86, N99, Q119, N120. N131, N152, N171, N176, N187, Q201, N203, N234, Q247, N266, N275, N276, N280, N287, Q299, N320, N327, N342, Q366, N371, N375, N401, N436, N454, N468, N474, Q500, N507, N513, Q526, N575, Q581, N621, Q624 and N664.

In more preferred embodiment, the variant of a maltogenic alpha-amylase raft comprises a substitution corresponding to one or more of the following substitutions in the amino acid sequence set forth in SEQ ID NO: 2:

Q13S/T/A/V/L/I/F/M, N26S/T/A/V/L/I, N77S/T/A/V/L/I, N86S/T/A/N/V/L/I, N99T/S/V/L, Q119T/S, N120S/T/A/V/L/I, N131S/T/A/V/L/I, N152T/S/V/L, N171Y/D/S/T, N176S/T/A/V/L/I, Q20S/T/A/V/L/I/F/M, N203D/S/T/A/V/L/I, N234S/T/A/V/L/I, Q247S/T/A/V/L/I/F/M, N266S/T/A/V/L/I, N275S/T/A/V/L/I, N276S/T/A/V/L/I, N280S/T/A/V/L/I, N287S/T/A/V/L/I, Q299L/T/S, N320S/T/A/V/L/I, N327S/T/A/V/L/I, N342S/T/A/V/L/I, Q365S/T/A/V/L/I, N371S/T/A/V/L/I, N375S/T/A/V/L/I, N401 S/T/A/V/L/I, N436S/T/A/V/L/I, N454D/S/T/A/V/L/I, N468D/S/T/A/V/L/I, N474D/S/T/A/V/L/I, Q500S/T/A/V/L/I/F/M, N507S/T/A/V/L/I, N513S/T/A/V/L/I, Q526D/S/T/A/V/L/I, N575S/T/A/V/L/I, Q581S/T/A/V/L/I/F/M, N621S/T/A/V/L/I Q624S/T/A/V/L/I/F/M and N664S/T/A/V/L/I.

Another embodiment of the invention relates to a variant of a parent maltogenic alpha-amylase which has improved stability and improved hydrogen bond contacts as compared to said parent, wherein said variant comprises a modification in a position corresponding to one or more of the following positions in SEQ ID NO: 2:

I16, L35, M45, P73, D76, D79, A192, 1100, A148, A163+G172, L268, V281, D285, L321, F297, $N_3O_5$, K316, S573, A341, M378, A381, F389, A483, A486, I510, A564, F586, K589, F636, K645, A629, and/or T681. In a preferred embodiment, the modification corresponds to one or more of the following:

I16T/D/N, L35Q, M45K, P73Q, D76E, D79E/Y, A192S/D/N, I100TS/D/N/E/Q, A148D/N/E/Q/S/T/R/K, A163Y+G172S/D/N, L268R/K, V281/Q, D285R/K, L321Q, F297N/D/Q/E, N305K/R, K316N/D, S573N/D, A341R/K, M378R/K, A381S/D/N, F389Y, A483S/D/N, A486Q/E, I510R/K, A564S/D/N, F586S/D/N, K589S/D/Q/N, F636Y, K645T, A629N/D/E/Q, and/or T681 D/N/E/Q/S.

Similar substitutions may be introduced in equivalent positions of other maltogenic alpha-amylases. Substitutions of particular interest are any combination of one or more of the above with any of the other modifications disclosed herein.

Before actually constructing a maltogenic alpha-amylase variant to achieve any of the above objectives, it may be convenient to evaluate whether or not the contemplated amino acid modification can be accommodated into the maltogenic alpha-amylase structure, e.g. into a model of the three-dimensional structure of the parent maltogenic alpha-amylase.

Maltogenic Alpha-Amylase Variants with Altered Thermostability and/or Altered Temperature Dependent Activity Profile The invention further relates to a variant of a parent maltogenic alpha-amylase, which results from substitution, deletion or insertion of one or more amino acid residues so as to obtain a variant having an altered thermostability or temperature dependent activity profile.

The structure of the maltogenic alpha-amylase contains a number of unique internal cavities which may contain water and a number of crevices. In order to increase the thermostability of the polypeptide it may be desirable to reduce the number or size of cavities and crevices, e.g., by introducing one or more hydrophobic contacts, preferably achieved by introducing amino acids with bulkier side groups in the vicinity or surroundings of the cavity. For instance, the amino acid residues to be modified are those which are involved in the formation of the cavity.

Accordingly, in a further aspect the present invention relates to a method of increasing the thermostability and/or altering the temperature dependent activity profile of a parent maltogenic alpha-amylase, which method comprises:

i) identifying an internal cavity or a crevice of the parent maltogenic alpha-amylase in the three-dimensional structure of said polypeptide;

ii) substituting, in the structure, one or more amino acid residues in the neighbourhood of the cavity or crevice identified in step i) with another amino acid residue which, from structural or functional considerations, is determined to increase the hydrophobic interaction and to fill out or reduce the size of the cavity or crevice; and iii) constructing a variant of the parent maltogenic alpha-amylase resulting from step ii) and testing the thermostability and/or temperature dependent activity of the variant.

The structure identified in Appendix 1 may be used for identifying the cavity or crevice of the parent maltogenic alpha-amylase.

It will be understood that the cavity or crevice is identified by the amino acid residues surrounding said cavity or crevice, and that modification of said amino acid residues are of importance for filling or reducing the size of said cavity or crevice. Preferably, the modification is a substitution with a bulkier amino acid residue, i.e. one with a greater side chain volume. For example, all the amino acids are bulkier than Gly, whereas Tyr and Trp are bulkier than Phe. The particular amino acid residues referred to below are those which in a crystal structure have been found to flank the cavity or crevice in question.

In a preferred embodiment, the variant of a maltogenic alpha-amylase, in order to fill, either completely or partly, cavities located internally in the structure, comprises a substitution of an amino acid residue corresponding to one or more of the following residues of the amino acid sequence set forth in SEQ ID NO: 2:

L51, L75, L78, G88, G91, T94, V114, I125, V126, T134, G157, L217, S235, G236, V254, V279, V281, L286, V289, 1290, V308, L321, 1325, D326, L343, F349, S353, I359, I405, L448, Q449, L452, I470, G509, V515, S583, G625, L627, L628 and A670.

L71, S72, V74, L75, L78, T80, L81, G83, T84, D85, N86, T87, G88, Y89, H90, G91, T94, R95, D96, F97, Y167, F168, H169, H170, N171, G172, D173, 1174, S175, N176, D178, D179, R180, Y181, E182, A183, Q184, K186, N187, F188, T189, D190, A192, G193, F194, S195, L196.

In a more preferred embodiment, the variant of a maltogenic alpha-amylase comprises one or more substitutions corresponding to the following substitutions in the amino acid sequence set forth in SEQ ID NO: 2:

L217 in combination with L75 (e.g. L217F/Y in combination with L75F/Y), L51W, L75F/Y, L78I, G88A/V/T, G91T/S/V/N, T94V/I/L, V114V/I/L, I125L/M/F/W V126I/L, T134V/I/L/M/F/Y/W, G157A/V/I/L, L217V/I/M/F/Y/W, S235I/L/M/F/Y/W, G236A/V/I/L/M/F/Y/W, V254I/L/M/F/Y/W, V279M/I/L/F, V281/L/M/F/Y/W, L286F, V289I/L/R, I290M/L/F, V308I/L/M/F/Y/W, L321I/M/F/Y/W, 1325L/M/F/Y/W, D326E/Q, L343M/F/Y/W, F349W/Y, S353V/I/L, I359L/M/F/Y/W, I405M/L/Y/F/W, L448Y, Q449Y, L452M/Y/F/W, I470M/L/F, G509A/V/I/L/M/S/T/D/N, V515I/L, S583V/I/L/N, G625A/V/I/L/M/F/Y/W, L627M/F/Y, L628M/I/F/Y/W and A670V/I/L/M/F/Y/W, L71I, S72C, V74I, L75N/D/Q/I/V, L78N/I, T80I/L/V/S/N/G, L81I/V/S/T/N/Q/K/H, G83A/S/T/N/Q/E/D/R/H/L, T84S/A/N/D/G, D85A/T/S/N/G, N86Q/E/D/Y/H/K, T87S/I, G88A/S/T, Y89F, H90N/Q/K, G91A/S/T, T94N/D/A/M/V/I, R95K/Q, D96N/V/Q/I, F97Y, Y167F/R/C, F168Y, H169N/Q/K, H170N/Q/K, N171D/E/Q/H/R/K/G, G172A/T/S, D173N/S/T/Y/R/G, I174N/Q/L, S175T/A/N/D, N176S/T/H/Q/P, D178N/Q/E/K/H, D179Y/N/H, R180W, Y181R/F/C/L, E182D, A183S/C/G, Q184E, K186R, N187Q/E/L/F/H/K/V/L, F188Y/L/I/H/N, T 89N/D/A/S/H/Y/G, D190E/Q/H/N/K, A192T/D/E/N/K, G193A/S/T, F194Y, S195N/D/E/R/K/G, L196I.

Similar substitutions may be introduced in equivalent positions of other maltogenic alpha-amylases. Variants of particular interest have a combination of one or more of the above with any of the other modifications disclosed herein.

Maltogenic Alpha-Amylase Variants with an Altered Cleavage Pattern

One aim of the present invention is to change the degradation characteristics of a maltogenic alpha-amylase. Thus, Novamyl hydrolyzes starch to form predominantly maltose (G2) and a small amount of glucose (G1), but virtually no higher oligosaccharides (G3+). It may be desirable to change this cleavage pattern, e.g. so as to form higher amounts of higher oligosaccharides, such as maltotriose (G3), maltotetraose (G4) and maltopentaose (G5).

A variant of a parent maltogenic alpha-amylase in which the substrate cleavage pattern is altered as compared to said parent may be constructed by a method which comprises:

i) identifying the substrate binding area of the parent maltogenic alpha-amylase in a model of the three-dimensional structure, e.g. within a sphere of 4 Å from the substrate binding site as defined in the section above entitled "Substrate Binding Site";

ii) substituting in the model one or more amino acid residues of the substrate binding area of the cleft identified in i) which is or are believed to be responsible for the cleavage pattern of the parent with another amino acid residue which from structural or functional considerations is believed to result in an altered substrate cleavage pattern, or deleting one or more amino acid residues of the substrate binding area contemplated to introduce favorable interactions to the substrate or adding one or more amino acid residues to the substrate binding area contemplated to introduce favorable interactions to the substrate; and iii) constructing a maltogenic alpha-amylase variant resulting from step ii) and testing the substrate cleavage pattern of the variant.

Accordingly, another aspect of the invention relates to a variant of a parent maltogenic alpha-amylase which has an altered substrate binding site as compared to said parent, which variant comprises a modification in a position corresponding to one or both of the following positions in SEQ ID NO: 2:

In a preferred embodiment, the variant comprises a modification corresponding to:

V281 Q and/or A629N/D1E/Q.

Similar modifications may be introduced in equivalent positions of other maltogenic alpha-amylases. Substitutions of particular interest are any combination of one or both of the above with any of the other modifications disclosed herein.

Maltogenic Alpha-Amylase Variants with Improved Ability to Reduce Retrogradation of Starch and/or Staling of Bread The invention provides maltogenic alpha-amylase variants having improved ability to reduce the retrogradation of starch and/or the staling of bread. Preferred variants comprise a modification at one or more positions corresponding to the following amino acid residues in SEQ ID NO: 2:

A30, K40, N115, T142, F188, T189, P191, A192, G193, F194, S195, D261, N327, K425, K520 and N595.

In a more preferred embodiment, the variant comprises one or more modifications corresponding to the following in SEQ ID NO: 2:

A30D, K40R, N115D, T142A, F188L, T189Y, A (191–195), D261G, D261G, N327S, K425E, K520R and N595I.

Determination of Residues within 10 Å from Calcium Ions

The coordinates of Appendix 1 are read into the INSIGHT program (BIOSYM Technologies). The spatial coordinates are presented showing the bonds between the atoms. The ions are presented as well as the water atoms. The part of the program package for creating subsets was used to create a 10 Å subset around the calcium ions in the structure by using the command ZONE. All residues identified as having an atom within the designated 10 Å distance from a calcium ion are compiled and listed by using the command LIST MOLECULE. By giving the ions the name "VAT CA" in the coordinate file, a 10 Å sphere around all atoms called "VAT CA" is compiled. The specific residues identified in this manner are given further above in the section entitled "Calcium binding".

Determination of Cavities

The solved structure of Novamyl with the structural coordinates set forth in Appendix 1 reveals many internal crevices and cavities. When analysing for such cavities the Connolly program is normally used (Lee, B. and Richards, F. M. (1971) J. Mol. Biol. 55:379400). The program uses a probe with radius to search the external and internal surface of the protein. The smallest crevice observable in this way has the probe radius.

To analyse the solved structure a modified version of the Connolly program included in the program of INSIGHT was used. In the first step, the water molecules and the ions were removed by unmerging these atoms from the solved structure. By using the command MOLECULE SURFACE SOLVENT the solvent accessible surface area was calculated for all atoms and residues using a probe radius of 1.4 Å, and displayed graphically together with the model of the solved structure. The internal cavities are then seen as dot surfaces with no connections to the external surface.

Suggestions for specific modifications to fill out the cavities are given above in the section entitled "Variants with altered thermostability and/or altered temperature dependent activity profile"). By using the homology built structures or/and comparisons based on sequence alignment, mutations for homologous structures of maltogenic alpha-amylases can be made.

Nomenclature for Amino Acid Modifications

The nomenclature used herein for defining mutations is essentially as described in WO 92/05249. Thus, F188H indicates a substitution of the-amino acid F (Phe) in position 188 with the amino acid H (His). V129S8T/GN indicates a substitution of V129 with S, T. G or V. Δ (191–195) or Δ (191–195) indicates a deletion of amino acids in positions 191–195, 192-A-193 indicates an insertion of A between amino acids 192 and 193.

Polypeptide Sequence Identity

For purposes of the present invention, the degree of identity may be suitably determined according to the method described in Needleman, S. B. and Wunsch, C. D., (1970), Journal of Molecular Biology, 48, 443–45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version 8, August 1994, Genetics Computer Group, 575 Science Drive, Madison, Wis., USA 53711).

The variants of the invention have an amino acid identity with amino acids 1686 of SEQ ID NO: 2 of at least 70%, preferably at least 80%, e.g. at least 90%, particularly at least 95% or at least 98%.

Hybridization

Suitable experimental conditions for determining hybridization between a nucleotide probe and a homologous DNA or RNA sequence involves presoaking of the filter containing the DNA fragments or RNA to hybridize in 5×SSC (sodium chloride/sodium citrate, Sambrook, et al., 1989) for 10 min, and prehybridization of the filter in a solution of 5×SSC, 5× Denhardt's solution (Sambrook, et al., 1989), 0.5% SDS and 100 µg/ml of denatured sonicated salmon sperm DNA (Sambrook, et al., 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/µg) probe for 12 hours at ca. 45° C. The filter is then washed twice for 30 minutes in 2×SSC, 0.5% SDS at least 55° C. (low stringency), preferably at least 60° C. (medium stringency), more preferably at least 65° C. (medium/high stringency), more preferably at least 70° C. (high stringency), even more preferably at least 75° C. (very high stringency).

Molecules which hybridize to the oligonucleotide probe under these conditions are detected by exposure to x-ray film.

Methods of Preparing Variants of Maltogenic Alpha-Amylases

Cloning a DNA Sequence Encoding a Novamyl-Like Polypeptide

The DNA sequence encoding a parent maltogenic alpha-amylase may be isolated from any cell or microorganism producing the maltogenic alpha-amylase in question, using various methods well known in the art, for example, from the *Bacillus* strain NCIB 11837.

First, a genomic DNA and/or cDNA library should be constructed using chromosomal DNA or messenger RNA from the organism that produces the maltogenic alpha-amylase to be studied. Then, if the amino acid sequence of the α-amylase is known, homologous, labelled oligonucleotide probes may be synthesised and used to identify maltogenic alpha-amylase-encoding clones from a genomic library prepared from the organism in question. Alternatively, a labelled oligonucleotide probe containing sequences homologous to a known α-amylase gene could be used as a probe to identify maltogenic alpha-amylase-encoding clones, using hybridization and washing conditions of lower stringency.

Another method for identifying maltogenic alpha-amylase-encoding clones involves inserting fragments of genomic DNA into an expression vector, such as a plasmid, transforming x-amylase negative bacteria with the resulting genomic DNA library, and then plating the transformed bacteria onto agar containing a substrate for maltogenic alpha-amylase, thereby allowing clones expressing maltogenic alpha-amylase activity to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin, wherein the fragments correspond to various parts of the entire DNA sequence, in accordance with techniques well known in the art. The DNA sequence may also be prepared by polymerase chain reaction (PCR) using specific primers, for instance as described in U.S. Pat. No. 4,683,202 or R. K. Saiki et al. (1988).

Site-Directed Mutagenesis

Once a maltogenic alpha-amylase-encoding DNA sequence has been isolated, and desirable sites for modification identified, modifications may be introduced using synthetic oligonucleotides. These oligonucleotides contain nucleotide sequences flanking the desired modification sites; mutant nucleotides are inserted during oligonucleotide synthesis. In a specific method, a single-stranded gap of DNA, bridging the maltogenic alpha-amylase-encoding sequence, is created in a vector carrying the maltogenic alpha-amylase gene. Then the synthetic nucleotide, bearing the desired modification, is annealed to a homologous portion of the single-stranded DNA. The remaining gap is then filled in with DNA polymerase 1 (Klenow fragment) and the construct is ligated using T4 ligase. A specific example of this method is described in Morinaga et al. (1984). U.S. Pat. No. 4,760,025 discloses the introduction of oligonucleotides encoding multiple modifications by performing minor alterations of the cassette. However, an even greater variety of modifications can be introduced at any one time by the Morinaga method because a multitude of oligonucleotides, of various lengths, can be introduced.

Another method of introducing modifications into a maltogenic alpha-amylase-encoding DNA sequences is described in Nelson and Long (1989). It involves a 3step generation of a PCR fragment containing the desired modification introduced by using a chemically synthesized DNA strand as one of the primers in the PCR reactions. From the PCR-generated fragment, a DNA fragment carrying the modification may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent maltogenic alpha-amylase may be conveniently performed by use of any method known in the art. In relation to the above, a further aspect of the present invention relates to a method for generating a variant of a parent Novamyl-like α-amylase, wherein the variant exhibits increased stability at low pH and at low calcium concentration relative to the parent, the method comprising:

(a) subjecting a DNA sequence encoding the parent Novamyl-like amylase to random mutagenesis, (b) expressing the mutated DNA sequence obtained in step (a) in a host cell, and (c) screening for host cells expressing a Novamyl-like α-amylase variant which has an altered property relative to the parent Novamyl-like α-amylase.

Step (a) of the above method of the invention is preferably performed using doped primers, as described in the working examples herein (tide infra). For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the maltogenic alpha-amylase enzyme by any published technique, using e.g. PCR, LCR or any DNA polymerase and ligase as deemed appropriate.

Preferably, the doping is carried out using 'constant random doping', in which the percentage of wild-type and modification in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% modifications in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent maltogenic alpha-amylase enzyme is subjected to PCR under conditions that increase the misincorporation of nucleotides (Deshler 1992, Leung et al., Technique, Vol. 1, 1989, pp. 11–15).

A mutator strain of E. coli (Fowler et al., Molec. Gen. Genet., 133, 1974, pp. 179–191), S. cereviseae or any other microbial organism may be used for the random mutagenesis of the DNA encoding the maltogenic alpha-amylase by, e.g., transforming a plasmid containing the parent enzyme into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the parent maltogenic alpha-amylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harbored in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment Examples of suitable host cells are the following: gram positive bacteria such as Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans or Streptomyces murinus; and gram negative bacteria such as E. coli.

The mutated DNA sequence may further comprise a DNA sequence encoding functions permitting expression of the mutated DNA sequence.

Localized Random Mutagenesis

The random mutagenesis may be advantageously localized to a part of the parent maltogenic alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

For region-specific random mutagenesis with a view to improving the stability of calcium binding of a parent maltogenic alpha-amylase, codon positions corresponding to the following amino acid residues from the amino acid sequence set forth in SEQ ID NO: 2 may appropriately be targeted:

Residues: Regions:
16–33, 35–36,40: 16–40
4654, 56:46–56
73–81: 73–81
87–89, 91, 93–96, 99–105, 109: 87–109
129–134, (145, 150): 129–134
167–172, 174, 177, 180–189: 167–189
196–202, 206–210:196–210
228–235, 237:228–237
378
637

With a view to achieving improved binding of a substrate, i.e., improved binding of a carbohydrate species, such as amylose or amylopectin, by a maltogenic alpha-amylase variant with a modified, e.g. higher, substrate specificity and/or a modified, e.g. higher, specificity with respect to cleavage, i.e. hydrolysis, of the substrate, it appears that the following codon positions in the following regions of the amino acid sequence shown in SEQ ID NO: 2, may particularly appropriately be targeted for modification by region-specific mutagenesis:

70–97, 127–143, 174–198, 226–233, 255–270, 282–292, 324–331, 370–376.

For region-specific random mutagenesis with a view to altering the substrate specificity and/or the pH dependent activity profile, the following regions of SEQ ID NO: 2 may be targeted: 70–97, 174–198.

For random mutagenesis with a view to improving the thermostability, the residues and regions described above may be targeted, particularly those described for altering stability, filling internal holes, improved Ca binding, interdomain and intradomain contacts, helix capping, proline substitution, and histidine substitution. In addition, the following regions may be targeted with a view to improving the thermostability: 70–109, 167–200. Also, any amino acid residue which is substituted in a variant having improved thermostability may be targeted, e.g. those in the following positions: 115, 342, 387, 422, 425, 483, 520, 594 and 600.

General Method for Random Mutagenesis by Use of the DOPE Program

The random mutagenesis may be carried out by the following steps:

1. Select regions of interest for modification in the parent enzyme
2. Decide on mutation sites and non-mutated sites in the selected region.
3. Decide on which kind of mutations should be carried out, e.g. with respect to the desired stability and/or performance of the variant to be constructed 4. Select structurally reasonable mutations
5. Adjust the residues selected by step 3 with regard to step 4.
6. Analyse by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting α-amylase variants by screening for the desired improved properties.

Suitable dope algorithms for use in step 6 are well known in the art. One such algorithm is described by Tomandl, D. et al., 1997, Journal of Computerided Molecular Design 11:29–38. Another algorithm is DOPE (Jensen, L J, Andersen, K V, Svendsen, A, and Kretzschmar, T (1998) Nucleic Acids Research 26:697–702).

Expression of Maltogenic Alpha-Amylase Variants

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

According to the invention, a DNA sequence encoding the variant produced by methods described above, or by any alternative methods known in the art, can be expressed, in the form of a protein or polypeptide, using an expression vector which typically includes control sequences encoding a promoter, operator, ribosome binding site, translation initiation signal, and, optionally, a repressor gene or various activator genes.

The recombinant expression vector carrying the DNA sequence encoding an maltogenic alpha-amylase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a maltogenic alpha-amylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyL), the promoters of the *Bacillus subtilis* xylA and xylB genes, etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the maltogenic alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracycline resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular. In general, the *Bacillus* α-amylase ls mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding maltogenic alpha-amylase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a maltogenic alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans. Bacillus lautus, Bacillus*

*megaterium, Bacillus thuringiensis,* or *Streptomyces lividans* or *Streptomyces murinus*, or gram negative bacteria such as *E. coli* The transformation of the bacteria may, for instance, be effected by protoplast transformation or by using competent cells in a manner known per se.

The yeast organism may favourably be selected from a species of *Saccharomyces* or *Schizosaccharomyces*, e.g. *Saccharomyces cerevisiae*. The filamentous fungus may advantageously belong to a species of *Aspergillus*, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing a maltogenic alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the maltogenic alpha-amylase variant of the invention. Suitable media are available from commercial suppliers or may be prepared according to published recipes (e.g. as described in catalogues of the American Type Culture Collection).

The maltogenic alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Testing of Maltogenic Alpha-Amylase Variants

Maltogenic alpha-amylase variants produced by any of the methods described above may be tested, either prior to or after purification, for amylolytic activity in a screening assay which measures the ability of the variant to degrade starch. The screening in step 10 in the above-mentioned random mutagenesis method of the invention may be conveniently performed by use of a filter assay based on the following procedure; A microorganism capable of expressing the mutated maltogenic alpha-amylase of interest is incubated on a suitable medium and under suitable conditions for secretion of the enzyme, the medium being covered with two filters comprising a protein-binding filter placed under a second filter exhibiting a low protein binding capability. The microorganism is grown on the second, top filter. Subsequent to the incubation, the bottom protein-binding filter comprising enzymes secreted from the microorganism is separated from the second filter-comprising the microorganism. The protein-binding filter is then subjected to screening for the desired enzymatic activity, and the corresponding microbial colonies present on the second filter are identified. The first filter used for binding the enzymatic activity may be any protein-binding filter, e.g., nylon or nitrocellulose. The second filter carrying the colonies of the expression organism may be any filter that has no or low affinity for binding proteins, e.g., cellulose acetate or Durapore™.

Screening consists of treating the first filter to which the secreted protein is bound with a substrate that allows detection of the α-amylase activity. The enzymatic activity may be detected by a dye, fluorescence, precipitation, pH indicator, IR-absorbance or any other known technique for detection of enzymatic activity. The detecting compound may be immobilized by any immobilizing agent e.g. agarose, agar, gelatine, polyacrylamide, starch, filter paper, cloth; or any combination of immobilizing agents. For example, α-amylase activity can be detected by Cibacron Red labelled amylopectin, which is immobilized in agarose. α-amylase activity on this substrate produces zones on the plate with reduced red color intensity. To screen for variants with increased stability, the filter with bound maltogenic alpha-amylase variants can be pretreated prior to the detection step described above to inactivate variants that do not have improved stability relative to the parent maltogenic alpha-amylase. This inactivation step may consist of, but is not limited to, incubation at a elevated temperatures in the presence of a buffered solution at any pH from pH 2 to 12, and/or in a buffer containing another compound known or thought to contribute to altered stability e.g., surfactants, EDTA, EGTA, wheat flour components, or any other relevant additives. Filters so treated for a specified time are then rinsed briefly in deionized water and placed on plates for activity detection as described above. The conditions are chosen such that stabilized variants show increased enzymatic activity relative to the parent after incubation on the detection media.

To screen for variants with altered thermostability, filters with bound variants are incubated in buffer at a given pH (e.g., in the range from pH 2–12) at an elevated temperature (e.g., in the range from 50°–110° C.) for a time period (e.g., from 1–20 minutes) to inactivate nearly all of the parent maltogenic alpha-amylase, rinsed in water, then placed directly on a detection plate containing immobilized Cibacron Red labelled amylopectin and incubated until activity is detectable. Similarly, pH dependent stability can be screened for by adjusting the pH of the buffer in the above inactivation step such that the parent maltogenic alpha-amylase is inactivated, thereby allowing detection of only those variants with increased stability at the pH in question. To screen for variants with increased calcium-dependent stability calcium chelators, such as ethylene glycol-bis(β-aminoethyl ether) N,N,N',N'-tetraacetic acid (EGTA), is added to the inactivation buffer at a concentration such that the parent maltogenic alpha-amylase is inactivated under conditions further defined, such as buffer pH, temperature or a specified length of incubation.

The variants of the invention may be suitably tested by assaying the starch-degrading activity of the variant, for instance by growing host cells transformed with a DNA sequence encoding a variant on a starch-containing agarose plate and identifying starch-degrading host cells as described above. Further testing in regard to altered properties, including specific activity, substrate specificity, cleavage pattern, thermoactivation, thermostability, pH dependent activity or optimum, pH dependent stability, temperature dependent activity or optimum, transglycosylation activity, stability, and any other parameter of interest, may be performed on purified variants in accordance with methods known in the art as described below.

Degradation of β-Limit Dextrin by Maltogenic Alpha-Amylase:

Another important parameter in the evaluation of the substrate specificity of maltogenic alpha-amylase variants may be the degree to which such enzymes are capable of degrading starch that has been exhaustively treated with the exoglycosylase β-amylase. To screen for variants which show patterns of degradation on such a substrate differing from the patterns produced by the parent maltogenic alpha-amylase the following assay is performed: limit dextrin is prepared by incubating 25 ml 1% amylopectin in McIlvane buffer (48.5 mM citrate and 193 mM sodium phosphate pH 5.0) with 24 μg/ml β-amylase overnight at 30° C. Unhydrolysed amylopectin (i.e., limit dextrin) is precipitated with 1 volume 98% ethanol, washed and redissolved in water. 1 ml delimit dextrin is incubated with 18 μl enzymes (at 2.2 mg/ml) and 100 μl 0.2 M citrate-phosphate pH 5.0 for 2 hrs at 30° C. and analysed by HPLC as described above. Total hydrolysis of β-limit dextrin is carried out in 2M HCl at 95° C. The concentration of reducing ends is measured by methods known in the art Calcium Binding Affinity Unfolding of maltogenic alpha-amylases by exposure to heat or to denaturants such as guanidine hydrochloride is accompanied by a decrease in fluorescence, and oss of calcium ions leads to unfolding. Thus, the affinity of a maltogenic alpha-amylase variant for calcium can be measured by fluorescence measurements before and after incubation of the variant (e.g., at a concentration of 10 mg/ml) in a buffer (e.g., 50 mM HEPES, pH 7) with different concentrations of calcium (e.g., in the range from 1 mM-100 mM) or of EGTA (e.g., in the range from 1–1000 mM) for a sufficiently long period of time (such as 22 hours at 55° C.).

The measured fluorescence, F, is composed of contributions form the folded and unfolded forms of the enzyme. The following equation can be derived to describe the dependence of F on calcium concentration ([Ca]):

$$F=[Ca]/(K_{diss}+[Ca])(a_N-b_N\log([Ca]))+K_{diss}(K_{diss}+[Ca])(a_U-b_U\log([Ca]))$$

where $a_N$ is the fluorescence of the native (folded) form of the enzyme, $b_N$ is the linear dependence of $a_N$ on the logarithm of the calcium concentration (as observed experimentally), $a_U$ is the fluorescence of the unfolded form and $b_U$ is the linear dependence of $a_U$ on the logarithm of the calcium concentration. $K_{diss}$ is the apparent calcium binding constant for an equilibrium process as follows:

$K_{diss}$

N–Ca<<U+Ca(N=native enzyme; U=unfolded enzyme)

In fact, unfolding proceeds extremely slowly and is irreversible. The rate of unfolding is dependent on calcium concentration, and such dependency for a given enzyme provides a measure of the calcium binding affinity of the enzyme. By defining a standard set of reaction conditions (e.g., 22 hours at 55° C.), a meaningful comparison of $K_{diss}$ for different maltogenic alpha-amylase variants can be made.

INDUSTRIAL APPLICATIONS

The maltogenic alpha-amylase variants of the invention possesses valuable properties which may be advantageously used in various industrial applications. In particular, the enzyme finds potential application for retarding or preventing retrogradation, and thus the staling, of starch based food such as common in the baking industry.

The variant may be used for the preparation of bread and other bread products in accordance with conventional techniques known in the art.

It is believed that the modification of the starch fraction by use of the present invention results in increased volume in baked products and improved organoleptic qualities, such as flavour, mouth feel, palatability, aroma and crust colour.

The maltogenic alpha-amylase variant may be used as the only enzyme or as a major enzymatic activity in combination with one or more additional enzymes, such as xylanase, lipase, glucose oxidase and other oxidoreductases, or an amylolytic enzyme.

The enzyme variants of the invention also find industrial applicability as a component in washing, dishwashing and hard-surface cleaning detergent compositions. Some variants are particularly useful in a process for the manufacture of linear oligosaccharides, or in the production of sweeteners and ethanol from starch, and/or for textile desizing. Conditions for conventional starch conversion processes, including starch liquefaction and/or saccharification processes, are described in, e.g., U.S. Pat. No. 3,912,590 and in EP patent publications Nos. 252,730 and 63,909.

The invention is further illustrated with reference to the following examples which are not intended to be in any way limiting to the scope of the invention as claimed.

Determination of Maltogenic Amylase in MANU

One Maltogenic Amylase Novo Unit (MANU) is the amount of enzyme which under standard will cleave one μmol maltotriose per minute. The standard conditions are 10 mg/ml maltotriose, 37° C., pH 5.0, 30 minutes reaction time.

The pH dependence is found by repeating this measurement at the same conditions, but at different pH values.

EXAMPLES

Example 1

Construction of a Variant of Novamyl with Altered pH Dependent Activity

Novamyl is expressed in *Bacillus subtilis* from a plasmid denoted herein as pLBei010. This plasmid contains amyM in which the expression of amyM is directed by its own promoter and the complete gene encoding Novamyl, e.g., as contained in the strain DSM 0.11837. The plasmid contains the origin of replication, on, from plasmid pUB110 and an kanamycin resistance marker for selection purposes. pLBei010 is shown in FIG. 1.

Primer Sequences

Site directed mutants of Novamyl were constructed by the megaprimer method essentially as described by Kammann et al. (1989). Briefly, a mutagenic oligonucleotide primer is used together in a PCR reaction with a suitable opposite DNA strand end primer to create a preliminary PCR product. This product is then used as a megaprimer together with another opposite DNA strand end primer to create a double-stranded DNA product. The product of the final PCR reaction was routinely used to replace a corresponding DNA fragment in the pLBei010 plasmid by standard cloning procedures. Mutants were transformed directly into *Bacillus subtillis* strain SHa273, a derivative of *Bacillus subtilis* 168 which is apr⁻, npr⁻, amyE⁻, amyR2⁻ and prepared by methods known in the art.

Oligonucleotide primers used in the construction of described variants are as listed below:

Variant Sequence (5'→3')
F188H: SEQ ID NO: 3
F188E: SEQ ID NO: 4
F284E: SEQ ID NO: 5
F284D: SEQ ID NO: 6
F284K: SEQ ID NO: 7
N327D: SEQ ID NO: 8
Variant Sequence (3'→5')
T288K: SEQ ID NO: 9
T28BR: SEQ ID NO: 10.

Aspartate variants of F284, T288 and N327 were obtained using primer A189 (SEQ ID NO: 11) and B649 (SEQ ID NO: 12) as end-primers.

F188-variants F188L, T189Y were obtained using primer A82 (SEQ ID NO: 13) and B346 (SEQ ID NO: 14) as end-primers.

PCR products with the desired modification(s) were purified, digested with appropriate enzymes, separated by agarose gel electrophoresis and extracted, ethanol precipitated in the presence of glycogen, resuspended in $H_2O$, ligated to pLBei010 which had been digested with the same appropriate enzymes, and transformed into *Bacillus subtilis* SHa273. Transformants were checked for size by colony PCR and for the insertion or removal of specific restriction sites by restriction enzyme digestion. Positive colonies were verified by DNA sequencing methods as described in the art.

Fermentation

The *B. subtilis* SHa273 mutant clones were grown overnight on LBKana (10 µg/ml) Starch plates at 37° C. The colonies from the plate were resuspended in 10 ml Luria broth. One-sixth of each of the suspensions were inoculated into a 500 ml shake flasks containing 100 ml PS-1 media, a soy meal/sucrose-based media, kanamycin for a final concentration of 10 µg/ml and 100 µl 5M NaOH. The pH was adjusted to 7.5 with NaOH before inoculation. The cultures were incubated for five days at 30° C., with shaking at 270–300 rpm.

Enzyme Purification

Large particles from the media were removed by flocculation before affinity chromatography. Superfloc C521 (American Cyanmide Company) was used as the cationic flocculant and Superfloc A130 (American Cyanmide Company) as the anionic flocculant.

The culture suspension was diluted 1:1 with deionized water and the pH was adjusted to approx. 7.5. A volume of 0.01 ml of $50^w/_w$ % CaCl, per ml diluted culture was added during stirring. A volume of 0.015 ml of $20^w/_w$ % Na-aluminate per ml diluted culture was titrated with 20% formic acid, while keeping the pH between 7 and 8. While stirring 0.025 ml $10^v/_v$ % of C521 per ml diluted culture was added, followed by 0.05 ml $1^w/_v$ % A130 per ml diluted culture, or until flocculation was observed. The solution was centrifuged at 4500 rpm for 30 minutes. Filtration was performed using a filter of pore size of 0.45 µm to exclude larger particles and any remaining bacteria. The filtered solution was stored at −20° C.

Immobilization of α-Cyclodextrin to DSV-Agarose

One hundred mg of α-cylcodextrin of molecular weight 972.86 g/mol (Fluka 28705) was dissolved in 20 ml coupling buffer (0.5M $Na_2CO_3$, pH 11). Ten ml of DSV-agarose (Mini-Leak, Medium 10–20 mmolyl of divinyl sulfone activated agarose (Kem En-Tec) was washed thoroughly with deionized water, then dried by suction and transferred to the a-cyclodextrin solution. After the mixture had stirred for 24 hr at ambient temperature, the gel was washed with deionized water, followed by 0.5M $KHCO_3$. The gel was transferred to the blocking buffer (20 ml 0.5M $KHCO_3$+1 ml mercaptoethanol), stirred for 2 hr at ambient temperature, then washed with deionized water.

Affinity Chromatography

The variants were purified by affinity chromatography using the Pharmacia FPLC System. A 0.04 volume of 1 M Na-acetate pH 5 was added to the filtrate obtained by flocculation to adjust pH and $CaCl_2$ was added to a final concentration of $10^{-10}$ M. The solution was filtered and degassed. A Pharmacia XK16 column was prepared with ten ml of the immobilised a-cyclodextrin, then equilibrated in the equilibration buffer (25 mM Na-acetate pH 5) by washing with approximately 10 times the column volume. The filtrate was applied to the XK16 column, which was then washed with the equilibration buffer until protein could no longer be detected in the washing buffer. The column was washed with the equilibration buffer containing 0.5M NaCl to elute nonspecific material, followed by another wash with 2–3 times the column volume of the equilibration buffer. All washings were performed using a flow rate of 10 ml/min. Specifically bound material was eluted using a solution of 2% α-cyclodextrin in the wash buffer and collected using the Pharmacia Liquid Chromatography Collector LCC-500 Plus using a flow rate of 5 ml/min.

Example 2 pH Dependent Activity of Variants

The variants prepared in the preceding Example were tested for activity at various pH values as follows.

A colorimetric glucose oxidase-peroxidase assay for liberated glucose from maltotriose or amylopectin was used to determine the pH activity profiles of the enzyme variants (Glucose/GOD-Perid® Method, Boehringer Mannheim, Indianapolis Ind.). Activity was assayed in a buffer of 25 mM citrate-phosphate, 0.1 mM $CaCl_2$ at pH values of 2, 2.5, 3, 3.5, 4, 4.5, 5, 5.5, 6, 6.5, 7, 7.5, 8 and 8.6. The buffer pH was adjusted using NaOH and enzymes were diluted in 25 mM citrate-phosphate buffer pH 5. Measurements, were taken in duplicate to obtain an average value. All values are relative to the pH at which the highest level of activity is seen.

The results, shown in the table below, indicate that each of the variants has an alteration in the pH dependent activity profile when compared to the parent Novamyl®. The highest level of activity for each variant is designated 100% and the activity of that variant measured at the other indicated pH values is a relative percentage of that maximum.

| | pH | | | | | | | | | | | | | | |
|---|---|---|---|---|---|---|---|---|---|---|---|---|---|---|---|
| Modifications | 2.0 | 2.5 | 3.0 | 3.5 | 4.0 | 4.5 | 5.0 | 5.5 | 6.0 | 6.5 | 7.0 | 7.5 | 8.0 | 8.6 |
| None (parent) | 0 | 0 | 0 | 8 | 47 | 80 | 100 | 95 | 91 | 80 | 66 | 39 | 35 | 30 |
| F188H | 1 | 0 | 0 | 1 | 3 | 29 | 77 | 99 | 100 | 88 | 59 | 39 | 31 | 27 |
| F188E | 0 | 0 | 0 | 2 | 27 | 62 | 89 | 100 | 93 | 71 | 46 | 28 | 20 | 18 |
| T288R | 0 | 0 | 0 | 8 | 51 | 77 | 94 | 100 | 86 | 73 | 50 | 34 | 27 | 12 |
| N327D | 1 | 1 | 7 | 27 | 67 | 95 | 100 | 98 | 77 | 33 | 19 | 11 | 5 | 0 |

Further, a number of Novamyl variants were tested for activity at pH 4.0 and 5.0, taking the activity of Novamyl at the same pH as 100%. The activity was determined by hydrolysis of maltotriose (10 mg/ml) at 60° C., 50 mM sodium acetate, 1 mM CaCl$_2$. The results are expressed as the ratio between activity at pH 5.0 and pH 4.0:

| Modifications | pH 5.0/pH 4.0 |
|---|---|
| N131D | 0.24 |
| I174Q | 0.31 |
| G397P | 0.40 |
| H103Y | 0.40 |
| Δ 262–266 | 0.47 |
| T142A + D261G + T288P + Q449R | 0.50 |
| S32Q | 0.53 |
| S32D | 0.55 |
| T142A + D261G | 0.62 |
| G370N + N371G | 0.66 |
| S32N | 0.68 |
| N176S | 0.79 |
| D17E | 0.80 |
| None (parent) | 1 |
| Δ 191 | 1.39 |
| 192-A-193 | 1.61 |
| I174E | 1.80 |
| 192-A-G-193 | 1.90 |
| Δ 192 | 2.22 |
| F188L + D261G + T288P | 2.47 |

The results demonstrate that variants with a higher or lower pH optimum can be obtained according to the invention.

Example 3

Thermostability of Variants
Incubation at 80° C.

The thermostability of a number of Novamyl variants was tested by incubating an aqueous solution at 8° C., pH 4.3, 50 mM acetate buffer, 1 mM CaCl$_2$, and measuring the residual amylase activity at various times. The parent enzyme, Novamyl, was included for comparison. The results are expressed as residual activity at various times in percent of initial activity:

| Variant | 0 | 5 min. | 10 min. | 15 min. | 20 min. | 25 min. |
|---|---|---|---|---|---|---|
| None (parent) | 100 | 23 | 9 | 3 | 1 | 0 |
| A197P + D261G + T288P + N342S | 100 | 36 | 28 | 14 | 16 | 9 |
| A30D + K40R + D261G | 100 | 38 | 24 | 15 | 13 | 10 |
| T288K | 100 | 64 | 31 | 18 | 7 | 4 |
| T142A + N327S + K425E + K520R + N595I | 100 | 47 | 39 | 25 | 19 | 11 |
| T142A + D261G + T288P + Q449R | 100 | 45 | 36 | 27 | 16 | 9 |
| K40R + F188L + D261G + A483T | 100 | 56 | 48 | 40 | 36 | 30 |
| F188L + V336L + T525A | 100 | 63 | 49 | 48 | 52 | 47 |
| F188I + Y422F + I660V | 100 | 71 | 60 | 51 | 43 | 38 |
| N115D + F188L | 100 | 73 | 60 | 51 | 44 | 39 |
| F188L + D261G + T288P | 100 | 60 | 67 | 66 | 63 | 67 |
| F188L + D261G + T288P + A483T | 100 | 66 | 72 | 73 | 75 | 78 |
| N26S + F188L + D261G + T288P + T594A + I600V | 100 | 80 | 80 | 82 | 84 | 84 |
| N26S + T80A + F188L + D261G + T288P + R291L | 100 | 80 | 75 | 82 | 83 | 87 |

The above data show a clearly improved thermostability for the variants compared to the parent amylase. Thus, after 15 minutes incubation at 8° C., a number of variants show at least 25% residual activity, and some even show at least 50% residual activity, whereas the parent enzyme has essentially lost its activity.

Incubation at 85° C.

The Novamyl variant S32E was tested by incubation with 1 mM Cam at 85° C. for 15 minutes. The variant showed a residual activity of 48% whereas the parent enzyme (Novamyl) showed 32% residual activity at the same conditions.

Incubation at 90'C'

Four variants and the parent enzyme were tested by incubating at 90° C., pH 5.0, 50 mM acetate buffer, 1 mM CaCl$_2$, and measuring the residual activity. The results were as follows:

| Variant | 0 | 10 min. | 20 min. | 30 min. |
|---|---|---|---|---|
| None (parent) | 100 | 5 | 0 | 0 |
| F188L + D261G + T288P | 100 | 70 | 41 | 28 |
| N26S + F188L + D261G + T288P + T594A + I600V | 100 | 71 | 54 | 39 |
| N26S + T80A + F188L + D261G + T288P + R291L | 100 | 43 | 26 | 13 |
| F188L + D261G + T288P + A483T | 100 | 54 | 39 | 26 |

The variants show a clearly improved thermostability. Thus, the variants retain more than 10% (or even more than 20%) relative activity after 30 minutes incubation at 90° C., whereas the parent enzyme loses all activity after 20 minutes.

DSC

Further, the thermostability was tested for some Novamyl variants by DSC (differential scanning calorimetry) at pH values in the range 4.0–5.5. Again, the parent amylase was included for comparison. The results are expressed as the denaturation temperature (Tm) at the given pH:

| Modifications | pH 4.0 | pH 4.3 | pH 5.0 | pH 5.5 |
|---|---|---|---|---|
| None (parent) | 64 C. | 79 C. | 83 C. | 88 C. |
| N115D + F188L | | 86 C. | | 92 C. |
| T142A + N327S + K425E + K520R + N595I | | | | 93 C. |
| F188L + D261G + T288P | 75 C. | | 95 C. | |

The results show improved thermostability for each variant. One variant shows an improvement of more than 1° C. at pH 4.0 and 5.5.

Example 4

Specific Activity of Variants

Amylase activity was determined by a colorimetric measurement after action on Phadebas tablets at pH 5.0 and 60° C. The results for two Novamyl variants, relative to Novamyl were as follows:

| Modifications | Relative amylase activity |
|---|---|
| None (parent) | 100 |
| 192-A-193 | 110 |
| Δ (191–195) | 300 |

The specific activity was further tested by action on maltotriose at pH 4.0, 60° C. by the MANU method described above. The results showed that the variant G370N, N371G has a maltotriose activity of 106% compared to Novamyl.

Example 5

Inhibition of Retrogradation

The efficiency of Novamyl and Novamyl variants to inhibit retrogradation was determined as follows:

730 mg of 50% (w/w) amylopectin slurry in 0.1 M sodium acetate, at a selected pH (3.7, 4.3 or 5.5) was mixed with 20 µl of an enzyme sample, and the mixture was incubated in a sealed ampoule for 1 hour at 40° C., followed by incubation at 100° C. for 1 hour in order to gelatinize the samples. The sample was then aged for 7 days at room temperature to allow recrystallization of the amylopectin. A control without enzyme was included.

After aging, DSC was performed on the sample by scanning from 5° C. to 95° C. at a constant scan rate of 90° C./hour. The area under the first endothermic peak in the thermogram was taken to represent the amount of retrograded amylopectin, and the relative inhibition of retrogradation was taken as the area reduction (in %) relative to the control without enzyme.

In the table below, the efficiency of the enzyme is expressed as the ratio of the relative inhibition of retrogradation to the enzyme dosage (in MANU/ml):

| pH | Modifications | MANU/ml | Relative inhibition | Efficiency |
|---|---|---|---|---|
| 3.7 | A30D + K40R + D261G | 0.23 | 0.38 | 1.7 |
| 3.7 | T142A + N327S + K425E + K520R + N595I | 0.07 | 0.29 | 4.1 |
| 3.7 | None (parent) | 0.27 | 0.38 | 1.4 |
| 4.3 | N115D + F188L | 0.01 | 0.18 | 18 |
| 4.3 | None (parent) | 0.27 | 0.43 | 1.6 |
| 5.5 | Δ (191–195) + F188L + T189Y | 0.02 | 0.12 | 6 |
| 5.5 | Δ (191–195) | 0.02 | 0.14 | 7 |
| 5.5 | Δ (191–195) | 0.05 | 0.31 | 6.2 |
| 5.5 | N115D + F188L | 0.01 | 0.39 | 39 |
| 5.5 | T142A + D261G | 0.14 | 0.53 | 3.8 |
| 5.5 | None (parent) | 0.27 | 0.49 | 1.8 |

The results demonstrate that a number of variants are more efficient than the parent amylase to inhibit retrogradation.

Example 6

Anti-Staling Effect of Variants

Bread was made by an European Straight Dough method (wheat flour, water, yeast, salt, sugar, ascorbic acid) or from a wheat sour dough (acidified with "Ireks ferdigsauer" from Balchem Co.) with or without addition of enzymes, and loaves were baked in lidded pans, to avoid volume effects. pH in the dough was measured by blending 10 g of the mixed dough with 100 ml of deionised water for 30 min before measurement of pH in the suspension. The bread was allowed to cool for 2 hours, and the texture was analyzed by a Texture Analyser TA-XT2 from Stable Micro Systems. The remaining loaves were then wrapped in plastic bags and stored at room temperature for texture analysis after 1, 4 and 7 days.

The texture analysis of each loaf was done by cutting 4 slices; the force was measured at 25% compression (P1), at 40% compression (P2) and after keeping 40% compression constant for 30 sec. (P3). P1 was taken as the firmness (in grams), and the ratio (P3/P2) was taken as the elasticity of the crumb. The extent of retrogradation after 7 days storage was determined by DSC as described in Example 7.

European Straight Dough (pH5.5–6.0)

A Novamyl variant (T142A+N327S+K425E+K520R+N595I) was tested at dosages in the range of 0–2 mg enzyme/kg flour, and the parent enzyme (Novamyl) was used for comparison.

The following results were obtained for elasticity (P3/P2) after two hours and 7 days and firmness (P1) after 7 days:

| Enzyme | Dosage mg/kg flour | Elasticity 2 hours | Elasticity 1 day | Elasticity 7 days | Firmness (P1) after 7 days |
|---|---|---|---|---|---|
| None | 0 | 0.69 | 0.60 | 0.44 | 2267 |
| Parent | 1 | 0.62 | 0.60 | 0.55 | 1192 |
|  | 2 | 0.58 | 0.57 | 0.54 | 1113 |
| Variant | 1 | 0.65 | 0.62 | 0.56 | 1022 |
|  | 2 | 0.63 | 0.61 | 0.58 | 905 |

The results after two hours and 1 day show that at equal dosages, the variant gives a better elasticity than the parent enzyme. The results after 7 days show that the variant at dosages of 1–2 mg/kg gives a softer crumb (lower firmness and higher elasticity) than the parent enzyme at the same dosage. Thus, the variant has a better anti-staling effect throughout a 7-day storage period.

Sour Dough (pH Approx. 4.51

A Novamyl variant (F188L+D261G+T288P) was tested in sour dough, and the parent enzyme (Novamyl) was used for comparison. The following results were obtained for firmness (P1) after 7 days, elasticity (P3/P2) after 4 and 7 days and retrogradation after 7 days:

| Enzyme | Dosage mg/kg flour | Firmness (P1) after 7 days | Elasticity 4 days | Elasticity 7 days | Retrogradation, 7 days (relative to control) |
|---|---|---|---|---|---|
| None | 0 | 2590 | 0.49 | 0.47 | 100% |
| Parent | 1 | 2031 | 0.51 | 0.52 | 100% |
|  | 3 | 1912 | 0.53 | 0.51 | 63% |
|  | 13 | 1570 | 0.53 | 0.51 | 32% |
| Variant | 1 | 1436 | 0.59 | 0.57 | 46% |
|  | 3 | 1226 | 0.57 | 0.58 | 20% |

The results show that the variant has a markedly improved effect on texture evaluated as firmness and elasticity in sour dough at pH 4.5. A dosage of 1–3 mg/kg of the variant is superior to 13 mg/kg of the parent enzyme on all parameters tested, and the elasticity achieved with the variant cannot be matched by the parent enzyme at any dosage.

pH-Profile in Wheat-Flour Bread (pH Approx. 4.4: 4.9: and 5.5)

The Novamyl variant (F188L+D261 G+T288P) was further tested in acidified wheat flour bread to measure the function over a broader pH range in baking application, while maintaining a comparable recipe. The parent enzyme (Novamyl) was used for comparison. Dosage of the parent enzyme was changed at the various pH to compensate for the lower activity of the parent enzyme at lower pH. The following results were obtained for firmness (P1) and elasticity (P31P2) after 0 (=2 hours), 1, 3 and 7 days.

|  |  |  | Firmness | | | | Elasticity | | | |
| --- | --- | --- | --- | --- | --- | --- | --- | --- | --- | --- |
| pH | Enzyme | Dosage mg/kg flour | 0 days | 1 day | 3 days | 7 days | 0 days | 1 day | 3 days | 7 days |
| pH 4.4 | None | 0 | 450 | 1144 | 1945 | 3020 | 0.70 | 0.61 | 0.53 | 0.48 |
|  | Variant | 0.5 | 392 | 939 | 1386 | 1664 | 0.70 | 0.63 | 0.59 | 0.56 |
|  | Parent | 15 | 870 | 1206 | 1220 | 1511 | 0.53 | 0.50 | 0.52 | 0.51 |
|  | Parent | 1 | 586 | 1127 | 2005 | 2312 | 0.65 | 0.60 | 0.55 | 0.51 |
| pH 4.9 | None | 0 | 330 | 764 | 1536 | 2005 | 0.71 | 0.64 | 0.55 | 0.49 |
|  | Variant | 0.5 | 287 | 687 | 767 | 1096 | 0.70 | 0.65 | 0.63 | 0.60 |
|  | Parent | 7 | 570 | 1075 | 984 | 1057 | 0.56 | 0.52 | 0.54 | 0.54 |
|  | Parent | 0.5 | 373 | 784 | 1170 | 1642 | 0.67 | 0.61 | 0.58 | 0.54 |
| pH 5.5 | None | 0 | 217 | 711 | 1123 | 1382 | 0.70 | 0.61 | 0.56 | 0.51 |
|  | Variant | 0.5 | 315 | 447 | 712 | 846 | 0.68 | 0.64 | 0.61 | 0.60 |
|  | Parent | 3.5 | 431 | 629 | 666 | 718 | 0.58 | 0.56 | 0.57 | 0.57 |
|  | Parent | 0.5 | 381 | 599 | 630 | 922 | 0.63 | 0.61 | 0.62 | 0.58 |

It is clearly observed, that the variant is much improved compared to the parent at all pH, and especially at lower pH. The elasticity is higher, and the crumb stays more soft over the measured time span.

Four Variants Tested in Wheat Sourdough Compared to Parent Enzyme

Four Novamyl variants were tested in another test series of acidified wheat flour bread to determine the performance in sourdough baking application. pH in the bread and dough was measured to be in the interval 4.30–4.40. The parent enzyme (Novamyl) was used for comparison. Dosage of the parent enzyme was chosen at 1 and 13 mg/kg flour, much higher than the variants, as we have experienced that this is needed to see effect of the parent enzyme in this specific application. The firmness (P1) and elasticity (P3/P2) were determined after 1, 3 and 7 days, and the extent of retrogradation after 7 days storage was determined as described above.

|  |  | Firmness | | | Elasticity | | | Retrogradation, 7 days |
| --- | --- | --- | --- | --- | --- | --- | --- | --- |
| Enzyme | Dosage mg/kg flour | 1 day | 3 days | 7 days | 1 day | 3 days | 7 days | (relative to control) |
| None | 0 | 789 | 1624 | 2054 | 0.63 | 0.55 | 0.48 | 100% |
| Parent | 1 | 745 | 1107 | 1685 | 0.64 | 0.57 | 0.49 | 67% |
|  | 13 | 722 | 967 | 1205 | 0.57 | 0.56 | 0.53 | 21% |
| N26S + F188L + D261G + T288P + T594A + I600V | 0.5 | 716 | 1170 | 1518 | 0.63 | 0.56 | 0.50 | 72% |
|  | 3 | 847 | 895 | 1188 | 0.61 | 0.59 | 0.57 | 18% |
| F188L + D261G + T288P | 0.5 | 689 | 1054 | 1457 | 0.64 | 0.58 | 0.53 | 53% |
| A197P + D261G + T288P + N342S | 0.5 | 638 | 1114 | 1631 | 0.64 | 0.57 | 0.50 | 59% |
| F188L + D261G + T288P + A483T | 0.5 | 643 | 983 | 1562 | 0.65 | 0.58 | 0.53 | 43% |
|  | 3 | 660 | 804 | 953 | 0.63 | 0.60 | 0.58 | 10% |

For antistaling (fresh-keeping) it is particularly important, that the bread is soft and elastic after several days storage. Therefore, most weight should be put on the textural properties after 7 days of storage. It is clearly observed, that the variants are much improved compared to the parent. The elasticity is higher, and the crumb stays more soft

Example 7

Cleavage Pattern of Variants

The cleavage pattern in starch hydrolysis was compared for two variants and the parent enzyme, Novamyl.

The results below indicate % by weight of each oligosaccharide (G1–G8) formed after 24 hours incubation in 1% (w/v) starch using 50 mM sodium acetate, 1 mM CaCl$_1$, pH 5.0 at 50° C. The oligosaccharides were identified and quantitated using HPLC.

| Oligosaccharide | Parent | Δ (191–195) | N115D + F188L |
| --- | --- | --- | --- |
| G8 | — | 1.7 | — |
| G7 | — | 2.6 | — |
| G6 | — | 7.5 | 1.4 |
| G5 | — | 10.1 | 2.1 |
| G4 | — | 21.1 | 11.3 |
| G3 | — | 28.7 | 10.7 |
| G2 | 96.5 | 28.3 | 61.9 |
| G1 | 3.5 | — | 12.6 |

The results demonstrate a significantly altered cleavage pattern. Novamyl after 24 hours produces mainly maltose and virtually no higher oligosaccharides. In contrast, the two variants produce significant amounts of maltotriose and higher oligosaccharides.

Example 8

Substrate Specificity of Variants

The activity of variants was tested on two different substrates: glucose release from maltotriose and color release from Phadebas colored starch. The parent enzyme (Novamyl) was tested for comparison. The measurements were made at pH 5, and each activity was expressed relative to the parent enzyme. The ratio of activities on the two substrates was found to be as follows:

| Variant | Activity ratio Starch/maltotriose |
|---|---|
| Parent enzyme | 1.0 |
| F188L, D261G, T288P | 3.6 |
| N26S + F188L, D261G, T288P, T594A, I600V | 5.5 |
| N26S, T80A, F188L, D2G1G, T288P, R291L | 1.9 |
| A197P, D261G, T288P, N342S | 1.5 |
| T142A, D261G, T288P, Q449R | 2.5 |
| F188L, D261G, T288P, A483T | 2.5 |

It is seen that the 6 variants have an increased activity on starch relative to maltotriose.

REFERENCES CITED

Klein, C., et al., *Biochemistry* 1992, 31, 8740–8746,
Mizuno, H., et al., *J. Mol. Biol.* (1993) 234, 1282–1283,
Chang, C., et al, *J. Mol. Biol.* (1993) 229, 235–238,
Larson, S. B., *J. Mol. Biol.* (1994) 235, 1560–1584,
Lawson, C. L., *J. Mol. Biol.* (1994) 236, 590–600,
Qian, M., et al., J. Mol. Biol. (1993) 231, 785–799,
Brady, R. L., et al., *Acta Crystallogr. sect. B,* 47, 527–535,
Swift, H. J., et al., *Acta Crystallogr. sect. B,* 47, 535544
A. Kadziola, Ph.D. Thesis: "An alpha-amylase from Barley and its Complex with Substrate. Analogue Inhibitor Studied by X-ray Crystallography", Department of Chemistry University of Copenhagen 1993
MacGregor, E. A., Food Hydrocolloids, 1987, Vol. 1, No. 5–6, p.
B. Diderichsen and L. Christiansen, Cloning of a maltogenic α-amylase from *Bacillus stearothermophilus*, FEMS Microbiol. letters: 56: pp. 53–60 (1988)
Hudson et al., Practical Immunology, Third edition (1989), Blackwell Scientific Publications,
Sambrook et al., *Molecular Cloning: A Laboratory Manual*, 2nd Ed., Cold Spring Harbor, 1989
S. L. Beaucage and M. H. Caruthers, *Tetrahedron Letters* 22, 1981, pp. 1859–869
Matthes et al., *The EMBO J.* 3, 1984, pp. 801–805.
R. K. Saiki et al., *Science* 239, 1988, pp. 487–491.
Moringa et al., (1984, Biotechnology 2:646–639)
Nelson and Long, *Analytical Biochemistry* 180, 1989, pp. 147–151
Hunkapiller et al., 1984, Nature 310:105–111
R. Higuchi, B. Krummel, and R. K. Saiki (1988). A general method of in vitro preparation and specific mutagenesis of DNA fragments: study of protein and DNA interactions. *Nucl. Acids Res.* 16:7351–7367.
Dubnau et al., 1971, *J. Mol. Biol.* 56, pp. 209–221.
Gryczan et al., 1978, *J. Bacteriol.* 134, pp. 318–329.
S. D. Erlich, 1977, *Proc. Natl. Acad. Sci.* 0.74 pp. 1680–1682.
Boel et al. 1990, *Biochemistry* 29, pp. 6244–6249.
Kammann, M Laufs, J Schell, J and Gronnenbom, B (1989) Nucleic Acids Research 20:4937–4938.

TABLE 1

Atom Coordinates from the Crystal Structure of NOVAMYL

| 1 | N | SER | A | 1 | 10.254 | 56.595 | 38.175 | 1.00 | 15.64 | 7 |
|---|---|---|---|---|---|---|---|---|---|---|
| 2 | CA | SER | A | 1 | 11.216 | 55.462 | 37.898 | 1.00 | 15.87 | 6 |
| 3 | C | SER | A | 1 | 12.466 | 55.723 | 38.726 | 1.00 | 14.53 | 6 |
| 4 | O | SER | A | 1 | 12.585 | 56.773 | 39.369 | 1.00 | 15.99 | 8 |
| 5 | CB | SER | A | 1 | 11.527 | 55.345 | 36.397 | 1.00 | 21.54 | 6 |
| 6 | OG | SER | A | 1 | 12.305 | 56.503 | 36.045 | 1.00 | 20.33 | 8 |
| 7 | N | SER | A | 2 | 13.466 | 54.795 | 38.551 | 1.00 | 18.07 | 7 |
| 8 | CA | SER | A | 2 | 14.705 | 55.061 | 39.291 | 1.00 | 19.33 | 6 |
| 9 | C | SER | A | 2 | 15.621 | 56.069 | 38.559 | 1.00 | 15.87 | 6 |
| 10 | O | SER | A | 2 | 16.573 | 56.563 | 39.209 | 1.00 | 16.73 | 8 |
| 11 | CB | SER | A | 2 | 15.490 | 53.735 | 39.422 | 1.00 | 26.53 | 6 |
| 12 | OG | SER | A | 2 | 15.918 | 53.392 | 38.123 | 1.00 | 21.07 | 8 |
| 13 | N | SER | A | 3 | 15.136 | 56.545 | 37.384 | 1.00 | 12.71 | 7 |
| 14 | CA | SER | A | 3 | 15.956 | 57.522 | 36.680 | 1.00 | 13.38 | 6 |
| 15 | C | SER | A | 3 | 15.873 | 58.916 | 37.316 | 1.00 | 12.57 | 6 |
| 16 | O | SER | A | 3 | 16.759 | 59.749 | 37.029 | 1.00 | 15.22 | 8 |
| 17 | CB | SER | A | 3 | 15.434 | 57.682 | 35.219 | 1.00 | 16.30 | 6 |
| 18 | OG | SER | A | 3 | 15.593 | 56.381 | 34.568 | 1.00 | 23.61 | 8 |
| 19 | N | ALA | A | 4 | 14.811 | 59.222 | 38.050 | 1.00 | 10.88 | 7 |
| 20 | CA | ALA | A | 4 | 14.574 | 60.623 | 38.384 | 1.00 | 11.38 | 6 |
| 21 | C | ALA | A | 4 | 15.599 | 61.115 | 39.409 | 1.00 | 12.81 | 6 |
| 22 | O | ALA | A | 4 | 15.888 | 62.314 | 39.355 | 1.00 | 12.58 | 8 |
| 23 | CB | ALA | A | 4 | 13.132 | 60.682 | 38.956 | 1.00 | 14.28 | 6 |
| 24 | N | SER | A | 5 | 15.968 | 60.306 | 40.380 | 1.00 | 13.21 | 7 |
| 25 | CA | SER | A | 5 | 16.905 | 60.780 | 41.427 | 1.00 | 14.29 | 6 |
| 26 | C | SER | A | 5 | 18.163 | 59.941 | 41.357 | 1.00 | 16.01 | 6 |
| 27 | O | SER | A | 5 | 18.053 | 58.724 | 41.237 | 1.00 | 16.41 | 8 |
| 28 | CB | SER | A | 5 | 16.218 | 60.613 | 42.785 | 1.00 | 15.57 | 6 |
| 29 | OG | SER | A | 5 | 17.193 | 60.855 | 43.843 | 1.00 | 13.17 | 8 |
| 30 | N | VAL | A | 6 | 19.340 | 60.530 | 41.476 | 1.00 | 10.07 | 7 |
| 31 | CA | VAL | A | 6 | 20.589 | 59.751 | 41.567 | 1.00 | 10.13 | 6 |
| 32 | C | VAL | A | 6 | 21.169 | 59.955 | 42.963 | 1.00 | 10.99 | 6 |
| 33 | O | VAL | A | 6 | 22.349 | 59.685 | 43.172 | 1.00 | 10.81 | 8 |
| 34 | CB | VAL | A | 6 | 21.639 | 60.160 | 40.513 | 1.00 | 13.85 | 6 |
| 35 | CG1 | VAL | A | 6 | 21.002 | 59.694 | 39.148 | 1.00 | 15.29 | 6 |
| 36 | CG2 | VAL | A | 6 | 21.874 | 61.656 | 40.459 | 1.00 | 12.12 | 6 |
| 37 | N | LYS | A | 7 | 20.369 | 60.349 | 43.964 | 1.00 | 10.30 | 7 |
| 38 | CA | LYS | A | 7 | 20.901 | 60.604 | 45.331 | 1.00 | 9.78 | 6 |
| 39 | C | LYS | A | 7 | 21.508 | 59.360 | 46.015 | 1.00 | 12.06 | 6 |

TABLE 1-continued

Atom Coordinates from the Crystal Structure of NOVAMYL

| 40 | O | LYS | A | 7 | 22.382 | 59.560 | 46.857 | 1.00 | 12.59 | 8 |
|---|---|---|---|---|---|---|---|---|---|---|
| 41 | CB | LYS | A | 7 | 19.830 | 61.187 | 46.264 | 1.00 | 11.40 | 6 |
| 42 | CG | LYS | A | 7 | 19.414 | 62.588 | 45.680 | 1.00 | 12.09 | 6 |
| 43 | CD | LYS | A | 7 | 18.160 | 63.123 | 46.350 | 1.00 | 9.80 | 6 |
| 44 | CE | LYS | A | 7 | 17.698 | 64.488 | 45.795 | 1.00 | 10.87 | 6 |
| 45 | NZ | LYS | A | 7 | 17.114 | 64.187 | 44.425 | 1.00 | 11.38 | 7 |
| 46 | N | GLY | A | 8 | 21.036 | 58.214 | 45.577 | 1.00 | 13.10 | 7 |
| 47 | CA | GLY | A | 8 | 21.604 | 56.982 | 46.166 | 1.00 | 12.31 | 6 |
| 48 | C | GLY | A | 8 | 22.718 | 56.358 | 45.340 | 1.00 | 14.02 | 6 |
| 49 | O | GLY | A | 8 | 23.109 | 55.205 | 45.579 | 1.00 | 13.36 | 8 |
| 50 | N | ASP | A | 9 | 23.133 | 57.048 | 44.293 | 1.00 | 11.90 | 7 |
| 51 | CA | ASP | A | 9 | 24.049 | 56.447 | 43.319 | 1.00 | 11.74 | 6 |
| 52 | C | ASP | A | 9 | 25.478 | 56.996 | 43.442 | 1.00 | 10.18 | 6 |
| 106 | CB | ILE | A | 15 | 37.192 | 59.653 | 28.343 | 1.00 | 10.73 | 6 |
| 107 | CG1 | ILE | A | 15 | 37.106 | 60.975 | 29.131 | 1.00 | 11.86 | 6 |
| 108 | CG2 | ILE | A | 15 | 37.626 | 60.014 | 26.904 | 1.00 | 12.56 | 6 |
| 109 | CD1 | ILE | A | 15 | 36.181 | 62.091 | 28.574 | 1.00 | 15.42 | 6 |
| 110 | N | ILE | A | 16 | 34.926 | 57.450 | 26.561 | 1.00 | 10.37 | 7 |
| 111 | CA | ILE | A | 16 | 34.728 | 56.178 | 25.868 | 1.00 | 11.03 | 6 |
| 112 | C | ILE | A | 16 | 35.990 | 55.729 | 25.099 | 1.00 | 12.23 | 6 |
| 113 | O | ILE | A | 16 | 36.342 | 54.511 | 25.184 | 1.00 | 11.07 | 8 |
| 114 | CB | ILE | A | 16 | 33.578 | 56.292 | 24.863 | 1.00 | 10.56 | 6 |
| 115 | CG1 | ILE | A | 16 | 32.240 | 56.387 | 25.709 | 1.00 | 11.92 | 6 |
| 116 | CG2 | ILE | A | 16 | 33.444 | 55.053 | 23.953 | 1.00 | 11.18 | 6 |
| 117 | CD1 | ILE | A | 16 | 31.115 | 56.958 | 24.823 | 1.00 | 13.67 | 6 |
| 118 | N | ASP | A | 17 | 36.565 | 56.624 | 24.314 | 1.00 | 10.08 | 7 |
| 119 | CA | ASP | A | 17 | 37.730 | 56.165 | 23.518 | 1.00 | 8.61 | 6 |
| 120 | C | ASP | A | 17 | 38.911 | 55.693 | 24.346 | 1.00 | 10.86 | 6 |
| 121 | O | ASP | A | 17 | 39.777 | 54.987 | 23.831 | 1.00 | 11.03 | 8 |
| 122 | CB | ASP | A | 17 | 38.184 | 57.422 | 22.675 | 1.00 | 11.30 | 6 |
| 123 | CG | ASP | A | 17 | 39.380 | 57.017 | 21.755 | 1.00 | 9.77 | 6 |
| 124 | OD1 | ASP | A | 17 | 39.105 | 56.206 | 20.852 | 1.00 | 11.65 | 8 |
| 125 | OD2 | ASP | A | 17 | 40.480 | 57.562 | 21.970 | 1.00 | 11.48 | 8 |
| 126 | N | ARG | A | 18 | 38.972 | 55.999 | 25.646 | 1.00 | 9.54 | 7 |
| 127 | CA | ARG | A | 18 | 40.113 | 55.719 | 26.527 | 1.00 | 8.38 | 6 |
| 128 | C | ARG | A | 18 | 39.826 | 54.720 | 27.608 | 1.00 | 9.97 | 6 |
| 129 | O | ARG | A | 18 | 40.643 | 54.490 | 28.501 | 1.00 | 13.32 | 8 |
| 130 | CB | ARG | A | 18 | 40.537 | 57.083 | 27.137 | 1.00 | 11.02 | 6 |
| 131 | CG | ARG | A | 18 | 40.931 | 58.139 | 26.063 | 1.00 | 9.63 | 6 |
| 132 | CD | ARG | A | 18 | 42.135 | 57.721 | 25.237 | 1.00 | 9.86 | 6 |
| 133 | NE | ARG | A | 18 | 42.280 | 58.523 | 23.969 | 1.00 | 10.16 | 7 |
| 134 | CZ | ARG | A | 18 | 43.103 | 59.578 | 23.903 | 1.00 | 13.46 | 6 |
| 135 | NH1 | ARG | A | 18 | 43.748 | 60.063 | 24.966 | 1.00 | 12.03 | 7 |
| 136 | NH2 | ARG | A | 18 | 43.350 | 60.181 | 22.725 | 1.00 | 10.43 | 7 |
| 137 | N | PHE | A | 19 | 38.648 | 54.007 | 27.497 | 1.00 | 11.25 | 7 |
| 138 | CA | PHE | A | 19 | 38.296 | 53.057 | 28.601 | 1.00 | 10.13 | 6 |
| 139 | C | PHE | A | 19 | 38.543 | 51.614 | 28.192 | 1.00 | 12.61 | 6 |
| 140 | O | PHE | A | 19 | 39.528 | 51.024 | 28.677 | 1.00 | 12.51 | 8 |
| 141 | CB | PHE | A | 19 | 36.798 | 53.294 | 28.945 | 1.00 | 13.20 | 6 |
| 142 | CG | PHE | A | 19 | 36.342 | 52.543 | 30.189 | 1.00 | 12.09 | 6 |
| 143 | CD1 | PHE | A | 19 | 36.849 | 52.908 | 31.423 | 1.00 | 12.96 | 6 |
| 144 | CD2 | PHE | A | 19 | 35.472 | 51.447 | 30.058 | 1.00 | 13.30 | 6 |
| 145 | CE1 | PHE | A | 19 | 36.500 | 52.187 | 32.563 | 1.00 | 16.46 | 6 |
| 146 | CE2 | PHE | A | 19 | 35.184 | 50.719 | 31.215 | 1.00 | 12.02 | 6 |
| 147 | CZ | PHE | A | 19 | 35.638 | 51.089 | 32.482 | 1.00 | 11.98 | 6 |
| 148 | N | TYR | A | 20 | 37.844 | 51.054 | 27.199 | 1.00 | 11.48 | 7 |
| 149 | CA | TYR | A | 20 | 38.154 | 49.694 | 26.772 | 1.00 | 11.40 | 6 |
| 150 | C | TYR | A | 20 | 37.730 | 49.476 | 25.321 | 1.00 | 10.89 | 6 |
| 151 | O | TYR | A | 20 | 36.593 | 49.813 | 24.934 | 1.00 | 11.80 | 8 |
| 152 | CB | TYR | A | 20 | 37.417 | 48.696 | 27.719 | 1.00 | 12.88 | 6 |
| 153 | CG | TYR | A | 20 | 37.927 | 47.270 | 27.504 | 1.00 | 13.88 | 6 |
| 154 | CD1 | TYR | A | 20 | 39.216 | 46.968 | 27.943 | 1.00 | 14.05 | 6 |
| 155 | CD2 | TYR | A | 20 | 37.160 | 46.285 | 26.932 | 1.00 | 15.80 | 6 |
| 156 | CE1 | TYR | A | 20 | 39.717 | 45.678 | 27.800 | 1.00 | 16.74 | 6 |
| 157 | CE2 | TYR | A | 20 | 37.658 | 44.982 | 26.795 | 1.00 | 19.32 | 6 |
| 158 | CZ | TYR | A | 20 | 39.835 | 44.710 | 27.214 | 1.00 | 19.70 | 6 |
| 159 | OH | TYR | A | 20 | 39.458 | 43.422 | 27.062 | 1.00 | 22.69 | 8 |
| 160 | N | ASP | A | 21 | 38.662 | 48.893 | 24.586 | 1.00 | 13.46 | 7 |
| 161 | CA | ASP | A | 21 | 38.414 | 48.628 | 23.134 | 1.00 | 14.35 | 6 |
| 162 | C | ASP | A | 21 | 37.754 | 47.226 | 23.097 | 1.00 | 14.61 | 6 |
| 163 | O | ASP | A | 21 | 38.426 | 46.196 | 23.063 | 1.00 | 13.84 | 8 |
| 164 | CB | ASP | A | 21 | 39.746 | 48.665 | 22.413 | 1.00 | 14.54 | 6 |
| 165 | CG | ASP | A | 21 | 39.678 | 48.444 | 20.909 | 1.00 | 17.30 | 6 |
| 166 | OD1 | ASP | A | 21 | 38.565 | 48.288 | 20.425 | 1.00 | 12.67 | 8 |
| 167 | OD2 | ASP | A | 21 | 40.759 | 48.450 | 20.282 | 1.00 | 15.87 | 8 |
| 168 | N | GLY | A | 22 | 36.430 | 47.219 | 23.040 | 1.00 | 12.11 | 7 |
| 169 | CA | GLY | A | 22 | 35.683 | 45.934 | 23.110 | 1.00 | 15.21 | 6 |

TABLE 1-continued

Atom Coordinates from the Crystal Structure of NOVAMYL

| 170 | C | GLY | A | 22 | 35.482 | 45.410 | 21.664 | 1.00 | 18.33 | 6 |
| 171 | O | GLY | A | 22 | 35.034 | 44.264 | 21.516 | 1.00 | 17.21 | 8 |
| 172 | N | ASP | A | 23 | 35.786 | 46.189 | 20.639 | 1.00 | 13.30 | 7 |
| 173 | CA | ASP | A | 23 | 35.505 | 45.770 | 19.261 | 1.00 | 14.68 | 6 |
| 174 | C | ASP | A | 23 | 36.634 | 46.389 | 18.425 | 1.00 | 14.54 | 6 |
| 175 | O | ASP | A | 23 | 36.570 | 47.597 | 18.138 | 1.00 | 13.39 | 8 |
| 176 | CB | ASP | A | 23 | 34.163 | 46.271 | 18.762 | 1.00 | 13.59 | 6 |
| 177 | CG | ASP | A | 23 | 33.889 | 45.785 | 17.319 | 1.00 | 16.74 | 6 |
| 178 | OD1 | ASP | A | 23 | 34.805 | 45.200 | 16.750 | 1.00 | 17.96 | 8 |
| 179 | OD2 | ASP | A | 23 | 32.782 | 46.058 | 16.872 | 1.00 | 16.43 | 8 |
| 180 | N | THR | A | 24 | 37.681 | 45.659 | 18.083 | 1.00 | 15.02 | 7 |
| 181 | CA | THR | A | 24 | 38.769 | 46.308 | 17.340 | 1.00 | 16.37 | 6 |
| 182 | C | THR | A | 24 | 38.381 | 46.606 | 15.923 | 1.00 | 15.39 | 6 |
| 183 | O | THR | A | 24 | 39.124 | 47.376 | 15.252 | 1.00 | 16.40 | 8 |
| 184 | CB | THR | A | 24 | 40.033 | 45.402 | 17.367 | 1.00 | 18.68 | 6 |
| 185 | OG1 | THR | A | 24 | 39.710 | 44.147 | 16.673 | 1.00 | 17.99 | 8 |
| 186 | CG2 | THR | A | 24 | 40.478 | 45.112 | 18.772 | 1.00 | 22.45 | 6 |
| 187 | N | THR | A | 25 | 37.228 | 46.150 | 15.423 | 1.00 | 16.09 | 7 |
| 188 | CA | THR | A | 25 | 36.864 | 46.330 | 14.019 | 1.00 | 16.07 | 6 |
| 189 | C | THR | A | 25 | 36.349 | 47.743 | 13.724 | 1.00 | 16.52 | 6 |
| 190 | O | THR | A | 25 | 36.215 | 48.013 | 12.538 | 1.00 | 20.25 | 8 |
| 191 | CB | THR | A | 25 | 35.780 | 45.366 | 13.475 | 1.00 | 20.06 | 6 |
| 192 | OG1 | THR | A | 25 | 34.475 | 45.532 | 14.010 | 1.00 | 18.04 | 8 |
| 193 | CG2 | THR | A | 25 | 36.248 | 43.924 | 13.739 | 1.00 | 21.26 | 6 |
| 194 | N | ASN | A | 26 | 36.066 | 48.509 | 14.802 | 1.00 | 13.98 | 7 |
| 195 | CA | ASN | A | 26 | 35.577 | 49.871 | 14.471 | 1.00 | 12.49 | 6 |
| 196 | C | ASN | A | 26 | 36.689 | 50.862 | 14.772 | 1.00 | 13.05 | 6 |
| 197 | O | ASN | A | 26 | 36.435 | 52.053 | 14.825 | 1.00 | 11.58 | 8 |
| 198 | CB | ASN | A | 26 | 34.283 | 50.103 | 15.246 | 1.00 | 13.85 | 6 |
| 199 | CG | ASN | A | 26 | 34.435 | 49.981 | 16.739 | 1.00 | 15.62 | 6 |
| 200 | OD1 | ASN | A | 26 | 35.558 | 50.066 | 17.224 | 1.00 | 12.89 | 8 |
| 201 | ND2 | ASN | A | 26 | 33.339 | 49.796 | 17.497 | 1.00 | 16.36 | 7 |
| 202 | N | ASN | A | 27 | 37.946 | 50.401 | 14.890 | 1.00 | 14.79 | 7 |
| 203 | CA | ASN | A | 27 | 38.972 | 51.353 | 15.290 | 1.00 | 12.19 | 6 |
| 204 | C | ASN | A | 27 | 39.404 | 52.337 | 14.189 | 1.00 | 13.62 | 6 |
| 205 | O | ASN | A | 27 | 39.775 | 53.461 | 14.499 | 1.00 | 14.13 | 8 |
| 206 | CB | ASN | A | 27 | 40.235 | 50.575 | 15.662 | 1.00 | 12.10 | 6 |
| 207 | CG | ASN | A | 27 | 40.150 | 49.884 | 17.001 | 1.00 | 15.80 | 6 |
| 208 | OD1 | ASN | A | 27 | 39.065 | 49.932 | 17.554 | 1.00 | 12.92 | 8 |
| 209 | ND2 | ASN | A | 27 | 41.187 | 49.291 | 17.571 | 1.00 | 15.14 | 7 |
| 210 | N | ASN | A | 28 | 39.211 | 51.954 | 12.920 | 1.00 | 14.26 | 7 |
| 211 | CA | ASN | A | 28 | 39.604 | 52.918 | 11.854 | 1.00 | 15.71 | 6 |
| 212 | C | ASN | A | 28 | 38.672 | 52.705 | 10.661 | 1.00 | 14.39 | 6 |
| 213 | O | ASN | A | 28 | 39.059 | 52.148 | 9.622 | 1.00 | 16.82 | 8 |
| 214 | CB | ASN | A | 28 | 41.036 | 52.497 | 11.478 | 1.00 | 13.79 | 6 |
| 215 | CG | ASN | A | 28 | 41.790 | 53.538 | 10.656 | 1.00 | 21.29 | 6 |
| 216 | OD1 | ASN | A | 28 | 41.391 | 54.685 | 10.535 | 1.00 | 17.46 | 8 |
| 217 | ND1 | ASN | A | 28 | 42.936 | 53.086 | 10.108 | 1.00 | 24.72 | 7 |
| 218 | N | PRO | A | 29 | 37.442 | 53.154 | 10.790 | 1.00 | 15.04 | 7 |
| 219 | CA | PRO | A | 29 | 36.430 | 52.993 | 9.742 | 1.00 | 17.37 | 6 |
| 220 | C | PRO | A | 29 | 36.734 | 53.802 | 8.507 | 1.00 | 18.08 | 6 |
| 221 | O | PRO | A | 29 | 37.259 | 54.906 | 8.580 | 1.00 | 16.51 | 8 |
| 222 | CB | PRO | A | 29 | 35.087 | 53.483 | 10.312 | 1.00 | 17.71 | 6 |
| 223 | CG | PRO | A | 29 | 35.394 | 53.615 | 11.787 | 1.00 | 17.95 | 6 |
| 224 | CD | PRO | A | 29 | 36.907 | 53.841 | 11.957 | 1.00 | 15.54 | 6 |
| 225 | N | ALA | A | 30 | 36.329 | 53.244 | 7.331 | 1.00 | 16.99 | 7 |
| 226 | CA | ALA | A | 30 | 36.533 | 54.024 | 6.117 | 1.00 | 19.06 | 6 |
| 227 | C | ALA | A | 30 | 35.841 | 55.375 | 6.161 | 1.00 | 16.15 | 6 |
| 228 | O | ALA | A | 30 | 36.398 | 56.355 | 5.599 | 1.00 | 18.27 | 8 |
| 229 | CB | ALA | A | 30 | 35.998 | 53.268 | 4.880 | 1.00 | 21.27 | 6 |
| 230 | N | LYS | A | 31 | 34.697 | 55.514 | 6.833 | 1.00 | 15.01 | 7 |
| 231 | CA | LYS | A | 31 | 34.012 | 56.812 | 6.886 | 1.00 | 14.64 | 6 |
| 232 | C | LYS | A | 31 | 34.944 | 57.908 | 7.416 | 1.00 | 15.07 | 6 |
| 233 | O | LYS | A | 31 | 34.722 | 59.094 | 7.172 | 1.00 | 14.25 | 8 |
| 234 | CB | LYS | A | 31 | 32.771 | 56.667 | 7.818 | 1.00 | 13.99 | 6 |
| 235 | CG | LYS | A | 31 | 31.981 | 57.980 | 8.050 | 1.00 | 13.23 | 6 |
| 236 | CD | LYS | A | 31 | 30.617 | 57.569 | 8.669 | 1.00 | 16.17 | 6 |
| 237 | CE | LYS | A | 31 | 29.763 | 58.766 | 9.053 | 1.00 | 14.65 | 6 |
| 238 | NZ | LYS | A | 31 | 30.427 | 59.568 | 10.156 | 1.00 | 12.05 | 7 |
| 239 | N | SER | A | 32 | 35.822 | 57.610 | 8.364 | 1.00 | 16.27 | 7 |
| 240 | CA | SER | A | 32 | 36.675 | 58.587 | 9.038 | 1.00 | 14.39 | 6 |
| 241 | C | SER | A | 32 | 38.087 | 57.989 | 9.161 | 1.00 | 17.62 | 6 |
| 242 | O | SER | A | 32 | 38.770 | 57.968 | 10.193 | 1.00 | 17.19 | 8 |
| 243 | CB | SER | A | 32 | 36.100 | 58.851 | 10.460 | 1.00 | 12.32 | 6 |
| 244 | OG | SER | A | 32 | 35.874 | 57.664 | 11.167 | 1.00 | 12.92 | 8 |
| 245 | N | TYR | A | 33 | 38.596 | 57.524 | 8.010 | 1.00 | 14.71 | 7 |
| 246 | CA | TYR | A | 33 | 39.875 | 56.801 | 8.045 | 1.00 | 15.23 | 6 |

TABLE 1-continued

Atom Coordinates from the Crystal Structure of NOVAMYL

| 247 | C | TYR | A | 33 | 41.051 | 57.676 | 8.444 | 1.00 | 14.94 | 6 |
|---|---|---|---|---|---|---|---|---|---|---|
| 248 | O | TYR | A | 33 | 41.042 | 58.848 | 8.023 | 1.00 | 17.62 | 8 |
| 249 | CB | TYR | A | 33 | 40.075 | 56.295 | 6.582 | 1.00 | 18.09 | 6 |
| 250 | CG | TYR | A | 33 | 41.166 | 55.254 | 6.536 | 1.00 | 20.46 | 6 |
| 251 | CD1 | TYR | A | 33 | 40.982 | 53.978 | 7.004 | 1.00 | 26.95 | 6 |
| 252 | CD2 | TYR | A | 33 | 42.408 | 55.618 | 6.002 | 1.00 | 31.14 | 6 |
| 253 | CE2 | TYR | A | 33 | 41.994 | 53.027 | 6.944 | 1.00 | 33.56 | 6 |
| 254 | CE2 | TYR | A | 33 | 43.422 | 54.670 | 5.943 | 1.00 | 31.30 | 6 |
| 255 | CZ | TYR | A | 33 | 43.210 | 53.409 | 6.402 | 1.00 | 33.88 | 6 |
| 256 | OH | TYR | A | 33 | 44.235 | 52.483 | 6.334 | 1.00 | 44.90 | 8 |
| 257 | N | GLY | A | 34 | 42.039 | 57.105 | 9.114 | 1.00 | 12.92 | 7 |
| 258 | CA | GLY | A | 34 | 43.281 | 57.836 | 9.403 | 1.00 | 14.92 | 6 |
| 259 | C | GLY | A | 34 | 43.255 | 58.672 | 10.686 | 1.00 | 15.08 | 6 |
| 260 | O | GLY | A | 34 | 44.274 | 59.342 | 10.956 | 1.00 | 15.24 | 8 |
| 261 | N | LEU | A | 35 | 42.253 | 58.417 | 11.548 | 1.00 | 12.52 | 7 |
| 262 | CA | LEU | A | 35 | 42.215 | 59.140 | 12.846 | 1.00 | 11.02 | 6 |
| 263 | C | LEU | A | 35 | 42.519 | 58.271 | 14.028 | 1.00 | 15.01 | 6 |
| 264 | O | LEU | A | 35 | 42.472 | 58.755 | 15.182 | 1.00 | 14.18 | 8 |
| 265 | CB | LEU | A | 35 | 40.784 | 59.737 | 13.090 | 1.00 | 10.53 | 6 |
| 266 | CG | LEU | A | 35 | 40.170 | 60.460 | 11.891 | 1.00 | 12.89 | 6 |
| 267 | CD1 | LEU | A | 35 | 38.783 | 61.033 | 12.240 | 1.00 | 13.47 | 6 |
| 268 | CD2 | LEU | A | 35 | 41.090 | 61.613 | 11.433 | 1.00 | 15.36 | 6 |
| 269 | N | TYR | A | 36 | 43.025 | 57.036 | 13.757 | 1.00 | 13.30 | 7 |
| 270 | CA | TYR | A | 36 | 43.335 | 56.061 | 14.796 | 1.00 | 13.00 | 6 |
| 271 | C | TYR | A | 36 | 44.826 | 55.913 | 15.032 | 1.00 | 15.18 | 6 |
| 272 | O | TYR | A | 36 | 45.610 | 55.855 | 14.049 | 1.00 | 15.86 | 8 |
| 273 | CB | TYR | A | 36 | 42.749 | 54.728 | 14.291 | 1.00 | 13.61 | 6 |
| 274 | CG | TYR | A | 36 | 43.149 | 53.492 | 15.076 | 1.00 | 12.30 | 6 |
| 275 | CD1 | TYR | A | 36 | 42.927 | 53.383 | 16.454 | 1.00 | 14.21 | 6 |
| 276 | CD2 | TYR | A | 36 | 43.807 | 52.460 | 14.391 | 1.00 | 16.88 | 6 |
| 277 | CE1 | TYR | A | 36 | 43.317 | 52.206 | 17.122 | 1.00 | 14.97 | 6 |
| 278 | CE2 | TYR | A | 36 | 44.182 | 51.320 | 15.075 | 1.00 | 19.02 | 6 |
| 279 | CZ | TYR | A | 36 | 43.930 | 51.206 | 16.416 | 1.00 | 17.90 | 6 |
| 280 | OH | TYR | A | 36 | 44.299 | 50.063 | 17.135 | 1.00 | 18.88 | 8 |
| 281 | N | ASP | A | 37 | 45.211 | 55.848 | 16.289 | 1.00 | 12.45 | 7 |
| 282 | CA | ASP | A | 37 | 46.646 | 55.624 | 16.621 | 1.00 | 12.80 | 6 |
| 283 | C | ASP | A | 37 | 46.700 | 54.350 | 17.441 | 1.00 | 14.03 | 6 |
| 284 | O | ASP | A | 37 | 46.507 | 54.281 | 18.673 | 1.00 | 13.32 | 8 |
| 285 | CB | ASP | A | 37 | 47.120 | 56.834 | 17.463 | 1.00 | 13.46 | 6 |
| 286 | CG | ASP | A | 37 | 48.543 | 56.543 | 17.991 | 1.00 | 20.57 | 6 |
| 287 | OD1 | ASP | A | 37 | 49.278 | 55.720 | 17.366 | 1.00 | 17.00 | 8 |
| 288 | OD2 | ASP | A | 37 | 48.902 | 57.113 | 19.028 | 1.00 | 17.32 | 8 |
| 289 | N | PRO | A | 38 | 47.163 | 53.245 | 16.821 | 1.00 | 15.62 | 7 |
| 290 | CA | PRO | A | 38 | 47.375 | 52.024 | 17.548 | 1.00 | 15.67 | 6 |
| 291 | C | PRO | A | 38 | 48.484 | 52.056 | 18.558 | 1.00 | 15.69 | 6 |
| 292 | O | PRO | A | 38 | 48.513 | 51.189 | 19.436 | 1.00 | 18.95 | 8 |
| 293 | CB | PRO | A | 38 | 47.669 | 50.946 | 16.450 | 1.00 | 17.01 | 6 |
| 294 | CG | PRO | A | 38 | 48.367 | 51.843 | 15.437 | 1.00 | 18.68 | 6 |
| 295 | CD | PRO | A | 38 | 47.570 | 53.192 | 15.409 | 1.00 | 18.22 | 6 |
| 296 | N | THR | A | 39 | 49.385 | 53.031 | 18.514 | 1.00 | 15.60 | 7 |
| 297 | CA | THR | A | 39 | 50.469 | 53.080 | 19.499 | 1.00 | 14.85 | 6 |
| 298 | C | THR | A | 39 | 50.126 | 53.773 | 20.822 | 1.00 | 17.68 | 6 |
| 299 | O | THR | A | 39 | 50.961 | 53.777 | 21.719 | 1.00 | 17.01 | 8 |
| 300 | CB | THR | A | 39 | 51.692 | 53.847 | 18.947 | 1.00 | 19.14 | 6 |
| 301 | OG1 | THR | A | 39 | 51.503 | 55.239 | 18.723 | 1.00 | 16.66 | 8 |
| 302 | CG2 | THR | A | 39 | 52.083 | 53.233 | 17.573 | 1.00 | 22.20 | 6 |
| 303 | N | LYS | A | 40 | 48.983 | 54.487 | 20.832 | 1.00 | 14.93 | 7 |
| 304 | CA | LYS | A | 40 | 48.588 | 55.225 | 22.041 | 1.00 | 14.22 | 6 |
| 305 | C | LYS | A | 40 | 49.736 | 56.141 | 22.483 | 1.00 | 17.80 | 6 |
| 306 | O | LYS | A | 40 | 50.009 | 56.348 | 23.685 | 1.00 | 17.78 | 8 |
| 307 | CB | LYS | A | 40 | 48.104 | 54.324 | 23.207 | 1.00 | 19.03 | 6 |
| 308 | CG | LYS | A | 40 | 47.023 | 53.320 | 22.775 | 1.00 | 18.65 | 6 |
| 309 | CD | LYS | A | 40 | 46.535 | 52.543 | 24.031 | 1.00 | 21.38 | 6 |
| 310 | CE | LYS | A | 40 | 45.432 | 51.573 | 23.590 | 1.00 | 22.34 | 6 |
| 311 | NZ | LYS | A | 40 | 45.883 | 50.563 | 22.605 | 1.00 | 21.85 | 7 |
| 312 | N | SER | A | 41 | 50.307 | 56.831 | 21.475 | 1.00 | 16.33 | 7 |
| 313 | CA | SER | A | 41 | 51.307 | 57.853 | 21.746 | 1.00 | 17.21 | 6 |
| 314 | C | SER | A | 41 | 50.929 | 59.210 | 21.203 | 1.00 | 16.87 | 6 |
| 315 | O | SER | A | 41 | 51.606 | 60.250 | 21.492 | 1.00 | 16.04 | 8 |
| 316 | CB | SER | A | 41 | 52.714 | 57.429 | 21.198 | 1.00 | 17.96 | 6 |
| 317 | OG | SER | A | 41 | 52.625 | 57.387 | 19.782 | 1.00 | 20.42 | 8 |
| 318 | N | LYS | A | 42 | 49.895 | 59.315 | 20.388 | 1.00 | 13.73 | 7 |
| 319 | CA | LYS | A | 42 | 49.446 | 60.589 | 19.836 | 1.00 | 12.77 | 6 |
| 320 | C | LYS | A | 42 | 48.152 | 60.921 | 20.603 | 1.00 | 13.20 | 6 |
| 321 | O | LYS | A | 42 | 47.111 | 60.351 | 20.317 | 1.00 | 12.98 | 8 |
| 322 | CB | LYS | A | 42 | 49.193 | 60.477 | 18.321 | 1.00 | 14.60 | 6 |
| 323 | CG | LYS | A | 42 | 50.523 | 60.079 | 17.606 | 1.00 | 19.41 | 6 |

TABLE 1-continued

Atom Coordinates from the Crystal Structure of NOVAMYL

| 324 | CD | LYS | A | 42 | 50.228 | 60.163 | 16.078 | 1.00 | 25.03 | 6 |
|---|---|---|---|---|---|---|---|---|---|---|
| 325 | CE | LYS | A | 42 | 51.611 | 60.340 | 15.395 | 1.00 | 34.65 | 6 |
| 326 | NZ | LYS | A | 42 | 52.071 | 58.949 | 15.130 | 1.00 | 41.02 | 7 |
| 327 | N | TRP | A | 43 | 48.256 | 61.858 | 21.565 | 1.00 | 11.08 | 7 |
| 328 | CA | TRP | A | 43 | 47.235 | 61.925 | 22.643 | 1.00 | 13.35 | 6 |
| 329 | C | TRP | A | 43 | 45.915 | 62.494 | 22.162 | 1.00 | 11.08 | 6 |
| 330 | O | TRP | A | 43 | 45.002 | 62.429 | 22.997 | 1.00 | 13.47 | 8 |
| 331 | CB | TRP | A | 43 | 47.831 | 62.848 | 23.743 | 1.00 | 14.15 | 6 |
| 332 | CG | TRP | A | 43 | 48.739 | 61.957 | 24.592 | 1.00 | 12.91 | 6 |
| 333 | CD1 | TRP | A | 43 | 50.014 | 61.590 | 24.338 | 1.00 | 14.88 | 6 |
| 334 | CD2 | TRP | A | 43 | 48.362 | 61.357 | 25.845 | 1.00 | 12.18 | 6 |
| 335 | NE1 | TRP | A | 43 | 50.507 | 60.770 | 25.364 | 1.00 | 16.61 | 7 |
| 336 | CE2 | TRP | A | 43 | 49.467 | 60.633 | 26.297 | 1.00 | 17.08 | 6 |
| 337 | CE3 | TRP | A | 43 | 47.186 | 61.367 | 26.617 | 1.00 | 13.97 | 6 |
| 338 | CZ2 | TRP | A | 43 | 49.497 | 59.891 | 27.501 | 1.00 | 19.44 | 6 |
| 339 | CZ3 | TRP | A | 43 | 47.223 | 60.644 | 27.814 | 1.00 | 14.34 | 6 |
| 340 | CH2 | TRP | A | 43 | 48.333 | 59.925 | 28.265 | 1.00 | 15.92 | 6 |
| 341 | N | LYS | A | 44 | 45.846 | 63.088 | 20.972 | 1.00 | 11.78 | 7 |
| 342 | CA | LYS | A | 44 | 44.532 | 63.606 | 20.529 | 1.00 | 10.59 | 6 |
| 343 | C | LYS | A | 44 | 43.959 | 62.797 | 19.362 | 1.00 | 11.15 | 6 |
| 344 | O | LYS | A | 44 | 43.021 | 63.227 | 18.707 | 1.00 | 11.48 | 8 |
| 345 | CB | LYS | A | 44 | 44.647 | 65.112 | 20.097 | 1.00 | 11.58 | 6 |
| 346 | CG | LYS | A | 44 | 45.053 | 65.911 | 21.382 | 1.00 | 11.48 | 6 |
| 347 | CD | LYS | A | 44 | 44.928 | 67.435 | 21.011 | 1.00 | 12.19 | 6 |
| 348 | CE | LYS | A | 44 | 45.254 | 68.171 | 22.334 | 1.00 | 15.83 | 6 |
| 349 | NZ | LYS | A | 44 | 45.125 | 69.681 | 22.068 | 1.00 | 18.92 | 7 |
| 350 | N | MET | A | 45 | 44.473 | 61.576 | 19.114 | 1.00 | 10.42 | 7 |
| 351 | CA | MET | A | 45 | 43.881 | 60.686 | 18.112 | 1.00 | 12.24 | 6 |
| 352 | C | MET | A | 45 | 42.952 | 59.664 | 18.768 | 1.00 | 11.36 | 6 |
| 353 | O | MET | A | 45 | 43.011 | 59.512 | 19.985 | 1.00 | 12.88 | 8 |
| 354 | CB | MET | A | 45 | 45.028 | 59.874 | 17.442 | 1.00 | 13.26 | 6 |
| 355 | CG | AMET | A | 45 | 46.067 | 60.710 | 16.692 | 0.50 | 14.78 | 6 |
| 356 | SD | AMET | A | 45 | 45.379 | 61.237 | 15.135 | 0.50 | 13.95 | 16 |
| 357 | CE | AMET | A | 45 | 45.728 | 60.040 | 13.903 | 0.50 | 12.41 | 6 |
| 356 | SD | BMET | A | 45 | 46.918 | 60.290 | 15.431 | 0.50 | 16.20 | 16 |
| 357 | CE | BMET | A | 45 | 45.864 | 59.453 | 14.271 | 0.50 | 18.11 | 6 |
| 358 | N | TYR | A | 46 | 42.122 | 58.961 | 17.976 | 1.00 | 10.91 | 7 |
| 359 | CA | TYR | A | 46 | 41.356 | 57.880 | 18.584 | 1.00 | 13.29 | 6 |
| 360 | C | TYR | A | 46 | 42.263 | 56.691 | 18.938 | 1.00 | 13.10 | 6 |
| 361 | O | TYR | A | 46 | 43.076 | 56.318 | 18.094 | 1.00 | 12.46 | 8 |
| 362 | CB | TYR | A | 46 | 40.258 | 57.364 | 17.660 | 1.00 | 12.44 | 6 |
| 363 | CG | TYR | A | 46 | 39.031 | 58.210 | 17.416 | 1.00 | 13.02 | 6 |
| 364 | CD1 | TYR | A | 46 | 39.075 | 59.210 | 16.436 | 1.00 | 11.30 | 6 |
| 365 | CD2 | TYR | A | 46 | 37.846 | 57.978 | 18.105 | 1.00 | 12.45 | 6 |
| 366 | CE1 | TYR | A | 46 | 37.940 | 59.997 | 16.146 | 1.00 | 12.75 | 6 |
| 367 | CE2 | TYR | A | 46 | 36.683 | 58.746 | 17.838 | 1.00 | 9.77 | 6 |
| 368 | CZ | TYR | A | 46 | 36.789 | 59.707 | 16.881 | 1.00 | 10.60 | 6 |
| 369 | OH | TYR | A | 46 | 35.703 | 60.490 | 16.547 | 1.00 | 11.65 | 8 |
| 370 | N | TRP | A | 47 | 42.097 | 56.222 | 20.188 | 1.00 | 9.67 | 7 |
| 371 | CA | TRP | A | 47 | 42.866 | 55.089 | 20.664 | 1.00 | 11.50 | 6 |
| 372 | C | TRP | A | 47 | 42.065 | 53.770 | 20.579 | 1.00 | 12.29 | 6 |
| 373 | O | TRP | A | 47 | 42.633 | 52.676 | 20.711 | 1.00 | 12.20 | 8 |
| 374 | CB | TRP | A | 47 | 43.430 | 55.285 | 22.077 | 1.00 | 12.80 | 6 |
| 375 | CG | TRP | A | 47 | 44.548 | 56.316 | 22.086 | 1.00 | 10.46 | 6 |
| 376 | CD1 | TRP | A | 47 | 45.068 | 57.007 | 21.037 | 1.00 | 11.88 | 6 |
| 377 | CD2 | TRP | A | 47 | 45.300 | 56.687 | 23.218 | 1.00 | 10.01 | 6 |
| 378 | NE1 | TRP | A | 47 | 46.060 | 57.853 | 21.485 | 1.00 | 11.36 | 7 |
| 379 | CE2 | TRP | A | 47 | 46.219 | 57.700 | 22.820 | 1.00 | 12.07 | 6 |
| 380 | CE3 | TRP | A | 47 | 45.198 | 56.392 | 24.603 | 1.00 | 12.09 | 6 |
| 381 | CZ2 | TRP | A | 47 | 47.103 | 58.301 | 23.715 | 1.00 | 13.05 | 6 |
| 382 | CZ3 | TRP | A | 47 | 46.072 | 56.974 | 25.484 | 1.00 | 15.07 | 6 |
| 383 | CH2 | TRP | A | 47 | 47.002 | 57.939 | 25.033 | 1.00 | 16.33 | 6 |
| 384 | N | GLY | A | 48 | 40.752 | 53.875 | 20.442 | 1.00 | 10.96 | 7 |
| 385 | CA | GLY | A | 48 | 39.995 | 52.631 | 20.097 | 1.00 | 11.53 | 6 |
| 386 | C | GLY | A | 48 | 38.960 | 52.197 | 21.106 | 1.00 | 11.03 | 6 |
| 387 | O | GLY | A | 48 | 38.208 | 51.215 | 20.845 | 1.00 | 12.01 | 8 |
| 388 | N | GLY | A | 49 | 38.834 | 52.862 | 22.221 | 1.00 | 12.42 | 7 |
| 389 | CA | GLY | A | 49 | 37.789 | 52.443 | 23.230 | 1.00 | 12.08 | 6 |
| 390 | C | GLY | A | 49 | 36.451 | 52.679 | 22.614 | 1.00 | 9.81 | 6 |
| 391 | O | GLY | A | 49 | 36.173 | 53.629 | 21.880 | 1.00 | 10.92 | 8 |
| 392 | N | ASP | A | 50 | 35.433 | 51.851 | 23.065 | 1.00 | 10.42 | 7 |
| 393 | CA | ASP | A | 50 | 34.135 | 51.985 | 22.429 | 1.00 | 11.91 | 6 |
| 394 | C | ASP | A | 50 | 32.977 | 51.516 | 23.344 | 1.00 | 11.85 | 6 |
| 395 | O | ASP | A | 50 | 33.188 | 51.228 | 24.489 | 1.00 | 12.76 | 8 |
| 396 | CB | ASP | A | 50 | 34.148 | 51.188 | 21.094 | 1.00 | 10.66 | 6 |
| 397 | CG | ASP | A | 50 | 34.693 | 49.790 | 21.327 | 1.00 | 14.50 | 6 |
| 398 | OD1 | ASP | A | 50 | 34.446 | 49.184 | 22.384 | 1.00 | 11.19 | 8 |

TABLE 1-continued

Atom Coordinates from the Crystal Structure of NOVAMYL

| 399 | OD2 | ASP | A | 50 | 35.425 | 49.205 | 20.532 | 1.00 | 11.87 | 8 |
|---|---|---|---|---|---|---|---|---|---|---|
| 400 | N | LEU | A | 51 | 31.762 | 51.615 | 22.778 | 1.00 | 11.80 | 7 |
| 401 | CA | LEU | A | 51 | 30.580 | 51.320 | 23.617 | 1.00 | 11.32 | 6 |
| 402 | C | LEU | A | 51 | 30.568 | 49.843 | 23.973 | 1.00 | 13.43 | 6 |
| 403 | O | LEU | A | 51 | 30.145 | 49.499 | 25.090 | 1.00 | 11.80 | 8 |
| 404 | CB | LEU | A | 51 | 29.272 | 51.662 | 22.869 | 1.00 | 12.03 | 6 |
| 405 | CG | LEU | A | 51 | 29.178 | 53.205 | 22.638 | 1.00 | 11.71 | 6 |
| 406 | CD1 | LEU | A | 51 | 28.036 | 53.389 | 21.666 | 1.00 | 13.88 | 6 |
| 407 | CD2 | LEU | A | 51 | 28.915 | 53.930 | 23.954 | 1.00 | 15.76 | 6 |
| 408 | N | GLU | A | 52 | 30.942 | 48.987 | 23.037 | 1.00 | 12.67 | 7 |
| 409 | CA | GLU | A | 52 | 30.995 | 47.541 | 23.443 | 1.00 | 12.25 | 6 |
| 410 | C | GLU | A | 52 | 32.024 | 47.239 | 24.516 | 1.00 | 12.73 | 6 |
| 411 | O | GLU | A | 52 | 31.816 | 46.375 | 25.382 | 1.00 | 13.32 | 8 |
| 412 | CB | GLU | A | 52 | 31.182 | 46.786 | 22.122 | 1.00 | 16.82 | 6 |
| 413 | CG | GLU | A | 52 | 31.390 | 45.298 | 22.295 | 1.00 | 22.57 | 6 |
| 414 | CD | GLU | A | 52 | 30.227 | 44.545 | 22.992 | 1.00 | 12.69 | 6 |
| 415 | OE1 | GLU | A | 52 | 29.097 | 45.029 | 23.005 | 1.00 | 17.98 | 8 |
| 416 | OE2 | GLU | A | 52 | 30.680 | 43.475 | 23.419 | 1.00 | 16.49 | 8 |
| 417 | N | GLY | A | 53 | 33.114 | 48.012 | 24.628 | 1.00 | 12.03 | 7 |
| 418 | CA | GLY | A | 53 | 34.108 | 47.857 | 25.680 | 1.00 | 13.18 | 6 |
| 419 | C | GLY | A | 53 | 33.471 | 48.292 | 27.005 | 1.00 | 12.67 | 6 |
| 420 | O | GLY | A | 53 | 33.737 | 47.586 | 28.000 | 1.00 | 11.91 | 8 |
| 421 | N | VAL | A | 54 | 32.653 | 49.355 | 27.005 | 1.00 | 11.80 | 7 |
| 422 | CA | VAL | A | 54 | 31.996 | 49.680 | 28.280 | 1.00 | 10.05 | 6 |
| 423 | C | VAL | A | 54 | 31.078 | 48.502 | 28.715 | 1.00 | 12.37 | 6 |
| 424 | O | VAL | A | 54 | 31.055 | 48.111 | 29.879 | 1.00 | 12.15 | 8 |
| 425 | CB | VAL | A | 54 | 31.154 | 50.947 | 28.220 | 1.00 | 11.03 | 6 |
| 426 | CG1 | VAL | A | 54 | 30.449 | 51.255 | 29.552 | 1.00 | 13.86 | 6 |
| 427 | CG2 | VAL | A | 54 | 32.100 | 52.143 | 27.853 | 1.00 | 11.86 | 6 |
| 428 | N | ARG | A | 55 | 30.387 | 47.952 | 27.708 | 1.00 | 9.95 | 7 |
| 429 | CA | ARG | A | 55 | 29.382 | 46.875 | 28.101 | 1.00 | 13.29 | 6 |
| 430 | C | ARG | A | 55 | 30.112 | 45.671 | 28.652 | 1.00 | 12.91 | 6 |
| 431 | O | ARG | A | 55 | 29.684 | 44.943 | 29.596 | 1.00 | 13.96 | 8 |
| 432 | CB | ARG | A | 55 | 28.627 | 46.458 | 26.819 | 1.00 | 13.43 | 6 |
| 433 | CG | ARG | A | 55 | 27.364 | 45.611 | 27.165 | 1.00 | 13.64 | 6 |
| 434 | CD | ARG | A | 55 | 26.723 | 44.974 | 25.877 | 1.00 | 13.15 | 6 |
| 435 | NE | ARG | A | 55 | 27.745 | 44.040 | 25.358 | 1.00 | 13.30 | 7 |
| 436 | CZ | ARG | A | 55 | 28.117 | 42.905 | 25.921 | 1.00 | 14.35 | 6 |
| 437 | NH1 | ARG | A | 55 | 27.475 | 42.404 | 27.011 | 1.00 | 15.82 | 7 |
| 438 | NH2 | ARG | A | 55 | 29.125 | 42.171 | 25.446 | 1.00 | 17.12 | 7 |
| 439 | N | GLN | A | 56 | 31.265 | 45.354 | 28.031 | 1.00 | 11.75 | 7 |
| 440 | CA | GLN | A | 56 | 32.050 | 44.171 | 28.503 | 1.00 | 12.69 | 6 |
| 441 | C | GLN | A | 56 | 32.530 | 44.339 | 29.945 | 1.00 | 14.76 | 6 |
| 442 | O | GLN | A | 56 | 32.895 | 43.338 | 30.611 | 1.00 | 15.16 | 8 |
| 443 | CB | GLN | A | 56 | 33.249 | 43.948 | 27.536 | 1.00 | 12.12 | 6 |
| 444 | CG | GLN | A | 56 | 32.718 | 43.310 | 26.223 | 1.00 | 12.45 | 6 |
| 445 | CD | GLN | A | 56 | 33.748 | 43.189 | 25.110 | 1.00 | 18.74 | 6 |
| 446 | OE1 | GLN | A | 56 | 33.441 | 43.161 | 23.879 | 1.00 | 21.22 | 8 |
| 447 | NE2 | GLN | A | 56 | 34.957 | 43.066 | 25.540 | 1.00 | 13.29 | 7 |
| 448 | N | LYS | A | 57 | 32.816 | 45.574 | 30.355 | 1.00 | 13.93 | 7 |
| 449 | CA | LYS | A | 57 | 33.243 | 45.881 | 31.703 | 1.00 | 11.77 | 6 |
| 450 | C | LYS | A | 57 | 32.146 | 46.200 | 32.702 | 1.00 | 13.05 | 6 |
| 451 | O | LYS | A | 57 | 32.397 | 46.651 | 33.834 | 1.00 | 12.11 | 8 |
| 452 | CB | LYS | A | 57 | 34.240 | 47.112 | 31.625 | 1.00 | 12.27 | 6 |
| 453 | CG | LYS | A | 57 | 35.508 | 46.752 | 30.818 | 1.00 | 13.15 | 6 |
| 454 | CD | LYS | A | 57 | 36.167 | 45.442 | 31.318 | 1.00 | 13.38 | 6 |
| 455 | CE | LYS | A | 57 | 37.577 | 45.277 | 30.729 | 1.00 | 16.88 | 6 |
| 456 | NZ | LYS | A | 57 | 38.170 | 43.960 | 31.261 | 1.00 | 17.21 | 7 |
| 457 | N | LEU | A | 58 | 30.883 | 45.891 | 32.388 | 1.00 | 12.90 | 7 |
| 458 | CA | LEU | A | 58 | 29.789 | 46.048 | 33.338 | 1.00 | 14.31 | 6 |
| 459 | C | LEU | A | 58 | 29.981 | 45.299 | 34.668 | 1.00 | 12.68 | 6 |
| 460 | O | LEU | A | 58 | 29.737 | 45.865 | 35.732 | 1.00 | 13.94 | 8 |
| 461 | CB | LEU | A | 58 | 28.407 | 45.779 | 32.723 | 1.00 | 12.52 | 6 |
| 462 | CG | LEU | A | 58 | 27.963 | 46.878 | 31.718 | 1.00 | 12.14 | 6 |
| 463 | CD1 | LEU | A | 58 | 26.709 | 46.366 | 30.943 | 1.00 | 14.87 | 6 |
| 464 | CD2 | LEU | A | 58 | 27.586 | 48.136 | 32.488 | 1.00 | 15.84 | 6 |
| 465 | N | PRO | A | 59 | 30.555 | 44.107 | 34.670 | 1.00 | 13.13 | 7 |
| 466 | CA | PRO | A | 59 | 30.776 | 43.396 | 35.937 | 1.00 | 14.64 | 6 |
| 467 | C | PRO | A | 59 | 31.759 | 44.139 | 36.827 | 1.00 | 14.63 | 6 |
| 468 | O | PRO | A | 59 | 31.532 | 44.250 | 38.038 | 1.00 | 15.79 | 8 |
| 469 | CB | PRO | A | 59 | 31.436 | 42.034 | 35.525 | 1.00 | 15.40 | 6 |
| 470 | CG | PRO | A | 59 | 30.719 | 41.845 | 34.161 | 1.00 | 16.79 | 6 |
| 471 | CD | PRO | A | 59 | 30.807 | 43.247 | 33.514 | 1.00 | 16.71 | 6 |
| 472 | N | TYR | A | 60 | 32.806 | 44.717 | 36.210 | 1.00 | 12.89 | 7 |
| 473 | CA | TYR | A | 60 | 33.789 | 45.511 | 36.994 | 1.00 | 12.47 | 6 |
| 474 | C | TYR | A | 60 | 33.072 | 46.731 | 37.584 | 1.00 | 12.64 | 6 |
| 475 | O | TYR | A | 60 | 33.237 | 46.994 | 38.797 | 1.00 | 13.63 | 8 |

TABLE 1-continued

Atom Coordinates from the Crystal Structure of NOVAMYL

| | | | | | | | | | | |
|---|---|---|---|---|---|---|---|---|---|---|
| 476 | CB | TYR | A | 60 | 34.918 | 45.920 | 36.026 | 1.00 | 12.16 | 6 |
| 477 | CG | TYR | A | 60 | 35.856 | 46.938 | 36.667 | 1.00 | 12.17 | 6 |
| 478 | CD1 | TYR | A | 60 | 36.917 | 46.528 | 37.462 | 1.00 | 13.23 | 6 |
| 479 | CD2 | TYR | A | 60 | 35.602 | 48.293 | 36.453 | 1.00 | 12.24 | 6 |
| 480 | CE1 | TYR | A | 60 | 37.730 | 47.509 | 38.049 | 1.00 | 12.99 | 6 |
| 481 | CE2 | TYR | A | 60 | 36.438 | 49.268 | 37.022 | 1.00 | 14.93 | 6 |
| 482 | CZ | TYR | A | 60 | 37.473 | 48.852 | 37.823 | 1.00 | 14.75 | 6 |
| 483 | OH | TYR | A | 60 | 38.287 | 49.782 | 38.464 | 1.00 | 13.93 | 8 |
| 484 | N | LEU | A | 61 | 32.298 | 47.410 | 36.735 | 1.00 | 11.74 | 7 |
| 485 | CA | LEU | A | 61 | 31.622 | 48.610 | 37.225 | 1.00 | 11.91 | 6 |
| 486 | C | LEU | A | 61 | 30.570 | 48.316 | 38.272 | 1.00 | 14.11 | 6 |
| 487 | O | LEU | A | 61 | 30.508 | 49.022 | 39.283 | 1.00 | 13.33 | 8 |
| 488 | CB | LEU | A | 61 | 30.993 | 49.382 | 36.051 | 1.00 | 12.06 | 6 |
| 489 | CG | LEU | A | 61 | 32.030 | 49.809 | 34.992 | 1.00 | 13.18 | 6 |
| 490 | CD1 | LEU | A | 61 | 31.263 | 50.310 | 33.753 | 1.00 | 15.35 | 6 |
| 491 | CD2 | LEU | A | 61 | 32.865 | 50.971 | 35.605 | 1.00 | 16.34 | 6 |
| 492 | N | LYS | A | 62 | 29.850 | 47.217 | 38.162 | 1.00 | 12.47 | 7 |
| 493 | CA | LYS | A | 62 | 28.890 | 46.844 | 39.202 | 1.00 | 13.25 | 6 |
| 494 | C | LYS | A | 62 | 29.614 | 46.558 | 40.535 | 1.00 | 13.60 | 6 |
| 495 | O | LYS | A | 62 | 29.149 | 47.032 | 41.576 | 1.00 | 15.97 | 8 |
| 496 | CB | LYS | A | 62 | 28.117 | 45.588 | 38.730 | 1.00 | 14.71 | 6 |
| 497 | CG | LYS | A | 62 | 27.011 | 45.263 | 39.764 | 1.00 | 17.27 | 6 |
| 498 | CD | LYS | A | 62 | 25.908 | 44.363 | 39.223 | 1.00 | 30.17 | 6 |
| 499 | CE | LYS | A | 62 | 24.879 | 44.088 | 40.343 | 1.00 | 25.52 | 6 |
| 500 | NZ | LYS | A | 62 | 23.887 | 45.203 | 40.515 | 1.00 | 24.63 | 7 |
| 501 | N | GLN | A | 63 | 30.722 | 45.781 | 40.455 | 1.00 | 12.05 | 7 |
| 502 | CA | GLN | A | 63 | 31.437 | 45.448 | 41.660 | 1.00 | 10.80 | 6 |
| 503 | C | GLN | A | 63 | 32.010 | 46.705 | 42.325 | 1.00 | 13.71 | 6 |
| 504 | O | GLN | A | 63 | 32.200 | 46.751 | 43.544 | 1.00 | 13.66 | 8 |
| 505 | CB | AGLN | A | 63 | 32.582 | 44.501 | 41.262 | 0.66 | 17.93 | 6 |
| 506 | CG | AGLN | A | 63 | 32.178 | 43.092 | 40.865 | 0.66 | 27.01 | 6 |
| 507 | CD | AGLN | A | 63 | 33.421 | 42.362 | 40.343 | 0.66 | 35.95 | 6 |
| 508 | OE1 | AGLN | A | 63 | 34.283 | 42.022 | 41.149 | 0.66 | 40.99 | 8 |
| 509 | NE2 | AGLN | A | 63 | 33.525 | 42.128 | 39.043 | 0.66 | 36.04 | 7 |
| 505 | CB | BGLN | A | 63 | 32.511 | 44.387 | 41.345 | 0.33 | 7.59 | 6 |
| 506 | CG | BGLN | A | 63 | 33.072 | 43.793 | 42.621 | 0.33 | 8.29 | 6 |
| 507 | CD | BGLN | A | 63 | 34.234 | 42.824 | 42.408 | 0.33 | 8.28 | 6 |
| 508 | OE1 | BGLN | A | 63 | 34.480 | 42.416 | 41.279 | 0.33 | 14.24 | 8 |
| 509 | NE2 | BGLN | A | 63 | 34.884 | 42.519 | 43.537 | 0.33 | 12.44 | 7 |
| 510 | N | LEU | A | 64 | 32.481 | 47.646 | 41.498 | 1.00 | 10.99 | 7 |
| 511 | CA | LEU | A | 64 | 32.993 | 48.909 | 42.087 | 1.00 | 15.73 | 6 |
| 512 | C | LEU | A | 64 | 31.893 | 49.656 | 42.837 | 1.00 | 14.21 | 6 |
| 513 | O | LEU | A | 64 | 32.253 | 50.516 | 43.659 | 1.00 | 14.81 | 8 |
| 514 | CB | LEU | A | 64 | 33.536 | 49.777 | 40.930 | 1.00 | 14.15 | 6 |
| 515 | CG | LEU | A | 64 | 34.050 | 51.201 | 41.274 | 1.00 | 13.04 | 6 |
| 516 | CD1 | LEU | A | 64 | 35.177 | 51.132 | 42.303 | 1.00 | 12.46 | 6 |
| 517 | CD2 | LEU | A | 64 | 34.587 | 51.825 | 39.963 | 1.00 | 12.70 | 6 |
| 518 | N | GLY | A | 65 | 30.605 | 49.492 | 42.566 | 1.00 | 14.23 | 7 |
| 519 | CA | GLY | A | 65 | 29.537 | 50.247 | 43.205 | 1.00 | 13.78 | 6 |
| 520 | C | GLY | A | 65 | 28.987 | 51.337 | 42.311 | 1.00 | 14.56 | 6 |
| 521 | O | GLY | A | 65 | 28.207 | 52.222 | 42.758 | 1.00 | 13.13 | 8 |
| 522 | N | VAL | A | 66 | 29.343 | 51.265 | 41.014 | 1.00 | 12.13 | 7 |
| 523 | CA | VAL | A | 66 | 28.773 | 52.267 | 40.114 | 1.00 | 10.77 | 6 |
| 524 | C | VAL | A | 66 | 27.297 | 52.007 | 39.842 | 1.00 | 13.82 | 6 |
| 525 | O | VAL | A | 66 | 26.933 | 50.836 | 39.617 | 1.00 | 13.38 | 8 |
| 526 | CB | VAL | A | 66 | 29.491 | 52.192 | 38.744 | 1.00 | 11.10 | 6 |
| 527 | CG1 | VAL | A | 66 | 28.892 | 53.220 | 37.731 | 1.00 | 12.12 | 6 |
| 528 | CG2 | VAL | A | 66 | 30.961 | 52.489 | 38.974 | 1.00 | 14.48 | 6 |
| 529 | N | THR | A | 67 | 26.431 | 53.016 | 39.992 | 1.00 | 10.70 | 7 |
| 530 | CA | THR | A | 67 | 25.022 | 52.822 | 39.675 | 1.00 | 12.22 | 6 |
| 531 | C | THR | A | 67 | 24.526 | 53.737 | 38.565 | 1.00 | 13.77 | 6 |
| 532 | O | THR | A | 67 | 23.404 | 53.538 | 38.103 | 1.00 | 13.29 | 8 |
| 533 | CB | THR | A | 67 | 24.072 | 52.926 | 40.898 | 1.00 | 14.25 | 6 |
| 534 | OG1 | THR | A | 67 | 24.680 | 53.791 | 41.874 | 1.00 | 13.89 | 8 |
| 535 | CG2 | THR | A | 67 | 24.085 | 51.519 | 41.584 | 1.00 | 14.96 | 6 |
| 536 | N | THR | A | 68 | 25.351 | 54.723 | 38.156 | 1.00 | 12.63 | 7 |
| 537 | CA | THR | A | 68 | 25.042 | 55.479 | 36.914 | 1.00 | 10.68 | 6 |
| 538 | C | THR | A | 68 | 26.379 | 55.684 | 36.193 | 1.00 | 9.37 | 6 |
| 539 | O | THR | A | 68 | 27.313 | 56.214 | 36.775 | 1.00 | 11.86 | 8 |
| 540 | CB | THR | A | 68 | 24.388 | 56.837 | 37.236 | 1.00 | 13.89 | 6 |
| 541 | OG1 | THR | A | 68 | 23.094 | 56.649 | 37.793 | 1.00 | 13.19 | 8 |
| 542 | CG2 | THR | A | 68 | 24.269 | 57.734 | 35.965 | 1.00 | 14.32 | 6 |
| 543 | N | ILE | A | 69 | 26.394 | 55.287 | 34.896 | 1.00 | 9.42 | 7 |
| 544 | CA | ILE | A | 69 | 27.605 | 55.600 | 34.073 | 1.00 | 8.17 | 6 |
| 545 | C | ILE | A | 69 | 27.249 | 56.897 | 33.377 | 1.00 | 11.16 | 6 |
| 546 | O | ILE | A | 69 | 26.200 | 57.080 | 32.734 | 1.00 | 12.50 | 8 |
| 547 | CB | ILE | A | 69 | 27.714 | 54.510 | 32.986 | 1.00 | 12.66 | 6 |

TABLE 1-continued

Atom Coordinates from the Crystal Structure of NOVAMYL

| 548 | CG1 | ILE | A | 69 | 28.160 | 53.214 | 33.736 | 1.00 | 14.05 | 6 |
|---|---|---|---|---|---|---|---|---|---|---|
| 549 | CG2 | ILE | A | 69 | 28.737 | 54.893 | 31.900 | 1.00 | 11.22 | 6 |
| 550 | CD1 | ILE | A | 69 | 27.937 | 52.008 | 32.775 | 1.00 | 13.93 | 6 |
| 551 | N | TRP | A | 70 | 28.196 | 57.872 | 33.425 | 1.00 | 9.74 | 7 |
| 552 | CA | TRP | A | 70 | 28.095 | 59.093 | 32.600 | 1.00 | 13.34 | 6 |
| 553 | C | TRP | A | 70 | 28.991 | 58.790 | 31.403 | 1.00 | 11.63 | 6 |
| 554 | O | TRP | A | 70 | 30.214 | 58.751 | 31.558 | 1.00 | 11.51 | 8 |
| 555 | CB | TRP | A | 70 | 28.494 | 60.327 | 33.441 | 1.00 | 9.83 | 6 |
| 556 | CG | TRP | A | 70 | 28.954 | 61.558 | 32.738 | 1.00 | 8.81 | 6 |
| 557 | CD1 | TRP | A | 70 | 29.050 | 61.770 | 31.360 | 1.00 | 13.03 | 6 |
| 558 | CD2 | TRP | A | 70 | 29.591 | 62.698 | 33.356 | 1.00 | 10.57 | 6 |
| 559 | NE1 | TRP | A | 70 | 29.645 | 63.016 | 31.118 | 1.00 | 12.41 | 7 |
| 560 | CE2 | TRP | A | 70 | 30.017 | 63.558 | 32.338 | 1.00 | 10.48 | 6 |
| 561 | CE3 | TRP | A | 70 | 29.830 | 63.007 | 34.699 | 1.00 | 12.18 | 6 |
| 562 | CZ2 | TRP | A | 70 | 30.721 | 64.729 | 32.587 | 1.00 | 9.61 | 6 |
| 563 | CZ3 | TRP | A | 70 | 30.426 | 64.234 | 34.950 | 1.00 | 11.62 | 6 |
| 564 | CH2 | TRP | A | 70 | 30.896 | 65.061 | 33.914 | 1.00 | 13.98 | 6 |
| 565 | N | LEU | A | 71 | 28.373 | 58.542 | 30.225 | 1.00 | 10.83 | 7 |
| 566 | CA | LEU | A | 71 | 29.219 | 58.311 | 29.023 | 1.00 | 11.92 | 6 |
| 567 | C | LEU | A | 71 | 29.585 | 59.691 | 28.439 | 1.00 | 10.49 | 6 |
| 568 | O | LEU | A | 71 | 28.669 | 60.552 | 28.276 | 1.00 | 10.64 | 8 |
| 569 | CB | LEU | A | 71 | 28.342 | 57.617 | 27.923 | 1.00 | 11.13 | 6 |
| 570 | CG | LEU | A | 71 | 27.991 | 56.159 | 28.240 | 1.00 | 11.31 | 6 |
| 571 | CD1 | LEU | A | 71 | 27.073 | 55.665 | 27.096 | 1.00 | 10.98 | 6 |
| 572 | CD2 | LEU | A | 71 | 29.253 | 55.314 | 28.322 | 1.00 | 11.96 | 6 |
| 573 | N | SER | A | 72 | 30.870 | 59.865 | 28.066 | 1.00 | 10.17 | 7 |
| 574 | CA | SER | A | 72 | 31.250 | 60.995 | 27.218 | 1.00 | 9.81 | 6 |
| 575 | C | SER | A | 72 | 30.455 | 60.988 | 25.920 | 1.00 | 11.22 | 6 |
| 576 | O | SER | A | 72 | 29.733 | 60.011 | 25.572 | 1.00 | 10.33 | 8 |
| 577 | CB | SER | A | 72 | 32.773 | 60.898 | 26.944 | 1.00 | 10.62 | 6 |
| 578 | OG | SER | A | 72 | 33.092 | 59.694 | 26.237 | 1.00 | 11.62 | 8 |
| 579 | N | PRO | A | 73 | 30.447 | 62.034 | 25.128 | 1.00 | 11.10 | 7 |
| 580 | CA | PRO | A | 73 | 29.427 | 62.188 | 24.048 | 1.00 | 11.86 | 6 |
| 581 | C | PRO | A | 73 | 29.521 | 61.057 | 23.042 | 1.00 | 13.54 | 6 |
| 582 | O | PRO | A | 73 | 30.653 | 60.649 | 22.674 | 1.00 | 11.75 | 8 |
| 583 | CB | PRO | A | 73 | 29.672 | 63.563 | 23.414 | 1.00 | 10.32 | 6 |
| 584 | CG | PRO | A | 73 | 30.360 | 64.313 | 24.557 | 1.00 | 10.23 | 6 |
| 585 | CD | PRO | A | 73 | 31.228 | 63.286 | 25.358 | 1.00 | 11.09 | 6 |
| 586 | N | VAL | A | 74 | 28.345 | 60.538 | 22.623 | 1.00 | 11.02 | 7 |
| 587 | CA | VAL | A | 74 | 28.351 | 59.338 | 21.794 | 1.00 | 9.14 | 6 |
| 588 | C | VAL | A | 74 | 27.998 | 59.628 | 20.344 | 1.00 | 9.79 | 6 |
| 589 | O | VAL | A | 74 | 28.041 | 58.700 | 19.549 | 1.00 | 10.96 | 8 |
| 590 | CB | VAL | A | 74 | 27.260 | 58.313 | 22.311 | 1.00 | 9.29 | 6 |
| 591 | CG1 | VAL | A | 74 | 27.541 | 57.935 | 23.780 | 1.00 | 11.66 | 6 |
| 592 | CG2 | VAL | A | 74 | 25.882 | 58.894 | 22.161 | 1.00 | 10.26 | 6 |
| 593 | N | LEU | A | 75 | 27.708 | 60.912 | 19.980 | 1.00 | 10.62 | 7 |
| 594 | CA | LEU | A | 75 | 27.182 | 61.136 | 18.619 | 1.00 | 10.48 | 6 |
| 595 | C | LEU | A | 75 | 28.305 | 61.464 | 17.620 | 1.00 | 12.02 | 6 |
| 596 | O | LEU | A | 75 | 29.436 | 61.678 | 18.016 | 1.00 | 11.28 | 8 |
| 597 | CB | LEU | A | 75 | 26.111 | 62.279 | 18.660 | 1.00 | 10.81 | 6 |
| 598 | CG | LEU | A | 75 | 24.952 | 61.966 | 19.634 | 1.00 | 11.49 | 6 |
| 599 | CD1 | LEU | A | 75 | 24.074 | 63.178 | 19.911 | 1.00 | 11.47 | 6 |
| 600 | CD2 | LEU | A | 75 | 24.074 | 60.864 | 18.960 | 1.00 | 11.05 | 6 |
| 601 | N | ASP | A | 76 | 27.958 | 61.296 | 16.347 | 1.00 | 10.11 | 7 |
| 602 | CA | ASP | A | 76 | 29.020 | 61.292 | 15.299 | 1.00 | 9.23 | 6 |
| 603 | C | ASP | A | 76 | 29.821 | 62.605 | 15.351 | 1.00 | 9.60 | 6 |
| 604 | O | ASP | A | 76 | 29.263 | 63.683 | 15.155 | 1.00 | 11.11 | 8 |
| 605 | CB | ASP | A | 76 | 28.264 | 61.153 | 13.979 | 1.00 | 9.89 | 6 |
| 606 | CG | ASP | A | 76 | 29.177 | 61.079 | 12.745 | 1.00 | 12.56 | 6 |
| 607 | OD1 | ASP | A | 76 | 30.380 | 60.856 | 12.895 | 1.00 | 12.97 | 8 |
| 608 | OD2 | ASP | A | 76 | 28.617 | 61.239 | 11.641 | 1.00 | 11.97 | 8 |
| 609 | N | ASN | A | 77 | 31.131 | 62.435 | 15.524 | 1.00 | 9.80 | 7 |
| 610 | CA | ASN | A | 77 | 32.043 | 63.570 | 15.534 | 1.00 | 9.86 | 6 |
| 611 | C | ASN | A | 77 | 32.766 | 63.691 | 14.180 | 1.00 | 10.69 | 6 |
| 612 | O | ASN | A | 77 | 32.797 | 62.759 | 13.385 | 1.00 | 10.51 | 8 |
| 613 | CB | ASN | A | 77 | 33.117 | 63.370 | 16.619 | 1.00 | 10.13 | 6 |
| 614 | CG | ASN | A | 77 | 32.685 | 63.988 | 17.945 | 1.00 | 13.40 | 6 |
| 615 | OD1 | ASN | A | 77 | 33.515 | 64.636 | 18.600 | 1.00 | 10.92 | 8 |
| 616 | ND2 | ASN | A | 77 | 31.412 | 63.908 | 18.341 | 1.00 | 11.73 | 7 |
| 617 | N | LEU | A | 78 | 33.296 | 64.886 | 13.967 | 1.00 | 10.62 | 7 |
| 618 | CA | LEU | A | 78 | 34.240 | 65.195 | 12.866 | 1.00 | 11.24 | 6 |
| 619 | C | LEU | A | 78 | 34.929 | 63.977 | 12.309 | 1.00 | 8.87 | 6 |
| 620 | O | LEU | A | 78 | 35.632 | 63.257 | 13.026 | 1.00 | 12.04 | 8 |
| 621 | CB | LEU | A | 78 | 35.257 | 66.197 | 13.506 | 1.00 | 9.81 | 6 |
| 622 | CG | LEU | A | 78 | 36.289 | 66.679 | 12.399 | 1.00 | 9.30 | 6 |
| 623 | CD1 | LEU | A | 78 | 35.622 | 67.597 | 11.418 | 1.00 | 11.34 | 6 |
| 624 | CD2 | LEU | A | 78 | 37.382 | 67.439 | 13.176 | 1.00 | 13.04 | 6 |

TABLE 1-continued

Atom Coordinates from the Crystal Structure of NOVAMYL

| 625 | N | ASP | A | 79 | 34.801 | 63.867 | 10.945 | 1.00 | 11.36 | 7 |
|---|---|---|---|---|---|---|---|---|---|---|
| 626 | CA | ASP | A | 79 | 35.393 | 62.670 | 10.348 | 1.00 | 9.32 | 6 |
| 627 | C | ASP | A | 79 | 36.754 | 62.947 | 9.688 | 1.00 | 12.70 | 6 |
| 628 | O | ASP | A | 79 | 37.275 | 62.042 | 9.026 | 1.00 | 14.30 | 8 |
| 629 | CB | ASP | A | 79 | 34.468 | 62.189 | 9.168 | 1.00 | 14.19 | 6 |
| 630 | CG | ASP | A | 79 | 33.217 | 61.518 | 9.658 | 1.00 | 15.14 | 6 |
| 631 | OD1 | ASP | A | 79 | 33.208 | 61.150 | 10.841 | 1.00 | 12.50 | 8 |
| 632 | OD2 | ASP | A | 79 | 32.239 | 61.307 | 8.931 | 1.00 | 12.26 | 8 |
| 633 | N | THR | A | 80 | 37.307 | 64.115 | 9.950 | 1.00 | 12.57 | 7 |
| 634 | CA | THR | A | 80 | 38.652 | 64.479 | 9.456 | 1.00 | 14.13 | 6 |
| 635 | C | THR | A | 80 | 39.521 | 64.930 | 10.635 | 1.00 | 13.16 | 6 |
| 636 | O | THR | A | 80 | 39.072 | 64.981 | 11.769 | 1.00 | 12.58 | 8 |
| 637 | CB | THR | A | 80 | 38.583 | 65.712 | 8.534 | 1.00 | 14.19 | 6 |
| 638 | OG1 | THR | A | 80 | 38.265 | 66.927 | 9.264 | 1.00 | 15.46 | 8 |
| 639 | CG2 | THR | A | 80 | 37.593 | 65.645 | 7.372 | 1.00 | 19.78 | 6 |
| 640 | N | LEU | A | 81 | 40.809 | 65.216 | 10.327 | 1.00 | 13.37 | 7 |
| 641 | CA | LEU | A | 81 | 41.651 | 65.864 | 11.341 | 1.00 | 10.22 | 6 |
| 642 | C | LEU | A | 81 | 41.263 | 67.297 | 11.488 | 1.00 | 12.10 | 6 |
| 643 | O | LEU | A | 81 | 40.635 | 67.900 | 10.595 | 1.00 | 12.72 | 8 |
| 644 | CB | LEU | A | 81 | 43.143 | 65.818 | 10.830 | 1.00 | 10.42 | 6 |
| 645 | CG | LEU | A | 81 | 43.643 | 64.345 | 10.809 | 1.00 | 15.27 | 6 |
| 646 | CD1 | LEU | A | 81 | 44.897 | 64.351 | 9.927 | 1.00 | 21.14 | 6 |
| 647 | CD2 | LEU | A | 81 | 44.059 | 63.885 | 12.244 | 1.00 | 14.05 | 6 |
| 648 | N | ALA | A | 82 | 41.647 | 67.888 | 12.629 | 1.00 | 11.74 | 7 |
| 649 | CA | ALA | A | 82 | 41.548 | 69.320 | 12.798 | 1.00 | 13.34 | 6 |
| 650 | C | ALA | A | 82 | 42.941 | 69.801 | 13.202 | 1.00 | 12.91 | 6 |
| 651 | O | ALA | A | 82 | 43.208 | 70.247 | 14.316 | 1.00 | 11.11 | 8 |
| 652 | CB | ALA | A | 82 | 40.566 | 69.586 | 13.989 | 1.00 | 14.40 | 6 |
| 653 | N | GLY | A | 83 | 43.811 | 69.835 | 12.180 | 1.00 | 12.89 | 7 |
| 654 | CA | GLY | A | 83 | 45.245 | 70.145 | 12.484 | 1.00 | 11.52 | 6 |
| 655 | C | GLY | A | 83 | 45.960 | 68.860 | 12.923 | 1.00 | 12.02 | 6 |
| 656 | O | GLY | A | 83 | 45.405 | 67.737 | 13.060 | 1.00 | 11.47 | 8 |
| 657 | N | THR | A | 84 | 47.262 | 68.987 | 13.230 | 1.00 | 12.31 | 7 |
| 658 | CA | THR | A | 84 | 48.160 | 67.879 | 13.444 | 1.00 | 11.91 | 6 |
| 659 | C | THR | A | 84 | 47.716 | 66.883 | 14.496 | 1.00 | 10.74 | 6 |
| 660 | O | THR | A | 84 | 47.554 | 67.213 | 15.687 | 1.00 | 11.33 | 8 |
| 661 | CB | THR | A | 84 | 49.570 | 68.477 | 13.888 | 1.00 | 10.32 | 6 |
| 662 | OG1 | THR | A | 84 | 49.942 | 69.432 | 12.873 | 1.00 | 12.17 | 8 |
| 663 | CG2 | THR | A | 84 | 50.533 | 67.298 | 14.074 | 1.00 | 13.58 | 6 |
| 664 | N | ASP | A | 85 | 47.462 | 65.652 | 14.019 | 1.00 | 12.06 | 7 |
| 665 | CA | ASP | A | 85 | 47.117 | 64.552 | 14.933 | 1.00 | 10.80 | 6 |
| 666 | C | ASP | A | 85 | 45.981 | 64.902 | 15.894 | 1.00 | 12.31 | 6 |
| 667 | O | ASP | A | 85 | 45.986 | 64.416 | 17.030 | 1.00 | 13.43 | 8 |
| 668 | CB | ASP | A | 85 | 48.356 | 64.077 | 15.747 | 1.00 | 14.44 | 6 |
| 669 | CG | ASP | A | 85 | 49.500 | 63.600 | 14.831 | 1.00 | 22.31 | 6 |
| 670 | OD1 | ASP | A | 85 | 49.284 | 63.065 | 13.744 | 1.00 | 14.91 | 8 |
| 671 | OD2 | ASP | A | 85 | 50.645 | 63.782 | 15.275 | 1.00 | 23.25 | 8 |
| 672 | N | ASN | A | 86 | 45.024 | 65.712 | 15.418 | 1.00 | 10.53 | 7 |
| 673 | CA | ASN | A | 86 | 44.024 | 66.196 | 16.401 | 1.00 | 10.12 | 6 |
| 674 | C | ASN | A | 86 | 42.644 | 65.784 | 15.880 | 1.00 | 9.75 | 6 |
| 675 | O | ASN | A | 86 | 42.241 | 66.073 | 14.747 | 1.00 | 12.30 | 8 |
| 676 | CB | ASN | A | 86 | 44.190 | 67.732 | 16.468 | 1.00 | 11.52 | 6 |
| 677 | CG | ASN | A | 86 | 43.470 | 68.295 | 17.677 | 1.00 | 13.68 | 6 |
| 678 | OD1 | ASN | A | 86 | 42.743 | 67.535 | 18.341 | 1.00 | 14.08 | 8 |
| 679 | ND2 | ASN | A | 86 | 43.644 | 69.546 | 18.063 | 1.00 | 15.21 | 7 |
| 680 | N | THR | A | 87 | 41.877 | 65.099 | 16.705 | 1.00 | 10.11 | 7 |
| 681 | CA | THR | A | 87 | 40.619 | 64.459 | 16.251 | 1.00 | 10.70 | 6 |
| 682 | C | THR | A | 87 | 39.525 | 64.643 | 17.317 | 1.00 | 11.84 | 6 |
| 683 | O | THR | A | 87 | 39.764 | 65.021 | 18.471 | 1.00 | 11.11 | 8 |
| 684 | CB | THR | A | 87 | 40.745 | 62.924 | 16.124 | 1.00 | 12.30 | 6 |
| 685 | OG1 | THR | A | 87 | 40.840 | 62.298 | 17.444 | 1.00 | 11.34 | 8 |
| 686 | CG2 | THR | A | 87 | 41.961 | 62.467 | 15.375 | 1.00 | 11.19 | 6 |
| 687 | N | GLY | A | 88 | 38.307 | 64.357 | 16.903 | 1.00 | 11.28 | 7 |
| 688 | CA | GLY | A | 88 | 37.184 | 64.329 | 17.887 | 1.00 | 10.27 | 6 |
| 689 | C | GLY | A | 88 | 37.107 | 63.063 | 18.721 | 1.00 | 10.54 | 6 |
| 690 | O | GLY | A | 88 | 35.954 | 62.712 | 19.121 | 1.00 | 10.21 | 8 |
| 691 | N | TYR | A | 89 | 38.196 | 62.404 | 19.087 | 1.00 | 10.33 | 7 |
| 692 | CA | TYR | A | 89 | 38.134 | 61.241 | 19.955 | 1.00 | 10.06 | 6 |
| 693 | C | TYR | A | 89 | 37.314 | 61.476 | 21.204 | 1.00 | 11.70 | 6 |
| 694 | O | TYR | A | 89 | 36.760 | 60.489 | 21.732 | 1.00 | 11.42 | 8 |
| 695 | CB | TYR | A | 89 | 39.564 | 60.769 | 20.316 | 1.00 | 9.10 | 6 |
| 696 | CG | TYR | A | 89 | 40.152 | 61.653 | 21.412 | 1.00 | 11.07 | 6 |
| 697 | CD1 | TYR | A | 89 | 40.732 | 62.857 | 21.106 | 1.00 | 10.61 | 6 |
| 698 | CD2 | TYR | A | 89 | 40.058 | 61.256 | 22.750 | 1.00 | 9.12 | 6 |
| 699 | CE1 | TYR | A | 89 | 41.243 | 63.688 | 22.115 | 1.00 | 9.21 | 6 |
| 700 | CE2 | TYR | A | 89 | 40.505 | 62.054 | 23.777 | 1.00 | 11.90 | 6 |
| 701 | CZ | TYR | A | 89 | 41.098 | 63.267 | 23.443 | 1.00 | 10.92 | 6 |

TABLE 1-continued

Atom Coordinates from the Crystal Structure of NOVAMYL

| 702 | OH | TYR | A | 89 | 41.593 | 64.126 | 24.411 | 1.00 | 10.82 | 8 |
|---|---|---|---|---|---|---|---|---|---|---|
| 703 | N | HIS | A | 90 | 37.283 | 62.703 | 21.748 | 1.00 | 10.85 | 7 |
| 704 | CA | HIS | A | 90 | 36.623 | 62.983 | 23.011 | 1.00 | 9.54 | 6 |
| 705 | C | HIS | A | 90 | 35.095 | 63.104 | 22.837 | 1.00 | 7.69 | 6 |
| 706 | O | HIS | A | 90 | 34.392 | 63.040 | 23.856 | 1.00 | 9.02 | 8 |
| 707 | CB | HIS | A | 90 | 37.178 | 64.338 | 23.555 | 1.00 | 10.73 | 6 |
| 708 | CG | HIS | A | 90 | 37.294 | 65.403 | 22.507 | 1.00 | 11.48 | 6 |
| 709 | ND1 | HIS | A | 90 | 36.210 | 66.035 | 21.926 | 1.00 | 9.73 | 7 |
| 710 | CD2 | HIS | A | 90 | 38.405 | 65.898 | 21.906 | 1.00 | 8.93 | 6 |
| 711 | CE1 | HIS | A | 90 | 36.686 | 66.903 | 21.010 | 1.00 | 10.94 | 6 |
| 712 | NE2 | HIS | A | 90 | 37.988 | 66.862 | 20.995 | 1.00 | 10.18 | 7 |
| 713 | N | GLY | A | 91 | 34.616 | 63.356 | 21.629 | 1.00 | 9.66 | 7 |
| 714 | CA | GLY | A | 91 | 33.143 | 63.393 | 21.404 | 1.00 | 9.79 | 6 |
| 715 | C | GLY | A | 91 | 32.505 | 64.768 | 21.395 | 1.00 | 10.82 | 6 |
| 716 | O | GLY | A | 91 | 31.287 | 64.916 | 21.102 | 1.00 | 11.09 | 8 |
| 717 | N | TYR | A | 92 | 33.288 | 65.840 | 21.633 | 1.00 | 10.15 | 7 |
| 718 | CA | TYR | A | 92 | 32.653 | 67.152 | 21.753 | 1.00 | 10.44 | 6 |
| 719 | C | TYR | A | 92 | 32.556 | 67.935 | 20.459 | 1.00 | 8.85 | 6 |
| 720 | O | TYR | A | 92 | 32.132 | 69.141 | 20.520 | 1.00 | 9.64 | 8 |
| 721 | CB | TYR | A | 92 | 33.461 | 67.977 | 22.837 | 1.00 | 10.08 | 6 |
| 722 | CG | TYR | A | 92 | 33.217 | 67.385 | 24.219 | 1.00 | 10.98 | 6 |
| 723 | CD1 | TYR | A | 92 | 32.091 | 67.719 | 24.974 | 1.00 | 10.25 | 6 |
| 724 | CD2 | TYR | A | 92 | 34.112 | 66.472 | 24.730 | 1.00 | 10.46 | 6 |
| 725 | CE1 | TYR | A | 92 | 31.905 | 67.143 | 26.247 | 1.00 | 10.96 | 6 |
| 726 | CE2 | TYR | A | 92 | 33.932 | 65.888 | 25.983 | 1.00 | 14.14 | 6 |
| 727 | CZ | TYR | A | 92 | 32.829 | 66.237 | 26.715 | 1.00 | 11.56 | 6 |
| 728 | OH | TYR | A | 92 | 32.648 | 65.665 | 27.970 | 1.00 | 12.31 | 8 |
| 729 | N | TRP | A | 93 | 32.968 | 67.343 | 19.345 | 1.00 | 10.19 | 7 |
| 730 | CA | TRP | A | 93 | 32.914 | 68.040 | 18.039 | 1.00 | 11.73 | 6 |
| 731 | C | TRP | A | 93 | 31.949 | 67.307 | 17.103 | 1.00 | 9.84 | 6 |
| 732 | O | TRP | A | 93 | 32.336 | 66.443 | 16.294 | 1.00 | 10.83 | 8 |
| 733 | CB | TRP | A | 93 | 34.322 | 68.024 | 17.415 | 1.00 | 12.42 | 6 |
| 734 | CG | TRP | A | 93 | 35.359 | 68.775 | 18.253 | 1.00 | 11.75 | 6 |
| 735 | CD1 | TRP | A | 93 | 35.181 | 69.659 | 19.258 | 1.00 | 12.58 | 6 |
| 736 | CD2 | TRP | A | 93 | 36.786 | 68.657 | 18.020 | 1.00 | 11.96 | 6 |
| 737 | NE1 | TRP | A | 93 | 36.448 | 70.120 | 19.694 | 1.00 | 13.60 | 7 |
| 738 | CE2 | TRP | A | 93 | 37.397 | 69.501 | 18.932 | 1.00 | 14.78 | 6 |
| 739 | CE3 | TRP | A | 93 | 37.559 | 67.884 | 17.130 | 1.00 | 13.74 | 6 |
| 740 | CZ2 | TRP | A | 93 | 38.808 | 69.626 | 19.040 | 1.00 | 15.96 | 6 |
| 741 | CZ3 | TRP | A | 93 | 38.959 | 68.021 | 17.209 | 1.00 | 10.95 | 6 |
| 742 | CH2 | TRP | A | 93 | 39.526 | 68.880 | 18.171 | 1.00 | 9.91 | 6 |
| 743 | N | THR | A | 94 | 30.669 | 67.534 | 17.237 | 1.00 | 10.45 | 7 |
| 744 | CA | THR | A | 94 | 29.603 | 66.690 | 16.661 | 1.00 | 9.91 | 6 |
| 745 | C | THR | A | 94 | 29.244 | 67.242 | 15.270 | 1.00 | 11.32 | 6 |
| 746 | O | THR | A | 94 | 28.854 | 68.415 | 15.074 | 1.00 | 11.48 | 8 |
| 747 | CB | THR | A | 94 | 28.302 | 66.837 | 17.495 | 1.00 | 9.85 | 6 |
| 748 | OG1 | THR | A | 94 | 28.643 | 66.563 | 18.891 | 1.00 | 11.49 | 8 |
| 749 | CG2 | THR | A | 94 | 27.263 | 65.739 | 17.079 | 1.00 | 11.23 | 6 |
| 750 | N | ARG | A | 95 | 29.315 | 66.299 | 14.292 | 1.00 | 10.33 | 7 |
| 751 | CA | ARG | A | 95 | 28.819 | 66.623 | 12.945 | 1.00 | 11.51 | 6 |
| 752 | C | ARG | A | 95 | 27.382 | 66.123 | 12.703 | 1.00 | 13.19 | 6 |
| 753 | O | ARG | A | 95 | 26.834 | 66.523 | 11.700 | 1.00 | 12.00 | 8 |
| 754 | CB | ARG | A | 95 | 29.766 | 65.999 | 11.920 | 1.00 | 12.95 | 6 |
| 755 | CG | ARG | A | 95 | 29.739 | 64.437 | 11.900 | 1.00 | 9.03 | 6 |
| 756 | CD | ARG | A | 95 | 30.894 | 63.964 | 11.008 | 1.00 | 12.99 | 6 |
| 757 | NE | ARG | A | 95 | 30.917 | 64.346 | 9.584 | 1.00 | 13.10 | 7 |
| 758 | CZ | ARG | A | 95 | 30.216 | 63.680 | 8.633 | 1.00 | 13.74 | 6 |
| 759 | NH1 | ARG | A | 95 | 29.307 | 62.746 | 8.918 | 1.00 | 13.30 | 7 |
| 760 | NH2 | ARG | A | 95 | 30.477 | 64.026 | 7.380 | 1.00 | 15.12 | 7 |
| 761 | N | ASP | A | 96 | 26.880 | 65.176 | 13.503 | 1.00 | 11.44 | 7 |
| 762 | CA | ASP | A | 96 | 25.536 | 64.640 | 13.218 | 1.00 | 11.75 | 6 |
| 763 | C | ASP | A | 96 | 24.977 | 64.166 | 14.570 | 1.00 | 10.37 | 6 |
| 764 | O | ASP | A | 96 | 25.448 | 63.154 | 15.091 | 1.00 | 12.67 | 8 |
| 765 | CB | ASP | A | 96 | 25.622 | 63.467 | 12.217 | 1.00 | 10.69 | 6 |
| 766 | CG | ASP | A | 96 | 24.238 | 63.012 | 11.732 | 1.00 | 14.77 | 6 |
| 767 | OD1 | ASP | A | 96 | 23.229 | 63.251 | 12.412 | 1.00 | 11.10 | 8 |
| 768 | OD2 | ASP | A | 96 | 24.218 | 62.343 | 10.651 | 1.00 | 15.82 | 8 |
| 769 | N | PHE | A | 97 | 24.007 | 64.989 | 15.033 | 1.00 | 9.84 | 7 |
| 770 | CA | PHE | A | 97 | 23.482 | 64.615 | 16.377 | 1.00 | 10.91 | 6 |
| 771 | C | PHE | A | 97 | 22.504 | 63.426 | 16.336 | 1.00 | 13.19 | 6 |
| 772 | O | PHE | A | 97 | 21.945 | 63.125 | 17.373 | 1.00 | 13.15 | 8 |
| 773 | CB | PHE | A | 97 | 22.818 | 65.844 | 16.982 | 1.00 | 10.58 | 6 |
| 774 | CG | PHE | A | 97 | 23.783 | 66.935 | 17.422 | 1.00 | 14.29 | 6 |
| 775 | CD1 | PHE | A | 97 | 24.438 | 67.807 | 16.532 | 1.00 | 13.03 | 6 |
| 776 | CD2 | PHE | A | 97 | 23.979 | 67.062 | 18.799 | 1.00 | 13.39 | 6 |
| 777 | CE1 | PHE | A | 97 | 25.321 | 68.786 | 17.067 | 1.00 | 11.37 | 6 |
| 778 | CE2 | PHE | A | 97 | 24.780 | 68.073 | 19.296 | 1.00 | 9.92 | 6 |

TABLE 1-continued

Atom Coordinates from the Crystal Structure of NOVAMYL

| | | | | | | | | | | |
|---|---|---|---|---|---|---|---|---|---|---|
| 779 | CZ | PHE | A | 97 | 25.489 | 68.930 | 18.467 | 1.00 | 9.67 | 6 |
| 780 | N | LYS | A | 98 | 22.220 | 62.889 | 15.152 | 1.00 | 11.59 | 7 |
| 781 | CA | LYS | A | 98 | 21.249 | 61.786 | 15.105 | 1.00 | 10.99 | 6 |
| 782 | C | LYS | A | 98 | 21.893 | 60.424 | 14.982 | 1.00 | 13.58 | 6 |
| 783 | O | LYS | A | 98 | 21.136 | 59.437 | 14.991 | 1.00 | 14.00 | 8 |
| 784 | CB | LYS | A | 98 | 20.375 | 61.999 | 13.835 | 1.00 | 10.72 | 6 |
| 785 | CG | LYS | A | 98 | 19.595 | 63.337 | 13.915 | 1.00 | 11.63 | 6 |
| 786 | CD | LYS | A | 98 | 18.627 | 63.408 | 15.091 | 1.00 | 16.21 | 6 |
| 787 | CE | LYS | A | 98 | 17.808 | 64.707 | 15.036 | 1.00 | 16.03 | 6 |
| 788 | NZ | LYS | A | 98 | 16.876 | 64.605 | 13.828 | 1.00 | 15.90 | 7 |
| 789 | N | GLN | A | 99 | 23.233 | 60.336 | 14.853 | 1.00 | 9.90 | 7 |
| 790 | CA | GLN | A | 99 | 23.900 | 59.079 | 14.613 | 1.00 | 11.53 | 6 |
| 791 | C | GLN | A | 99 | 25.042 | 58.866 | 15.625 | 1.00 | 12.11 | 6 |
| 792 | O | GLN | A | 99 | 25.610 | 59.842 | 16.118 | 1.00 | 13.41 | 8 |
| 793 | CB | GLN | A | 99 | 24.657 | 58.975 | 13.225 | 1.00 | 13.31 | 6 |
| 794 | CG | GLN | A | 99 | 23.575 | 58.962 | 12.137 | 1.00 | 20.81 | 6 |
| 795 | CD | GLN | A | 99 | 24.005 | 57.830 | 11.187 | 1.00 | 47.61 | 6 |
| 796 | OE1 | GLN | A | 99 | 23.966 | 56.639 | 11.540 | 1.00 | 38.44 | 8 |
| 797 | NE2 | GLN | A | 99 | 24.435 | 58.330 | 10.031 | 1.00 | 51.18 | 7 |
| 798 | N | ILE | A | 100 | 25.139 | 57.581 | 16.003 | 1.00 | 11.97 | 7 |
| 799 | CA | ILE | A | 100 | 26.265 | 57.291 | 16.916 | 1.00 | 9.69 | 6 |
| 800 | C | ILE | A | 100 | 27.586 | 57.395 | 16.160 | 1.00 | 11.29 | 6 |
| 801 | O | ILE | A | 100 | 27.744 | 57.032 | 14.974 | 1.00 | 13.58 | 8 |
| 802 | CB | ILE | A | 100 | 26.080 | 55.834 | 17.385 | 1.00 | 11.20 | 6 |
| 803 | CG1 | ILE | A | 100 | 24.767 | 55.651 | 18.197 | 1.00 | 13.05 | 6 |
| 804 | CG2 | ILE | A | 100 | 27.229 | 55.284 | 18.240 | 1.00 | 10.14 | 6 |
| 805 | CD1 | ILE | A | 100 | 24.692 | 56.541 | 19.489 | 1.00 | 13.82 | 6 |
| 806 | N | GLU | A | 101 | 28.607 | 57.861 | 16.898 | 1.00 | 11.66 | 7 |
| 807 | CA | GLU | A | 101 | 29.968 | 57.886 | 16.322 | 1.00 | 11.19 | 6 |
| 808 | C | GLU | A | 101 | 30.443 | 56.478 | 15.956 | 1.00 | 11.88 | 6 |
| 809 | O | GLU | A | 101 | 30.430 | 55.545 | 16.758 | 1.00 | 12.38 | 8 |
| 810 | CB | GLU | A | 101 | 30.918 | 58.478 | 17.400 | 1.00 | 11.53 | 6 |
| 811 | CG | GLU | A | 101 | 32.427 | 58.256 | 17.126 | 1.00 | 10.12 | 6 |
| 812 | CD | GLU | A | 101 | 32.796 | 58.791 | 15.715 | 1.00 | 10.82 | 6 |
| 813 | OE1 | GLU | A | 101 | 32.328 | 59.903 | 15.389 | 1.00 | 11.74 | 8 |
| 814 | OE2 | GLU | A | 101 | 33.577 | 58.059 | 15.099 | 1.00 | 12.29 | 8 |
| 815 | N | GLU | A | 102 | 30.874 | 56.411 | 14.662 | 1.00 | 12.51 | 7 |
| 816 | CA | GLU | A | 102 | 31.192 | 55.081 | 14.116 | 1.00 | 11.29 | 6 |
| 817 | C | GLU | A | 102 | 32.387 | 54.443 | 14.766 | 1.00 | 12.50 | 6 |
| 818 | O | GLU | A | 102 | 32.460 | 53.176 | 14.813 | 1.00 | 11.57 | 8 |
| 819 | CB | GLU | A | 102 | 31.402 | 55.182 | 12.553 | 1.00 | 11.80 | 6 |
| 820 | CG | GLU | A | 102 | 32.656 | 55.982 | 12.107 | 1.00 | 12.52 | 6 |
| 821 | CD | GLU | A | 102 | 32.465 | 57.475 | 12.181 | 1.00 | 12.69 | 6 |
| 822 | OE1 | GLU | A | 102 | 31.368 | 58.018 | 12.431 | 1.00 | 14.09 | 8 |
| 823 | OE2 | GLU | A | 102 | 33.493 | 58.174 | 11.930 | 1.00 | 15.94 | 8 |
| 824 | N | HIS | A | 103 | 33.391 | 55.145 | 15.324 | 1.00 | 9.73 | 7 |
| 825 | CA | HIS | A | 103 | 34.429 | 54.494 | 16.120 | 1.00 | 9.99 | 6 |
| 826 | C | HIS | A | 103 | 33.862 | 53.874 | 17.376 | 1.00 | 11.88 | 6 |
| 827 | O | HIS | A | 103 | 34.531 | 52.943 | 17.864 | 1.00 | 12.86 | 8 |
| 828 | CB | HIS | A | 103 | 35.470 | 55.578 | 16.584 | 1.00 | 12.93 | 6 |
| 829 | CG | HIS | A | 103 | 36.364 | 56.049 | 15.481 | 1.00 | 11.28 | 6 |
| 830 | ND1 | HIS | A | 103 | 36.015 | 57.085 | 14.639 | 1.00 | 12.54 | 7 |
| 831 | CD2 | HIS | A | 103 | 37.595 | 55.655 | 15.123 | 1.00 | 14.43 | 6 |
| 832 | CE1 | HIS | A | 103 | 37.021 | 57.288 | 13.749 | 1.00 | 13.58 | 6 |
| 833 | NE2 | HIS | A | 103 | 37.965 | 56.434 | 14.054 | 1.00 | 13.95 | 7 |
| 834 | N | PHE | A | 104 | 32.662 | 54.253 | 17.819 | 1.00 | 9.60 | 7 |
| 835 | CA | PHE | A | 104 | 32.171 | 53.727 | 19.103 | 1.00 | 10.30 | 6 |
| 836 | C | PHE | A | 104 | 31.116 | 52.625 | 18.924 | 1.00 | 13.76 | 6 |
| 837 | O | PHE | A | 104 | 30.969 | 51.851 | 19.894 | 1.00 | 13.23 | 8 |
| 838 | CB | PHE | A | 104 | 31.583 | 54.855 | 19.953 | 1.00 | 10.00 | 6 |
| 839 | CG | PHE | A | 104 | 32.587 | 55.933 | 20.330 | 1.00 | 13.59 | 6 |
| 840 | CD1 | PHE | A | 104 | 33.954 | 55.782 | 20.204 | 1.00 | 11.92 | 6 |
| 841 | CD2 | PHE | A | 104 | 32.082 | 57.130 | 20.834 | 1.00 | 13.49 | 6 |
| 842 | CE1 | PHE | A | 104 | 34.854 | 56.802 | 20.561 | 1.00 | 12.32 | 6 |
| 843 | CE2 | PHE | A | 104 | 32.981 | 58.161 | 21.193 | 1.00 | 11.48 | 6 |
| 844 | CZ | PHE | A | 104 | 34.365 | 58.005 | 21.053 | 1.00 | 13.46 | 6 |
| 845 | N | GLY | A | 105 | 30.491 | 52.584 | 17.759 | 1.00 | 14.42 | 7 |
| 846 | CA | GLY | A | 105 | 29.462 | 51.533 | 17.546 | 1.00 | 16.52 | 6 |
| 847 | C | GLY | A | 105 | 28.362 | 52.143 | 16.670 | 1.00 | 17.63 | 6 |
| 848 | O | GLY | A | 105 | 28.624 | 53.104 | 15.927 | 1.00 | 14.43 | 8 |
| 849 | N | ASN | A | 106 | 27.169 | 51.558 | 16.664 | 1.00 | 14.15 | 7 |
| 850 | CA | ASN | A | 106 | 26.017 | 52.150 | 15.960 | 1.00 | 11.27 | 6 |
| 851 | C | ASN | A | 106 | 24.864 | 52.149 | 16.958 | 1.00 | 13.27 | 6 |
| 852 | O | ASN | A | 106 | 25.081 | 51.890 | 18.174 | 1.00 | 13.00 | 8 |
| 853 | CB | ASN | A | 106 | 25.756 | 51.332 | 14.677 | 1.00 | 13.55 | 6 |
| 854 | CG | ASN | A | 106 | 25.465 | 49.876 | 14.958 | 1.00 | 18.28 | 6 |
| 855 | OD1 | ASN | A | 106 | 25.093 | 49.459 | 16.033 | 1.00 | 17.05 | 8 |

TABLE 1-continued

Atom Coordinates from the Crystal Structure of NOVAMYL

| | | | | | | | | | | |
|---|---|---|---|---|---|---|---|---|---|---|
| 856 | ND2 | ASN | A | 106 | 25.576 | 49.021 | 13.910 | 1.00 | 22.96 | 7 |
| 857 | N | TRP | A | 107 | 23.668 | 52.508 | 16.525 | 1.00 | 12.62 | 7 |
| 858 | CA | TRP | A | 107 | 22.554 | 52.559 | 17.465 | 1.00 | 13.67 | 6 |
| 859 | C | TRP | A | 107 | 22.296 | 51.203 | 18.121 | 1.00 | 14.10 | 6 |
| 860 | O | TRP | A | 107 | 21.827 | 51.121 | 19.274 | 1.00 | 14.66 | 8 |
| 861 | CB | TRP | A | 107 | 21.268 | 53.087 | 16.802 | 1.00 | 14.53 | 6 |
| 862 | CG | TRP | A | 107 | 21.256 | 54.576 | 16.836 | 1.00 | 16.29 | 6 |
| 863 | CD1 | TRP | A | 107 | 21.351 | 55.357 | 15.696 | 1.00 | 17.56 | 6 |
| 864 | CD2 | TRP | A | 107 | 21.131 | 55.454 | 17.949 | 1.00 | 15.71 | 6 |
| 865 | NE1 | TRP | A | 107 | 21.279 | 56.677 | 16.088 | 1.00 | 16.73 | 7 |
| 866 | CE2 | TRP | A | 107 | 21.186 | 56.759 | 17.451 | 1.00 | 14.24 | 6 |
| 867 | CE2 | TRP | A | 107 | 20.995 | 55.256 | 19.345 | 1.00 | 13.30 | 6 |
| 868 | CZ2 | TRP | A | 107 | 21.082 | 57.915 | 18.240 | 1.00 | 14.74 | 6 |
| 869 | CZ3 | TRP | A | 107 | 20.919 | 56.410 | 20.131 | 1.00 | 16.80 | 6 |
| 870 | CH2 | TRP | A | 107 | 20.927 | 57.717 | 19.596 | 1.00 | 13.00 | 6 |
| 871 | N | THR | A | 108 | 22.439 | 50.097 | 17.351 | 1.00 | 14.29 | 7 |
| 872 | CA | THR | A | 108 | 22.316 | 48.792 | 18.020 | 1.00 | 14.34 | 6 |
| 873 | C | THR | A | 108 | 23.305 | 48.617 | 19.154 | 1.00 | 16.18 | 6 |
| 874 | O | THR | A | 108 | 22.945 | 48.095 | 20.224 | 1.00 | 14.57 | 8 |
| 875 | CB | THR | A | 108 | 22.508 | 47.669 | 16.969 | 1.00 | 16.38 | 6 |
| 876 | OG1 | THR | A | 108 | 21.473 | 47.841 | 16.005 | 1.00 | 18.39 | 8 |
| 877 | CG2 | THR | A | 108 | 22.386 | 46.276 | 17.600 | 1.00 | 20.41 | 6 |
| 878 | N | THR | A | 109 | 24.581 | 49.043 | 18.959 | 1.00 | 12.36 | 7 |
| 879 | CA | THR | A | 109 | 25.556 | 48.897 | 20.029 | 1.00 | 13.35 | 6 |
| 880 | C | THR | A | 109 | 25.149 | 49.732 | 21.248 | 1.00 | 12.11 | 6 |
| 881 | O | THR | A | 109 | 25.318 | 49.282 | 22.382 | 1.00 | 12.78 | 8 |
| 882 | CB | THR | A | 109 | 26.960 | 49.404 | 19.545 | 1.00 | 13.85 | 6 |
| 883 | OG1 | THR | A | 109 | 27.201 | 49.021 | 18.155 | 1.00 | 14.22 | 8 |
| 884 | CG2 | THR | A | 109 | 28.048 | 48.783 | 20.429 | 1.00 | 15.14 | 6 |
| 885 | N | PHE | A | 110 | 24.673 | 50.945 | 20.982 | 1.00 | 12.96 | 7 |
| 886 | CA | PHE | A | 110 | 24.247 | 51.800 | 22.126 | 1.00 | 12.43 | 6 |
| 887 | C | PHE | A | 110 | 23.058 | 51.137 | 22.830 | 1.00 | 13.48 | 6 |
| 888 | O | PHE | A | 110 | 23.061 | 51.036 | 24.060 | 1.00 | 12.36 | 8 |
| 889 | CB | PHE | A | 110 | 23.823 | 53.160 | 21.525 | 1.00 | 14.28 | 6 |
| 890 | CG | PHE | A | 110 | 23.320 | 54.128 | 22.611 | 1.00 | 15.08 | 6 |
| 891 | CD1 | PHE | A | 110 | 24.190 | 54.941 | 23.252 | 1.00 | 13.29 | 6 |
| 892 | CD2 | PHE | A | 110 | 21.975 | 54.202 | 22.913 | 1.00 | 14.29 | 6 |
| 893 | CE1 | PHE | A | 110 | 23.764 | 55.850 | 24.247 | 1.00 | 13.20 | 6 |
| 894 | CE2 | PHE | A | 110 | 21.487 | 55.055 | 23.876 | 1.00 | 12.89 | 6 |
| 895 | CZ | PHE | A | 110 | 22.377 | 55.898 | 24.558 | 1.00 | 13.20 | 6 |
| 896 | N | ASP | A | 111 | 22.056 | 50.645 | 22.065 | 1.00 | 13.15 | 7 |
| 897 | CA | ASP | A | 111 | 20.916 | 49.993 | 22.755 | 1.00 | 12.63 | 6 |
| 898 | C | ASP | A | 111 | 21.337 | 48.770 | 23.517 | 1.00 | 14.08 | 6 |
| 899 | O | ASP | A | 111 | 20.917 | 48.606 | 24.698 | 1.00 | 14.41 | 8 |
| 900 | CB | ASP | A | 111 | 19.966 | 49.513 | 21.610 | 1.00 | 13.40 | 6 |
| 901 | CG | ASP | A | 111 | 19.224 | 50.603 | 20.937 | 1.00 | 18.96 | 6 |
| 902 | OD1 | ASP | A | 111 | 19.343 | 51.768 | 21.305 | 1.00 | 17.72 | 8 |
| 903 | OD2 | ASP | A | 111 | 18.498 | 50.291 | 19.945 | 1.00 | 18.78 | 8 |
| 904 | N | THR | A | 112 | 22.284 | 48.006 | 22.997 | 1.00 | 13.38 | 7 |
| 905 | CA | THR | A | 112 | 22.756 | 46.828 | 23.718 | 1.00 | 14.87 | 6 |
| 906 | C | THR | A | 112 | 23.450 | 47.184 | 25.017 | 1.00 | 14.48 | 6 |
| 907 | O | THR | A | 112 | 23.224 | 46.583 | 26.069 | 1.00 | 15.04 | 8 |
| 908 | CB | THR | A | 112 | 23.680 | 45.966 | 22.829 | 1.00 | 15.99 | 6 |
| 909 | OG1 | THR | A | 112 | 22.844 | 45.644 | 21.711 | 1.00 | 16.67 | 8 |
| 910 | CG2 | THR | A | 112 | 24.006 | 44.662 | 23.576 | 1.00 | 18.86 | 6 |
| 911 | N | LEU | A | 113 | 24.321 | 48.221 | 24.968 | 1.00 | 11.85 | 7 |
| 912 | CA | LEU | A | 113 | 24.982 | 48.631 | 26.219 | 1.00 | 12.44 | 6 |
| 913 | C | LEU | A | 113 | 23.992 | 49.138 | 27.242 | 1.00 | 12.26 | 6 |
| 914 | O | LEU | A | 113 | 24.057 | 48.793 | 28.403 | 1.00 | 12.86 | 8 |
| 915 | CB | LEU | A | 113 | 25.988 | 49.772 | 25.811 | 1.00 | 10.14 | 6 |
| 916 | CG | LEU | A | 113 | 26.404 | 50.629 | 27.037 | 1.00 | 13.26 | 6 |
| 917 | CD1 | LEU | A | 113 | 27.184 | 49.772 | 28.040 | 1.00 | 13.59 | 6 |
| 918 | CD2 | LEU | A | 113 | 27.295 | 51.825 | 26.664 | 1.00 | 12.75 | 6 |
| 919 | N | VAL | A | 114 | 23.020 | 49.971 | 26.823 | 1.00 | 11.82 | 7 |
| 920 | CA | VAL | A | 114 | 22.073 | 50.545 | 27.762 | 1.00 | 12.84 | 6 |
| 921 | C | VAL | A | 114 | 21.215 | 49.449 | 28.384 | 1.00 | 13.48 | 6 |
| 922 | O | VAL | A | 114 | 20.973 | 49.402 | 29.577 | 1.00 | 13.54 | 8 |
| 923 | CB | VAL | A | 114 | 21.264 | 51.680 | 27.090 | 1.00 | 13.71 | 6 |
| 924 | CG1 | VAL | A | 114 | 20.144 | 52.091 | 28.032 | 1.00 | 18.18 | 6 |
| 925 | CG2 | VAL | A | 114 | 22.209 | 52.885 | 26.815 | 1.00 | 15.06 | 6 |
| 926 | N | ASN | A | 115 | 20.760 | 48.534 | 27.512 | 1.00 | 13.50 | 7 |
| 927 | CA | ASN | A | 115 | 19.912 | 47.430 | 28.013 | 1.00 | 11.60 | 6 |
| 928 | C | ASN | A | 115 | 20.678 | 46.553 | 28.961 | 1.00 | 12.99 | 6 |
| 929 | O | ASN | A | 115 | 20.121 | 46.160 | 29.987 | 1.00 | 15.11 | 8 |
| 930 | CB | ASN | A | 115 | 19.372 | 46.637 | 26.820 | 1.00 | 15.99 | 6 |
| 931 | CG | ASN | A | 115 | 18.200 | 47.261 | 26.118 | 1.00 | 22.41 | 6 |
| 932 | OD1 | ASN | A | 115 | 18.061 | 47.131 | 24.868 | 1.00 | 26.38 | 8 |

TABLE 1-continued

Atom Coordinates from the Crystal Structure of NOVAMYL

| | | | | | | | | | |
|---|---|---|---|---|---|---|---|---|---|
| 933 | ND2 | ASN | A | 115 | 17.304 | 47.937 | 26.823 | 1.00 | 22.30 | 7 |
| 934 | N | ASP | A | 116 | 21.940 | 46.229 | 28.669 | 1.00 | 12.94 | 7 |
| 935 | CA | ASP | A | 116 | 22.731 | 45.386 | 29.561 | 1.00 | 12.20 | 6 |
| 936 | C | ASP | A | 116 | 23.087 | 46.144 | 30.835 | 1.00 | 12.69 | 6 |
| 937 | O | ASP | A | 116 | 23.070 | 45.584 | 31.933 | 1.00 | 12.40 | 8 |
| 938 | CB | ASP | A | 116 | 23.989 | 44.814 | 28.887 | 1.00 | 13.19 | 6 |
| 939 | CG | ASP | A | 116 | 23.648 | 43.698 | 27.896 | 1.00 | 19.33 | 6 |
| 940 | OD1 | ASP | A | 116 | 22.461 | 43.487 | 27.582 | 1.00 | 23.80 | 8 |
| 941 | OD2 | ASP | A | 116 | 24.583 | 42.967 | 27.460 | 1.00 | 22.90 | 8 |
| 942 | N | ALA | A | 117 | 23.342 | 47.453 | 30.753 | 1.00 | 12.25 | 7 |
| 943 | CA | ALA | A | 117 | 23.561 | 48.208 | 32.005 | 1.00 | 12.13 | 6 |
| 944 | C | ALA | A | 117 | 22.314 | 48.146 | 32.878 | 1.00 | 10.66 | 6 |
| 945 | O | ALA | A | 117 | 22.425 | 47.887 | 34.083 | 1.00 | 12.92 | 8 |
| 946 | CB | ALA | A | 117 | 23.877 | 49.692 | 31.625 | 1.00 | 13.05 | 6 |
| 947 | N | HIS | A | 118 | 21.149 | 48.403 | 32.291 | 1.00 | 12.02 | 7 |
| 948 | CA | HIS | A | 118 | 19.948 | 48.334 | 33.131 | 1.00 | 10.66 | 6 |
| 949 | C | HIS | A | 118 | 19.727 | 46.929 | 33.683 | 1.00 | 12.65 | 6 |
| 950 | O | HIS | A | 118 | 19.267 | 46.870 | 34.838 | 1.00 | 14.87 | 8 |
| 951 | CB | HIS | A | 118 | 18.714 | 48.622 | 32.200 | 1.00 | 10.79 | 6 |
| 952 | CG | HIS | A | 118 | 18.691 | 50.088 | 31.789 | 1.00 | 11.37 | 6 |
| 953 | ND1 | HIS | A | 118 | 17.881 | 50.557 | 30.773 | 1.00 | 14.86 | 7 |
| 954 | CD2 | HIS | A | 118 | 19.340 | 51.157 | 32.359 | 1.00 | 13.69 | 6 |
| 955 | CE1 | HIS | A | 118 | 18.020 | 51.897 | 30.708 | 1.00 | 15.91 | 6 |
| 956 | NE2 | HIS | A | 118 | 18.912 | 52.260 | 31.644 | 1.00 | 11.99 | 7 |
| 957 | N | GLN | A | 119 | 20.028 | 45.871 | 32.935 | 1.00 | 11.93 | 7 |
| 958 | CA | GLN | A | 119 | 19.843 | 44.545 | 33.592 | 1.00 | 12.22 | 6 |
| 959 | C | GLN | A | 119 | 20.770 | 44.412 | 34.781 | 1.00 | 15.02 | 6 |
| 960 | O | GLN | A | 119 | 20.519 | 43.615 | 35.694 | 1.00 | 15.33 | 8 |
| 961 | CB | GLN | A | 119 | 20.340 | 43.445 | 32.620 | 1.00 | 16.20 | 6 |
| 962 | CG | GLN | A | 119 | 19.327 | 43.169 | 31.521 | 1.00 | 17.09 | 6 |
| 963 | CD | GLN | A | 119 | 20.028 | 41.969 | 30.765 | 1.00 | 21.33 | 6 |
| 964 | OE1 | GLN | A | 119 | 20.575 | 41.051 | 31.363 | 1.00 | 29.71 | 8 |
| 965 | NE2 | GLN | A | 119 | 19.985 | 42.085 | 29.522 | 1.00 | 20.93 | 7 |
| 966 | N | ASN | A | 120 | 21.939 | 45.127 | 34.806 | 1.00 | 15.33 | 7 |
| 967 | CA | ASN | A | 120 | 22.853 | 45.072 | 35.932 | 1.00 | 16.39 | 6 |
| 968 | C | ASN | A | 120 | 22.541 | 46.148 | 36.970 | 1.00 | 14.25 | 6 |
| 969 | O | ASN | A | 120 | 23.358 | 46.337 | 37.876 | 1.00 | 15.65 | 8 |
| 970 | CB | ASN | A | 120 | 24.337 | 45.189 | 35.481 | 1.00 | 12.26 | 6 |
| 971 | CG | ASN | A | 120 | 24.753 | 43.901 | 34.799 | 1.00 | 20.80 | 6 |
| 972 | OD1 | ASN | A | 120 | 24.778 | 43.805 | 33.576 | 1.00 | 23.34 | 8 |
| 973 | ND1 | ASN | A | 120 | 25.076 | 42.912 | 35.627 | 1.00 | 18.29 | 7 |
| 974 | N | GLY | A | 121 | 21.398 | 46.801 | 36.951 | 1.00 | 13.35 | 7 |
| 975 | CA | GLY | A | 121 | 20.994 | 47.834 | 37.885 | 1.00 | 16.91 | 6 |
| 976 | C | GLY | A | 121 | 21.840 | 49.129 | 37.772 | 1.00 | 13.99 | 6 |
| 977 | O | GLY | A | 121 | 21.866 | 49.890 | 38.747 | 1.00 | 15.35 | 8 |
| 978 | N | ILE | A | 122 | 22.262 | 49.397 | 36.527 | 1.00 | 12.67 | 7 |
| 979 | CA | ILE | A | 122 | 23.128 | 50.569 | 36.322 | 1.00 | 13.01 | 6 |
| 980 | C | ILE | A | 122 | 22.464 | 51.454 | 35.289 | 1.00 | 13.96 | 6 |
| 981 | O | ILE | A | 122 | 22.075 | 50.945 | 34.227 | 1.00 | 12.86 | 8 |
| 982 | CB | ILE | A | 122 | 24.556 | 50.129 | 35.886 | 1.00 | 12.06 | 6 |
| 983 | CG1 | ILE | A | 122 | 25.320 | 49.424 | 37.040 | 1.00 | 15.35 | 6 |
| 984 | CG2 | ILE | A | 122 | 25.415 | 51.348 | 35.506 | 1.00 | 13.36 | 6 |
| 985 | CD1 | ILE | A | 122 | 26.569 | 48.709 | 36.465 | 1.00 | 15.31 | 6 |
| 986 | N | LYS | A | 123 | 22.344 | 52.752 | 35.609 | 1.00 | 11.45 | 7 |
| 987 | CA | LYS | A | 123 | 21.767 | 53.718 | 34.652 | 1.00 | 11.74 | 6 |
| 988 | C | LYS | A | 123 | 22.865 | 54.362 | 33.786 | 1.00 | 11.74 | 6 |
| 989 | O | LYS | A | 123 | 24.052 | 54.129 | 34.057 | 1.00 | 11.17 | 8 |
| 990 | CB | LYS | A | 123 | 21.051 | 54.811 | 35.457 | 1.00 | 11.34 | 6 |
| 991 | CG | LYS | A | 123 | 19.832 | 54.205 | 36.163 | 1.00 | 12.23 | 6 |
| 992 | CD | LYS | A | 123 | 18.994 | 55.310 | 36.815 | 1.00 | 16.30 | 6 |
| 993 | CE | LYS | A | 123 | 19.601 | 56.014 | 38.025 | 1.00 | 21.38 | 6 |
| 994 | NZ | LYS | A | 123 | 20.133 | 55.054 | 39.000 | 1.00 | 25.83 | 7 |
| 995 | N | VAL | A | 124 | 22.372 | 54.936 | 32.656 | 1.00 | 9.54 | 7 |
| 996 | CA | VAL | A | 124 | 23.343 | 55.533 | 31.740 | 1.00 | 9.53 | 6 |
| 997 | C | VAL | A | 124 | 22.856 | 56.954 | 31.460 | 1.00 | 12.31 | 6 |
| 998 | O | VAL | A | 124 | 21.723 | 57.168 | 30.990 | 1.00 | 12.23 | 8 |
| 999 | CB | VAL | A | 124 | 23.372 | 54.748 | 30.408 | 1.00 | 12.71 | 6 |
| 1000 | CG1 | VAL | A | 124 | 24.327 | 55.480 | 29.398 | 1.00 | 12.93 | 6 |
| 1001 | CG2 | VAL | A | 124 | 23.875 | 53.313 | 30.661 | 1.00 | 11.85 | 6 |
| 1002 | N | ILE | A | 125 | 23.726 | 57.937 | 31.756 | 1.00 | 10.85 | 7 |
| 1003 | CA | ILE | A | 125 | 23.419 | 59.311 | 31.352 | 1.00 | 10.22 | 6 |
| 1004 | C | ILE | A | 125 | 24.430 | 59.676 | 30.232 | 1.00 | 11.59 | 6 |
| 1005 | O | ILE | A | 125 | 25.549 | 59.113 | 30.220 | 1.00 | 12.11 | 8 |
| 1006 | CB | ILE | A | 125 | 23.403 | 60.385 | 32.474 | 1.00 | 10.25 | 6 |
| 1007 | CG1 | ILE | A | 125 | 24.811 | 60.531 | 33.089 | 1.00 | 13.12 | 6 |
| 1008 | CG2 | ILE | A | 125 | 22.304 | 60.035 | 33.484 | 1.00 | 9.99 | 6 |
| 1009 | CD1 | ILE | A | 125 | 24.770 | 61.746 | 34.084 | 1.00 | 17.03 | 6 |

TABLE 1-continued

Atom Coordinates from the Crystal Structure of NOVAMYL

| 1010 | N | VAL | A | 126 | 23.971 | 60.450 | 29.252 | 1.00 | 9.62 | 7 |
|---|---|---|---|---|---|---|---|---|---|---|
| 1011 | CA | VAL | A | 126 | 24.864 | 60.725 | 28.102 | 1.00 | 10.33 | 6 |
| 1012 | C | VAL | A | 126 | 25.247 | 62.207 | 28.081 | 1.00 | 12.61 | 6 |
| 1013 | O | VAL | A | 126 | 24.413 | 63.080 | 28.254 | 1.00 | 11.41 | 8 |
| 1014 | CB | VAL | A | 126 | 24.039 | 60.356 | 26.823 | 1.00 | 11.44 | 6 |
| 1015 | CG1 | VAL | A | 126 | 24.892 | 60.704 | 25.575 | 1.00 | 12.92 | 6 |
| 1016 | CG2 | VAL | A | 126 | 23.704 | 58.883 | 26.856 | 1.00 | 11.52 | 6 |
| 1017 | N | ASP | A | 127 | 26.535 | 62.445 | 27.771 | 1.00 | 8.46 | 7 |
| 1018 | CA | ASP | A | 127 | 27.011 | 63.870 | 27.661 | 1.00 | 9.67 | 6 |
| 1019 | C | ASP | A | 127 | 26.509 | 64.374 | 26.283 | 1.00 | 10.71 | 6 |
| 1020 | O | ASP | A | 127 | 26.837 | 63.710 | 25.279 | 1.00 | 11.36 | 8 |
| 1021 | CB | ASP | A | 127 | 28.552 | 63.719 | 27.694 | 1.00 | 9.91 | 6 |
| 1022 | CG | ASP | A | 127 | 29.305 | 64.951 | 28.135 | 1.00 | 11.94 | 6 |
| 1023 | OD1 | ASP | A | 127 | 28.822 | 66.041 | 27.747 | 1.00 | 11.17 | 8 |
| 1024 | OD2 | ASP | A | 127 | 30.335 | 64.880 | 28.865 | 1.00 | 10.63 | 8 |
| 1025 | N | PHE | A | 128 | 25.802 | 65.484 | 26.325 | 1.00 | 8.41 | 7 |
| 1026 | CA | PHE | A | 128 | 25.134 | 65.952 | 25.077 | 1.00 | 9.40 | 6 |
| 1027 | C | PHE | A | 128 | 25.609 | 67.394 | 24.887 | 1.00 | 9.48 | 6 |
| 1028 | O | PHE | A | 128 | 25.752 | 68.163 | 25.858 | 1.00 | 10.67 | 8 |
| 1029 | CB | PHE | A | 128 | 23.609 | 66.006 | 25.437 | 1.00 | 9.59 | 6 |
| 1030 | CG | PHE | A | 128 | 22.760 | 66.405 | 24.223 | 1.00 | 8.93 | 6 |
| 1031 | CD1 | PHE | A | 128 | 22.719 | 65.597 | 23.104 | 1.00 | 12.26 | 6 |
| 1032 | CD2 | PHE | A | 128 | 22.095 | 67.627 | 24.315 | 1.00 | 10.12 | 6 |
| 1033 | CE1 | PHE | A | 128 | 21.907 | 66.014 | 22.027 | 1.00 | 12.04 | 6 |
| 1034 | CE2 | PHE | A | 128 | 21.325 | 67.993 | 23.183 | 1.00 | 10.05 | 6 |
| 1035 | CZ | PHE | A | 128 | 21.229 | 67.218 | 22.070 | 1.00 | 10.20 | 6 |
| 1036 | N | VAL | A | 129 | 25.985 | 67.736 | 23.647 | 1.00 | 8.13 | 7 |
| 1037 | CA | VAL | A | 129 | 26.851 | 68.932 | 23.398 | 1.00 | 9.78 | 6 |
| 1038 | C | VAL | A | 129 | 26.171 | 69.845 | 22.412 | 1.00 | 9.18 | 6 |
| 1039 | O | VAL | A | 129 | 26.494 | 70.026 | 21.210 | 1.00 | 10.74 | 8 |
| 1040 | CB | VAL | A | 129 | 28.178 | 68.381 | 22.804 | 1.00 | 11.28 | 6 |
| 1041 | CG1 | VAL | A | 129 | 29.206 | 69.539 | 22.719 | 1.00 | 12.02 | 6 |
| 1042 | CG2 | VAL | A | 129 | 28.829 | 67.246 | 23.590 | 1.00 | 10.62 | 6 |
| 1043 | N | PRO | A | 130 | 25.165 | 70.638 | 22.855 | 1.00 | 10.64 | 7 |
| 1044 | CA | PRO | A | 130 | 24.341 | 71.474 | 21.986 | 1.00 | 10.69 | 6 |
| 1045 | C | PRO | A | 130 | 24.946 | 72.802 | 21.588 | 1.00 | 11.36 | 6 |
| 1046 | O | PRO | A | 130 | 24.336 | 73.565 | 20.814 | 1.00 | 11.49 | 8 |
| 1047 | CB | PRO | A | 130 | 22.983 | 71.673 | 22.735 | 1.00 | 10.77 | 6 |
| 1048 | CG | PRO | A | 130 | 23.480 | 71.602 | 24.189 | 1.00 | 12.02 | 6 |
| 1049 | CD | PRO | A | 130 | 24.593 | 70.514 | 24.205 | 1.00 | 11.44 | 6 |
| 1050 | N | ASN | A | 131 | 26.107 | 73.181 | 22.144 | 1.00 | 9.48 | 7 |
| 1051 | CA | ASN | A | 131 | 26.687 | 74.481 | 21.859 | 1.00 | 10.43 | 6 |
| 1052 | C | ASN | A | 131 | 27.244 | 74.637 | 20.438 | 1.00 | 11.66 | 6 |
| 1053 | O | ASN | A | 131 | 27.256 | 75.724 | 19.881 | 1.00 | 11.65 | 8 |
| 1054 | CB | ASN | A | 131 | 27.756 | 74.902 | 22.877 | 1.00 | 10.94 | 6 |
| 1055 | CG | ASN | A | 131 | 28.233 | 76.316 | 22.592 | 1.00 | 10.72 | 6 |
| 1056 | OD1 | ASN | A | 131 | 27.396 | 77.205 | 22.783 | 1.00 | 10.02 | 8 |
| 1057 | ND2 | ASN | A | 131 | 29.516 | 76.447 | 22.224 | 1.00 | 10.08 | 7 |
| 1058 | N | HIS | A | 132 | 27.676 | 73.513 | 19.855 | 1.00 | 10.71 | 7 |
| 1059 | CA | HIS | A | 132 | 28.476 | 73.726 | 18.632 | 1.00 | 9.32 | 6 |
| 1060 | C | HIS | A | 132 | 28.552 | 72.441 | 17.845 | 1.00 | 9.83 | 6 |
| 1061 | O | HIS | A | 132 | 28.256 | 71.362 | 18.361 | 1.00 | 12.46 | 8 |
| 1062 | CB | HIS | A | 132 | 29.896 | 74.227 | 19.005 | 1.00 | 11.52 | 6 |
| 1063 | CG | HIS | A | 132 | 30.560 | 73.394 | 20.080 | 1.00 | 10.70 | 6 |
| 1064 | ND1 | HIS | A | 132 | 30.616 | 73.869 | 21.372 | 1.00 | 11.00 | 7 |
| 1065 | CD2 | HIS | A | 132 | 31.084 | 72.152 | 20.032 | 1.00 | 9.99 | 6 |
| 1066 | CE1 | HIS | A | 132 | 31.189 | 72.945 | 22.154 | 1.00 | 12.39 | 6 |
| 1067 | NE2 | HIS | A | 132 | 31.445 | 71.929 | 21.368 | 1.00 | 10.00 | 7 |
| 1068 | N | SER | A | 133 | 28.999 | 72.608 | 16.584 | 1.00 | 10.23 | 7 |
| 1069 | CA | SER | A | 133 | 29.365 | 71.428 | 15.787 | 1.00 | 10.30 | 6 |
| 1070 | C | SER | A | 133 | 30.876 | 71.239 | 15.861 | 1.00 | 11.64 | 6 |
| 1071 | O | SER | A | 133 | 31.319 | 70.652 | 16.863 | 1.00 | 11.94 | 8 |
| 1072 | CB | SER | A | 133 | 28.807 | 71.514 | 14.344 | 1.00 | 10.65 | 6 |
| 1073 | OG | SER | A | 133 | 29.342 | 72.683 | 13.700 | 1.00 | 11.57 | 8 |
| 1074 | N | THR | A | 134 | 31.611 | 71.535 | 14.805 | 1.00 | 11.30 | 7 |
| 1075 | CA | THR | A | 134 | 33.034 | 71.082 | 14.740 | 1.00 | 10.51 | 6 |
| 1076 | C | THR | A | 134 | 33.959 | 72.251 | 14.424 | 1.00 | 8.56 | 6 |
| 1077 | O | THR | A | 134 | 33.553 | 73.376 | 14.121 | 1.00 | 10.40 | 8 |
| 1078 | CB | THR | A | 134 | 33.119 | 70.005 | 13.630 | 1.00 | 9.65 | 6 |
| 1079 | OG1 | THR | A | 134 | 32.559 | 70.596 | 12.429 | 1.00 | 11.51 | 8 |
| 1080 | CG2 | THR | A | 134 | 32.295 | 68.752 | 13.956 | 1.00 | 11.00 | 6 |
| 1081 | N | PRO | A | 135 | 35.256 | 71.959 | 14.489 | 1.00 | 10.51 | 7 |
| 1082 | CA | PRO | A | 135 | 36.320 | 72.955 | 14.289 | 1.00 | 12.33 | 6 |
| 1083 | C | PRO | A | 135 | 36.264 | 73.606 | 12.899 | 1.00 | 12.27 | 6 |
| 1084 | O | PRO | A | 135 | 36.014 | 72.968 | 11.868 | 1.00 | 13.19 | 8 |
| 1085 | CB | PRO | A | 135 | 37.627 | 72.145 | 14.405 | 1.00 | 11.11 | 6 |
| 1086 | CG | PRO | A | 135 | 37.241 | 71.129 | 15.486 | 1.00 | 11.56 | 6 |

TABLE 1-continued

Atom Coordinates from the Crystal Structure of NOVAMYL

| 1087 | CD  | PRO | A | 135 | 35.809 | 70.746 | 15.111 | 1.00 | 11.98 | 6 |
|------|-----|-----|---|-----|--------|--------|--------|------|-------|---|
| 1088 | N   | PHE | A | 136 | 36.500 | 74.966 | 12.885 | 1.00 | 10.88 | 7 |
| 1089 | CA  | PHE | A | 136 | 36.606 | 75.628 | 11.597 | 1.00 | 11.37 | 6 |
| 1090 | C   | PHE | A | 136 | 37.536 | 76.830 | 11.718 | 1.00 | 11.99 | 6 |
| 1091 | O   | PHE | A | 136 | 37.856 | 77.248 | 12.827 | 1.00 | 12.95 | 8 |
| 1092 | CB  | PHE | A | 136 | 35.176 | 76.074 | 11.125 | 1.00 | 13.36 | 6 |
| 1093 | CG  | PHE | A | 136 | 34.690 | 77.341 | 11.793 | 1.00 | 15.31 | 6 |
| 1094 | CD1 | PHE | A | 136 | 34.201 | 77.311 | 13.100 | 1.00 | 12.18 | 6 |
| 1095 | CD2 | PHE | A | 136 | 34.801 | 78.565 | 11.134 | 1.00 | 13.24 | 6 |
| 1096 | CE1 | PHE | A | 136 | 33.813 | 78.477 | 13.738 | 1.00 | 13.44 | 6 |
| 1097 | CE2 | PHE | A | 136 | 34.451 | 79.741 | 11.779 | 1.00 | 12.17 | 6 |
| 1098 | CZ  | PHE | A | 136 | 33.903 | 79.708 | 13.087 | 1.00 | 15.41 | 6 |
| 1099 | N   | LYS | A | 137 | 38.037 | 77.258 | 10.547 | 1.00 | 11.70 | 7 |
| 1100 | CA  | LYS | A | 137 | 38.710 | 78.567 | 10.479 | 1.00 | 10.33 | 6 |
| 1101 | C   | LYS | A | 137 | 37.859 | 79.484 | 9.618  | 1.00 | 13.10 | 6 |
| 1102 | O   | LYS | A | 137 | 37.493 | 79.111 | 8.490  | 1.00 | 12.91 | 8 |
| 1103 | CB  | LYS | A | 137 | 40.060 | 78.360 | 9.724  | 1.00 | 17.76 | 6 |
| 1104 | CG  | LYS | A | 137 | 41.153 | 77.554 | 10.411 | 1.00 | 19.69 | 6 |
| 1105 | CD  | LYS | A | 137 | 41.439 | 78.049 | 11.810 | 1.00 | 22.72 | 6 |
| 1106 | CE  | LYS | A | 137 | 42.145 | 79.366 | 12.006 | 1.00 | 31.41 | 6 |
| 1107 | NZ  | LYS | A | 137 | 43.212 | 79.771 | 11.035 | 1.00 | 25.39 | 7 |
| 1108 | N   | ALA | A | 138 | 37.657 | 80.688 | 10.158 | 1.00 | 12.09 | 7 |
| 1109 | CA  | ALA | A | 138 | 36.683 | 81.510 | 9.375  | 1.00 | 12.57 | 6 |
| 1110 | C   | ALA | A | 138 | 37.267 | 81.873 | 8.017  | 1.00 | 14.60 | 6 |
| 1111 | O   | ALA | A | 138 | 36.469 | 82.176 | 7.094  | 1.00 | 14.01 | 8 |
| 1112 | CB  | ALA | A | 138 | 36.410 | 82.806 | 10.148 | 1.00 | 15.45 | 6 |
| 1113 | N   | ASN | A | 139 | 38.597 | 81.986 | 7.900  | 1.00 | 13.25 | 7 |
| 1114 | CA  | ASN | A | 139 | 39.165 | 82.359 | 6.608  | 1.00 | 14.41 | 6 |
| 1115 | C   | ASN | A | 139 | 39.444 | 81.212 | 5.682  | 1.00 | 14.25 | 6 |
| 1116 | O   | ASN | A | 139 | 40.047 | 81.349 | 4.562  | 1.00 | 14.82 | 8 |
| 1117 | CB  | ASN | A | 139 | 40.443 | 83.188 | 6.852  | 1.00 | 16.78 | 6 |
| 1118 | CG  | ASN | A | 139 | 41.666 | 82.292 | 7.083  | 1.00 | 22.27 | 6 |
| 1119 | OD1 | ASN | A | 139 | 41.484 | 81.167 | 7.486  | 1.00 | 25.66 | 8 |
| 1120 | ND2 | ASN | A | 139 | 42.853 | 82.762 | 6.773  | 1.00 | 21.53 | 7 |
| 1121 | N   | ASP | A | 140 | 39.150 | 79.955 | 6.052  | 1.00 | 14.76 | 7 |
| 1122 | CA  | ASP | A | 140 | 39.433 | 78.835 | 5.203  | 1.00 | 13.60 | 6 |
| 1123 | C   | ASP | A | 140 | 38.470 | 77.674 | 5.337  | 1.00 | 16.09 | 6 |
| 1124 | O   | ASP | A | 140 | 38.607 | 76.905 | 6.339  | 1.00 | 13.95 | 8 |
| 1125 | CB  | ASP | A | 140 | 40.885 | 78.382 | 5.557  | 1.00 | 12.14 | 6 |
| 1126 | CG  | ASP | A | 140 | 41.331 | 77.260 | 4.643  | 1.00 | 16.87 | 6 |
| 1127 | OD1 | ASP | A | 140 | 40.616 | 76.705 | 3.810  | 1.00 | 17.82 | 8 |
| 1128 | OD2 | ASP | A | 140 | 42.569 | 76.954 | 4.814  | 1.00 | 25.09 | 8 |
| 1129 | N   | SER | A | 141 | 37.529 | 77.555 | 4.414  | 1.00 | 15.21 | 7 |
| 1130 | CA  | SER | A | 141 | 36.508 | 76.520 | 4.501  | 1.00 | 16.63 | 6 |
| 1131 | C   | SER | A | 141 | 37.048 | 75.092 | 4.285  | 1.00 | 17.44 | 6 |
| 1132 | O   | SER | A | 141 | 36.349 | 74.129 | 4.607  | 1.00 | 18.28 | 8 |
| 1133 | CB  | SER | A | 141 | 35.372 | 76.746 | 3.493  | 1.00 | 19.52 | 6 |
| 1134 | OG  | SER | A | 141 | 35.867 | 76.579 | 2.144  | 1.00 | 16.38 | 8 |
| 1135 | N   | THR | A | 142 | 38.302 | 74.958 | 3.839  | 1.00 | 14.08 | 7 |
| 1136 | CA  | THR | A | 142 | 38.889 | 73.615 | 3.649  | 1.00 | 15.63 | 6 |
| 1137 | C   | THR | A | 142 | 39.445 | 73.036 | 4.933  | 1.00 | 16.91 | 6 |
| 1138 | O   | THR | A | 142 | 39.798 | 71.840 | 4.961  | 1.00 | 15.67 | 8 |
| 1139 | CB  | THR | A | 142 | 40.105 | 73.658 | 2.622  | 1.00 | 16.69 | 6 |
| 1140 | OG1 | THR | A | 142 | 41.261 | 74.288 | 3.211  | 1.00 | 18.35 | 8 |
| 1141 | CG2 | THR | A | 142 | 39.653 | 74.352 | 1.368  | 1.00 | 25.03 | 6 |
| 1142 | N   | PHE | A | 143 | 39.533 | 73.874 | 6.007  | 1.00 | 15.48 | 7 |
| 1143 | CA  | PHE | A | 143 | 40.027 | 73.314 | 7.285  | 1.00 | 12.99 | 6 |
| 1144 | C   | PHE | A | 143 | 38.953 | 72.384 | 7.908  | 1.00 | 14.57 | 6 |
| 1145 | O   | PHE | A | 143 | 37.807 | 72.837 | 8.026  | 1.00 | 12.49 | 8 |
| 1146 | CB  | PHE | A | 143 | 40.412 | 74.481 | 8.238  | 1.00 | 14.72 | 6 |
| 1147 | CG  | PHE | A | 143 | 40.905 | 73.939 | 9.546  | 1.00 | 13.33 | 6 |
| 1148 | CD1 | PHE | A | 143 | 42.192 | 73.454 | 9.669  | 1.00 | 14.66 | 6 |
| 1149 | CD2 | PHE | A | 143 | 40.054 | 73.908 | 10.679 | 1.00 | 10.60 | 6 |
| 1150 | CE1 | PHE | A | 143 | 42.677 | 72.946 | 10.878 | 1.00 | 14.87 | 6 |
| 1151 | CE2 | PHE | A | 143 | 40.556 | 73.381 | 11.849 | 1.00 | 12.09 | 6 |
| 1152 | CZ  | PHE | A | 143 | 41.842 | 72.912 | 11.975 | 1.00 | 16.30 | 6 |
| 1153 | N   | ALA | A | 144 | 39.342 | 71.174 | 8.264  | 1.00 | 14.83 | 7 |
| 1154 | CA  | ALA | A | 144 | 38.380 | 70.250 | 8.884  | 1.00 | 14.49 | 6 |
| 1155 | C   | ALA | A | 144 | 37.165 | 70.136 | 7.976  | 1.00 | 14.94 | 6 |
| 1156 | O   | ALA | A | 144 | 37.369 | 69.878 | 6.784  | 1.00 | 13.97 | 8 |
| 1157 | CB  | ALA | A | 144 | 37.990 | 70.683 | 10.323 | 1.00 | 12.28 | 6 |
| 1158 | N   | GLU | A | 145 | 35.942 | 70.135 | 8.506  | 1.00 | 11.43 | 7 |
| 1159 | CA  | GLU | A | 145 | 34.744 | 70.061 | 7.645  | 1.00 | 10.19 | 6 |
| 1160 | C   | GLU | A | 145 | 34.063 | 71.386 | 7.520  | 1.00 | 10.66 | 6 |
| 1161 | O   | GLU | A | 145 | 32.824 | 71.513 | 7.266  | 1.00 | 11.84 | 8 |
| 1162 | CB  | GLU | A | 145 | 33.771 | 68.943 | 8.180  | 1.00 | 11.91 | 6 |
| 1163 | CG  | GLU | A | 145 | 34.408 | 67.577 | 8.042  | 1.00 | 11.68 | 6 |

TABLE 1-continued

Atom Coordinates from the Crystal Structure of NOVAMYL

| 1164 | CD  | GLU | A | 145 | 33.591 | 66.467 | 8.697  | 1.00 | 15.77 | 6 |
|------|-----|-----|---|-----|--------|--------|--------|------|-------|---|
| 1165 | OE1 | GLU | A | 145 | 32.530 | 66.660 | 9.208  | 1.00 | 20.95 | 8 |
| 1166 | OE2 | GLU | A | 145 | 34.122 | 65.351 | 8.743  | 1.00 | 21.22 | 8 |
| 1167 | N   | GLY | A | 146 | 34.677 | 72.533 | 7.898  | 1.00 | 12.55 | 7 |
| 1168 | CA  | GLY | A | 146 | 34.021 | 73.826 | 7.783  | 1.00 | 12.03 | 6 |
| 1169 | C   | GLY | A | 146 | 32.799 | 73.976 | 8.739  | 1.00 | 15.18 | 6 |
| 1170 | O   | GLY | A | 146 | 32.025 | 74.880 | 8.511  | 1.00 | 13.95 | 8 |
| 1171 | N   | GLY | A | 147 | 32.774 | 73.157 | 9.790  | 1.00 | 12.57 | 7 |
| 1172 | CA  | GLY | A | 147 | 31.639 | 73.265 | 10.703 | 1.00 | 12.28 | 6 |
| 1173 | C   | GLY | A | 147 | 30.439 | 72.415 | 10.267 | 1.00 | 14.09 | 6 |
| 1174 | O   | GLY | A | 147 | 29.372 | 72.644 | 10.903 | 1.00 | 11.87 | 8 |
| 1175 | N   | ALA | A | 148 | 30.552 | 71.583 | 9.258  | 1.00 | 11.40 | 7 |
| 1176 | CA  | ALA | A | 148 | 29.343 | 70.942 | 8.707  | 1.00 | 13.48 | 6 |
| 1177 | C   | ALA | A | 148 | 28.495 | 70.132 | 9.729  | 1.00 | 11.58 | 6 |
| 1178 | O   | ALA | A | 148 | 29.025 | 69.390 | 10.557 | 1.00 | 12.14 | 8 |
| 1179 | CB  | ALA | A | 148 | 29.861 | 69.927 | 7.660  | 1.00 | 14.52 | 6 |
| 1180 | N   | LEU | A | 149 | 27.188 | 70.305 | 9.543  | 1.00 | 12.19 | 7 |
| 1181 | CA  | LEU | A | 149 | 26.192 | 69.594 | 10.365 | 1.00 | 10.39 | 6 |
| 1182 | C   | LEU | A | 149 | 25.298 | 68.798 | 9.407  | 1.00 | 10.91 | 6 |
| 1183 | O   | LEU | A | 149 | 24.907 | 69.311 | 8.313  | 1.00 | 14.52 | 8 |
| 1184 | CB  | LEU | A | 149 | 25.345 | 70.684 | 11.028 | 1.00 | 10.56 | 6 |
| 1185 | CG  | LEU | A | 149 | 24.344 | 70.222 | 12.098 | 1.00 | 14.34 | 6 |
| 1186 | CD1 | LEU | A | 149 | 25.067 | 69.618 | 13.294 | 1.00 | 16.21 | 6 |
| 1187 | CD2 | LEU | A | 149 | 23.436 | 71.409 | 12.447 | 1.00 | 15.60 | 6 |
| 1188 | N   | TYR | A | 150 | 25.047 | 67.560 | 9.836  | 1.00 | 12.69 | 7 |
| 1189 | CA  | TYR | A | 150 | 24.178 | 66.675 | 9.057  | 1.00 | 11.91 | 6 |
| 1190 | C   | TYR | A | 150 | 23.007 | 66.234 | 9.957  | 1.00 | 13.54 | 6 |
| 1191 | O   | TYR | A | 150 | 23.116 | 66.203 | 11.188 | 1.00 | 12.53 | 8 |
| 1192 | CB  | TYR | A | 150 | 24.945 | 65.392 | 8.671  | 1.00 | 12.62 | 6 |
| 1193 | CG  | TYR | A | 150 | 26.104 | 65.699 | 7.694  | 1.00 | 10.80 | 6 |
| 1194 | CD1 | TYR | A | 150 | 27.275 | 66.240 | 8.185  | 1.00 | 13.28 | 6 |
| 1195 | CD2 | TYR | A | 150 | 25.983 | 65.330 | 6.359  | 1.00 | 14.10 | 6 |
| 1196 | CE1 | TYR | A | 150 | 28.295 | 66.545 | 7.273  | 1.00 | 14.81 | 6 |
| 1197 | CE2 | TYR | A | 150 | 27.004 | 65.609 | 5.479  | 1.00 | 17.28 | 6 |
| 1198 | CZ  | TYR | A | 150 | 28.139 | 66.206 | 5.959  | 1.00 | 17.89 | 6 |
| 1199 | OH  | TYR | A | 150 | 29.227 | 66.444 | 5.082  | 1.00 | 18.31 | 8 |
| 1200 | N   | ASN | A | 151 | 21.932 | 65.787 | 9.288  | 1.00 | 11.59 | 7 |
| 1201 | CA  | ASN | A | 151 | 20.774 | 65.261 | 10.048 | 1.00 | 13.13 | 6 |
| 1202 | C   | ASN | A | 151 | 20.582 | 63.801 | 9.659  | 1.00 | 14.46 | 6 |
| 1203 | O   | ASN | A | 151 | 20.020 | 63.527 | 8.595  | 1.00 | 15.41 | 8 |
| 1204 | CB  | ASN | A | 151 | 19.542 | 66.068 | 9.633  | 1.00 | 12.78 | 6 |
| 1205 | CG  | ASN | A | 151 | 18.280 | 65.607 | 10.386 | 1.00 | 15.85 | 6 |
| 1206 | OD1 | ASN | A | 151 | 18.376 | 65.084 | 11.460 | 1.00 | 14.91 | 8 |
| 1207 | ND2 | ASN | A | 151 | 17.115 | 65.851 | 9.790  | 1.00 | 23.13 | 7 |
| 1208 | N   | ASN | A | 152 | 21.153 | 62.881 | 10.455 | 1.00 | 11.88 | 7 |
| 1209 | CA  | ASN | A | 152 | 21.160 | 61.460 | 10.056 | 1.00 | 12.91 | 6 |
| 1210 | C   | ASN | A | 152 | 21.628 | 61.265 | 8.619  | 1.00 | 17.10 | 6 |
| 1211 | O   | ASN | A | 152 | 21.059 | 60.495 | 7.804  | 1.00 | 18.15 | 8 |
| 1212 | CB  | ASN | A | 152 | 19.763 | 60.894 | 10.305 | 1.00 | 15.18 | 6 |
| 1213 | CG  | ASN | A | 152 | 19.772 | 59.363 | 10.289 | 1.00 | 28.25 | 6 |
| 1214 | OD1 | ASN | A | 152 | 20.803 | 58.741 | 10.579 | 1.00 | 25.62 | 8 |
| 1215 | ND2 | ASN | A | 152 | 18.647 | 58.722 | 9.925  | 1.00 | 26.09 | 7 |
| 1216 | N   | GLY | A | 153 | 22.797 | 61.857 | 8.344  | 1.00 | 11.86 | 7 |
| 1217 | CA  | GLY | A | 153 | 23.494 | 61.698 | 7.061  | 1.00 | 15.63 | 6 |
| 1218 | C   | GLY | A | 153 | 23.096 | 62.727 | 6.007  | 1.00 | 17.70 | 6 |
| 1219 | O   | GLY | A | 153 | 23.819 | 62.836 | 4.994  | 1.00 | 16.41 | 8 |
| 1220 | N   | THR | A | 154 | 21.975 | 63.414 | 6.209  | 1.00 | 13.77 | 7 |
| 1221 | CA  | THR | A | 154 | 21.535 | 64.406 | 5.220  | 1.00 | 14.28 | 6 |
| 1222 | C   | THR | A | 154 | 22.181 | 65.781 | 5.538  | 1.00 | 14.24 | 6 |
| 1223 | O   | THR | A | 154 | 22.048 | 66.264 | 6.650  | 1.00 | 15.31 | 8 |
| 1224 | CB  | THR | A | 154 | 20.008 | 64.592 | 5.212  | 1.00 | 21.10 | 6 |
| 1225 | OG1 | THR | A | 154 | 19.488 | 63.334 | 4.709  | 1.00 | 20.66 | 8 |
| 1226 | CG2 | THR | A | 154 | 19.569 | 65.711 | 4.260  | 1.00 | 21.99 | 6 |
| 1227 | N   | TYR | A | 155 | 22.977 | 66.280 | 4.566  | 1.00 | 14.57 | 7 |
| 1228 | CA  | TYR | A | 155 | 23.613 | 67.573 | 4.928  | 1.00 | 15.65 | 6 |
| 1229 | C   | TYR | A | 155 | 22.652 | 68.698 | 5.184  | 1.00 | 17.55 | 6 |
| 1230 | O   | TYR | A | 155 | 21.639 | 68.912 | 4.487  | 1.00 | 16.44 | 8 |
| 1231 | CB  | TYR | A | 155 | 24.440 | 67.984 | 3.678  | 1.00 | 16.08 | 6 |
| 1232 | CG  | TYR | A | 155 | 25.238 | 69.243 | 3.820  | 1.00 | 16.71 | 6 |
| 1233 | CD1 | TYR | A | 155 | 26.324 | 69.277 | 4.693  | 1.00 | 16.20 | 6 |
| 1234 | CD2 | TYR | A | 155 | 24.989 | 70.381 | 3.075  | 1.00 | 16.54 | 6 |
| 1235 | CE1 | TYR | A | 155 | 27.139 | 70.407 | 4.789  | 1.00 | 16.44 | 6 |
| 1236 | CE2 | TYR | A | 155 | 25.773 | 71.530 | 3.162  | 1.00 | 14.17 | 6 |
| 1237 | CZ  | TYR | A | 155 | 26.843 | 71.515 | 4.015  | 1.00 | 16.83 | 6 |
| 1238 | OH  | TYR | A | 155 | 27.673 | 72.601 | 4.142  | 1.00 | 15.80 | 8 |
| 1239 | N   | MET | A | 156 | 22.895 | 69.456 | 6.272  | 1.00 | 12.36 | 7 |
| 1240 | CA  | MET | A | 156 | 22.120 | 70.658 | 6.595  | 1.00 | 12.72 | 6 |

TABLE 1-continued

Atom Coordinates from the Crystal Structure of NOVAMYL

| 1241 | C   | MET | A | 156 | 22.877 | 71.939 | 6.202  | 1.00 | 14.70 | 6  |
|------|-----|-----|---|-----|--------|--------|--------|------|-------|----|
| 1242 | O   | MET | A | 156 | 22.290 | 72.876 | 5.628  | 1.00 | 14.86 | 8  |
| 1243 | CB  | MET | A | 156 | 21.886 | 70.683 | 8.141  | 1.00 | 14.72 | 6  |
| 1244 | CG  | MET | A | 156 | 21.045 | 69.510 | 8.543  | 1.00 | 13.16 | 6  |
| 1245 | SD  | MET | A | 156 | 20.812 | 69.391 | 10.354 | 1.00 | 16.44 | 16 |
| 1246 | CE  | MET | A | 156 | 19.828 | 70.788 | 10.735 | 1.00 | 16.14 | 6  |
| 1247 | N   | GLY | A | 157 | 24.138 | 72.003 | 6.634  | 1.00 | 15.28 | 7  |
| 1248 | CA  | GLY | A | 157 | 24.888 | 73.257 | 6.260  | 1.00 | 12.22 | 6  |
| 1249 | C   | GLY | A | 157 | 26.169 | 73.337 | 7.061  | 1.00 | 15.29 | 6  |
| 1250 | O   | GLY | A | 157 | 26.402 | 72.513 | 7.965  | 1.00 | 13.96 | 8  |
| 1251 | N   | ASN | A | 158 | 26.981 | 74.369 | 6.736  | 1.00 | 13.19 | 7  |
| 1252 | CA  | ASN | A | 158 | 28.205 | 74.586 | 7.485  | 1.00 | 12.06 | 6  |
| 1253 | C   | ASN | A | 158 | 28.353 | 76.085 | 7.759  | 1.00 | 8.80  | 6  |
| 1254 | O   | ASN | A | 158 | 27.377 | 76.850 | 7.583  | 1.00 | 11.73 | 8  |
| 1255 | CB  | ASN | A | 158 | 29.438 | 73.957 | 6.787  | 1.00 | 12.79 | 6  |
| 1256 | CG  | ASN | A | 158 | 29.783 | 74.647 | 5.457  | 1.00 | 16.08 | 6  |
| 1257 | OD1 | ASN | A | 158 | 29.311 | 75.727 | 5.160  | 1.00 | 12.69 | 8  |
| 1258 | ND2 | ASN | A | 158 | 30.650 | 74.060 | 4.603  | 1.00 | 20.88 | 7  |
| 1259 | N   | TYR | A | 159 | 29.559 | 76.484 | 8.260  | 1.00 | 10.67 | 7  |
| 1260 | CA  | TYR | A | 159 | 29.714 | 77.924 | 8.640  | 1.00 | 11.67 | 6  |
| 1261 | C   | TYR | A | 159 | 29.665 | 78.827 | 7.432  | 1.00 | 12.87 | 6  |
| 1262 | O   | TYR | A | 159 | 29.444 | 80.029 | 7.605  | 1.00 | 12.70 | 8  |
| 1263 | CB  | TYR | A | 159 | 31.055 | 78.072 | 9.434  | 1.00 | 11.86 | 6  |
| 1264 | CG  | TYR | A | 159 | 31.171 | 79.475 | 10.063 | 1.00 | 11.61 | 6  |
| 1265 | CD1 | TYR | A | 159 | 30.414 | 79.868 | 11.149 | 1.00 | 14.86 | 6  |
| 1266 | CD2 | TYR | A | 159 | 31.962 | 80.402 | 9.380  | 1.00 | 13.87 | 6  |
| 1267 | CE1 | TYR | A | 159 | 30.576 | 81.181 | 11.600 | 1.00 | 15.19 | 6  |
| 1268 | CE2 | TYR | A | 159 | 32.069 | 81.716 | 9.811  | 1.00 | 19.88 | 6  |
| 1269 | CZ  | TYR | A | 159 | 31.387 | 82.088 | 10.926 | 1.00 | 16.15 | 6  |
| 1270 | OH  | TYR | A | 159 | 31.377 | 83.383 | 11.432 | 1.00 | 16.24 | 8  |
| 1271 | N   | PHE | A | 160 | 29.904 | 78.307 | 6.253  | 1.00 | 13.52 | 7  |
| 1272 | CA  | PHE | A | 160 | 30.073 | 79.126 | 5.029  | 1.00 | 12.84 | 6  |
| 1273 | C   | PHE | A | 160 | 28.855 | 79.182 | 4.153  | 1.00 | 12.34 | 6  |
| 1274 | O   | PHE | A | 160 | 28.803 | 80.101 | 3.300  | 1.00 | 14.63 | 8  |
| 1275 | CB  | PHE | A | 160 | 31.228 | 78.421 | 4.234  | 1.00 | 12.99 | 6  |
| 1276 | CG  | PHE | A | 160 | 32.504 | 78.508 | 5.080  | 1.00 | 14.21 | 6  |
| 1277 | CD1 | PHE | A | 160 | 33.310 | 79.662 | 4.935  | 1.00 | 12.64 | 6  |
| 1278 | CD2 | PHE | A | 160 | 32.804 | 77.488 | 5.965  | 1.00 | 12.84 | 6  |
| 1279 | CE1 | PHE | A | 160 | 34.466 | 79.772 | 5.737  | 1.00 | 14.91 | 6  |
| 1280 | CE2 | PHE | A | 160 | 33.940 | 77.621 | 6.761  | 1.00 | 14.27 | 6  |
| 1281 | CZ  | PHE | A | 160 | 34.769 | 78.740 | 6.653  | 1.00 | 13.93 | 6  |
| 1282 | N   | ASP | A | 161 | 27.917 | 78.220 | 4.232  | 1.00 | 14.16 | 7  |
| 1283 | CA  | ASP | A | 161 | 26.731 | 78.329 | 3.371  | 1.00 | 14.46 | 6  |
| 1284 | C   | ASP | A | 161 | 25.486 | 78.622 | 4.217  | 1.00 | 14.25 | 6  |
| 1285 | O   | ASP | A | 161 | 24.375 | 78.215 | 3.808  | 1.00 | 15.23 | 8  |
| 1286 | CB  | ASP | A | 161 | 26.557 | 77.031 | 2.565  | 1.00 | 12.66 | 6  |
| 1287 | CG  | ASP | A | 161 | 26.500 | 75.766 | 3.373  | 1.00 | 15.72 | 6  |
| 1288 | OD1 | ASP | A | 161 | 26.191 | 75.896 | 4.579  | 1.00 | 13.04 | 8  |
| 1289 | OD2 | ASP | A | 161 | 26.767 | 74.716 | 2.766  | 1.00 | 20.26 | 8  |
| 1290 | N   | ASP | A | 162 | 25.656 | 79.460 | 5.227  | 1.00 | 13.84 | 7  |
| 1291 | CA  | ASP | A | 162 | 24.557 | 79.667 | 6.196  | 1.00 | 14.60 | 6  |
| 1292 | C   | ASP | A | 162 | 23.787 | 80.939 | 5.979  | 1.00 | 16.54 | 6  |
| 1293 | O   | ASP | A | 162 | 22.840 | 81.252 | 6.726  | 1.00 | 18.25 | 8  |
| 1294 | CB  | ASP | A | 162 | 25.253 | 79.785 | 7.584  | 1.00 | 12.11 | 6  |
| 1295 | CG  | ASP | A | 162 | 24.264 | 79.524 | 8.717  | 1.00 | 13.12 | 6  |
| 1296 | OD1 | ASP | A | 162 | 23.408 | 78.624 | 8.551  | 1.00 | 12.76 | 8  |
| 1297 | OD2 | ASP | A | 162 | 24.417 | 80.201 | 9.775  | 1.00 | 12.76 | 8  |
| 1298 | N   | ALA | A | 163 | 24.109 | 81.725 | 4.949  | 1.00 | 16.09 | 7  |
| 1299 | CA  | ALA | A | 163 | 23.428 | 83.019 | 4.792  | 1.00 | 16.11 | 6  |
| 1300 | C   | ALA | A | 163 | 21.914 | 82.901 | 4.848  | 1.00 | 17.25 | 6  |
| 1301 | O   | ALA | A | 163 | 21.341 | 83.825 | 5.467  | 1.00 | 24.30 | 8  |
| 1302 | CB  | ALA | A | 163 | 23.828 | 83.609 | 3.414  | 1.00 | 19.57 | 6  |
| 1303 | N   | THR | A | 164 | 21.317 | 81.987 | 4.145  | 1.00 | 19.25 | 7  |
| 1304 | CA  | THR | A | 164 | 19.845 | 81.973 | 4.121  | 1.00 | 24.11 | 6  |
| 1305 | C   | THR | A | 164 | 19.237 | 81.014 | 5.149  | 1.00 | 25.86 | 6  |
| 1306 | O   | THR | A | 164 | 18.055 | 80.605 | 5.002  | 1.00 | 25.38 | 8  |
| 1307 | CB  | THR | A | 164 | 19.384 | 81.502 | 2.723  | 1.00 | 21.33 | 6  |
| 1308 | OG1 | THR | A | 164 | 19.834 | 80.146 | 2.496  | 1.00 | 29.22 | 8  |
| 1309 | CG2 | THR | A | 164 | 20.062 | 82.359 | 1.658  | 1.00 | 32.67 | 6  |
| 1310 | N   | LYS | A | 165 | 20.086 | 80.431 | 6.008  | 1.00 | 19.16 | 7  |
| 1311 | CA  | LYS | A | 165 | 19.577 | 79.430 | 6.929  | 1.00 | 16.62 | 6  |
| 1312 | C   | LYS | A | 165 | 19.714 | 79.888 | 8.391  | 1.00 | 18.03 | 6  |
| 1313 | O   | LYS | A | 165 | 18.735 | 79.767 | 9.173  | 1.00 | 17.25 | 8  |
| 1314 | CB  | LYS | A | 165 | 20.423 | 78.140 | 6.826  | 1.00 | 13.80 | 6  |
| 1315 | CG  | LYS | A | 165 | 20.215 | 77.497 | 5.423  | 1.00 | 21.49 | 6  |
| 1316 | CD  | LYS | A | 165 | 20.913 | 76.186 | 5.334  | 1.00 | 30.47 | 6  |
| 1317 | CE  | LYS | A | 165 | 22.394 | 76.297 | 5.245  | 1.00 | 26.09 | 6  |

TABLE 1-continued

Atom Coordinates from the Crystal Structure of NOVAMYL

| | | | | | | | | | | |
|---|---|---|---|---|---|---|---|---|---|---|
| 1318 | NZ | LYS | A | 165 | 23.067 | 75.308 | 4.349 | 1.00 | 18.44 | 7 |
| 1319 | N | GLY | A | 166 | 20.839 | 80.499 | 8.700 | 1.00 | 14.27 | 7 |
| 1320 | CA | GLY | A | 166 | 21.048 | 81.024 | 10.082 | 1.00 | 14.43 | 6 |
| 1321 | C | GLY | A | 166 | 21.103 | 79.863 | 11.109 | 1.00 | 14.80 | 6 |
| 1322 | O | GLY | A | 166 | 20.730 | 80.096 | 12.287 | 1.00 | 14.92 | 8 |
| 1323 | N | TYR | A | 167 | 21.732 | 78.765 | 10.734 | 1.00 | 12.78 | 7 |
| 1324 | CA | TYR | A | 167 | 21.882 | 77.692 | 11.732 | 1.00 | 12.54 | 6 |
| 1325 | C | TYR | A | 167 | 22.991 | 78.009 | 12.739 | 1.00 | 12.62 | 6 |
| 1326 | O | TYR | A | 167 | 23.085 | 77.349 | 13.776 | 1.00 | 11.78 | 8 |
| 1327 | CB | TYR | A | 167 | 22.226 | 76.374 | 11.022 | 1.00 | 10.92 | 6 |
| 1328 | CG | TYR | A | 167 | 21.127 | 75.836 | 10.103 | 1.00 | 14.63 | 6 |
| 1329 | CD1 | TYR | A | 167 | 19.810 | 76.232 | 10.291 | 1.00 | 13.59 | 6 |
| 1330 | CD2 | TYR | A | 167 | 21.490 | 74.921 | 9.121 | 1.00 | 15.06 | 6 |
| 1331 | CE1 | TYR | A | 167 | 18.836 | 75.722 | 9.421 | 1.00 | 13.53 | 6 |
| 1332 | CE2 | TYR | A | 167 | 20.503 | 74.385 | 8.254 | 1.00 | 12.93 | 6 |
| 1333 | CZ | TYR | A | 167 | 19.211 | 74.809 | 8.469 | 1.00 | 15.10 | 6 |
| 1334 | OH | TYR | A | 167 | 18.235 | 74.289 | 7.594 | 1.00 | 18.52 | 8 |
| 1335 | N | PHE | A | 168 | 23.963 | 78.870 | 12.342 | 1.00 | 11.36 | 7 |
| 1336 | CA | PHE | A | 168 | 25.072 | 79.208 | 13.244 | 1.00 | 11.20 | 6 |
| 1337 | C | PHE | A | 168 | 25.097 | 80.677 | 13.551 | 1.00 | 12.02 | 6 |
| 1338 | O | PHE | A | 168 | 24.515 | 81.539 | 12.854 | 1.00 | 11.21 | 8 |
| 1339 | CB | PHE | A | 168 | 26.432 | 78.934 | 12.493 | 1.00 | 13.41 | 6 |
| 1340 | CG | PHE | A | 168 | 26.552 | 77.459 | 12.174 | 1.00 | 11.52 | 6 |
| 1341 | CD1 | PHE | A | 168 | 27.044 | 76.583 | 13.130 | 1.00 | 10.63 | 6 |
| 1342 | CD2 | PHE | A | 168 | 26.171 | 77.007 | 10.899 | 1.00 | 13.81 | 6 |
| 1343 | CE1 | PHE | A | 168 | 27.122 | 75.214 | 12.765 | 1.00 | 12.04 | 6 |
| 1344 | CE2 | PHE | A | 168 | 26.250 | 75.639 | 10.574 | 1.00 | 12.05 | 6 |
| 1345 | CZ | PHE | A | 168 | 26.752 | 74.751 | 11.518 | 1.00 | 12.13 | 6 |
| 1346 | N | HIS | A | 169 | 25.665 | 81.067 | 14.709 | 1.00 | 11.43 | 7 |
| 1347 | CA | HIS | A | 169 | 25.979 | 82.473 | 14.979 | 1.00 | 12.52 | 6 |
| 1348 | C | HIS | A | 169 | 27.266 | 82.836 | 14.195 | 1.00 | 11.69 | 6 |
| 1349 | O | HIS | A | 169 | 28.109 | 82.035 | 13.921 | 1.00 | 11.66 | 8 |
| 1350 | CB | HIS | A | 169 | 26.361 | 82.658 | 16.482 | 1.00 | 11.57 | 6 |
| 1351 | CG | HIS | A | 169 | 25.157 | 82.347 | 17.376 | 1.00 | 11.97 | 6 |
| 1352 | ND1 | HIS | A | 169 | 25.403 | 81.657 | 18.588 | 1.00 | 11.36 | 7 |
| 1353 | CD2 | HIS | A | 169 | 23.838 | 82.604 | 17.274 | 1.00 | 11.55 | 6 |
| 1354 | CE1 | HIS | A | 169 | 24.195 | 81.518 | 19.195 | 1.00 | 12.02 | 6 |
| 1355 | NE2 | HIS | A | 169 | 23.233 | 82.111 | 18.427 | 1.00 | 10.80 | 7 |
| 1356 | N | HIS | A | 170 | 27.295 | 84.147 | 13.797 | 1.00 | 11.77 | 7 |
| 1357 | CA | HIS | A | 170 | 28.474 | 84.629 | 13.015 | 1.00 | 12.20 | 6 |
| 1358 | C | HIS | A | 170 | 29.029 | 85.872 | 13.672 | 1.00 | 14.93 | 6 |
| 1359 | O | HIS | A | 170 | 29.174 | 86.974 | 13.053 | 1.00 | 16.92 | 8 |
| 1360 | CB | HIS | A | 170 | 28.083 | 84.949 | 11.533 | 1.00 | 13.28 | 6 |
| 1361 | CG | HIS | A | 170 | 27.535 | 83.698 | 10.888 | 1.00 | 12.02 | 6 |
| 1362 | ND1 | HIS | A | 170 | 28.327 | 82.925 | 10.069 | 1.00 | 15.51 | 7 |
| 1363 | CD2 | HIS | A | 170 | 26.306 | 83.088 | 10.915 | 1.00 | 13.12 | 6 |
| 1364 | CE1 | HIS | A | 170 | 27.639 | 81.863 | 9.689 | 1.00 | 16.69 | 6 |
| 1365 | NE2 | HIS | A | 170 | 26.409 | 81.953 | 10.156 | 1.00 | 13.32 | 7 |
| 1366 | N | ASN | A | 171 | 29.387 | 85.778 | 14.962 | 1.00 | 12.58 | 7 |
| 1367 | CA | ASN | A | 171 | 29.735 | 86.967 | 15.733 | 1.00 | 12.76 | 6 |
| 1368 | C | ASN | A | 171 | 31.201 | 87.040 | 16.147 | 1.00 | 13.34 | 6 |
| 1369 | O | ASN | A | 171 | 31.554 | 87.947 | 16.949 | 1.00 | 17.31 | 8 |
| 1370 | CB | ASN | A | 171 | 28.916 | 86.961 | 17.054 | 1.00 | 13.40 | 6 |
| 1371 | CG | ASN | A | 171 | 27.430 | 86.948 | 16.719 | 1.00 | 17.12 | 6 |
| 1372 | OD1 | ASN | A | 171 | 26.595 | 86.168 | 17.252 | 1.00 | 16.54 | 8 |
| 1373 | ND2 | ASN | A | 171 | 27.046 | 87.866 | 15.861 | 1.00 | 12.82 | 7 |
| 1374 | N | GLY | A | 172 | 32.013 | 86.197 | 15.601 | 1.00 | 13.14 | 7 |
| 1375 | CA | GLY | A | 172 | 33.444 | 86.166 | 15.964 | 1.00 | 15.42 | 6 |
| 1376 | C | GLY | A | 172 | 33.728 | 85.275 | 17.210 | 1.00 | 16.69 | 6 |
| 1377 | O | GLY | A | 172 | 32.817 | 84.706 | 17.722 | 1.00 | 14.98 | 8 |
| 1378 | N | ASP | A | 173 | 34.993 | 85.180 | 17.526 | 1.00 | 14.76 | 7 |
| 1379 | CA | ASP | A | 173 | 35.473 | 84.346 | 18.622 | 1.00 | 12.93 | 6 |
| 1380 | C | ASP | A | 173 | 35.292 | 84.996 | 19.976 | 1.00 | 12.76 | 6 |
| 1381 | O | ASP | A | 173 | 35.410 | 86.248 | 20.131 | 1.00 | 11.79 | 8 |
| 1382 | CB | ASP | A | 173 | 36.980 | 84.152 | 18.369 | 1.00 | 14.28 | 6 |
| 1383 | CG | ASP | A | 173 | 37.273 | 83.139 | 17.268 | 1.00 | 24.98 | 6 |
| 1384 | OD1 | ASP | A | 173 | 36.398 | 82.387 | 16.822 | 1.00 | 17.11 | 8 |
| 1385 | OD2 | ASP | A | 173 | 38.451 | 83.124 | 16.815 | 1.00 | 23.71 | 8 |
| 1386 | N | ILE | A | 174 | 35.073 | 84.127 | 20.969 | 1.00 | 12.58 | 7 |
| 1387 | CA | ILE | A | 174 | 35.136 | 84.670 | 22.362 | 1.00 | 11.65 | 6 |
| 1388 | C | ILE | A | 174 | 36.500 | 85.307 | 22.646 | 1.00 | 14.87 | 6 |
| 1389 | O | ILE | A | 174 | 37.508 | 84.670 | 22.337 | 1.00 | 15.09 | 8 |
| 1390 | CB | ILE | A | 174 | 34.896 | 83.495 | 23.357 | 1.00 | 13.27 | 6 |
| 1391 | CG1 | ILE | A | 174 | 33.431 | 83.005 | 23.177 | 1.00 | 10.95 | 6 |
| 1392 | CG2 | ILE | A | 174 | 35.145 | 84.016 | 24.806 | 1.00 | 12.74 | 6 |
| 1393 | CD1 | ILE | A | 174 | 33.220 | 81.690 | 24.000 | 1.00 | 11.77 | 6 |
| 1394 | N | SER | A | 175 | 36.441 | 86.493 | 23.260 | 1.00 | 14.22 | 7 |

TABLE 1-continued

Atom Coordinates from the Crystal Structure of NOVAMYL

| 1395 | CA | SER | A | 175 | 37.710 | 87.093 | 23.770 | 1.00 | 16.89 | 6 |
|---|---|---|---|---|---|---|---|---|---|---|
| 1396 | C | SER | A | 175 | 37.712 | 87.131 | 25.291 | 1.00 | 18.02 | 6 |
| 1397 | O | SER | A | 175 | 38.617 | 86.587 | 25.938 | 1.00 | 19.20 | 8 |
| 1398 | CB | SER | A | 175 | 37.868 | 88.470 | 23.138 | 1.00 | 17.86 | 6 |
| 1399 | OG | SER | A | 175 | 39.049 | 89.044 | 23.724 | 1.00 | 24.28 | 8 |
| 1400 | N | ASN | A | 176 | 36.650 | 87.662 | 25.854 | 1.00 | 14.39 | 7 |
| 1401 | CA | ASN | A | 176 | 36.515 | 87.678 | 27.336 | 1.00 | 13.41 | 6 |
| 1402 | C | ASN | A | 176 | 35.511 | 86.561 | 27.678 | 1.00 | 12.76 | 6 |
| 1403 | O | ASN | A | 176 | 34.286 | 86.760 | 27.482 | 1.00 | 13.43 | 8 |
| 1404 | CB | ASN | A | 176 | 35.898 | 89.032 | 27.724 | 1.00 | 15.61 | 6 |
| 1405 | CG | ASN | A | 176 | 35.749 | 89.123 | 29.243 | 1.00 | 17.91 | 6 |
| 1406 | OD1 | ASN | A | 176 | 35.963 | 88.166 | 29.982 | 1.00 | 15.18 | 8 |
| 1407 | ND2 | ASN | A | 176 | 35.402 | 90.347 | 29.694 | 1.00 | 22.13 | 7 |
| 1408 | N | TRP | A | 177 | 36.085 | 85.465 | 28.237 | 1.00 | 14.29 | 7 |
| 1409 | CA | TRP | A | 177 | 35.172 | 84.361 | 28.558 | 1.00 | 13.39 | 6 |
| 1410 | C | TRP | A | 177 | 34.248 | 84.677 | 29.724 | 1.00 | 15.05 | 6 |
| 1411 | O | TRP | A | 177 | 33.279 | 83.898 | 29.909 | 1.00 | 14.25 | 8 |
| 1412 | CB | TRP | A | 177 | 36.054 | 83.145 | 28.953 | 1.00 | 16.12 | 6 |
| 1413 | CG | TRP | A | 177 | 36.712 | 82.559 | 27.721 | 1.00 | 14.43 | 6 |
| 1414 | CD1 | TRP | A | 177 | 37.745 | 83.101 | 26.998 | 1.00 | 16.58 | 6 |
| 1415 | CD2 | TRP | A | 177 | 36.399 | 81.291 | 27.142 | 1.00 | 13.92 | 6 |
| 1416 | NE1 | TRP | A | 177 | 38.070 | 82.235 | 25.940 | 1.00 | 18.57 | 7 |
| 1417 | CE2 | TRP | A | 177 | 37.234 | 81.131 | 26.014 | 1.00 | 18.68 | 6 |
| 1418 | CE3 | TRP | A | 177 | 35.437 | 80.298 | 27.392 | 1.00 | 17.34 | 6 |
| 1419 | CZ2 | TRP | A | 177 | 37.148 | 80.031 | 25.169 | 1.00 | 14.28 | 6 |
| 1420 | CZ3 | TRP | A | 177 | 35.379 | 79.182 | 26.574 | 1.00 | 17.20 | 6 |
| 1421 | CH2 | TRP | A | 177 | 36.253 | 79.045 | 25.441 | 1.00 | 18.00 | 6 |
| 1422 | N | ASP | A | 178 | 34.477 | 85.795 | 30.469 | 1.00 | 12.43 | 7 |
| 1423 | CA | ASP | A | 178 | 33.507 | 86.126 | 31.517 | 1.00 | 11.08 | 6 |
| 1424 | C | ASP | A | 178 | 32.454 | 87.115 | 31.053 | 1.00 | 12.88 | 6 |
| 1425 | O | ASP | A | 178 | 31.586 | 87.420 | 31.881 | 1.00 | 15.73 | 8 |
| 1426 | CB | ASP | A | 178 | 34.243 | 86.717 | 32.739 | 1.00 | 17.78 | 6 |
| 1427 | CG | ASP | A | 178 | 35.201 | 85.739 | 33.362 | 1.00 | 24.33 | 6 |
| 1428 | OD1 | ASP | A | 178 | 34.916 | 84.535 | 33.440 | 1.00 | 18.07 | 8 |
| 1429 | OD2 | ASP | A | 178 | 36.317 | 86.155 | 33.777 | 1.00 | 24.77 | 8 |
| 1430 | N | ASP | A | 179 | 32.527 | 87.608 | 29.810 | 1.00 | 11.79 | 7 |
| 1431 | CA | ASP | A | 179 | 31.448 | 88.502 | 29.357 | 1.00 | 11.42 | 6 |
| 1432 | C | ASP | A | 179 | 30.292 | 87.603 | 28.903 | 1.00 | 12.33 | 6 |
| 1433 | O | ASP | A | 179 | 30.537 | 86.725 | 28.067 | 1.00 | 12.08 | 8 |
| 1434 | CB | ASP | A | 179 | 31.997 | 89.341 | 28.184 | 1.00 | 15.43 | 6 |
| 1435 | CG | ASP | A | 179 | 30.831 | 90.225 | 27.763 | 1.00 | 18.80 | 6 |
| 1436 | OD1 | ASP | A | 179 | 30.462 | 91.232 | 28.431 | 1.00 | 20.56 | 8 |
| 1437 | OD2 | ASP | A | 179 | 30.213 | 89.893 | 26.753 | 1.00 | 13.51 | 8 |
| 1438 | N | ARG | A | 180 | 29.115 | 87.768 | 29.477 | 1.00 | 13.02 | 7 |
| 1439 | CA | ARG | A | 180 | 28.057 | 86.771 | 29.205 | 1.00 | 11.54 | 6 |
| 1440 | C | ARG | A | 180 | 27.585 | 86.833 | 27.757 | 1.00 | 10.36 | 6 |
| 1441 | O | ARG | A | 180 | 27.261 | 85.746 | 27.225 | 1.00 | 11.27 | 8 |
| 1442 | CB | ARG | A | 180 | 26.893 | 87.051 | 30.172 | 1.00 | 13.31 | 6 |
| 1443 | CG | ARG | A | 180 | 27.286 | 86.796 | 31.654 | 1.00 | 12.49 | 6 |
| 1444 | CD | ARG | A | 180 | 27.797 | 85.340 | 31.899 | 1.00 | 10.75 | 6 |
| 1445 | NE | ARG | A | 180 | 26.694 | 84.389 | 31.571 | 1.00 | 11.38 | 7 |
| 1446 | CZ | ARG | A | 180 | 26.896 | 83.305 | 30.812 | 1.00 | 11.55 | 6 |
| 1447 | NH1 | ARG | A | 180 | 28.090 | 82.893 | 30.359 | 1.00 | 11.21 | 7 |
| 1448 | NH2 | ARG | A | 180 | 25.769 | 82.597 | 30.589 | 1.00 | 13.64 | 7 |
| 1449 | N | TYR | A | 181 | 27.508 | 87.990 | 27.113 | 1.00 | 10.51 | 7 |
| 1450 | CA | TYR | A | 181 | 27.104 | 87.980 | 25.688 | 1.00 | 10.68 | 6 |
| 1451 | C | TYR | A | 181 | 28.195 | 87.277 | 24.870 | 1.00 | 11.14 | 6 |
| 1452 | O | TYR | A | 181 | 27.826 | 86.403 | 24.044 | 1.00 | 10.66 | 8 |
| 1453 | CB | TYR | A | 181 | 26.915 | 89.446 | 25.196 | 1.00 | 12.30 | 6 |
| 1454 | CG | TYR | A | 181 | 26.645 | 89.417 | 23.698 | 1.00 | 12.16 | 6 |
| 1455 | CD1 | TYR | A | 181 | 25.446 | 89.009 | 23.179 | 1.00 | 13.07 | 6 |
| 1456 | CD2 | TYR | A | 181 | 27.712 | 89.736 | 22.837 | 1.00 | 15.09 | 6 |
| 1457 | CE1 | TYR | A | 181 | 25.242 | 88.936 | 21.808 | 1.00 | 18.03 | 6 |
| 1458 | CE2 | TYR | A | 181 | 27.510 | 89.688 | 21.457 | 1.00 | 16.90 | 6 |
| 1459 | CZ | TYR | A | 181 | 26.275 | 89.265 | 20.988 | 1.00 | 19.76 | 6 |
| 1460 | OH | TYR | A | 181 | 26.097 | 89.156 | 19.614 | 1.00 | 17.30 | 8 |
| 1461 | N | GLU | A | 182 | 29.473 | 87.528 | 25.083 | 1.00 | 13.50 | 7 |
| 1462 | CA | GLU | A | 182 | 30.468 | 86.836 | 24.265 | 1.00 | 12.35 | 6 |
| 1463 | C | GLU | A | 182 | 30.442 | 85.311 | 24.504 | 1.00 | 10.45 | 6 |
| 1464 | O | GLU | A | 182 | 30.482 | 84.533 | 23.582 | 1.00 | 11.45 | 8 |
| 1465 | CB | GLU | A | 182 | 31.939 | 87.266 | 24.571 | 1.00 | 10.48 | 6 |
| 1466 | CG | GLU | A | 182 | 32.131 | 88.769 | 24.214 | 1.00 | 12.66 | 6 |
| 1467 | CD | GLU | A | 182 | 33.640 | 89.046 | 24.246 | 1.00 | 19.30 | 6 |
| 1468 | OE1 | GLU | A | 182 | 34.487 | 88.229 | 23.958 | 1.00 | 15.48 | 8 |
| 1469 | OE2 | GLU | A | 182 | 34.009 | 90.199 | 24.690 | 1.00 | 30.95 | 8 |
| 1470 | N | ALA | A | 183 | 30.314 | 84.945 | 25.796 | 1.00 | 10.17 | 7 |
| 1471 | CA | ALA | A | 183 | 30.436 | 83.521 | 26.110 | 1.00 | 11.02 | 6 |

TABLE 1-continued

Atom Coordinates from the Crystal Structure of NOVAMYL

| 1472 | C   | ALA | A | 183 | 29.302 | 82.709 | 25.471 | 1.00 | 11.67 | 6 |
|------|-----|-----|---|-----|--------|--------|--------|------|-------|---|
| 1473 | O   | ALA | A | 183 | 29.555 | 81.542 | 25.197 | 1.00 | 10.91 | 8 |
| 1474 | CB  | ALA | A | 183 | 30.290 | 83.352 | 27.664 | 1.00 | 11.34 | 6 |
| 1475 | N   | GLN | A | 184 | 28.196 | 83.381 | 25.172 | 1.00 | 10.70 | 7 |
| 1476 | CA  | GLN | A | 184 | 27.046 | 82.624 | 24.601 | 1.00 | 8.62  | 6 |
| 1477 | C   | GLN | A | 184 | 26.939 | 82.844 | 23.102 | 1.00 | 10.69 | 6 |
| 1478 | O   | GLN | A | 184 | 26.509 | 81.913 | 22.388 | 1.00 | 10.72 | 8 |
| 1479 | CB  | GLN | A | 184 | 25.772 | 83.078 | 25.330 | 1.00 | 12.35 | 6 |
| 1480 | CG  | GLN | A | 184 | 25.730 | 82.584 | 26.785 | 1.00 | 9.80  | 6 |
| 1481 | CD  | GLN | A | 184 | 24.603 | 83.315 | 27.538 | 1.00 | 12.56 | 6 |
| 1482 | OE1 | GLN | A | 184 | 24.739 | 84.527 | 27.890 | 1.00 | 15.21 | 8 |
| 1483 | NE2 | GLN | A | 184 | 23.536 | 82.580 | 27.775 | 1.00 | 8.78  | 7 |
| 1484 | N   | TRP | A | 185 | 27.186 | 84.018 | 22.585 | 1.00 | 11.90 | 7 |
| 1485 | CA  | TRP | A | 185 | 26.968 | 84.285 | 21.148 | 1.00 | 9.74  | 6 |
| 1486 | C   | TRP | A | 185 | 28.252 | 84.298 | 20.318 | 1.00 | 10.30 | 6 |
| 1487 | O   | TRP | A | 185 | 28.093 | 84.277 | 19.065 | 1.00 | 11.67 | 8 |
| 1488 | CB  | TRP | A | 185 | 26.201 | 85.647 | 20.965 | 1.00 | 12.61 | 6 |
| 1489 | CG  | TRP | A | 185 | 24.696 | 85.390 | 21.039 | 1.00 | 10.95 | 6 |
| 1490 | CD1 | TRP | A | 185 | 23.863 | 85.166 | 19.989 | 1.00 | 12.59 | 6 |
| 1491 | CD2 | TRP | A | 185 | 23.898 | 85.345 | 22.226 | 1.00 | 12.07 | 6 |
| 1492 | NE1 | TRP | A | 185 | 22.561 | 84.887 | 20.428 | 1.00 | 14.15 | 7 |
| 1493 | CE2 | TRP | A | 185 | 22.600 | 85.003 | 21.805 | 1.00 | 13.63 | 6 |
| 1494 | CE3 | TRP | A | 185 | 24.154 | 85.530 | 23.587 | 1.00 | 13.34 | 6 |
| 1495 | CZ2 | TRP | A | 185 | 21.534 | 84.846 | 22.703 | 1.00 | 14.01 | 6 |
| 1496 | CZ3 | TRP | A | 185 | 23.083 | 85.361 | 24.494 | 1.00 | 14.75 | 6 |
| 1497 | CH2 | TRP | A | 185 | 21.812 | 85.004 | 24.035 | 1.00 | 13.91 | 6 |
| 1498 | N   | LYS | A | 186 | 29.413 | 84.254 | 20.924 | 1.00 | 11.31 | 7 |
| 1499 | CA  | LYS | A | 186 | 30.655 | 84.170 | 20.127 | 1.00 | 12.29 | 6 |
| 1500 | C   | LYS | A | 186 | 31.228 | 82.764 | 20.238 | 1.00 | 14.72 | 6 |
| 1501 | O   | LYS | A | 186 | 30.718 | 81.896 | 20.981 | 1.00 | 12.47 | 8 |
| 1502 | CB  | LYS | A | 186 | 31.682 | 85.224 | 20.582 | 1.00 | 11.09 | 6 |
| 1503 | CG  | LYS | A | 186 | 31.145 | 86.646 | 20.243 | 1.00 | 14.74 | 6 |
| 1504 | CD  | LYS | A | 186 | 32.295 | 87.655 | 20.601 | 1.00 | 14.53 | 6 |
| 1505 | CE  | LYS | A | 186 | 31.688 | 89.051 | 20.286 | 1.00 | 20.29 | 6 |
| 1506 | NZ  | LYS | A | 186 | 32.744 | 89.943 | 19.726 | 1.00 | 28.67 | 7 |
| 1507 | N   | ASN | A | 187 | 32.217 | 82.446 | 19.379 | 1.00 | 13.16 | 7 |
| 1508 | CA  | ASN | A | 187 | 32.653 | 81.074 | 19.195 | 1.00 | 13.22 | 6 |
| 1509 | C   | ASN | A | 187 | 33.587 | 80.604 | 20.314 | 1.00 | 15.43 | 6 |
| 1510 | O   | ASN | A | 187 | 34.587 | 81.250 | 20.646 | 1.00 | 12.76 | 8 |
| 1511 | CB  | ASN | A | 187 | 33.386 | 80.850 | 17.862 | 1.00 | 12.72 | 6 |
| 1512 | CG  | ASN | A | 187 | 32.673 | 81.537 | 16.697 | 1.00 | 18.84 | 6 |
| 1513 | OD1 | ASN | A | 187 | 31.447 | 81.456 | 16.631 | 1.00 | 15.46 | 8 |
| 1514 | ND2 | ASN | A | 187 | 33.426 | 82.219 | 15.839 | 1.00 | 16.94 | 7 |
| 1515 | N   | PHE | A | 188 | 33.369 | 79.356 | 20.719 | 1.00 | 11.91 | 7 |
| 1516 | CA  | PHE | A | 188 | 34.321 | 78.658 | 21.604 | 1.00 | 10.93 | 6 |
| 1517 | C   | PHE | A | 188 | 35.600 | 78.457 | 20.806 | 1.00 | 13.95 | 6 |
| 1518 | O   | PHE | A | 188 | 35.534 | 78.128 | 19.632 | 1.00 | 13.55 | 8 |
| 1519 | CB  | PHE | A | 188 | 33.682 | 77.259 | 21.822 | 1.00 | 11.05 | 6 |
| 1520 | CG  | PHE | A | 188 | 34.177 | 76.552 | 23.071 | 1.00 | 11.08 | 6 |
| 1521 | CD1 | PHE | A | 188 | 35.431 | 75.953 | 23.060 | 1.00 | 14.39 | 6 |
| 1522 | CD2 | PHE | A | 188 | 33.364 | 76.492 | 24.194 | 1.00 | 14.52 | 6 |
| 1523 | CE1 | PHE | A | 188 | 35.865 | 75.309 | 24.204 | 1.00 | 15.63 | 6 |
| 1524 | CE2 | PHE | A | 188 | 33.821 | 75.818 | 25.327 | 1.00 | 14.28 | 6 |
| 1525 | CZ  | PHE | A | 188 | 35.081 | 75.233 | 25.350 | 1.00 | 12.75 | 6 |
| 1526 | N   | THR | A | 189 | 36.737 | 78.710 | 21.504 | 1.00 | 11.89 | 7 |
| 1527 | CA  | THR | A | 189 | 38.000 | 78.578 | 20.769 | 1.00 | 11.77 | 6 |
| 1528 | C   | THR | A | 189 | 38.851 | 77.524 | 21.457 | 1.00 | 13.65 | 6 |
| 1529 | O   | THR | A | 189 | 38.630 | 77.149 | 22.589 | 1.00 | 14.67 | 8 |
| 1530 | CB  | THR | A | 189 | 38.826 | 79.904 | 20.788 | 1.00 | 12.56 | 6 |
| 1531 | OG1 | THR | A | 189 | 39.066 | 80.215 | 22.180 | 1.00 | 15.52 | 8 |
| 1532 | CG2 | THR | A | 189 | 38.012 | 81.045 | 20.136 | 1.00 | 13.79 | 6 |
| 1533 | N   | ASP | A | 190 | 39.773 | 76.961 | 20.639 | 1.00 | 11.10 | 7 |
| 1534 | CA  | ASP | A | 190 | 40.736 | 75.985 | 21.186 | 1.00 | 11.48 | 6 |
| 1535 | C   | ASP | A | 190 | 42.109 | 76.575 | 20.929 | 1.00 | 11.63 | 6 |
| 1536 | O   | ASP | A | 190 | 42.403 | 77.103 | 19.861 | 1.00 | 13.03 | 8 |
| 1537 | CB  | ASP | A | 190 | 40.530 | 74.703 | 20.365 | 1.00 | 11.07 | 6 |
| 1538 | CG  | ASP | A | 190 | 41.445 | 73.591 | 20.781 | 1.00 | 12.55 | 6 |
| 1539 | OD1 | ASP | A | 190 | 42.691 | 73.716 | 20.943 | 1.00 | 14.12 | 8 |
| 1540 | OD2 | ASP | A | 190 | 40.937 | 72.422 | 20.956 | 1.00 | 14.32 | 8 |
| 1541 | N   | PRO | A | 191 | 43.013 | 76.539 | 21.885 | 1.00 | 12.39 | 7 |
| 1542 | CA  | PRO | A | 191 | 44.344 | 77.094 | 21.756 | 1.00 | 16.15 | 6 |
| 1543 | C   | PRO | A | 191 | 45.205 | 76.488 | 20.648 | 1.00 | 17.03 | 6 |
| 1544 | O   | PRO | A | 191 | 46.194 | 77.139 | 20.258 | 1.00 | 17.33 | 8 |
| 1545 | CB  | PRO | A | 191 | 45.077 | 76.806 | 23.067 | 1.00 | 15.82 | 6 |
| 1546 | CG  | PRO | A | 191 | 43.951 | 76.489 | 24.024 | 1.00 | 19.99 | 6 |
| 1547 | CD  | PRO | A | 191 | 42.769 | 75.960 | 23.220 | 1.00 | 15.14 | 6 |
| 1548 | N   | ALA | A | 192 | 44.778 | 75.374 | 20.102 | 1.00 | 12.41 | 7 |

TABLE 1-continued

Atom Coordinates from the Crystal Structure of NOVAMYL

| 1549 | CA  | ALA | A | 192 | 45.446 | 74.851 | 18.871 | 1.00 | 16.29 | 6 |
|------|-----|-----|---|-----|--------|--------|--------|------|-------|---|
| 1550 | C   | ALA | A | 192 | 45.279 | 75.807 | 17.697 | 1.00 | 21.11 | 6 |
| 1551 | O   | ALA | A | 192 | 46.014 | 75.779 | 16.675 | 1.00 | 19.85 | 8 |
| 1552 | CB  | ALA | A | 192 | 44.978 | 73.466 | 18.579 | 1.00 | 20.48 | 6 |
| 1553 | N   | GLY | A | 193 | 44.317 | 76.695 | 17.671 | 1.00 | 16.93 | 7 |
| 1554 | CA  | GLY | A | 193 | 44.199 | 77.733 | 16.641 | 1.00 | 17.03 | 6 |
| 1555 | C   | GLY | A | 193 | 42.919 | 77.582 | 15.819 | 1.00 | 17.85 | 6 |
| 1556 | O   | GLY | A | 193 | 42.991 | 77.960 | 14.651 | 1.00 | 17.03 | 8 |
| 1557 | N   | PHE | A | 194 | 41.888 | 76.955 | 16.373 | 1.00 | 13.47 | 7 |
| 1558 | CA  | PHE | A | 194 | 40.612 | 76.976 | 15.567 | 1.00 | 11.84 | 6 |
| 1559 | C   | PHE | A | 194 | 39.441 | 77.265 | 16.536 | 1.00 | 11.03 | 6 |
| 1560 | O   | PHE | A | 194 | 39.621 | 77.423 | 17.750 | 1.00 | 11.69 | 8 |
| 1561 | CB  | PHE | A | 194 | 40.411 | 75.629 | 14.855 | 1.00 | 10.98 | 6 |
| 1562 | CG  | PHE | A | 194 | 40.568 | 74.412 | 15.767 | 1.00 | 11.46 | 6 |
| 1563 | CD1 | PHE | A | 194 | 39.545 | 74.063 | 16.649 | 1.00 | 11.56 | 6 |
| 1564 | CD2 | PHE | A | 194 | 41.707 | 73.656 | 15.747 | 1.00 | 15.24 | 6 |
| 1565 | CE1 | PHE | A | 194 | 39.688 | 72.942 | 17.460 | 1.00 | 11.26 | 6 |
| 1566 | CE2 | PHE | A | 194 | 41.871 | 72.533 | 16.574 | 1.00 | 12.49 | 6 |
| 1567 | CZ  | PHE | A | 194 | 40.860 | 72.181 | 17.450 | 1.00 | 12.03 | 6 |
| 1568 | N   | SER | A | 195 | 38.283 | 77.497 | 15.895 | 1.00 | 10.73 | 7 |
| 1569 | CA  | SER | A | 195 | 37.097 | 77.782 | 16.704 | 1.00 | 11.52 | 6 |
| 1570 | C   | SER | A | 195 | 36.081 | 76.649 | 16.423 | 1.00 | 11.92 | 6 |
| 1571 | O   | SER | A | 195 | 36.284 | 75.902 | 15.519 | 1.00 | 10.36 | 8 |
| 1572 | CB  | SER | A | 195 | 36.416 | 79.059 | 16.186 | 1.00 | 16.30 | 6 |
| 1573 | OG  | SER | A | 195 | 37.442 | 80.119 | 16.216 | 1.00 | 22.79 | 8 |
| 1574 | N   | LEU | A | 196 | 35.060 | 76.594 | 17.262 | 1.00 | 12.22 | 7 |
| 1575 | CA  | LEU | A | 196 | 34.007 | 75.622 | 17.060 | 1.00 | 12.16 | 6 |
| 1576 | C   | LEU | A | 196 | 32.756 | 76.384 | 16.584 | 1.00 | 7.60  | 6 |
| 1577 | O   | LEU | A | 196 | 32.364 | 77.416 | 17.112 | 1.00 | 13.16 | 8 |
| 1578 | CB  | LEU | A | 196 | 33.660 | 74.883 | 18.410 | 1.00 | 10.95 | 6 |
| 1579 | CG  | LEU | A | 196 | 34.880 | 74.298 | 19.107 | 1.00 | 10.75 | 6 |
| 1580 | CD1 | LEU | A | 196 | 34.439 | 73.454 | 20.334 | 1.00 | 11.59 | 6 |
| 1581 | CD2 | LEU | A | 196 | 35.719 | 73.384 | 18.134 | 1.00 | 12.48 | 6 |
| 1582 | N   | ALA | A | 197 | 32.139 | 75.877 | 15.481 | 1.00 | 9.97  | 7 |
| 1583 | CA  | ALA | A | 197 | 30.995 | 76.637 | 14.905 | 1.00 | 10.64 | 6 |
| 1584 | C   | ALA | A | 197 | 29.788 | 76.658 | 15.830 | 1.00 | 14.16 | 6 |
| 1585 | O   | ALA | A | 197 | 29.362 | 75.622 | 16.314 | 1.00 | 11.22 | 8 |
| 1586 | CB  | ALA | A | 197 | 30.629 | 75.928 | 13.565 | 1.00 | 10.95 | 6 |
| 1587 | N   | ASP | A | 198 | 29.429 | 77.869 | 16.236 | 1.00 | 10.28 | 7 |
| 1588 | CA  | ASP | A | 198 | 28.459 | 78.009 | 17.350 | 1.00 | 10.50 | 6 |
| 1589 | C   | ASP | A | 198 | 27.030 | 77.880 | 16.795 | 1.00 | 11.99 | 6 |
| 1590 | O   | ASP | A | 198 | 26.607 | 78.731 | 15.993 | 1.00 | 13.33 | 8 |
| 1591 | CB  | ASP | A | 198 | 28.744 | 79.433 | 17.900 | 1.00 | 12.29 | 6 |
| 1592 | CG  | ASP | A | 198 | 28.236 | 79.529 | 19.353 | 1.00 | 10.72 | 6 |
| 1593 | OD1 | ASP | A | 198 | 28.683 | 78.683 | 20.172 | 1.00 | 11.33 | 8 |
| 1594 | OD2 | ASP | A | 198 | 27.401 | 80.452 | 19.671 | 1.00 | 10.45 | 8 |
| 1595 | N   | LEU | A | 199 | 26.310 | 76.847 | 17.247 | 1.00 | 10.29 | 7 |
| 1596 | CA  | LEU | A | 199 | 24.927 | 76.690 | 16.763 | 1.00 | 8.80  | 6 |
| 1597 | C   | LEU | A | 199 | 24.086 | 77.821 | 17.321 | 1.00 | 9.88  | 6 |
| 1598 | O   | LEU | A | 199 | 24.246 | 78.320 | 18.449 | 1.00 | 11.27 | 8 |
| 1599 | CB  | LEU | A | 199 | 24.452 | 75.296 | 17.279 | 1.00 | 9.52  | 6 |
| 1600 | CG  | LEU | A | 199 | 25.178 | 74.135 | 16.526 | 1.00 | 10.88 | 6 |
| 1601 | CD1 | LEU | A | 199 | 24.799 | 72.879 | 17.321 | 1.00 | 12.59 | 6 |
| 1602 | CD2 | LEU | A | 199 | 24.658 | 74.045 | 15.071 | 1.00 | 14.19 | 6 |
| 1603 | N   | SER | A | 200 | 23.024 | 78.144 | 16.505 | 1.00 | 11.57 | 7 |
| 1604 | CA  | SER | A | 200 | 22.055 | 79.160 | 16.950 | 1.00 | 10.26 | 6 |
| 1605 | C   | SER | A | 200 | 20.810 | 78.424 | 17.499 | 1.00 | 11.50 | 6 |
| 1606 | O   | SER | A | 200 | 19.994 | 77.917 | 16.741 | 1.00 | 11.79 | 8 |
| 1607 | CB  | SER | A | 200 | 21.636 | 80.012 | 15.731 | 1.00 | 14.77 | 6 |
| 1608 | OG  | SER | A | 200 | 20.723 | 81.011 | 16.249 | 1.00 | 13.69 | 8 |
| 1609 | N   | GLN | A | 201 | 20.786 | 78.294 | 18.837 | 1.00 | 10.61 | 7 |
| 1610 | CA  | GLN | A | 201 | 19.599 | 77.668 | 19.473 | 1.00 | 11.55 | 6 |
| 1611 | C   | GLN | A | 201 | 18.421 | 78.648 | 19.371 | 1.00 | 11.79 | 6 |
| 1612 | O   | GLN | A | 201 | 17.305 | 78.161 | 19.700 | 1.00 | 12.43 | 8 |
| 1613 | CB  | GLN | A | 201 | 19.852 | 77.359 | 20.969 | 1.00 | 11.94 | 6 |
| 1614 | CG  | GLN | A | 201 | 21.042 | 76.370 | 21.151 | 1.00 | 10.05 | 6 |
| 1615 | CD  | GLN | A | 201 | 22.393 | 77.086 | 21.126 | 1.00 | 10.84 | 6 |
| 1616 | OE1 | GLN | A | 201 | 22.499 | 78.298 | 21.208 | 1.00 | 11.60 | 8 |
| 1617 | NE2 | GLN | A | 201 | 23.465 | 76.231 | 21.079 | 1.00 | 9.83  | 7 |
| 1618 | N   | GLU | A | 202 | 18.590 | 79.860 | 18.862 | 1.00 | 10.41 | 7 |
| 1619 | CA  | GLU | A | 202 | 17.434 | 80.763 | 18.667 | 1.00 | 11.55 | 6 |
| 1620 | C   | GLU | A | 202 | 16.849 | 80.531 | 17.277 | 1.00 | 14.51 | 6 |
| 1621 | O   | GLU | A | 202 | 15.856 | 81.166 | 16.903 | 1.00 | 16.57 | 8 |
| 1622 | CB  | GLU | A | 202 | 17.877 | 82.226 | 18.875 | 1.00 | 10.69 | 6 |
| 1623 | CG  | GLU | A | 202 | 18.522 | 82.442 | 20.252 | 1.00 | 9.01  | 6 |
| 1624 | CD  | GLU | A | 202 | 20.002 | 82.069 | 20.330 | 1.00 | 12.78 | 6 |
| 1625 | OE1 | GLU | A | 202 | 20.680 | 82.031 | 19.299 | 1.00 | 16.62 | 8 |

TABLE 1-continued

Atom Coordinates from the Crystal Structure of NOVAMYL

| 1626 | OE2 | GLU | A | 202 | 20.457 | 81.782 | 21.434 | 1.00 | 12.31 | 8 |
|---|---|---|---|---|---|---|---|---|---|---|
| 1627 | N | ASN | A | 203 | 17.507 | 79.704 | 16.435 | 1.00 | 11.04 | 7 |
| 1628 | CA | ASN | A | 203 | 16.939 | 79.318 | 15.142 | 1.00 | 10.64 | 6 |
| 1629 | C | ASN | A | 203 | 16.020 | 78.098 | 15.372 | 1.00 | 13.48 | 6 |
| 1630 | O | ASN | A | 203 | 16.441 | 77.148 | 16.008 | 1.00 | 12.81 | 8 |
| 1631 | CB | ASN | A | 203 | 18.105 | 78.892 | 14.217 | 1.00 | 11.71 | 6 |
| 1632 | CG | ASN | A | 203 | 17.604 | 78.307 | 12.930 | 1.00 | 15.36 | 6 |
| 1633 | OD1 | ASN | A | 203 | 17.271 | 77.124 | 12.838 | 1.00 | 15.37 | 8 |
| 1634 | ND2 | ASN | A | 203 | 17.611 | 79.108 | 11.829 | 1.00 | 15.33 | 7 |
| 1635 | N | GLY | A | 204 | 14.797 | 78.219 | 14.831 | 1.00 | 13.94 | 7 |
| 1636 | CA | GLY | A | 204 | 13.813 | 77.115 | 15.175 | 1.00 | 14.96 | 6 |
| 1637 | C | GLY | A | 204 | 14.202 | 75.766 | 14.593 | 1.00 | 12.98 | 6 |
| 1638 | O | GLY | A | 204 | 13.891 | 74.775 | 15.243 | 1.00 | 14.33 | 8 |
| 1639 | N | THR | A | 205 | 14.802 | 75.705 | 13.401 | 1.00 | 11.88 | 7 |
| 1640 | CA | THR | A | 205 | 15.279 | 74.405 | 12.894 | 1.00 | 12.45 | 6 |
| 1641 | C | THR | A | 205 | 16.275 | 73.780 | 13.856 | 1.00 | 11.35 | 6 |
| 1642 | O | THR | A | 205 | 16.161 | 72.621 | 14.172 | 1.00 | 11.84 | 8 |
| 1643 | CB | THR | A | 205 | 15.866 | 74.603 | 11.497 | 1.00 | 14.40 | 6 |
| 1644 | OG1 | THR | A | 205 | 14.760 | 75.060 | 10.662 | 1.00 | 18.35 | 8 |
| 1645 | CG2 | THR | A | 205 | 16.344 | 73.256 | 10.930 | 1.00 | 16.31 | 6 |
| 1646 | N | ILE | A | 206 | 17.295 | 74.586 | 14.188 | 1.00 | 10.89 | 7 |
| 1647 | CA | ILE | A | 206 | 18.330 | 73.996 | 15.081 | 1.00 | 10.54 | 6 |
| 1648 | C | ILE | A | 206 | 17.736 | 73.689 | 16.457 | 1.00 | 9.48 | 6 |
| 1649 | O | ILE | A | 206 | 18.081 | 72.638 | 17.051 | 1.00 | 10.61 | 8 |
| 1650 | CB | ILE | A | 206 | 19.481 | 75.017 | 15.212 | 1.00 | 9.16 | 6 |
| 1651 | CG1 | ILE | A | 206 | 20.193 | 75.155 | 13.844 | 1.00 | 12.29 | 6 |
| 1652 | CG2 | ILE | A | 206 | 20.550 | 74.624 | 16.273 | 1.00 | 11.91 | 6 |
| 1653 | CD1 | ILE | A | 206 | 20.691 | 73.847 | 13.218 | 1.00 | 12.69 | 6 |
| 1654 | N | ALA | A | 207 | 16.912 | 74.562 | 17.021 | 1.00 | 10.30 | 7 |
| 1655 | CA | ALA | A | 207 | 16.350 | 74.185 | 18.339 | 1.00 | 12.45 | 6 |
| 1656 | C | ALA | A | 207 | 15.583 | 72.871 | 18.311 | 1.00 | 12.96 | 6 |
| 1657 | O | ALA | A | 207 | 15.714 | 72.053 | 19.217 | 1.00 | 13.37 | 8 |
| 1658 | CB | ALA | A | 207 | 15.511 | 75.359 | 18.883 | 1.00 | 13.30 | 6 |
| 1659 | N | GLN | A | 208 | 14.749 | 72.676 | 17.282 | 1.00 | 10.55 | 7 |
| 1660 | CA | GLN | A | 208 | 13.968 | 71.431 | 17.236 | 1.00 | 11.60 | 6 |
| 1661 | C | GLN | A | 208 | 14.842 | 70.256 | 16.877 | 1.00 | 14.22 | 6 |
| 1662 | O | GLN | A | 208 | 14.627 | 69.200 | 17.426 | 1.00 | 11.79 | 8 |
| 1663 | CB | GLN | A | 208 | 12.869 | 71.573 | 16.136 | 1.00 | 13.62 | 6 |
| 1664 | CG | GLN | A | 208 | 11.847 | 70.429 | 16.197 | 1.00 | 14.37 | 6 |
| 1665 | CD | GLN | A | 208 | 11.089 | 70.392 | 17.513 | 1.00 | 15.09 | 6 |
| 1666 | OE1 | GLN | A | 208 | 10.565 | 71.371 | 17.957 | 1.00 | 14.67 | 8 |
| 1667 | NE2 | GLN | A | 208 | 11.168 | 69.230 | 18.180 | 1.00 | 14.23 | 7 |
| 1668 | N | TYR | A | 209 | 15.876 | 70.454 | 16.062 | 1.00 | 11.41 | 7 |
| 1669 | CA | TYR | A | 209 | 16.807 | 69.372 | 15.724 | 1.00 | 10.71 | 6 |
| 1670 | C | TYR | A | 209 | 17.570 | 68.930 | 16.979 | 1.00 | 10.31 | 6 |
| 1671 | O | TYR | A | 209 | 17.634 | 67.727 | 17.231 | 1.00 | 11.12 | 8 |
| 1672 | CB | TYR | A | 209 | 17.840 | 69.989 | 14.743 | 1.00 | 11.54 | 6 |
| 1673 | CG | TYR | A | 209 | 19.072 | 69.148 | 14.457 | 1.00 | 12.56 | 6 |
| 1674 | CD1 | TYR | A | 209 | 19.031 | 68.083 | 13.584 | 1.00 | 11.38 | 6 |
| 1675 | CD2 | TYR | A | 209 | 20.269 | 69.485 | 15.060 | 1.00 | 12.87 | 6 |
| 1676 | CE1 | TYR | A | 209 | 20.184 | 67.341 | 13.286 | 1.00 | 16.27 | 6 |
| 1677 | CE2 | TYR | A | 209 | 21.432 | 68.739 | 14.794 | 1.00 | 13.55 | 6 |
| 1678 | CZ | TYR | A | 209 | 21.368 | 67.676 | 13.915 | 1.00 | 13.50 | 6 |
| 1679 | OH | TYR | A | 209 | 22.527 | 66.968 | 13.654 | 1.00 | 14.21 | 8 |
| 1680 | N | LEU | A | 210 | 17.985 | 69.883 | 17.821 | 1.00 | 10.88 | 7 |
| 1681 | CA | LEU | A | 210 | 18.731 | 69.461 | 19.027 | 1.00 | 10.76 | 6 |
| 1682 | C | LEU | A | 210 | 17.776 | 68.829 | 20.049 | 1.00 | 11.52 | 6 |
| 1683 | O | LEU | A | 210 | 18.178 | 67.863 | 20.687 | 1.00 | 11.55 | 8 |
| 1684 | CB | LEU | A | 210 | 19.388 | 70.688 | 19.713 | 1.00 | 10.40 | 6 |
| 1685 | CG | LEU | A | 210 | 20.603 | 71.237 | 18.893 | 1.00 | 10.20 | 6 |
| 1686 | CD1 | LEU | A | 210 | 20.918 | 72.628 | 19.480 | 1.00 | 12.47 | 6 |
| 1687 | CD2 | LEU | A | 210 | 21.766 | 70.260 | 18.920 | 1.00 | 13.21 | 6 |
| 1688 | N | THR | A | 211 | 16.539 | 69.327 | 20.069 | 1.00 | 9.66 | 7 |
| 1689 | CA | THR | A | 211 | 15.520 | 68.689 | 20.933 | 1.00 | 11.98 | 6 |
| 1690 | C | THR | A | 211 | 15.294 | 67.272 | 20.496 | 1.00 | 11.93 | 6 |
| 1691 | O | THR | A | 211 | 15.311 | 66.354 | 21.335 | 1.00 | 11.42 | 8 |
| 1692 | CB | THR | A | 211 | 14.193 | 69.502 | 20.889 | 1.00 | 12.29 | 6 |
| 1693 | OG1 | THR | A | 211 | 14.488 | 70.842 | 21.373 | 1.00 | 11.73 | 8 |
| 1694 | CG2 | THR | A | 211 | 13.137 | 68.832 | 21.808 | 1.00 | 10.37 | 6 |
| 1695 | N | ASP | A | 212 | 15.071 | 67.084 | 19.170 | 1.00 | 12.47 | 7 |
| 1696 | CA | ASP | A | 212 | 14.813 | 65.738 | 18.671 | 1.00 | 10.73 | 6 |
| 1697 | C | ASP | A | 212 | 15.998 | 64.812 | 18.997 | 1.00 | 12.42 | 6 |
| 1698 | O | ASP | A | 212 | 15.748 | 63.598 | 19.194 | 1.00 | 12.22 | 8 |
| 1699 | CB | ASP | A | 212 | 14.605 | 65.829 | 17.159 | 1.00 | 12.33 | 6 |
| 1700 | CG | ASP | A | 212 | 13.253 | 66.477 | 16.797 | 1.00 | 15.18 | 6 |
| 1701 | OD1 | ASP | A | 212 | 12.379 | 66.643 | 17.667 | 1.00 | 13.61 | 8 |
| 1702 | OD2 | ASP | A | 212 | 13.100 | 66.828 | 15.585 | 1.00 | 14.64 | 8 |

TABLE 1-continued

Atom Coordinates from the Crystal Structure of NOVAMYL

| 1703 | N | ALA | A | 213 | 17.230 | 65.326 | 18.830 | 1.00 | 10.02 | 7 |
|---|---|---|---|---|---|---|---|---|---|---|
| 1704 | CA | ALA | A | 213 | 18.376 | 64.422 | 19.084 | 1.00 | 10.72 | 6 |
| 1705 | C | ALA | A | 213 | 18.422 | 64.023 | 20.552 | 1.00 | 10.18 | 6 |
| 1706 | O | ALA | A | 213 | 18.819 | 62.882 | 20.861 | 1.00 | 11.96 | 8 |
| 1707 | CB | ALA | A | 213 | 19.679 | 65.163 | 18.735 | 1.00 | 10.83 | 6 |
| 1708 | N | ALA | A | 214 | 18.155 | 64.970 | 21.448 | 1.00 | 12.55 | 7 |
| 1709 | CA | ALA | A | 214 | 18.185 | 64.599 | 22.892 | 1.00 | 10.81 | 6 |
| 1710 | C | ALA | A | 214 | 17.073 | 63.631 | 23.235 | 1.00 | 11.35 | 6 |
| 1711 | O | ALA | A | 214 | 17.246 | 62.667 | 23.953 | 1.00 | 12.75 | 8 |
| 1712 | CB | ALA | A | 214 | 18.038 | 65.876 | 23.757 | 1.00 | 10.21 | 6 |
| 1713 | N | VAL | A | 215 | 15.885 | 63.854 | 22.677 | 1.00 | 10.82 | 7 |
| 1714 | CA | VAL | A | 215 | 14.724 | 62.923 | 22.875 | 1.00 | 11.60 | 6 |
| 1715 | C | VAL | A | 215 | 15.035 | 61.577 | 22.302 | 1.00 | 13.68 | 6 |
| 1716 | O | VAL | A | 215 | 14.673 | 60.552 | 22.903 | 1.00 | 15.03 | 8 |
| 1717 | CB | VAL | A | 215 | 13.462 | 63.523 | 22.283 | 1.00 | 14.89 | 6 |
| 1718 | CG1 | VAL | A | 215 | 12.285 | 62.514 | 22.234 | 1.00 | 16.68 | 6 |
| 1719 | CG2 | VAL | A | 215 | 12.982 | 64.740 | 23.099 | 1.00 | 15.78 | 6 |
| 1720 | N | GLN | A | 216 | 15.759 | 61.496 | 21.193 | 1.00 | 12.25 | 7 |
| 1721 | CA | GLN | A | 216 | 16.153 | 60.192 | 20.632 | 1.00 | 13.52 | 6 |
| 1722 | C | GLN | A | 216 | 17.023 | 59.404 | 21.577 | 1.00 | 13.62 | 6 |
| 1723 | O | GLN | A | 216 | 16.864 | 58.192 | 21.706 | 1.00 | 12.75 | 8 |
| 1724 | CB | GLN | A | 216 | 16.814 | 60.382 | 19.232 | 1.00 | 12.82 | 6 |
| 1725 | CG | GLN | A | 216 | 17.225 | 59.032 | 18.639 | 1.00 | 14.36 | 6 |
| 1726 | CD | GLN | A | 216 | 17.856 | 59.162 | 17.261 | 1.00 | 18.32 | 6 |
| 1727 | OE1 | GLN | A | 216 | 18.762 | 59.976 | 16.980 | 1.00 | 21.98 | 8 |
| 1728 | NE2 | GLN | A | 216 | 17.392 | 58.348 | 16.335 | 1.00 | 19.07 | 7 |
| 1729 | N | LEU | A | 217 | 17.996 | 60.043 | 22.269 | 1.00 | 11.16 | 7 |
| 1730 | CA | LEU | A | 217 | 18.781 | 59.317 | 23.261 | 1.00 | 11.02 | 6 |
| 1731 | C | LEU | A | 217 | 17.885 | 58.756 | 24.396 | 1.00 | 10.47 | 6 |
| 1732 | O | LEU | A | 217 | 18.106 | 57.631 | 24.754 | 1.00 | 13.19 | 8 |
| 1733 | CB | LEU | A | 217 | 19.847 | 60.252 | 23.876 | 1.00 | 12.00 | 6 |
| 1734 | CG | LEU | A | 217 | 20.974 | 60.577 | 22.859 | 1.00 | 10.07 | 6 |
| 1735 | CD1 | LEU | A | 217 | 21.770 | 61.789 | 23.418 | 1.00 | 10.56 | 6 |
| 1736 | CD2 | LEU | A | 217 | 21.953 | 59.383 | 22.787 | 1.00 | 12.18 | 6 |
| 1737 | N | VAL | A | 218 | 16.940 | 59.584 | 24.844 | 1.00 | 10.50 | 7 |
| 1738 | CA | VAL | A | 218 | 16.027 | 59.030 | 25.884 | 1.00 | 14.12 | 6 |
| 1739 | C | VAL | A | 218 | 15.114 | 57.918 | 25.304 | 1.00 | 12.90 | 6 |
| 1740 | O | VAL | A | 218 | 14.914 | 56.898 | 25.978 | 1.00 | 14.29 | 8 |
| 1741 | CB | VAL | A | 218 | 15.121 | 60.168 | 26.376 | 1.00 | 11.91 | 6 |
| 1742 | CG1 | VAL | A | 218 | 14.131 | 59.671 | 27.428 | 1.00 | 14.89 | 6 |
| 1743 | CG2 | VAL | A | 218 | 16.045 | 61.169 | 27.107 | 1.00 | 14.59 | 6 |
| 1744 | N | ALA | A | 219 | 14.717 | 57.992 | 24.051 | 1.00 | 14.93 | 7 |
| 1745 | CA | ALA | A | 219 | 13.868 | 56.915 | 23.478 | 1.00 | 14.21 | 6 |
| 1746 | C | ALA | A | 219 | 14.647 | 55.619 | 23.377 | 1.00 | 16.64 | 6 |
| 1747 | O | ALA | A | 219 | 14.072 | 54.517 | 23.401 | 1.00 | 14.94 | 8 |
| 1748 | CB | ALA | A | 219 | 13.379 | 57.270 | 22.059 | 1.00 | 15.54 | 6 |
| 1749 | N | HIS | A | 220 | 15.959 | 55.702 | 23.258 | 1.00 | 12.54 | 7 |
| 1750 | CA | HIS | A | 220 | 16.853 | 54.570 | 23.215 | 1.00 | 14.41 | 6 |
| 1751 | C | HIS | A | 220 | 17.305 | 54.124 | 24.611 | 1.00 | 12.25 | 6 |
| 1752 | O | HIS | A | 220 | 18.194 | 53.243 | 24.711 | 1.00 | 13.99 | 8 |
| 1753 | CB | HIS | A | 220 | 18.055 | 54.802 | 22.293 | 1.00 | 11.69 | 6 |
| 1754 | CG | HIS | A | 220 | 17.630 | 54.760 | 20.840 | 1.00 | 14.69 | 6 |
| 1755 | ND1 | HIS | A | 220 | 17.984 | 53.694 | 20.064 | 1.00 | 14.71 | 7 |
| 1756 | CD2 | HIS | A | 220 | 16.928 | 55.624 | 20.077 | 1.00 | 16.42 | 6 |
| 1757 | CE1 | HIS | A | 220 | 17.518 | 53.916 | 18.823 | 1.00 | 16.42 | 6 |
| 1758 | NE2 | HIS | A | 220 | 16.855 | 55.077 | 18.794 | 1.00 | 17.85 | 7 |
| 1759 | N | GLY | A | 221 | 16.735 | 54.666 | 25.655 | 1.00 | 11.47 | 7 |
| 1760 | CA | GLY | A | 221 | 16.964 | 54.129 | 26.999 | 1.00 | 11.21 | 6 |
| 1761 | C | GLY | A | 221 | 17.655 | 55.060 | 27.965 | 1.00 | 13.22 | 6 |
| 1762 | O | GLY | A | 221 | 17.875 | 54.635 | 29.095 | 1.00 | 13.24 | 8 |
| 1763 | N | ALA | A | 222 | 18.297 | 56.111 | 27.426 | 1.00 | 12.29 | 7 |
| 1764 | CA | ALA | A | 222 | 19.139 | 56.912 | 28.356 | 1.00 | 14.03 | 6 |
| 1765 | C | ALA | A | 222 | 18.325 | 57.381 | 29.553 | 1.00 | 13.32 | 6 |
| 1766 | O | ALA | A | 222 | 17.138 | 57.794 | 29.459 | 1.00 | 10.61 | 8 |
| 1767 | CB | ALA | A | 222 | 19.700 | 58.136 | 27.618 | 1.00 | 12.95 | 6 |
| 1768 | N | ASP | A | 223 | 19.009 | 57.376 | 30.709 | 1.00 | 11.67 | 7 |
| 1769 | CA | ASP | A | 223 | 18.391 | 57.768 | 31.951 | 1.00 | 10.83 | 6 |
| 1770 | C | ASP | A | 223 | 18.621 | 59.249 | 32.306 | 1.00 | 12.58 | 6 |
| 1771 | O | ASP | A | 223 | 18.116 | 59.667 | 33.356 | 1.00 | 11.47 | 8 |
| 1772 | CB | ASP | A | 223 | 18.997 | 56.964 | 33.123 | 1.00 | 9.67 | 6 |
| 1773 | CG | ASP | A | 223 | 18.744 | 55.469 | 32.925 | 1.00 | 12.72 | 6 |
| 1774 | OD1 | ASP | A | 223 | 17.554 | 55.095 | 33.224 | 1.00 | 15.35 | 8 |
| 1775 | OD2 | ASP | A | 223 | 19.610 | 54.686 | 32.482 | 1.00 | 10.77 | 8 |
| 1776 | N | GLY | A | 224 | 19.186 | 59.972 | 31.348 | 1.00 | 11.00 | 7 |
| 1777 | CA | GLY | A | 224 | 19.393 | 61.413 | 31.651 | 1.00 | 11.62 | 6 |
| 1778 | C | GLY | A | 224 | 20.641 | 61.861 | 30.809 | 1.00 | 9.62 | 6 |
| 1779 | O | GLY | A | 224 | 21.069 | 61.107 | 29.928 | 1.00 | 9.69 | 8 |

TABLE 1-continued

Atom Coordinates from the Crystal Structure of NOVAMYL

| 1780 | N | LEU | A | 225 | 20.869 | 63.123 | 30.983 | 1.00 | 10.32 | 7 |
| 1781 | CA | LEU | A | 225 | 21.962 | 63.749 | 30.177 | 1.00 | 9.63 | 6 |
| 1782 | C | LEU | A | 225 | 22.828 | 64.566 | 31.128 | 1.00 | 10.99 | 6 |
| 1783 | O | LEU | A | 225 | 22.356 | 65.110 | 32.097 | 1.00 | 10.86 | 8 |
| 1784 | CB | LEU | A | 225 | 21.389 | 64.780 | 29.172 | 1.00 | 9.89 | 6 |
| 1785 | CG | LEU | A | 225 | 20.424 | 64.212 | 28.122 | 1.00 | 10.00 | 6 |
| 1786 | CD1 | LEU | A | 225 | 19.806 | 65.361 | 27.279 | 1.00 | 12.69 | 6 |
| 1787 | CD2 | LEU | A | 225 | 21.003 | 63.092 | 27.243 | 1.00 | 13.97 | 6 |
| 1788 | N | ARG | A | 226 | 24.135 | 64.671 | 30.790 | 1.00 | 10.52 | 7 |
| 1789 | CA | ARG | A | 226 | 24.993 | 65.777 | 31.295 | 1.00 | 9.01 | 6 |
| 1790 | C | ARG | A | 226 | 25.093 | 66.744 | 30.110 | 1.00 | 10.97 | 6 |
| 1791 | O | ARG | A | 226 | 25.628 | 66.348 | 29.083 | 1.00 | 10.94 | 8 |
| 1792 | CB | ARG | A | 226 | 26.337 | 65.159 | 31.691 | 1.00 | 9.10 | 6 |
| 1793 | CG | ARG | A | 226 | 27.381 | 66.213 | 32.158 | 1.00 | 8.52 | 6 |
| 1794 | CD | ARG | A | 226 | 28.248 | 66.648 | 30.956 | 1.00 | 9.82 | 6 |
| 1795 | NE | ARG | A | 226 | 29.438 | 67.400 | 31.425 | 1.00 | 9.22 | 7 |
| 1796 | CZ | ARG | A | 226 | 30.251 | 68.074 | 30.592 | 1.00 | 9.27 | 6 |
| 1797 | NH1 | ARG | A | 226 | 29.978 | 68.191 | 29.289 | 1.00 | 9.46 | 7 |
| 1798 | NH2 | ARG | A | 226 | 31.311 | 68.687 | 31.114 | 1.00 | 10.94 | 7 |
| 1799 | N | ILE | A | 227 | 24.590 | 67.940 | 30.262 | 1.00 | 10.46 | 7 |
| 1800 | CA | ILE | A | 227 | 24.553 | 68.901 | 29.124 | 1.00 | 7.87 | 6 |
| 1801 | C | ILE | A | 227 | 25.807 | 69.751 | 29.238 | 1.00 | 8.86 | 6 |
| 1802 | O | ILE | A | 227 | 26.042 | 70.450 | 30.199 | 1.00 | 11.29 | 8 |
| 1803 | CB | ILE | A | 227 | 23.295 | 69.783 | 29.269 | 1.00 | 9.62 | 6 |
| 1804 | CG1 | ILE | A | 227 | 22.096 | 68.814 | 29.378 | 1.00 | 10.28 | 6 |
| 1805 | CG2 | ILE | A | 227 | 23.196 | 70.601 | 27.964 | 1.00 | 11.21 | 6 |
| 1806 | CD1 | ILE | A | 227 | 20.743 | 69.547 | 29.412 | 1.00 | 15.31 | 6 |
| 1807 | N | ASP | A | 228 | 26.544 | 69.672 | 28.125 | 1.00 | 9.30 | 7 |
| 1808 | CA | ASP | A | 228 | 27.846 | 70.399 | 28.079 | 1.00 | 9.30 | 6 |
| 1809 | C | ASP | A | 228 | 27.672 | 71.915 | 27.904 | 1.00 | 9.50 | 6 |
| 1810 | O | ASP | A | 228 | 26.757 | 72.338 | 27.189 | 1.00 | 9.88 | 8 |
| 1811 | CB | ASP | A | 228 | 28.521 | 69.865 | 26.769 | 1.00 | 9.23 | 6 |
| 1812 | CG | ASP | A | 228 | 29.904 | 70.442 | 26.587 | 1.00 | 10.24 | 6 |
| 1813 | OD1 | ASP | A | 228 | 30.725 | 70.228 | 27.505 | 1.00 | 10.28 | 8 |
| 1814 | OD2 | ASP | A | 228 | 30.208 | 71.128 | 25.574 | 1.00 | 9.89 | 8 |
| 1815 | N | ALA | A | 229 | 28.575 | 72.633 | 28.582 | 1.00 | 8.93 | 7 |
| 1816 | CA | ALA | A | 229 | 28.745 | 74.068 | 28.257 | 1.00 | 9.72 | 6 |
| 1817 | C | ALA | A | 229 | 27.455 | 74.868 | 28.324 | 1.00 | 10.58 | 6 |
| 1818 | O | ALA | A | 229 | 27.123 | 75.695 | 27.464 | 1.00 | 10.73 | 8 |
| 1819 | CB | ALA | A | 229 | 29.355 | 74.180 | 26.841 | 1.00 | 9.90 | 6 |
| 1820 | N | VAL | A | 230 | 26.729 | 74.708 | 29.487 | 1.00 | 9.05 | 7 |
| 1821 | CA | VAL | A | 230 | 25.421 | 75.392 | 29.548 | 1.00 | 9.09 | 6 |
| 1822 | C | VAL | A | 230 | 25.547 | 76.905 | 29.753 | 1.00 | 10.83 | 6 |
| 1823 | O | VAL | A | 230 | 24.587 | 77.636 | 29.573 | 1.00 | 12.48 | 8 |
| 1824 | CB | VAL | A | 230 | 24.469 | 74.836 | 30.634 | 1.00 | 10.80 | 6 |
| 1825 | CG1 | VAL | A | 230 | 24.119 | 73.389 | 30.262 | 1.00 | 9.84 | 6 |
| 1826 | CG2 | VAL | A | 230 | 25.084 | 74.934 | 32.048 | 1.00 | 11.19 | 6 |
| 1827 | N | LYS | A | 231 | 26.753 | 77.312 | 30.189 | 1.00 | 9.10 | 7 |
| 1828 | CA | LYS | A | 231 | 26.988 | 78.763 | 30.234 | 1.00 | 7.91 | 6 |
| 1829 | C | LYS | A | 231 | 27.304 | 79.391 | 28.883 | 1.00 | 11.01 | 6 |
| 1830 | O | LYS | A | 231 | 27.398 | 80.604 | 28.809 | 1.00 | 13.02 | 8 |
| 1831 | CB | LYS | A | 231 | 28.173 | 79.043 | 31.209 | 1.00 | 10.48 | 6 |
| 1832 | CG | LYS | A | 231 | 29.567 | 78.801 | 30.602 | 1.00 | 10.63 | 6 |
| 1833 | CD | LYS | A | 231 | 30.599 | 78.817 | 31.758 | 1.00 | 13.70 | 6 |
| 1834 | CE | LYS | A | 231 | 30.937 | 80.205 | 32.236 | 1.00 | 13.75 | 6 |
| 1835 | NZ | LYS | A | 231 | 32.215 | 80.157 | 33.104 | 1.00 | 11.49 | 7 |
| 1836 | N | HIS | A | 232 | 27.364 | 78.589 | 27.814 | 1.00 | 9.37 | 7 |
| 1837 | CA | HIS | A | 232 | 27.744 | 79.081 | 26.480 | 1.00 | 12.72 | 6 |
| 1838 | C | HIS | A | 232 | 26.576 | 79.044 | 25.537 | 1.00 | 12.48 | 6 |
| 1839 | O | HIS | A | 232 | 26.698 | 79.505 | 24.388 | 1.00 | 9.62 | 8 |
| 1840 | CB | HIS | A | 232 | 28.849 | 78.129 | 25.915 | 1.00 | 9.94 | 6 |
| 1841 | CG | HIS | A | 232 | 30.145 | 78.345 | 26.709 | 1.00 | 9.35 | 6 |
| 1842 | ND1 | HIS | A | 232 | 30.780 | 79.598 | 26.674 | 1.00 | 11.03 | 7 |
| 1843 | CD2 | HIS | A | 232 | 30.803 | 77.530 | 27.554 | 1.00 | 11.85 | 6 |
| 1844 | CE1 | HIS | A | 232 | 31.838 | 79.483 | 27.513 | 1.00 | 12.22 | 6 |
| 1845 | NE2 | HIS | A | 232 | 31.882 | 78.243 | 28.049 | 1.00 | 11.68 | 7 |
| 1846 | N | PHE | A | 233 | 25.342 | 78.757 | 25.941 | 1.00 | 9.67 | 7 |
| 1847 | CA | PHE | A | 233 | 24.165 | 78.957 | 25.062 | 1.00 | 10.57 | 6 |
| 1848 | C | PHE | A | 233 | 23.015 | 79.437 | 25.991 | 1.00 | 9.21 | 6 |
| 1849 | O | PHE | A | 233 | 23.073 | 79.254 | 27.225 | 1.00 | 11.50 | 8 |
| 1850 | CB | PHE | A | 233 | 23.792 | 77.705 | 24.295 | 1.00 | 9.50 | 6 |
| 1851 | CG | PHE | A | 233 | 23.382 | 76.523 | 25.145 | 1.00 | 10.66 | 6 |
| 1852 | CD1 | PHE | A | 233 | 24.335 | 75.588 | 25.559 | 1.00 | 12.13 | 6 |
| 1853 | CD2 | PHE | A | 233 | 22.023 | 76.331 | 25.466 | 1.00 | 11.40 | 6 |
| 1854 | CE1 | PHE | A | 233 | 23.982 | 74.503 | 26.347 | 1.00 | 12.18 | 6 |
| 1855 | CE2 | PHE | A | 233 | 21.642 | 75.219 | 26.237 | 1.00 | 10.50 | 6 |
| 1856 | CZ | PHE | A | 233 | 22.629 | 74.340 | 26.657 | 1.00 | 11.82 | 6 |

TABLE 1-continued

Atom Coordinates from the Crystal Structure of NOVAMYL

| 1857 | N | ASN | A | 234 | 22.051 | 80.148 | 25.349 | 1.00 | 12.13 | 7 |
|---|---|---|---|---|---|---|---|---|---|---|
| 1858 | CA | ASN | A | 234 | 21.093 | 80.799 | 26.253 | 1.00 | 8.31 | 6 |
| 1859 | C | ASN | A | 234 | 20.367 | 79.859 | 27.214 | 1.00 | 9.45 | 6 |
| 1860 | O | ASN | A | 234 | 20.112 | 78.722 | 26.829 | 1.00 | 9.94 | 8 |
| 1861 | CB | ASN | A | 234 | 20.132 | 81.662 | 25.369 | 1.00 | 10.71 | 6 |
| 1862 | CG | ASN | A | 234 | 18.981 | 80.871 | 24.740 | 1.00 | 12.93 | 6 |
| 1863 | OD1 | ASN | A | 234 | 18.070 | 80.516 | 25.519 | 1.00 | 12.50 | 8 |
| 1864 | ND2 | ASN | A | 234 | 18.975 | 80.590 | 23.448 | 1.00 | 10.79 | 7 |
| 1865 | N | SER | A | 235 | 20.023 | 80.451 | 28.374 | 1.00 | 10.78 | 7 |
| 1866 | CA | SER | A | 235 | 19.401 | 79.586 | 29.396 | 1.00 | 8.67 | 6 |
| 1867 | C | SER | A | 235 | 17.906 | 79.375 | 29.177 | 1.00 | 11.06 | 6 |
| 1868 | O | SER | A | 235 | 17.399 | 78.402 | 29.759 | 1.00 | 11.56 | 8 |
| 1869 | CB | ASER | A | 235 | 19.594 | 80.196 | 30.792 | 0.60 | 11.41 | 6 |
| 1870 | OG | ASER | A | 235 | 20.974 | 80.269 | 31.098 | 0.60 | 10.81 | 8 |
| 1869 | CB | BSER | A | 235 | 19.679 | 80.067 | 30.817 | 0.40 | 10.03 | 6 |
| 1870 | OG | BSER | A | 235 | 19.311 | 81.423 | 30.914 | 0.40 | 7.85 | 8 |
| 1871 | N | GLY | A | 236 | 17.301 | 80.140 | 28.312 | 1.00 | 10.81 | 7 |
| 1872 | CA | GLY | A | 236 | 15.906 | 79.857 | 27.882 | 1.00 | 11.83 | 6 |
| 1873 | C | GLY | A | 236 | 15.821 | 78.448 | 27.289 | 1.00 | 12.34 | 6 |
| 1874 | O | GLY | A | 236 | 14.942 | 77.638 | 27.552 | 1.00 | 11.07 | 8 |
| 1875 | N | PHE | A | 237 | 16.742 | 78.158 | 26.370 | 1.00 | 10.75 | 7 |
| 1876 | CA | PHE | A | 237 | 16.793 | 76.864 | 25.702 | 1.00 | 9.60 | 6 |
| 1877 | C | PHE | A | 237 | 17.034 | 75.738 | 26.715 | 1.00 | 10.90 | 6 |
| 1878 | O | PHE | A | 237 | 16.476 | 74.641 | 26.526 | 1.00 | 10.74 | 8 |
| 1879 | CB | PHE | A | 237 | 17.714 | 76.891 | 24.467 | 1.00 | 12.14 | 6 |
| 1880 | CG | PHE | A | 237 | 17.642 | 75.595 | 23.691 | 1.00 | 12.02 | 6 |
| 1881 | CD1 | PHE | A | 237 | 16.442 | 75.242 | 23.048 | 1.00 | 12.55 | 6 |
| 1882 | CD2 | PHE | A | 237 | 18.751 | 74.740 | 23.659 | 1.00 | 11.64 | 6 |
| 1883 | CE1 | PHE | A | 237 | 16.367 | 74.046 | 22.358 | 1.00 | 12.60 | 6 |
| 1884 | CE2 | PHE | A | 237 | 18.634 | 73.533 | 22.952 | 1.00 | 11.39 | 6 |
| 1885 | CZ | PHE | A | 237 | 17.468 | 73.200 | 22.301 | 1.00 | 13.43 | 6 |
| 1886 | N | SER | A | 238 | 17.965 | 75.939 | 27.658 | 1.00 | 10.56 | 7 |
| 1887 | CA | SER | A | 238 | 18.119 | 74.844 | 28.637 | 1.00 | 11.43 | 6 |
| 1888 | C | SER | A | 238 | 16.762 | 74.489 | 29.289 | 1.00 | 10.24 | 6 |
| 1889 | O | SER | A | 238 | 16.416 | 73.312 | 29.442 | 1.00 | 10.58 | 8 |
| 1890 | CB | SER | A | 238 | 19.069 | 75.303 | 29.776 | 1.00 | 11.86 | 6 |
| 1891 | OG | SER | A | 238 | 20.432 | 75.070 | 29.404 | 1.00 | 12.16 | 8 |
| 1892 | N | LYS | A | 239 | 16.053 | 75.523 | 29.757 | 1.00 | 10.06 | 7 |
| 1893 | CA | LYS | A | 239 | 14.749 | 75.262 | 30.433 | 1.00 | 10.43 | 6 |
| 1894 | C | LYS | A | 239 | 13.712 | 74.684 | 29.505 | 1.00 | 10.95 | 6 |
| 1895 | O | LYS | A | 239 | 13.006 | 73.718 | 29.879 | 1.00 | 11.91 | 8 |
| 1896 | CB | LYS | A | 239 | 14.259 | 76.598 | 31.123 | 1.00 | 8.56 | 6 |
| 1897 | CG | LYS | A | 239 | 12.889 | 76.329 | 31.861 | 1.00 | 12.08 | 6 |
| 1898 | CD | LYS | A | 239 | 12.577 | 77.644 | 32.648 | 1.00 | 11.14 | 6 |
| 1899 | CE | LYS | A | 239 | 11.131 | 77.442 | 33.240 | 1.00 | 11.14 | 6 |
| 1900 | NZ | LYS | A | 239 | 10.797 | 78.668 | 34.098 | 1.00 | 10.40 | 7 |
| 1901 | N | SER | A | 240 | 13.600 | 75.153 | 28.279 | 1.00 | 9.61 | 7 |
| 1902 | CA | SER | A | 240 | 12.611 | 74.583 | 27.330 | 1.00 | 9.08 | 6 |
| 1903 | C | SER | A | 240 | 13.006 | 73.207 | 26.957 | 1.00 | 10.90 | 6 |
| 1904 | O | SER | A | 240 | 12.160 | 72.320 | 26.790 | 1.00 | 10.77 | 8 |
| 1905 | CB | SER | A | 240 | 12.560 | 75.572 | 26.136 | 1.00 | 11.38 | 6 |
| 1906 | OG | SER | A | 240 | 11.488 | 75.039 | 25.266 | 1.00 | 12.68 | 8 |
| 1907 | N | LEU | A | 241 | 14.300 | 72.896 | 26.747 | 1.00 | 10.43 | 7 |
| 1908 | CA | LEU | A | 241 | 14.726 | 71.560 | 26.389 | 1.00 | 10.29 | 6 |
| 1909 | C | LEU | A | 241 | 14.420 | 70.599 | 27.539 | 1.00 | 11.73 | 6 |
| 1910 | O | LEU | A | 241 | 13.924 | 69.507 | 27.303 | 1.00 | 11.15 | 8 |
| 1911 | CB | LEU | A | 241 | 16.255 | 71.582 | 26.077 | 1.00 | 10.07 | 6 |
| 1912 | CG | LEU | A | 241 | 16.816 | 70.170 | 25.829 | 1.00 | 12.71 | 6 |
| 1913 | CD1 | LEU | A | 241 | 16.205 | 69.502 | 24.577 | 1.00 | 13.39 | 6 |
| 1914 | CD2 | LEU | A | 241 | 18.333 | 70.350 | 25.611 | 1.00 | 12.90 | 6 |
| 1915 | N | ALA | A | 242 | 14.710 | 71.055 | 28.778 | 1.00 | 11.25 | 7 |
| 1916 | CA | ALA | A | 242 | 14.427 | 70.181 | 29.912 | 1.00 | 10.06 | 6 |
| 1917 | C | ALA | A | 242 | 12.923 | 69.852 | 29.969 | 1.00 | 10.68 | 6 |
| 1918 | O | ALA | A | 242 | 12.565 | 68.703 | 30.215 | 1.00 | 10.97 | 8 |
| 1919 | CB | ALA | A | 242 | 14.910 | 70.889 | 31.196 | 1.00 | 10.49 | 6 |
| 1920 | N | ASP | A | 243 | 12.062 | 70.870 | 29.712 | 1.00 | 10.40 | 7 |
| 1921 | CA | ASP | A | 243 | 10.609 | 70.595 | 29.694 | 1.00 | 11.54 | 6 |
| 1922 | C | ASP | A | 243 | 10.365 | 69.448 | 28.700 | 1.00 | 12.78 | 6 |
| 1923 | O | ASP | A | 243 | 9.636 | 68.474 | 29.006 | 1.00 | 12.31 | 8 |
| 1924 | CB | ASP | A | 243 | 9.930 | 71.904 | 29.186 | 1.00 | 11.95 | 6 |
| 1925 | CG | ASP | A | 243 | 8.507 | 71.717 | 28.674 | 1.00 | 13.21 | 6 |
| 1926 | OD1 | ASP | A | 243 | 7.668 | 71.113 | 29.422 | 1.00 | 12.98 | 8 |
| 1927 | OD2 | ASP | A | 243 | 8.223 | 72.178 | 27.546 | 1.00 | 12.92 | 8 |
| 1928 | N | LYS | A | 244 | 10.825 | 69.536 | 27.451 | 1.00 | 10.42 | 7 |
| 1929 | CA | LYS | A | 244 | 10.523 | 68.449 | 26.484 | 1.00 | 10.94 | 6 |
| 1930 | C | LYS | A | 244 | 10.997 | 67.097 | 26.998 | 1.00 | 13.31 | 6 |
| 1931 | O | LYS | A | 244 | 10.349 | 66.061 | 26.763 | 1.00 | 12.24 | 8 |

TABLE 1-continued

Atom Coordinates from the Crystal Structure of NOVAMYL

| 1932 | CB | LYS | A | 244 | 11.232 | 68.728 | 25.122 | 1.00 | 11.69 | 6 |
|---|---|---|---|---|---|---|---|---|---|---|
| 1933 | CG | LYS | A | 244 | 10.924 | 70.142 | 24.580 | 1.00 | 14.16 | 6 |
| 1934 | CD | LYS | A | 244 | 9.398 | 70.400 | 24.483 | 1.00 | 13.14 | 6 |
| 1935 | CE | LYS | A | 244 | 9.129 | 71.869 | 24.133 | 1.00 | 13.82 | 6 |
| 1936 | NZ | LYS | A | 244 | 9.582 | 72.780 | 25.269 | 1.00 | 12.11 | 7 |
| 1937 | N | LEU | A | 245 | 12.213 | 67.068 | 27.593 | 1.00 | 11.20 | 7 |
| 1938 | CA | LEU | A | 245 | 12.730 | 65.762 | 28.039 | 1.00 | 11.98 | 6 |
| 1939 | C | LEU | A | 245 | 11.936 | 65.200 | 29.205 | 1.00 | 12.96 | 6 |
| 1940 | O | LEU | A | 245 | 11.665 | 63.996 | 29.219 | 1.00 | 12.16 | 8 |
| 1941 | CB | LEU | A | 245 | 14.221 | 65.961 | 28.461 | 1.00 | 10.88 | 6 |
| 1942 | CG | LEU | A | 245 | 15.091 | 66.282 | 27.206 | 1.00 | 15.60 | 6 |
| 1943 | CD1 | LEU | A | 245 | 16.493 | 66.701 | 27.692 | 1.00 | 14.87 | 6 |
| 1944 | CD2 | LEU | A | 245 | 15.227 | 65.052 | 26.282 | 1.00 | 19.24 | 6 |
| 1945 | N | TYR | A | 246 | 11.480 | 66.037 | 30.136 | 1.00 | 11.31 | 7 |
| 1946 | CA | TYR | A | 246 | 10.676 | 65.529 | 31.258 | 1.00 | 11.13 | 6 |
| 1947 | C | TYR | A | 246 | 9.294 | 65.090 | 30.770 | 1.00 | 11.59 | 6 |
| 1948 | O | TYR | A | 246 | 8.674 | 64.306 | 31.500 | 1.00 | 13.03 | 8 |
| 1949 | CB | TYR | A | 246 | 10.582 | 66.586 | 32.359 | 1.00 | 12.53 | 6 |
| 1950 | CG | TYR | A | 246 | 11.928 | 66.907 | 32.995 | 1.00 | 9.85 | 6 |
| 1951 | CD1 | TYR | A | 246 | 12.882 | 65.941 | 33.210 | 1.00 | 11.79 | 6 |
| 1952 | CD2 | TYR | A | 246 | 12.163 | 68.228 | 33.408 | 1.00 | 10.52 | 6 |
| 1953 | CE1 | TYR | A | 246 | 14.103 | 66.245 | 33.830 | 1.00 | 11.71 | 6 |
| 1954 | CE2 | TYR | A | 246 | 13.379 | 68.569 | 34.021 | 1.00 | 10.59 | 6 |
| 1955 | CZ | TYR | A | 246 | 14.319 | 67.562 | 34.208 | 1.00 | 11.60 | 6 |
| 1956 | OH | TYR | A | 246 | 15.536 | 67.856 | 34.816 | 1.00 | 11.49 | 8 |
| 1957 | N | GLN | A | 247 | 8.769 | 65.623 | 29.672 | 1.00 | 12.54 | 7 |
| 1958 | CA | GLN | A | 247 | 7.501 | 65.088 | 29.112 | 1.00 | 13.07 | 6 |
| 1959 | C | GLN | A | 247 | 7.677 | 63.690 | 28.587 | 1.00 | 13.75 | 6 |
| 1960 | O | GLN | A | 247 | 6.712 | 62.875 | 28.651 | 1.00 | 16.16 | 8 |
| 1961 | CB | GLN | A | 247 | 7.016 | 66.001 | 27.940 | 1.00 | 12.33 | 6 |
| 1962 | CG | GLN | A | 247 | 6.530 | 67.357 | 28.518 | 1.00 | 13.62 | 6 |
| 1963 | CD | GLN | A | 247 | 6.016 | 68.220 | 27.397 | 1.00 | 16.89 | 6 |
| 1964 | OE1 | GLN | A | 247 | 5.355 | 67.699 | 26.462 | 1.00 | 18.89 | 8 |
| 1965 | NE2 | GLN | A | 247 | 6.372 | 69.518 | 27.387 | 1.00 | 14.76 | 7 |
| 1966 | N | LYS | A | 248 | 8.881 | 63.349 | 28.162 | 1.00 | 14.17 | 7 |
| 1967 | CA | LYS | A | 248 | 9.163 | 61.979 | 27.702 | 1.00 | 15.18 | 6 |
| 1968 | C | LYS | A | 248 | 9.328 | 61.000 | 28.836 | 1.00 | 15.52 | 6 |
| 1969 | O | LYS | A | 248 | 8.839 | 59.868 | 28.746 | 1.00 | 16.45 | 8 |
| 1970 | CB | ALYS | A | 248 | 10.397 | 61.994 | 26.793 | 0.50 | 13.40 | 6 |
| 1971 | CG | ALYS | A | 248 | 10.116 | 62.793 | 25.528 | 0.50 | 14.14 | 6 |
| 1972 | CD | ALYS | A | 248 | 8.958 | 62.165 | 24.749 | 0.50 | 17.69 | 6 |
| 1973 | CE | ALYS | A | 248 | 8.449 | 63.068 | 23.657 | 0.50 | 18.41 | 6 |
| 1974 | NZ | ALYS | A | 248 | 7.682 | 62.378 | 22.577 | 0.50 | 25.68 | 7 |
| 1970 | CB | BLYS | A | 248 | 10.414 | 62.030 | 26.816 | 0.50 | 17.60 | 6 |
| 1971 | CG | BLYS | A | 248 | 10.840 | 60.676 | 26.292 | 0.50 | 22.20 | 6 |
| 1972 | CD | BLYS | A | 248 | 11.561 | 60.755 | 24.977 | 0.50 | 29.85 | 6 |
| 1973 | CE | BLYS | A | 248 | 11.495 | 59.497 | 24.150 | 0.50 | 18.09 | 6 |
| 1974 | NZ | BLYS | A | 248 | 10.779 | 58.367 | 24.885 | 0.50 | 21.86 | 7 |
| 1975 | N | LYS | A | 249 | 10.131 | 61.400 | 29.830 | 1.00 | 12.97 | 7 |
| 1976 | CA | LYS | A | 249 | 10.424 | 60.442 | 30.917 | 1.00 | 14.04 | 6 |
| 1977 | C | LYS | A | 249 | 10.983 | 61.213 | 32.084 | 1.00 | 11.94 | 6 |
| 1978 | O | LYS | A | 249 | 11.520 | 62.316 | 31.876 | 1.00 | 13.26 | 8 |
| 1979 | CB | LYS | A | 249 | 11.514 | 59.423 | 30.462 | 1.00 | 15.09 | 6 |
| 1980 | CG | LYS | A | 249 | 11.674 | 58.358 | 31.542 | 1.00 | 15.17 | 6 |
| 1981 | CD | LYS | A | 249 | 12.552 | 57.175 | 31.147 | 1.00 | 23.08 | 6 |
| 1982 | CE | LYS | A | 249 | 12.451 | 56.111 | 32.249 | 1.00 | 27.89 | 6 |
| 1983 | NZ | LYS | A | 249 | 13.149 | 54.836 | 31.875 | 1.00 | 36.10 | 7 |
| 1984 | N | ASP | A | 250 | 10.870 | 60.678 | 33.288 | 1.00 | 11.41 | 7 |
| 1985 | CA | ASP | A | 250 | 11.406 | 61.336 | 34.494 | 1.00 | 12.04 | 6 |
| 1986 | C | ASP | A | 250 | 12.918 | 61.011 | 34.626 | 1.00 | 11.51 | 6 |
| 1987 | O | ASP | A | 250 | 13.348 | 60.354 | 35.546 | 1.00 | 13.89 | 8 |
| 1988 | CB | ASP | A | 250 | 10.638 | 60.891 | 35.728 | 1.00 | 11.54 | 6 |
| 1989 | CG | ASP | A | 250 | 10.618 | 59.405 | 36.030 | 1.00 | 15.08 | 6 |
| 1990 | OD1 | ASP | A | 250 | 10.695 | 58.618 | 35.085 | 1.00 | 15.58 | 8 |
| 1991 | OD2 | ASP | A | 250 | 10.448 | 59.027 | 37.224 | 1.00 | 15.73 | 8 |
| 1992 | N | ILE | A | 251 | 13.644 | 61.541 | 33.607 | 1.00 | 11.19 | 7 |
| 1993 | CA | ILE | A | 251 | 15.093 | 61.346 | 33.593 | 1.00 | 12.04 | 6 |
| 1994 | C | ILE | A | 251 | 15.777 | 62.413 | 34.467 | 1.00 | 12.14 | 6 |
| 1995 | O | ILE | A | 251 | 15.148 | 63.303 | 34.990 | 1.00 | 13.37 | 8 |
| 1996 | CB | ILE | A | 251 | 15.610 | 61.331 | 32.164 | 1.00 | 15.29 | 6 |
| 1997 | CG1 | ILE | A | 251 | 14.988 | 62.477 | 31.361 | 1.00 | 23.77 | 6 |
| 1998 | CG2 | ILE | A | 251 | 15.204 | 60.064 | 31.402 | 1.00 | 16.73 | 6 |
| 1999 | CD1 | ILE | A | 251 | 15.645 | 63.784 | 31.503 | 1.00 | 25.03 | 6 |
| 2000 | N | PHE | A | 252 | 17.122 | 62.248 | 34.639 | 1.00 | 9.99 | 7 |
| 2001 | CA | PHE | A | 252 | 17.885 | 63.182 | 35.420 | 1.00 | 9.59 | 6 |
| 2002 | C | PHE | A | 252 | 18.690 | 64.105 | 34.501 | 1.00 | 11.26 | 6 |
| 2003 | O | PHE | A | 252 | 19.347 | 63.587 | 33.596 | 1.00 | 12.38 | 8 |

TABLE 1-continued

Atom Coordinates from the Crystal Structure of NOVAMYL

| | | | | | | | | | |
|---|---|---|---|---|---|---|---|---|---|
| 2004 | CB | PHE | A | 252 | 18.916 | 62.372 | 36.275 | 1.00 | 13.00 | 6 |
| 2005 | CG | PHE | A | 252 | 19.748 | 63.290 | 37.145 | 1.00 | 11.27 | 6 |
| 2006 | CD1 | PHE | A | 252 | 19.182 | 63.951 | 38.241 | 1.00 | 12.24 | 6 |
| 2007 | CD2 | PHE | A | 252 | 21.094 | 63.494 | 36.838 | 1.00 | 12.52 | 6 |
| 2008 | CE1 | PHE | A | 252 | 19.907 | 64.802 | 39.029 | 1.00 | 11.05 | 6 |
| 2009 | CE2 | PHE | A | 252 | 21.843 | 64.327 | 37.664 | 1.00 | 11.26 | 6 |
| 2010 | CZ | PHE | A | 252 | 21.263 | 65.031 | 38.750 | 1.00 | 10.84 | 6 |
| 2011 | N | LEU | A | 253 | 18.740 | 65.389 | 34.772 | 1.00 | 12.09 | 7 |
| 2012 | CA | LEU | A | 253 | 19.592 | 66.278 | 33.936 | 1.00 | 9.30 | 6 |
| 2013 | C | LEU | A | 253 | 20.498 | 67.083 | 34.913 | 1.00 | 9.94 | 6 |
| 2014 | O | LEU | A | 253 | 20.094 | 67.647 | 35.914 | 1.00 | 11.26 | 8 |
| 2015 | CB | LEU | A | 253 | 18.694 | 67.378 | 33.282 | 1.00 | 8.72 | 6 |
| 2016 | CG | LEU | A | 253 | 17.749 | 66.766 | 32.216 | 1.00 | 10.91 | 6 |
| 2017 | CD1 | LEU | A | 253 | 16.881 | 67.891 | 31.562 | 1.00 | 10.35 | 6 |
| 2018 | CD2 | LEU | A | 253 | 18.508 | 66.051 | 31.089 | 1.00 | 12.13 | 6 |
| 2019 | N | VAL | A | 254 | 21.761 | 67.179 | 34.422 | 1.00 | 11.23 | 7 |
| 2020 | CA | VAL | A | 254 | 22.750 | 68.015 | 35.077 | 1.00 | 11.09 | 6 |
| 2021 | C | VAL | A | 254 | 23.423 | 68.807 | 33.921 | 1.00 | 10.26 | 6 |
| 2022 | O | VAL | A | 254 | 23.707 | 68.196 | 32.892 | 1.00 | 10.32 | 8 |
| 2023 | CB | VAL | A | 254 | 23.722 | 67.184 | 35.947 | 1.00 | 9.61 | 6 |
| 2024 | CG1 | VAL | A | 254 | 24.552 | 66.161 | 35.161 | 1.00 | 10.99 | 6 |
| 2025 | CG2 | VAL | A | 254 | 24.688 | 68.131 | 36.685 | 1.00 | 11.22 | 6 |
| 2026 | N | GLY | A | 255 | 23.762 | 70.047 | 34.194 | 1.00 | 10.96 | 7 |
| 2027 | CA | GLY | A | 255 | 24.492 | 70.879 | 33.243 | 1.00 | 11.43 | 6 |
| 2028 | C | GLY | A | 255 | 25.877 | 71.193 | 33.731 | 1.00 | 11.23 | 6 |
| 2029 | O | GLY | A | 255 | 26.095 | 71.404 | 34.967 | 1.00 | 10.31 | 8 |
| 2030 | N | GLU | A | 256 | 26.828 | 71.308 | 32.765 | 1.00 | 10.72 | 7 |
| 2031 | CA | GLU | A | 256 | 28.159 | 71.786 | 33.187 | 1.00 | 10.84 | 6 |
| 2032 | C | GLU | A | 256 | 28.236 | 73.315 | 33.013 | 1.00 | 11.33 | 6 |
| 2033 | O | GLU | A | 256 | 28.295 | 73.820 | 31.871 | 1.00 | 10.36 | 8 |
| 2034 | CB | GLU | A | 256 | 29.172 | 71.178 | 32.167 | 1.00 | 10.52 | 6 |
| 2035 | CG | GLU | A | 256 | 30.603 | 71.617 | 32.605 | 1.00 | 10.70 | 6 |
| 2036 | CD | GLU | A | 256 | 31.442 | 72.059 | 31.414 | 1.00 | 11.32 | 6 |
| 2037 | OE1 | GLU | A | 256 | 30.925 | 72.467 | 30.347 | 1.00 | 10.78 | 8 |
| 2038 | OE2 | GLU | A | 256 | 32.696 | 71.998 | 31.517 | 1.00 | 11.88 | 8 |
| 2039 | N | TRP | A | 257 | 28.173 | 74.038 | 34.120 | 1.00 | 9.79 | 7 |
| 2040 | CA | TRP | A | 257 | 28.409 | 75.480 | 34.158 | 1.00 | 9.57 | 6 |
| 2041 | C | TRP | A | 257 | 29.798 | 75.608 | 34.799 | 1.00 | 10.84 | 6 |
| 2042 | O | TRP | A | 257 | 29.908 | 75.560 | 36.037 | 1.00 | 10.82 | 8 |
| 2043 | CB | TRP | A | 257 | 27.301 | 76.175 | 34.997 | 1.00 | 9.83 | 6 |
| 2044 | CG | TRP | A | 257 | 27.449 | 77.700 | 34.854 | 1.00 | 8.59 | 6 |
| 2045 | CD1 | TRP | A | 257 | 28.566 | 78.442 | 35.196 | 1.00 | 12.90 | 6 |
| 2046 | CD2 | TRP | A | 257 | 26.431 | 78.592 | 34.412 | 1.00 | 10.35 | 6 |
| 2047 | NE1 | TRP | A | 257 | 28.295 | 79.753 | 34.937 | 1.00 | 12.55 | 7 |
| 2048 | CE2 | TRP | A | 257 | 27.020 | 79.891 | 34.459 | 1.00 | 12.29 | 6 |
| 2049 | CE3 | TRP | A | 257 | 25.124 | 78.425 | 33.946 | 1.00 | 13.94 | 6 |
| 2050 | CZ2 | TRP | A | 257 | 26.317 | 81.041 | 34.055 | 1.00 | 10.73 | 6 |
| 2051 | CZ3 | TRP | A | 257 | 24.385 | 79.544 | 33.527 | 1.00 | 13.32 | 6 |
| 2052 | CH2 | TRP | A | 257 | 25.026 | 80.793 | 33.599 | 1.00 | 11.64 | 6 |
| 2053 | N | TYR | A | 258 | 30.831 | 75.725 | 33.986 | 1.00 | 11.79 | 7 |
| 2054 | CA | TRY | A | 258 | 32.211 | 75.619 | 34.524 | 1.00 | 11.80 | 6 |
| 2055 | C | TYR | A | 258 | 32.527 | 76.859 | 35.355 | 1.00 | 12.06 | 6 |
| 2056 | O | TYR | A | 258 | 32.370 | 77.988 | 34.869 | 1.00 | 13.57 | 8 |
| 2057 | CB | TYR | A | 258 | 33.189 | 75.508 | 33.335 | 1.00 | 11.31 | 6 |
| 2058 | CG | TYR | A | 258 | 34.562 | 74.978 | 33.723 | 1.00 | 11.97 | 6 |
| 2059 | CD1 | TYR | A | 258 | 35.452 | 75.687 | 34.524 | 1.00 | 13.71 | 6 |
| 2060 | CD2 | TYR | A | 258 | 34.932 | 73.734 | 33.234 | 1.00 | 11.78 | 6 |
| 2061 | CE1 | TYR | A | 258 | 36.707 | 75.160 | 34.859 | 1.00 | 15.77 | 6 |
| 2062 | CE2 | TYR | A | 258 | 36.179 | 73.226 | 33.564 | 1.00 | 13.38 | 6 |
| 2063 | CZ | TYR | A | 258 | 37.037 | 73.908 | 34.376 | 1.00 | 16.44 | 6 |
| 2064 | OH | TYR | A | 258 | 38.277 | 73.304 | 34.631 | 1.00 | 20.59 | 8 |
| 2065 | N | GLY | A | 259 | 33.030 | 76.605 | 36.550 | 1.00 | 9.86 | 7 |
| 2066 | CA | GLY | A | 259 | 33.584 | 77.705 | 37.361 | 1.00 | 12.24 | 6 |
| 2067 | C | GLY | A | 259 | 32.510 | 78.690 | 37.891 | 1.00 | 11.55 | 6 |
| 2068 | O | GLY | A | 259 | 31.417 | 78.276 | 38.227 | 1.00 | 12.61 | 8 |
| 2069 | N | ASP | A | 260 | 32.921 | 79.963 | 37.891 | 1.00 | 11.45 | 7 |
| 2070 | CA | ASP | A | 260 | 32.064 | 81.004 | 38.486 | 1.00 | 10.59 | 6 |
| 2071 | C | ASP | A | 260 | 31.718 | 80.614 | 39.947 | 1.00 | 12.08 | 6 |
| 2072 | O | ASP | A | 260 | 30.554 | 80.528 | 40.317 | 1.00 | 11.34 | 8 |
| 2073 | CB | ASP | A | 260 | 30.792 | 81.286 | 37.665 | 1.00 | 13.01 | 6 |
| 2074 | CG | ASP | A | 260 | 31.160 | 81.807 | 36.269 | 1.00 | 16.43 | 6 |
| 2075 | OD1 | ASP | A | 260 | 32.136 | 82.593 | 36.148 | 1.00 | 13.58 | 6 |
| 2076 | OD2 | ASP | A | 260 | 30.486 | 81.502 | 35.274 | 1.00 | 14.47 | 8 |
| 2077 | N | ASP | A | 261 | 32.812 | 80.528 | 40.708 | 1.00 | 10.89 | 7 |
| 2078 | CA | ASP | A | 261 | 32.709 | 80.239 | 42.158 | 1.00 | 13.96 | 6 |
| 2079 | C | ASP | A | 261 | 32.059 | 81.369 | 42.936 | 1.00 | 12.00 | 6 |
| 2080 | O | ASP | A | 261 | 31.920 | 82.528 | 42.502 | 1.00 | 13.08 | 8 |

TABLE 1-continued

Atom Coordinates from the Crystal Structure of NOVAMYL

| 2081 | CB | ASP | A | 261 | 34.125 | 79.875 | 42.610 | 1.00 | 17.34 | 6 |
|---|---|---|---|---|---|---|---|---|---|---|
| 2082 | CG | ASP | A | 261 | 34.615 | 78.518 | 42.074 | 1.00 | 18.47 | 6 |
| 2083 | OD1 | ASP | A | 261 | 33.990 | 77.881 | 41.181 | 1.00 | 22.23 | 8 |
| 2084 | OD2 | ASP | A | 261 | 35.642 | 78.035 | 42.569 | 1.00 | 20.46 | 8 |
| 2085 | N | PRO | A | 262 | 31.751 | 81.124 | 44.230 | 1.00 | 11.36 | 7 |
| 2086 | CA | PRO | A | 262 | 31.155 | 82.197 | 45.033 | 1.00 | 13.50 | 6 |
| 2087 | C | PRO | A | 262 | 32.085 | 83.428 | 45.042 | 1.00 | 15.27 | 6 |
| 2088 | O | PRO | A | 262 | 33.325 | 83.254 | 45.078 | 1.00 | 17.80 | 8 |
| 2089 | CB | PRO | A | 262 | 30.973 | 81.583 | 46.445 | 1.00 | 14.74 | 6 |
| 2090 | CG | PRO | A | 262 | 30.818 | 80.086 | 46.071 | 1.00 | 13.76 | 6 |
| 2091 | CD | PRO | A | 262 | 31.873 | 79.856 | 44.938 | 1.00 | 11.66 | 6 |
| 2092 | N | GLY | A | 263 | 31.385 | 84.560 | 45.069 | 1.00 | 20.11 | 7 |
| 2093 | CA | GLY | A | 263 | 32.178 | 85.810 | 45.091 | 1.00 | 20.82 | 6 |
| 2094 | C | GLY | A | 263 | 32.444 | 86.343 | 43.693 | 1.00 | 22.93 | 6 |
| 2095 | O | GLY | A | 263 | 33.030 | 87.433 | 43.565 | 1.00 | 26.12 | 8 |
| 2096 | N | THR | A | 264 | 32.204 | 85.581 | 42.640 | 1.00 | 16.30 | 7 |
| 2097 | CA | THR | A | 264 | 32.579 | 85.990 | 41.270 | 1.00 | 15.29 | 6 |
| 2098 | C | THR | A | 264 | 31.378 | 86.647 | 40.599 | 1.00 | 14.14 | 6 |
| 2099 | O | THR | A | 264 | 30.225 | 86.490 | 41.019 | 1.00 | 15.14 | 8 |
| 2100 | CB | THR | A | 264 | 33.154 | 84.890 | 40.377 | 1.00 | 17.00 | 6 |
| 2101 | OG1 | THR | A | 264 | 32.185 | 83.864 | 40.214 | 1.00 | 17.20 | 8 |
| 2102 | CG2 | THR | A | 264 | 34.455 | 84.302 | 40.998 | 1.00 | 18.53 | 6 |
| 2103 | N | ALA | A | 265 | 31.684 | 87.407 | 39.536 | 1.00 | 14.47 | 7 |
| 2104 | CA | ALA | A | 265 | 30.579 | 88.206 | 38.957 | 1.00 | 16.68 | 6 |
| 2105 | C | ALA | A | 265 | 29.455 | 87.387 | 38.348 | 1.00 | 14.50 | 6 |
| 2106 | O | ALA | A | 265 | 28.315 | 87.921 | 38.316 | 1.00 | 15.71 | 8 |
| 2107 | CB | ALA | A | 265 | 31.153 | 89.034 | 37.793 | 1.00 | 18.93 | 6 |
| 2108 | N | ASN | A | 266 | 29.808 | 86.186 | 37.837 | 1.00 | 11.26 | 7 |
| 2109 | CA | ASN | A | 266 | 28.739 | 85.402 | 37.199 | 1.00 | 12.93 | 6 |
| 2110 | C | ASN | A | 266 | 28.140 | 84.338 | 38.110 | 1.00 | 13.52 | 6 |
| 2111 | O | ASN | A | 266 | 27.364 | 83.484 | 37.632 | 1.00 | 11.82 | 8 |
| 2112 | CB | ASN | A | 266 | 29.289 | 84.792 | 35.855 | 1.00 | 15.03 | 6 |
| 2113 | CG | ASN | A | 266 | 29.632 | 85.944 | 34.889 | 1.00 | 15.26 | 6 |
| 2114 | OD1 | ASN | A | 266 | 28.938 | 86.955 | 34.822 | 1.00 | 13.24 | 8 |
| 2115 | ND2 | ASN | A | 266 | 30.698 | 85.797 | 34.146 | 1.00 | 14.64 | 7 |
| 2116 | N | HIS | A | 267 | 28.621 | 84.306 | 39.353 | 1.00 | 12.23 | 7 |
| 2117 | CA | HIS | A | 267 | 28.106 | 83.276 | 40.271 | 1.00 | 13.10 | 6 |
| 2118 | C | HIS | A | 267 | 26.596 | 83.276 | 40.469 | 1.00 | 13.44 | 6 |
| 2119 | O | HIS | A | 267 | 25.999 | 82.182 | 40.399 | 1.00 | 12.11 | 8 |
| 2120 | CB | HIS | A | 267 | 28.852 | 83.439 | 41.616 | 1.00 | 10.82 | 6 |
| 2121 | CG | HIS | A | 267 | 28.469 | 82.306 | 42.563 | 1.00 | 12.37 | 6 |
| 2122 | ND1 | HIS | A | 267 | 28.877 | 81.020 | 42.410 | 1.00 | 11.65 | 7 |
| 2123 | CD2 | HIS | A | 267 | 27.637 | 82.360 | 43.640 | 1.00 | 15.29 | 6 |
| 2124 | CE1 | HIS | A | 267 | 28.355 | 80.278 | 43.375 | 1.00 | 12.97 | 6 |
| 2125 | NE2 | HIS | A | 267 | 27.608 | 81.080 | 44.153 | 1.00 | 11.63 | 7 |
| 2126 | N | LEU | A | 268 | 26.001 | 84.430 | 40.726 | 1.00 | 10.81 | 7 |
| 2127 | CA | LEU | A | 268 | 24.548 | 84.455 | 40.988 | 1.00 | 13.40 | 6 |
| 2128 | C | LEU | A | 268 | 23.766 | 83.997 | 39.768 | 1.00 | 11.02 | 6 |
| 2129 | O | LEU | A | 268 | 22.745 | 83.268 | 39.957 | 1.00 | 12.74 | 8 |
| 2130 | CB | LEU | A | 268 | 24.169 | 85.889 | 41.374 | 1.00 | 14.95 | 6 |
| 2131 | CG | LEU | A | 268 | 22.599 | 86.052 | 41.471 | 1.00 | 19.99 | 6 |
| 2132 | CD1 | LEU | A | 268 | 22.040 | 85.151 | 42.563 | 1.00 | 24.25 | 6 |
| 2133 | CD2 | LEU | A | 268 | 22.298 | 87.536 | 41.677 | 1.00 | 25.18 | 6 |
| 2134 | N | GLU | A | 269 | 24.210 | 84.274 | 38.549 | 1.00 | 11.51 | 7 |
| 2135 | CA | GLU | A | 269 | 23.495 | 83.760 | 37.381 | 1.00 | 11.81 | 6 |
| 2136 | C | GLU | A | 269 | 23.525 | 82.221 | 37.386 | 1.00 | 10.11 | 6 |
| 2137 | O | GLU | A | 269 | 22.512 | 81.596 | 37.067 | 1.00 | 11.07 | 8 |
| 2138 | CB | GLU | A | 269 | 24.190 | 84.360 | 36.122 | 1.00 | 13.26 | 6 |
| 2139 | CG | GLU | A | 269 | 23.490 | 83.803 | 34.867 | 1.00 | 11.45 | 6 |
| 2140 | CD | GLU | A | 269 | 24.122 | 84.417 | 33.582 | 1.00 | 13.11 | 6 |
| 2141 | OE1 | GLU | A | 269 | 24.906 | 85.369 | 33.643 | 1.00 | 12.92 | 8 |
| 2142 | OE2 | GLU | A | 269 | 23.720 | 83.906 | 32.525 | 1.00 | 12.17 | 8 |
| 2143 | N | LYS | A | 270 | 24.678 | 81.608 | 37.720 | 1.00 | 9.00 | 7 |
| 2144 | CA | LYS | A | 270 | 24.754 | 80.156 | 37.787 | 1.00 | 9.72 | 6 |
| 2145 | C | LYS | A | 270 | 23.806 | 79.578 | 38.862 | 1.00 | 10.98 | 6 |
| 2146 | O | LYS | A | 270 | 23.079 | 78.613 | 38.609 | 1.00 | 10.64 | 8 |
| 2147 | CB | LYS | A | 270 | 26.221 | 79.709 | 38.063 | 1.00 | 10.49 | 6 |
| 2148 | CG | LYS | A | 270 | 26.259 | 78.174 | 38.299 | 1.00 | 10.05 | 6 |
| 2149 | CD | LYS | A | 270 | 27.725 | 77.682 | 38.502 | 1.00 | 8.77 | 6 |
| 2150 | CE | LYS | A | 270 | 28.236 | 78.181 | 39.869 | 1.00 | 9.57 | 6 |
| 2151 | NZ | LYS | A | 270 | 29.600 | 77.515 | 40.161 | 1.00 | 11.56 | 7 |
| 2152 | N | VAL | A | 271 | 23.765 | 80.218 | 40.038 | 1.00 | 11.90 | 7 |
| 2153 | CA | VAL | A | 271 | 22.847 | 79.712 | 41.105 | 1.00 | 10.97 | 6 |
| 2154 | C | VAL | A | 271 | 21.392 | 79.835 | 40.608 | 1.00 | 10.81 | 6 |
| 2155 | O | VAL | A | 271 | 20.583 | 78.951 | 40.827 | 1.00 | 11.67 | 8 |
| 2156 | CB | VAL | A | 271 | 23.044 | 80.608 | 42.346 | 1.00 | 13.53 | 6 |
| 2157 | CG1 | VAL | A | 271 | 22.016 | 80.248 | 43.435 | 1.00 | 12.11 | 6 |

TABLE 1-continued

Atom Coordinates from the Crystal Structure of NOVAMYL

| | | | | | | | | | |
|---|---|---|---|---|---|---|---|---|---|
| 2158 | CG2 | VAL | A | 271 | 24.455 | 80.307 | 42.888 | 1.00 | 12.46 | 6 |
| 2159 | N | ARG | A | 272 | 21.064 | 80.978 | 39.983 | 1.00 | 11.20 | 7 |
| 2160 | CA | ARG | A | 272 | 19.668 | 81.127 | 39.458 | 1.00 | 11.53 | 6 |
| 2161 | C | ARG | A | 272 | 19.328 | 80.041 | 38.439 | 1.00 | 10.29 | 6 |
| 2162 | O | ARG | A | 272 | 18.208 | 79.506 | 38.389 | 1.00 | 11.34 | 8 |
| 2163 | CB | ARG | A | 272 | 19.462 | 82.540 | 38.859 | 1.00 | 9.74 | 6 |
| 2164 | CG | ARG | A | 272 | 19.220 | 83.552 | 40.027 | 1.00 | 11.97 | 6 |
| 2165 | CD | ARG | A | 272 | 19.405 | 85.000 | 39.483 | 1.00 | 10.96 | 6 |
| 2166 | NE | ARG | A | 272 | 18.600 | 85.394 | 38.306 | 1.00 | 12.10 | 7 |
| 2167 | CZ | ARG | A | 272 | 17.297 | 85.759 | 38.377 | 1.00 | 14.61 | 6 |
| 2168 | NH1 | ARG | A | 272 | 16.541 | 85.765 | 39.493 | 1.00 | 12.14 | 7 |
| 2169 | NH2 | ARG | A | 272 | 16.734 | 86.132 | 37.232 | 1.00 | 12.07 | 7 |
| 2170 | N | TYR | A | 273 | 20.329 | 79.790 | 37.553 | 1.00 | 10.33 | 7 |
| 2171 | CA | TYR | A | 273 | 20.116 | 78.669 | 36.589 | 1.00 | 11.57 | 6 |
| 2172 | C | TYR | A | 273 | 19.882 | 77.355 | 37.328 | 1.00 | 9.14 | 6 |
| 2173 | O | TYR | A | 273 | 18.931 | 76.590 | 36.993 | 1.00 | 12.29 | 8 |
| 2174 | CB | TYR | A | 273 | 21.415 | 78.569 | 35.742 | 1.00 | 9.07 | 6 |
| 2175 | CG | TYR | A | 273 | 21.388 | 77.445 | 34.693 | 1.00 | 8.78 | 6 |
| 2176 | CD1 | TYR | A | 273 | 21.708 | 76.144 | 35.110 | 1.00 | 11.52 | 6 |
| 2177 | CD2 | TYR | A | 273 | 21.054 | 77.630 | 33.363 | 1.00 | 9.55 | 6 |
| 2178 | CE1 | TYR | A | 273 | 21.663 | 75.071 | 34.218 | 1.00 | 9.62 | 6 |
| 2179 | CE2 | TYR | A | 273 | 21.087 | 76.577 | 32.482 | 1.00 | 8.45 | 6 |
| 2180 | CZ | TYR | A | 273 | 21.366 | 75.301 | 32.885 | 1.00 | 10.47 | 6 |
| 2181 | OH | TYR | A | 273 | 21.365 | 74.258 | 31.956 | 1.00 | 11.35 | 8 |
| 2182 | N | ALA | A | 274 | 20.678 | 77.001 | 38.308 | 1.00 | 10.68 | 7 |
| 2183 | CA | ALA | A | 274 | 20.449 | 75.697 | 39.008 | 1.00 | 10.66 | 6 |
| 2184 | C | ALA | A | 274 | 19.062 | 75.725 | 39.677 | 1.00 | 10.79 | 6 |
| 2185 | O | ALA | A | 274 | 18.478 | 74.649 | 39.796 | 1.00 | 11.53 | 8 |
| 2186 | CB | ALA | A | 274 | 21.539 | 75.560 | 40.092 | 1.00 | 12.82 | 6 |
| 2187 | N | ASN | A | 275 | 18.692 | 76.887 | 40.217 | 1.00 | 11.15 | 7 |
| 2188 | CA | ASN | A | 275 | 17.443 | 76.882 | 40.998 | 1.00 | 11.26 | 6 |
| 2189 | C | ASN | A | 275 | 16.199 | 77.051 | 40.131 | 1.00 | 10.88 | 6 |
| 2190 | O | ASN | A | 275 | 15.082 | 76.705 | 40.606 | 1.00 | 11.83 | 8 |
| 2191 | CB | ASN | A | 275 | 17.490 | 78.056 | 42.004 | 1.00 | 11.31 | 6 |
| 2192 | CG | ASN | A | 275 | 18.495 | 77.768 | 43.107 | 1.00 | 11.97 | 6 |
| 2193 | OD1 | ASN | A | 275 | 18.987 | 76.661 | 43.214 | 1.00 | 12.55 | 8 |
| 2194 | ND2 | ASN | A | 275 | 18.759 | 78.816 | 43.934 | 1.00 | 12.55 | 7 |
| 2195 | N | ASN | A | 276 | 16.322 | 77.453 | 38.842 | 1.00 | 11.20 | 7 |
| 2196 | CA | ASN | A | 276 | 15.129 | 77.705 | 38.045 | 1.00 | 12.25 | 6 |
| 2197 | C | ASN | A | 276 | 15.023 | 76.992 | 36.720 | 1.00 | 14.18 | 6 |
| 2198 | O | ASN | A | 276 | 13.932 | 76.820 | 36.165 | 1.00 | 11.89 | 8 |
| 2199 | CB | ASN | A | 276 | 15.134 | 79.197 | 37.632 | 1.00 | 9.94 | 6 |
| 2200 | CG | ASN | A | 276 | 14.629 | 80.023 | 38.806 | 1.00 | 14.75 | 6 |
| 2201 | OD1 | ASN | A | 276 | 13.365 | 80.089 | 38.826 | 1.00 | 16.83 | 8 |
| 2202 | ND2 | ASN | A | 276 | 15.551 | 80.529 | 39.612 | 1.00 | 16.12 | 7 |
| 2203 | N | SER | A | 277 | 16.151 | 76.504 | 36.173 | 1.00 | 10.52 | 7 |
| 2204 | CA | SER | A | 277 | 16.064 | 75.974 | 34.811 | 1.00 | 11.82 | 6 |
| 2205 | C | SER | A | 277 | 15.497 | 74.585 | 34.678 | 1.00 | 11.16 | 6 |
| 2206 | O | SER | A | 277 | 15.204 | 74.178 | 33.545 | 1.00 | 12.16 | 8 |
| 2207 | CB | SER | A | 277 | 17.502 | 75.911 | 34.204 | 1.00 | 11.66 | 6 |
| 2208 | OG | SER | A | 277 | 18.257 | 74.877 | 34.872 | 1.00 | 12.14 | 8 |
| 2209 | N | GLY | A | 278 | 15.371 | 73.851 | 35.795 | 1.00 | 11.36 | 7 |
| 2210 | CA | GLY | A | 278 | 15.051 | 72.411 | 35.697 | 1.00 | 11.40 | 6 |
| 2211 | C | GLY | A | 278 | 16.263 | 71.565 | 35.375 | 1.00 | 11.97 | 6 |
| 2212 | O | GLY | A | 278 | 16.115 | 70.348 | 35.279 | 1.00 | 13.61 | 8 |
| 2213 | N | VAL | A | 279 | 17.442 | 72.180 | 35.342 | 1.00 | 12.14 | 7 |
| 2214 | CA | VAL | A | 279 | 18.673 | 71.427 | 35.090 | 1.00 | 10.48 | 6 |
| 2215 | C | VAL | A | 279 | 19.552 | 71.645 | 36.348 | 1.00 | 11.31 | 6 |
| 2216 | O | VAL | A | 279 | 19.814 | 72.782 | 36.732 | 1.00 | 12.60 | 8 |
| 2217 | CB | VAL | A | 279 | 19.362 | 71.989 | 33.830 | 1.00 | 11.56 | 6 |
| 2218 | CG1 | VAL | A | 279 | 20.628 | 71.191 | 33.543 | 1.00 | 10.87 | 6 |
| 2219 | CG2 | VAL | A | 279 | 18.429 | 71.824 | 32.592 | 1.00 | 13.38 | 6 |
| 2220 | N | ASN | A | 280 | 20.053 | 70.556 | 36.919 | 1.00 | 10.03 | 7 |
| 2221 | CA | ASN | A | 280 | 20.918 | 70.714 | 38.122 | 1.00 | 10.49 | 6 |
| 2222 | C | ASN | A | 280 | 22.294 | 71.095 | 37.572 | 1.00 | 13.05 | 6 |
| 2223 | O | ASN | A | 280 | 22.506 | 71.116 | 36.365 | 1.00 | 12.57 | 8 |
| 2224 | CB | ASN | A | 280 | 20.968 | 69.368 | 38.864 | 1.00 | 11.26 | 6 |
| 2225 | CG | ASN | A | 280 | 19.492 | 69.056 | 39.263 | 1.00 | 9.85 | 6 |
| 2226 | OD1 | ASN | A | 280 | 18.839 | 69.805 | 39.990 | 1.00 | 10.91 | 8 |
| 2227 | ND2 | ASN | A | 280 | 18.974 | 67.913 | 38.787 | 1.00 | 10.65 | 7 |
| 2228 | N | VAL | A | 281 | 23.262 | 71.312 | 38.492 | 1.00 | 11.45 | 7 |
| 2229 | CA | VAL | A | 281 | 24.622 | 71.621 | 37.977 | 1.00 | 9.71 | 6 |
| 2230 | C | VAL | A | 281 | 25.671 | 70.782 | 38.660 | 1.00 | 11.24 | 6 |
| 2231 | O | VAL | A | 281 | 25.581 | 70.318 | 39.799 | 1.00 | 11.15 | 8 |
| 2232 | CB | VAL | A | 281 | 25.013 | 73.104 | 38.187 | 1.00 | 9.82 | 6 |
| 2233 | CG1 | VAL | A | 281 | 24.019 | 74.024 | 37.397 | 1.00 | 10.47 | 6 |
| 2234 | CG2 | VAL | A | 281 | 25.038 | 73.569 | 39.638 | 1.00 | 11.52 | 6 |

TABLE 1-continued

Atom Coordinates from the Crystal Structure of NOVAMYL

| 2235 | N | LEU | A | 282 | 26.786 | 70.675 | 37.904 | 1.00 | 9.31 | 7 |
|---|---|---|---|---|---|---|---|---|---|---|
| 2236 | CA | LEU | A | 282 | 28.031 | 70.087 | 38.460 | 1.00 | 10.27 | 6 |
| 2237 | C | LEU | A | 282 | 28.631 | 71.063 | 39.476 | 1.00 | 11.17 | 6 |
| 2238 | O | LEU | A | 282 | 28.577 | 72.295 | 39.298 | 1.00 | 12.65 | 8 |
| 2239 | CB | LEU | A | 282 | 29.022 | 69.883 | 37.283 | 1.00 | 10.13 | 6 |
| 2240 | CG | LEU | A | 282 | 28.650 | 68.558 | 36.538 | 1.00 | 11.97 | 6 |
| 2241 | CD1 | LEU | A | 282 | 29.159 | 68.726 | 35.102 | 1.00 | 16.51 | 6 |
| 2242 | CD2 | LEU | A | 282 | 29.314 | 67.351 | 37.196 | 1.00 | 12.93 | 6 |
| 2243 | N | ASP | A | 283 | 29.128 | 70.458 | 40.581 | 1.00 | 9.33 | 7 |
| 2244 | CA | ASP | A | 283 | 29.503 | 71.304 | 41.764 | 1.00 | 11.76 | 6 |
| 2245 | C | ASP | A | 283 | 30.935 | 71.778 | 41.696 | 1.00 | 11.31 | 6 |
| 2246 | O | ASP | A | 283 | 31.877 | 71.275 | 42.316 | 1.00 | 11.22 | 8 |
| 2247 | CB | ASP | A | 283 | 29.212 | 70.451 | 43.014 | 1.00 | 8.73 | 6 |
| 2248 | CG | ASP | A | 283 | 29.282 | 71.343 | 44.271 | 1.00 | 11.60 | 6 |
| 2249 | OD1 | ASP | A | 283 | 29.655 | 72.526 | 44.259 | 1.00 | 10.06 | 8 |
| 2250 | OD2 | ASP | A | 283 | 28.866 | 70.758 | 45.290 | 1.00 | 11.95 | 8 |
| 2251 | N | PHE | A | 284 | 31.108 | 72.815 | 40.834 | 1.00 | 10.41 | 7 |
| 2252 | CA | PHE | A | 284 | 32.439 | 73.424 | 40.731 | 1.00 | 10.33 | 6 |
| 2253 | C | PHE | A | 284 | 32.746 | 74.271 | 41.966 | 1.00 | 11.21 | 6 |
| 2254 | O | PHE | A | 284 | 33.941 | 74.331 | 42.313 | 1.00 | 12.52 | 8 |
| 2255 | CB | PHE | A | 284 | 32.509 | 74.409 | 39.517 | 1.00 | 10.51 | 6 |
| 2256 | CG | PHE | A | 284 | 32.750 | 73.575 | 38.227 | 1.00 | 10.01 | 6 |
| 2257 | CD1 | PHE | A | 284 | 31.725 | 72.991 | 37.520 | 1.00 | 11.07 | 6 |
| 2258 | CD2 | PHE | A | 284 | 34.073 | 73.416 | 37.765 | 1.00 | 11.57 | 6 |
| 2259 | CE1 | PHE | A | 284 | 31.925 | 72.232 | 36.386 | 1.00 | 12.29 | 6 |
| 2260 | CE2 | PHE | A | 284 | 34.292 | 72.665 | 36.596 | 1.00 | 11.45 | 6 |
| 2261 | CZ | PHE | A | 284 | 33.234 | 72.085 | 35.903 | 1.00 | 9.72 | 6 |
| 2262 | N | ASP | A | 285 | 31.729 | 74.753 | 42.687 | 1.00 | 9.13 | 7 |
| 2263 | CA | ASP | A | 285 | 32.061 | 75.575 | 43.882 | 1.00 | 10.61 | 6 |
| 2264 | C | ASP | A | 285 | 32.799 | 74.670 | 44.885 | 1.00 | 10.95 | 6 |
| 2265 | O | ASP | A | 285 | 33.806 | 75.092 | 45.468 | 1.00 | 11.00 | 8 |
| 2266 | CB | ASP | A | 285 | 30.773 | 76.068 | 44.545 | 1.00 | 9.55 | 6 |
| 2267 | CG | ASP | A | 285 | 29.979 | 77.042 | 43.692 | 1.00 | 10.92 | 6 |
| 2268 | OD1 | ASP | A | 285 | 30.499 | 77.631 | 42.710 | 1.00 | 12.04 | 8 |
| 2269 | OD2 | ASP | A | 285 | 28.773 | 77.214 | 44.043 | 1.00 | 12.59 | 8 |
| 2270 | N | LEU | A | 286 | 32.248 | 73.464 | 45.128 | 1.00 | 10.30 | 7 |
| 2271 | CA | LEU | A | 286 | 32.959 | 72.569 | 46.061 | 1.00 | 9.08 | 6 |
| 2272 | C | LEU | A | 286 | 34.219 | 71.940 | 45.505 | 1.00 | 9.26 | 6 |
| 2273 | O | LEU | A | 286 | 35.179 | 71.757 | 46.238 | 1.00 | 11.04 | 8 |
| 2274 | CB | LEU | A | 286 | 31.968 | 71.419 | 46.481 | 1.00 | 9.12 | 6 |
| 2275 | CG | LEU | A | 286 | 32.367 | 70.697 | 47.790 | 1.00 | 10.68 | 6 |
| 2276 | CD1 | LEU | A | 286 | 32.357 | 71.580 | 49.023 | 1.00 | 15.93 | 6 |
| 2277 | CD2 | LEU | A | 286 | 31.384 | 69.510 | 47.999 | 1.00 | 13.68 | 6 |
| 2278 | N | ASN | A | 287 | 34.226 | 71.683 | 44.168 | 1.00 | 9.32 | 7 |
| 2279 | CA | ASN | A | 287 | 35.441 | 71.091 | 43.586 | 1.00 | 10.65 | 6 |
| 2280 | C | ASN | A | 287 | 36.687 | 71.937 | 43.872 | 1.00 | 9.75 | 6 |
| 2281 | O | ASN | A | 287 | 37.751 | 71.401 | 44.184 | 1.00 | 10.35 | 8 |
| 2282 | CB | ASN | A | 287 | 35.269 | 71.000 | 42.039 | 1.00 | 8.74 | 6 |
| 2283 | CG | ASN | A | 287 | 36.571 | 70.507 | 41.392 | 1.00 | 11.79 | 6 |
| 2284 | OD1 | ASN | A | 287 | 37.171 | 71.318 | 40.654 | 1.00 | 11.65 | 8 |
| 2285 | ND2 | ASN | A | 287 | 36.866 | 69.245 | 41.597 | 1.00 | 9.92 | 7 |
| 2286 | N | THR | A | 288 | 36.588 | 73.275 | 43.719 | 1.00 | 9.52 | 7 |
| 2287 | CA | THR | A | 288 | 37.769 | 74.106 | 43.907 | 1.00 | 11.58 | 6 |
| 2288 | C | THR | A | 288 | 38.367 | 73.906 | 45.292 | 1.00 | 10.74 | 6 |
| 2289 | O | THR | A | 288 | 39.593 | 73.741 | 45.486 | 1.00 | 13.25 | 8 |
| 2290 | CB | THR | A | 288 | 37.365 | 75.596 | 43.745 | 1.00 | 15.82 | 6 |
| 2291 | OG1 | THR | A | 288 | 36.906 | 75.753 | 42.397 | 1.00 | 16.55 | 8 |
| 2292 | CG2 | THR | A | 288 | 38.641 | 76.459 | 43.984 | 1.00 | 14.43 | 6 |
| 2293 | N | VAL | A | 289 | 37.440 | 73.847 | 46.268 | 1.00 | 8.64 | 7 |
| 2294 | CA | VAL | A | 289 | 37.915 | 73.732 | 47.655 | 1.00 | 8.82 | 6 |
| 2295 | C | VAL | A | 289 | 38.401 | 72.341 | 47.985 | 1.00 | 11.04 | 6 |
| 2296 | O | VAL | A | 289 | 39.438 | 72.184 | 48.642 | 1.00 | 11.67 | 8 |
| 2297 | CB | VAL | A | 289 | 36.780 | 74.237 | 48.605 | 1.00 | 11.02 | 6 |
| 2298 | CG1 | VAL | A | 289 | 37.297 | 74.258 | 50.051 | 1.00 | 10.38 | 6 |
| 2299 | CG2 | VAL | A | 289 | 36.323 | 75.632 | 48.191 | 1.00 | 11.61 | 6 |
| 2300 | N | ILE | A | 290 | 37.764 | 71.287 | 47.430 | 1.00 | 9.86 | 7 |
| 2301 | CA | ILE | A | 290 | 38.262 | 69.911 | 47.642 | 1.00 | 8.30 | 6 |
| 2302 | C | ILE | A | 290 | 39.715 | 69.830 | 47.144 | 1.00 | 12.22 | 6 |
| 2303 | O | ILE | A | 290 | 40.554 | 69.251 | 47.806 | 1.00 | 10.89 | 8 |
| 2304 | CB | ILE | A | 290 | 37.342 | 68.979 | 46.851 | 1.00 | 9.93 | 6 |
| 2305 | CG1 | ILE | A | 290 | 36.004 | 68.833 | 47.591 | 1.00 | 11.46 | 6 |
| 2306 | CG2 | ILE | A | 290 | 38.025 | 67.579 | 46.690 | 1.00 | 11.35 | 6 |
| 2307 | CD1 | ILE | A | 290 | 34.964 | 68.108 | 46.700 | 1.00 | 11.71 | 6 |
| 2308 | N | ARG | A | 291 | 39.969 | 70.386 | 45.940 | 1.00 | 11.21 | 7 |
| 2309 | CA | ARG | A | 291 | 41.352 | 70.246 | 45.455 | 1.00 | 10.67 | 6 |
| 2310 | C | ARG | A | 291 | 42.343 | 71.071 | 46.293 | 1.00 | 9.59 | 6 |
| 2311 | O | ARG | A | 291 | 43.481 | 70.627 | 46.380 | 1.00 | 12.39 | 8 |

TABLE 1-continued

Atom Coordinates from the Crystal Structure of NOVAMYL

| | | | | | | | | | |
|---|---|---|---|---|---|---|---|---|---|
| 2312 | CB | ARG | A | 291 | 41.308 | 70.770 | 43.991 | 1.00 | 10.96 | 6 |
| 2313 | CG | ARG | A | 291 | 40.602 | 69.717 | 43.110 | 1.00 | 11.39 | 6 |
| 2314 | CD | ARG | A | 291 | 40.480 | 70.173 | 41.647 | 1.00 | 11.11 | 6 |
| 2315 | NE | ARG | A | 291 | 41.729 | 70.343 | 40.907 | 1.00 | 11.15 | 7 |
| 2316 | CZ | ARG | A | 291 | 42.225 | 69.361 | 40.109 | 1.00 | 12.12 | 6 |
| 2317 | NH1 | ARG | A | 291 | 41.706 | 68.126 | 40.068 | 1.00 | 11.32 | 7 |
| 2318 | NH2 | ARG | A | 291 | 43.322 | 69.593 | 39.363 | 1.00 | 12.38 | 7 |
| 2319 | N | ASN | A | 292 | 41.972 | 72.204 | 46.801 | 1.00 | 12.65 | 7 |
| 2320 | CA | ASN | A | 292 | 42.894 | 73.001 | 47.653 | 1.00 | 11.32 | 6 |
| 2321 | C | ASN | A | 292 | 42.983 | 72.376 | 49.051 | 1.00 | 11.68 | 6 |
| 2322 | O | ASN | A | 292 | 44.074 | 72.565 | 49.634 | 1.00 | 11.50 | 8 |
| 2323 | CB | ASN | A | 292 | 42.408 | 74.471 | 47.750 | 1.00 | 11.01 | 6 |
| 2324 | CG | ASN | A | 292 | 42.593 | 75.238 | 46.379 | 1.00 | 14.57 | 6 |
| 2325 | OD1 | ASN | A | 292 | 43.466 | 74.831 | 45.665 | 1.00 | 19.84 | 8 |
| 2326 | ND2 | ASN | A | 292 | 41.735 | 76.242 | 46.267 | 1.00 | 18.55 | 7 |
| 2327 | N | VAL | A | 293 | 42.009 | 71.574 | 49.542 | 1.00 | 10.40 | 7 |
| 2328 | CA | VAL | A | 293 | 42.157 | 71.075 | 50.940 | 1.00 | 10.24 | 6 |
| 2329 | C | VAL | A | 293 | 42.861 | 69.743 | 50.969 | 1.00 | 11.21 | 6 |
| 2330 | O | VAL | A | 293 | 43.748 | 69.520 | 51.783 | 1.00 | 11.98 | 8 |
| 2331 | CB | VAL | A | 293 | 40.703 | 70.961 | 51.499 | 1.00 | 10.95 | 6 |
| 2332 | CG1 | VAL | A | 293 | 40.707 | 70.175 | 52.820 | 1.00 | 12.97 | 6 |
| 2333 | CG2 | VAL | A | 293 | 40.153 | 72.364 | 51.736 | 1.00 | 13.88 | 6 |
| 2334 | N | PHE | A | 294 | 42.479 | 68.858 | 50.033 | 1.00 | 11.12 | 7 |
| 2335 | CA | PHE | A | 294 | 43.106 | 67.537 | 49.960 | 1.00 | 11.38 | 6 |
| 2336 | C | PHE | A | 294 | 44.255 | 67.464 | 48.964 | 1.00 | 11.51 | 6 |
| 2337 | O | PHE | A | 294 | 45.095 | 66.540 | 49.093 | 1.00 | 11.86 | 8 |
| 2338 | CB | PHE | A | 294 | 42.063 | 66.455 | 49.553 | 1.00 | 11.70 | 6 |
| 2339 | CG | PHE | A | 294 | 40.936 | 66.334 | 50.584 | 1.00 | 11.57 | 6 |
| 2340 | CD1 | PHE | A | 294 | 41.178 | 65.683 | 51.808 | 1.00 | 11.48 | 6 |
| 2341 | CD2 | PHE | A | 294 | 39.707 | 66.865 | 50.295 | 1.00 | 13.60 | 6 |
| 2342 | CE1 | PHE | A | 294 | 40.133 | 65.579 | 52.724 | 1.00 | 12.41 | 6 |
| 2343 | CE2 | PHE | A | 294 | 38.662 | 66.762 | 51.232 | 1.00 | 13.36 | 6 |
| 2344 | CZ | PHE | A | 294 | 38.880 | 66.104 | 52.463 | 1.00 | 13.22 | 6 |
| 2345 | N | GLY | A | 295 | 44.295 | 68.355 | 47.976 | 1.00 | 11.76 | 7 |
| 2346 | CA | GLY | A | 295 | 45.328 | 68.234 | 46.907 | 1.00 | 12.36 | 6 |
| 2347 | C | GLY | A | 295 | 46.504 | 69.187 | 47.187 | 1.00 | 10.85 | 6 |
| 2348 | O | GLY | A | 295 | 47.547 | 68.676 | 47.612 | 1.00 | 13.29 | 8 |
| 2349 | N | THR | A | 296 | 46.271 | 70.499 | 46.990 | 1.00 | 10.00 | 7 |
| 2350 | CA | THR | A | 296 | 47.441 | 71.394 | 47.123 | 1.00 | 11.19 | 6 |
| 2351 | C | THR | A | 296 | 47.675 | 71.894 | 48.549 | 1.00 | 13.50 | 6 |
| 2352 | O | THR | A | 296 | 48.755 | 72.436 | 48.874 | 1.00 | 12.22 | 8 |
| 2353 | CB | THR | A | 296 | 47.162 | 72.647 | 46.253 | 1.00 | 11.65 | 6 |
| 2354 | OG1 | THR | A | 296 | 46.005 | 73.276 | 46.812 | 1.00 | 15.42 | 8 |
| 2355 | CG2 | THR | A | 296 | 46.976 | 72.308 | 44.770 | 1.00 | 13.16 | 6 |
| 2356 | N | PHE | A | 297 | 46.760 | 71.647 | 49.472 | 1.00 | 11.24 | 7 |
| 2357 | CA | PHE | A | 297 | 46.917 | 72.026 | 50.881 | 1.00 | 12.10 | 6 |
| 2358 | C | PHE | A | 297 | 47.104 | 73.543 | 50.984 | 1.00 | 17.18 | 6 |
| 2359 | O | PHE | A | 297 | 47.719 | 74.035 | 51.952 | 1.00 | 17.61 | 8 |
| 2360 | CB | PHE | A | 297 | 48.052 | 71.271 | 51.610 | 1.00 | 11.80 | 6 |
| 2361 | CG | PHE | A | 297 | 47.630 | 69.924 | 52.199 | 1.00 | 14.38 | 6 |
| 2362 | CD1 | PHE | A | 297 | 47.153 | 68.917 | 51.385 | 1.00 | 13.09 | 6 |
| 2363 | CD2 | PHE | A | 297 | 47.760 | 69.711 | 53.565 | 1.00 | 11.70 | 6 |
| 2364 | CE1 | PHE | A | 297 | 46.821 | 67.656 | 51.854 | 1.00 | 12.95 | 6 |
| 2365 | CE2 | PHE | A | 297 | 47.438 | 68.444 | 54.064 | 1.00 | 12.92 | 6 |
| 2366 | CZ | PHE | A | 297 | 46.948 | 67.450 | 53.231 | 1.00 | 11.87 | 6 |
| 2367 | N | THR | A | 298 | 46.411 | 74.322 | 50.183 | 1.00 | 13.51 | 7 |
| 2368 | CA | THR | A | 298 | 46.398 | 75.773 | 50.270 | 1.00 | 13.52 | 6 |
| 2369 | C | THR | A | 298 | 45.131 | 76.303 | 50.925 | 1.00 | 13.29 | 6 |
| 2370 | O | THR | A | 298 | 45.018 | 77.505 | 51.220 | 1.00 | 15.14 | 8 |
| 2371 | CB | THR | A | 298 | 46.488 | 76.437 | 48.870 | 1.00 | 13.68 | 6 |
| 2372 | OG1 | THR | A | 298 | 45.446 | 75.982 | 48.035 | 1.00 | 12.95 | 8 |
| 2373 | CG2 | THR | A | 298 | 47.869 | 76.059 | 48.250 | 1.00 | 15.45 | 6 |
| 2374 | N | GLN | A | 299 | 44.162 | 75.400 | 51.194 | 1.00 | 10.17 | 7 |
| 2375 | CA | GLN | A | 299 | 43.009 | 75.785 | 51.975 | 1.00 | 13.00 | 6 |
| 2376 | C | GLN | A | 299 | 42.852 | 74.738 | 53.114 | 1.00 | 14.72 | 6 |
| 2377 | O | GLN | A | 299 | 43.624 | 73.753 | 53.094 | 1.00 | 14.92 | 8 |
| 2378 | CB | GLN | A | 299 | 41.654 | 75.808 | 51.214 | 1.00 | 11.79 | 6 |
| 2379 | CG | GLN | A | 299 | 41.692 | 77.072 | 50.299 | 1.00 | 14.80 | 6 |
| 2380 | CD | GLN | A | 299 | 40.301 | 77.320 | 49.668 | 1.00 | 16.23 | 6 |
| 2381 | OE1 | GLN | A | 299 | 39.959 | 76.525 | 48.827 | 1.00 | 15.11 | 8 |
| 2382 | NE2 | GLN | A | 299 | 39.635 | 78.376 | 50.107 | 1.00 | 17.75 | 7 |
| 2383 | N | THR | A | 300 | 42.031 | 75.020 | 54.106 | 1.00 | 13.71 | 7 |
| 2384 | CA | THR | A | 300 | 41.924 | 74.106 | 55.252 | 1.00 | 11.61 | 6 |
| 2385 | C | THR | A | 300 | 40.518 | 73.485 | 55.355 | 1.00 | 14.08 | 6 |
| 2386 | O | THR | A | 300 | 39.580 | 73.874 | 54.644 | 1.00 | 11.91 | 8 |
| 2387 | CB | THR | A | 300 | 42.152 | 74.850 | 56.601 | 1.00 | 15.34 | 6 |
| 2388 | OG1 | THR | A | 300 | 41.116 | 75.771 | 56.804 | 1.00 | 15.70 | 8 |

TABLE 1-continued

Atom Coordinates from the Crystal Structure of NOVAMYL

| 2389 | CG2 | THR | A | 300 | 43.511 | 75.587 | 56.464 | 1.00 | 16.98 | 6 |
|---|---|---|---|---|---|---|---|---|---|---|
| 2390 | N | MET | A | 301 | 40.337 | 72.672 | 56.443 | 1.00 | 11.88 | 7 |
| 2391 | CA | MET | A | 301 | 38.977 | 72.123 | 56.650 | 1.00 | 12.22 | 6 |
| 2392 | C | MET | A | 301 | 37.972 | 73.216 | 56.994 | 1.00 | 12.44 | 6 |
| 2393 | O | MET | A | 301 | 36.791 | 73.075 | 56.691 | 1.00 | 11.03 | 8 |
| 2394 | CB | MET | A | 301 | 38.935 | 71.065 | 57.800 | 1.00 | 12.80 | 6 |
| 2395 | CG | MET | A | 301 | 39.707 | 69.787 | 57.393 | 1.00 | 11.05 | 6 |
| 2396 | SD | MET | A | 301 | 39.027 | 69.014 | 55.895 | 1.00 | 12.28 | 16 |
| 2397 | CE | MET | A | 301 | 39.724 | 67.366 | 56.047 | 1.00 | 14.34 | 6 |
| 2398 | N | TYR | A | 302 | 38.408 | 74.374 | 57.555 | 1.00 | 12.00 | 7 |
| 2399 | CA | TYR | A | 302 | 37.462 | 75.453 | 57.759 | 1.00 | 10.79 | 6 |
| 2400 | C | TYR | A | 302 | 36.898 | 75.974 | 56.430 | 1.00 | 11.89 | 6 |
| 2401 | O | TYR | A | 302 | 35.694 | 76.181 | 56.325 | 1.00 | 12.65 | 8 |
| 2402 | CB | TYR | A | 302 | 38.131 | 76.626 | 58.505 | 1.00 | 10.20 | 6 |
| 2403 | CG | TYR | A | 302 | 38.409 | 76.271 | 59.983 | 1.00 | 11.51 | 6 |
| 2404 | CD1 | TYR | A | 302 | 37.375 | 76.197 | 60.914 | 1.00 | 16.19 | 6 |
| 2405 | CD2 | TYR | A | 302 | 39.739 | 76.057 | 60.344 | 1.00 | 17.97 | 6 |
| 2406 | CE1 | TYR | A | 302 | 37.736 | 75.884 | 62.236 | 1.00 | 18.06 | 6 |
| 2407 | CE2 | TYR | A | 302 | 40.062 | 75.723 | 61.683 | 1.00 | 15.93 | 6 |
| 2408 | CZ | TYR | A | 302 | 39.029 | 75.670 | 62.567 | 1.00 | 19.00 | 6 |
| 2409 | OH | TYR | A | 302 | 39.409 | 75.355 | 63.905 | 1.00 | 21.46 | 8 |
| 2410 | N | ASP | A | 303 | 37.763 | 76.026 | 55.418 | 1.00 | 13.06 | 7 |
| 2411 | CA | ASP | A | 303 | 37.256 | 76.434 | 54.104 | 1.00 | 12.54 | 6 |
| 2412 | C | ASP | A | 303 | 36.285 | 75.409 | 53.492 | 1.00 | 11.88 | 6 |
| 2413 | O | ASP | A | 303 | 35.330 | 75.782 | 52.785 | 1.00 | 13.46 | 8 |
| 2414 | CB | ASP | A | 303 | 38.419 | 76.666 | 53.133 | 1.00 | 10.93 | 6 |
| 2415 | CG | ASP | A | 303 | 39.386 | 77.734 | 53.654 | 1.00 | 14.78 | 6 |
| 2416 | OD1 | ASP | A | 303 | 38.879 | 78.877 | 53.849 | 1.00 | 13.77 | 8 |
| 2417 | OD2 | ASP | A | 303 | 40.573 | 77.435 | 53.832 | 1.00 | 13.10 | 8 |
| 2418 | N | LEU | A | 304 | 36.602 | 74.152 | 53.720 | 1.00 | 11.36 | 7 |
| 2419 | CA | LEU | A | 304 | 35.713 | 73.086 | 53.156 | 1.00 | 11.06 | 6 |
| 2420 | C | LEU | A | 304 | 34.348 | 73.181 | 53.841 | 1.00 | 12.95 | 6 |
| 2421 | O | LEU | A | 304 | 33.315 | 73.111 | 53.155 | 1.00 | 11.60 | 8 |
| 2422 | CB | LEU | A | 304 | 36.393 | 71.742 | 53.367 | 1.00 | 10.48 | 6 |
| 2423 | CG | LEU | A | 304 | 35.687 | 70.566 | 52.633 | 1.00 | 11.09 | 6 |
| 2424 | CD1 | LEU | A | 304 | 35.737 | 70.797 | 51.112 | 1.00 | 12.57 | 6 |
| 2425 | CD2 | LEU | A | 304 | 36.397 | 69.248 | 52.971 | 1.00 | 12.54 | 6 |
| 2426 | N | ASN | A | 305 | 34.290 | 73.255 | 55.180 | 1.00 | 11.76 | 7 |
| 2427 | CA | ASN | A | 305 | 32.999 | 73.422 | 55.887 | 1.00 | 12.74 | 6 |
| 2428 | C | ASN | A | 305 | 32.308 | 74.720 | 55.479 | 1.00 | 11.54 | 6 |
| 2429 | O | ASN | A | 305 | 31.100 | 74.673 | 55.259 | 1.00 | 13.50 | 8 |
| 2430 | CB | ASN | A | 305 | 33.331 | 73.448 | 57.405 | 1.00 | 12.22 | 6 |
| 2431 | CG | ASN | A | 305 | 32.014 | 73.551 | 58.210 | 1.00 | 12.84 | 6 |
| 2432 | OD1 | ASN | A | 305 | 31.174 | 72.669 | 58.097 | 1.00 | 13.98 | 8 |
| 2433 | ND2 | ASN | A | 305 | 31.910 | 74.651 | 58.967 | 1.00 | 17.24 | 7 |
| 2434 | N | ASN | A | 306 | 33.061 | 75.772 | 55.272 | 1.00 | 11.86 | 7 |
| 2435 | CA | ASN | A | 306 | 32.418 | 77.036 | 54.848 | 1.00 | 12.68 | 6 |
| 2436 | C | ASN | A | 306 | 31.740 | 76.830 | 53.499 | 1.00 | 13.44 | 6 |
| 2437 | O | ASN | A | 306 | 30.672 | 77.409 | 53.225 | 1.00 | 13.40 | 8 |
| 2438 | CB | ASN | A | 306 | 33.438 | 78.176 | 54.774 | 1.00 | 12.13 | 6 |
| 2439 | CG | ASN | A | 306 | 33.863 | 78.686 | 56.143 | 1.00 | 20.79 | 6 |
| 2440 | OD1 | ASN | A | 306 | 33.275 | 78.499 | 57.233 | 1.00 | 23.19 | 8 |
| 2441 | ND2 | ASN | A | 306 | 34.959 | 79.477 | 56.155 | 1.00 | 24.17 | 7 |
| 2442 | N | MET | A | 307 | 32.405 | 76.105 | 52.589 | 1.00 | 11.55 | 7 |
| 2443 | CA | MET | A | 307 | 31.750 | 75.915 | 51.254 | 1.00 | 11.38 | 6 |
| 2444 | C | MET | A | 307 | 30.590 | 74.957 | 51.272 | 1.00 | 12.48 | 6 |
| 2445 | O | MET | A | 307 | 29.639 | 75.156 | 50.512 | 1.00 | 13.10 | 8 |
| 2446 | CB | MET | A | 307 | 32.849 | 75.431 | 50.252 | 1.00 | 12.11 | 6 |
| 2447 | CG | MET | A | 307 | 32.375 | 75.462 | 48.767 | 1.00 | 12.14 | 6 |
| 2448 | SD | MET | A | 307 | 31.759 | 77.075 | 48.246 | 1.00 | 12.77 | 16 |
| 2449 | CE | MET | A | 307 | 33.282 | 78.010 | 48.324 | 1.00 | 13.86 | 6 |
| 2450 | N | VAL | A | 308 | 30.592 | 73.951 | 52.152 | 1.00 | 10.38 | 7 |
| 2451 | CA | VAL | A | 308 | 29.383 | 73.136 | 52.340 | 1.00 | 10.10 | 6 |
| 2452 | C | VAL | A | 308 | 28.272 | 74.049 | 52.822 | 1.00 | 11.64 | 6 |
| 2453 | O | VAL | A | 308 | 27.153 | 73.974 | 52.321 | 1.00 | 13.14 | 8 |
| 2454 | CB | VAL | A | 308 | 29.712 | 72.052 | 53.406 | 1.00 | 13.16 | 6 |
| 2455 | CG1 | VAL | A | 308 | 28.388 | 71.356 | 53.770 | 1.00 | 14.05 | 6 |
| 2456 | CG2 | VAL | A | 308 | 30.641 | 71.038 | 52.727 | 1.00 | 13.08 | 6 |
| 2457 | N | ASN | A | 309 | 28.541 | 74.952 | 53.784 | 1.00 | 12.04 | 7 |
| 2458 | CA | ASN | A | 309 | 27.479 | 75.848 | 54.264 | 1.00 | 12.56 | 6 |
| 2459 | C | ASN | A | 309 | 27.073 | 76.824 | 53.176 | 1.00 | 13.56 | 6 |
| 2460 | O | ASN | A | 309 | 25.875 | 77.017 | 53.030 | 1.00 | 15.38 | 8 |
| 2461 | CB | ASN | A | 309 | 27.997 | 76.680 | 55.470 | 1.00 | 14.00 | 6 |
| 2462 | CG | ASN | A | 309 | 28.109 | 75.761 | 56.684 | 1.00 | 20.56 | 6 |
| 2463 | OD1 | ASN | A | 309 | 27.432 | 74.725 | 56.748 | 1.00 | 26.71 | 8 |
| 2464 | ND2 | ASN | A | 309 | 28.967 | 76.208 | 57.595 | 1.00 | 21.18 | 7 |
| 2465 | N | GLN | A | 310 | 27.970 | 77.423 | 52.426 | 1.00 | 14.28 | 7 |

TABLE 1-continued

Atom Coordinates from the Crystal Structure of NOVAMYL

| 2466 | CA | GLN | A | 310 | 27.549 | 78.422 | 51.422 | 1.00 | 13.95 | 6 |
|---|---|---|---|---|---|---|---|---|---|---|
| 2467 | C | GLN | A | 310 | 26.734 | 77.754 | 50.319 | 1.00 | 13.50 | 6 |
| 2468 | O | GLN | A | 310 | 25.672 | 78.286 | 49.942 | 1.00 | 14.03 | 8 |
| 2469 | CB | GLN | A | 310 | 28.821 | 79.123 | 50.869 | 1.00 | 14.99 | 6 |
| 2470 | CG | GLN | A | 310 | 28.507 | 80.214 | 49.859 | 1.00 | 21.08 | 6 |
| 2471 | CD | GLN | A | 310 | 29.734 | 81.169 | 49.819 | 1.00 | 21.08 | 6 |
| 2472 | OE1 | GLN | A | 310 | 30.875 | 80.762 | 50.019 | 1.00 | 25.61 | 8 |
| 2473 | NE2 | GLN | A | 310 | 29.417 | 82.401 | 49.600 | 1.00 | 25.23 | 7 |
| 2474 | N | THR | A | 311 | 27.238 | 76.630 | 49.792 | 1.00 | 11.65 | 7 |
| 2475 | CA | THR | A | 311 | 26.432 | 75.983 | 48.711 | 1.00 | 11.52 | 6 |
| 2476 | C | THR | A | 311 | 25.089 | 75.459 | 49.257 | 1.00 | 12.57 | 6 |
| 2477 | O | THR | A | 311 | 24.039 | 75.572 | 48.599 | 1.00 | 13.81 | 8 |
| 2478 | CB | THR | A | 311 | 27.143 | 74.754 | 48.142 | 1.00 | 12.52 | 6 |
| 2479 | OG1 | THR | A | 311 | 27.593 | 73.909 | 49.194 | 1.00 | 13.67 | 8 |
| 2480 | CG2 | THR | A | 311 | 28.426 | 75.250 | 47.375 | 1.00 | 14.32 | 6 |
| 2481 | N | GLY | A | 312 | 25.096 | 75.107 | 50.561 | 1.00 | 11.69 | 7 |
| 2482 | CA | GLY | A | 312 | 23.812 | 74.642 | 51.137 | 1.00 | 14.78 | 6 |
| 2483 | C | GLY | A | 312 | 22.800 | 75.792 | 51.223 | 1.00 | 14.32 | 6 |
| 2484 | O | GLY | A | 312 | 21.573 | 75.473 | 51.276 | 1.00 | 16.33 | 8 |
| 2485 | N | ASN | A | 313 | 23.320 | 76.998 | 51.476 | 1.00 | 13.08 | 7 |
| 2486 | CA | ASN | A | 313 | 22.392 | 78.108 | 51.535 | 1.00 | 13.20 | 6 |
| 2487 | C | ASN | A | 313 | 21.980 | 78.575 | 50.150 | 1.00 | 14.89 | 6 |
| 2488 | O | ASN | A | 313 | 20.827 | 79.097 | 50.014 | 1.00 | 20.75 | 8 |
| 2489 | CB | ASN | A | 313 | 23.155 | 79.260 | 52.204 | 1.00 | 19.18 | 6 |
| 2490 | CG | ASN | A | 313 | 23.210 | 79.024 | 53.718 | 1.00 | 30.91 | 6 |
| 2491 | OD1 | ASN | A | 313 | 22.384 | 78.310 | 54.281 | 1.00 | 30.04 | 8 |
| 2492 | ND2 | ASN | A | 313 | 24.152 | 79.691 | 54.360 | 1.00 | 31.03 | 7 |
| 2493 | N | GLU | A | 314 | 22.802 | 78.394 | 49.111 | 1.00 | 12.83 | 7 |
| 2494 | CA | GLU | A | 314 | 22.396 | 79.060 | 47.822 | 1.00 | 11.95 | 6 |
| 2495 | C | GLU | A | 314 | 21.621 | 78.137 | 46.889 | 1.00 | 13.20 | 6 |
| 2496 | O | GLU | A | 314 | 20.733 | 78.689 | 46.175 | 1.00 | 13.02 | 8 |
| 2497 | CB | GLU | A | 314 | 23.753 | 79.394 | 47.117 | 1.00 | 10.17 | 6 |
| 2498 | CG | GLU | A | 314 | 24.503 | 80.510 | 47.842 | 1.00 | 12.02 | 6 |
| 2499 | CD | GLU | A | 314 | 25.715 | 80.987 | 46.985 | 1.00 | 15.94 | 6 |
| 2500 | OE1 | GLU | A | 314 | 26.285 | 80.206 | 46.232 | 1.00 | 15.22 | 8 |
| 2501 | OE2 | GLU | A | 314 | 26.164 | 82.100 | 47.284 | 1.00 | 24.00 | 8 |
| 2502 | N | TYR | A | 315 | 21.992 | 76.840 | 46.892 | 1.00 | 11.76 | 7 |
| 2503 | CA | TYR | A | 315 | 21.297 | 75.979 | 45.885 | 1.00 | 10.85 | 6 |
| 2504 | C | TYR | A | 315 | 20.032 | 75.368 | 46.506 | 1.00 | 12.73 | 6 |
| 2505 | O | TYR | A | 315 | 20.140 | 74.648 | 47.510 | 1.00 | 12.47 | 8 |
| 2506 | CB | TYR | A | 315 | 22.265 | 74.838 | 45.494 | 1.00 | 12.39 | 6 |
| 2507 | CG | TYR | A | 315 | 23.437 | 75.394 | 44.699 | 1.00 | 10.41 | 6 |
| 2508 | CD1 | TYR | A | 315 | 23.270 | 75.610 | 43.316 | 1.00 | 11.23 | 6 |
| 2509 | CD2 | TYR | A | 315 | 24.613 | 75.785 | 45.297 | 1.00 | 12.52 | 6 |
| 2510 | CE1 | TYR | A | 315 | 24.333 | 76.166 | 42.586 | 1.00 | 12.92 | 6 |
| 2511 | CE2 | TYR | A | 315 | 25.686 | 76.350 | 44.563 | 1.00 | 10.90 | 6 |
| 2512 | CZ | TYR | A | 315 | 25.510 | 76.507 | 43.187 | 1.00 | 12.76 | 6 |
| 2513 | OH | TYR | A | 315 | 26.595 | 77.056 | 42.517 | 1.00 | 13.74 | 8 |
| 2514 | N | LYS | A | 316 | 18.895 | 75.634 | 45.861 | 1.00 | 11.54 | 7 |
| 2515 | CA | LYS | A | 316 | 17.638 | 75.080 | 46.395 | 1.00 | 14.39 | 6 |
| 2516 | C | LYS | A | 316 | 17.578 | 73.555 | 46.454 | 1.00 | 15.27 | 6 |
| 2517 | O | LYS | A | 316 | 17.175 | 72.963 | 47.475 | 1.00 | 14.60 | 8 |
| 2518 | CB | LYS | A | 316 | 16.496 | 75.595 | 45.485 | 1.00 | 14.77 | 6 |
| 2519 | CG | LYS | A | 316 | 15.139 | 75.068 | 46.091 | 1.00 | 18.12 | 6 |
| 2520 | CD | LYS | A | 316 | 13.982 | 75.856 | 45.565 | 1.00 | 22.24 | 6 |
| 2521 | CE | LYS | A | 316 | 12.683 | 75.166 | 46.061 | 1.00 | 19.23 | 6 |
| 2522 | NZ | LYS | A | 316 | 12.432 | 75.635 | 47.468 | 1.00 | 22.20 | 7 |
| 2523 | N | TYR | A | 317 | 18.227 | 72.953 | 45.457 | 1.00 | 13.10 | 7 |
| 2524 | CA | TYR | A | 317 | 18.316 | 71.483 | 45.445 | 1.00 | 11.39 | 6 |
| 2525 | C | TYR | A | 317 | 19.805 | 71.123 | 45.506 | 1.00 | 10.31 | 6 |
| 2526 | O | TYR | A | 317 | 20.410 | 70.491 | 44.637 | 1.00 | 12.52 | 8 |
| 2527 | CB | TYR | A | 317 | 17.652 | 70.893 | 44.157 | 1.00 | 12.53 | 6 |
| 2528 | CG | TYR | A | 317 | 16.221 | 71.387 | 44.004 | 1.00 | 13.61 | 6 |
| 2529 | CD1 | TYR | A | 317 | 15.272 | 70.932 | 44.915 | 1.00 | 14.65 | 6 |
| 2530 | CD2 | TYR | A | 317 | 15.800 | 72.280 | 43.030 | 1.00 | 14.34 | 6 |
| 2531 | CE1 | TYR | A | 317 | 13.938 | 71.366 | 44.811 | 1.00 | 13.78 | 6 |
| 2532 | CE2 | TYR | A | 317 | 14.511 | 72.767 | 42.890 | 1.00 | 12.10 | 6 |
| 2533 | CZ | TYR | A | 317 | 13.604 | 72.246 | 43.832 | 1.00 | 15.19 | 6 |
| 2534 | OH | TYR | A | 317 | 12.275 | 72.682 | 43.733 | 1.00 | 14.53 | 8 |
| 2535 | N | LYS | A | 318 | 20.375 | 71.463 | 46.702 | 1.00 | 11.46 | 7 |
| 2536 | CA | LYS | A | 318 | 21.821 | 71.130 | 46.865 | 1.00 | 10.64 | 6 |
| 2537 | C | LYS | A | 318 | 22.053 | 69.651 | 46.865 | 1.00 | 10.21 | 6 |
| 2538 | O | LYS | A | 318 | 23.133 | 69.145 | 46.529 | 1.00 | 10.36 | 8 |
| 2539 | CB | LYS | A | 318 | 22.408 | 71.772 | 48.141 | 1.00 | 9.85 | 6 |
| 2540 | CG | LYS | A | 318 | 21.843 | 71.211 | 49.451 | 1.00 | 13.57 | 6 |
| 2541 | CD | LYS | A | 318 | 20.619 | 72.105 | 49.820 | 1.00 | 19.29 | 6 |
| 2542 | CE | LYS | A | 318 | 20.309 | 72.064 | 51.345 | 1.00 | 19.13 | 6 |

TABLE 1-continued

Atom Coordinates from the Crystal Structure of NOVAMYL

| | | | | | | | | | |
|---|---|---|---|---|---|---|---|---|---|
| 2543 | NZ | LYS | A | 318 | 19.066 | 72.819 | 51.636 | 1.00 | 20.57 | 7 |
| 2544 | N | GLU | A | 319 | 21.044 | 68.796 | 47.174 | 1.00 | 9.32 | 7 |
| 2545 | CA | GLU | A | 319 | 21.217 | 67.359 | 47.096 | 1.00 | 11.07 | 6 |
| 2546 | C | GLU | A | 319 | 21.164 | 66.802 | 45.667 | 1.00 | 12.26 | 6 |
| 2547 | O | GLU | A | 319 | 21.469 | 65.627 | 45.504 | 1.00 | 11.85 | 8 |
| 2548 | CB | GLU | A | 319 | 20.021 | 66.636 | 47.827 | 1.00 | 12.74 | 6 |
| 2549 | CG | GLU | A | 319 | 19.998 | 67.027 | 49.320 | 1.00 | 15.35 | 6 |
| 2550 | CD | GLU | A | 319 | 19.346 | 68.353 | 49.656 | 1.00 | 19.53 | 6 |
| 2551 | OE1 | GLU | A | 319 | 18.645 | 68.996 | 48.818 | 1.00 | 14.20 | 8 |
| 2552 | OE2 | GLU | A | 319 | 19.503 | 68.829 | 50.839 | 1.00 | 14.17 | 8 |
| 2553 | N | ASN | A | 320 | 21.033 | 67.681 | 44.664 | 1.00 | 9.38 | 7 |
| 2554 | CA | ASN | A | 320 | 21.155 | 67.324 | 43.285 | 1.00 | 9.77 | 6 |
| 2555 | C | ASN | A | 320 | 22.454 | 67.819 | 42.636 | 1.00 | 12.36 | 6 |
| 2556 | O | ASN | A | 320 | 22.736 | 67.591 | 41.442 | 1.00 | 10.93 | 8 |
| 2557 | CB | ASN | A | 320 | 19.995 | 67.901 | 42.402 | 1.00 | 10.57 | 6 |
| 2558 | CG | ASN | A | 320 | 18.660 | 67.290 | 42.784 | 1.00 | 14.03 | 6 |
| 2559 | OD1 | ASN | A | 320 | 18.619 | 66.275 | 43.445 | 1.00 | 13.17 | 8 |
| 2560 | ND2 | ASN | A | 320 | 17.558 | 67.901 | 42.323 | 1.00 | 10.64 | 7 |
| 2561 | N | LEU | A | 321 | 23.285 | 68.499 | 43.422 | 1.00 | 10.68 | 7 |
| 2562 | CA | LEU | A | 321 | 24.610 | 68.918 | 42.896 | 1.00 | 10.60 | 6 |
| 2563 | C | LEU | A | 321 | 25.415 | 67.643 | 42.685 | 1.00 | 10.70 | 6 |
| 2564 | O | LEU | A | 321 | 25.448 | 66.685 | 43.452 | 1.00 | 11.96 | 8 |
| 2565 | CB | LEU | A | 321 | 25.299 | 69.733 | 44.024 | 1.00 | 9.53 | 6 |
| 2566 | CG | LEU | A | 321 | 24.761 | 71.176 | 44.124 | 1.00 | 9.68 | 6 |
| 2567 | CD1 | LEU | A | 321 | 25.310 | 71.820 | 45.415 | 1.00 | 13.05 | 6 |
| 2568 | CD2 | LEU | A | 321 | 25.183 | 72.064 | 42.930 | 1.00 | 9.85 | 6 |
| 2569 | N | ILE | A | 322 | 26.185 | 67.671 | 41.566 | 1.00 | 9.04 | 7 |
| 2570 | CA | ILE | A | 322 | 27.014 | 66.478 | 41.265 | 1.00 | 9.68 | 6 |
| 2571 | C | ILE | A | 322 | 28.477 | 66.821 | 41.584 | 1.00 | 11.13 | 6 |
| 2572 | O | ILE | A | 322 | 29.071 | 67.716 | 40.935 | 1.00 | 10.40 | 8 |
| 2573 | CB | ILE | A | 322 | 26.872 | 66.118 | 39.767 | 1.00 | 10.10 | 6 |
| 2574 | CG1 | ILE | A | 322 | 25.387 | 65.842 | 39.384 | 1.00 | 9.96 | 6 |
| 2575 | CG2 | ILE | A | 322 | 27.793 | 64.954 | 39.396 | 1.00 | 12.80 | 6 |
| 2576 | CD1 | ILE | A | 322 | 24.773 | 64.698 | 40.258 | 1.00 | 9.05 | 6 |
| 2577 | N | THR | A | 323 | 29.019 | 66.133 | 42.594 | 1.00 | 9.87 | 7 |
| 2578 | CA | THR | A | 323 | 30.333 | 66.524 | 43.130 | 1.00 | 8.82 | 6 |
| 2579 | C | THR | A | 323 | 31.433 | 65.704 | 42.453 | 1.00 | 9.73 | 6 |
| 2580 | O | THR | A | 323 | 31.218 | 64.628 | 41.902 | 1.00 | 10.64 | 8 |
| 2581 | CB | THR | A | 323 | 30.364 | 66.302 | 44.652 | 1.00 | 10.77 | 6 |
| 2582 | OG1 | THR | A | 323 | 30.009 | 64.919 | 44.887 | 1.00 | 10.73 | 8 |
| 2583 | CG2 | THR | A | 323 | 29.314 | 67.237 | 45.318 | 1.00 | 10.06 | 6 |
| 2584 | N | PHE | A | 324 | 32.660 | 66.234 | 42.559 | 1.00 | 9.44 | 7 |
| 2585 | CA | PHE | A | 324 | 33.784 | 65.582 | 41.880 | 1.00 | 10.80 | 6 |
| 2586 | C | PHE | A | 324 | 35.086 | 66.205 | 42.385 | 1.00 | 9.58 | 6 |
| 2587 | O | PHE | A | 324 | 35.086 | 67.375 | 42.805 | 1.00 | 10.73 | 8 |
| 2588 | CB | PHE | A | 324 | 33.716 | 65.698 | 40.286 | 1.00 | 9.57 | 6 |
| 2589 | CG | PHE | A | 324 | 33.638 | 67.122 | 39.817 | 1.00 | 9.02 | 6 |
| 2590 | CD1 | PHE | A | 324 | 32.421 | 67.817 | 39.810 | 1.00 | 11.94 | 6 |
| 2591 | CD2 | PHE | A | 324 | 34.798 | 67.746 | 39.354 | 1.00 | 11.07 | 6 |
| 2592 | CE1 | PHE | A | 324 | 32.321 | 69.142 | 39.380 | 1.00 | 11.10 | 6 |
| 2593 | CE2 | PHE | A | 324 | 34.683 | 69.083 | 38.926 | 1.00 | 11.33 | 6 |
| 2594 | CZ | PHE | A | 324 | 33.498 | 69.788 | 38.931 | 1.00 | 13.68 | 6 |
| 2595 | N | ILE | A | 325 | 36.137 | 65.385 | 42.285 | 1.00 | 9.28 | 7 |
| 2596 | CA | ILE | A | 325 | 37.469 | 65.879 | 42.710 | 1.00 | 9.24 | 6 |
| 2597 | C | ILE | A | 325 | 38.277 | 66.277 | 41.480 | 1.00 | 9.67 | 6 |
| 2598 | O | ILE | A | 325 | 39.255 | 67.116 | 41.645 | 1.00 | 10.76 | 8 |
| 2599 | CB | AILE | A | 325 | 38.211 | 64.869 | 43.596 | 0.60 | 11.75 | 6 |
| 2600 | CG1 | AILE | A | 325 | 38.779 | 63.705 | 42.764 | 0.60 | 10.90 | 6 |
| 2601 | CG2 | AILE | A | 325 | 37.288 | 64.325 | 44.695 | 0.60 | 12.60 | 6 |
| 2602 | CD1 | AILE | A | 325 | 39.550 | 62.693 | 43.585 | 0.60 | 10.36 | 6 |
| 2599 | CB | BILE | A | 325 | 38.139 | 64.627 | 43.330 | 0.40 | 12.90 | 6 |
| 2600 | CG1 | BILE | A | 325 | 37.386 | 64.127 | 44.568 | 0.40 | 10.36 | 6 |
| 2601 | CG2 | BILE | A | 325 | 39.604 | 64.862 | 43.640 | 0.40 | 10.82 | 6 |
| 2602 | CD1 | BILE | A | 325 | 37.571 | 62.651 | 44.847 | 0.40 | 13.69 | 6 |
| 2603 | N | ASP | A | 326 | 38.028 | 65.680 | 40.350 | 1.00 | 9.63 | 7 |
| 2604 | CA | ASP | A | 326 | 38.762 | 65.987 | 39.107 | 1.00 | 10.15 | 6 |
| 2605 | C | ASP | A | 326 | 37.813 | 65.625 | 37.964 | 1.00 | 11.71 | 6 |
| 2606 | O | ASP | A | 326 | 36.678 | 65.102 | 38.209 | 1.00 | 10.86 | 8 |
| 2607 | CB | ASP | A | 326 | 40.149 | 65.323 | 39.050 | 1.00 | 12.00 | 6 |
| 2608 | CG | ASP | A | 326 | 40.166 | 63.807 | 39.089 | 1.00 | 12.49 | 6 |
| 2609 | OD1 | ASP | A | 326 | 39.080 | 63.207 | 38.870 | 1.00 | 12.13 | 8 |
| 2610 | OD2 | ASP | A | 326 | 41.228 | 63.200 | 39.354 | 1.00 | 11.72 | 8 |
| 2611 | N | ASN | A | 327 | 38.279 | 65.749 | 36.731 | 1.00 | 9.05 | 7 |
| 2612 | CA | ASN | A | 327 | 37.486 | 65.359 | 35.569 | 1.00 | 10.52 | 6 |
| 2613 | C | ASN | A | 327 | 38.334 | 65.556 | 34.352 | 1.00 | 9.98 | 6 |
| 2614 | O | ASN | A | 327 | 39.573 | 65.686 | 34.478 | 1.00 | 11.19 | 8 |
| 2615 | CB | ASN | A | 327 | 36.177 | 66.162 | 35.432 | 1.00 | 11.56 | 6 |

TABLE 1-continued

Atom Coordinates from the Crystal Structure of NOVAMYL

| 2616 | CG | ASN | A | 327 | 36.351 | 67.636 | 35.121 | 1.00 | 12.65 | 6 |
| 2617 | OD1 | ASN | A | 327 | 37.355 | 68.106 | 34.634 | 1.00 | 11.48 | 8 |
| 2618 | ND2 | ASN | A | 327 | 35.314 | 68.376 | 35.463 | 1.00 | 8.99 | 7 |
| 2619 | N | HIS | A | 328 | 37.802 | 65.385 | 33.178 | 1.00 | 9.23 | 7 |
| 2620 | CA | HIS | A | 328 | 38.599 | 65.393 | 31.958 | 1.00 | 11.14 | 6 |
| 2621 | C | HIS | A | 328 | 39.037 | 66.779 | 31.471 | 1.00 | 11.62 | 6 |
| 2622 | O | HIS | A | 328 | 39.744 | 66.836 | 30.450 | 1.00 | 11.55 | 8 |
| 2623 | CB | HIS | A | 328 | 37.726 | 64.740 | 30.844 | 1.00 | 10.61 | 6 |
| 2624 | CG | HIS | A | 328 | 36.511 | 65.577 | 30.526 | 1.00 | 9.76 | 6 |
| 2625 | ND1 | HIS | A | 328 | 35.652 | 65.938 | 31.572 | 1.00 | 11.58 | 7 |
| 2626 | CD2 | HIS | A | 328 | 36.012 | 66.093 | 29.370 | 1.00 | 11.35 | 6 |
| 2627 | CE1 | HIS | A | 328 | 34.648 | 66.668 | 31.066 | 1.00 | 12.44 | 6 |
| 2628 | NE2 | HIS | A | 328 | 34.853 | 66.756 | 29.733 | 1.00 | 11.88 | 7 |
| 2629 | N | ASP | A | 329 | 38.746 | 67.808 | 32.263 | 1.00 | 8.48 | 7 |
| 2630 | CA | ASP | A | 329 | 39.181 | 69.155 | 31.893 | 1.00 | 9.03 | 6 |
| 2631 | C | ASP | A | 329 | 40.073 | 69.793 | 32.960 | 1.00 | 12.15 | 6 |
| 2632 | O | ASP | A | 329 | 40.388 | 71.012 | 32.883 | 1.00 | 12.94 | 8 |
| 2633 | CB | ASP | A | 329 | 37.955 | 70.091 | 31.837 | 1.00 | 11.03 | 6 |
| 2634 | CG | ASP | A | 329 | 37.069 | 69.815 | 30.620 | 1.00 | 11.95 | 6 |
| 2635 | OD1 | ASP | A | 329 | 37.477 | 69.188 | 29.617 | 1.00 | 11.39 | 8 |
| 2636 | OD2 | ASP | A | 329 | 35.891 | 70.243 | 30.712 | 1.00 | 11.11 | 8 |
| 2637 | N | MET | A | 330 | 40.568 | 68.936 | 33.857 | 1.00 | 11.19 | 7 |
| 2638 | CA | MET | A | 330 | 41.533 | 69.433 | 34.857 | 1.00 | 9.36 | 6 |
| 2639 | C | MET | A | 330 | 42.537 | 68.330 | 35.211 | 1.00 | 9.51 | 6 |
| 2640 | O | MET | A | 330 | 42.224 | 67.156 | 34.927 | 1.00 | 11.47 | 8 |
| 2641 | CB | MET | A | 330 | 40.858 | 70.015 | 36.111 | 1.00 | 13.17 | 6 |
| 2642 | CG | MET | A | 330 | 40.005 | 68.973 | 36.857 | 1.00 | 11.23 | 6 |
| 2643 | SD | MET | A | 330 | 39.087 | 69.743 | 38.236 | 1.00 | 12.96 | 16 |
| 2644 | CE | MET | A | 330 | 37.923 | 70.706 | 37.364 | 1.00 | 13.78 | 6 |
| 2645 | N | SER | A | 331 | 43.702 | 68.680 | 35.765 | 1.00 | 10.04 | 7 |
| 2646 | CA | SER | A | 331 | 44.650 | 67.618 | 36.030 | 1.00 | 9.86 | 6 |
| 2647 | C | SER | A | 331 | 44.130 | 66.557 | 37.020 | 1.00 | 11.24 | 6 |
| 2648 | O | SER | A | 331 | 43.295 | 66.892 | 37.858 | 1.00 | 11.71 | 8 |
| 2649 | CB | SER | A | 331 | 46.009 | 68.207 | 36.629 | 1.00 | 11.21 | 6 |
| 2650 | OG | SER | A | 331 | 45.623 | 68.981 | 37.793 | 1.00 | 14.33 | 8 |
| 2651 | N | ARG | A | 332 | 44.540 | 65.321 | 36.833 | 1.00 | 11.49 | 7 |
| 2652 | CA | ARG | A | 332 | 44.057 | 64.272 | 37.749 | 1.00 | 11.49 | 6 |
| 2653 | C | ARG | A | 332 | 44.499 | 64.603 | 39.189 | 1.00 | 11.63 | 6 |
| 2654 | O | ARG | A | 332 | 45.591 | 65.103 | 39.412 | 1.00 | 12.21 | 8 |
| 2655 | CB | ARG | A | 332 | 44.667 | 62.914 | 37.387 | 1.00 | 13.45 | 6 |
| 2656 | CG | ARG | A | 332 | 43.997 | 62.516 | 36.049 | 1.00 | 16.61 | 6 |
| 2657 | CD | ARG | A | 332 | 43.560 | 61.101 | 36.061 | 1.00 | 20.26 | 6 |
| 2658 | NE | ARG | A | 332 | 43.017 | 60.592 | 34.777 | 1.00 | 15.50 | 7 |
| 2659 | CZ | ARG | A | 332 | 41.965 | 59.753 | 34.882 | 1.00 | 12.48 | 6 |
| 2660 | NH1 | ARG | A | 332 | 41.546 | 59.388 | 36.094 | 1.00 | 10.61 | 7 |
| 2661 | NH2 | ARG | A | 332 | 41.440 | 59.251 | 33.741 | 1.00 | 10.74 | 7 |
| 2662 | N | PHE | A | 333 | 43.654 | 64.168 | 40.153 | 1.00 | 9.55 | 7 |
| 2663 | CA | PHE | A | 333 | 44.019 | 64.431 | 41.533 | 1.00 | 10.54 | 6 |
| 2664 | O | PHE | A | 333 | 45.461 | 63.976 | 41.852 | 1.00 | 12.40 | 6 |
| 2665 | O | PHE | A | 333 | 46.170 | 64.709 | 42.515 | 1.00 | 13.01 | 8 |
| 2666 | CB | PHE | A | 333 | 43.007 | 63.676 | 42.481 | 1.00 | 11.67 | 6 |
| 2667 | CG | PHE | A | 333 | 43.365 | 64.006 | 43.958 | 1.00 | 12.76 | 6 |
| 2668 | CD1 | PHE | A | 333 | 44.315 | 63.230 | 44.587 | 1.00 | 15.62 | 6 |
| 2669 | CD2 | PHE | A | 333 | 42.718 | 65.041 | 44.556 | 1.00 | 18.86 | 6 |
| 2670 | CE1 | PHE | A | 333 | 44.651 | 63.513 | 45.905 | 1.00 | 19.61 | 6 |
| 2671 | CE2 | PHE | A | 333 | 43.014 | 65.342 | 45.906 | 1.00 | 15.77 | 6 |
| 2672 | CZ | PHE | A | 333 | 43.978 | 64.561 | 46.492 | 1.00 | 16.46 | 6 |
| 2673 | N | LEU | A | 334 | 45.825 | 62.763 | 41.462 | 1.00 | 10.49 | 7 |
| 2674 | CA | LEU | A | 334 | 47.183 | 62.257 | 41.835 | 1.00 | 14.60 | 6 |
| 2675 | C | LEU | A | 334 | 48.303 | 63.035 | 41.167 | 1.00 | 12.74 | 6 |
| 2676 | O | LEU | A | 334 | 49.456 | 62.864 | 41.627 | 1.00 | 13.05 | 8 |
| 2677 | CB | LEU | A | 334 | 47.269 | 60.748 | 41.476 | 1.00 | 13.94 | 6 |
| 2678 | CG | LEU | A | 334 | 46.461 | 59.910 | 42.484 | 1.00 | 13.29 | 6 |
| 2679 | CD1 | LEU | A | 334 | 46.488 | 58.447 | 41.969 | 1.00 | 14.98 | 6 |
| 2680 | CD2 | LEU | A | 334 | 47.045 | 59.905 | 43.909 | 1.00 | 13.51 | 6 |
| 2681 | N | SER | A | 335 | 48.014 | 63.857 | 40.144 | 1.00 | 11.98 | 7 |
| 2682 | CA | SER | A | 335 | 49.117 | 64.732 | 39.639 | 1.00 | 11.30 | 6 |
| 2683 | C | SER | A | 335 | 49.115 | 66.026 | 40.421 | 1.00 | 15.22 | 6 |
| 2684 | O | SER | A | 335 | 50.159 | 66.664 | 40.438 | 1.00 | 18.21 | 8 |
| 2685 | CB | SER | A | 335 | 48.843 | 65.113 | 38.179 | 1.00 | 14.88 | 6 |
| 2686 | OG | SER | A | 335 | 49.221 | 63.920 | 37.436 | 1.00 | 17.27 | 8 |
| 2687 | N | VAL | A | 336 | 48.041 | 66.315 | 41.169 | 1.00 | 11.92 | 7 |
| 2688 | CA | VAL | A | 336 | 48.092 | 67.455 | 42.094 | 1.00 | 14.73 | 6 |
| 2689 | C | VAL | A | 336 | 48.805 | 67.064 | 43.392 | 1.00 | 15.20 | 6 |
| 2690 | O | VAL | A | 336 | 49.593 | 67.825 | 43.962 | 1.00 | 16.13 | 8 |
| 2691 | CB | VAL | A | 336 | 46.691 | 67.970 | 42.447 | 1.00 | 14.37 | 6 |
| 2692 | CG1 | VAL | A | 336 | 46.646 | 69.120 | 43.441 | 1.00 | 16.05 | 6 |

TABLE 1-continued

Atom Coordinates from the Crystal Structure of NOVAMYL

| 2693 | CG2 | VAL | A | 336 | 45.970 | 68.386 | 41.154 | 1.00 | 18.05 | 6 |
|---|---|---|---|---|---|---|---|---|---|---|
| 2694 | N | ASN | A | 337 | 48.525 | 65.866 | 43.852 | 1.00 | 13.19 | 7 |
| 2695 | CA | ASN | A | 337 | 49.114 | 65.389 | 45.132 | 1.00 | 12.41 | 6 |
| 2696 | C | ASN | A | 337 | 49.153 | 63.870 | 44.976 | 1.00 | 12.10 | 6 |
| 2697 | O | ASN | A | 337 | 48.082 | 63.178 | 44.865 | 1.00 | 11.76 | 8 |
| 2698 | CB | ASN | A | 337 | 48.141 | 65.756 | 46.272 | 1.00 | 11.12 | 6 |
| 2699 | CG | ASN | A | 337 | 48.570 | 65.206 | 47.621 | 1.00 | 13.14 | 6 |
| 2700 | OD1 | ASN | A | 337 | 49.572 | 64.466 | 47.738 | 1.00 | 12.58 | 8 |
| 2701 | ND2 | ASN | A | 337 | 47.865 | 65.514 | 48.694 | 1.00 | 11.19 | 7 |
| 2702 | N | SER | A | 338 | 50.364 | 63.275 | 44.939 | 1.00 | 9.71 | 7 |
| 2703 | CA | SER | A | 338 | 50.477 | 61.849 | 44.747 | 1.00 | 13.36 | 6 |
| 2704 | C | SER | A | 338 | 50.257 | 60.983 | 45.993 | 1.00 | 11.43 | 6 |
| 2705 | O | SER | A | 338 | 50.294 | 59.759 | 45.858 | 1.00 | 14.29 | 8 |
| 2706 | CB | SER | A | 338 | 51.884 | 61.461 | 44.225 | 1.00 | 17.19 | 6 |
| 2707 | OG | SER | A | 338 | 52.871 | 61.883 | 45.154 | 1.00 | 17.12 | 8 |
| 2708 | N | ASN | A | 339 | 49.847 | 61.610 | 47.095 | 1.00 | 13.33 | 7 |
| 2709 | CA | ASN | A | 339 | 49.601 | 60.788 | 48.297 | 1.00 | 12.26 | 6 |
| 2710 | C | ASN | A | 339 | 48.267 | 60.043 | 48.193 | 1.00 | 12.82 | 6 |
| 2711 | O | ASN | A | 339 | 47.246 | 60.732 | 48.134 | 1.00 | 12.55 | 8 |
| 2712 | CB | ASN | A | 339 | 49.554 | 61.769 | 49.485 | 1.00 | 10.37 | 6 |
| 2713 | CG | ASN | A | 339 | 49.516 | 60.949 | 50.787 | 1.00 | 18.65 | 6 |
| 2714 | OD1 | ASN | A | 339 | 48.403 | 60.509 | 51.110 | 1.00 | 19.28 | 8 |
| 2715 | ND2 | ASN | A | 339 | 50.648 | 60.809 | 51.502 | 1.00 | 18.28 | 7 |
| 2716 | N | LYS | A | 340 | 48.283 | 58.708 | 48.148 | 1.00 | 12.73 | 7 |
| 2717 | CA | LYS | A | 340 | 47.008 | 58.021 | 47.941 | 1.00 | 11.20 | 6 |
| 2718 | C | LYS | A | 340 | 46.077 | 58.134 | 49.122 | 1.00 | 13.56 | 6 |
| 2719 | O | LYS | A | 340 | 44.859 | 58.103 | 48.906 | 1.00 | 12.11 | 8 |
| 2720 | CB | LYS | A | 340 | 47.345 | 56.523 | 47.665 | 1.00 | 12.59 | 6 |
| 2721 | CG | LYS | A | 340 | 48.006 | 56.401 | 46.279 | 1.00 | 12.90 | 6 |
| 2722 | CD | LYS | A | 340 | 48.318 | 54.903 | 46.055 | 1.00 | 18.47 | 6 |
| 2723 | CE | LYS | A | 340 | 48.937 | 54.658 | 44.699 | 1.00 | 18.65 | 6 |
| 2724 | NZ | LYS | A | 340 | 50.377 | 55.099 | 44.564 | 1.00 | 22.63 | 7 |
| 2725 | N | ALA | A | 341 | 46.585 | 58.363 | 50.345 | 1.00 | 12.85 | 7 |
| 2726 | CA | ALA | A | 341 | 45.626 | 58.557 | 51.453 | 1.00 | 14.45 | 6 |
| 2727 | C | ALA | A | 341 | 44.835 | 59.830 | 51.239 | 1.00 | 13.48 | 6 |
| 2728 | O | ALA | A | 341 | 43.661 | 59.855 | 51.568 | 1.00 | 11.31 | 8 |
| 2729 | CB | ALA | A | 341 | 46.346 | 58.628 | 52.806 | 1.00 | 15.23 | 6 |
| 2730 | N | ASN | A | 342 | 45.459 | 60.911 | 50.731 | 1.00 | 10.37 | 7 |
| 2731 | CA | ASN | A | 342 | 44.717 | 62.126 | 50.470 | 1.00 | 10.38 | 6 |
| 2732 | C | ASN | A | 342 | 43.687 | 61.897 | 49.359 | 1.00 | 10.62 | 6 |
| 2733 | O | ASN | A | 342 | 42.560 | 62.477 | 49.439 | 1.00 | 12.01 | 8 |
| 2734 | CB | ASN | A | 342 | 45.708 | 63.276 | 50.141 | 1.00 | 11.46 | 6 |
| 2735 | CG | ASN | A | 342 | 46.519 | 63.737 | 51.351 | 1.00 | 13.17 | 6 |
| 2736 | OD1 | ASN | A | 342 | 47.710 | 64.044 | 51.127 | 1.00 | 12.82 | 8 |
| 2737 | ND2 | ASN | A | 342 | 45.888 | 63.859 | 52.516 | 1.00 | 12.05 | 7 |
| 2738 | N | LEU | A | 343 | 44.001 | 61.049 | 48.344 | 1.00 | 10.66 | 7 |
| 2739 | CA | LEU | A | 343 | 42.953 | 60.715 | 47.377 | 1.00 | 10.18 | 6 |
| 2740 | C | LEU | A | 343 | 41.810 | 59.935 | 48.039 | 1.00 | 12.28 | 6 |
| 2741 | O | LEU | A | 343 | 40.635 | 60.288 | 47.781 | 1.00 | 11.44 | 8 |
| 2742 | CB | LEU | A | 343 | 43.581 | 59.854 | 46.229 | 1.00 | 10.02 | 6 |
| 2743 | CG | LEU | A | 343 | 42.546 | 59.182 | 45.295 | 1.00 | 10.27 | 6 |
| 2744 | CD1 | LEU | A | 343 | 41.847 | 60.288 | 44.550 | 1.00 | 13.59 | 6 |
| 2745 | CD2 | LEU | A | 343 | 43.309 | 58.294 | 44.283 | 1.00 | 12.64 | 6 |
| 2746 | N | HIS | A | 344 | 42.173 | 58.977 | 48.898 | 1.00 | 11.47 | 7 |
| 2747 | CA | HIS | A | 344 | 41.093 | 58.185 | 49.570 | 1.00 | 11.49 | 6 |
| 2748 | C | HIS | A | 344 | 40.189 | 59.122 | 50.370 | 1.00 | 13.40 | 6 |
| 2749 | O | HIS | A | 344 | 38.951 | 58.916 | 50.500 | 1.00 | 12.11 | 8 |
| 2750 | CB | HIS | A | 344 | 41.731 | 57.075 | 50.439 | 1.00 | 9.09 | 6 |
| 2751 | CG | HIS | A | 344 | 42.520 | 56.064 | 49.656 | 1.00 | 10.04 | 6 |
| 2752 | ND1 | HIS | A | 344 | 43.612 | 55.436 | 50.199 | 1.00 | 12.75 | 7 |
| 2753 | CD2 | HIS | A | 344 | 42.363 | 55.580 | 48.370 | 1.00 | 11.63 | 6 |
| 2754 | CE1 | HIS | A | 344 | 44.114 | 54.612 | 49.289 | 1.00 | 10.72 | 6 |
| 2755 | NE2 | HIS | A | 344 | 43.393 | 54.662 | 48.157 | 1.00 | 12.61 | 7 |
| 2756 | N | GLN | A | 345 | 40.834 | 60.100 | 51.024 | 1.00 | 10.53 | 7 |
| 2757 | CA | GLN | A | 345 | 40.049 | 61.036 | 51.831 | 1.00 | 10.43 | 6 |
| 2758 | C | GLN | A | 345 | 39.077 | 61.899 | 51.008 | 1.00 | 10.42 | 6 |
| 2759 | O | GLN | A | 345 | 37.888 | 62.067 | 51.324 | 1.00 | 10.38 | 8 |
| 2760 | CB | GLN | A | 345 | 40.996 | 62.012 | 52.564 | 1.00 | 11.01 | 6 |
| 2761 | CG | GLN | A | 345 | 41.847 | 61.258 | 53.641 | 1.00 | 9.73 | 6 |
| 2762 | CD | GLN | A | 345 | 43.142 | 62.041 | 53.786 | 1.00 | 10.78 | 6 |
| 2763 | OE1 | GLN | A | 345 | 43.232 | 63.196 | 53.279 | 1.00 | 12.69 | 8 |
| 2764 | NE2 | GLN | A | 345 | 44.170 | 61.448 | 54.428 | 1.00 | 12.87 | 7 |
| 2765 | N | ALA | A | 346 | 39.590 | 62.418 | 49.883 | 1.00 | 11.81 | 7 |
| 2766 | CA | ALA | A | 346 | 38.762 | 63.250 | 48.987 | 1.00 | 10.44 | 6 |
| 2767 | C | ALA | A | 346 | 37.604 | 62.379 | 48.462 | 1.00 | 11.17 | 6 |
| 2768 | O | ALA | A | 346 | 36.473 | 62.887 | 48.339 | 1.00 | 11.30 | 8 |
| 2769 | CB | ALA | A | 346 | 39.595 | 63.827 | 47.829 | 1.00 | 9.34 | 6 |

TABLE 1-continued

Atom Coordinates from the Crystal Structure of NOVAMYL

| 2770 | N   | LEU | A | 347 | 37.895 | 61.107 | 48.079 | 1.00 | 12.34 | 7 |
|------|-----|-----|---|-----|--------|--------|--------|------|-------|---|
| 2771 | CA  | LEU | A | 347 | 36.809 | 60.261 | 47.589 | 1.00 | 11.12 | 6 |
| 2772 | C   | LEU | A | 347 | 35.777 | 59.999 | 48.733 | 1.00 | 9.98  | 6 |
| 2773 | O   | LEU | A | 347 | 34.567 | 60.087 | 48.466 | 1.00 | 11.63 | 8 |
| 2774 | CB  | LEU | A | 347 | 37.367 | 58.885 | 47.187 | 1.00 | 11.26 | 6 |
| 2775 | CG  | LEU | A | 347 | 38.146 | 58.913 | 45.840 | 1.00 | 14.75 | 6 |
| 2776 | CD1 | LEU | A | 347 | 38.829 | 57.574 | 45.530 | 1.00 | 13.09 | 6 |
| 2777 | CD2 | LEU | A | 347 | 37.132 | 59.197 | 44.722 | 1.00 | 15.41 | 6 |
| 2778 | N   | ALA | A | 348 | 36.304 | 59.764 | 49.955 | 1.00 | 10.14 | 7 |
| 2779 | CA  | ALA | A | 348 | 35.269 | 59.479 | 51.003 | 1.00 | 10.67 | 6 |
| 2780 | C   | ALA | A | 348 | 34.432 | 60.725 | 51.273 | 1.00 | 12.22 | 6 |
| 2781 | O   | ALA | A | 348 | 33.231 | 60.600 | 51.534 | 1.00 | 11.88 | 8 |
| 2782 | CB  | ALA | A | 348 | 36.008 | 59.130 | 52.310 | 1.00 | 10.16 | 6 |
| 2783 | N   | PHE | A | 349 | 35.026 | 61.922 | 51.160 | 1.00 | 10.08 | 7 |
| 2784 | CA  | PHE | A | 349 | 34.258 | 63.149 | 51.330 | 1.00 | 10.26 | 6 |
| 2785 | C   | PHE | A | 349 | 33.120 | 63.213 | 50.282 | 1.00 | 9.67  | 6 |
| 2786 | O   | PHE | A | 349 | 31.942 | 63.422 | 50.717 | 1.00 | 11.25 | 8 |
| 2787 | CB  | PHE | A | 349 | 35.270 | 64.348 | 51.200 | 1.00 | 9.92  | 6 |
| 2788 | CG  | PHE | A | 349 | 34.515 | 65.659 | 51.357 | 1.00 | 8.60  | 6 |
| 2789 | CD1 | PHE | A | 349 | 34.016 | 66.030 | 52.605 | 1.00 | 11.80 | 6 |
| 2790 | CD2 | PHE | A | 349 | 34.340 | 66.526 | 50.249 | 1.00 | 11.51 | 6 |
| 2791 | CE1 | PHE | A | 349 | 33.296 | 67.247 | 52.714 | 1.00 | 11.90 | 6 |
| 2792 | CE2 | PHE | A | 349 | 33.638 | 67.709 | 50.409 | 1.00 | 10.49 | 6 |
| 2793 | CZ  | PHE | A | 349 | 33.069 | 68.068 | 51.660 | 1.00 | 12.88 | 6 |
| 2794 | N   | ILE | A | 350 | 33.411 | 63.030 | 49.005 | 1.00 | 8.49  | 7 |
| 2795 | CA  | ILE | A | 350 | 32.257 | 63.124 | 48.089 | 1.00 | 10.97 | 6 |
| 2796 | C   | ILE | A | 350 | 31.361 | 61.899 | 48.158 | 1.00 | 11.48 | 6 |
| 2797 | O   | ILE | A | 350 | 30.139 | 62.115 | 47.958 | 1.00 | 11.30 | 8 |
| 2798 | CB  | ILE | A | 350 | 32.676 | 63.380 | 46.605 | 1.00 | 11.26 | 6 |
| 2799 | CG1 | ILE | A | 350 | 33.451 | 62.279 | 45.983 | 1.00 | 11.16 | 6 |
| 2800 | CG2 | ILE | A | 350 | 33.429 | 64.742 | 46.556 | 1.00 | 12.07 | 6 |
| 2801 | CD1 | ILE | A | 350 | 33.748 | 62.454 | 44.463 | 1.00 | 9.59  | 6 |
| 2802 | N   | LEU | A | 351 | 31.873 | 60.731 | 48.548 | 1.00 | 9.78  | 7 |
| 2803 | CA  | LEU | A | 351 | 30.930 | 59.601 | 48.655 | 1.00 | 9.90  | 6 |
| 2804 | C   | LEU | A | 351 | 29.956 | 59.782 | 49.809 | 1.00 | 11.10 | 6 |
| 2805 | O   | LEU | A | 351 | 28.888 | 59.122 | 49.698 | 1.00 | 11.60 | 8 |
| 2806 | CB  | LEU | A | 351 | 31.813 | 58.349 | 48.879 | 1.00 | 11.35 | 6 |
| 2807 | CG  | LEU | A | 351 | 32.492 | 57.907 | 47.564 | 1.00 | 10.64 | 6 |
| 2808 | CD1 | LEU | A | 351 | 33.679 | 56.944 | 47.822 | 1.00 | 12.51 | 6 |
| 2809 | CD2 | LEU | A | 351 | 31.500 | 57.262 | 46.595 | 1.00 | 13.68 | 6 |
| 2810 | N   | THR | A | 352 | 30.267 | 60.590 | 50.850 | 1.00 | 9.74  | 7 |
| 2811 | CA  | THR | A | 352 | 29.310 | 60.657 | 51.960 | 1.00 | 11.34 | 6 |
| 2812 | C   | THR | A | 352 | 28.658 | 62.022 | 52.149 | 1.00 | 12.86 | 6 |
| 2813 | O   | THR | A | 352 | 27.822 | 62.214 | 53.022 | 1.00 | 13.09 | 8 |
| 2814 | CB  | THR | A | 352 | 30.099 | 60.375 | 53.296 | 1.00 | 11.44 | 6 |
| 2815 | OG1 | THR | A | 352 | 31.244 | 61.234 | 53.420 | 1.00 | 11.08 | 8 |
| 2816 | CG2 | THR | A | 352 | 30.607 | 58.939 | 53.324 | 1.00 | 9.52  | 6 |
| 2817 | N   | SER | A | 353 | 29.100 | 63.028 | 51.368 | 1.00 | 10.03 | 7 |
| 2818 | CA  | SER | A | 353 | 28.530 | 64.357 | 51.432 | 1.00 | 10.73 | 6 |
| 2819 | C   | SER | A | 353 | 27.299 | 64.574 | 50.536 | 1.00 | 9.28  | 6 |
| 2820 | O   | SER | A | 353 | 26.990 | 63.688 | 49.726 | 1.00 | 13.31 | 8 |
| 2821 | CB  | SER | A | 353 | 29.607 | 65.403 | 51.012 | 1.00 | 12.91 | 6 |
| 2822 | OG  | SER | A | 353 | 30.626 | 65.402 | 52.045 | 1.00 | 12.40 | 8 |
| 2823 | N   | ARG | A | 354 | 26.646 | 65.741 | 50.754 | 1.00 | 10.25 | 7 |
| 2824 | CA  | ARG | A | 354 | 25.379 | 65.920 | 50.024 | 1.00 | 10.03 | 6 |
| 2825 | C   | ARG | A | 354 | 25.611 | 65.997 | 48.533 | 1.00 | 10.84 | 6 |
| 2826 | O   | ARG | A | 354 | 26.704 | 66.369 | 48.085 | 1.00 | 11.59 | 8 |
| 2827 | CB  | ARG | A | 354 | 24.669 | 67.185 | 50.545 | 1.00 | 10.71 | 6 |
| 2828 | CG  | ARG | A | 354 | 25.099 | 68.504 | 49.838 | 1.00 | 11.61 | 6 |
| 2829 | CD  | ARG | A | 354 | 26.535 | 68.853 | 50.229 | 1.00 | 12.49 | 6 |
| 2830 | NE  | ARG | A | 354 | 26.964 | 70.130 | 49.548 | 1.00 | 12.69 | 7 |
| 2831 | CZ  | ARG | A | 354 | 27.455 | 70.157 | 48.317 | 1.00 | 12.54 | 6 |
| 2832 | NH1 | ARG | A | 354 | 27.638 | 69.113 | 47.497 | 1.00 | 12.15 | 7 |
| 2833 | NH2 | ARG | A | 354 | 27.867 | 71.370 | 47.894 | 1.00 | 11.14 | 7 |
| 2834 | N   | GLY | A | 355 | 24.542 | 65.707 | 47.780 | 1.00 | 11.00 | 7 |
| 2835 | CA  | GLY | A | 355 | 24.624 | 65.584 | 46.318 | 1.00 | 10.49 | 6 |
| 2836 | C   | GLY | A | 355 | 25.149 | 64.196 | 45.929 | 1.00 | 13.18 | 6 |
| 2837 | O   | GLY | A | 355 | 25.154 | 63.299 | 46.788 | 1.00 | 15.74 | 8 |
| 2838 | N   | THR | A | 356 | 25.546 | 64.007 | 44.688 | 1.00 | 10.24 | 7 |
| 2839 | CA  | THR | A | 356 | 25.885 | 62.648 | 44.202 | 1.00 | 10.01 | 6 |
| 2840 | C   | THR | A | 356 | 27.279 | 62.722 | 43.581 | 1.00 | 10.67 | 6 |
| 2841 | O   | THR | A | 356 | 27.512 | 63.621 | 42.769 | 1.00 | 10.61 | 8 |
| 2842 | CB  | THR | A | 356 | 24.908 | 62.301 | 43.066 | 1.00 | 13.21 | 6 |
| 2843 | OG1 | THR | A | 356 | 23.622 | 62.052 | 43.698 | 1.00 | 11.93 | 8 |
| 2844 | CG2 | THR | A | 356 | 25.332 | 60.948 | 42.433 | 1.00 | 11.53 | 6 |
| 2845 | N   | PRO | A | 357 | 28.184 | 61.868 | 43.967 | 1.00 | 10.42 | 7 |
| 2846 | CA  | PRO | A | 357 | 29.564 | 61.929 | 43.493 | 1.00 | 10.52 | 6 |

TABLE 1-continued

Atom Coordinates from the Crystal Structure of NOVAMYL

| | | | | | | | | | |
|---|---|---|---|---|---|---|---|---|---|
| 2847 | C | PRO | A | 357 | 29.689 | 61.366 | 42.092 | 1.00 | 11.14 | 6 |
| 2848 | O | PRO | A | 357 | 29.074 | 60.379 | 41.752 | 1.00 | 11.48 | 8 |
| 2849 | CB | PRO | A | 357 | 30.340 | 61.021 | 44.494 | 1.00 | 10.57 | 6 |
| 2850 | CG | PRO | A | 357 | 29.245 | 59.991 | 44.834 | 1.00 | 11.58 | 6 |
| 2851 | CD | PRO | A | 357 | 27.914 | 60.760 | 44.914 | 1.00 | 10.88 | 6 |
| 2852 | N | SER | A | 358 | 30.508 | 62.051 | 41.293 | 1.00 | 8.23 | 7 |
| 2853 | CA | SER | A | 358 | 31.003 | 61.558 | 40.001 | 1.00 | 9.73 | 6 |
| 2854 | C | SER | A | 358 | 32.509 | 61.272 | 40.069 | 1.00 | 10.56 | 6 |
| 2855 | O | SER | A | 358 | 33.323 | 62.183 | 40.331 | 1.00 | 11.97 | 8 |
| 2856 | CB | SER | A | 358 | 30.768 | 62.634 | 38.921 | 1.00 | 12.36 | 6 |
| 2857 | OG | SER | A | 358 | 31.301 | 62.159 | 37.653 | 1.00 | 13.42 | 8 |
| 2858 | N | ILE | A | 359 | 32.813 | 59.992 | 39.915 | 1.00 | 9.37 | 7 |
| 2859 | CA | ILE | A | 359 | 34.234 | 59.557 | 39.927 | 1.00 | 9.47 | 6 |
| 2860 | C | ILE | A | 359 | 34.703 | 59.350 | 38.492 | 1.00 | 12.04 | 6 |
| 2861 | O | ILE | A | 359 | 34.101 | 58.730 | 37.647 | 1.00 | 11.59 | 8 |
| 2862 | CB | ILE | A | 359 | 34.313 | 58.205 | 40.671 | 1.00 | 11.89 | 6 |
| 2863 | CG1 | ILE | A | 359 | 33.858 | 58.478 | 42.145 | 1.00 | 14.90 | 6 |
| 2864 | CG2 | ILE | A | 359 | 35.727 | 57.624 | 40.550 | 1.00 | 12.39 | 6 |
| 2865 | CD1 | ILE | A | 359 | 33.936 | 57.155 | 42.925 | 1.00 | 22.17 | 6 |
| 2866 | N | TYR | A | 360 | 35.810 | 60.088 | 38.176 | 1.00 | 9.52 | 7 |
| 2867 | CA | TYR | A | 360 | 36.364 | 60.076 | 36.807 | 1.00 | 8.41 | 6 |
| 2868 | C | TYR | A | 360 | 37.027 | 58.709 | 36.636 | 1.00 | 9.86 | 6 |
| 2869 | O | TYR | A | 360 | 37.780 | 58.227 | 37.510 | 1.00 | 10.81 | 8 |
| 2870 | CB | TYR | A | 360 | 37.399 | 61.247 | 36.796 | 1.00 | 9.51 | 6 |
| 2871 | CG | TYR | A | 360 | 37.935 | 61.510 | 35.363 | 1.00 | 9.64 | 6 |
| 2872 | CD1 | TYR | A | 360 | 37.191 | 61.428 | 34.206 | 1.00 | 10.11 | 6 |
| 2873 | CD2 | TYR | A | 360 | 39.279 | 61.882 | 35.294 | 1.00 | 9.54 | 6 |
| 2874 | CE1 | TYR | A | 360 | 37.818 | 61.650 | 32.960 | 1.00 | 10.79 | 6 |
| 2875 | CE2 | TYR | A | 360 | 39.927 | 62.148 | 34.066 | 1.00 | 10.73 | 6 |
| 2876 | CZ | TYR | A | 360 | 39.153 | 62.044 | 32.937 | 1.00 | 11.36 | 6 |
| 2877 | OH | TYR | A | 360 | 39.712 | 62.217 | 31.670 | 1.00 | 10.12 | 8 |
| 2878 | N | TYR | A | 361 | 36.808 | 56.146 | 35.418 | 1.00 | 10.09 | 7 |
| 2879 | CA | TYR | A | 361 | 37.279 | 56.773 | 35.210 | 1.00 | 10.66 | 6 |
| 2880 | C | TYR | A | 361 | 38.748 | 56.616 | 35.593 | 1.00 | 11.54 | 6 |
| 2881 | O | TYR | A | 361 | 39.556 | 57.488 | 35.297 | 1.00 | 11.37 | 8 |
| 2882 | CB | TYR | A | 361 | 37.051 | 56.287 | 33.730 | 1.00 | 9.71 | 6 |
| 2883 | CG | TYR | A | 361 | 38.086 | 56.846 | 32.765 | 1.00 | 10.50 | 6 |
| 2884 | CD1 | TYR | A | 361 | 37.937 | 58.150 | 32.332 | 1.00 | 10.91 | 6 |
| 2885 | CD2 | TYR | A | 361 | 39.176 | 56.052 | 32.383 | 1.00 | 10.62 | 6 |
| 2886 | CE1 | TYR | A | 361 | 38.913 | 58.715 | 31.480 | 1.00 | 10.92 | 6 |
| 2887 | CE2 | TYR | A | 361 | 40.155 | 56.601 | 31.520 | 1.00 | 9.87 | 6 |
| 2888 | CZ | TYR | A | 361 | 39.988 | 57.930 | 31.139 | 1.00 | 12.35 | 6 |
| 2889 | OH | TYR | A | 361 | 40.982 | 58.482 | 30.297 | 1.00 | 11.60 | 8 |
| 2890 | N | GLY | A | 362 | 39.069 | 55.475 | 36.171 | 1.00 | 11.61 | 7 |
| 2891 | CA | GLY | A | 362 | 40.454 | 55.099 | 36.513 | 1.00 | 12.01 | 6 |
| 2892 | C | GLY | A | 362 | 40.997 | 55.744 | 37.772 | 1.00 | 11.04 | 6 |
| 2893 | O | GLY | A | 362 | 42.168 | 55.431 | 38.093 | 1.00 | 12.36 | 8 |
| 2894 | N | THR | A | 363 | 40.222 | 56.614 | 38.446 | 1.00 | 12.35 | 7 |
| 2895 | CA | THR | A | 363 | 40.676 | 57.169 | 39.736 | 1.00 | 11.24 | 6 |
| 2896 | C | THR | A | 363 | 41.033 | 56.009 | 40.693 | 1.00 | 11.33 | 6 |
| 2897 | O | THR | A | 363 | 42.072 | 56.704 | 41.376 | 1.00 | 12.29 | 8 |
| 2898 | CB | THR | A | 363 | 39.528 | 57.957 | 40.387 | 1.00 | 11.07 | 6 |
| 2899 | OG1 | THR | A | 363 | 39.248 | 59.065 | 39.494 | 1.00 | 12.04 | 8 |
| 2900 | CG2 | THR | A | 363 | 40.024 | 58.554 | 41.730 | 1.00 | 11.22 | 6 |
| 2901 | N | GLU | A | 364 | 40.221 | 54.961 | 40.670 | 1.00 | 11.97 | 7 |
| 2902 | CA | GLU | A | 364 | 40.379 | 53.835 | 41.610 | 1.00 | 11.29 | 6 |
| 2903 | C | GLU | A | 364 | 41.520 | 52.938 | 41.198 | 1.00 | 12.77 | 6 |
| 2904 | O | GLU | A | 364 | 41.845 | 51.968 | 41.915 | 1.00 | 14.39 | 8 |
| 2905 | CB | GLU | A | 364 | 38.994 | 53.093 | 41.712 | 1.00 | 10.27 | 6 |
| 2906 | CG | GLU | A | 364 | 38.652 | 52.265 | 40.469 | 1.00 | 11.76 | 6 |
| 2907 | CD | GLU | A | 364 | 38.139 | 53.001 | 39.248 | 1.00 | 15.28 | 6 |
| 2908 | OE1 | GLU | A | 364 | 38.072 | 54.257 | 39.239 | 1.00 | 13.43 | 8 |
| 2909 | OE2 | GLU | A | 364 | 37.813 | 52.343 | 38.247 | 1.00 | 11.75 | 8 |
| 2910 | N | GLN | A | 365 | 42.046 | 53.105 | 39.993 | 1.00 | 10.80 | 7 |
| 2911 | CA | GLN | A | 365 | 43.256 | 52.398 | 39.542 | 1.00 | 11.28 | 6 |
| 2912 | C | GLN | A | 365 | 44.462 | 53.305 | 39.629 | 1.00 | 12.82 | 6 |
| 2913 | O | GLN | A | 365 | 45.606 | 52.953 | 39.219 | 1.00 | 12.70 | 8 |
| 2914 | CB | GLN | A | 365 | 43.138 | 51.923 | 38.088 | 1.00 | 12.65 | 6 |
| 2915 | CG | GLN | A | 365 | 41.964 | 50.951 | 37.828 | 1.00 | 9.91 | 6 |
| 2916 | CD | GLN | A | 365 | 42.043 | 49.690 | 38.693 | 1.00 | 14.70 | 6 |
| 2917 | OE1 | GLN | A | 365 | 41.016 | 49.200 | 39.269 | 1.00 | 17.54 | 8 |
| 2918 | NE2 | GLN | A | 365 | 43.204 | 49.142 | 38.847 | 1.00 | 12.05 | 7 |
| 2919 | N | TYR | A | 366 | 44.317 | 54.426 | 40.333 | 1.00 | 10.84 | 7 |
| 2920 | CA | TYR | A | 366 | 45.443 | 55.357 | 40.582 | 1.00 | 10.38 | 6 |
| 2921 | C | TYR | A | 366 | 46.039 | 55.921 | 39.308 | 1.00 | 13.18 | 6 |
| 2922 | O | TYR | A | 366 | 47.248 | 56.182 | 39.205 | 1.00 | 14.90 | 8 |
| 2923 | CB | TYR | A | 366 | 46.547 | 54.753 | 41.514 | 1.00 | 11.57 | 6 |

TABLE 1-continued

Atom Coordinates from the Crystal Structure of NOVAMYL

| | | | | | | | | | |
|---|---|---|---|---|---|---|---|---|---|
| 2924 | CG | TYR | A | 366 | 45.872 | 54.326 | 42.813 | 1.00 | 11.25 | 6 |
| 2925 | CD1 | TYR | A | 366 | 45.270 | 55.215 | 43.707 | 1.00 | 14.66 | 6 |
| 2926 | CD2 | TYR | A | 366 | 45.942 | 52.977 | 43.139 | 1.00 | 13.34 | 6 |
| 2927 | CE1 | TYR | A | 366 | 44.653 | 54.747 | 44.882 | 1.00 | 15.95 | 6 |
| 2928 | CE2 | TYR | A | 366 | 45.361 | 52.494 | 44.332 | 1.00 | 14.89 | 6 |
| 2929 | CZ | TYR | A | 366 | 44.711 | 53.395 | 45.154 | 1.00 | 12.93 | 6 |
| 2930 | OH | TYR | A | 366 | 44.118 | 52.939 | 46.302 | 1.00 | 12.26 | 8 |
| 2931 | N | MET | A | 367 | 45.147 | 56.315 | 38.357 | 1.00 | 12.15 | 7 |
| 2932 | CA | MET | A | 367 | 45.700 | 56.998 | 37.181 | 1.00 | 10.89 | 6 |
| 2933 | C | MET | A | 367 | 46.195 | 58.365 | 37.586 | 1.00 | 14.58 | 6 |
| 2934 | O | MET | A | 367 | 45.501 | 59.019 | 38.383 | 1.00 | 14.18 | 8 |
| 2935 | CB | MET | A | 367 | 44.602 | 57.163 | 36.115 | 1.00 | 11.31 | 6 |
| 2936 | CG | MET | A | 367 | 44.316 | 55.810 | 35.397 | 1.00 | 11.19 | 6 |
| 2937 | SD | MET | A | 367 | 42.994 | 56.012 | 34.139 | 1.00 | 13.40 | 16 |
| 2938 | CE | MET | A | 367 | 43.986 | 56.859 | 32.873 | 1.00 | 13.82 | 6 |
| 2939 | N | ALA | A | 368 | 47.271 | 58.817 | 36.904 | 1.00 | 12.72 | 7 |
| 2940 | CA | ALA | A | 368 | 47.689 | 60.193 | 37.152 | 1.00 | 14.30 | 6 |
| 2941 | C | ALA | A | 368 | 47.745 | 60.849 | 35.754 | 1.00 | 14.06 | 6 |
| 2942 | O | ALA | A | 368 | 47.702 | 60.187 | 34.694 | 1.00 | 19.49 | 8 |
| 2943 | CB | ALA | A | 368 | 49.047 | 60.184 | 37.904 | 1.00 | 15.40 | 6 |
| 2944 | N | GLY | A | 369 | 47.908 | 62.152 | 35.729 | 1.00 | 14.57 | 7 |
| 2945 | CA | GLY | A | 369 | 48.101 | 62.780 | 34.408 | 1.00 | 15.04 | 6 |
| 2946 | C | GLY | A | 369 | 47.715 | 64.242 | 34.571 | 1.00 | 16.47 | 6 |
| 2947 | O | GLY | A | 369 | 46.895 | 64.643 | 35.433 | 1.00 | 13.93 | 8 |
| 2948 | N | GLY | A | 370 | 48.524 | 65.045 | 33.872 | 1.00 | 12.36 | 7 |
| 2949 | CA | GLY | A | 370 | 48.282 | 66.487 | 33.864 | 1.00 | 15.60 | 6 |
| 2950 | C | GLY | A | 370 | 47.034 | 66.898 | 33.102 | 1.00 | 14.31 | 6 |
| 2951 | O | GLY | A | 370 | 46.202 | 66.015 | 32.888 | 1.00 | 18.42 | 8 |
| 2952 | N | ASN | A | 371 | 46.994 | 68.167 | 32.710 | 1.00 | 14.57 | 7 |
| 2953 | CA | ASN | A | 371 | 45.708 | 68.579 | 32.081 | 1.00 | 14.92 | 6 |
| 2954 | C | ASN | A | 371 | 45.594 | 68.064 | 30.645 | 1.00 | 14.23 | 6 |
| 2955 | O | ASN | A | 371 | 46.556 | 67.570 | 30.084 | 1.00 | 14.23 | 8 |
| 2956 | CB | AASN | A | 371 | 45.420 | 70.051 | 32.240 | 0.60 | 23.78 | 6 |
| 2957 | CG | AASN | A | 371 | 43.956 | 70.451 | 32.279 | 0.60 | 25.40 | 6 |
| 2958 | OD1 | AASN | A | 371 | 43.002 | 69.778 | 31.899 | 0.60 | 11.28 | 8 |
| 2959 | ND2 | AASN | A | 371 | 43.728 | 71.695 | 32.756 | 0.60 | 26.08 | 7 |
| 2956 | CB | BASN | A | 371 | 45.872 | 70.115 | 31.871 | 0.40 | 16.79 | 6 |
| 2957 | CG | BASN | A | 371 | 44.590 | 70.670 | 32.513 | 0.40 | 29.87 | 6 |
| 2958 | OD1 | BASN | A | 371 | 43.560 | 70.829 | 31.849 | 0.40 | 28.56 | 8 |
| 2959 | ND2 | BASN | A | 371 | 44.801 | 70.909 | 33.793 | 0.40 | 23.38 | 7 |
| 2960 | N | ASP | A | 372 | 44.373 | 68.230 | 30.152 | 1.00 | 12.86 | 7 |
| 2961 | CA | ASP | A | 372 | 44.018 | 67.780 | 28.792 | 1.00 | 12.97 | 6 |
| 2962 | C | ASP | A | 372 | 45.054 | 67.942 | 27.745 | 1.00 | 12.07 | 6 |
| 2963 | O | ASP | A | 372 | 45.503 | 69.093 | 27.614 | 1.00 | 13.32 | 8 |
| 2964 | CB | ASP | A | 372 | 42.737 | 68.624 | 28.451 | 1.00 | 10.31 | 6 |
| 2965 | CG | ASP | A | 372 | 42.153 | 68.351 | 27.084 | 1.00 | 11.02 | 6 |
| 2966 | OD1 | ASP | A | 372 | 42.556 | 67.384 | 26.464 | 1.00 | 12.81 | 8 |
| 2967 | OD2 | ASP | A | 372 | 41.293 | 69.190 | 26.659 | 1.00 | 12.58 | 8 |
| 2968 | N | PRO | A | 373 | 45.561 | 66.874 | 27.151 | 1.00 | 11.77 | 7 |
| 2969 | CA | PRO | A | 373 | 44.932 | 65.582 | 26.928 | 1.00 | 11.70 | 6 |
| 2970 | C | PRO | A | 373 | 45.436 | 64.544 | 27.918 | 1.00 | 11.76 | 6 |
| 2971 | O | PRO | A | 373 | 45.014 | 63.392 | 27.879 | 1.00 | 11.30 | 8 |
| 2972 | CB | PRO | A | 373 | 45.237 | 65.136 | 25.475 | 1.00 | 10.91 | 6 |
| 2973 | CG | PRO | A | 373 | 46.632 | 65.755 | 25.353 | 1.00 | 14.12 | 6 |
| 2974 | CD | PRO | A | 373 | 46.484 | 67.082 | 26.040 | 1.00 | 13.69 | 6 |
| 2975 | N | TYR | A | 374 | 46.374 | 64.933 | 28.815 | 1.00 | 9.68 | 7 |
| 2976 | CA | TYR | A | 374 | 47.139 | 63.921 | 29.579 | 1.00 | 10.60 | 6 |
| 2977 | C | TYR | A | 374 | 46.381 | 63.338 | 30.741 | 1.00 | 11.01 | 6 |
| 2978 | O | TYR | A | 374 | 46.896 | 62.356 | 31.346 | 1.00 | 12.41 | 8 |
| 2979 | CB | TYR | A | 374 | 48.493 | 64.515 | 30.101 | 1.00 | 12.69 | 6 |
| 2980 | CG | TYR | A | 374 | 49.258 | 65.009 | 28.884 | 1.00 | 14.15 | 6 |
| 2981 | CD1 | TYR | A | 374 | 49.738 | 64.107 | 27.954 | 1.00 | 14.25 | 6 |
| 2982 | CD2 | TYR | A | 374 | 49.457 | 66.382 | 28.664 | 1.00 | 19.98 | 6 |
| 2983 | CE1 | TYR | A | 374 | 50.385 | 64.536 | 26.798 | 1.00 | 19.01 | 6 |
| 2984 | CE2 | TYR | A | 374 | 50.125 | 66.791 | 27.525 | 1.00 | 18.34 | 6 |
| 2985 | CZ | TYR | A | 374 | 50.572 | 65.893 | 26.613 | 1.00 | 21.81 | 6 |
| 2986 | OH | TYR | A | 374 | 51.271 | 66.349 | 25.492 | 1.00 | 24.57 | 8 |
| 2987 | N | ASN | A | 375 | 45.203 | 63.895 | 31.004 | 1.00 | 10.61 | 7 |
| 2988 | CA | ASN | A | 375 | 44.295 | 63.320 | 31.991 | 1.00 | 9.59 | 6 |
| 2989 | C | ASN | A | 375 | 43.275 | 62.353 | 31.357 | 1.00 | 11.84 | 6 |
| 2990 | O | ASN | A | 375 | 42.406 | 61.795 | 32.073 | 1.00 | 12.18 | 8 |
| 2991 | CB | ASN | A | 375 | 43.489 | 64.456 | 32.649 | 1.00 | 10.84 | 6 |
| 2992 | CG | ASN | A | 375 | 42.822 | 65.356 | 31.632 | 1.00 | 13.47 | 6 |
| 2993 | OD1 | ASN | A | 375 | 42.889 | 65.147 | 30.378 | 1.00 | 14.66 | 8 |
| 2994 | ND2 | ASN | A | 375 | 42.188 | 66.403 | 32.155 | 1.00 | 11.13 | 7 |
| 2995 | N | ARG | A | 376 | 48.519 | 62.009 | 30.071 | 1.00 | 11.23 | 7 |
| 2996 | CA | ARG | A | 376 | 42.622 | 61.074 | 29.366 | 1.00 | 12.81 | 6 |

TABLE 1-continued

Atom Coordinates from the Crystal Structure of NOVAMYL

| | | | | | | | | | |
|---|---|---|---|---|---|---|---|---|---|
| 2997 | C | ARG | A | 376 | 43.410 | 59.886 | 28.872 | 1.00 | 11.47 | 6 |
| 2998 | O | ARG | A | 376 | 43.286 | 59.389 | 27.744 | 1.00 | 11.36 | 8 |
| 2999 | CB | ARG | A | 376 | 41.975 | 61.789 | 28.128 | 1.00 | 11.93 | 6 |
| 3000 | CG | ARG | A | 376 | 41.111 | 62.997 | 28.659 | 1.00 | 11.44 | 6 |
| 3001 | CD | ARG | A | 376 | 40.908 | 63.980 | 27.521 | 1.00 | 13.66 | 6 |
| 3002 | NE | ARG | A | 376 | 40.177 | 65.214 | 28.005 | 1.00 | 13.05 | 7 |
| 3003 | CZ | ARG | A | 376 | 39.567 | 66.011 | 27.137 | 1.00 | 11.35 | 6 |
| 3004 | NH1 | ARG | A | 376 | 39.569 | 65.752 | 25.825 | 1.00 | 9.57 | 7 |
| 3005 | NH2 | ARG | A | 376 | 38.944 | 67.071 | 27.646 | 1.00 | 10.95 | 7 |
| 3006 | N | GLY | A | 377 | 44.270 | 59.361 | 29.749 | 1.00 | 9.89 | 7 |
| 3007 | CA | GLY | A | 377 | 45.084 | 58.173 | 29.407 | 1.00 | 10.61 | 6 |
| 3008 | C | GLY | A | 377 | 44.162 | 56.943 | 29.297 | 1.00 | 11.99 | 6 |
| 3009 | O | GLY | A | 377 | 42.974 | 56.949 | 29.658 | 1.00 | 10.52 | 8 |
| 3010 | N | MET | A | 378 | 44.783 | 55.861 | 28.718 | 1.00 | 12.46 | 7 |
| 3011 | CA | MET | A | 378 | 43.968 | 54.622 | 28.638 | 1.00 | 11.69 | 6 |
| 3012 | C | MET | A | 378 | 43.777 | 54.021 | 30.032 | 1.00 | 11.73 | 6 |
| 3013 | O | MET | A | 378 | 44.769 | 53.836 | 30.804 | 1.00 | 12.80 | 8 |
| 3014 | CB | MET | A | 378 | 44.714 | 53.606 | 27.749 | 1.00 | 13.64 | 6 |
| 3015 | CG | MET | A | 378 | 43.750 | 52.572 | 27.113 | 1.00 | 12.65 | 6 |
| 3016 | SD | MET | A | 378 | 42.871 | 53.357 | 25.713 | 1.00 | 14.01 | 16 |
| 3017 | CE | MET | A | 378 | 41.543 | 52.139 | 25.530 | 1.00 | 15.94 | 6 |
| 3018 | N | MET | A | 379 | 42.575 | 53.515 | 30.324 | 1.00 | 11.68 | 7 |
| 3019 | CA | MET | A | 379 | 42.364 | 52.843 | 31.637 | 1.00 | 11.67 | 6 |
| 3020 | C | MET | A | 379 | 43.364 | 51.711 | 31.705 | 1.00 | 14.11 | 6 |
| 3021 | O | MET | A | 379 | 43.463 | 50.864 | 30.812 | 1.00 | 12.85 | 8 |
| 3022 | CB | MET | A | 379 | 40.896 | 52.323 | 31.558 | 1.00 | 12.77 | 6 |
| 3023 | CG | MET | A | 379 | 40.572 | 51.443 | 32.790 | 1.00 | 13.09 | 6 |
| 3024 | SD | MET | A | 379 | 40.355 | 52.467 | 34.277 | 1.00 | 13.28 | 16 |
| 3025 | CE | MET | A | 379 | 39.369 | 51.269 | 35.254 | 1.00 | 13.26 | 6 |
| 3026 | N | PRO | A | 380 | 44.193 | 51.636 | 32.750 | 1.00 | 12.95 | 7 |
| 3027 | CA | PRO | A | 380 | 45.398 | 50.827 | 32.726 | 1.00 | 14.01 | 6 |
| 3028 | C | PRO | A | 380 | 45.170 | 49.402 | 33.204 | 1.00 | 17.99 | 6 |
| 3029 | O | PRO | A | 380 | 46.005 | 48.554 | 32.914 | 1.00 | 17.24 | 8 |
| 3030 | CB | PRO | A | 380 | 46.384 | 51.501 | 33.699 | 1.00 | 14.68 | 6 |
| 3031 | CG | PRO | A | 380 | 45.418 | 52.190 | 34.636 | 1.00 | 16.71 | 6 |
| 3032 | CD | PRO | A | 380 | 44.300 | 52.693 | 33.751 | 1.00 | 14.00 | 6 |
| 3033 | N | ALA | A | 381 | 44.099 | 49.232 | 33.975 | 1.00 | 15.78 | 7 |
| 3034 | CA | ALA | A | 381 | 43.895 | 47.955 | 34.625 | 1.00 | 13.86 | 6 |
| 3035 | C | ALA | A | 381 | 42.477 | 47.891 | 35.190 | 1.00 | 13.98 | 6 |
| 3036 | O | ALA | A | 381 | 41.859 | 48.952 | 35.215 | 1.00 | 13.69 | 8 |
| 3037 | CB | ALA | A | 381 | 44.854 | 47.608 | 35.761 | 1.00 | 17.52 | 6 |
| 3038 | N | PHE | A | 382 | 42.029 | 46.671 | 35.497 | 1.00 | 14.05 | 7 |
| 3039 | CA | PHE | A | 382 | 40.701 | 46.466 | 36.094 | 1.00 | 12.60 | 6 |
| 3040 | C | PHE | A | 382 | 40.791 | 45.644 | 37.393 | 1.00 | 12.68 | 6 |
| 3041 | O | PHE | A | 382 | 39.963 | 44.765 | 37.641 | 1.00 | 15.80 | 8 |
| 3042 | CB | PHE | A | 382 | 39.742 | 45.806 | 35.052 | 1.00 | 15.36 | 6 |
| 3043 | CG | PHE | A | 382 | 39.619 | 46.669 | 33.826 | 1.00 | 14.57 | 6 |
| 3044 | CD1 | PHE | A | 382 | 40.475 | 46.629 | 32.737 | 1.00 | 14.43 | 6 |
| 3045 | CD2 | PHE | A | 382 | 38.572 | 47.618 | 33.775 | 1.00 | 16.09 | 6 |
| 3046 | CE1 | PHE | A | 382 | 40.327 | 47.480 | 31.670 | 1.00 | 17.87 | 6 |
| 3047 | CE2 | PHE | A | 382 | 38.414 | 48.469 | 32.699 | 1.00 | 12.38 | 6 |
| 3048 | CZ | PHE | A | 382 | 39.293 | 48.395 | 31.613 | 1.00 | 15.80 | 6 |
| 3049 | N | ASP | A | 383 | 41.721 | 46.138 | 38.224 | 1.00 | 13.84 | 7 |
| 3050 | CA | ASP | A | 383 | 42.065 | 45.402 | 39.467 | 1.00 | 15.38 | 6 |
| 3051 | C | ASP | A | 383 | 41.067 | 45.732 | 40.552 | 1.00 | 15.05 | 6 |
| 3052 | O | ASP | A | 383 | 40.864 | 46.868 | 40.943 | 1.00 | 16.64 | 8 |
| 3053 | CB | ASP | A | 383 | 43.457 | 45.826 | 39.901 | 1.00 | 13.18 | 6 |
| 3054 | CG | ASP | A | 383 | 44.015 | 45.155 | 41.165 | 1.00 | 18.89 | 6 |
| 3055 | OD1 | ASP | A | 383 | 43.286 | 44.428 | 41.805 | 1.00 | 20.99 | 8 |
| 3056 | OD2 | ASP | A | 383 | 45.229 | 45.408 | 41.363 | 1.00 | 21.43 | 8 |
| 3057 | N | THR | A | 384 | 40.302 | 44.680 | 40.950 | 1.00 | 13.75 | 7 |
| 3058 | CA | THR | A | 384 | 39.215 | 44.894 | 41.930 | 1.00 | 12.49 | 6 |
| 3059 | C | THR | A | 384 | 39.773 | 44.871 | 43.345 | 1.00 | 13.78 | 6 |
| 3060 | O | THR | A | 384 | 38.951 | 44.852 | 44.298 | 1.00 | 18.13 | 8 |
| 3061 | CB | THR | A | 384 | 38.098 | 43.831 | 41.755 | 1.00 | 16.42 | 6 |
| 3062 | OG1 | THR | A | 384 | 38.725 | 42.525 | 41.937 | 1.00 | 18.75 | 8 |
| 3063 | CG2 | THR | A | 384 | 37.515 | 43.943 | 40.342 | 1.00 | 20.28 | 6 |
| 3064 | N | THR | A | 385 | 41.088 | 44.832 | 43.573 | 1.00 | 14.37 | 7 |
| 3065 | CA | THR | A | 385 | 41.648 | 44.691 | 44.906 | 1.00 | 16.71 | 6 |
| 3066 | C | THR | A | 385 | 42.313 | 45.974 | 45.424 | 1.00 | 16.63 | 6 |
| 3067 | O | THR | A | 385 | 42.873 | 45.952 | 46.539 | 1.00 | 14.22 | 8 |
| 3068 | CB | THR | A | 385 | 42.693 | 43.546 | 45.009 | 1.00 | 19.15 | 6 |
| 3069 | OG1 | THR | A | 385 | 43.883 | 43.878 | 44.288 | 1.00 | 17.99 | 8 |
| 3070 | CG2 | THR | A | 385 | 42.075 | 42.234 | 44.541 | 1.00 | 24.33 | 6 |
| 3071 | N | THR | A | 386 | 42.254 | 47.039 | 44.606 | 1.00 | 14.92 | 7 |
| 3072 | CA | THR | A | 386 | 42.952 | 48.254 | 45.131 | 1.00 | 13.63 | 6 |
| 3073 | C | THR | A | 386 | 42.175 | 48.801 | 46.328 | 1.00 | 11.22 | 6 |

TABLE 1-continued

Atom Coordinates from the Crystal Structure of NOVAMYL

| 3074 | O | THR | A | 386 | 40.990 | 48.649 | 46.478 | 1.00 | 12.74 | 8 |
|---|---|---|---|---|---|---|---|---|---|---|
| 3075 | CB | THR | A | 386 | 43.101 | 49.344 | 44.054 | 1.00 | 13.50 | 6 |
| 3076 | OG1 | THR | A | 386 | 41.805 | 49.919 | 43.822 | 1.00 | 12.14 | 8 |
| 3077 | CG2 | THR | A | 386 | 43.656 | 48.809 | 42.719 | 1.00 | 17.62 | 6 |
| 3078 | N | THR | A | 387 | 42.886 | 49.552 | 47.184 | 1.00 | 14.21 | 7 |
| 3079 | CA | THR | A | 387 | 42.237 | 50.167 | 48.316 | 1.00 | 11.44 | 6 |
| 3080 | C | THR | A | 387 | 41.127 | 51.134 | 47.887 | 1.00 | 12.54 | 6 |
| 3081 | O | THR | A | 387 | 40.045 | 51.113 | 48.437 | 1.00 | 12.57 | 8 |
| 3082 | CB | THR | A | 387 | 43.277 | 50.926 | 49.145 | 1.00 | 17.16 | 6 |
| 3083 | OG1 | THR | A | 387 | 44.177 | 49.939 | 49.669 | 1.00 | 15.42 | 8 |
| 3084 | CG2 | THR | A | 387 | 42.644 | 51.724 | 50.273 | 1.00 | 14.27 | 6 |
| 3085 | N | ALA | A | 388 | 41.441 | 51.910 | 46.838 | 1.00 | 13.30 | 7 |
| 3086 | CA | ALA | A | 388 | 40.376 | 52.785 | 46.360 | 1.00 | 10.83 | 6 |
| 3087 | C | ALA | A | 388 | 39.162 | 52.083 | 45.808 | 1.00 | 12.23 | 6 |
| 3088 | O | ALA | A | 388 | 38.030 | 52.497 | 46.001 | 1.00 | 11.44 | 8 |
| 3089 | CB | ALA | A | 388 | 40.968 | 53.700 | 45.239 | 1.00 | 10.26 | 6 |
| 3090 | N | PHE | A | 389 | 39.347 | 50.956 | 45.084 | 1.00 | 12.53 | 7 |
| 3091 | CA | PHE | A | 389 | 38.202 | 50.182 | 44.579 | 1.00 | 13.64 | 6 |
| 3092 | C | PHE | A | 389 | 37.361 | 49.746 | 45.779 | 1.00 | 13.47 | 6 |
| 3093 | O | PHE | A | 389 | 36.157 | 49.895 | 45.789 | 1.00 | 12.37 | 8 |
| 3094 | CB | PHE | A | 389 | 38.766 | 48.975 | 43.763 | 1.00 | 11.46 | 6 |
| 3095 | CG | PHE | A | 389 | 37.627 | 48.178 | 43.141 | 1.00 | 12.01 | 6 |
| 3096 | CD1 | PHE | A | 389 | 36.936 | 47.248 | 43.916 | 1.00 | 16.87 | 6 |
| 3097 | CD2 | PHE | A | 389 | 37.375 | 48.299 | 41.777 | 1.00 | 14.39 | 6 |
| 3098 | CE1 | PHE | A | 389 | 35.869 | 46.515 | 43.383 | 1.00 | 14.50 | 6 |
| 3099 | CE2 | PHE | A | 389 | 36.340 | 47.536 | 41.216 | 1.00 | 12.44 | 6 |
| 3100 | CZ | PHE | A | 389 | 35.646 | 46.648 | 42.031 | 1.00 | 13.69 | 6 |
| 3101 | N | LYS | A | 390 | 38.053 | 49.160 | 46.775 | 1.00 | 12.03 | 7 |
| 3102 | CA | LYS | A | 390 | 37.303 | 48.672 | 47.936 | 1.00 | 12.63 | 6 |
| 3103 | C | LYS | A | 390 | 36.544 | 49.767 | 48.699 | 1.00 | 14.75 | 6 |
| 3104 | O | LYS | A | 390 | 35.438 | 49.556 | 49.197 | 1.00 | 12.66 | 8 |
| 3105 | CB | LYS | A | 390 | 38.291 | 48.000 | 48.917 | 1.00 | 12.06 | 6 |
| 3106 | CG | LYS | A | 390 | 38.798 | 46.712 | 48.243 | 1.00 | 15.90 | 6 |
| 3107 | CD | LYS | A | 390 | 39.589 | 45.970 | 49.325 | 1.00 | 25.81 | 6 |
| 3108 | CE | LYS | A | 390 | 40.980 | 46.524 | 49.440 | 1.00 | 29.79 | 6 |
| 3109 | NZ | LYS | A | 390 | 41.835 | 45.465 | 50.107 | 1.00 | 41.01 | 7 |
| 3110 | N | GLU | A | 391 | 37.256 | 50.908 | 48.782 | 1.00 | 11.21 | 7 |
| 3111 | CA | GLU | A | 391 | 36.636 | 52.048 | 49.475 | 1.00 | 11.43 | 6 |
| 3112 | C | GLU | A | 391 | 35.375 | 52.482 | 48.742 | 1.00 | 12.51 | 6 |
| 3113 | O | GLU | A | 391 | 34.300 | 52.735 | 49.337 | 1.00 | 10.64 | 8 |
| 3114 | CB | GLU | A | 391 | 37.670 | 53.223 | 49.487 | 1.00 | 10.44 | 6 |
| 3115 | CG | GLU | A | 391 | 36.957 | 54.519 | 49.997 | 1.00 | 10.67 | 6 |
| 3116 | CD | GLU | A | 391 | 37.870 | 55.744 | 49.810 | 1.00 | 12.38 | 6 |
| 3117 | OE1 | GLU | A | 391 | 38.974 | 55.628 | 49.226 | 1.00 | 13.12 | 8 |
| 3118 | OE2 | GLU | A | 391 | 37.458 | 56.841 | 50.284 | 1.00 | 12.94 | 8 |
| 3119 | N | VLA | A | 392 | 35.455 | 52.675 | 47.403 | 1.00 | 11.36 | 7 |
| 3120 | CA | VAL | A | 392 | 34.279 | 53.176 | 46.653 | 1.00 | 12.25 | 6 |
| 3121 | C | VAL | A | 392 | 33.156 | 52.128 | 46.716 | 1.00 | 12.76 | 6 |
| 3122 | O | VAL | A | 392 | 31.968 | 52.481 | 46.930 | 1.00 | 12.77 | 8 |
| 3123 | CB | VAL | A | 392 | 34.667 | 53.410 | 45.175 | 1.00 | 14.39 | 6 |
| 3124 | CG1 | VAL | A | 392 | 33.434 | 53.661 | 44.296 | 1.00 | 13.75 | 6 |
| 3125 | CG2 | VAL | A | 392 | 35.702 | 54.570 | 45.061 | 1.00 | 12.07 | 6 |
| 3126 | N | SER | A | 393 | 33.487 | 50.846 | 46.628 | 1.00 | 10.90 | 7 |
| 3127 | CA | SER | A | 393 | 32.426 | 49.822 | 46.686 | 1.00 | 12.19 | 6 |
| 3128 | C | SER | A | 393 | 31.708 | 49.782 | 48.021 | 1.00 | 10.96 | 6 |
| 3129 | O | SER | A | 393 | 30.469 | 49.774 | 48.186 | 1.00 | 12.48 | 8 |
| 3130 | CB | SER | A | 393 | 33.059 | 48.431 | 46.394 | 1.00 | 12.79 | 6 |
| 3131 | OG | SER | A | 393 | 31.944 | 47.538 | 46.423 | 1.00 | 19.93 | 8 |
| 3132 | N | THR | A | 394 | 32.493 | 49.942 | 49.099 | 1.00 | 11.04 | 7 |
| 3133 | CA | THR | A | 394 | 31.920 | 49.922 | 50.445 | 1.00 | 12.34 | 6 |
| 3134 | C | THR | A | 394 | 31.061 | 51.130 | 50.682 | 1.00 | 11.80 | 6 |
| 3135 | O | THR | A | 394 | 29.935 | 51.097 | 51.169 | 1.00 | 11.63 | 8 |
| 3136 | CB | THR | A | 394 | 33.039 | 49.889 | 51.509 | 1.00 | 12.40 | 6 |
| 3137 | OG1 | THR | A | 394 | 33.699 | 48.614 | 51.401 | 1.00 | 14.67 | 8 |
| 3138 | CG2 | THR | A | 394 | 32.443 | 50.011 | 52.927 | 1.00 | 14.84 | 6 |
| 3139 | N | LEU | A | 395 | 31.600 | 52.334 | 50.322 | 1.00 | 12.76 | 7 |
| 3140 | CA | LEU | A | 395 | 30.858 | 53.558 | 50.592 | 1.00 | 11.35 | 6 |
| 3141 | C | LEU | A | 395 | 29.666 | 53.709 | 49.624 | 1.00 | 10.18 | 6 |
| 3142 | O | LEU | A | 395 | 28.676 | 54.373 | 49.976 | 1.00 | 11.69 | 8 |
| 3143 | CB | LEU | A | 395 | 31.784 | 54.804 | 50.604 | 1.00 | 13.30 | 6 |
| 3144 | CG | LEU | A | 395 | 32.795 | 54.745 | 51.811 | 1.00 | 12.96 | 6 |
| 3145 | CD1 | LEU | A | 395 | 33.641 | 56.019 | 51.748 | 1.00 | 13.55 | 6 |
| 3146 | CD2 | LEU | A | 395 | 32.059 | 54.747 | 53.145 | 1.00 | 14.45 | 6 |
| 3147 | N | ALA | A | 396 | 29.852 | 53.116 | 48.444 | 1.00 | 11.70 | 7 |
| 3148 | CA | ALA | A | 396 | 28.636 | 53.182 | 47.557 | 1.00 | 12.78 | 6 |
| 3149 | C | ALA | A | 396 | 27.498 | 52.378 | 48.163 | 1.00 | 13.72 | 6 |
| 3150 | O | ALA | A | 396 | 26.345 | 52.797 | 48.075 | 1.00 | 10.99 | 8 |

TABLE 1-continued

Atom Coordinates from the Crystal Structure of NOVAMYL

| 3151 | CB | ALA | A | 396 | 29.035 | 52.530 | 46.203 | 1.00 | 12.34 | 6 |
|---|---|---|---|---|---|---|---|---|---|---|
| 3152 | N | GLY | A | 397 | 27.797 | 51.244 | 48.825 | 1.00 | 11.86 | 7 |
| 3153 | CA | GLY | A | 397 | 26.710 | 50.490 | 49.510 | 1.00 | 12.95 | 6 |
| 3154 | C | GLY | A | 397 | 26.096 | 51.295 | 50.656 | 1.00 | 12.93 | 6 |
| 3155 | O | GLY | A | 397 | 24.865 | 51.276 | 50.842 | 1.00 | 15.22 | 8 |
| 3156 | N | LEU | A | 398 | 26.948 | 52.018 | 51.404 | 1.00 | 12.12 | 7 |
| 3157 | CA | LEU | A | 398 | 26.336 | 52.833 | 52.491 | 1.00 | 10.40 | 6 |
| 3158 | C | LEU | A | 398 | 25.388 | 53.871 | 51.900 | 1.00 | 13.47 | 6 |
| 3159 | O | LEU | A | 398 | 24.310 | 54.166 | 52.434 | 1.00 | 13.29 | 8 |
| 3160 | CB | LEU | A | 398 | 27.503 | 53.525 | 53.229 | 1.00 | 10.78 | 6 |
| 3161 | CG | LEU | A | 398 | 26.999 | 54.426 | 54.353 | 1.00 | 11.76 | 6 |
| 3162 | CD1 | LEU | A | 398 | 26.326 | 53.660 | 55.479 | 1.00 | 15.25 | 6 |
| 3163 | CD2 | LEU | A | 398 | 28.230 | 55.206 | 54.909 | 1.00 | 16.57 | 6 |
| 3164 | N | ARG | A | 399 | 25.832 | 54.478 | 50.754 | 1.00 | 11.98 | 7 |
| 3165 | CA | ARG | A | 399 | 24.988 | 55.539 | 50.164 | 1.00 | 12.52 | 6 |
| 3166 | C | ARG | A | 399 | 23.712 | 54.952 | 49.579 | 1.00 | 13.24 | 6 |
| 3167 | O | ARG | A | 399 | 22.661 | 55.603 | 49.688 | 1.00 | 14.42 | 8 |
| 3168 | CB | ARG | A | 399 | 25.789 | 56.271 | 49.068 | 1.00 | 11.24 | 6 |
| 3169 | CG | ARG | A | 399 | 24.974 | 57.205 | 48.158 | 1.00 | 11.40 | 6 |
| 3170 | CD | ARG | A | 399 | 25.933 | 57.875 | 47.182 | 1.00 | 11.42 | 6 |
| 3171 | NE | ARG | A | 399 | 26.620 | 59.029 | 47.799 | 1.00 | 10.92 | 7 |
| 3172 | CZ | ARG | A | 399 | 26.193 | 60.279 | 47.877 | 1.00 | 14.21 | 6 |
| 3173 | NH1 | ARG | A | 399 | 24.965 | 60.565 | 47.446 | 1.00 | 10.96 | 7 |
| 3174 | NH2 | ARG | A | 399 | 26.954 | 61.245 | 48.436 | 1.00 | 11.76 | 7 |
| 3175 | N | ARG | A | 400 | 23.713 | 53.697 | 49.131 | 1.00 | 12.24 | 7 |
| 3176 | CA | ARG | A | 400 | 22.456 | 53.111 | 48.675 | 1.00 | 12.96 | 6 |
| 3177 | C | ARG | A | 400 | 21.533 | 52.789 | 49.852 | 1.00 | 13.71 | 6 |
| 3178 | O | ARG | A | 400 | 20.311 | 52.762 | 49.629 | 1.00 | 17.33 | 8 |
| 3179 | CB | ARG | A | 400 | 22.748 | 51.783 | 47.930 | 1.00 | 14.09 | 6 |
| 3180 | CG | ARG | A | 400 | 23.460 | 51.918 | 46.578 | 1.00 | 14.91 | 6 |
| 3181 | CD | ARG | A | 400 | 23.412 | 50.634 | 45.761 | 1.00 | 16.08 | 6 |
| 3182 | NE | ARG | A | 400 | 24.141 | 49.517 | 46.399 | 1.00 | 14.78 | 7 |
| 3183 | CZ | ARG | A | 400 | 25.452 | 49.279 | 46.343 | 1.00 | 14.12 | 6 |
| 3184 | NH1 | ARG | A | 400 | 26.214 | 50.128 | 45.640 | 1.00 | 15.84 | 7 |
| 3185 | NH2 | ARG | A | 400 | 25.957 | 48.216 | 46.978 | 1.00 | 16.89 | 7 |
| 3186 | N | ASN | A | 401 | 22.154 | 52.394 | 50.972 | 1.00 | 14.24 | 7 |
| 3187 | CA | ASN | A | 401 | 21.271 | 51.879 | 52.060 | 1.00 | 14.18 | 6 |
| 3188 | C | ASN | A | 401 | 20.967 | 52.828 | 53.189 | 1.00 | 15.56 | 6 |
| 3189 | O | ASN | A | 401 | 19.976 | 52.564 | 53.935 | 1.00 | 17.91 | 8 |
| 3190 | CB | ASN | A | 401 | 21.990 | 50.632 | 52.590 | 1.00 | 16.43 | 6 |
| 3191 | CG | ASN | A | 401 | 21.827 | 49.617 | 51.404 | 1.00 | 25.29 | 6 |
| 3192 | OD1 | ASN | A | 401 | 22.805 | 49.256 | 50.797 | 1.00 | 33.03 | 8 |
| 3193 | ND2 | ASN | A | 401 | 20.619 | 49.215 | 51.102 | 1.00 | 40.20 | 7 |
| 3194 | N | ASN | A | 402 | 21.705 | 53.948 | 53.373 | 1.00 | 13.76 | 7 |
| 3195 | CA | ASN | A | 402 | 21.449 | 54.851 | 54.506 | 1.00 | 13.71 | 6 |
| 3196 | C | ASN | A | 402 | 20.938 | 56.175 | 53.980 | 1.00 | 14.67 | 6 |
| 3197 | O | ASN | A | 402 | 21.601 | 56.923 | 53.249 | 1.00 | 13.53 | 8 |
| 3198 | CB | ASN | A | 402 | 22.753 | 55.036 | 55.311 | 1.00 | 13.24 | 6 |
| 3199 | CG | ASN | A | 402 | 22.397 | 55.744 | 56.604 | 1.00 | 14.53 | 6 |
| 3200 | OD1 | ASN | A | 402 | 21.722 | 56.787 | 56.564 | 1.00 | 14.56 | 8 |
| 3201 | ND2 | ASN | A | 402 | 22.839 | 55.186 | 57.762 | 1.00 | 11.48 | 7 |
| 3202 | N | ALA | A | 403 | 19.633 | 56.460 | 54.202 | 1.00 | 12.55 | 7 |
| 3203 | CA | ALA | A | 403 | 19.017 | 57.672 | 53.679 | 1.00 | 12.81 | 6 |
| 3204 | C | ALA | A | 403 | 19.622 | 58.961 | 54.144 | 1.00 | 14.88 | 6 |
| 3205 | O | ALA | A | 403 | 19.421 | 59.958 | 53.422 | 1.00 | 13.18 | 8 |
| 3206 | CB | ALA | A | 403 | 17.511 | 57.608 | 54.092 | 1.00 | 12.99 | 6 |
| 3207 | N | ALA | A | 404 | 20.407 | 58.945 | 55.229 | 1.00 | 11.82 | 7 |
| 3208 | CA | ALA | A | 404 | 21.107 | 60.187 | 55.611 | 1.00 | 11.98 | 6 |
| 3209 | C | ALA | A | 404 | 22.095 | 60.641 | 54.524 | 1.00 | 11.49 | 6 |
| 3210 | O | ALA | A | 404 | 22.259 | 61.857 | 54.383 | 1.00 | 12.58 | 8 |
| 3211 | CB | ALA | A | 404 | 21.874 | 60.008 | 56.930 | 1.00 | 15.02 | 6 |
| 3212 | N | ILE | A | 405 | 22.707 | 59.716 | 53.830 | 1.00 | 11.27 | 7 |
| 3213 | CA | ILE | A | 405 | 23.702 | 60.168 | 52.791 | 1.00 | 11.62 | 6 |
| 3214 | C | ILE | A | 405 | 22.936 | 60.722 | 51.581 | 1.00 | 13.21 | 6 |
| 3215 | O | ILE | A | 405 | 23.353 | 61.696 | 50.964 | 1.00 | 12.14 | 8 |
| 3216 | CB | ILE | A | 405 | 24.538 | 58.973 | 52.331 | 1.00 | 14.54 | 6 |
| 3217 | CG1 | ILE | A | 405 | 25.425 | 58.253 | 53.392 | 1.00 | 15.40 | 6 |
| 3218 | CG2 | ILE | A | 405 | 25.511 | 59.410 | 51.202 | 1.00 | 11.30 | 6 |
| 3219 | CD1 | ILE | A | 405 | 26.170 | 59.266 | 54.247 | 1.00 | 17.36 | 6 |
| 3220 | N | GLN | A | 406 | 21.759 | 60.152 | 51.297 | 1.00 | 11.32 | 7 |
| 3221 | CA | GLN | A | 406 | 20.992 | 60.545 | 50.107 | 1.00 | 11.87 | 6 |
| 3222 | C | GLN | A | 406 | 20.335 | 61.902 | 50.300 | 1.00 | 14.28 | 6 |
| 3223 | O | GLN | A | 406 | 20.265 | 62.707 | 49.360 | 1.00 | 11.82 | 8 |
| 3224 | CB | GLN | A | 406 | 19.875 | 59.494 | 49.869 | 1.00 | 12.00 | 6 |
| 3225 | CG | GLN | A | 406 | 20.511 | 58.136 | 49.549 | 1.00 | 12.17 | 6 |
| 3226 | CD | GLN | A | 406 | 19.521 | 56.983 | 49.392 | 1.00 | 22.22 | 6 |
| 3227 | OE1 | GLN | A | 406 | 19.847 | 55.775 | 49.395 | 1.00 | 20.31 | 8 |

TABLE 1-continued

Atom Coordinates from the Crystal Structure of NOVAMYL

| 3228 | NE2 | GLN | A | 406 | 18.272 | 57.356 | 49.223 | 1.00 | 24.04 | 7 |
| 3229 | N | TYR | A | 407 | 19.757 | 62.154 | 51.499 | 1.00 | 13.05 | 7 |
| 3230 | CA | TYR | A | 407 | 18.848 | 63.261 | 51.702 | 1.00 | 13.56 | 6 |
| 3231 | C | TYR | A | 407 | 19.168 | 64.182 | 52.885 | 1.00 | 10.35 | 6 |
| 3232 | O | TYR | A | 407 | 18.463 | 65.190 | 53.047 | 1.00 | 12.85 | 8 |
| 3233 | CB | TYR | A | 407 | 17.440 | 62.678 | 52.068 | 1.00 | 14.06 | 6 |
| 3234 | CG | TYR | A | 407 | 16.935 | 61.567 | 51.144 | 1.00 | 12.51 | 6 |
| 3235 | CD1 | TYR | A | 407 | 16.929 | 61.748 | 49.759 | 1.00 | 11.68 | 6 |
| 3236 | CD2 | TYR | A | 407 | 16.397 | 60.418 | 51.708 | 1.00 | 11.57 | 6 |
| 3237 | CE1 | TYR | A | 407 | 16.441 | 60.742 | 48.918 | 1.00 | 12.71 | 6 |
| 3238 | CE2 | TYR | A | 407 | 15.910 | 59.420 | 50.894 | 1.00 | 14.60 | 6 |
| 3239 | CZ | TYR | A | 407 | 15.933 | 59.595 | 49.515 | 1.00 | 15.50 | 6 |
| 3240 | OH | TYR | A | 407 | 15.433 | 58.598 | 48.707 | 1.00 | 15.89 | 8 |
| 3241 | N | GLY | A | 408 | 20.152 | 63.743 | 53.678 | 1.00 | 12.31 | 7 |
| 3242 | CA | GLY | A | 408 | 20.277 | 64.361 | 55.005 | 1.00 | 14.17 | 6 |
| 3243 | C | GLY | A | 408 | 20.830 | 65.790 | 55.030 | 1.00 | 13.76 | 6 |
| 3244 | O | GLY | A | 408 | 21.566 | 66.253 | 54.133 | 1.00 | 13.31 | 8 |
| 3245 | N | THR | A | 409 | 20.636 | 66.393 | 56.207 | 1.00 | 12.33 | 7 |
| 3246 | CA | THR | A | 409 | 21.322 | 67.645 | 56.558 | 1.00 | 14.50 | 6 |
| 3247 | C | THR | A | 409 | 22.822 | 67.370 | 56.707 | 1.00 | 13.72 | 6 |
| 3248 | O | THR | A | 409 | 23.222 | 66.229 | 56.777 | 1.00 | 12.71 | 8 |
| 3249 | CB | THR | A | 409 | 20.812 | 68.210 | 57.928 | 1.00 | 16.13 | 6 |
| 3250 | OG1 | THR | A | 409 | 20.849 | 67.169 | 58.916 | 1.00 | 16.69 | 8 |
| 3251 | CG2 | THR | A | 409 | 19.360 | 68.677 | 57.762 | 1.00 | 18.70 | 6 |
| 3252 | N | THR | A | 410 | 23.605 | 68.449 | 56.790 | 1.00 | 12.28 | 7 |
| 3253 | CA | THR | A | 410 | 25.062 | 68.261 | 57.141 | 1.00 | 12.15 | 6 |
| 3254 | C | THR | A | 410 | 25.332 | 69.229 | 58.321 | 1.00 | 12.71 | 6 |
| 3255 | O | THR | A | 410 | 25.041 | 70.423 | 58.225 | 1.00 | 13.99 | 8 |
| 3256 | CB | THR | A | 410 | 25.943 | 68.740 | 55.952 | 1.00 | 11.34 | 6 |
| 3257 | OG1 | THR | A | 410 | 25.541 | 67.959 | 54.786 | 1.00 | 13.77 | 8 |
| 3258 | CG2 | THR | A | 410 | 27.425 | 68.392 | 56.192 | 1.00 | 13.33 | 6 |
| 3259 | N | THR | A | 411 | 25.996 | 68.665 | 59.342 | 1.00 | 12.78 | 7 |
| 3260 | CA | THR | A | 411 | 26.301 | 69.430 | 60.568 | 1.00 | 12.27 | 6 |
| 3261 | C | THR | A | 411 | 27.765 | 69.192 | 60.919 | 1.00 | 13.51 | 6 |
| 3262 | O | THR | A | 411 | 28.168 | 68.039 | 61.036 | 1.00 | 14.10 | 8 |
| 3263 | CB | THR | A | 411 | 25.386 | 68.891 | 61.718 | 1.00 | 13.83 | 6 |
| 3264 | OG1 | THR | A | 411 | 24.000 | 69.120 | 61.364 | 1.00 | 15.26 | 8 |
| 3265 | CG2 | THR | A | 411 | 25.620 | 69.676 | 62.991 | 1.00 | 17.79 | 6 |
| 3266 | N | GLN | A | 412 | 28.501 | 70.302 | 61.110 | 1.00 | 12.74 | 7 |
| 3267 | CA | GLN | A | 412 | 29.899 | 70.153 | 61.592 | 1.00 | 13.61 | 6 |
| 3268 | C | GLN | A | 412 | 29.894 | 69.765 | 63.062 | 1.00 | 13.43 | 6 |
| 3269 | O | GLN | A | 412 | 29.218 | 70.451 | 63.824 | 1.00 | 15.64 | 8 |
| 3270 | CB | GLN | A | 412 | 30.556 | 71.523 | 61.335 | 1.00 | 14.70 | 6 |
| 3271 | CG | GLN | A | 412 | 31.999 | 71.615 | 61.876 | 1.00 | 22.99 | 6 |
| 3272 | CD | GLN | A | 412 | 31.918 | 72.168 | 63.334 | 1.00 | 22.07 | 6 |
| 3273 | OE1 | GLN | A | 412 | 32.409 | 71.438 | 64.163 | 1.00 | 19.41 | 8 |
| 3274 | NE2 | GLN | A | 412 | 31.358 | 73.310 | 63.633 | 1.00 | 25.10 | 7 |
| 3275 | N | ARG | A | 413 | 30.694 | 68.721 | 63.330 | 1.00 | 11.94 | 7 |
| 3276 | CA | ARG | A | 413 | 30.768 | 68.223 | 64.700 | 1.00 | 11.40 | 6 |
| 3277 | C | ARG | A | 413 | 32.184 | 68.430 | 65.276 | 1.00 | 12.19 | 6 |
| 3278 | O | ARG | A | 413 | 32.263 | 68.482 | 66.510 | 1.00 | 12.20 | 8 |
| 3279 | CB | ARG | A | 413 | 30.356 | 66.756 | 64.815 | 1.00 | 16.20 | 6 |
| 3280 | CG | ARG | A | 413 | 28.840 | 66.557 | 64.562 | 1.00 | 13.09 | 6 |
| 3281 | CD | ARG | A | 413 | 27.968 | 67.296 | 65.579 | 1.00 | 13.13 | 6 |
| 3282 | NE | ARG | A | 413 | 26.611 | 66.668 | 65.580 | 1.00 | 14.79 | 7 |
| 3283 | CZ | ARG | A | 413 | 25.684 | 66.909 | 66.515 | 1.00 | 19.43 | 6 |
| 3284 | NH1 | ARG | A | 413 | 25.974 | 67.784 | 67.503 | 1.00 | 16.73 | 7 |
| 3285 | NH2 | ARG | A | 413 | 24.529 | 66.233 | 66.470 | 1.00 | 18.22 | 7 |
| 3286 | N | TRP | A | 414 | 33.228 | 68.466 | 64.474 | 1.00 | 11.18 | 7 |
| 3287 | CA | TRP | A | 414 | 34.548 | 68.752 | 65.082 | 1.00 | 12.61 | 6 |
| 3288 | C | TRP | A | 414 | 35.444 | 69.243 | 63.947 | 1.00 | 13.80 | 6 |
| 3289 | O | TRP | A | 414 | 35.295 | 68.712 | 62.833 | 1.00 | 13.58 | 8 |
| 3290 | CB | TRP | A | 414 | 35.121 | 67.438 | 65.651 | 1.00 | 14.04 | 6 |
| 3291 | CG | TRP | A | 414 | 36.181 | 67.603 | 66.709 | 1.00 | 14.49 | 6 |
| 3292 | CD1 | TRP | A | 414 | 35.921 | 67.473 | 68.075 | 1.00 | 15.45 | 6 |
| 3293 | CD2 | TRP | A | 414 | 37.583 | 67.864 | 66.591 | 1.00 | 15.74 | 6 |
| 3294 | NE1 | TRP | A | 414 | 37.112 | 67.622 | 68.773 | 1.00 | 16.17 | 7 |
| 3295 | CE2 | TRP | A | 414 | 38.123 | 67.884 | 67.898 | 1.00 | 15.43 | 6 |
| 3296 | CE3 | TRP | A | 414 | 38.421 | 68.101 | 65.507 | 1.00 | 14.89 | 6 |
| 3297 | CZ2 | TRP | A | 414 | 39.489 | 68.090 | 68.138 | 1.00 | 20.21 | 6 |
| 3298 | CZ3 | TRP | A | 414 | 39.805 | 68.279 | 65.725 | 1.00 | 15.42 | 6 |
| 3299 | CH2 | TRP | A | 414 | 40.310 | 68.296 | 67.066 | 1.00 | 17.01 | 6 |
| 3300 | N | ILE | A | 415 | 36.215 | 70.337 | 64.186 | 1.00 | 12.40 | 7 |
| 3301 | CA | ILE | A | 415 | 37.021 | 70.828 | 63.038 | 1.00 | 11.33 | 6 |
| 3302 | C | ILE | A | 415 | 38.296 | 71.491 | 63.524 | 1.00 | 15.04 | 6 |
| 3303 | O | ILE | A | 415 | 38.300 | 72.134 | 64.600 | 1.00 | 15.39 | 8 |
| 3304 | CB | ILE | A | 415 | 36.153 | 71.827 | 62.253 | 1.00 | 15.29 | 6 |

TABLE 1-continued

Atom Coordinates from the Crystal Structure of NOVAMYL

| | | | | | | | | | | |
|---|---|---|---|---|---|---|---|---|---|---|
| 3305 | CG1 | ILE | A | 415 | 36.843 | 72.197 | 60.923 | 1.00 | 15.07 | 6 |
| 3306 | CG2 | ILE | A | 415 | 35.782 | 73.061 | 63.054 | 1.00 | 20.69 | 6 |
| 3307 | CD1 | ILE | A | 415 | 35.862 | 72.686 | 59.854 | 1.00 | 18.18 | 6 |
| 3308 | N | ASN | A | 416 | 39.349 | 71.266 | 62.797 | 1.00 | 13.47 | 7 |
| 3309 | CA | ASN | A | 416 | 40.517 | 72.152 | 62.912 | 1.00 | 14.63 | 6 |
| 3310 | C | ASN | A | 416 | 41.103 | 72.198 | 61.526 | 1.00 | 13.17 | 6 |
| 3311 | O | ASN | A | 416 | 40.399 | 71.879 | 60.536 | 1.00 | 12.76 | 8 |
| 3312 | CB | ASN | A | 416 | 41.480 | 71.607 | 63.994 | 1.00 | 14.61 | 6 |
| 3313 | CG | ASN | A | 416 | 42.250 | 70.394 | 63.669 | 1.00 | 16.07 | 6 |
| 3314 | OD1 | ASN | A | 416 | 42.250 | 70.394 | 63.669 | 1.00 | 12.99 | 8 |
| 3315 | ND2 | ASN | A | 416 | 43.129 | 69.947 | 64.597 | 1.00 | 16.12 | 7 |
| 3316 | N | ASN | A | 417 | 42.356 | 72.644 | 61.313 | 1.00 | 13.23 | 7 |
| 3317 | CA | ASN | A | 417 | 42.755 | 72.836 | 59.907 | 1.00 | 13.30 | 6 |
| 3318 | C | ASN | A | 417 | 42.767 | 71.526 | 59.103 | 1.00 | 13.34 | 6 |
| 3319 | O | ASN | A | 417 | 42.621 | 71.524 | 57.886 | 1.00 | 12.55 | 8 |
| 3320 | CB | ASN | A | 417 | 44.185 | 73.410 | 59.931 | 1.00 | 16.87 | 6 |
| 3321 | CG | ASN | A | 417 | 44.190 | 74.929 | 59.999 | 1.00 | 23.81 | 6 |
| 3322 | OD1 | ASN | A | 417 | 43.170 | 75.585 | 60.178 | 1.00 | 21.65 | 8 |
| 3323 | ND2 | ASN | A | 417 | 45.415 | 75.482 | 59.839 | 1.00 | 24.48 | 7 |
| 3324 | N | ASP | A | 418 | 43.109 | 70.439 | 59.874 | 1.00 | 12.62 | 7 |
| 3325 | CA | ASP | A | 418 | 43.295 | 69.150 | 59.209 | 1.00 | 10.76 | 6 |
| 3326 | C | ASP | A | 418 | 42.126 | 68.157 | 59.319 | 1.00 | 12.08 | 6 |
| 3327 | O | ASP | A | 418 | 42.093 | 67.177 | 58.533 | 1.00 | 11.98 | 8 |
| 3328 | CB | ASP | A | 418 | 44.520 | 68.478 | 59.846 | 1.00 | 13.38 | 6 |
| 3329 | CG | ASP | A | 418 | 45.842 | 69.080 | 59.483 | 1.00 | 16.78 | 6 |
| 3330 | OD1 | ASP | A | 418 | 46.040 | 69.609 | 58.372 | 1.00 | 13.55 | 8 |
| 3331 | OD2 | ASP | A | 418 | 46.759 | 69.017 | 60.342 | 1.00 | 13.98 | 8 |
| 3332 | N | VAL | A | 419 | 41.304 | 68.369 | 60.363 | 1.00 | 11.52 | 7 |
| 3333 | CA | VAL | A | 419 | 40.281 | 67.366 | 60.644 | 1.00 | 10.52 | 6 |
| 3334 | C | VAL | A | 419 | 38.910 | 67.958 | 60.419 | 1.00 | 12.12 | 6 |
| 3335 | O | VAL | A | 419 | 38.606 | 69.052 | 60.846 | 1.00 | 12.25 | 8 |
| 3336 | CB | VAL | A | 419 | 40.384 | 66.958 | 62.145 | 1.00 | 11.46 | 6 |
| 3337 | CG1 | VAL | A | 419 | 39.231 | 65.959 | 62.481 | 1.00 | 11.88 | 6 |
| 3338 | CG2 | VAL | A | 419 | 41.737 | 66.266 | 62.444 | 1.00 | 12.56 | 6 |
| 3339 | N | TYR | A | 420 | 38.034 | 67.172 | 59.764 | 1.00 | 11.92 | 7 |
| 3340 | CA | TYR | A | 420 | 36.628 | 67.548 | 59.636 | 1.00 | 10.72 | 6 |
| 3341 | C | TYR | A | 420 | 35.772 | 66.328 | 59.977 | 1.00 | 10.50 | 6 |
| 3342 | O | TYR | A | 420 | 35.908 | 65.254 | 59.383 | 1.00 | 13.20 | 8 |
| 3343 | CB | TYR | A | 420 | 36.410 | 67.866 | 58.138 | 1.00 | 9.44 | 6 |
| 3344 | CG | TYR | A | 420 | 35.063 | 68.583 | 57.856 | 1.00 | 10.31 | 6 |
| 3345 | CD1 | TYR | A | 420 | 34.258 | 69.238 | 58.754 | 1.00 | 13.30 | 6 |
| 3346 | CD2 | TYR | A | 420 | 34.669 | 68.523 | 56.512 | 1.00 | 13.25 | 6 |
| 3347 | CE1 | TYR | A | 420 | 33.045 | 69.865 | 58.379 | 1.00 | 11.70 | 6 |
| 3348 | CE2 | TYR | A | 420 | 33.476 | 69.131 | 56.115 | 1.00 | 14.40 | 6 |
| 3349 | CZ | TYR | A | 420 | 32.692 | 69.780 | 57.021 | 1.00 | 15.49 | 6 |
| 3350 | OH | TYR | A | 420 | 31.503 | 70.412 | 56.683 | 1.00 | 15.26 | 8 |
| 3351 | N | ILE | A | 421 | 35.000 | 66.508 | 61.075 | 1.00 | 11.61 | 7 |
| 3352 | CA | ILE | A | 421 | 34.037 | 65.462 | 61.458 | 1.00 | 9.13 | 6 |
| 3353 | C | ILE | A | 421 | 32.649 | 66.076 | 61.282 | 1.00 | 10.90 | 6 |
| 3354 | O | ILE | A | 421 | 32.379 | 67.148 | 61.788 | 1.00 | 13.13 | 8 |
| 3355 | CB | ILE | A | 421 | 34.238 | 64.997 | 62.941 | 1.00 | 11.03 | 6 |
| 3356 | CG1 | ILE | A | 421 | 35.689 | 64.584 | 63.133 | 1.00 | 11.76 | 6 |
| 3357 | CG2 | ILE | A | 421 | 33.251 | 63.841 | 63.198 | 1.00 | 14.22 | 6 |
| 3358 | CD1 | ILE | A | 421 | 35.980 | 63.871 | 64.484 | 1.00 | 14.70 | 6 |
| 3359 | N | TYR | A | 422 | 31.889 | 65.498 | 60.276 | 1.00 | 10.51 | 7 |
| 3360 | CA | TYR | A | 422 | 30.571 | 66.072 | 60.004 | 1.00 | 11.77 | 6 |
| 3361 | C | TYR | A | 422 | 29.510 | 64.963 | 60.053 | 1.00 | 11.33 | 6 |
| 3362 | O | TYR | A | 422 | 29.877 | 63.774 | 59.986 | 1.00 | 11.55 | 8 |
| 3363 | CB | TYR | A | 422 | 30.570 | 66.791 | 58.623 | 1.00 | 11.55 | 6 |
| 3364 | CG | TYR | A | 422 | 31.000 | 65.881 | 57.458 | 1.00 | 12.40 | 6 |
| 3365 | CD1 | TYR | A | 422 | 30.094 | 65.103 | 56.724 | 1.00 | 11.81 | 6 |
| 3366 | CD2 | TYR | A | 422 | 32.354 | 65.851 | 57.140 | 1.00 | 11.72 | 6 |
| 3367 | CE1 | TYR | A | 422 | 30.559 | 64.305 | 55.668 | 1.00 | 12.09 | 6 |
| 3368 | CE2 | TYR | A | 422 | 32.853 | 65.051 | 56.094 | 1.00 | 11.73 | 6 |
| 3369 | CZ | TYR | A | 422 | 31.935 | 64.298 | 55.377 | 1.00 | 13.04 | 6 |
| 3370 | OH | TYR | A | 422 | 32.365 | 63.520 | 54.338 | 1.00 | 11.43 | 8 |
| 3371 | N | GLU | A | 423 | 28.257 | 65.380 | 60.139 | 1.00 | 11.98 | 7 |
| 3372 | CA | GLU | A | 423 | 27.202 | 64.378 | 60.362 | 1.00 | 11.04 | 6 |
| 3373 | C | GLU | A | 423 | 26.064 | 64.598 | 59.383 | 1.00 | 11.74 | 6 |
| 3374 | O | GLU | A | 423 | 25.644 | 65.748 | 59.205 | 1.00 | 13.56 | 8 |
| 3375 | CB | GLU | A | 423 | 26.633 | 64.609 | 61.806 | 1.00 | 14.91 | 6 |
| 3376 | CG | GLU | A | 423 | 25.731 | 63.465 | 62.258 | 1.00 | 12.27 | 6 |
| 3377 | CD | GLU | A | 423 | 25.459 | 63.688 | 63.796 | 1.00 | 13.28 | 6 |
| 3378 | OE1 | GLU | A | 423 | 24.947 | 64.750 | 64.099 | 1.00 | 18.28 | 8 |
| 3379 | OE2 | GLU | A | 423 | 25.800 | 62.682 | 64.408 | 1.00 | 17.49 | 8 |
| 3380 | N | ARG | A | 424 | 25.648 | 63.541 | 58.699 | 1.00 | 12.31 | 7 |
| 3381 | CA | ARG | A | 424 | 24.457 | 63.621 | 57.847 | 1.00 | 11.64 | 6 |

TABLE 1-continued

Atom Coordinates from the Crystal Structure of NOVAMYL

| 3382 | C | ARG | A | 424 | 23.268 | 63.035 | 58.643 | 1.00 | 13.19 | 6 |
|---|---|---|---|---|---|---|---|---|---|---|
| 3383 | O | ARG | A | 424 | 23.515 | 62.077 | 59.367 | 1.00 | 13.04 | 8 |
| 3384 | CB | ARG | A | 424 | 24.665 | 62.689 | 56.620 | 1.00 | 10.72 | 6 |
| 3385 | CG | ARG | A | 424 | 25.961 | 63.049 | 55.805 | 1.00 | 10.81 | 6 |
| 3386 | CD | ARG | A | 424 | 25.862 | 64.465 | 55.212 | 1.00 | 11.09 | 6 |
| 3387 | NE | ARG | A | 424 | 24.666 | 64.721 | 54.412 | 1.00 | 10.91 | 7 |
| 3388 | CZ | ARG | A | 424 | 24.420 | 64.168 | 53.207 | 1.00 | 11.39 | 6 |
| 3389 | NH1 | ARG | A | 424 | 25.240 | 63.308 | 52.620 | 1.00 | 10.62 | 7 |
| 3390 | NH2 | ARG | A | 424 | 23.239 | 64.512 | 52.596 | 1.00 | 10.78 | 7 |
| 3391 | N | LYS | A | 425 | 22.068 | 63.623 | 58.542 | 1.00 | 11.90 | 7 |
| 3392 | CA | LYS | A | 425 | 20.937 | 63.080 | 59.290 | 1.00 | 11.75 | 6 |
| 3393 | C | LYS | A | 425 | 19.685 | 63.233 | 58.443 | 1.00 | 15.39 | 6 |
| 3394 | O | LYS | A | 425 | 19.444 | 64.340 | 58.036 | 1.00 | 14.23 | 8 |
| 3395 | CB | LYS | A | 425 | 20.801 | 63.854 | 60.626 | 1.00 | 13.68 | 6 |
| 3396 | CG | LYS | A | 425 | 19.617 | 63.271 | 61.494 | 1.00 | 14.44 | 6 |
| 3397 | CD | LYS | A | 425 | 19.721 | 63.992 | 62.863 | 1.00 | 19.53 | 6 |
| 3398 | CE | LYS | A | 425 | 18.739 | 63.342 | 63.856 | 1.00 | 20.97 | 6 |
| 3399 | NZ | LYS | A | 425 | 17.322 | 63.663 | 63.509 | 1.00 | 23.72 | 7 |
| 3400 | N | PHE | A | 426 | 18.908 | 62.144 | 58.357 | 1.00 | 12.33 | 7 |
| 3401 | CA | PHE | A | 426 | 17.583 | 62.238 | 57.709 | 1.00 | 12.03 | 6 |
| 3402 | C | PHE | A | 426 | 16.651 | 61.481 | 58.706 | 1.00 | 11.05 | 6 |
| 3403 | O | PHE | A | 426 | 16.657 | 60.252 | 58.693 | 1.00 | 13.03 | 8 |
| 3404 | CB | PHE | A | 426 | 17.608 | 61.450 | 56.397 | 1.00 | 13.23 | 6 |
| 3405 | CG | PHE | A | 426 | 16.260 | 61.449 | 55.699 | 1.00 | 12.58 | 6 |
| 3406 | CD1 | PHE | A | 426 | 15.838 | 62.659 | 55.147 | 1.00 | 14.04 | 6 |
| 3407 | CD2 | PHE | A | 426 | 15.515 | 60.300 | 55.571 | 1.00 | 14.55 | 6 |
| 3408 | CE1 | PHE | A | 426 | 14.594 | 62.715 | 54.490 | 1.00 | 13.58 | 6 |
| 3409 | CE2 | PHE | A | 426 | 14.264 | 60.345 | 54.906 | 1.00 | 15.67 | 6 |
| 3410 | CZ | PHE | A | 426 | 13.839 | 61.552 | 54.398 | 1.00 | 15.62 | 6 |
| 3411 | N | PHE | A | 427 | 15.916 | 62.357 | 59.408 | 1.00 | 14.34 | 7 |
| 3412 | CA | PHE | A | 427 | 15.024 | 61.773 | 60.490 | 1.00 | 16.20 | 6 |
| 3413 | C | PHE | A | 427 | 15.781 | 60.836 | 61.400 | 1.00 | 17.32 | 6 |
| 3414 | O | PHE | A | 427 | 16.737 | 61.354 | 62.070 | 1.00 | 19.10 | 8 |
| 3415 | CB | PHE | A | 427 | 13.772 | 61.132 | 59.840 | 1.00 | 18.52 | 6 |
| 3416 | CG | PHE | A | 427 | 12.888 | 62.175 | 59.193 | 1.00 | 17.73 | 6 |
| 3417 | CD1 | PHE | A | 427 | 11.972 | 62.918 | 59.905 | 1.00 | 21.55 | 6 |
| 3418 | CD2 | PHE | A | 427 | 13.018 | 62.396 | 57.830 | 1.00 | 14.51 | 6 |
| 3419 | CE1 | PHE | A | 427 | 11.188 | 63.858 | 59.276 | 1.00 | 18.85 | 6 |
| 3420 | CE2 | PHE | A | 427 | 12.246 | 63.336 | 57.185 | 1.00 | 16.68 | 6 |
| 3421 | CZ | PHE | A | 427 | 11.311 | 64.087 | 57.906 | 1.00 | 19.85 | 6 |
| 3422 | N | ASN | A | 428 | 15.546 | 59.522 | 61.442 | 1.00 | 15.71 | 7 |
| 3423 | CA | ASN | A | 428 | 16.284 | 58.735 | 62.433 | 1.00 | 17.74 | 6 |
| 3424 | C | ASN | A | 428 | 17.573 | 58.173 | 61.837 | 1.00 | 18.72 | 6 |
| 3425 | O | ASN | A | 428 | 18.307 | 57.587 | 62.639 | 1.00 | 17.57 | 8 |
| 3426 | CB | ASN | A | 428 | 15.484 | 57.591 | 63.008 | 1.00 | 22.35 | 6 |
| 3427 | CG | ASN | A | 428 | 14.267 | 58.214 | 63.733 | 1.00 | 36.36 | 6 |
| 3428 | OD1 | ASN | A | 428 | 14.452 | 59.092 | 64.570 | 1.00 | 38.45 | 8 |
| 3429 | ND2 | ASN | A | 428 | 13.103 | 57.735 | 63.325 | 1.00 | 44.64 | 7 |
| 3430 | N | ASP | A | 429 | 17.867 | 58.370 | 60.547 | 1.00 | 15.06 | 7 |
| 3431 | CA | ASP | A | 429 | 19.091 | 57.810 | 59.986 | 1.00 | 14.19 | 6 |
| 3432 | C | ASP | A | 429 | 20.222 | 58.816 | 60.103 | 1.00 | 11.55 | 6 |
| 3433 | O | ASP | A | 429 | 20.026 | 60.024 | 59.967 | 1.00 | 13.16 | 8 |
| 3434 | CB | ASP | A | 429 | 18.927 | 57.501 | 58.471 | 1.00 | 12.81 | 6 |
| 3435 | CG | ASP | A | 429 | 17.766 | 56.561 | 58.255 | 1.00 | 28.25 | 6 |
| 3436 | OD1 | ASP | A | 429 | 17.727 | 55.530 | 58.940 | 1.00 | 20.84 | 8 |
| 3437 | OD2 | ASP | A | 429 | 16.804 | 56.870 | 57.490 | 1.00 | 27.47 | 8 |
| 3438 | N | VAL | A | 430 | 21.384 | 58.297 | 60.600 | 1.00 | 12.85 | 7 |
| 3439 | CA | VAL | A | 430 | 22.502 | 59.192 | 60.876 | 1.00 | 11.51 | 6 |
| 3440 | C | VAL | A | 430 | 23.816 | 58.621 | 60.371 | 1.00 | 13.31 | 6 |
| 3441 | O | VAL | A | 430 | 23.993 | 57.405 | 60.522 | 1.00 | 12.49 | 8 |
| 3442 | CB | VAL | A | 430 | 22.632 | 59.315 | 62.427 | 1.00 | 14.21 | 6 |
| 3443 | CG1 | VAL | A | 430 | 23.828 | 60.233 | 62.734 | 1.00 | 14.56 | 6 |
| 3444 | CG2 | VAL | A | 430 | 21.373 | 59.955 | 63.033 | 1.00 | 14.79 | 6 |
| 3445 | N | VAL | A | 431 | 24.721 | 59.432 | 59.826 | 1.00 | 12.54 | 7 |
| 3446 | CA | VAL | A | 431 | 26.043 | 58.933 | 59.434 | 1.00 | 11.58 | 6 |
| 3447 | C | VAL | A | 431 | 27.051 | 59.978 | 59.912 | 1.00 | 11.43 | 6 |
| 3448 | O | VAL | A | 431 | 26.847 | 61.129 | 59.603 | 1.00 | 12.12 | 8 |
| 3449 | CB | VAL | A | 431 | 26.250 | 58.685 | 57.905 | 1.00 | 12.54 | 6 |
| 3450 | CG1 | VAL | A | 431 | 27.698 | 58.199 | 57.615 | 1.00 | 10.81 | 6 |
| 3451 | CG2 | VAL | A | 431 | 25.254 | 57.657 | 57.400 | 1.00 | 13.14 | 6 |
| 3452 | N | LEU | A | 432 | 27.976 | 59.557 | 60.800 | 1.00 | 10.48 | 7 |
| 3453 | CA | LEU | A | 432 | 29.015 | 60.512 | 61.285 | 1.00 | 11.27 | 6 |
| 3454 | C | LEU | A | 432 | 30.317 | 60.140 | 60.583 | 1.00 | 11.12 | 6 |
| 3455 | O | LEU | A | 432 | 30.708 | 58.961 | 60.577 | 1.00 | 13.28 | 8 |
| 3456 | CB | LEU | A | 432 | 29.087 | 60.224 | 62.831 | 1.00 | 11.86 | 6 |
| 3457 | CG | LEU | A | 432 | 30.033 | 61.205 | 63.562 | 1.00 | 11.74 | 6 |
| 3458 | CD1 | LEU | A | 432 | 29.574 | 62.643 | 63.510 | 1.00 | 11.18 | 6 |

TABLE 1-continued

Atom Coordinates from the Crystal Structure of NOVAMYL

| 3459 | CD2 | LEU | A | 432 | 30.119 | 60.744 | 65.044 | 1.00 | 14.23 | 6 |
|---|---|---|---|---|---|---|---|---|---|---|
| 3460 | N | VAL | A | 433 | 30.987 | 61.141 | 59.978 | 1.00 | 11.73 | 7 |
| 3461 | CA | VAL | A | 433 | 32.162 | 60.867 | 59.131 | 1.00 | 9.07 | 6 |
| 3462 | C | VAL | A | 433 | 33.328 | 61.667 | 59.702 | 1.00 | 9.49 | 6 |
| 3463 | O | VAL | A | 433 | 33.158 | 62.864 | 59.844 | 1.00 | 10.58 | 8 |
| 3464 | CB | VAL | A | 433 | 31.899 | 61.334 | 57.674 | 1.00 | 10.62 | 6 |
| 3465 | CG1 | VAL | A | 433 | 33.173 | 61.088 | 56.812 | 1.00 | 11.05 | 6 |
| 3466 | CG2 | VAL | A | 433 | 30.693 | 60.564 | 57.072 | 1.00 | 11.15 | 6 |
| 3467 | N | ALA | A | 434 | 34.455 | 61.000 | 60.017 | 1.00 | 10.65 | 7 |
| 3468 | CA | ALA | A | 434 | 35.643 | 61.757 | 60.409 | 1.00 | 10.07 | 6 |
| 3469 | C | ALA | A | 434 | 36.742 | 61.603 | 59.363 | 1.00 | 11.73 | 6 |
| 3470 | O | ALA | A | 434 | 37.030 | 60.489 | 58.924 | 1.00 | 11.96 | 8 |
| 3471 | CB | ALA | A | 434 | 36.199 | 61.171 | 61.742 | 1.00 | 10.24 | 6 |
| 3472 | N | ILE | A | 435 | 37.345 | 62.744 | 58.992 | 1.00 | 10.23 | 7 |
| 3472 | CA | ILE | A | 435 | 38.438 | 62.741 | 58.008 | 1.00 | 8.82 | 6 |
| 3474 | C | ILE | A | 435 | 39.571 | 63.587 | 58.558 | 1.00 | 10.58 | 6 |
| 3475 | O | ILE | A | 435 | 39.366 | 64.734 | 58.922 | 1.00 | 10.88 | 8 |
| 3476 | CB | ILE | A | 435 | 37.961 | 63.408 | 56.674 | 1.00 | 10.84 | 6 |
| 3477 | CG1 | ILE | A | 435 | 36.749 | 62.608 | 56.120 | 1.00 | 11.49 | 6 |
| 3478 | CG2 | ILE | A | 435 | 39.146 | 63.352 | 55.689 | 1.00 | 10.37 | 6 |
| 3479 | CD1 | ILE | A | 435 | 36.230 | 63.228 | 54.758 | 1.00 | 13.59 | 6 |
| 3480 | N | ASN | A | 436 | 40.741 | 62.933 | 58.596 | 1.00 | 10.83 | 7 |
| 3481 | CA | ASN | A | 436 | 41.963 | 63.646 | 58.943 | 1.00 | 11.64 | 6 |
| 3482 | C | ASN | A | 436 | 42.852 | 63.653 | 57.715 | 1.00 | 9.83 | 6 |
| 3483 | O | ASN | A | 436 | 43.367 | 62.621 | 57.309 | 1.00 | 12.85 | 8 |
| 3484 | CB | ASN | A | 436 | 42.711 | 62.821 | 60.036 | 1.00 | 12.59 | 6 |
| 3485 | CG | ASN | A | 436 | 44.030 | 63.480 | 60.383 | 1.00 | 12.87 | 6 |
| 3486 | OD1 | ASN | A | 436 | 44.422 | 64.602 | 60.026 | 1.00 | 13.07 | 8 |
| 3487 | ND1 | ASN | A | 436 | 44.789 | 62.721 | 61.224 | 1.00 | 13.56 | 7 |
| 3488 | N | ARG | A | 437 | 43.055 | 64.891 | 57.181 | 1.00 | 10.03 | 7 |
| 3489 | CA | ARG | A | 437 | 43.878 | 64.887 | 55.958 | 1.00 | 9.39 | 6 |
| 3490 | C | ARG | A | 437 | 45.362 | 64.725 | 56.267 | 1.00 | 10.71 | 6 |
| 3491 | O | ARG | A | 437 | 46.117 | 64.552 | 55.310 | 1.00 | 12.32 | 8 |
| 3492 | CB | ARG | A | 437 | 43.673 | 66.201 | 55.161 | 1.00 | 12.80 | 6 |
| 3493 | CG | ARG | A | 437 | 44.296 | 67.415 | 55.869 | 1.00 | 13.58 | 6 |
| 3494 | CD | ARG | A | 437 | 44.031 | 68.719 | 55.043 | 1.00 | 11.13 | 6 |
| 3495 | NE | ARG | A | 437 | 44.772 | 69.847 | 55.738 | 1.00 | 10.90 | 7 |
| 3496 | CZ | ARG | A | 437 | 44.957 | 71.046 | 55.195 | 1.00 | 14.88 | 6 |
| 3497 | NH1 | ARG | A | 437 | 44.521 | 71.299 | 53.948 | 1.00 | 11.67 | 7 |
| 3498 | NH2 | ARG | A | 437 | 45.406 | 72.058 | 55.947 | 1.00 | 13.84 | 7 |
| 3499 | N | ASN | A | 438 | 45.779 | 65.035 | 57.513 | 1.00 | 11.11 | 7 |
| 3500 | CA | ASN | A | 438 | 47.255 | 65.048 | 57.734 | 1.00 | 12.20 | 6 |
| 3501 | C | ASN | A | 438 | 47.780 | 63.623 | 57.869 | 1.00 | 13.73 | 6 |
| 3502 | O | ASN | A | 438 | 47.440 | 62.900 | 58.830 | 1.00 | 12.56 | 8 |
| 3503 | CB | ASN | A | 438 | 47.474 | 65.787 | 59.071 | 1.00 | 13.49 | 6 |
| 3504 | CG | ASN | A | 438 | 48.921 | 66.167 | 59.255 | 1.00 | 13.92 | 6 |
| 3505 | OD1 | ASN | A | 438 | 49.775 | 65.335 | 58.985 | 1.00 | 15.45 | 8 |
| 3506 | ND2 | ASN | A | 438 | 49.263 | 67.376 | 59.700 | 1.00 | 13.51 | 7 |
| 3507 | N | THR | A | 439 | 48.650 | 63.224 | 56.949 | 1.00 | 11.49 | 7 |
| 3508 | CA | THR | A | 439 | 49.087 | 61.822 | 56.883 | 1.00 | 12.77 | 6 |
| 3509 | C | THR | A | 439 | 50.271 | 61.585 | 57.846 | 1.00 | 14.69 | 6 |
| 3510 | O | THR | A | 439 | 50.750 | 60.450 | 57.917 | 1.00 | 16.23 | 8 |
| 3511 | CB | THR | A | 439 | 49.518 | 61.431 | 55.456 | 1.00 | 16.48 | 6 |
| 3512 | OG1 | THR | A | 439 | 50.542 | 62.330 | 54.990 | 1.00 | 17.73 | 8 |
| 3513 | CG2 | THR | A | 439 | 48.284 | 61.611 | 54.554 | 1.00 | 15.47 | 6 |
| 3514 | N | GLN | A | 440 | 50.666 | 62.669 | 58.501 | 1.00 | 14.00 | 7 |
| 3515 | CA | GLN | A | 440 | 51.778 | 62.467 | 59.481 | 1.00 | 16.61 | 6 |
| 3516 | C | GLN | A | 440 | 51.339 | 62.729 | 60.910 | 1.00 | 19.80 | 6 |
| 3517 | O | GLN | A | 440 | 52.198 | 62.543 | 61.812 | 1.00 | 18.55 | 8 |
| 3518 | CB | GLN | A | 440 | 52.905 | 63.422 | 59.081 | 1.00 | 23.60 | 6 |
| 3519 | CG | GLN | A | 440 | 53.543 | 62.971 | 57.761 | 1.00 | 37.17 | 6 |
| 3520 | CD | GLN | A | 440 | 54.248 | 61.634 | 57.810 | 1.00 | 48.48 | 6 |
| 3521 | OE1 | GLN | A | 440 | 55.292 | 61.462 | 58.444 | 1.00 | 57.64 | 8 |
| 3522 | NE2 | GLN | A | 440 | 53.729 | 60.605 | 57.127 | 1.00 | 54.59 | 7 |
| 3523 | N | SER | A | 441 | 50.115 | 63.161 | 61.192 | 1.00 | 13.09 | 7 |
| 3524 | CA | SER | A | 441 | 49.738 | 63.516 | 62.559 | 1.00 | 13.14 | 6 |
| 3525 | C | SER | A | 441 | 48.481 | 62.739 | 62.958 | 1.00 | 18.60 | 6 |
| 3526 | O | SER | A | 441 | 47.524 | 62.718 | 62.168 | 1.00 | 15.27 | 8 |
| 3527 | CB | SER | A | 441 | 49.451 | 65.025 | 62.702 | 1.00 | 16.00 | 6 |
| 3528 | OG | SER | A | 441 | 50.658 | 65.770 | 62.516 | 1.00 | 17.34 | 8 |
| 3529 | N | SER | A | 442 | 48.417 | 62.251 | 64.198 | 1.00 | 13.46 | 7 |
| 3530 | CA | SER | A | 442 | 47.177 | 61.703 | 64.730 | 1.00 | 13.64 | 6 |
| 3531 | C | SER | A | 442 | 46.581 | 62.835 | 65.599 | 1.00 | 14.33 | 6 |
| 3532 | O | SER | A | 442 | 47.366 | 63.761 | 65.974 | 1.00 | 15.22 | 8 |
| 3533 | CB | SER | A | 442 | 47.452 | 60.598 | 65.791 | 1.00 | 15.48 | 6 |
| 3534 | OG | SER | A | 442 | 48.033 | 59.420 | 65.203 | 1.00 | 19.49 | 8 |
| 3535 | N | TYR | A | 443 | 45.302 | 62.845 | 65.817 | 1.00 | 13.24 | 7 |

TABLE 1-continued

Atom Coordinates from the Crystal Structure of NOVAMYL

| 3536 | CA | TYR | A | 443 | 44.693 | 63.886 | 66.694 | 1.00 | 12.26 | 6 |
|---|---|---|---|---|---|---|---|---|---|---|
| 3537 | C | TYR | A | 443 | 43.877 | 63.156 | 67.749 | 1.00 | 14.89 | 6 |
| 3538 | O | TYR | A | 443 | 43.032 | 62.293 | 67.451 | 1.00 | 14.44 | 8 |
| 3539 | CB | TYR | A | 443 | 43.772 | 64.824 | 65.860 | 1.00 | 13.59 | 6 |
| 3540 | CG | TYR | A | 443 | 44.592 | 65.807 | 65.009 | 1.00 | 10.92 | 6 |
| 3541 | CD1 | TYR | A | 443 | 45.124 | 66.940 | 65.629 | 1.00 | 12.95 | 6 |
| 3542 | CD2 | TYR | A | 443 | 44.836 | 65.549 | 63.667 | 1.00 | 12.89 | 6 |
| 3543 | CE1 | TYR | A | 443 | 45.908 | 67.843 | 64.882 | 1.00 | 11.89 | 6 |
| 3544 | CE2 | TYR | A | 443 | 45.595 | 66.474 | 62.914 | 1.00 | 11.54 | 6 |
| 3545 | CZ | TYR | A | 443 | 46.107 | 67.595 | 63.551 | 1.00 | 12.16 | 6 |
| 3546 | OH | TYR | A | 443 | 46.871 | 68.508 | 62.811 | 1.00 | 15.42 | 8 |
| 3547 | N | SER | A | 444 | 43.976 | 63.663 | 69.008 | 1.00 | 14.60 | 7 |
| 3548 | CA | SER | A | 444 | 43.034 | 63.232 | 70.040 | 1.00 | 14.67 | 6 |
| 3549 | C | SER | A | 444 | 41.698 | 64.002 | 69.912 | 1.00 | 13.95 | 6 |
| 3550 | O | SER | A | 444 | 41.739 | 65.229 | 69.879 | 1.00 | 16.35 | 8 |
| 3551 | CB | SER | A | 444 | 43.620 | 63.684 | 71.418 | 1.00 | 17.27 | 6 |
| 3552 | OG | SER | A | 444 | 44.701 | 62.764 | 71.733 | 1.00 | 18.88 | 8 |
| 3553 | N | ILE | A | 445 | 40.628 | 63.265 | 69.758 | 1.00 | 15.00 | 7 |
| 3554 | CA | ILE | A | 445 | 39.303 | 63.892 | 69.559 | 1.00 | 13.10 | 6 |
| 3555 | C | ILE | A | 445 | 38.498 | 63.757 | 70.863 | 1.00 | 14.11 | 6 |
| 3556 | O | ILE | A | 445 | 37.935 | 62.703 | 71.131 | 1.00 | 17.51 | 8 |
| 3557 | CB | ILE | A | 445 | 38.537 | 63.188 | 68.403 | 1.00 | 14.59 | 6 |
| 3558 | CG1 | ILE | A | 445 | 39.386 | 63.120 | 67.136 | 1.00 | 15.39 | 6 |
| 3559 | CG2 | ILE | A | 445 | 37.159 | 63.906 | 68.223 | 1.00 | 16.44 | 6 |
| 3560 | CD1 | ILE | A | 445 | 39.772 | 64.500 | 66.533 | 1.00 | 15.53 | 6 |
| 3561 | N | SER | A | 446 | 38.309 | 64.925 | 71.501 | 1.00 | 15.73 | 7 |
| 3562 | CA | SER | A | 446 | 37.450 | 65.018 | 72.680 | 1.00 | 16.64 | 6 |
| 3563 | C | SER | A | 446 | 36.394 | 66.091 | 72.415 | 1.00 | 18.39 | 6 |
| 3564 | O | SER | A | 446 | 36.592 | 67.021 | 71.653 | 1.00 | 18.43 | 8 |
| 3565 | CB | SER | A | 446 | 38.248 | 65.398 | 73.972 | 1.00 | 18.77 | 6 |
| 3566 | OG | SER | A | 446 | 38.784 | 66.689 | 73.750 | 1.00 | 24.38 | 8 |
| 3567 | N | GLY | A | 447 | 35.263 | 65.958 | 73.091 | 1.00 | 19.05 | 7 |
| 3568 | CA | GLY | A | 447 | 34.169 | 66.916 | 73.050 | 1.00 | 17.05 | 6 |
| 3569 | C | GLY | A | 447 | 33.253 | 66.660 | 71.829 | 1.00 | 20.26 | 6 |
| 3570 | O | GLY | A | 447 | 32.491 | 67.554 | 71.467 | 1.00 | 19.38 | 8 |
| 3571 | N | LEU | A | 448 | 33.487 | 65.502 | 71.171 | 1.00 | 13.94 | 7 |
| 3572 | CA | LEU | A | 448 | 32.625 | 65.262 | 69.967 | 1.00 | 15.40 | 6 |
| 3573 | C | LEU | A | 448 | 31.245 | 64.853 | 70.386 | 1.00 | 16.78 | 6 |
| 3574 | O | LEU | A | 448 | 31.018 | 63.906 | 71.155 | 1.00 | 17.47 | 8 |
| 3575 | CB | LEU | A | 448 | 33.312 | 64.155 | 69.144 | 1.00 | 14.08 | 6 |
| 3576 | CG | LEU | A | 448 | 32.578 | 63.628 | 67.903 | 1.00 | 15.34 | 6 |
| 3577 | CD1 | LEU | A | 448 | 32.403 | 64.740 | 66.845 | 1.00 | 16.18 | 6 |
| 3578 | CD2 | LEU | A | 448 | 33.283 | 62.449 | 67.256 | 1.00 | 13.42 | 6 |
| 3579 | N | GLN | A | 449 | 30.221 | 65.509 | 69.814 | 1.00 | 13.16 | 7 |
| 3580 | CA | GLN | A | 449 | 28.812 | 65.224 | 70.018 | 1.00 | 14.91 | 6 |
| 3581 | C | GLN | A | 449 | 28.209 | 64.630 | 68.734 | 1.00 | 16.76 | 6 |
| 3582 | O | GLN | A | 449 | 28.754 | 64.827 | 67.645 | 1.00 | 13.94 | 8 |
| 3583 | CB | AGLN | A | 449 | 28.054 | 66.486 | 70.470 | 0.50 | 18.23 | 6 |
| 3584 | CG | AGLN | A | 449 | 28.884 | 67.206 | 71.540 | 0.05 | 24.01 | 6 |
| 3585 | CD | AGLN | A | 449 | 28.211 | 68.188 | 72.449 | 0.50 | 23.44 | 6 |
| 3586 | OE1 | AGLN | A | 449 | 28.812 | 68.606 | 73.455 | 0.50 | 32.55 | 8 |
| 3587 | NE2 | AGLN | A | 449 | 26.984 | 68.573 | 72.134 | 0.50 | 32.22 | 7 |
| 3583 | CB | BGLN | A | 449 | 27.974 | 66.473 | 70.339 | 0.50 | 13.26 | 6 |
| 3584 | CG | BGLN | A | 449 | 28.536 | 67.122 | 71.620 | 0.50 | 17.72 | 6 |
| 3585 | CD | BGLN | A | 449 | 28.037 | 66.396 | 72.844 | 0.50 | 16.00 | 6 |
| 3586 | OE1 | BGLN | A | 449 | 28.776 | 65.702 | 73.511 | 0.50 | 22.43 | 8 |
| 3587 | NE2 | BGLN | A | 449 | 26.759 | 66.550 | 73.145 | 0.50 | 23.34 | 7 |
| 3588 | N | THR | A | 450 | 27.085 | 63.965 | 68.897 | 1.00 | 15.61 | 7 |
| 3589 | CA | THR | A | 450 | 26.481 | 63.264 | 67.761 | 1.00 | 13.97 | 6 |
| 3590 | C | THR | A | 450 | 24.998 | 63.001 | 67.994 | 1.00 | 16.43 | 6 |
| 3591 | O | THR | A | 450 | 24.528 | 62.925 | 69.160 | 1.00 | 16.61 | 8 |
| 3592 | CB | THR | A | 450 | 27.216 | 61.912 | 67.566 | 1.00 | 15.00 | 6 |
| 3593 | OG1 | THR | A | 450 | 26.686 | 61.176 | 66.471 | 1.00 | 15.07 | 8 |
| 3594 | CG2 | THR | A | 450 | 27.007 | 61.016 | 68.814 | 1.00 | 18.27 | 6 |
| 3595 | N | ALA | A | 451 | 24.286 | 62.806 | 66.886 | 1.00 | 15.10 | 7 |
| 3596 | CA | ALA | A | 451 | 22.898 | 62.330 | 66.941 | 1.00 | 16.96 | 6 |
| 3597 | C | ALA | A | 451 | 22.799 | 60.830 | 66.879 | 1.00 | 15.04 | 6 |
| 3598 | O | ALA | A | 451 | 21.681 | 60.282 | 66.900 | 1.00 | 15.44 | 8 |
| 3599 | CB | ALA | A | 451 | 22.212 | 62.946 | 65.681 | 1.00 | 16.26 | 6 |
| 3600 | N | LEU | A | 452 | 23.929 | 60.083 | 66.788 | 1.00 | 14.57 | 7 |
| 3601 | CA | LEU | A | 452 | 23.803 | 58.623 | 66.814 | 1.00 | 12.45 | 6 |
| 3602 | C | LEU | A | 452 | 23.170 | 58.200 | 68.158 | 1.00 | 17.32 | 6 |
| 3603 | O | LEU | A | 452 | 23.505 | 58.727 | 69.218 | 1.00 | 17.00 | 8 |
| 3604 | CB | LEU | A | 452 | 25.201 | 57.989 | 66.779 | 1.00 | 14.27 | 6 |
| 3605 | CG | LEU | A | 452 | 25.854 | 58.082 | 65.380 | 1.00 | 14.43 | 6 |
| 3606 | CD1 | LEU | A | 452 | 27.344 | 57.716 | 65.610 | 1.00 | 13.81 | 6 |
| 3607 | CD2 | LEU | A | 452 | 25.263 | 57.102 | 64.375 | 1.00 | 14.40 | 6 |

TABLE 1-continued

Atom Coordinates from the Crystal Structure of NOVAMYL

| 3608 | N   | PRO | A | 453 | 22.383 | 57.163 | 68.080 | 1.00 | 16.12 | 7 |
|------|-----|-----|---|-----|--------|--------|--------|------|-------|---|
| 3609 | CA  | PRO | A | 453 | 21.808 | 56.539 | 69.305 | 1.00 | 18.87 | 6 |
| 3610 | C   | PRO | A | 453 | 22.936 | 55.882 | 70.090 | 1.00 | 19.68 | 6 |
| 3611 | O   | PRO | A | 453 | 24.039 | 55.532 | 69.686 | 1.00 | 18.19 | 8 |
| 3612 | CB  | PRO | A | 453 | 20.796 | 55.523 | 68.880 | 1.00 | 20.41 | 6 |
| 3613 | CG  | PRO | A | 453 | 20.615 | 55.743 | 67.392 | 1.00 | 21.35 | 6 |
| 3614 | CD  | PRO | A | 453 | 21.806 | 56.582 | 66.872 | 1.00 | 16.78 | 6 |
| 3615 | N   | ASN | A | 454 | 22.619 | 55.684 | 71.406 | 1.00 | 14.58 | 7 |
| 3616 | CA  | ASN | A | 454 | 23.630 | 55.025 | 72.244 | 1.00 | 14.89 | 6 |
| 3617 | C   | ASN | A | 454 | 24.085 | 53.704 | 71.712 | 1.00 | 18.47 | 6 |
| 3618 | O   | ASN | A | 454 | 23.320 | 52.881 | 71.168 | 1.00 | 17.84 | 8 |
| 3619 | CB  | ASN | A | 454 | 22.851 | 54.705 | 73.573 | 1.00 | 17.80 | 6 |
| 3620 | CG  | ASN | A | 454 | 22.656 | 55.933 | 74.421 | 1.00 | 24.08 | 6 |
| 3621 | OD1 | ASN | A | 454 | 23.071 | 57.055 | 74.201 | 1.00 | 19.24 | 8 |
| 3622 | ND2 | ASN | A | 454 | 21.941 | 55.757 | 75.554 | 1.00 | 24.42 | 7 |
| 3623 | N   | GLY | A | 455 | 25.378 | 53.451 | 71.950 | 1.00 | 17.75 | 7 |
| 3624 | CA  | GLY | A | 455 | 25.919 | 52.156 | 71.553 | 1.00 | 20.13 | 6 |
| 3625 | C   | GLY | A | 455 | 27.422 | 52.289 | 71.172 | 1.00 | 17.39 | 6 |
| 3626 | O   | GLY | A | 455 | 27.899 | 53.393 | 71.080 | 1.00 | 19.07 | 8 |
| 3627 | N   | SER | A | 456 | 27.916 | 51.112 | 70.814 | 1.00 | 18.37 | 7 |
| 3628 | CA  | SER | A | 456 | 29.286 | 51.073 | 70.261 | 1.00 | 17.34 | 6 |
| 3629 | C   | SER | A | 456 | 29.173 | 50.927 | 68.725 | 1.00 | 17.80 | 6 |
| 3630 | O   | SER | A | 456 | 28.322 | 50.199 | 68.220 | 1.00 | 20.53 | 8 |
| 3631 | CB  | SER | A | 456 | 29.916 | 49.747 | 70.778 | 1.00 | 22.39 | 6 |
| 3632 | OG  | SER | A | 456 | 30.178 | 49.998 | 72.161 | 1.00 | 30.42 | 8 |
| 3633 | N   | TYR | A | 457 | 30.024 | 51.683 | 68.013 | 1.00 | 15.08 | 7 |
| 3634 | CA  | TYR | A | 457 | 29.941 | 51.627 | 66.559 | 1.00 | 13.18 | 6 |
| 3635 | C   | TYR | A | 457 | 31.301 | 51.229 | 65.961 | 1.00 | 14.20 | 6 |
| 3636 | O   | TYR | A | 457 | 32.257 | 51.915 | 66.259 | 1.00 | 16.66 | 8 |
| 3637 | CB  | TYR | A | 457 | 29.564 | 53.017 | 65.941 | 1.00 | 17.47 | 6 |
| 3638 | CG  | TYR | A | 457 | 28.122 | 53.387 | 66.241 | 1.00 | 15.26 | 6 |
| 3639 | CD1 | TYR | A | 457 | 27.799 | 53.933 | 67.497 | 1.00 | 15.37 | 6 |
| 3640 | CD2 | TYR | A | 457 | 27.077 | 53.174 | 65.325 | 1.00 | 16.16 | 6 |
| 3641 | CE1 | TYR | A | 457 | 26.521 | 54.297 | 67.873 | 1.00 | 15.82 | 6 |
| 3642 | CE2 | TYR | A | 457 | 25.768 | 53.516 | 65.671 | 1.00 | 15.99 | 6 |
| 3643 | CZ  | TYR | A | 457 | 25.523 | 54.070 | 66.928 | 1.00 | 16.37 | 6 |
| 3644 | OH  | TYR | A | 457 | 24.210 | 54.401 | 67.218 | 1.00 | 16.11 | 8 |
| 3645 | N   | ALA | A | 458 | 31.329 | 50.211 | 65.128 | 1.00 | 14.59 | 7 |
| 3646 | CA  | ALA | A | 458 | 32.601 | 49.943 | 64.445 | 1.00 | 17.03 | 6 |
| 3647 | C   | ALA | A | 458 | 32.686 | 50.915 | 63.247 | 1.00 | 14.66 | 6 |
| 3648 | O   | ALA | A | 458 | 31.654 | 51.326 | 62.731 | 1.00 | 14.84 | 8 |
| 3649 | CB  | ALA | A | 458 | 32.638 | 48.538 | 63.857 | 1.00 | 17.50 | 6 |
| 3650 | N   | ASP | A | 459 | 33.942 | 51.128 | 62.831 | 1.00 | 13.42 | 7 |
| 3651 | CA  | ASP | A | 459 | 34.082 | 51.858 | 61.521 | 1.00 | 11.91 | 6 |
| 3652 | C   | ASP | A | 459 | 33.472 | 51.048 | 60.410 | 1.00 | 12.75 | 6 |
| 3653 | O   | ASP | A | 459 | 33.679 | 49.834 | 60.222 | 1.00 | 13.42 | 8 |
| 3654 | CB  | ASP | A | 459 | 35.567 | 52.007 | 61.258 | 1.00 | 12.66 | 6 |
| 3655 | CG  | ASP | A | 459 | 35.984 | 52.522 | 59.876 | 1.00 | 13.56 | 6 |
| 3656 | OD1 | ASP | A | 459 | 35.143 | 53.232 | 59.328 | 1.00 | 12.36 | 8 |
| 3657 | OD2 | ASP | A | 459 | 37.109 | 52.170 | 59.441 | 1.00 | 14.11 | 8 |
| 3658 | N   | TYR | A | 460 | 32.581 | 51.730 | 59.662 | 1.00 | 11.96 | 7 |
| 3659 | CA  | TYR | A | 460 | 31.927 | 51.022 | 58.513 | 1.00 | 13.29 | 6 |
| 3660 | C   | TYR | A | 460 | 32.905 | 50.541 | 57.467 | 1.00 | 16.04 | 6 |
| 3661 | O   | TYR | A | 460 | 32.617 | 49.627 | 56.683 | 1.00 | 15.32 | 8 |
| 3662 | CB  | TYR | A | 460 | 30.909 | 52.021 | 57.931 | 1.00 | 13.60 | 6 |
| 3663 | CG  | TYR | A | 460 | 29.970 | 51.418 | 56.899 | 1.00 | 13.06 | 6 |
| 3664 | CD1 | TYR | A | 460 | 28.809 | 50.815 | 57.400 | 1.00 | 11.63 | 6 |
| 3665 | CD2 | TYR | A | 460 | 30.215 | 51.365 | 55.532 | 1.00 | 16.49 | 6 |
| 3666 | CE1 | TYR | A | 460 | 27.838 | 50.274 | 56.514 | 1.00 | 15.86 | 6 |
| 3667 | CE2 | TYR | A | 460 | 29.278 | 50.783 | 54.662 | 1.00 | 15.66 | 6 |
| 3668 | CZ  | TYR | A | 460 | 28.098 | 50.257 | 55.165 | 1.00 | 17.45 | 6 |
| 3669 | OH  | TYR | A | 460 | 27.209 | 49.696 | 54.262 | 1.00 | 16.44 | 8 |
| 3670 | N   | LEU | A | 461 | 34.057 | 51.242 | 57.374 | 1.00 | 13.04 | 7 |
| 3671 | CA  | LEU | A | 461 | 35.137 | 50.814 | 56.424 | 1.00 | 13.89 | 6 |
| 3672 | C   | LEU | A | 461 | 36.026 | 49.742 | 57.023 | 1.00 | 14.71 | 6 |
| 3673 | O   | LEU | A | 461 | 36.992 | 49.331 | 56.369 | 1.00 | 13.39 | 8 |
| 3674 | CB  | LEU | A | 461 | 35.968 | 52.115 | 56.171 | 1.00 | 13.08 | 6 |
| 3675 | CG  | LEU | A | 461 | 35.299 | 53.075 | 55.149 | 1.00 | 13.44 | 6 |
| 3676 | CD1 | LEU | A | 461 | 35.968 | 54.453 | 55.284 | 1.00 | 14.44 | 6 |
| 3677 | CD2 | LEU | A | 461 | 35.485 | 52.526 | 53.743 | 1.00 | 16.37 | 6 |
| 3678 | N   | SER | A | 462 | 35.746 | 49.218 | 58.222 | 1.00 | 15.11 | 7 |
| 3679 | CA  | SER | A | 462 | 36.521 | 48.122 | 58.810 | 1.00 | 16.17 | 6 |
| 3680 | C   | SER | A | 462 | 38.011 | 48.422 | 58.907 | 1.00 | 17.10 | 6 |
| 3681 | O   | SER | A | 462 | 38.878 | 47.546 | 58.763 | 1.00 | 16.40 | 8 |
| 3682 | CB  | SER | A | 462 | 36.316 | 46.813 | 57.987 | 1.00 | 19.17 | 6 |
| 3683 | OG  | SER | A | 462 | 34.914 | 46.479 | 57.974 | 1.00 | 20.76 | 8 |
| 3684 | N   | GLY | A | 463 | 38.369 | 49.689 | 59.115 | 1.00 | 13.98 | 7 |

TABLE 1-continued

Atom Coordinates from the Crystal Structure of NOVAMYL

| 3685 | CA | GLY | A | 463 | 39.781 | 50.089 | 59.271 | 1.00 | 14.97 | 6 |
|---|---|---|---|---|---|---|---|---|---|---|
| 3686 | C | GLY | A | 463 | 40.533 | 50.140 | 57.949 | 1.00 | 15.42 | 6 |
| 3687 | O | GLY | A | 463 | 41.745 | 50.387 | 57.984 | 1.00 | 15.84 | 8 |
| 3688 | N | LEU | A | 464 | 39.816 | 50.043 | 56.808 | 1.00 | 12.86 | 7 |
| 3689 | CA | LEU | A | 464 | 40.559 | 50.113 | 55.525 | 1.00 | 10.93 | 6 |
| 3690 | C | LEU | A | 464 | 41.370 | 51.420 | 55.427 | 1.00 | 12.62 | 6 |
| 3691 | O | LEU | A | 464 | 42.484 | 51.408 | 54.854 | 1.00 | 14.36 | 8 |
| 3692 | CB | LEU | A | 464 | 39.487 | 50.148 | 54.402 | 1.00 | 13.24 | 6 |
| 3693 | CG | LEU | A | 464 | 40.083 | 50.223 | 52.969 | 1.00 | 14.42 | 6 |
| 3694 | CD1 | LEU | A | 464 | 40.800 | 48.892 | 52.620 | 1.00 | 15.93 | 6 |
| 3695 | CD2 | LEU | A | 465 | 38.971 | 50.469 | 51.967 | 1.00 | 14.00 | 6 |
| 3696 | N | LEU | A | 465 | 40.797 | 52.526 | 55.872 | 1.00 | 11.79 | 7 |
| 3697 | CA | LEU | A | 465 | 41.473 | 53.824 | 55.761 | 1.00 | 12.51 | 6 |
| 3698 | C | LEU | A | 465 | 41.953 | 54.319 | 57.114 | 1.00 | 13.32 | 6 |
| 3699 | O | LEU | A | 465 | 41.873 | 55.518 | 57.401 | 1.00 | 16.12 | 8 |
| 3700 | CB | LEU | A | 465 | 40.510 | 54.894 | 55.130 | 1.00 | 12.90 | 6 |
| 3701 | CG | LEU | A | 465 | 40.090 | 54.441 | 53.714 | 1.00 | 12.88 | 6 |
| 3702 | CD1 | LEU | A | 465 | 39.162 | 55.509 | 53.111 | 1.00 | 14.96 | 6 |
| 3703 | CD2 | LEU | A | 465 | 41.263 | 54.191 | 52.777 | 1.00 | 14.83 | 6 |
| 3704 | N | GLY | A | 466 | 42.237 | 53.348 | 58.043 | 1.00 | 14.06 | 7 |
| 3705 | CA | GLY | A | 466 | 42.789 | 53.800 | 59.336 | 1.00 | 14.74 | 6 |
| 3706 | C | GLY | A | 466 | 41.735 | 54.095 | 60.400 | 1.00 | 14.06 | 6 |
| 3707 | O | GLY | A | 466 | 42.061 | 54.643 | 61.479 | 1.00 | 15.13 | 8 |
| 3708 | N | GLY | A | 467 | 40.451 | 53.817 | 60.125 | 1.00 | 13.86 | 7 |
| 3709 | CA | GLY | A | 467 | 39.357 | 54.137 | 61.045 | 1.00 | 11.80 | 6 |
| 3710 | C | GLY | A | 467 | 39.321 | 53.244 | 62.311 | 1.00 | 14.35 | 6 |
| 3711 | O | GLY | A | 467 | 40.083 | 52.261 | 62.394 | 1.00 | 16.59 | 8 |
| 3712 | N | ASN | A | 468 | 38.509 | 53.696 | 63.236 | 1.00 | 15.29 | 7 |
| 3713 | CA | ASN | A | 468 | 38.483 | 53.050 | 64.569 | 1.00 | 14.61 | 6 |
| 3714 | C | ASN | A | 468 | 37.007 | 52.960 | 64.963 | 1.00 | 15.14 | 6 |
| 3715 | O | ASN | A | 468 | 36.145 | 53.679 | 64.418 | 1.00 | 15.07 | 8 |
| 3716 | CB | ASN | A | 468 | 39.253 | 54.012 | 65.515 | 1.00 | 16.45 | 6 |
| 3717 | CG | ASN | A | 468 | 38.730 | 55.429 | 65.538 | 1.00 | 17.15 | 6 |
| 3718 | OD1 | ASN | A | 468 | 39.013 | 56.375 | 64.739 | 1.00 | 19.92 | 8 |
| 3719 | ND2 | ASN | A | 468 | 37.812 | 55.710 | 66.490 | 1.00 | 16.39 | 7 |
| 3720 | N | GLY | A | 469 | 36.787 | 52.285 | 66.076 | 1.00 | 16.49 | 7 |
| 3721 | CA | GLY | A | 469 | 35.415 | 52.189 | 66.624 | 1.00 | 16.85 | 6 |
| 3722 | C | GLY | A | 469 | 35.261 | 53.309 | 67.640 | 1.00 | 14.55 | 6 |
| 3723 | O | GLY | A | 469 | 36.191 | 53.919 | 68.176 | 1.00 | 17.51 | 8 |
| 3724 | N | ILE | A | 470 | 33.976 | 53.624 | 67.954 | 1.00 | 14.83 | 7 |
| 3725 | CA | ILE | A | 470 | 33.623 | 54.650 | 68.921 | 1.00 | 14.09 | 6 |
| 3726 | C | ILE | A | 470 | 32.518 | 54.102 | 69.860 | 1.00 | 13.92 | 6 |
| 3727 | O | ILE | A | 470 | 31.867 | 53.108 | 69.553 | 1.00 | 19.57 | 8 |
| 3728 | CB | ILE | A | 470 | 33.155 | 56.004 | 68.368 | 1.00 | 16.37 | 6 |
| 3729 | CG1 | ILE | A | 470 | 31.948 | 55.753 | 67.429 | 1.00 | 17.51 | 6 |
| 3730 | CG2 | ILE | A | 470 | 34.319 | 56.652 | 67.581 | 1.00 | 16.76 | 6 |
| 3731 | CD1 | ILE | A | 470 | 31.315 | 57.104 | 67.032 | 1.00 | 15.78 | 6 |
| 3732 | N | SER | A | 471 | 32.408 | 54.804 | 70.980 | 1.00 | 15.71 | 7 |
| 3733 | CA | SER | A | 471 | 31.268 | 54.477 | 71.903 | 1.00 | 14.51 | 6 |
| 3734 | C | SER | A | 471 | 30.497 | 55.755 | 72.165 | 1.00 | 14.83 | 6 |
| 3735 | O | SER | A | 471 | 31.107 | 56.814 | 72.402 | 1.00 | 17.55 | 8 |
| 3736 | CB | SER | A | 471 | 32.024 | 54.018 | 73.220 | 1.00 | 22.00 | 6 |
| 3737 | OG | SER | A | 471 | 30.967 | 53.933 | 74.176 | 1.00 | 27.40 | 8 |
| 3738 | N | VAL | A | 472 | 29.172 | 55.712 | 72.054 | 1.00 | 14.69 | 7 |
| 3739 | CA | VAL | A | 472 | 28.298 | 56.834 | 72.186 | 1.00 | 14.15 | 6 |
| 3740 | C | VAL | A | 472 | 27.380 | 56.696 | 73.425 | 1.00 | 15.07 | 6 |
| 3741 | O | VAL | A | 472 | 26.764 | 55.638 | 73.563 | 1.00 | 19.05 | 8 |
| 3742 | CB | VAL | A | 472 | 27.433 | 56.903 | 70.900 | 1.00 | 15.53 | 6 |
| 3743 | CG1 | VAL | A | 472 | 26.446 | 58.057 | 70.970 | 1.00 | 14.81 | 6 |
| 3744 | CG2 | VAL | A | 472 | 28.376 | 57.153 | 69.691 | 1.00 | 18.40 | 6 |
| 3745 | N | SER | A | 473 | 27.351 | 57.767 | 74.184 | 1.00 | 15.80 | 7 |
| 3746 | CA | SER | A | 473 | 26.386 | 57.736 | 75.312 | 1.00 | 16.44 | 6 |
| 3747 | C | SER | A | 473 | 25.711 | 59.073 | 75.420 | 1.00 | 16.40 | 6 |
| 3748 | O | SER | A | 473 | 26.435 | 60.084 | 75.548 | 1.00 | 19.98 | 8 |
| 3749 | CB | SER | A | 473 | 27.214 | 57.446 | 76.594 | 1.00 | 21.00 | 6 |
| 3750 | OG | SER | A | 473 | 26.284 | 57.573 | 77.686 | 1.00 | 31.70 | 8 |
| 3751 | N | ASN | A | 474 | 24.396 | 59.107 | 75.308 | 1.00 | 18.40 | 7 |
| 3752 | CA | ASN | A | 474 | 23.632 | 60.348 | 75.444 | 1.00 | 19.45 | 6 |
| 3753 | C | ASN | A | 474 | 24.194 | 61.523 | 74.646 | 1.00 | 19.99 | 6 |
| 3754 | O | ASN | A | 474 | 24.363 | 62.658 | 75.103 | 1.00 | 15.86 | 8 |
| 3755 | CB | ASN | A | 474 | 23.685 | 60.707 | 76.968 | 1.00 | 22.35 | 6 |
| 3756 | CG | ASN | A | 474 | 22.991 | 59.572 | 77.722 | 1.00 | 31.24 | 6 |
| 3757 | OD1 | ASN | A | 474 | 22.086 | 58.887 | 77.191 | 1.00 | 33.57 | 8 |
| 3758 | ND2 | ASN | A | 474 | 23.579 | 59.303 | 78.890 | 1.00 | 32.67 | 7 |
| 3759 | N | GLY | A | 475 | 24.452 | 61.223 | 73.341 | 1.00 | 17.78 | 7 |
| 3760 | CA | GLY | A | 475 | 24.866 | 62.311 | 72.438 | 1.00 | 20.56 | 6 |
| 3761 | C | GLY | A | 475 | 26.369 | 62.573 | 72.430 | 1.00 | 18.34 | 6 |

TABLE 1-continued

Atom Coordinates from the Crystal Structure of NOVAMYL

| 3762 | O   | GLY  | A | 475 | 26.807 | 63.464 | 71.690 | 1.00 | 20.59 | 8 |
|------|-----|------|---|-----|--------|--------|--------|------|-------|---|
| 3763 | N   | SER  | A | 476 | 27.146 | 61.894 | 73.305 | 1.00 | 18.39 | 7 |
| 3764 | CA  | SER  | A | 476 | 28.563 | 62.222 | 73.451 | 1.00 | 14.26 | 6 |
| 3765 | C   | SER  | A | 476 | 29.384 | 61.026 | 72.974 | 1.00 | 17.38 | 6 |
| 3766 | O   | SER  | A | 476 | 29.103 | 59.902 | 73.358 | 1.00 | 18.38 | 8 |
| 3767 | CB  | ASER | A | 476 | 28.931 | 62.557 | 74.900 | 0.70 | 19.66 | 6 |
| 3768 | OG  | ASER | A | 476 | 28.330 | 63.803 | 75.257 | 0.70 | 22.12 | 8 |
| 3767 | CB  | BSER | A | 476 | 28.870 | 62.465 | 74.932 | 0.30 | 18.16 | 6 |
| 3768 | OG  | BSER | A | 476 | 30.220 | 62.822 | 75.127 | 0.30 | 20.85 | 8 |
| 3769 | N   | VAL  | A | 477 | 30.430 | 61.284 | 72.188 | 1.00 | 15.08 | 7 |
| 3770 | CA  | VAL  | A | 477 | 31.322 | 60.248 | 71.766 | 1.00 | 16.01 | 6 |
| 3771 | C   | VAL  | A | 477 | 32.549 | 60.211 | 72.699 | 1.00 | 14.42 | 6 |
| 3772 | O   | VAL  | A | 477 | 33.117 | 61.277 | 72.913 | 1.00 | 16.73 | 8 |
| 3773 | CB  | VAL  | A | 477 | 31.852 | 60.539 | 70.320 | 1.00 | 12.17 | 6 |
| 3774 | CG1 | VAL  | A | 477 | 32.718 | 59.377 | 69.872 | 1.00 | 15.08 | 6 |
| 3775 | CG2 | VAL  | A | 477 | 30.665 | 60.682 | 69.389 | 1.00 | 13.12 | 6 |
| 3776 | N   | ALA  | A | 478 | 32.802 | 59.035 | 73.236 | 1.00 | 17.39 | 7 |
| 3777 | CA  | ALA  | A | 478 | 33.956 | 58.962 | 74.181 | 1.00 | 17.45 | 6 |
| 3778 | C   | ALA  | A | 478 | 35.248 | 59.401 | 73.501 | 1.00 | 19.79 | 6 |
| 3779 | O   | ALA  | A | 478 | 35.398 | 59.204 | 72.298 | 1.00 | 15.95 | 8 |
| 3780 | CB  | ALA  | A | 478 | 34.031 | 57.543 | 74.731 | 1.00 | 18.76 | 6 |
| 3781 | N   | SER  | A | 479 | 36.152 | 60.069 | 74.181 | 1.00 | 15.72 | 7 |
| 3782 | CA  | SER  | A | 479 | 37.405 | 60.518 | 73.501 | 1.00 | 17.20 | 6 |
| 3783 | C   | SER  | A | 479 | 38.170 | 59.392 | 72.855 | 1.00 | 16.18 | 6 |
| 3784 | O   | SER  | A | 479 | 38.177 | 58.231 | 73.329 | 1.00 | 16.38 | 8 |
| 3785 | CB  | SER  | A | 479 | 38.262 | 61.218 | 74.569 | 1.00 | 23.12 | 6 |
| 3786 | OG  | SER  | A | 479 | 37.554 | 62.348 | 75.047 | 1.00 | 22.40 | 8 |
| 3787 | N   | PHE  | A | 480 | 38.774 | 59.656 | 71.674 | 1.00 | 16.00 | 7 |
| 3788 | CA  | PHE  | A | 480 | 39.449 | 58.638 | 70.881 | 1.00 | 15.01 | 6 |
| 3789 | C   | PHE  | A | 480 | 40.575 | 59.308 | 70.092 | 1.00 | 14.53 | 6 |
| 3790 | O   | PHE  | A | 480 | 40.568 | 60.548 | 70.019 | 1.00 | 17.08 | 8 |
| 3791 | CB  | PHE  | A | 480 | 38.538 | 57.834 | 69.938 | 1.00 | 14.92 | 6 |
| 3792 | CG  | PHE  | A | 480 | 37.888 | 58.695 | 68.846 | 1.00 | 15.98 | 6 |
| 3793 | CD1 | PHE  | A | 480 | 36.748 | 59.437 | 69.087 | 1.00 | 14.48 | 6 |
| 3794 | CD2 | PHE  | A | 480 | 38.493 | 58.728 | 67.589 | 1.00 | 14.19 | 6 |
| 3795 | CE1 | PHE  | A | 480 | 36.160 | 60.227 | 68.092 | 1.00 | 18.16 | 6 |
| 3796 | CE2 | PHE  | A | 480 | 37.899 | 59.513 | 66.609 | 1.00 | 18.21 | 6 |
| 3797 | CZ  | PHE  | A | 480 | 36.770 | 60.255 | 66.848 | 1.00 | 19.62 | 6 |
| 3798 | N   | THR  | A | 481 | 41.459 | 58.476 | 69.565 | 1.00 | 15.04 | 7 |
| 3799 | CA  | THR  | A | 481 | 42.525 | 59.036 | 69.696 | 1.00 | 12.66 | 6 |
| 3800 | C   | THR  | A | 481 | 42.186 | 58.783 | 67.223 | 1.00 | 14.82 | 6 |
| 3801 | O   | THR  | A | 481 | 41.811 | 57.641 | 66.885 | 1.00 | 16.40 | 8 |
| 3802 | CB  | THR  | A | 481 | 43.859 | 58.332 | 69.002 | 1.00 | 19.94 | 6 |
| 3803 | OG1 | THR  | A | 481 | 44.253 | 58.543 | 70.360 | 1.00 | 21.84 | 8 |
| 3804 | CG2 | THR  | A | 481 | 44.953 | 58.894 | 68.091 | 1.00 | 20.55 | 6 |
| 3805 | N   | LEU  | A | 482 | 42.216 | 59.860 | 66.454 | 1.00 | 14.98 | 7 |
| 3806 | CA  | LEU  | A | 482 | 42.004 | 59.690 | 64.991 | 1.00 | 13.06 | 6 |
| 3807 | C   | LEU  | A | 482 | 43.383 | 59.527 | 64.394 | 1.00 | 14.32 | 6 |
| 3808 | O   | LEU  | A | 482 | 44.199 | 60.432 | 64.487 | 1.00 | 15.20 | 8 |
| 3809 | CB  | LEU  | A | 482 | 41.231 | 60.917 | 64.486 | 1.00 | 13.14 | 6 |
| 3810 | CG  | LEU  | A | 482 | 40.812 | 60.936 | 62.999 | 1.00 | 14.96 | 6 |
| 3811 | CD1 | LEU  | A | 482 | 39.938 | 59.717 | 62.720 | 1.00 | 16.24 | 6 |
| 3812 | CD2 | LEU  | A | 482 | 40.073 | 62.242 | 62.727 | 1.00 | 14.36 | 6 |
| 3813 | N   | ALA  | A | 483 | 43.621 | 58.414 | 63.680 | 1.00 | 12.65 | 7 |
| 3814 | CA  | ALA  | A | 483 | 44.961 | 58.090 | 63.175 | 1.00 | 13.54 | 6 |
| 3815 | C   | ALA  | A | 483 | 45.370 | 58.961 | 62.000 | 1.00 | 13.15 | 6 |
| 3816 | O   | ALA  | A | 483 | 44.562 | 59.723 | 61.387 | 1.00 | 13.10 | 8 |
| 3817 | CB  | ALA  | A | 483 | 44.892 | 56.581 | 62.782 | 1.00 | 12.82 | 6 |
| 3818 | N   | PRO  | A | 484 | 46.637 | 58.980 | 61.687 | 1.00 | 14.66 | 7 |
| 3819 | CA  | PRO  | A | 484 | 47.183 | 59.827 | 60.632 | 1.00 | 11.27 | 6 |
| 3820 | C   | PRO  | A | 484 | 46.509 | 59.496 | 59.301 | 1.00 | 12.98 | 6 |
| 3821 | O   | PRO  | A | 484 | 46.374 | 58.331 | 58.884 | 1.00 | 13.40 | 8 |
| 3822 | CB  | PRO  | A | 484 | 48.704 | 59.546 | 60.545 | 1.00 | 15.48 | 6 |
| 3823 | CG  | PRO  | A | 484 | 48.959 | 58.945 | 61.936 | 1.00 | 15.92 | 6 |
| 3824 | CD  | PRO  | A | 484 | 47.698 | 58.160 | 62.333 | 1.00 | 15.61 | 6 |
| 3825 | N   | GLY  | A | 485 | 45.977 | 60.548 | 58.671 | 1.00 | 14.03 | 7 |
| 3826 | CA  | GLY  | A | 485 | 45.399 | 60.352 | 57.309 | 1.00 | 13.19 | 6 |
| 3827 | C   | GLY  | A | 485 | 44.067 | 59.600 | 57.376 | 1.00 | 16.21 | 6 |
| 3828 | O   | GLY  | A | 485 | 43.561 | 59.235 | 56.271 | 1.00 | 13.21 | 8 |
| 3829 | N   | ALA  | A | 486 | 43.508 | 59.349 | 58.553 | 1.00 | 11.65 | 7 |
| 3830 | CA  | ALA  | A | 486 | 42.375 | 58.395 | 58.545 | 1.00 | 13.98 | 6 |
| 3831 | C   | ALA  | A | 486 | 41.058 | 58.969 | 58.068 | 1.00 | 15.41 | 6 |
| 3832 | O   | ALA  | A | 486 | 40.730 | 60.148 | 58.196 | 1.00 | 13.33 | 8 |
| 3833 | CB  | ALA  | A | 486 | 42.233 | 57.937 | 60.002 | 1.00 | 14.43 | 6 |
| 3834 | N   | VAL  | A | 487 | 40.213 | 58.008 | 57.647 | 1.00 | 12.17 | 7 |
| 3835 | CA  | VAL  | A | 487 | 38.776 | 58.220 | 57.403 | 1.00 | 9.79  | 6 |
| 3836 | C   | VAL  | A | 487 | 38.057 | 57.174 | 58.257 | 1.00 | 9.96  | 6 |

TABLE 1-continued

Atom Coordinates from the Crystal Structure of NOVAMYL

| | | | | | | | | | | |
|---|---|---|---|---|---|---|---|---|---|---|
| 3837 | O | VAL | A | 487 | 38.406 | 55.970 | 58.179 | 1.00 | 12.30 | 8 |
| 3838 | CB | VAL | A | 487 | 38.428 | 58.022 | 55.919 | 1.00 | 10.95 | 6 |
| 3839 | CG1 | VAL | A | 487 | 36.871 | 58.150 | 55.762 | 1.00 | 12.89 | 6 |
| 3840 | CG2 | VAL | A | 487 | 39.127 | 58.990 | 54.964 | 1.00 | 15.13 | 6 |
| 3841 | N | SER | A | 488 | 37.112 | 57.635 | 59.078 | 1.00 | 11.84 | 7 |
| 3842 | CA | SER | A | 488 | 36.335 | 56.623 | 59.865 | 1.00 | 12.18 | 6 |
| 3843 | C | SER | A | 488 | 34.867 | 56.972 | 59.699 | 1.00 | 11.64 | 6 |
| 3844 | O | SER | A | 488 | 34.519 | 58.154 | 59.650 | 1.00 | 12.81 | 8 |
| 3845 | CB | SER | A | 488 | 36.850 | 56.705 | 61.336 | 1.00 | 15.82 | 6 |
| 3846 | OG | SER | A | 488 | 36.431 | 55.439 | 61.907 | 1.00 | 19.75 | 8 |
| 3847 | N | VAL | A | 489 | 33.950 | 55.975 | 59.626 | 1.00 | 11.85 | 7 |
| 3848 | CA | VAL | A | 489 | 32.567 | 56.313 | 59.340 | 1.00 | 11.74 | 6 |
| 3849 | C | VAL | A | 489 | 31.685 | 55.457 | 60.269 | 1.00 | 12.51 | 6 |
| 3850 | O | VAL | A | 489 | 31.910 | 54.276 | 60.410 | 1.00 | 13.59 | 8 |
| 3851 | CB | VAL | A | 489 | 32.231 | 55.903 | 57.882 | 1.00 | 12.50 | 6 |
| 3852 | CG1 | VAL | A | 489 | 30.712 | 56.154 | 57.650 | 1.00 | 11.14 | 6 |
| 3853 | CG2 | VAL | A | 489 | 32.978 | 56.812 | 56.882 | 1.00 | 13.14 | 6 |
| 3854 | N | TRP | A | 490 | 30.771 | 56.135 | 60.914 | 1.00 | 11.35 | 7 |
| 3855 | CA | TRP | A | 490 | 29.900 | 55.413 | 61.883 | 1.00 | 11.90 | 6 |
| 3856 | C | TRP | A | 490 | 28.446 | 55.715 | 61.508 | 1.00 | 13.16 | 6 |
| 3857 | O | TRP | A | 490 | 28.103 | 56.878 | 61.324 | 1.00 | 16.40 | 8 |
| 3858 | CB | TRP | A | 490 | 30.222 | 55.953 | 63.283 | 1.00 | 12.61 | 6 |
| 3859 | CG | TRP | A | 490 | 31.708 | 55.807 | 63.639 | 1.00 | 12.91 | 6 |
| 3860 | CD1 | TRP | A | 490 | 32.381 | 54.628 | 63.904 | 1.00 | 14.71 | 6 |
| 3861 | CD2 | TRP | A | 490 | 32.632 | 56.884 | 63.716 | 1.00 | 14.18 | 6 |
| 3862 | NE1 | TRP | A | 490 | 33.717 | 54.969 | 64.166 | 1.00 | 13.76 | 7 |
| 3863 | CE2 | TRP | A | 490 | 33.883 | 56.328 | 64.049 | 1.00 | 14.41 | 6 |
| 3864 | CE3 | TRP | A | 490 | 32.509 | 58.271 | 63.546 | 1.00 | 16.82 | 6 |
| 3865 | CZ2 | TRP | A | 490 | 35.020 | 57.117 | 64.216 | 1.00 | 13.91 | 6 |
| 3866 | CZ3 | TRP | A | 490 | 33.641 | 59.052 | 63.701 | 1.00 | 14.61 | 6 |
| 3867 | CH2 | TRP | A | 490 | 34.894 | 58.461 | 64.044 | 1.00 | 14.54 | 6 |
| 3868 | N | GLN | A | 491 | 27.680 | 54.618 | 61.394 | 1.00 | 11.75 | 7 |
| 3869 | CA | GLN | A | 491 | 26.332 | 54.869 | 60.903 | 1.00 | 12.20 | 6 |
| 3870 | C | GLN | A | 491 | 25.221 | 54.121 | 61.637 | 1.00 | 13.63 | 6 |
| 3871 | O | GLN | A | 491 | 25.472 | 53.092 | 62.207 | 1.00 | 13.45 | 8 |
| 3872 | CB | GLN | A | 491 | 26.259 | 54.452 | 59.410 | 1.00 | 12.17 | 6 |
| 3873 | CG | GLN | A | 491 | 26.541 | 52.972 | 59.117 | 1.00 | 12.78 | 6 |
| 3874 | CD | GLN | A | 491 | 25.208 | 52.219 | 58.993 | 1.00 | 19.79 | 6 |
| 3875 | OE1 | GLN | A | 491 | 24.222 | 52.726 | 58.485 | 1.00 | 16.61 | 8 |
| 3876 | NE2 | GLN | A | 491 | 25.214 | 50.952 | 59.455 | 1.00 | 19.28 | 7 |
| 3877 | N | TYR | A | 492 | 24.024 | 54.698 | 61.523 | 1.00 | 13.67 | 7 |
| 3878 | CA | TYR | A | 492 | 22.819 | 54.043 | 62.092 | 1.00 | 14.21 | 6 |
| 3879 | C | TYR | A | 492 | 21.665 | 54.203 | 61.102 | 1.00 | 17.30 | 6 |
| 3880 | O | TYR | A | 492 | 21.507 | 55.341 | 60.614 | 1.00 | 14.76 | 8 |
| 3881 | CB | TYR | A | 492 | 22.452 | 54.774 | 63.393 | 1.00 | 15.27 | 6 |
| 3882 | CG | TYR | A | 492 | 21.152 | 54.219 | 63.984 | 1.00 | 15.56 | 6 |
| 3883 | CD1 | TYR | A | 492 | 21.146 | 53.010 | 64.638 | 1.00 | 20.95 | 6 |
| 3884 | CD2 | TYR | A | 492 | 19.963 | 54.959 | 63.800 | 1.00 | 18.48 | 6 |
| 3885 | CE1 | TYR | A | 492 | 19.956 | 52.511 | 65.176 | 1.00 | 21.55 | 6 |
| 3886 | CE2 | TYR | A | 492 | 18.770 | 54.444 | 64.324 | 1.00 | 19.51 | 6 |
| 3887 | CZ | TYR | A | 492 | 18.817 | 53.254 | 65.003 | 1.00 | 22.52 | 6 |
| 3888 | OH | TYR | A | 492 | 17.596 | 52.781 | 65.511 | 1.00 | 24.89 | 8 |
| 3889 | N | SER | A | 493 | 20.879 | 53.151 | 60.925 | 1.00 | 15.17 | 7 |
| 3890 | CA | SER | A | 493 | 19.666 | 53.363 | 60.096 | 1.00 | 14.91 | 6 |
| 3891 | C | SER | A | 493 | 18.548 | 52.462 | 60.616 | 1.00 | 20.17 | 6 |
| 3892 | O | SER | A | 493 | 18.887 | 51.457 | 61.265 | 1.00 | 22.90 | 8 |
| 3893 | CB | SER | A | 493 | 19.867 | 53.083 | 58.619 | 1.00 | 23.97 | 6 |
| 3894 | OG | SER | A | 493 | 20.148 | 51.710 | 58.532 | 1.00 | 30.62 | 8 |
| 3895 | N | THR | A | 494 | 17.344 | 52.991 | 60.393 | 1.00 | 15.89 | 7 |
| 3896 | CA | THR | A | 494 | 16.243 | 52.127 | 60.906 | 1.00 | 18.40 | 6 |
| 3897 | C | THR | A | 494 | 14.999 | 52.406 | 60.060 | 1.00 | 20.14 | 6 |
| 3898 | O | THR | A | 494 | 14.967 | 53.429 | 59.367 | 1.00 | 20.45 | 8 |
| 3899 | CB | THR | A | 494 | 15.993 | 52.424 | 62.396 | 1.00 | 24.38 | 6 |
| 3900 | OG1 | THR | A | 494 | 15.137 | 51.363 | 62.864 | 1.00 | 25.66 | 8 |
| 3901 | CG2 | THR | A | 494 | 15.368 | 53.751 | 62.737 | 1.00 | 27.09 | 6 |
| 3902 | N | SER | A | 495 | 14.017 | 51.534 | 60.157 | 1.00 | 22.56 | 7 |
| 3903 | CA | SER | A | 495 | 12.772 | 51.870 | 59.422 | 1.00 | 19.72 | 6 |
| 3904 | C | SER | A | 495 | 12.082 | 53.049 | 60.021 | 1.00 | 19.50 | 6 |
| 3905 | O | SER | A | 495 | 12.132 | 53.418 | 61.188 | 1.00 | 21.11 | 8 |
| 3906 | CB | ASER | A | 495 | 11.766 | 50.698 | 59.444 | 0.60 | 26.59 | 6 |
| 3907 | OG | ASER | A | 495 | 12.447 | 49.487 | 59.259 | 0.60 | 31.40 | 8 |
| 3907 | CB | BSER | A | 495 | 11.888 | 50.603 | 59.441 | 0.40 | 20.10 | 6 |
| 3908 | OG | BSER | A | 495 | 11.922 | 50.184 | 60.798 | 0.40 | 20.04 | 8 |
| 3908 | N | ALA | A | 496 | 11.315 | 53.727 | 59.141 | 1.00 | 20.53 | 7 |
| 3909 | CA | ALA | A | 496 | 10.529 | 54.893 | 59.493 | 1.00 | 21.55 | 6 |
| 3910 | C | ALA | A | 496 | 9.094 | 54.492 | 59.960 | 1.00 | 24.11 | 6 |
| 3911 | O | ALA | A | 496 | 8.536 | 53.596 | 59.350 | 1.00 | 29.93 | 8 |

TABLE 1-continued

Atom Coordinates from the Crystal Structure of NOVAMYL

| 3912 | CB  | ALA | A | 496 | 10.354 | 55.717 | 58.189 | 1.00 | 22.92 | 6 |
|------|-----|-----|---|-----|--------|--------|--------|------|-------|---|
| 3913 | N   | SER | A | 497 | 8.599  | 55.279 | 60.902 | 1.00 | 26.84 | 7 |
| 3914 | CA  | SER | A | 497 | 7.226  | 54.967 | 61.354 | 1.00 | 32.64 | 6 |
| 3915 | C   | SER | A | 497 | 6.242  | 56.009 | 60.853 | 1.00 | 31.20 | 6 |
| 3916 | O   | SER | A | 497 | 5.049  | 55.788 | 61.090 | 1.00 | 33.40 | 8 |
| 3917 | CB  | SER | A | 497 | 7.183  | 54.836 | 62.875 | 1.00 | 35.13 | 6 |
| 3918 | OG  | SER | A | 497 | 7.578  | 56.030 | 63.515 | 1.00 | 39.06 | 8 |
| 3919 | N   | ALA | A | 498 | 6.685  | 56.920 | 59.967 | 1.00 | 25.21 | 7 |
| 3920 | CA  | ALA | A | 498 | 5.749  | 57.878 | 59.354 | 1.00 | 21.05 | 6 |
| 3921 | C   | ALA | A | 498 | 6.350  | 58.189 | 57.975 | 1.00 | 22.00 | 6 |
| 3922 | O   | ALA | A | 498 | 7.541  | 57.907 | 57.763 | 1.00 | 18.25 | 8 |
| 3923 | CB  | ALA | A | 498 | 5.737  | 59.103 | 60.231 | 1.00 | 22.15 | 6 |
| 3924 | N   | PRO | A | 499 | 5.633  | 58.771 | 57.054 | 1.00 | 18.84 | 7 |
| 3925 | CA  | PRO | A | 499 | 6.176  | 59.058 | 55.718 | 1.00 | 19.31 | 6 |
| 3926 | C   | PRO | A | 499 | 7.174  | 60.210 | 55.762 | 1.00 | 15.69 | 6 |
| 3927 | O   | PRO | A | 499 | 6.934  | 61.242 | 56.370 | 1.00 | 16.96 | 8 |
| 3928 | CB  | PRO | A | 499 | 4.930  | 59.294 | 54.823 | 1.00 | 20.07 | 6 |
| 3929 | CG  | PRO | A | 499 | 3.927  | 59.790 | 55.829 | 1.00 | 23.72 | 6 |
| 3930 | CD  | PRO | A | 499 | 4.205  | 59.113 | 57.173 | 1.00 | 23.70 | 6 |
| 3931 | N   | GLN | A | 500 | 8.288  | 59.975 | 55.037 | 1.00 | 18.24 | 7 |
| 3932 | CA  | GLN | A | 500 | 9.423  | 60.939 | 55.075 | 1.00 | 13.65 | 6 |
| 3933 | C   | GLN | A | 500 | 9.921  | 61.084 | 53.596 | 1.00 | 12.93 | 6 |
| 3934 | O   | GLN | A | 500 | 10.256 | 60.065 | 53.014 | 1.00 | 15.78 | 8 |
| 3935 | CB  | GLN | A | 500 | 10.601 | 60.286 | 55.860 | 1.00 | 15.18 | 6 |
| 3936 | CG  | GLN | A | 500 | 10.189 | 60.048 | 57.328 | 1.00 | 16.32 | 6 |
| 3937 | CD  | GLN | A | 500 | 11.284 | 59.264 | 58.126 | 1.00 | 15.95 | 6 |
| 3938 | OE1 | GLN | A | 500 | 12.239 | 58.781 | 57.571 | 1.00 | 17.99 | 8 |
| 3939 | NE2 | GLN | A | 500 | 11.008 | 59.238 | 59.419 | 1.00 | 20.52 | 7 |
| 3940 | N   | ILE | A | 501 | 9.662  | 62.283 | 53.054 | 1.00 | 12.81 | 7 |
| 3941 | CA  | ILE | A | 501 | 10.101 | 62.501 | 51.667 | 1.00 | 12.56 | 6 |
| 3942 | C   | ILE | A | 501 | 11.594 | 62.914 | 51.642 | 1.00 | 13.47 | 6 |
| 3943 | O   | ILE | A | 501 | 11.899 | 63.905 | 52.301 | 1.00 | 14.35 | 8 |
| 3944 | CB  | ILE | A | 501 | 9.262  | 63.635 | 51.032 | 1.00 | 12.51 | 6 |
| 3945 | CG1 | ILE | A | 501 | 7.788  | 63.216 | 50.842 | 1.00 | 14.81 | 6 |
| 3946 | CG2 | ILE | A | 501 | 9.888  | 63.939 | 49.629 | 1.00 | 12.71 | 6 |
| 3947 | CD1 | ILE | A | 501 | 6.897  | 64.308 | 50.244 | 1.00 | 15.70 | 6 |
| 3948 | N   | GLY | A | 502 | 12.383 | 62.169 | 50.872 | 1.00 | 12.33 | 7 |
| 3949 | CA  | GLY | A | 502 | 13.793 | 62.673 | 50.746 | 1.00 | 12.41 | 6 |
| 3950 | C   | GLY | A | 502 | 13.915 | 63.416 | 49.403 | 1.00 | 11.68 | 6 |
| 3951 | O   | GLY | A | 502 | 14.806 | 64.300 | 49.332 | 1.00 | 12.18 | 8 |
| 3952 | N   | SER | A | 503 | 13.120 | 63.068 | 48.395 | 1.00 | 12.99 | 7 |
| 3953 | CA  | SER | A | 503 | 13.334 | 63.710 | 47.073 | 1.00 | 12.73 | 6 |
| 3954 | C   | SER | A | 503 | 11.970 | 63.672 | 46.342 | 1.00 | 14.01 | 6 |
| 3955 | O   | SER | A | 503 | 11.263 | 62.678 | 46.449 | 1.00 | 14.22 | 8 |
| 3956 | CB  | SER | A | 503 | 14.364 | 62.853 | 46.296 | 1.00 | 12.66 | 6 |
| 3957 | OG  | SER | A | 503 | 14.467 | 63.267 | 44.940 | 1.00 | 12.94 | 8 |
| 3958 | N   | VAL | A | 504 | 11.736 | 64.763 | 45.625 | 1.00 | 12.13 | 7 |
| 3959 | CA  | VAL | A | 504 | 10.738 | 64.716 | 44.521 | 1.00 | 11.27 | 6 |
| 3960 | C   | VAL | A | 504 | 11.521 | 65.159 | 43.243 | 1.00 | 11.68 | 6 |
| 3961 | O   | VAL | A | 504 | 12.287 | 66.121 | 43.321 | 1.00 | 11.43 | 8 |
| 3962 | CB  | VAL | A | 504 | 9.614  | 65.700 | 44.790 | 1.00 | 12.52 | 6 |
| 3963 | CG1 | VAL | A | 504 | 8.670  | 65.766 | 43.563 | 1.00 | 15.49 | 6 |
| 3964 | CG2 | VAL | A | 504 | 8.740  | 65.263 | 46.021 | 1.00 | 12.38 | 6 |
| 3965 | N   | ALA | A | 505 | 11.424 | 64.285 | 42.236 | 1.00 | 11.00 | 7 |
| 3966 | CA  | ALA | A | 505 | 12.174 | 64.595 | 41.003 | 1.00 | 10.56 | 6 |
| 3967 | C   | ALA | A | 505 | 11.447 | 64.174 | 39.798 | 1.00 | 12.28 | 6 |
| 3968 | O   | ALA | A | 505 | 10.738 | 63.165 | 39.919 | 1.00 | 13.54 | 8 |
| 3969 | CB  | ALA | A | 505 | 13.567 | 63.894 | 41.072 | 1.00 | 11.90 | 6 |
| 3970 | N   | PRO | A | 506 | 11.674 | 64.766 | 38.661 | 1.00 | 12.95 | 7 |
| 3971 | CA  | PRO | A | 506 | 12.353 | 66.020 | 38.410 | 1.00 | 11.12 | 6 |
| 3972 | C   | PRO | A | 506 | 11.747 | 67.182 | 39.194 | 1.00 | 12.55 | 6 |
| 3973 | O   | PRO | A | 506 | 10.711 | 67.015 | 39.862 | 1.00 | 12.33 | 8 |
| 3974 | CB  | PRO | A | 506 | 12.227 | 66.313 | 36.887 | 1.00 | 13.30 | 6 |
| 3975 | CG  | PRO | A | 506 | 11.545 | 65.090 | 36.310 | 1.00 | 15.76 | 6 |
| 3976 | CD  | PRO | A | 506 | 11.007 | 64.329 | 37.471 | 1.00 | 14.19 | 6 |
| 3977 | N   | ASN | A | 507 | 12.364 | 68.381 | 39.142 | 1.00 | 10.92 | 7 |
| 3978 | CA  | ASN | A | 507 | 11.835 | 69.493 | 39.909 | 1.00 | 11.12 | 6 |
| 3979 | C   | ASN | A | 507 | 10.940 | 70.447 | 39.087 | 1.00 | 10.54 | 6 |
| 3980 | O   | ASN | A | 507 | 10.497 | 71.416 | 39.701 | 1.00 | 12.30 | 8 |
| 3981 | CB  | ASN | A | 507 | 13.043 | 70.353 | 40.401 | 1.00 | 11.79 | 6 |
| 3982 | CG  | ASN | A | 507 | 14.033 | 69.459 | 41.196 | 1.00 | 14.07 | 6 |
| 3983 | OD1 | ASN | A | 507 | 15.192 | 69.361 | 40.778 | 1.00 | 13.37 | 8 |
| 3984 | ND2 | ASN | A | 507 | 13.592 | 68.845 | 42.261 | 1.00 | 13.47 | 7 |
| 3985 | N   | MET | A | 508 | 10.654 | 70.046 | 37.850 | 1.00 | 10.20 | 7 |
| 3986 | CA  | MET | A | 508 | 9.823  | 70.957 | 37.021 | 1.00 | 11.04 | 6 |
| 3987 | C   | MET | A | 508 | 9.102  | 70.087 | 36.027 | 1.00 | 11.63 | 6 |
| 3988 | O   | MET | A | 508 | 9.633  | 69.029 | 35.633 | 1.00 | 12.66 | 8 |

TABLE 1-continued

Atom Coordinates from the Crystal Structure of NOVAMYL

| | | | | | | | | | |
|---|---|---|---|---|---|---|---|---|---|
| 3989 | CB | MET | A | 508 | 10.929 | 71.782 | 36.219 | 1.00 | 12.80 | 6 |
| 3990 | CG | MET | A | 508 | 10.270 | 72.808 | 35.305 | 1.00 | 15.57 | 6 |
| 3991 | SD | MET | A | 508 | 11.558 | 73.692 | 34.325 | 1.00 | 12.60 | 16 |
| 3992 | CE | MET | A | 508 | 11.921 | 72.582 | 33.003 | 1.00 | 11.82 | 6 |
| 3993 | N | GLY | A | 509 | 7.935 | 70.545 | 35.550 | 1.00 | 11.36 | 7 |
| 3994 | CA | GLY | A | 509 | 7.253 | 69.739 | 34.528 | 1.00 | 10.02 | 6 |
| 3995 | C | GLY | A | 509 | 5.851 | 70.331 | 34.276 | 1.00 | 13.18 | 6 |
| 3996 | O | GLY | A | 509 | 5.506 | 71.321 | 34.889 | 1.00 | 13.82 | 8 |
| 3997 | N | ILE | A | 510 | 5.070 | 69.599 | 33.480 | 1.00 | 11.23 | 7 |
| 3998 | CA | ILE | A | 510 | 3.674 | 70.061 | 33.192 | 1.00 | 12.19 | 6 |
| 3999 | C | ILE | A | 510 | 2.746 | 68.964 | 33.701 | 1.00 | 11.61 | 6 |
| 4000 | O | ILE | A | 510 | 3.156 | 67.806 | 33.903 | 1.00 | 13.58 | 8 |
| 4001 | CB | ILE | A | 510 | 3.456 | 70.272 | 31.683 | 1.00 | 12.75 | 6 |
| 4002 | CG1 | ILE | A | 510 | 3.840 | 69.011 | 30.868 | 1.00 | 11.82 | 6 |
| 4003 | CG2 | ILE | A | 510 | 4.241 | 71.485 | 31.163 | 1.00 | 14.82 | 6 |
| 4004 | CD1 | ILE | A | 510 | 3.293 | 69.108 | 29.417 | 1.00 | 18.53 | 6 |
| 4005 | N | PRO | A | 511 | 1.462 | 69.267 | 33.824 | 1.00 | 13.51 | 7 |
| 4006 | CA | PRO | A | 511 | 0.442 | 68.291 | 34.164 | 1.00 | 14.15 | 6 |
| 4007 | C | PRO | A | 511 | 0.531 | 67.082 | 33.263 | 1.00 | 13.29 | 6 |
| 4008 | O | PRO | A | 511 | 0.780 | 67.180 | 32.026 | 1.00 | 13.86 | 8 |
| 4009 | CB | PRO | A | 511 | −0.913 | 69.037 | 33.810 | 1.00 | 13.10 | 6 |
| 4010 | CG | PRO | A | 511 | −0.528 | 70.435 | 34.265 | 1.00 | 15.94 | 6 |
| 4011 | CD | PRO | A | 511 | 0.925 | 70.625 | 33.729 | 1.00 | 16.03 | 6 |
| 4012 | N | GLY | A | 512 | 0.462 | 65.892 | 33.876 | 1.00 | 12.55 | 7 |
| 4013 | CA | GLY | A | 512 | 0.554 | 64.629 | 33.165 | 1.00 | 14.21 | 6 |
| 4014 | C | GLY | A | 512 | 1.950 | 63.971 | 33.170 | 1.00 | 13.76 | 6 |
| 4015 | O | GLY | A | 512 | 2.002 | 62.765 | 32.923 | 1.00 | 15.31 | 8 |
| 4016 | N | ASN | A | 513 | 2.994 | 64.789 | 33.454 | 1.00 | 12.18 | 7 |
| 4017 | CA | ASN | A | 513 | 4.306 | 64.154 | 33.561 | 1.00 | 10.79 | 6 |
| 4018 | C | ASN | A | 513 | 4.360 | 63.144 | 34.731 | 1.00 | 15.27 | 6 |
| 4019 | O | ASN | A | 513 | 3.699 | 63.392 | 35.738 | 1.00 | 13.64 | 8 |
| 4020 | CB | ASN | A | 513 | 5.408 | 65.230 | 33.833 | 1.00 | 11.43 | 6 |
| 4021 | CG | ASN | A | 513 | 5.762 | 66.023 | 32.583 | 1.00 | 11.94 | 6 |
| 4022 | OD1 | ASN | A | 513 | 6.738 | 66.874 | 32.746 | 1.00 | 16.21 | 8 |
| 4023 | ND2 | ASN | A | 513 | 5.078 | 65.931 | 31.505 | 1.00 | 8.90 | 7 |
| 4024 | N | VAL | A | 514 | 5.280 | 62.177 | 34.576 | 1.00 | 11.74 | 7 |
| 4025 | CA | VAL | A | 514 | 5.505 | 61.269 | 35.745 | 1.00 | 11.63 | 6 |
| 4026 | C | VAL | A | 514 | 6.594 | 61.894 | 36.612 | 1.00 | 13.73 | 6 |
| 4027 | O | VAL | A | 514 | 7.617 | 62.379 | 36.131 | 1.00 | 15.35 | 8 |
| 4028 | CB | VAL | A | 514 | 6.072 | 59.931 | 35.221 | 1.00 | 13.67 | 6 |
| 4029 | CG1 | VAL | A | 514 | 6.529 | 59.036 | 36.390 | 1.00 | 14.35 | 6 |
| 4030 | CG2 | VAL | A | 514 | 5.042 | 59.176 | 34.393 | 1.00 | 16.73 | 6 |
| 4031 | N | VAL | A | 515 | 6.335 | 61.959 | 37.923 | 1.00 | 10.41 | 7 |
| 4032 | CA | VAL | A | 515 | 7.256 | 62.496 | 38.927 | 1.00 | 12.67 | 6 |
| 4033 | C | VAL | A | 515 | 7.433 | 61.442 | 40.001 | 1.00 | 13.31 | 6 |
| 4034 | O | VAL | A | 515 | 6.495 | 60.711 | 40.306 | 1.00 | 14.78 | 8 |
| 4035 | CB | VAL | A | 515 | 6.563 | 63.772 | 39.511 | 1.00 | 14.30 | 6 |
| 4036 | CG1 | VAL | A | 515 | 7.228 | 64.271 | 40.775 | 1.00 | 18.11 | 6 |
| 4037 | CG2 | VAL | A | 515 | 6.678 | 64.883 | 38.435 | 1.00 | 16.90 | 6 |
| 4038 | N | THR | A | 516 | 8.669 | 61.321 | 40.514 | 1.00 | 11.19 | 7 |
| 4039 | CA | THR | A | 516 | 8.900 | 60.252 | 41.495 | 1.00 | 11.78 | 6 |
| 4040 | C | THR | A | 516 | 9.271 | 60.860 | 42.835 | 1.00 | 11.71 | 6 |
| 4041 | O | THR | A | 516 | 10.092 | 61.763 | 42.959 | 1.00 | 12.89 | 8 |
| 4042 | CB | THR | A | 516 | 10.107 | 59.384 | 41.001 | 1.00 | 14.88 | 6 |
| 4043 | OG1 | THR | A | 516 | 9.696 | 58.789 | 39.742 | 1.00 | 14.59 | 8 |
| 4044 | CG2 | THR | A | 516 | 10.446 | 58.275 | 42.004 | 1.00 | 14.18 | 6 |
| 4045 | N | ILE | A | 517 | 8.600 | 60.281 | 43.863 | 1.00 | 9.66 | 7 |
| 4046 | CA | ILE | A | 517 | 8.878 | 60.681 | 45.251 | 1.00 | 10.17 | 6 |
| 4047 | C | ILE | A | 517 | 9.670 | 59.586 | 45.920 | 1.00 | 13.57 | 6 |
| 4048 | O | ILE | A | 517 | 9.172 | 58.427 | 45.949 | 1.00 | 13.82 | 8 |
| 4049 | CB | ILE | A | 517 | 7.493 | 60.899 | 45.948 | 1.00 | 12.16 | 6 |
| 4050 | CG1 | ILE | A | 517 | 6.659 | 61.984 | 45.278 | 1.00 | 15.38 | 6 |
| 4051 | CG2 | ILE | A | 517 | 7.745 | 61.419 | 47.392 | 1.00 | 14.69 | 6 |
| 4052 | CD1 | ILE | A | 517 | 5.200 | 61.951 | 45.779 | 1.00 | 22.16 | 6 |
| 4053 | N | ASP | A | 518 | 10.911 | 59.861 | 46.363 | 1.00 | 13.29 | 7 |
| 4054 | CA | ASP | A | 518 | 11.743 | 58.802 | 46.976 | 1.00 | 14.12 | 6 |
| 4055 | C | ASP | A | 518 | 11.868 | 59.161 | 48.435 | 1.00 | 13.11 | 6 |
| 4056 | O | ASP | A | 518 | 11.922 | 60.347 | 48.791 | 1.00 | 14.37 | 8 |
| 4057 | CB | ASP | A | 518 | 13.159 | 58.791 | 46.351 | 1.00 | 14.49 | 6 |
| 4058 | CG | ASP | A | 518 | 13.106 | 58.207 | 44.962 | 1.00 | 17.62 | 6 |
| 4059 | OD1 | ASP | A | 518 | 12.858 | 56.963 | 44.888 | 1.00 | 17.47 | 8 |
| 4060 | OD2 | ASP | A | 518 | 13.289 | 58.874 | 43.931 | 1.00 | 16.96 | 8 |
| 4061 | N | GLY | A | 519 | 11.769 | 58.138 | 49.315 | 1.00 | 13.39 | 7 |
| 4062 | CA | GLY | A | 519 | 11.872 | 58.484 | 50.757 | 1.00 | 14.21 | 6 |
| 4063 | C | GLY | A | 519 | 11.716 | 57.152 | 51.549 | 1.00 | 13.61 | 6 |
| 4064 | O | GLY | A | 519 | 12.278 | 56.130 | 51.134 | 1.00 | 15.70 | 8 |
| 4065 | N | LYS | A | 520 | 11.059 | 57.319 | 52.696 | 1.00 | 17.22 | 7 |

TABLE 1-continued

Atom Coordinates from the Crystal Structure of NOVAMYL

| 4066 | CA  | LYS | A | 520 | 10.867 | 56.091 | 53.545 | 1.00 | 15.85 | 6 |
|------|-----|-----|---|-----|--------|--------|--------|------|-------|---|
| 4067 | C   | LYS | A | 520 | 9.539  | 56.230 | 54.256 | 1.00 | 16.54 | 6 |
| 4068 | O   | LYS | A | 520 | 9.004  | 57.334 | 54.385 | 1.00 | 17.43 | 8 |
| 4069 | CB  | LYS | A | 520 | 11.866 | 56.344 | 54.747 | 1.00 | 17.75 | 6 |
| 4070 | CG  | LYS | A | 520 | 13.318 | 56.307 | 54.421 | 1.00 | 24.98 | 6 |
| 4071 | CD  | LYS | A | 520 | 14.147 | 56.512 | 55.698 | 1.00 | 22.21 | 6 |
| 4072 | CE  | LYS | A | 520 | 14.074 | 55.145 | 56.459 | 1.00 | 23.54 | 6 |
| 4073 | NZ  | LYS | A | 520 | 15.426 | 54.879 | 57.005 | 1.00 | 27.08 | 7 |
| 4074 | N   | GLY | A | 521 | 9.021  | 55.065 | 54.728 | 1.00 | 16.42 | 7 |
| 4075 | CA  | GLY | A | 521 | 7.870  | 55.223 | 55.627 | 1.00 | 16.98 | 6 |
| 4076 | C   | GLY | A | 521 | 6.540  | 55.347 | 54.874 | 1.00 | 19.49 | 6 |
| 4077 | O   | GLY | A | 521 | 5.533  | 55.716 | 55.525 | 1.00 | 18.22 | 8 |
| 4078 | N   | PHE | A | 522 | 6.569  | 55.053 | 53.560 | 1.00 | 19.15 | 7 |
| 4079 | CA  | PHE | A | 522 | 5.299  | 55.230 | 52.839 | 1.00 | 17.53 | 6 |
| 4080 | C   | PHE | A | 522 | 4.344  | 54.037 | 53.029 | 1.00 | 20.57 | 6 |
| 4081 | O   | PHE | A | 522 | 3.173  | 54.222 | 52.638 | 1.00 | 20.45 | 8 |
| 4082 | CB  | PHE | A | 522 | 5.587  | 55.448 | 51.342 | 1.00 | 17.55 | 6 |
| 4083 | CG  | PHE | A | 522 | 6.513  | 56.605 | 51.009 | 1.00 | 15.40 | 6 |
| 4084 | CD1 | PHE | A | 522 | 6.601  | 57.740 | 51.763 | 1.00 | 17.48 | 6 |
| 4085 | CD2 | PHE | A | 522 | 7.262  | 56.452 | 49.824 | 1.00 | 17.80 | 6 |
| 4086 | CE1 | PHE | A | 522 | 7.480  | 58.778 | 51.376 | 1.00 | 20.21 | 6 |
| 4087 | CE2 | PHE | A | 522 | 8.142  | 57.475 | 49.422 | 1.00 | 16.35 | 6 |
| 4088 | CZ  | PHE | A | 522 | 8.257  | 58.607 | 50.214 | 1.00 | 14.66 | 6 |
| 4089 | N   | GLY | A | 523 | 4.826  | 52.902 | 53.488 | 1.00 | 23.38 | 7 |
| 4090 | CA  | GLY | A | 523 | 3.947  | 51.721 | 53.586 | 1.00 | 26.21 | 6 |
| 4091 | C   | GLY | A | 523 | 3.753  | 51.037 | 52.260 | 1.00 | 27.39 | 6 |
| 4092 | O   | GLY | A | 523 | 4.082  | 51.536 | 51.167 | 1.00 | 21.64 | 8 |
| 4093 | N   | THR | A | 524 | 3.204  | 49.785 | 52.316 | 1.00 | 26.00 | 7 |
| 4094 | CA  | THR | A | 524 | 3.043  | 49.010 | 51.103 | 1.00 | 24.30 | 6 |
| 4095 | C   | THR | A | 524 | 1.636  | 49.241 | 50.556 | 1.00 | 26.74 | 6 |
| 4096 | O   | THR | A | 524 | 1.433  | 48.984 | 49.372 | 1.00 | 34.03 | 8 |
| 4097 | CB  | THR | A | 524 | 3.314  | 47.505 | 51.308 | 1.00 | 36.63 | 6 |
| 4098 | OG1 | THR | A | 524 | 2.403  | 47.020 | 52.315 | 1.00 | 34.71 | 8 |
| 4099 | CG2 | THR | A | 524 | 4.711  | 47.251 | 51.862 | 1.00 | 34.40 | 6 |
| 4100 | N   | THR | A | 525 | 0.748  | 49.673 | 51.432 | 1.00 | 27.38 | 7 |
| 4101 | CA  | THR | A | 525 | -0.646 | 49.948 | 51.027 | 1.00 | 29.73 | 6 |
| 4102 | C   | THR | A | 525 | -0.696 | 51.367 | 50.456 | 1.00 | 29.44 | 6 |
| 4103 | O   | THR | A | 525 | -0.315 | 52.313 | 51.159 | 1.00 | 28.46 | 8 |
| 4104 | CB  | THR | A | 525 | -1.558 | 49.835 | 52.265 | 1.00 | 31.59 | 6 |
| 4105 | OG1 | THR | A | 525 | -1.416 | 48.485 | 52.779 | 1.00 | 34.50 | 8 |
| 4106 | CG2 | THR | A | 525 | -3.020 | 50.076 | 51.920 | 1.00 | 33.53 | 6 |
| 4107 | N   | GLN | A | 526 | -1.341 | 51.530 | 49.304 | 1.00 | 26.38 | 7 |
| 4108 | CA  | GLN | A | 526 | -1.383 | 52.864 | 48.695 | 1.00 | 27.25 | 6 |
| 4109 | C   | GLN | A | 526 | -2.090 | 53.867 | 49.574 | 1.00 | 29.32 | 6 |
| 4110 | O   | GLN | A | 526 | -3.264 | 53.665 | 49.960 | 1.00 | 25.61 | 8 |
| 4111 | CB  | GLN | A | 526 | -2.101 | 52.757 | 47.340 | 1.00 | 28.17 | 6 |
| 4112 | CG  | GLN | A | 526 | -2.028 | 53.996 | 46.486 | 1.00 | 30.46 | 6 |
| 4113 | CD  | GLN | A | 526 | -2.542 | 53.744 | 45.055 | 1.00 | 28.73 | 6 |
| 4114 | OE1 | GLN | A | 526 | -3.419 | 54.518 | 44.679 | 1.00 | 33.21 | 8 |
| 4115 | NE2 | GLN | A | 526 | -1.951 | 52.750 | 44.438 | 1.00 | 31.17 | 7 |
| 4116 | N   | GLY | A | 527 | -1.476 | 55.032 | 49.820 | 1.00 | 22.05 | 7 |
| 4117 | CA  | GLY | A | 527 | -2.091 | 56.150 | 50.508 | 1.00 | 20.00 | 6 |
| 4118 | C   | GLY | A | 527 | -2.415 | 57.258 | 49.471 | 1.00 | 19.58 | 6 |
| 4119 | O   | GLY | A | 527 | -2.894 | 56.897 | 48.405 | 1.00 | 21.95 | 8 |
| 4120 | N   | THR | A | 528 | -2.136 | 58.506 | 49.804 | 1.00 | 21.30 | 7 |
| 4121 | CA  | THR | A | 528 | -2.428 | 59.597 | 48.884 | 1.00 | 18.42 | 6 |
| 4122 | C   | THR | A | 528 | -1.268 | 60.584 | 48.808 | 1.00 | 21.48 | 6 |
| 4123 | O   | THR | A | 528 | -0.375 | 60.642 | 49.647 | 1.00 | 20.31 | 8 |
| 4124 | CB  | THR | A | 528 | -3.685 | 60.387 | 49.320 | 1.00 | 24.98 | 6 |
| 4125 | OG1 | THR | A | 528 | -3.522 | 60.782 | 50.657 | 1.00 | 30.73 | 8 |
| 4126 | CG2 | THR | A | 528 | -4.933 | 59.511 | 49.240 | 1.00 | 26.25 | 6 |
| 4127 | N   | VAL | A | 529 | -1.209 | 61.255 | 47.667 | 1.00 | 16.67 | 7 |
| 4128 | CA  | VAL | A | 529 | -0.167 | 62.275 | 47.425 | 1.00 | 15.19 | 6 |
| 4129 | C   | VAL | A | 529 | -0.924 | 63.532 | 46.987 | 1.00 | 16.18 | 6 |
| 4130 | O   | VAL | A | 529 | -1.825 | 63.328 | 46.155 | 1.00 | 16.64 | 8 |
| 4131 | CB  | VAL | A | 529 | 0.700  | 61.851 | 46.216 | 1.00 | 14.16 | 6 |
| 4132 | CG1 | VAL | A | 529 | 1.664  | 62.995 | 45.841 | 1.00 | 17.46 | 6 |
| 4133 | CG2 | VAL | A | 529 | 1.483  | 60.594 | 46.604 | 1.00 | 18.23 | 6 |
| 4134 | N   | THR | A | 530 | -0.533 | 64.669 | 47.531 | 1.00 | 14.50 | 7 |
| 4135 | CA  | THR | A | 530 | -1.148 | 65.900 | 47.016 | 1.00 | 14.78 | 6 |
| 4136 | C   | THR | A | 530 | -0.038 | 66.814 | 46.492 | 1.00 | 17.57 | 6 |
| 4137 | O   | THR | A | 530 | 1.076  | 66.792 | 47.027 | 1.00 | 15.22 | 8 |
| 4138 | CB  | THR | A | 530 | -1.954 | 66.621 | 48.090 | 1.00 | 15.93 | 6 |
| 4139 | OG1 | THR | A | 530 | -1.209 | 66.722 | 49.308 | 1.00 | 17.69 | 8 |
| 4140 | CG2 | THR | A | 530 | -3.279 | 65.858 | 48.340 | 1.00 | 17.39 | 6 |
| 4141 | N   | PHE | A | 531 | -0.395 | 67.691 | 45.569 | 1.00 | 14.04 | 7 |
| 4142 | CA  | PHE | A | 531 | 0.458  | 68.822 | 45.142 | 1.00 | 13.01 | 6 |

TABLE 1-continued

Atom Coordinates from the Crystal Structure of NOVAMYL

| 4143 | CA  | PHE | A | 531 | -0.344 | 70.073 | 45.496 | 1.00 | 15.03 | 6 |
|------|-----|-----|---|-----|--------|--------|--------|------|-------|---|
| 4144 | O   | PHE | A | 531 | -1.454 | 70.292 | 44.989 | 1.00 | 16.16 | 8 |
| 4145 | CB  | PHE | A | 531 | 0.659  | 68.823 | 43.604 | 1.00 | 13.87 | 6 |
| 4146 | CG  | PHE | A | 531 | 1.611  | 67.777 | 43.040 | 1.00 | 13.21 | 6 |
| 4147 | CD1 | PHE | A | 531 | 1.438  | 66.431 | 43.191 | 1.00 | 14.34 | 6 |
| 4148 | CD2 | PHE | A | 531 | 2.662  | 68.228 | 42.240 | 1.00 | 14.96 | 6 |
| 4149 | CE1 | PHE | A | 531 | 2.288  | 65.515 | 42.629 | 1.00 | 16.70 | 6 |
| 4150 | CE2 | PHE | A | 531 | 3.545  | 67.306 | 41.691 | 1.00 | 13.81 | 6 |
| 4151 | CZ  | PHE | A | 531 | 3.385  | 65.943 | 41.836 | 1.00 | 16.70 | 6 |
| 4152 | N   | GLY | A | 532 | 0.118  | 70.806 | 46.490 | 1.00 | 14.18 | 7 |
| 4153 | CA  | GLY | A | 532 | -0.569 | 72.077 | 46.884 | 1.00 | 15.57 | 6 |
| 4154 | C   | GLY | A | 532 | -1.992 | 71.702 | 47.378 | 1.00 | 19.88 | 6 |
| 4155 | O   | GLY | A | 532 | -2.928 | 72.482 | 47.068 | 1.00 | 18.91 | 8 |
| 4156 | N   | GLY | A | 533 | -2.193 | 70.510 | 47.921 | 1.00 | 17.41 | 7 |
| 4157 | CA  | GLY | A | 533 | -3.524 | 70.089 | 48.400 | 1.00 | 18.31 | 6 |
| 4158 | C   | GLY | A | 533 | -4.368 | 69.372 | 47.370 | 1.00 | 20.08 | 6 |
| 4159 | O   | GLY | A | 533 | -5.463 | 68.817 | 47.637 | 1.00 | 19.31 | 8 |
| 4160 | N   | VAL | A | 534 | -3.923 | 69.391 | 46.097 | 1.00 | 16.06 | 7 |
| 4161 | CA  | VAL | A | 534 | -4.592 | 68.721 | 44.999 | 1.00 | 15.11 | 6 |
| 4162 | C   | VAL | A | 534 | -4.197 | 67.275 | 44.894 | 1.00 | 15.67 | 6 |
| 4163 | O   | VAL | A | 534 | -3.019 | 66.888 | 44.712 | 1.00 | 17.94 | 8 |
| 4164 | CB  | VAL | A | 534 | -4.368 | 69.480 | 43.645 | 1.00 | 13.67 | 6 |
| 4165 | CG1 | VAL | A | 534 | -5.101 | 68.739 | 42.509 | 1.00 | 15.45 | 6 |
| 4166 | CG2 | VAL | A | 534 | -4.807 | 70.937 | 43.768 | 1.00 | 16.93 | 6 |
| 4167 | N   | THR | A | 535 | -5.185 | 66.334 | 44.967 | 1.00 | 13.93 | 7 |
| 4168 | CA  | THR | A | 535 | -4.827 | 64.927 | 44.890 | 1.00 | 16.87 | 6 |
| 4169 | C   | THR | A | 535 | -4.271 | 64.521 | 43.536 | 1.00 | 20.28 | 6 |
| 4170 | O   | THR | A | 535 | -4.796 | 64.893 | 42.462 | 1.00 | 17.64 | 8 |
| 4171 | CB  | THR | A | 535 | -6.065 | 64.042 | 45.192 | 1.00 | 20.23 | 6 |
| 4172 | OG1 | THR | A | 535 | -6.446 | 64.284 | 46.576 | 1.00 | 20.94 | 8 |
| 4173 | CG2 | THR | A | 535 | -5.787 | 62.565 | 45.026 | 1.00 | 24.73 | 6 |
| 4174 | N   | ALA | A | 536 | -3.162 | 63.773 | 43.562 | 1.00 | 15.87 | 7 |
| 4175 | CA  | ALA | A | 536 | -2.521 | 63.324 | 42.337 | 1.00 | 17.27 | 6 |
| 4176 | C   | ALA | A | 536 | -2.808 | 61.859 | 42.042 | 1.00 | 20.29 | 6 |
| 4177 | O   | ALA | A | 536 | -2.929 | 61.111 | 43.030 | 1.00 | 20.32 | 8 |
| 4178 | CB  | ALA | A | 536 | -0.976 | 63.441 | 42.384 | 1.00 | 17.03 | 6 |
| 4179 | N   | THR | A | 537 | -2.937 | 61.461 | 40.791 | 1.00 | 16.03 | 7 |
| 4180 | CA  | THR | A | 537 | -3.151 | 60.043 | 40.489 | 1.00 | 15.38 | 6 |
| 4181 | C   | THR | A | 537 | -1.865 | 59.242 | 40.679 | 1.00 | 19.21 | 6 |
| 4182 | O   | THR | A | 537 | -0.823 | 59.697 | 40.166 | 1.00 | 19.02 | 8 |
| 4183 | CB  | THR | A | 537 | -3.564 | 59.955 | 38.998 | 1.00 | 18.90 | 6 |
| 4184 | OG1 | THR | A | 537 | -4.828 | 60.651 | 38.950 | 1.00 | 19.30 | 8 |
| 4185 | CG2 | THR | A | 537 | -3.697 | 58.508 | 38.591 | 1.00 | 18.81 | 6 |
| 4186 | N   | VAL | A | 538 | -1.925 | 58.176 | 41.415 | 1.00 | 16.51 | 7 |
| 4187 | CA  | VAL | A | 538 | -0.704 | 57.394 | 41.746 | 1.00 | 16.38 | 6 |
| 4188 | C   | VAL | A | 538 | -0.516 | 56.415 | 40.613 | 1.00 | 18.34 | 6 |
| 4189 | O   | VAL | A | 538 | -1.390 | 55.599 | 40.252 | 1.00 | 20.80 | 8 |
| 4190 | CB  | VAL | A | 538 | -0.896 | 56.665 | 43.080 | 1.00 | 17.97 | 6 |
| 4191 | CG1 | VAL | A | 538 | 0.219  | 55.621 | 43.337 | 1.00 | 16.03 | 6 |
| 4192 | CG2 | VAL | A | 538 | -1.016 | 57.646 | 44.226 | 1.00 | 19.59 | 6 |
| 4193 | N   | LYS | A | 539 | 0.696  | 56.340 | 40.055 | 1.00 | 15.64 | 7 |
| 4194 | CA  | LYS | A | 539 | 1.119  | 55.341 | 39.108 | 1.00 | 14.97 | 6 |
| 4195 | C   | LYS | A | 539 | 1.626  | 54.044 | 39.732 | 1.00 | 17.57 | 6 |
| 4196 | O   | LYS | A | 539 | 1.313  | 52.885 | 39.375 | 1.00 | 18.05 | 8 |
| 4197 | CB  | LYS | A | 539 | 2.264  | 55.914 | 38.209 | 1.00 | 17.15 | 6 |
| 4198 | CG  | LYS | A | 539 | 2.814  | 54.859 | 37.246 | 1.00 | 20.63 | 6 |
| 4199 | CD  | LYS | A | 539 | 3.860  | 55.636 | 36.368 | 1.00 | 25.39 | 6 |
| 4200 | CE  | LYS | A | 539 | 3.601  | 55.199 | 34.949 | 1.00 | 41.98 | 6 |
| 4201 | NZ  | LYS | A | 539 | 4.369  | 53.976 | 34.672 | 1.00 | 30.47 | 7 |
| 4202 | N   | SER | A | 540 | 2.424  | 54.212 | 40.787 | 1.00 | 15.53 | 7 |
| 4203 | CA  | SER | A | 540 | 2.919  | 53.073 | 41.587 | 1.00 | 16.52 | 6 |
| 4204 | C   | SER | A | 540 | 3.231  | 53.502 | 42.999 | 1.00 | 17.69 | 6 |
| 4205 | O   | SER | A | 540 | 3.482  | 54.680 | 43.306 | 1.00 | 16.82 | 8 |
| 4206 | CB  | SER | A | 540 | 4.136  | 52.424 | 40.903 | 1.00 | 20.58 | 6 |
| 4207 | OG  | SER | A | 540 | 5.270  | 53.317 | 41.043 | 1.00 | 19.05 | 8 |
| 4208 | N   | TRP | A | 541 | 3.206  | 52.536 | 43.953 | 1.00 | 16.64 | 7 |
| 4209 | CA  | TRP | A | 541 | 3.361  | 52.905 | 45.378 | 1.00 | 15.40 | 6 |
| 4210 | C   | TRP | A | 541 | 4.148  | 51.785 | 46.053 | 1.00 | 20.16 | 6 |
| 4211 | O   | TRP | A | 541 | 3.682  | 50.647 | 46.008 | 1.00 | 21.11 | 8 |
| 4212 | CB  | TRP | A | 541 | 2.034  | 53.084 | 46.101 | 1.00 | 17.49 | 6 |
| 4213 | CG  | TRP | A | 541 | 2.124  | 53.605 | 47.502 | 1.00 | 15.27 | 6 |
| 4214 | CD1 | TRP | A | 541 | 2.645  | 52.924 | 48.584 | 1.00 | 18.64 | 6 |
| 4215 | CD2 | TRP | A | 541 | 1.689  | 54.854 | 48.006 | 1.00 | 15.30 | 6 |
| 4216 | NE1 | TRP | A | 541 | 2.542  | 53.673 | 49.715 | 1.00 | 19.85 | 7 |
| 4217 | CE2 | TRP | A | 541 | 1.976  | 54.894 | 49.381 | 1.00 | 17.27 | 6 |
| 4218 | CE3 | TRP | A | 541 | 1.086  | 55.984 | 47.440 | 1.00 | 15.92 | 6 |
| 4219 | CZ2 | TRP | A | 541 | 1.703  | 55.983 | 50.201 | 1.00 | 18.49 | 6 |

TABLE 1-continued

Atom Coordinates from the Crystal Structure of NOVAMYL

| 4220 | CZ3 | TRP | A | 541 | 0.787 | 57.054 | 48.223 | 1.00 | 19.66 | 6 |
|---|---|---|---|---|---|---|---|---|---|---|
| 4221 | CH2 | TRP | A | 541 | 1.076 | 57.063 | 49.619 | 1.00 | 21.41 | 6 |
| 4222 | N | THR | A | 542 | 5.297 | 52.107 | 46.615 | 1.00 | 18.77 | 7 |
| 4223 | CA | THR | A | 542 | 6.111 | 51.224 | 47.437 | 1.00 | 20.27 | 6 |
| 4224 | C | THR | A | 542 | 6.477 | 51.972 | 48.690 | 1.00 | 21.74 | 6 |
| 4225 | O | THR | A | 542 | 6.369 | 53.228 | 48.814 | 1.00 | 17.27 | 8 |
| 4226 | CB | THR | A | 542 | 7.356 | 50.641 | 46.743 | 1.00 | 24.92 | 6 |
| 4227 | OG1 | THR | A | 542 | 8.305 | 51.745 | 46.576 | 1.00 | 21.04 | 8 |
| 4228 | CG2 | THR | A | 542 | 7.091 | 49.930 | 45.442 | 1.00 | 26.69 | 6 |
| 4229 | N | SER | A | 543 | 7.123 | 51.252 | 49.648 | 1.00 | 18.34 | 7 |
| 4230 | CA | SER | A | 543 | 7.474 | 51.808 | 50.923 | 1.00 | 18.96 | 6 |
| 4231 | C | SER | A | 543 | 8.463 | 52.975 | 50.734 | 1.00 | 17.37 | 6 |
| 4232 | O | SER | A | 543 | 8.525 | 53.808 | 51.615 | 1.00 | 19.43 | 8 |
| 4233 | CB | SER | A | 543 | 8.201 | 50.711 | 51.743 | 1.00 | 24.79 | 6 |
| 4234 | OG | SER | A | 543 | 7.254 | 49.673 | 51.954 | 1.00 | 38.42 | 8 |
| 4235 | N | ASN | A | 544 | 9.313 | 52.865 | 49.721 | 1.00 | 17.78 | 7 |
| 4236 | CA | ASN | A | 544 | 10.349 | 53.917 | 49.575 | 1.00 | 14.67 | 6 |
| 4237 | C | ASN | A | 544 | 10.208 | 54.723 | 48.287 | 1.00 | 15.24 | 6 |
| 4238 | O | ASN | A | 544 | 11.018 | 55.668 | 48.072 | 1.00 | 16.63 | 8 |
| 4239 | CB | AASN | A | 544 | 11.734 | 53.252 | 49.583 | 0.50 | 18.64 | 6 |
| 4240 | CG | AASN | A | 544 | 12.145 | 52.868 | 51.005 | 0.50 | 24.93 | 6 |
| 4241 | OD1 | AASN | A | 544 | 11.394 | 53.024 | 51.976 | 0.50 | 27.01 | 8 |
| 4242 | ND2 | AASN | A | 544 | 13.359 | 52.364 | 51.118 | 0.50 | 19.54 | 7 |
| 4240 | CB | BASN | A | 544 | 11.746 | 53.263 | 49.523 | 0.50 | 15.95 | 6 |
| 4241 | CG | BASN | A | 544 | 11.998 | 52.552 | 50.860 | 0.50 | 20.57 | 6 |
| 4242 | OD1 | BASN | A | 544 | 12.195 | 53.205 | 51.884 | 0.50 | 23.06 | 8 |
| 4243 | ND2 | BASN | A | 544 | 11.914 | 51.250 | 50.767 | 0.50 | 19.16 | 7 |
| 4243 | N | ARG | A | 545 | 9.224 | 54.409 | 47.426 | 1.00 | 14.40 | 7 |
| 4244 | CA | ARG | A | 545 | 9.193 | 55.190 | 46.167 | 1.00 | 16.44 | 6 |
| 4245 | C | ARG | A | 545 | 7.727 | 55.246 | 45.682 | 1.00 | 19.39 | 6 |
| 4246 | O | ARG | A | 545 | 7.083 | 54.204 | 45.539 | 1.00 | 17.25 | 8 |
| 4247 | CB | ARG | A | 545 | 10.085 | 54.589 | 45.084 | 1.00 | 17.96 | 6 |
| 4248 | CG | ARG | A | 545 | 9.964 | 55.404 | 43.794 | 1.00 | 17.03 | 6 |
| 4249 | CD | ARG | A | 545 | 10.778 | 54.728 | 42.653 | 1.00 | 15.55 | 6 |
| 4250 | NE | ARG | A | 545 | 12.186 | 54.934 | 43.045 | 1.00 | 17.92 | 7 |
| 4251 | CZ | ARG | A | 545 | 13.164 | 54.094 | 42.735 | 1.00 | 27.70 | 6 |
| 4252 | NH1 | ARG | A | 545 | 12.923 | 53.020 | 41.999 | 1.00 | 26.35 | 7 |
| 4253 | NH2 | ARG | A | 545 | 14.392 | 54.343 | 43.179 | 1.00 | 26.80 | 7 |
| 4254 | N | ILE | A | 546 | 7.282 | 56.458 | 45.332 | 1.00 | 18.00 | 7 |
| 4255 | CA | ILE | A | 546 | 5.908 | 56.613 | 44.793 | 1.00 | 14.23 | 6 |
| 4256 | C | ILE | A | 546 | 6.077 | 57.267 | 43.406 | 1.00 | 17.86 | 6 |
| 4257 | O | ILE | A | 546 | 6.771 | 58.296 | 43.389 | 1.00 | 15.62 | 8 |
| 4258 | CB | ILE | A | 546 | 5.039 | 57.498 | 45.668 | 1.00 | 13.38 | 6 |
| 4259 | CG1 | ILE | A | 546 | 4.895 | 56.781 | 47.045 | 1.00 | 15.14 | 6 |
| 4260 | CG2 | ILE | A | 546 | 3.624 | 57.682 | 45.030 | 1.00 | 14.12 | 6 |
| 4261 | CD1 | ILE | A | 546 | 4.473 | 57.773 | 48.119 | 1.00 | 13.44 | 6 |
| 4262 | N | GLU | A | 547 | 5.424 | 56.777 | 42.400 | 1.00 | 14.74 | 7 |
| 4263 | CA | GLU | A | 547 | 5.338 | 57.543 | 41.134 | 1.00 | 14.58 | 6 |
| 4264 | C | GLU | A | 547 | 3.943 | 58.116 | 40.945 | 1.00 | 15.30 | 6 |
| 4265 | O | GLU | A | 547 | 2.977 | 57.405 | 41.270 | 1.00 | 15.50 | 8 |
| 4266 | CB | GLU | A | 547 | 5.537 | 56.644 | 39.913 | 1.00 | 14.75 | 6 |
| 4267 | CG | GLU | A | 547 | 6.987 | 56.074 | 39.890 | 1.00 | 17.63 | 6 |
| 4268 | CD | GLU | A | 547 | 7.105 | 55.058 | 38.781 | 1.00 | 21.54 | 6 |
| 4269 | OE1 | GLU | A | 547 | 6.335 | 54.046 | 38.730 | 1.00 | 18.28 | 8 |
| 4270 | OE2 | GLU | A | 547 | 7.924 | 55.225 | 37.834 | 1.00 | 16.92 | 8 |
| 4271 | N | VAL | A | 548 | 3.865 | 59.377 | 40.603 | 1.00 | 12.67 | 7 |
| 4272 | CA | VAL | A | 548 | 2.565 | 60.033 | 40.428 | 1.00 | 13.16 | 6 |
| 4273 | C | VAL | A | 548 | 2.565 | 60.764 | 39.095 | 1.00 | 15.52 | 6 |
| 4274 | O | VAL | A | 548 | 3.587 | 61.028 | 38.477 | 1.00 | 14.55 | 8 |
| 4275 | CB | VAL | A | 548 | 2.266 | 61.100 | 41.499 | 1.00 | 15.22 | 6 |
| 4276 | CG1 | VAL | A | 548 | 2.134 | 60.409 | 42.872 | 1.00 | 17.06 | 6 |
| 4277 | CG2 | VAL | A | 548 | 3.376 | 62.179 | 41.584 | 1.00 | 16.26 | 6 |
| 4278 | N | TYR | A | 549 | 1.338 | 61.119 | 38.644 | 1.00 | 12.92 | 7 |
| 4279 | CA | TYR | A | 549 | 1.226 | 61.997 | 37.481 | 1.00 | 14.43 | 6 |
| 4280 | C | TYR | A | 549 | 0.902 | 63.397 | 37.975 | 1.00 | 13.16 | 6 |
| 4281 | O | TYR | A | 549 | 0.223 | 63.571 | 39.016 | 1.00 | 14.84 | 8 |
| 4282 | CB | TYR | A | 549 | 0.000 | 61.611 | 36.605 | 1.00 | 14.89 | 6 |
| 4283 | CG | TYR | A | 549 | 0.208 | 60.240 | 36.037 | 1.00 | 14.21 | 6 |
| 4284 | CD1 | TYR | A | 549 | 1.049 | 60.058 | 34.934 | 1.00 | 17.04 | 6 |
| 4285 | CD2 | TYR | A | 549 | −0.398 | 59.160 | 36.628 | 1.00 | 14.96 | 6 |
| 4286 | CE1 | TYR | A | 549 | 1.252 | 58.788 | 34.395 | 1.00 | 19.51 | 6 |
| 4287 | CE2 | TYR | A | 549 | −0.214 | 57.885 | 36.081 | 1.00 | 20.11 | 6 |
| 4288 | CZ | TYR | A | 549 | 0.577 | 57.730 | 34.984 | 1.00 | 20.28 | 6 |
| 4289 | OH | TYR | A | 549 | 0.789 | 56.436 | 34.508 | 1.00 | 21.51 | 8 |
| 4290 | N | VAL | A | 550 | 1.626 | 64.446 | 37.496 | 1.00 | 12.41 | 7 |
| 4291 | CA | VAL | A | 550 | 1.317 | 65.794 | 37.957 | 1.00 | 13.30 | 6 |
| 4292 | C | VAL | A | 550 | −0.145 | 66.139 | 37.602 | 1.00 | 12.86 | 6 |

TABLE 1-continued

Atom Coordinates from the Crystal Structure of NOVAMYL

| 4293 | O | VAL | A | 550 | −0.589 | 65.893 | 36.503 | 1.00 | 15.42 | 8 |
|---|---|---|---|---|---|---|---|---|---|---|
| 4294 | CB | VAL | A | 550 | 2.195 | 66.791 | 37.131 | 1.00 | 12.38 | 6 |
| 4295 | CG1 | VAL | A | 550 | 1.968 | 68.236 | 37.581 | 1.00 | 13.91 | 6 |
| 4296 | CG2 | VAL | A | 550 | 3.657 | 66.404 | 37.542 | 1.00 | 16.31 | 6 |
| 4297 | N | PRO | A | 551 | −0.828 | 66.685 | 38.603 | 1.00 | 13.48 | 7 |
| 4298 | CA | PRO | A | 551 | −2.272 | 66.942 | 38.387 | 1.00 | 16.42 | 6 |
| 4299 | C | PRO | A | 551 | −2.447 | 68.081 | 37.424 | 1.00 | 16.09 | 6 |
| 4300 | O | PRO | A | 551 | −1.599 | 68.955 | 37.236 | 1.00 | 16.43 | 8 |
| 4301 | CB | PRO | A | 551 | −2.869 | 67.337 | 39.755 | 1.00 | 20.53 | 6 |
| 4302 | CG | PRO | A | 551 | −1.772 | 66.991 | 40.707 | 1.00 | 20.55 | 6 |
| 4303 | CD | PRO | A | 551 | −0.427 | 66.849 | 39.973 | 1.00 | 17.00 | 6 |
| 4304 | N | ASN | A | 552 | −3.658 | 68.150 | 36.821 | 1.00 | 15.47 | 7 |
| 4305 | CA | ASN | A | 552 | −4.017 | 69.248 | 35.941 | 1.00 | 15.18 | 6 |
| 4306 | C | ASN | A | 552 | −4.401 | 70.475 | 36.748 | 1.00 | 19.54 | 6 |
| 4307 | O | ASN | A | 552 | −5.630 | 70.744 | 36.917 | 1.00 | 19.65 | 8 |
| 4308 | CB | ASN | A | 552 | −5.198 | 68.759 | 35.075 | 1.00 | 19.00 | 6 |
| 4309 | CG | ASN | A | 552 | −5.522 | 69.706 | 33.925 | 1.00 | 23.61 | 6 |
| 4310 | OD1 | ASN | A | 552 | −4.763 | 70.583 | 33.553 | 1.00 | 29.14 | 8 |
| 4311 | ND2 | ASN | A | 552 | −6.635 | 69.481 | 33.239 | 1.00 | 23.65 | 7 |
| 4312 | N | MET | A | 553 | −3.487 | 71.146 | 37.402 | 1.00 | 13.46 | 7 |
| 4313 | CA | MET | A | 553 | −3.722 | 72.208 | 38.346 | 1.00 | 11.50 | 6 |
| 4314 | C | MET | A | 553 | −3.003 | 73.456 | 37.901 | 1.00 | 15.54 | 6 |
| 4315 | O | MET | A | 553 | −2.319 | 73.427 | 36.881 | 1.00 | 17.61 | 8 |
| 4316 | CB | MET | A | 553 | −3.328 | 71.835 | 39.803 | 1.00 | 16.46 | 6 |
| 4317 | CG | MET | A | 553 | −1.826 | 71.490 | 39.883 | 1.00 | 14.92 | 6 |
| 4318 | SD | MET | A | 553 | −1.364 | 70.962 | 41.579 | 1.00 | 17.71 | 16 |
| 4319 | CE | MET | A | 553 | −1.416 | 72.450 | 42.426 | 1.00 | 16.59 | 6 |
| 4320 | N | ALA | A | 554 | −3.278 | 74.532 | 38.619 | 1.00 | 17.19 | 7 |
| 4321 | CA | ALA | A | 554 | −2.711 | 75.834 | 38.289 | 1.00 | 21.10 | 6 |
| 4322 | C | ALA | A | 554 | −1.169 | 75.788 | 38.321 | 1.00 | 17.79 | 6 |
| 4323 | O | ALA | A | 554 | −0.631 | 75.032 | 39.141 | 1.00 | 17.24 | 8 |
| 4324 | CB | ALA | A | 554 | −3.075 | 76.757 | 39.471 | 1.00 | 24.10 | 6 |
| 4325 | N | ALA | A | 555 | −0.537 | 76.591 | 37.500 | 1.00 | 14.57 | 7 |
| 4326 | CA | ALA | A | 555 | 0.947 | 76.567 | 37.489 | 1.00 | 13.27 | 6 |
| 4327 | C | ALA | A | 555 | 1.568 | 77.356 | 38.600 | 1.00 | 13.78 | 6 |
| 4328 | O | ALA | A | 555 | 1.051 | 78.305 | 39.204 | 1.00 | 14.85 | 8 |
| 4329 | CB | ALA | A | 555 | 1.375 | 77.200 | 36.142 | 1.00 | 16.26 | 6 |
| 4330 | N | GLY | A | 556 | 2.874 | 76.966 | 38.857 | 1.00 | 12.02 | 7 |
| 4331 | CA | GLY | A | 556 | 3.602 | 77.675 | 39.947 | 1.00 | 14.17 | 6 |
| 4332 | C | GLY | A | 556 | 4.312 | 76.639 | 40.815 | 1.00 | 12.79 | 6 |
| 4333 | O | GLY | A | 556 | 4.121 | 75.415 | 40.670 | 1.00 | 12.92 | 8 |
| 4334 | N | LEU | A | 557 | 5.203 | 77.130 | 41.670 | 1.00 | 14.81 | 7 |
| 4335 | CA | LEU | A | 557 | 5.876 | 76.232 | 42.626 | 1.00 | 13.54 | 6 |
| 4336 | C | LEU | A | 557 | 4.918 | 75.806 | 43.737 | 1.00 | 12.41 | 6 |
| 4337 | O | LEU | A | 557 | 4.110 | 76.659 | 44.188 | 1.00 | 14.95 | 8 |
| 4338 | CB | LEU | A | 557 | 7.091 | 76.999 | 43.221 | 1.00 | 13.41 | 6 |
| 4339 | CG | LEU | A | 557 | 8.018 | 76.123 | 44.069 | 1.00 | 15.11 | 6 |
| 4340 | CD1 | LEU | A | 557 | 8.847 | 75.220 | 43.141 | 1.00 | 13.33 | 6 |
| 4341 | CD2 | LEU | A | 557 | 8.965 | 77.046 | 44.898 | 1.00 | 17.39 | 6 |
| 4342 | N | THR | A | 558 | 4.801 | 74.500 | 43.858 | 1.00 | 13.24 | 7 |
| 4343 | CA | THR | A | 558 | 3.807 | 73.941 | 44.818 | 1.00 | 13.26 | 6 |
| 4344 | C | THR | A | 558 | 4.469 | 72.927 | 45.741 | 1.00 | 16.19 | 6 |
| 4345 | O | THR | A | 558 | 5.520 | 72.402 | 45.379 | 1.00 | 16.82 | 8 |
| 4346 | CB | THR | A | 558 | 2.616 | 73.378 | 44.044 | 1.00 | 17.75 | 6 |
| 4347 | OG1 | THR | A | 558 | 1.566 | 73.153 | 45.010 | 1.00 | 18.46 | 8 |
| 4348 | CG2 | THR | A | 558 | 2.886 | 72.099 | 43.320 | 1.00 | 14.65 | 6 |
| 4349 | N | ASP | A | 559 | 3.750 | 72.559 | 46.821 | 1.00 | 13.53 | 7 |
| 4350 | CA | ASP | A | 559 | 4.351 | 71.569 | 47.739 | 1.00 | 13.26 | 6 |
| 4351 | C | ASP | A | 559 | 3.718 | 70.202 | 47.564 | 1.00 | 17.40 | 6 |
| 4352 | O | ASP | A | 559 | 2.469 | 70.015 | 47.579 | 1.00 | 17.26 | 8 |
| 4353 | CB | ASP | A | 559 | 4.129 | 72.027 | 49.195 | 1.00 | 13.77 | 8 |
| 4354 | CG | ASP | A | 559 | 4.998 | 73.219 | 49.580 | 1.00 | 25.94 | 6 |
| 4355 | OD1 | ASP | A | 559 | 6.174 | 73.267 | 49.201 | 1.00 | 23.88 | 8 |
| 4356 | OD2 | ASP | A | 559 | 4.468 | 74.127 | 50.251 | 1.00 | 28.55 | 8 |
| 4357 | N | VAL | A | 560 | 4.576 | 69.205 | 47.465 | 1.00 | 12.44 | 7 |
| 4358 | CA | VAL | A | 560 | 4.161 | 67.801 | 47.392 | 1.00 | 11.28 | 6 |
| 4359 | C | VAL | A | 560 | 4.193 | 67.207 | 48.826 | 1.00 | 14.98 | 6 |
| 4360 | O | VAL | A | 560 | 5.085 | 67.470 | 49.616 | 1.00 | 15.44 | 8 |
| 4361 | CB | VAL | A | 560 | 5.144 | 66.953 | 46.555 | 1.00 | 11.93 | 6 |
| 4362 | CG1 | VAL | A | 560 | 4.738 | 65.496 | 46.488 | 1.00 | 16.58 | 6 |
| 4363 | CG2 | VAL | A | 560 | 5.186 | 67.516 | 45.122 | 1.00 | 14.73 | 6 |
| 4364 | N | LYS | A | 561 | 3.136 | 66.439 | 49.097 | 1.00 | 15.49 | 7 |
| 4365 | CA | LYS | A | 561 | 2.989 | 65.835 | 50.443 | 1.00 | 14.90 | 6 |
| 4366 | C | LYS | A | 561 | 2.427 | 64.452 | 50.269 | 1.00 | 15.23 | 6 |
| 4367 | O | LYS | A | 561 | 1.502 | 64.157 | 49.522 | 1.00 | 16.90 | 8 |
| 4368 | CB | LYS | A | 561 | 1.960 | 66.720 | 51.206 | 1.00 | 18.50 | 6 |
| 4369 | CG | LYS | A | 561 | 1.847 | 66.177 | 52.656 | 1.00 | 22.42 | 6 |

TABLE 1-continued

Atom Coordinates from the Crystal Structure of NOVAMYL

| | | | | | | | | | | |
|---|---|---|---|---|---|---|---|---|---|---|
| 4370 | CD | LYS | A | 561 | 1.025 | 67.110 | 53.523 | 1.00 | 25.69 | 6 |
| 4371 | CE | LYS | A | 561 | −0.461 | 66.912 | 53.312 | 1.00 | 33.13 | 6 |
| 4372 | NZ | LYS | A | 561 | −1.198 | 68.004 | 54.033 | 1.00 | 37.04 | 7 |
| 4373 | N | VAL | A | 562 | 2.947 | 63.489 | 51.047 | 1.00 | 16.07 | 7 |
| 4374 | CA | VAL | A | 562 | 2.525 | 62.108 | 51.051 | 1.00 | 14.01 | 6 |
| 4375 | C | VAL | A | 562 | 1.751 | 61.827 | 52.382 | 1.00 | 14.81 | 6 |
| 4376 | O | VAL | A | 562 | 2.150 | 62.324 | 53.398 | 1.00 | 17.73 | 8 |
| 4377 | CB | VAL | A | 562 | 3.735 | 61.158 | 51.036 | 1.00 | 16.60 | 6 |
| 4378 | CG1 | VAL | A | 562 | 3.312 | 59.677 | 51.185 | 1.00 | 16.48 | 6 |
| 4379 | CG2 | VAL | A | 562 | 4.473 | 61.228 | 49.672 | 1.00 | 17.80 | 6 |
| 4380 | N | THR | A | 563 | 0.603 | 61.156 | 52.140 | 1.00 | 17.67 | 7 |
| 4381 | CA | THR | A | 563 | −0.181 | 60.806 | 53.380 | 1.00 | 18.18 | 6 |
| 4382 | C | THR | A | 563 | −0.261 | 59.308 | 53.412 | 1.00 | 18.30 | 6 |
| 4383 | O | THR | A | 563 | −0.679 | 58.642 | 52.456 | 1.00 | 19.93 | 8 |
| 4384 | CB | THR | A | 563 | −1.542 | 61.496 | 53.361 | 1.00 | 18.11 | 6 |
| 4385 | OG1 | THR | A | 563 | −1.367 | 62.891 | 53.406 | 1.00 | 19.44 | 8 |
| 4386 | CG2 | THR | A | 563 | −2.281 | 61.112 | 54.705 | 1.00 | 20.36 | 6 |
| 4387 | N | ALA | A | 564 | 0.154 | 58.701 | 54.548 | 1.00 | 21.05 | 7 |
| 4388 | CA | ALA | A | 564 | 0.245 | 57.258 | 54.649 | 1.00 | 24.26 | 6 |
| 4389 | C | ALA | A | 564 | −0.234 | 56.845 | 56.060 | 1.00 | 23.28 | 6 |
| 4390 | O | ALA | A | 564 | 0.104 | 57.536 | 57.008 | 1.00 | 21.58 | 8 |
| 4391 | CB | ALA | A | 564 | 1.658 | 56.711 | 54.437 | 1.00 | 25.03 | 6 |
| 4392 | N | GLY | A | 565 | −1.218 | 55.968 | 56.140 | 1.00 | 30.08 | 7 |
| 4393 | CA | GLY | A | 565 | −1.857 | 55.701 | 57.443 | 1.00 | 31.09 | 6 |
| 4394 | C | GLY | A | 565 | −2.488 | 56.887 | 58.121 | 1.00 | 35.06 | 6 |
| 4395 | O | GLY | A | 565 | −2.493 | 56.983 | 59.363 | 1.00 | 31.36 | 8 |
| 4396 | N | GLY | A | 566 | −3.025 | 57.873 | 57.403 | 1.00 | 32.22 | 7 |
| 4397 | CA | GLY | A | 566 | −3.549 | 59.083 | 58.011 | 1.00 | 31.70 | 6 |
| 4398 | C | GLY | A | 566 | −2.523 | 60.107 | 58.438 | 1.00 | 31.07 | 6 |
| 4399 | O | GLY | A | 566 | −2.936 | 61.213 | 58.829 | 1.00 | 32.69 | 8 |
| 4400 | N | VAL | A | 567 | −1.202 | 59.887 | 58.271 | 1.00 | 26.17 | 7 |
| 4401 | CA | VAL | A | 567 | −0.186 | 60.798 | 58.776 | 1.00 | 21.45 | 6 |
| 4402 | C | VAL | A | 567 | 0.537 | 61.488 | 57.557 | 1.00 | 17.95 | 6 |
| 4403 | O | VAL | A | 567 | 0.692 | 60.707 | 56.658 | 1.00 | 18.75 | 8 |
| 4404 | CB | VAL | A | 567 | 0.945 | 60.023 | 59.500 | 1.00 | 26.89 | 6 |
| 4405 | CG1 | VAL | A | 567 | 1.981 | 60.946 | 60.096 | 1.00 | 30.00 | 6 |
| 4406 | CG2 | VAL | A | 567 | 0.308 | 59.088 | 60.567 | 1.00 | 33.86 | 6 |
| 4407 | N | SER | A | 568 | 0.687 | 62.774 | 57.699 | 1.00 | 19.77 | 7 |
| 4408 | CA | SER | A | 568 | 1.267 | 63.410 | 56.486 | 1.00 | 19.16 | 6 |
| 4409 | C | SER | A | 568 | 2.770 | 63.585 | 56.688 | 1.00 | 19.28 | 6 |
| 4410 | O | SER | A | 568 | 3.351 | 63.752 | 57.763 | 1.00 | 21.35 | 8 |
| 4411 | CB | SER | A | 568 | 0.574 | 64.705 | 56.156 | 1.00 | 29.69 | 6 |
| 4412 | OG | SER | A | 568 | 0.595 | 65.549 | 57.266 | 1.00 | 41.18 | 8 |
| 4413 | N | SER | A | 569 | 3.399 | 63.581 | 55.503 | 1.00 | 19.22 | 7 |
| 4414 | CA | SER | A | 569 | 4.867 | 63.784 | 55.480 | 1.00 | 17.43 | 6 |
| 4415 | C | SER | A | 569 | 5.229 | 65.245 | 55.568 | 1.00 | 17.17 | 6 |
| 4416 | O | SER | A | 569 | 4.519 | 66.266 | 55.502 | 1.00 | 17.53 | 8 |
| 4417 | CB | SER | A | 569 | 5.381 | 63.220 | 54.137 | 1.00 | 17.58 | 6 |
| 4418 | OG | SER | A | 569 | 5.066 | 64.083 | 53.025 | 1.00 | 15.50 | 8 |
| 4419 | N | ASN | A | 570 | 6.572 | 65.473 | 55.538 | 1.00 | 14.77 | 7 |
| 4420 | CA | ASN | A | 570 | 7.143 | 66.776 | 55.253 | 1.00 | 13.84 | 6 |
| 4421 | C | ASN | A | 570 | 6.848 | 67.107 | 53.752 | 1.00 | 13.33 | 6 |
| 4422 | O | ASN | A | 570 | 6.527 | 66.217 | 52.996 | 1.00 | 16.50 | 8 |
| 4423 | CB | ASN | A | 570 | 8.670 | 66.723 | 55.435 | 1.00 | 17.22 | 6 |
| 4424 | CG | ASN | A | 570 | 9.363 | 65.581 | 54.758 | 1.00 | 16.95 | 6 |
| 4425 | OD1 | ASN | A | 570 | 9.038 | 64.399 | 54.745 | 1.00 | 15.12 | 8 |
| 4426 | ND2 | ASN | A | 570 | 10.455 | 65.853 | 54.023 | 1.00 | 16.51 | 7 |
| 4427 | N | LEU | A | 571 | 7.108 | 68.381 | 53.486 | 1.00 | 14.82 | 7 |
| 4428 | CA | LEU | A | 571 | 6.705 | 68.878 | 52.131 | 1.00 | 12.49 | 6 |
| 4429 | C | LEU | A | 571 | 7.959 | 69.019 | 51.282 | 1.00 | 15.87 | 6 |
| 4430 | O | LEU | A | 571 | 9.024 | 69.355 | 51.828 | 1.00 | 16.79 | 8 |
| 4431 | CB | LEU | A | 571 | 6.147 | 70.286 | 52.340 | 1.00 | 15.18 | 6 |
| 4432 | CG | LEU | A | 571 | 4.911 | 70.396 | 53.250 | 1.00 | 22.77 | 6 |
| 4433 | CD1 | LEU | A | 571 | 4.368 | 71.807 | 53.300 | 1.00 | 22.26 | 6 |
| 4434 | CD2 | LEU | A | 571 | 3.834 | 69.448 | 52.757 | 1.00 | 22.04 | 6 |
| 4435 | N | TYR | A | 572 | 7.747 | 68.878 | 49.946 | 1.00 | 13.65 | 7 |
| 4436 | CA | TYR | A | 572 | 8.930 | 69.100 | 49.067 | 1.00 | 12.87 | 6 |
| 4437 | C | TYR | A | 572 | 8.322 | 69.878 | 47.880 | 1.00 | 14.52 | 6 |
| 4438 | O | TYR | A | 572 | 7.347 | 69.399 | 47.262 | 1.00 | 14.71 | 8 |
| 4439 | CB | TYR | A | 572 | 9.480 | 67.704 | 48.701 | 1.00 | 12.62 | 6 |
| 4440 | CG | TYR | A | 572 | 10.887 | 67.679 | 48.121 | 1.00 | 13.61 | 6 |
| 4441 | CD1 | TYR | A | 572 | 11.079 | 68.175 | 46.835 | 1.00 | 13.57 | 6 |
| 4442 | CD2 | TYR | A | 572 | 11.946 | 67.161 | 48.845 | 1.00 | 15.40 | 6 |
| 4443 | CE1 | TYR | A | 572 | 12.361 | 68.168 | 46.257 | 1.00 | 13.80 | 6 |
| 4444 | CE2 | TYR | A | 572 | 13.221 | 67.135 | 48.283 | 1.00 | 12.70 | 6 |
| 4445 | CZ | TYR | A | 572 | 13.400 | 67.629 | 47.002 | 1.00 | 14.33 | 6 |
| 4446 | OH | TYR | A | 572 | 14.710 | 67.607 | 46.466 | 1.00 | 13.40 | 8 |

TABLE 1-continued

Atom Coordinates from the Crystal Structure of NOVAMYL

| 4447 | N   | SER  | A | 573 | 9.060  | 70.874 | 47.387 | 1.00 | 13.37 | 7 |
|------|-----|------|---|-----|--------|--------|--------|------|-------|---|
| 4448 | CA  | SER  | A | 573 | 8.571  | 71.734 | 46.294 | 1.00 | 12.21 | 6 |
| 4449 | C   | SER  | A | 573 | 8.665  | 71.055 | 44.920 | 1.00 | 12.75 | 6 |
| 4450 | O   | SER  | A | 573 | 9.520  | 70.234 | 44.703 | 1.00 | 12.64 | 8 |
| 4451 | CB  | ASER | A | 573 | 9.436  | 72.999 | 46.162 | 0.60 | 17.33 | 6 |
| 4452 | OG  | ASER | A | 573 | 9.459  | 73.767 | 47.331 | 0.60 | 22.77 | 8 |
| 4452 | CB  | BSER | A | 573 | 9.408  | 73.025 | 46.276 | 0.40 | 15.40 | 6 |
| 4453 | OG  | BSER | A | 573 | 10.793 | 72.728 | 46.149 | 0.40 | 16.17 | 8 |
| 4453 | N   | TYR  | A | 574 | 7.838  | 71.568 | 44.000 | 1.00 | 11.56 | 7 |
| 4454 | CA  | TYR  | A | 574 | 7.912  | 71.077 | 42.604 | 1.00 | 10.89 | 6 |
| 4455 | C   | TYR  | A | 574 | 7.374  | 72.249 | 41.771 | 1.00 | 13.28 | 6 |
| 4456 | O   | TYR  | A | 574 | 6.344  | 72.860 | 42.138 | 1.00 | 12.17 | 8 |
| 4457 | CB  | TYR  | A | 574 | 7.041  | 69.857 | 42.405 | 1.00 | 11.94 | 6 |
| 4458 | CG  | TYR  | A | 574 | 6.917  | 69.379 | 40.971 | 1.00 | 11.37 | 6 |
| 4459 | CD1 | TYR  | A | 574 | 7.921  | 68.521 | 40.467 | 1.00 | 12.69 | 6 |
| 4460 | CD2 | TYR  | A | 574 | 5.867  | 69.781 | 40.162 | 1.00 | 11.85 | 6 |
| 4461 | CE1 | TYR  | A | 574 | 7.863  | 68.052 | 39.154 | 1.00 | 13.23 | 6 |
| 4462 | CE2 | TYR  | A | 574 | 5.792  | 69.313 | 38.834 | 1.00 | 13.93 | 6 |
| 4463 | CZ  | TYR  | A | 574 | 6.796  | 68.466 | 38.366 | 1.00 | 11.32 | 6 |
| 4464 | OH  | TYR  | A | 574 | 6.679  | 68.006 | 37.078 | 1.00 | 12.54 | 8 |
| 4465 | N   | ASN  | A | 575 | 7.992  | 72.510 | 40.627 | 1.00 | 12.18 | 7 |
| 4466 | CA  | ASN  | A | 575 | 7.578  | 73.682 | 39.820 | 1.00 | 12.18 | 6 |
| 4467 | C   | ASN  | A | 575 | 6.738  | 73.306 | 38.608 | 1.00 | 12.59 | 6 |
| 4468 | O   | ASN  | A | 575 | 7.171  | 72.699 | 37.598 | 1.00 | 12.20 | 8 |
| 4469 | CB  | ASN  | A | 575 | 8.898  | 74.351 | 39.331 | 1.00 | 12.02 | 6 |
| 4470 | CG  | ASN  | A | 575 | 8.635  | 75.707 | 38.700 | 1.00 | 17.00 | 6 |
| 4471 | OD1 | ASN  | A | 575 | 7.562  | 76.292 | 38.872 | 1.00 | 14.54 | 8 |
| 4472 | ND2 | ASN  | A | 575 | 9.608  | 76.223 | 37.934 | 1.00 | 13.02 | 7 |
| 4473 | N   | ILE  | A | 576 | 5.400  | 73.515 | 38.739 | 1.00 | 10.95 | 7 |
| 4474 | CA  | ILE  | A | 576 | 4.506  | 73.221 | 37.604 | 1.00 | 10.36 | 6 |
| 4475 | C   | ILE  | A | 576 | 4.485  | 74.374 | 36.602 | 1.00 | 12.05 | 6 |
| 4476 | O   | ILE  | A | 576 | 4.145  | 75.497 | 36.930 | 1.00 | 13.39 | 8 |
| 4477 | CB  | ILE  | A | 576 | 3.036  | 73.061 | 38.127 | 1.00 | 12.95 | 6 |
| 4478 | CG1 | ILE  | A | 576 | 3.082  | 71.956 | 39.190 | 1.00 | 13.10 | 6 |
| 4479 | CG2 | ILE  | A | 576 | 2.079  | 72.677 | 36.966 | 1.00 | 14.18 | 6 |
| 4480 | CD1 | ILE  | A | 576 | 1.709  | 71.488 | 39.691 | 1.00 | 15.07 | 6 |
| 4481 | N   | LEU  | A | 577 | 4.883  | 74.054 | 35.368 | 1.00 | 10.51 | 7 |
| 4482 | CA  | LEU  | A | 577 | 4.908  | 75.052 | 34.303 | 1.00 | 12.74 | 6 |
| 4483 | C   | LEU  | A | 577 | 3.480  | 75.308 | 33.772 | 1.00 | 11.80 | 6 |
| 4484 | O   | LEU  | A | 577 | 2.572  | 74.474 | 34.021 | 1.00 | 13.37 | 8 |
| 4485 | CB  | LEU  | A | 577 | 5.757  | 74.463 | 33.137 | 1.00 | 11.48 | 6 |
| 4486 | CG  | LEU  | A | 577 | 7.226  | 74.238 | 33.569 | 1.00 | 12.21 | 6 |
| 4487 | CD1 | LEU  | A | 577 | 7.982  | 73.601 | 32.421 | 1.00 | 13.03 | 6 |
| 4488 | CD2 | LEU  | A | 577 | 7.897  | 75.576 | 33.989 | 1.00 | 13.85 | 6 |
| 4489 | N   | SER  | A | 578 | 3.398  | 76.385 | 33.006 | 1.00 | 11.76 | 7 |
| 4490 | CA  | SER  | A | 578 | 2.037  | 76.726 | 32.475 | 1.00 | 15.00 | 6 |
| 4491 | C   | SER  | A | 578 | 1.681  | 75.960 | 31.215 | 1.00 | 17.37 | 6 |
| 4492 | O   | SER  | A | 578 | 0.553  | 76.134 | 30.685 | 1.00 | 17.93 | 8 |
| 4493 | CB  | SER  | A | 578 | 2.081  | 78.230 | 32.132 | 1.00 | 13.25 | 6 |
| 4494 | OG  | SER  | A | 578 | 2.321  | 78.967 | 33.305 | 1.00 | 14.45 | 8 |
| 4495 | N   | GLY  | A | 579 | 2.538  | 75.095 | 30.688 | 1.00 | 15.28 | 7 |
| 4496 | CA  | GLY  | A | 579 | 2.266  | 74.270 | 29.497 | 1.00 | 14.88 | 6 |
| 4497 | C   | GLY  | A | 579 | 3.627  | 74.010 | 28.818 | 1.00 | 13.39 | 6 |
| 4498 | O   | GLY  | A | 579 | 4.670  | 74.450 | 29.318 | 1.00 | 14.78 | 8 |
| 4499 | N   | THR  | A | 580 | 3.518  | 73.227 | 27.740 | 1.00 | 11.35 | 7 |
| 4500 | CA  | THR  | A | 580 | 4.803  | 72.961 | 27.005 | 1.00 | 13.16 | 6 |
| 4501 | C   | THR  | A | 580 | 5.419  | 74.292 | 26.647 | 1.00 | 14.61 | 6 |
| 4502 | O   | THR  | A | 580 | 4.747  | 75.282 | 26.349 | 1.00 | 14.26 | 8 |
| 4503 | CB  | THR  | A | 580 | 4.517  | 72.009 | 25.835 | 1.00 | 13.57 | 6 |
| 4504 | OG1 | THR  | A | 580 | 5.753  | 71.676 | 25.176 | 1.00 | 16.06 | 8 |
| 4505 | CG2 | THR  | A | 580 | 3.688  | 72.715 | 24.732 | 1.00 | 20.75 | 6 |
| 4506 | N   | GLN  | A | 581 | 6.787  | 74.346 | 26.706 | 1.00 | 11.89 | 7 |
| 4507 | CA  | GLN  | A | 581 | 7.454  | 75.658 | 26.609 | 1.00 | 10.06 | 6 |
| 4508 | C   | GLN  | A | 581 | 8.012  | 75.905 | 25.148 | 1.00 | 10.19 | 6 |
| 4509 | O   | GLN  | A | 581 | 8.163  | 75.020 | 24.338 | 1.00 | 12.94 | 8 |
| 4510 | CB  | GLN  | A | 581 | 8.751  | 75.601 | 27.465 | 1.00 | 11.27 | 6 |
| 4511 | CG  | GLN  | A | 581 | 8.407  | 75.301 | 28.975 | 1.00 | 10.49 | 6 |
| 4512 | CD  | GLN  | A | 581 | 7.920  | 76.579 | 29.654 | 1.00 | 12.45 | 6 |
| 4513 | OE1 | GLN  | A | 581 | 8.545  | 77.588 | 29.921 | 1.00 | 13.44 | 8 |
| 4514 | NE2 | GLN  | A | 581 | 6.582  | 76.528 | 30.002 | 1.00 | 11.11 | 7 |
| 4515 | N   | THR  | A | 582 | 8.202  | 77.209 | 24.953 | 1.00 | 9.52  | 7 |
| 4516 | CA  | THR  | A | 582 | 8.978  | 77.646 | 23.772 | 1.00 | 10.13 | 6 |
| 4517 | C   | THR  | A | 582 | 10.049 | 78.609 | 24.293 | 1.00 | 10.70 | 6 |
| 4518 | O   | THR  | A | 582 | 9.921  | 79.235 | 25.313 | 1.00 | 12.73 | 8 |
| 4519 | CB  | THR  | A | 582 | 8.018  | 78.306 | 22.763 | 1.00 | 12.88 | 6 |
| 4520 | OG1 | THR  | A | 582 | 8.736  | 78.798 | 21.599 | 1.00 | 12.92 | 8 |
| 4521 | CG2 | THR  | A | 582 | 7.265  | 79.504 | 23.359 | 1.00 | 11.55 | 6 |

TABLE 1-continued

Atom Coordinates from the Crystal Structure of NOVAMYL

| 4522 | N | SRE | A | 583 | 11.166 | 78.712 | 23.507 | 1.00 | 11.67 | 7 |
|---|---|---|---|---|---|---|---|---|---|---|
| 4523 | CA | SER | A | 583 | 12.321 | 79.527 | 23.931 | 1.00 | 12.58 | 6 |
| 4524 | C | SER | A | 583 | 12.300 | 80.783 | 23.061 | 1.00 | 11.58 | 6 |
| 4525 | O | SER | A | 583 | 12.496 | 80.687 | 21.844 | 1.00 | 12.44 | 8 |
| 4526 | CB | SER | A | 583 | 13.612 | 78.697 | 23.747 | 1.00 | 12.53 | 6 |
| 4527 | OG | SER | A | 583 | 14.755 | 79.449 | 24.240 | 1.00 | 14.73 | 8 |
| 4528 | N | VAL | A | 584 | 12.118 | 81.899 | 23.781 | 1.00 | 10.19 | 7 |
| 4529 | CA | VAL | A | 584 | 11.741 | 83.141 | 23.016 | 1.00 | 9.76 | 6 |
| 4530 | C | VAL | A | 584 | 12.721 | 84.268 | 23.298 | 1.00 | 11.27 | 6 |
| 4531 | O | VAL | A | 584 | 13.066 | 84.570 | 24.440 | 1.00 | 11.87 | 8 |
| 4532 | CB | VAL | A | 584 | 10.358 | 83.645 | 23.506 | 1.00 | 12.33 | 6 |
| 4533 | CG1 | VAL | A | 584 | 10.041 | 84.968 | 22.757 | 1.00 | 14.53 | 6 |
| 4534 | CG2 | VAL | A | 584 | 9.279 | 82.604 | 23.220 | 1.00 | 12.71 | 6 |
| 4535 | N | VAL | A | 585 | 13.307 | 84.868 | 22.244 | 1.00 | 10.77 | 7 |
| 4536 | CA | VAL | A | 585 | 14.166 | 86.030 | 22.421 | 1.00 | 9.69 | 6 |
| 4537 | C | VAL | A | 585 | 13.244 | 87.219 | 22.693 | 1.00 | 12.06 | 6 |
| 4538 | O | VAL | A | 585 | 12.450 | 87.576 | 21.803 | 1.00 | 14.60 | 8 |
| 4539 | CB | VAL | A | 585 | 14.882 | 86.310 | 21.064 | 1.00 | 11.53 | 6 |
| 4540 | CG1 | VAL | A | 585 | 15.712 | 87.605 | 21.158 | 1.00 | 15.03 | 6 |
| 4541 | CG2 | VAL | A | 585 | 15.750 | 85.111 | 20.717 | 1.00 | 14.67 | 6 |
| 4542 | N | PHE | A | 586 | 13.361 | 87.762 | 23.908 | 1.00 | 12.32 | 7 |
| 4543 | CA | PHE | A | 586 | 12.622 | 88.986 | 24.243 | 1.00 | 12.19 | 6 |
| 4544 | C | PHE | A | 586 | 13.584 | 90.161 | 24.063 | 1.00 | 14.77 | 6 |
| 4545 | O | PHE | A | 586 | 14.668 | 90.209 | 24.709 | 1.00 | 12.38 | 8 |
| 4546 | CB | PHE | A | 586 | 12.174 | 88.944 | 25.704 | 1.00 | 12.57 | 6 |
| 4547 | CG | PHE | A | 586 | 10.886 | 88.184 | 25.987 | 1.00 | 11.39 | 6 |
| 4548 | CD1 | PHE | A | 586 | 10.879 | 86.809 | 26.009 | 1.00 | 13.56 | 6 |
| 4549 | CD2 | PHE | A | 586 | 9.694 | 88.868 | 26.231 | 1.00 | 13.70 | 6 |
| 4550 | CE1 | PHE | A | 586 | 9.758 | 86.060 | 26.284 | 1.00 | 13.86 | 6 |
| 4551 | CE2 | PHE | A | 586 | 8.543 | 88.102 | 26.520 | 1.00 | 12.32 | 6 |
| 4552 | CZ | PHE | A | 586 | 8.577 | 86.707 | 26.558 | 1.00 | 11.70 | 6 |
| 4553 | N | THR | A | 587 | 13.189 | 91.146 | 23.239 | 1.00 | 14.16 | 7 |
| 4554 | CA | THR | A | 587 | 14.016 | 92.324 | 23.066 | 1.00 | 12.96 | 6 |
| 4555 | C | THR | A | 587 | 13.247 | 93.561 | 23.468 | 1.00 | 13.58 | 6 |
| 4556 | O | THR | A | 587 | 12.072 | 93.651 | 23.058 | 1.00 | 15.22 | 8 |
| 4557 | CB | THR | A | 587 | 14.421 | 92.464 | 21.555 | 1.00 | 11.66 | 6 |
| 4558 | OG1 | THR | A | 587 | 15.145 | 91.299 | 21.141 | 1.00 | 15.06 | 8 |
| 4559 | CG2 | THR | A | 587 | 15.331 | 93.708 | 21.318 | 1.00 | 13.37 | 6 |
| 4560 | N | VAL | A | 588 | 13.829 | 94.487 | 24.195 | 1.00 | 14.03 | 7 |
| 4561 | CA | VAL | A | 588 | 13.156 | 95.779 | 24.469 | 1.00 | 14.79 | 6 |
| 4562 | C | VAL | A | 588 | 14.079 | 96.867 | 23.912 | 1.00 | 14.40 | 6 |
| 4563 | O | VAL | A | 588 | 15.258 | 97.015 | 24.225 | 1.00 | 15.56 | 8 |
| 4564 | CB | VAL | A | 588 | 12.863 | 95.933 | 25.971 | 1.00 | 14.24 | 6 |
| 4565 | CG1 | VAL | A | 588 | 14.111 | 95.935 | 26.870 | 1.00 | 14.60 | 6 |
| 4566 | CG2 | VAL | A | 588 | 12.079 | 97.255 | 26.232 | 1.00 | 13.38 | 6 |
| 4567 | N | LYS | A | 589 | 13.478 | 97.570 | 22.915 | 1.00 | 15.39 | 7 |
| 4568 | CA | LYS | A | 589 | 14.212 | 98.670 | 22.258 | 1.00 | 16.20 | 6 |
| 4569 | C | LYS | A | 589 | 14.180 | 100.009 | 22.953 | 1.00 | 18.01 | 6 |
| 4570 | O | LYS | A | 589 | 13.230 | 100.355 | 23.652 | 1.00 | 15.39 | 8 |
| 4571 | CB | LYS | A | 589 | 13.597 | 98.820 | 20.860 | 1.00 | 16.23 | 6 |
| 4572 | CG | LYS | A | 589 | 13.908 | 97.588 | 20.008 | 1.00 | 17.01 | 6 |
| 4573 | CD | LYS | A | 589 | 13.275 | 97.825 | 18.634 | 1.00 | 24.71 | 6 |
| 4574 | CE | LYS | A | 589 | 13.494 | 96.582 | 17.792 | 1.00 | 37.49 | 6 |
| 4575 | NZ | LYS | A | 589 | 13.368 | 96.852 | 16.321 | 1.00 | 51.36 | 7 |
| 4576 | N | SER | A | 590 | 15.302 | 100.747 | 22.828 | 1.00 | 16.34 | 7 |
| 4577 | CA | SER | A | 590 | 15.371 | 102.116 | 23.293 | 1.00 | 19.32 | 6 |
| 4578 | C | SER | A | 590 | 15.006 | 102.295 | 24.746 | 1.00 | 19.68 | 6 |
| 4579 | O | SER | A | 590 | 14.185 | 103.146 | 25.151 | 1.00 | 17.24 | 8 |
| 4580 | CB | SER | A | 590 | 14.448 | 103.009 | 22.421 | 1.00 | 20.32 | 6 |
| 4581 | OG | SER | A | 590 | 14.867 | 102.933 | 21.046 | 1.00 | 22.81 | 8 |
| 4582 | N | ALA | A | 591 | 15.698 | 101.514 | 25.612 | 1.00 | 17.08 | 7 |
| 4583 | CA | ALA | A | 591 | 15.458 | 101.617 | 27.048 | 1.00 | 16.02 | 6 |
| 4584 | C | ALA | A | 591 | 16.178 | 102.871 | 27.530 | 1.00 | 18.06 | 6 |
| 4585 | O | ALA | A | 591 | 17.152 | 103.325 | 26.878 | 1.00 | 15.85 | 8 |
| 4586 | CB | ALA | A | 591 | 16.045 | 100.326 | 27.695 | 1.00 | 15.17 | 6 |
| 4587 | N | PRO | A | 592 | 15.872 | 103.303 | 28.730 | 1.00 | 18.28 | 7 |
| 4588 | CA | PRO | A | 592 | 16.493 | 104.529 | 29.298 | 1.00 | 18.18 | 6 |
| 4589 | C | PRO | A | 592 | 17.967 | 104.319 | 29.512 | 1.00 | 22.69 | 6 |
| 4590 | O | PRO | A | 592 | 18.463 | 103.180 | 29.693 | 1.00 | 19.12 | 8 |
| 4591 | CB | PRO | A | 592 | 15.762 | 104.797 | 30.621 | 1.00 | 19.23 | 6 |
| 4592 | CG | PRO | A | 592 | 14.433 | 104.085 | 30.387 | 1.00 | 23.18 | 6 |
| 4593 | CD | PRO | A | 592 | 14.795 | 102.833 | 29.585 | 1.00 | 17.71 | 6 |
| 4594 | N | PRO | A | 593 | 18.778 | 105.367 | 29.550 | 1.00 | 21.02 | 7 |
| 4595 | CA | PRO | A | 593 | 20.204 | 105.252 | 29.779 | 1.00 | 20.83 | 6 |
| 4596 | C | PRO | A | 593 | 20.494 | 104.537 | 31.094 | 1.00 | 20.17 | 6 |
| 4597 | O | PRO | A | 593 | 19.811 | 104.784 | 32.102 | 1.00 | 21.50 | 8 |
| 4598 | CB | PRO | A | 593 | 20.715 | 106.727 | 29.941 | 1.00 | 22.70 | 6 |

TABLE 1-continued

Atom Coordinates from the Crystal Structure of NOVAMYL

| | | | | | | | | | | |
|---|---|---|---|---|---|---|---|---|---|---|
| 4599 | CG | PRO | A | 593 | 19.643 | 107.491 | 29.165 | 1.00 | 24.71 | 6 |
| 4600 | CD | PRO | A | 593 | 18.337 | 106.774 | 29.432 | 1.00 | 23.44 | 6 |
| 4601 | N | THR | A | 594 | 21.530 | 103.723 | 31.165 | 1.00 | 19.91 | 7 |
| 4602 | CA | THR | A | 594 | 21.909 | 103.060 | 32.402 | 1.00 | 21.78 | 6 |
| 4603 | C | THR | A | 594 | 23.380 | 103.366 | 32.686 | 1.00 | 23.13 | 6 |
| 4604 | O | THR | A | 594 | 24.138 | 103.737 | 31.787 | 1.00 | 23.96 | 8 |
| 4605 | CB | THR | A | 594 | 21.729 | 101.521 | 32.292 | 1.00 | 23.27 | 6 |
| 4606 | OG1 | THR | A | 594 | 22.466 | 101.094 | 31.140 | 1.00 | 20.06 | 8 |
| 4607 | CG2 | THR | A | 594 | 20.245 | 101.183 | 32.157 | 1.00 | 21.33 | 6 |
| 4608 | N | ASN | A | 595 | 23.764 | 103.210 | 33.928 | 1.00 | 23.96 | 7 |
| 4609 | CA | ASN | A | 595 | 25.142 | 103.193 | 34.370 | 1.00 | 28.93 | 6 |
| 4610 | C | ASN | A | 595 | 25.614 | 101.791 | 34.716 | 1.00 | 31.88 | 6 |
| 4611 | O | ASN | A | 595 | 24.847 | 100.849 | 34.915 | 1.00 | 22.74 | 8 |
| 4612 | CB | ASN | A | 595 | 25.285 | 104.099 | 35.620 | 1.00 | 34.82 | 6 |
| 4613 | CG | ASN | A | 595 | 24.970 | 105.532 | 35.180 | 1.00 | 36.76 | 6 |
| 4614 | OD1 | ASN | A | 595 | 24.047 | 106.190 | 35.647 | 1.00 | 42.57 | 8 |
| 4615 | ND2 | ASN | A | 595 | 25.738 | 106.004 | 34.208 | 1.00 | 38.16 | 7 |
| 4616 | N | LEU | A | 596 | 26.939 | 101.654 | 34.839 | 1.00 | 34.83 | 7 |
| 4617 | CA | LEU | A | 596 | 27.559 | 100.380 | 35.212 | 1.00 | 37.55 | 6 |
| 4618 | C | LEU | A | 596 | 26.947 | 99.803 | 36.488 | 1.00 | 31.76 | 6 |
| 4619 | O | LEU | A | 596 | 26.589 | 100.502 | 37.435 | 1.00 | 35.49 | 8 |
| 4620 | CB | LEU | A | 596 | 29.051 | 100.642 | 35.407 | 1.00 | 48.79 | 6 |
| 4621 | CG | LEU | A | 596 | 30.042 | 99.528 | 35.681 | 1.00 | 52.60 | 6 |
| 4622 | CD1 | LEU | A | 596 | 29.894 | 98.971 | 37.092 | 1.00 | 56.16 | 6 |
| 4623 | CD2 | LEU | A | 596 | 29.934 | 98.433 | 34.628 | 1.00 | 56.63 | 6 |
| 4624 | N | GLY | A | 597 | 26.492 | 98.556 | 36.348 | 1.00 | 30.34 | 7 |
| 4625 | CA | GLY | A | 597 | 25.861 | 97.860 | 37.473 | 1.00 | 30.50 | 6 |
| 4626 | C | GLY | A | 597 | 24.337 | 97.822 | 37.288 | 1.00 | 25.20 | 6 |
| 4627 | O | GLY | A | 597 | 23.705 | 96.996 | 37.949 | 1.00 | 23.57 | 8 |
| 4628 | N | ASP | A | 598 | 23.780 | 98.803 | 36.544 | 1.00 | 21.92 | 7 |
| 4629 | CA | ASP | A | 598 | 22.315 | 98.799 | 36.399 | 1.00 | 18.64 | 6 |
| 4630 | C | ASP | A | 598 | 21.982 | 97.666 | 35.429 | 1.00 | 21.53 | 6 |
| 4631 | O | ASP | A | 598 | 22.702 | 97.563 | 34.399 | 1.00 | 20.69 | 8 |
| 4632 | CB | ASP | A | 598 | 21.814 | 100.096 | 35.763 | 1.00 | 17.61 | 6 |
| 4633 | CG | ASP | A | 598 | 22.046 | 101.382 | 36.536 | 1.00 | 20.17 | 6 |
| 4634 | OD1 | ASP | A | 598 | 22.364 | 101.347 | 37.751 | 1.00 | 19.25 | 8 |
| 4635 | OD2 | ASP | A | 598 | 21.858 | 102.432 | 35.868 | 1.00 | 22.20 | 8 |
| 4636 | N | LYS | A | 599 | 20.861 | 96.919 | 35.612 | 1.00 | 18.66 | 7 |
| 4637 | CA | LYS | A | 599 | 20.593 | 95.891 | 34.605 | 1.00 | 15.76 | 6 |
| 4638 | C | LYS | A | 599 | 19.056 | 95.824 | 34.461 | 1.00 | 11.90 | 6 |
| 4639 | O | LYS | A | 599 | 18.320 | 96.237 | 35.358 | 1.00 | 19.04 | 8 |
| 4640 | CB | LYS | A | 599 | 21.049 | 94.484 | 35.006 | 1.00 | 23.86 | 6 |
| 4641 | CG | LYS | A | 599 | 22.597 | 94.419 | 35.031 | 1.00 | 25.32 | 6 |
| 4642 | CD | LYS | A | 599 | 23.118 | 93.007 | 35.252 | 1.00 | 26.43 | 6 |
| 4643 | CE | LYS | A | 599 | 24.656 | 93.063 | 35.120 | 1.00 | 32.43 | 6 |
| 4644 | NZ | LYS | A | 599 | 25.179 | 91.656 | 35.106 | 1.00 | 35.89 | 7 |
| 4645 | N | ILE | A | 600 | 18.623 | 95.442 | 33.287 | 1.00 | 13.51 | 7 |
| 4646 | CA | ILE | A | 600 | 17.178 | 95.336 | 33.021 | 1.00 | 12.20 | 6 |
| 4647 | C | ILE | A | 600 | 16.746 | 93.886 | 33.130 | 1.00 | 13.74 | 6 |
| 4648 | O | ILE | A | 600 | 17.476 | 92.927 | 32.799 | 1.00 | 14.24 | 8 |
| 4649 | CB | ILE | A | 600 | 16.938 | 95.829 | 31.554 | 1.00 | 13.87 | 6 |
| 4650 | CG1 | ILE | A | 600 | 17.249 | 97.335 | 31.566 | 1.00 | 21.52 | 6 |
| 4651 | CG2 | ILE | A | 600 | 15.499 | 95.618 | 31.051 | 1.00 | 15.85 | 6 |
| 4652 | CD1 | ILE | A | 600 | 16.798 | 98.104 | 30.313 | 1.00 | 23.52 | 6 |
| 4653 | N | TYR | A | 601 | 15.545 | 93.745 | 33.676 | 1.00 | 13.09 | 7 |
| 4654 | CA | TYR | A | 601 | 14.926 | 92.453 | 33.883 | 1.00 | 12.76 | 6 |
| 4655 | C | TYR | A | 601 | 13.531 | 92.475 | 33.288 | 1.00 | 13.27 | 6 |
| 4656 | O | TYR | A | 601 | 12.914 | 93.491 | 32.986 | 1.00 | 15.09 | 8 |
| 4657 | CB | TYR | A | 601 | 14.751 | 92.119 | 35.387 | 1.00 | 14.11 | 6 |
| 4658 | CG | TYR | A | 601 | 16.065 | 91.805 | 36.078 | 1.00 | 11.98 | 6 |
| 4659 | CD1 | TYR | A | 601 | 16.902 | 92.834 | 36.502 | 1.00 | 12.52 | 6 |
| 4660 | CD2 | TYR | A | 601 | 16.473 | 90.490 | 36.242 | 1.00 | 12.95 | 6 |
| 4661 | CE1 | TYR | A | 601 | 18.138 | 92.544 | 37.097 | 1.00 | 13.54 | 6 |
| 4662 | CE2 | TYR | A | 601 | 17.673 | 90.213 | 36.888 | 1.00 | 14.26 | 6 |
| 4663 | CZ | TYR | A | 601 | 18.499 | 91.239 | 37.276 | 1.00 | 15.84 | 6 |
| 4664 | OH | TYR | A | 601 | 19.691 | 90.903 | 37.935 | 1.00 | 16.92 | 8 |
| 4665 | N | LEU | A | 602 | 12.986 | 91.285 | 33.068 | 1.00 | 11.99 | 7 |
| 4666 | CA | LEU | A | 602 | 11.657 | 91.057 | 32.494 | 1.00 | 13.20 | 6 |
| 4667 | C | LEU | A | 602 | 10.762 | 90.434 | 33.580 | 1.00 | 14.26 | 6 |
| 4668 | O | LEU | A | 602 | 11.148 | 89.522 | 34.284 | 1.00 | 13.06 | 8 |
| 4669 | CB | LEU | A | 602 | 11.794 | 90.060 | 31.334 | 1.00 | 13.29 | 6 |
| 4670 | CG | LEU | A | 602 | 10.506 | 89.432 | 30.800 | 1.00 | 10.59 | 6 |
| 4671 | CD1 | LEU | A | 602 | 9.579 | 90.481 | 30.155 | 1.00 | 14.08 | 6 |
| 4672 | CD2 | LEU | A | 602 | 10.864 | 88.385 | 29.704 | 1.00 | 11.83 | 6 |
| 4673 | N | THR | A | 603 | 9.482 | 90.861 | 33.649 | 1.00 | 12.02 | 7 |
| 4674 | CA | THR | A | 603 | 8.570 | 90.233 | 34.635 | 1.00 | 12.81 | 6 |
| 4675 | C | THR | A | 603 | 7.158 | 90.267 | 34.066 | 1.00 | 12.50 | 6 |

TABLE 1-continued

Atom Coordinates from the Crystal Structure of NOVAMYL

| 4676 | O | THR | A | 603 | 6.876 | 91.096 | 33.183 | 1.00 | 14.59 | 8 |
|---|---|---|---|---|---|---|---|---|---|---|
| 4677 | CB | THR | A | 603 | 8.711 | 90.983 | 35.969 | 1.00 | 14.38 | 6 |
| 4678 | OG1 | THR | A | 603 | 7.971 | 90.241 | 36.987 | 1.00 | 14.53 | 8 |
| 4679 | CG2 | THR | A | 603 | 8.152 | 92.414 | 35.971 | 1.00 | 15.35 | 6 |
| 4680 | N | GLY | A | 604 | 6.310 | 89.331 | 34.489 | 1.00 | 11.51 | 7 |
| 4681 | CA | GLY | A | 604 | 4.995 | 89.274 | 33.787 | 1.00 | 11.82 | 6 |
| 4682 | C | GLY | A | 604 | 4.042 | 88.348 | 34.530 | 1.00 | 12.03 | 6 |
| 4683 | O | GLY | A | 604 | 4.358 | 87.909 | 35.636 | 1.00 | 13.68 | 8 |
| 4684 | N | ASN | A | 605 | 2.911 | 88.082 | 33.859 | 1.00 | 12.03 | 7 |
| 4685 | CA | ASN | A | 605 | 1.782 | 87.516 | 34.637 | 1.00 | 11.85 | 6 |
| 4686 | C | ASN | A | 605 | 1.680 | 86.017 | 34.575 | 1.00 | 12.50 | 6 |
| 4687 | O | ASN | A | 605 | 0.615 | 85.441 | 34.625 | 1.00 | 14.07 | 8 |
| 4688 | CB | ASN | A | 605 | 0.481 | 88.161 | 34.031 | 1.00 | 13.77 | 6 |
| 4689 | CG | ASN | A | 605 | 0.265 | 87.610 | 32.629 | 1.00 | 17.19 | 6 |
| 4690 | OD1 | ASN | A | 605 | 1.080 | 87.101 | 31.828 | 1.00 | 13.63 | 8 |
| 4691 | ND1 | ASN | A | 605 | −1.025 | 87.681 | 32.165 | 1.00 | 16.36 | 7 |
| 4692 | N | ILE | A | 606 | 2.823 | 85.308 | 34.560 | 1.00 | 13.26 | 7 |
| 4693 | CA | ILE | A | 606 | 2.836 | 83.860 | 34.628 | 1.00 | 11.73 | 6 |
| 4694 | C | ILE | A | 606 | 4.099 | 83.493 | 35.448 | 1.00 | 13.02 | 6 |
| 4695 | O | ILE | A | 606 | 5.005 | 84.349 | 35.511 | 1.00 | 13.34 | 8 |
| 4696 | CB | ILE | A | 606 | 2.995 | 83.184 | 33.259 | 1.00 | 11.81 | 6 |
| 4697 | CG1 | ILE | A | 606 | 4.029 | 83.874 | 32.346 | 1.00 | 12.94 | 6 |
| 4698 | CG2 | ILE | A | 606 | 1.625 | 83.138 | 32.550 | 1.00 | 15.56 | 6 |
| 4699 | CD1 | ILE | A | 606 | 4.300 | 82.981 | 31.113 | 1.00 | 15.13 | 6 |
| 4700 | N | PRO | A | 607 | 4.181 | 82.331 | 36.033 | 1.00 | 13.09 | 7 |
| 4701 | CA | PRO | A | 607 | 5.294 | 81.982 | 36.937 | 1.00 | 12.68 | 6 |
| 4702 | C | PRO | A | 607 | 6.616 | 81.880 | 36.189 | 1.00 | 10.98 | 6 |
| 4703 | O | PRO | A | 607 | 7.700 | 82.258 | 36.671 | 1.00 | 14.73 | 8 |
| 4704 | CB | PRO | A | 607 | 4.895 | 80.647 | 37.607 | 1.00 | 13.69 | 6 |
| 4705 | CG | PRO | A | 607 | 3.818 | 80.118 | 36.675 | 1.00 | 16.48 | 6 |
| 4706 | CD | PRO | A | 607 | 3.081 | 81.335 | 36.098 | 1.00 | 16.43 | 6 |
| 4707 | N | GLU | A | 608 | 6.531 | 81.525 | 34.880 | 1.00 | 11.74 | 7 |
| 4708 | CA | GLU | A | 608 | 7.747 | 81.559 | 34.031 | 1.00 | 10.58 | 6 |
| 4709 | C | GLU | A | 608 | 8.382 | 82.958 | 33.994 | 1.00 | 13.60 | 6 |
| 4710 | O | GLU | A | 608 | 9.606 | 83.060 | 33.731 | 1.00 | 11.79 | 8 |
| 4711 | CB | GLU | A | 608 | 7.437 | 81.056 | 32.616 | 1.00 | 11.09 | 6 |
| 4712 | CG | GLU | A | 608 | 7.145 | 79.550 | 32.522 | 1.00 | 10.94 | 6 |
| 4713 | CD | GLU | A | 608 | 5.674 | 79.163 | 32.699 | 1.00 | 14.31 | 6 |
| 4714 | OE1 | GLU | A | 608 | 4.875 | 79.973 | 33.221 | 1.00 | 12.87 | 8 |
| 4715 | OE1 | GLU | A | 608 | 5.344 | 78.040 | 32.280 | 1.00 | 13.22 | 8 |
| 4716 | N | LEU | A | 609 | 7.571 | 83.999 | 34.112 | 1.00 | 11.31 | 7 |
| 4717 | CA | LEU | A | 609 | 8.093 | 85.359 | 34.095 | 1.00 | 11.00 | 6 |
| 4718 | C | LEU | A | 609 | 7.944 | 86.002 | 35.453 | 1.00 | 12.01 | 6 |
| 4719 | O | LEU | A | 609 | 7.959 | 87.224 | 35.602 | 1.00 | 14.24 | 8 |
| 4720 | CB | LEU | A | 609 | 7.249 | 86.188 | 33.078 | 1.00 | 14.30 | 6 |
| 4721 | CG | LEU | A | 609 | 7.424 | 85.668 | 31.627 | 1.00 | 13.57 | 6 |
| 4722 | CD1 | LEU | A | 609 | 6.672 | 86.643 | 30.695 | 1.00 | 18.28 | 6 |
| 4723 | CD2 | LEU | A | 609 | 8.912 | 85.648 | 31.238 | 1.00 | 14.71 | 6 |
| 4724 | N | GLY | A | 610 | 7.854 | 85.194 | 36.525 | 1.00 | 10.78 | 7 |
| 4725 | CA | GLY | A | 610 | 7.950 | 85.729 | 37.864 | 1.00 | 10.94 | 6 |
| 4726 | C | GLY | A | 610 | 6.664 | 86.230 | 38.554 | 1.00 | 13.37 | 6 |
| 4727 | O | GLY | A | 610 | 6.767 | 86.832 | 39.647 | 1.00 | 13.90 | 8 |
| 4728 | N | ASN | A | 611 | 5.525 | 86.174 | 37.906 | 1.00 | 13.56 | 7 |
| 4729 | CA | ASN | A | 611 | 4.262 | 86.696 | 38.463 | 1.00 | 14.13 | 6 |
| 4730 | C | ASN | A | 611 | 4.462 | 88.079 | 39.072 | 1.00 | 13.68 | 6 |
| 4731 | O | ASN | A | 611 | 4.063 | 88.427 | 40.207 | 1.00 | 14.78 | 8 |
| 4732 | CB | ASN | A | 611 | 3.695 | 85.782 | 39.555 | 1.00 | 13.73 | 6 |
| 4733 | CG | ASN | A | 611 | 3.110 | 84.538 | 38.890 | 1.00 | 16.98 | 6 |
| 4734 | OD1 | ASN | A | 611 | 2.353 | 84.585 | 37.897 | 1.00 | 17.26 | 8 |
| 4735 | ND2 | ASN | A | 611 | 3.501 | 83.420 | 39.478 | 1.00 | 16.08 | 7 |
| 4736 | N | TRP | A | 612 | 5.010 | 88.962 | 38.242 | 1.00 | 13.00 | 7 |
| 4737 | CA | TRP | A | 612 | 5.298 | 90.339 | 38.534 | 1.00 | 13.35 | 6 |
| 4738 | C | TRP | A | 612 | 6.284 | 90.676 | 39.608 | 1.00 | 14.25 | 6 |
| 4739 | O | TRP | A | 612 | 6.420 | 91.775 | 40.107 | 1.00 | 15.26 | 8 |
| 4740 | CB | TRP | A | 612 | 3.915 | 91.044 | 38.832 | 1.00 | 13.65 | 6 |
| 4741 | CG | TRP | A | 612 | 2.965 | 91.036 | 37.664 | 1.00 | 13.25 | 6 |
| 4742 | CD1 | TRP | A | 612 | 1.775 | 90.359 | 37.632 | 1.00 | 13.84 | 6 |
| 4743 | CD2 | TRP | A | 612 | 3.138 | 91.564 | 36.359 | 1.00 | 14.07 | 6 |
| 4744 | NE1 | TRP | A | 612 | 1.160 | 90.489 | 36.402 | 1.00 | 13.90 | 7 |
| 4745 | CE2 | TRP | A | 612 | 1.983 | 91.288 | 35.617 | 1.00 | 16.64 | 6 |
| 4746 | CE3 | TRP | A | 612 | 4.148 | 92.402 | 35.815 | 1.00 | 15.91 | 6 |
| 4747 | CZ2 | TRP | A | 612 | 1.843 | 91.676 | 34.288 | 1.00 | 14.35 | 6 |
| 4748 | CZ3 | TRP | A | 612 | 3.980 | 92.856 | 34.506 | 1.00 | 14.55 | 6 |
| 4749 | CH2 | TRP | A | 612 | 2.844 | 92.490 | 33.747 | 1.00 | 14.05 | 6 |
| 4750 | N | SER | A | 613 | 7.114 | 89.674 | 40.049 | 1.00 | 14.59 | 7 |
| 4751 | CA | SER | A | 613 | 8.136 | 89.943 | 41.025 | 1.00 | 16.76 | 6 |
| 4752 | C | SER | A | 613 | 9.171 | 90.916 | 40.471 | 1.00 | 15.94 | 6 |

TABLE 1-continued

Atom Coordinates from the Crystal Structure of NOVAMYL

| 4753 | O | SER | A | 613 | 9.510 | 90.841 | 39.281 | 1.00 | 15.44 | 8 |
|---|---|---|---|---|---|---|---|---|---|---|
| 4754 | CB | SER | A | 613 | 8.804 | 88.572 | 41.315 | 1.00 | 14.15 | 6 |
| 4755 | OG | SER | A | 613 | 9.842 | 88.719 | 42.250 | 1.00 | 15.35 | 8 |
| 4756 | N | THR | A | 614 | 9.821 | 91.648 | 41.406 | 1.00 | 13.40 | 7 |
| 4757 | CA | THR | A | 614 | 11.021 | 92.394 | 41.037 | 1.00 | 13.18 | 6 |
| 4758 | C | THR | A | 614 | 12.238 | 91.869 | 41.796 | 1.00 | 12.85 | 6 |
| 4759 | O | THR | A | 614 | 13.311 | 92.464 | 41.777 | 1.00 | 15.88 | 8 |
| 4760 | CB | THR | A | 614 | 10.895 | 93.904 | 41.297 | 1.00 | 16.41 | 6 |
| 4761 | OG1 | THR | A | 614 | 10.626 | 94.073 | 42.724 | 1.00 | 18.07 | 8 |
| 4762 | CG2 | THR | A | 614 | 9.718 | 94.523 | 40.520 | 1.00 | 18.09 | 6 |
| 4763 | N | ASP | A | 615 | 12.033 | 90.680 | 42.425 | 1.00 | 13.65 | 7 |
| 4764 | CA | ASP | A | 615 | 13.138 | 90.024 | 43.143 | 1.00 | 15.24 | 6 |
| 4765 | C | ASP | A | 615 | 14.084 | 89.416 | 42.093 | 1.00 | 12.74 | 6 |
| 4766 | O | ASP | A | 615 | 13.582 | 88.794 | 41.143 | 1.00 | 13.71 | 8 |
| 4767 | CB | ASP | A | 615 | 12.511 | 88.981 | 44.075 | 1.00 | 14.77 | 6 |
| 4768 | CG | ASP | A | 615 | 13.634 | 88.423 | 44.970 | 1.00 | 21.15 | 6 |
| 4769 | OD1 | ASP | A | 615 | 13.956 | 88.932 | 46.048 | 1.00 | 23.65 | 8 |
| 4770 | OD2 | ASP | A | 615 | 14.204 | 87.431 | 44.586 | 1.00 | 18.42 | 8 |
| 4771 | N | THR | A | 616 | 15.390 | 89.536 | 42.350 | 1.00 | 12.77 | 7 |
| 4772 | CA | THR | A | 616 | 16.387 | 89.067 | 41.365 | 1.00 | 13.57 | 6 |
| 4773 | C | THR | A | 616 | 17.391 | 88.146 | 42.072 | 1.00 | 15.88 | 6 |
| 4774 | O | THR | A | 616 | 18.487 | 87.902 | 41.566 | 1.00 | 14.89 | 8 |
| 4775 | CB | THR | A | 616 | 17.144 | 90.224 | 40.674 | 1.00 | 14.32 | 6 |
| 4776 | OG1 | THR | A | 616 | 17.752 | 91.045 | 41.713 | 1.00 | 15.99 | 8 |
| 4777 | CG2 | THR | A | 616 | 16.189 | 91.128 | 39.884 | 1.00 | 16.33 | 6 |
| 4778 | N | SER | A | 617 | 16.981 | 87.590 | 43.216 | 1.00 | 13.15 | 7 |
| 4779 | CA | SER | A | 617 | 17.813 | 86.641 | 43.956 | 1.00 | 12.49 | 6 |
| 4780 | C | SER | A | 617 | 17.759 | 85.265 | 43.312 | 1.00 | 13.68 | 6 |
| 4781 | O | SER | A | 617 | 17.193 | 85.034 | 42.235 | 1.00 | 12.79 | 8 |
| 4782 | CB | SER | A | 617 | 17.271 | 86.583 | 45.396 | 1.00 | 14.38 | 6 |
| 4783 | OG | SER | A | 617 | 16.056 | 85.882 | 45.441 | 1.00 | 15.10 | 8 |
| 4784 | N | GLY | A | 618 | 18.327 | 84.268 | 44.080 | 1.00 | 15.05 | 7 |
| 4785 | CA | GLY | A | 618 | 18.300 | 82.869 | 43.621 | 1.00 | 13.01 | 6 |
| 4786 | C | GLY | A | 618 | 16.967 | 82.147 | 43.811 | 1.00 | 13.49 | 6 |
| 4787 | O | GLY | A | 618 | 16.835 | 80.938 | 43.552 | 1.00 | 15.47 | 8 |
| 4788 | N | ALA | A | 619 | 15.893 | 82.847 | 44.200 | 1.00 | 13.99 | 7 |
| 4789 | CA | ALA | A | 619 | 14.592 | 82.218 | 44.333 | 1.00 | 14.93 | 6 |
| 4790 | C | ALA | A | 619 | 14.033 | 81.691 | 43.015 | 1.00 | 15.28 | 6 |
| 4791 | O | ALA | A | 619 | 14.489 | 82.043 | 41.907 | 1.00 | 15.28 | 8 |
| 4792 | CB | ALA | A | 619 | 13.582 | 83.263 | 44.854 | 1.00 | 17.52 | 6 |
| 4793 | N | VAL | A | 620 | 13.043 | 80.805 | 43.172 | 1.00 | 11.74 | 7 |
| 4794 | CA | VAL | A | 620 | 12.419 | 80.230 | 41.967 | 1.00 | 12.25 | 6 |
| 4795 | C | VAL | A | 620 | 11.259 | 81.126 | 41.502 | 1.00 | 12.14 | 6 |
| 4796 | O | VAL | A | 620 | 10.533 | 81.679 | 42.344 | 1.00 | 14.38 | 8 |
| 4797 | CB | VAL | A | 620 | 11.796 | 78.892 | 42.436 | 1.00 | 15.46 | 6 |
| 4798 | CG1 | VAL | A | 620 | 11.242 | 78.231 | 41.173 | 1.00 | 13.86 | 6 |
| 4799 | CG2 | VAL | A | 620 | 12.924 | 77.941 | 42.923 | 1.00 | 15.04 | 6 |
| 4800 | N | ASN | A | 621 | 11.157 | 81.254 | 40.168 | 1.00 | 12.23 | 7 |
| 4801 | CA | ASN | A | 621 | 10.066 | 82.044 | 39.571 | 1.00 | 12.45 | 6 |
| 4802 | C | ASN | A | 621 | 9.968 | 83.484 | 40.032 | 1.00 | 12.62 | 6 |
| 4803 | O | ASN | A | 621 | 8.860 | 83.896 | 40.480 | 1.00 | 12.87 | 8 |
| 4804 | CB | ASN | A | 621 | 8.676 | 81.346 | 39.732 | 1.00 | 10.99 | 6 |
| 4805 | CG | ASN | A | 621 | 8.656 | 79.972 | 39.084 | 1.00 | 11.13 | 6 |
| 4806 | OD1 | ASN | A | 621 | 9.398 | 79.689 | 38.141 | 1.00 | 13.90 | 8 |
| 4807 | ND2 | ASN | A | 621 | 7.742 | 79.105 | 39.596 | 1.00 | 13.32 | 7 |
| 4808 | N | ASN | A | 622 | 11.106 | 84.199 | 40.048 | 1.00 | 13.97 | 7 |
| 4809 | CA | ASN | A | 622 | 11.116 | 85.623 | 40.322 | 1.00 | 11.35 | 6 |
| 4810 | C | ASN | A | 622 | 11.418 | 86.389 | 39.037 | 1.00 | 12.47 | 6 |
| 4811 | O | ASN | A | 622 | 11.090 | 85.862 | 37.960 | 1.00 | 12.66 | 8 |
| 4812 | CB | ASN | A | 622 | 12.073 | 85.956 | 41.471 | 1.00 | 12.54 | 6 |
| 4813 | CG | ASN | A | 622 | 13.543 | 85.545 | 41.151 | 1.00 | 12.82 | 6 |
| 4814 | OD1 | ASN | A | 622 | 13.811 | 85.093 | 40.044 | 1.00 | 12.70 | 8 |
| 4815 | ND2 | ASN | A | 622 | 14.377 | 85.753 | 42.196 | 1.00 | 13.72 | 7 |
| 4816 | N | ALA | A | 623 | 11.883 | 87.626 | 39.098 | 1.00 | 11.27 | 7 |
| 4817 | CA | ALA | A | 623 | 12.088 | 88.339 | 37.812 | 1.00 | 12.38 | 6 |
| 4818 | C | ALA | A | 623 | 13.107 | 87.592 | 36.947 | 1.00 | 13.25 | 6 |
| 4819 | O | ALA | A | 623 | 14.035 | 87.018 | 37.469 | 1.00 | 13.43 | 8 |
| 4820 | CB | ALA | A | 623 | 12.586 | 89.748 | 38.120 | 1.00 | 14.46 | 6 |
| 4821 | N | GLN | A | 624 | 12.905 | 87.740 | 35.631 | 1.00 | 12.11 | 7 |
| 4822 | CA | GLN | A | 624 | 13.742 | 87.034 | 34.660 | 1.00 | 11.87 | 6 |
| 4823 | C | GLN | A | 624 | 14.828 | 89.912 | 34.071 | 1.00 | 12.70 | 6 |
| 4824 | O | GLN | A | 624 | 14.646 | 89.092 | 33.762 | 1.00 | 13.14 | 8 |
| 4825 | CB | GLN | A | 624 | 12.880 | 86.477 | 33.521 | 1.00 | 14.55 | 6 |
| 4826 | CG | GLN | A | 624 | 11.779 | 85.492 | 34.084 | 1.00 | 13.33 | 6 |
| 4827 | CD | GLN | A | 624 | 12.451 | 84.323 | 34.754 | 1.00 | 14.35 | 6 |
| 4828 | OE1 | GLN | A | 624 | 13.213 | 83.546 | 34.096 | 1.00 | 15.81 | 8 |
| 4829 | NE2 | GLN | A | 634 | 12.268 | 84.078 | 36.040 | 1.00 | 14.08 | 7 |

TABLE 1-continued

Atom Coordinates from the Crystal Structure of NOVAMYL

| 4830 | N | GLY | A | 625 | 15.989 | 87.264 | 33.941 | 1.00 | 12.93 | 7 |
|---|---|---|---|---|---|---|---|---|---|---|
| 4831 | CA | GLY | A | 625 | 17.183 | 87.950 | 33.418 | 1.00 | 12.61 | 6 |
| 4832 | C | GLY | A | 625 | 18.392 | 87.917 | 34.310 | 1.00 | 12.24 | 6 |
| 4833 | O | GLY | A | 625 | 18.497 | 86.888 | 34.934 | 1.00 | 13.82 | 8 |
| 4834 | N | PRO | A | 626 | 19.296 | 88.815 | 34.131 | 1.00 | 12.81 | 7 |
| 4835 | CA | PRO | A | 626 | 19.237 | 90.097 | 33.510 | 1.00 | 15.64 | 6 |
| 4836 | C | PRO | A | 626 | 19.288 | 89.998 | 32.003 | 1.00 | 15.42 | 6 |
| 4837 | O | PRO | A | 626 | 19.675 | 88.992 | 31.364 | 1.00 | 15.65 | 8 |
| 4838 | CB | PRO | A | 626 | 20.374 | 91.012 | 34.019 | 1.00 | 15.71 | 6 |
| 4839 | CG | PRO | A | 626 | 21.401 | 89.927 | 34.320 | 1.00 | 14.63 | 6 |
| 4840 | CD | PRO | A | 626 | 20.565 | 88.780 | 34.858 | 1.00 | 13.83 | 6 |
| 4841 | N | LEU | A | 627 | 18.725 | 91.061 | 31.332 | 1.00 | 13.98 | 7 |
| 4842 | CA | LEU | A | 627 | 18.935 | 91.116 | 29.881 | 1.00 | 13.16 | 6 |
| 4843 | C | LEU | A | 627 | 20.364 | 91.609 | 29.649 | 1.00 | 14.14 | 6 |
| 4844 | O | LEU | A | 627 | 21.024 | 92.215 | 30.527 | 1.00 | 14.86 | 8 |
| 4845 | CB | LEU | A | 627 | 17.906 | 92.080 | 29.214 | 1.00 | 13.73 | 6 |
| 4846 | CG | LEU | A | 627 | 16.549 | 91.433 | 28.919 | 1.00 | 13.68 | 6 |
| 4847 | CD1 | LEU | A | 627 | 15.771 | 91.075 | 30.200 | 1.00 | 16.08 | 6 |
| 4848 | CD2 | LEU | A | 627 | 15.630 | 92.370 | 28.084 | 1.00 | 16.33 | 6 |
| 4849 | N | LEU | A | 628 | 20.804 | 91.374 | 28.421 | 1.00 | 12.55 | 7 |
| 4850 | CA | LEU | A | 628 | 22.139 | 91.805 | 27.919 | 1.00 | 12.76 | 6 |
| 4851 | C | LEU | A | 628 | 21.994 | 92.999 | 26.973 | 1.00 | 15.67 | 6 |
| 4852 | O | LEU | A | 628 | 20.910 | 93.197 | 26.394 | 1.00 | 14.76 | 8 |
| 4853 | CB | LEU | A | 628 | 22.746 | 90.663 | 27.111 | 1.00 | 14.06 | 6 |
| 4854 | CG | LEU | A | 628 | 22.848 | 89.332 | 27.886 | 1.00 | 14.72 | 6 |
| 4855 | CD1 | LEU | A | 628 | 23.526 | 88.239 | 27.056 | 1.00 | 12.14 | 6 |
| 4856 | CD2 | LEU | A | 628 | 23.659 | 89.508 | 29.185 | 1.00 | 20.12 | 6 |
| 4857 | N | ALA | A | 629 | 23.117 | 93.699 | 26.702 | 1.00 | 16.33 | 7 |
| 4858 | CA | ALA | A | 629 | 22.871 | 94.875 | 25.787 | 1.00 | 16.83 | 6 |
| 4859 | C | ALA | A | 629 | 23.983 | 95.083 | 24.795 | 1.00 | 15.77 | 6 |
| 4860 | O | ALA | A | 629 | 24.610 | 96.177 | 24.707 | 1.00 | 15.92 | 8 |
| 4861 | CB | ALA | A | 629 | 22.674 | 96.098 | 26.674 | 1.00 | 19.56 | 6 |
| 4862 | N | PRO | A | 630 | 24.278 | 94.136 | 23.970 | 1.00 | 16.96 | 7 |
| 4863 | CA | PRO | A | 630 | 25.237 | 94.281 | 22.873 | 1.00 | 19.28 | 6 |
| 4864 | C | PRO | A | 630 | 24.773 | 95.400 | 21.940 | 1.00 | 21.06 | 6 |
| 4865 | O | PRO | A | 630 | 25.633 | 96.015 | 21.314 | 1.00 | 23.58 | 8 |
| 4866 | CB | PRO | A | 630 | 25.314 | 92.944 | 22.123 | 1.00 | 17.59 | 6 |
| 4867 | CG | PRO | A | 630 | 23.928 | 92.367 | 22.442 | 1.00 | 18.42 | 6 |
| 4868 | CD | PRO | A | 630 | 23.644 | 92.807 | 23.877 | 1.00 | 18.05 | 6 |
| 4869 | N | ASN | A | 631 | 23.464 | 95.562 | 21.768 | 1.00 | 17.93 | 7 |
| 4870 | CA | ASN | A | 631 | 22.935 | 96.635 | 20.926 | 1.00 | 17.58 | 6 |
| 4871 | C | ASN | A | 631 | 22.382 | 97.779 | 21.748 | 1.00 | 17.45 | 6 |
| 4872 | O | ASN | A | 631 | 21.359 | 98.370 | 21.354 | 1.00 | 18.41 | 8 |
| 4873 | CB | ASN | A | 631 | 21.902 | 96.082 | 19.950 | 1.00 | 18.61 | 6 |
| 4874 | CG | ASN | A | 631 | 22.400 | 94.876 | 19.161 | 1.00 | 28.21 | 6 |
| 4875 | OD1 | ASN | A | 631 | 21.838 | 93.764 | 19.168 | 1.00 | 27.73 | 8 |
| 4876 | ND2 | ASN | A | 631 | 23.476 | 95.224 | 18.455 | 1.00 | 19.54 | 7 |
| 4877 | N | TYR | A | 632 | 22.980 | 98.110 | 22.883 | 1.00 | 16.27 | 7 |
| 4878 | CA | TYR | A | 632 | 22.570 | 99.229 | 23.700 | 1.00 | 17.84 | 6 |
| 4879 | C | TYR | A | 632 | 22.255 | 100.496 | 22.909 | 1.00 | 19.89 | 6 |
| 4880 | O | TYR | A | 632 | 23.030 | 100.672 | 21.982 | 1.00 | 19.89 | 8 |
| 4881 | CB | TYR | A | 632 | 23.749 | 99.537 | 24.643 | 1.00 | 18.23 | 6 |
| 4882 | CG | TYR | A | 632 | 23.520 | 100.604 | 25.654 | 1.00 | 20.78 | 6 |
| 4883 | CD1 | TYR | A | 632 | 22.919 | 100.369 | 26.875 | 1.00 | 20.07 | 6 |
| 4884 | CD2 | TYR | A | 632 | 23.839 | 101.933 | 25.333 | 1.00 | 22.98 | 6 |
| 4885 | CE1 | TYR | A | 632 | 22.700 | 101.367 | 27.797 | 1.00 | 22.62 | 6 |
| 4886 | CE2 | TYR | A | 632 | 23.578 | 102.953 | 26.223 | 1.00 | 23.64 | 6 |
| 4887 | CZ | TYR | A | 632 | 23.051 | 102.671 | 27.457 | 1.00 | 27.32 | 6 |
| 4888 | OH | TYR | A | 632 | 22.814 | 103.670 | 28.369 | 1.00 | 23.27 | 8 |
| 4889 | N | PRO | A | 633 | 21.113 | 101.067 | 23.157 | 1.00 | 19.06 | 7 |
| 4890 | CA | PRO | A | 633 | 20.194 | 101.103 | 24.225 | 1.00 | 16.58 | 6 |
| 4891 | C | PRO | A | 633 | 19.087 | 100.033 | 24.123 | 1.00 | 15.76 | 6 |
| 4892 | O | PRO | A | 633 | 18.188 | 100.153 | 24.954 | 1.00 | 16.24 | 8 |
| 4893 | CB | PRO | A | 633 | 19.474 | 102.498 | 24.311 | 1.00 | 19.94 | 6 |
| 4894 | CG | PRO | A | 633 | 19.449 | 102.810 | 22.846 | 1.00 | 24.00 | 6 |
| 4895 | CD | PRO | A | 633 | 20.772 | 102.271 | 22.369 | 1.00 | 24.76 | 6 |
| 4896 | N | ASP | A | 634 | 19.272 | 99.094 | 23.169 | 1.00 | 16.18 | 7 |
| 4897 | CA | ASP | A | 634 | 18.330 | 97.978 | 23.121 | 1.00 | 16.48 | 6 |
| 4898 | C | ASP | A | 634 | 18.923 | 96.792 | 23.937 | 1.00 | 15.97 | 6 |
| 4899 | O | ASP | A | 634 | 20.153 | 96.671 | 24.058 | 1.00 | 16.27 | 8 |
| 4900 | CB | ASP | A | 634 | 18.133 | 97.402 | 21.731 | 1.00 | 15.05 | 6 |
| 4901 | CG | ASP | A | 634 | 17.626 | 98.434 | 20.695 | 1.00 | 20.07 | 6 |
| 4902 | OD1 | ASP | A | 634 | 17.138 | 99.519 | 21.100 | 1.00 | 17.34 | 8 |
| 4903 | OD2 | ASP | A | 634 | 17.728 | 98.097 | 19.503 | 1.00 | 19.32 | 8 |
| 4904 | N | TRP | A | 635 | 18.009 | 96.147 | 24.656 | 1.00 | 14.45 | 7 |
| 4905 | CA | TRP | A | 635 | 18.413 | 95.017 | 25.510 | 1.00 | 16.15 | 6 |
| 4906 | C | TRP | A | 635 | 17.708 | 93.736 | 25.085 | 1.00 | 13.84 | 6 |

TABLE 1-continued

Atom Coordinates from the Crystal Structure of NOVAMYL

| 4907 | O   | TRP | A | 635 | 16.590 | 93.820 | 24.606 | 1.00 | 13.90 | 8 |
|------|-----|-----|---|-----|--------|--------|--------|------|-------|---|
| 4908 | CB  | TRP | A | 635 | 18.024 | 95.299 | 26.962 | 1.00 | 15.52 | 6 |
| 4909 | CG  | TRP | A | 635 | 18.818 | 96.421 | 27.587 | 1.00 | 14.07 | 6 |
| 4910 | CD1 | TRP | A | 635 | 18.737 | 97.739 | 27.178 | 1.00 | 14.13 | 6 |
| 4911 | CD2 | TRP | A | 635 | 19.713 | 96.407 | 28.694 | 1.00 | 16.17 | 6 |
| 4912 | NE1 | TRP | A | 635 | 19.561 | 98.533 | 27.989 | 1.00 | 15.61 | 7 |
| 4913 | CE2 | TRP | A | 635 | 20.179 | 97.706 | 28.908 | 1.00 | 17.77 | 6 |
| 4914 | CE3 | TRP | A | 635 | 20.179 | 95.350 | 29.511 | 1.00 | 18.51 | 6 |
| 4915 | CZ2 | TRP | A | 635 | 21.071 | 98.018 | 29.935 | 1.00 | 19.26 | 6 |
| 4916 | CZ3 | TRP | A | 635 | 21.100 | 95.671 | 30.515 | 1.00 | 23.17 | 6 |
| 4917 | CH2 | TRP | A | 635 | 21.514 | 96.992 | 30.735 | 1.00 | 20.92 | 6 |
| 4918 | N   | PHE | A | 636 | 18.294 | 92.561 | 25.372 | 1.00 | 12.41 | 7 |
| 4919 | CA  | PHE | A | 636 | 17.562 | 91.335 | 24.947 | 1.00 | 11.57 | 6 |
| 4920 | C   | PHE | A | 636 | 18.071 | 90.195 | 25.855 | 1.00 | 12.41 | 6 |
| 4921 | O   | PHE | A | 636 | 19.204 | 90.239 | 26.345 | 1.00 | 13.24 | 8 |
| 4922 | CB  | PHE | A | 636 | 17.761 | 90.971 | 23.435 | 1.00 | 12.03 | 6 |
| 4923 | CG  | PHE | A | 636 | 19.030 | 90.118 | 23.261 | 1.00 | 12.15 | 6 |
| 4924 | CD1 | PHE | A | 636 | 20.287 | 90.667 | 23.292 | 1.00 | 17.38 | 6 |
| 4925 | CD2 | PHE | A | 636 | 18.856 | 88.751 | 23.095 | 1.00 | 11.02 | 6 |
| 4926 | CE1 | PHE | A | 636 | 21.417 | 89.860 | 23.207 | 1.00 | 19.56 | 6 |
| 4927 | CE2 | PHE | A | 636 | 19.996 | 87.906 | 22.997 | 1.00 | 12.49 | 6 |
| 4928 | CZ  | PHE | A | 636 | 21.250 | 88.466 | 23.034 | 1.00 | 17.21 | 6 |
| 4929 | N   | TYR | A | 637 | 17.229 | 89.170 | 25.966 | 1.00 | 12.09 | 7 |
| 4930 | CA  | TYR | A | 637 | 17.759 | 87.841 | 26.425 | 1.00 | 12.35 | 6 |
| 4931 | C   | TYR | A | 637 | 16.714 | 86.848 | 25.989 | 1.00 | 12.24 | 6 |
| 4932 | O   | TYR | A | 637 | 15.911 | 87.135 | 25.088 | 1.00 | 12.49 | 8 |
| 4933 | CB  | TYR | A | 637 | 18.183 | 87.770 | 27.903 | 1.00 | 12.77 | 6 |
| 4934 | CG  | TYR | A | 637 | 19.035 | 86.513 | 28.195 | 1.00 | 13.33 | 6 |
| 4935 | CD1 | TYR | A | 637 | 20.253 | 86.244 | 27.548 | 1.00 | 12.60 | 6 |
| 4936 | CD2 | TYR | A | 637 | 18.595 | 85.573 | 29.127 | 1.00 | 10.55 | 6 |
| 4937 | CE1 | TYR | A | 637 | 21.022 | 85.134 | 27.792 | 1.00 | 11.85 | 6 |
| 4938 | CE2 | TYR | A | 637 | 19.321 | 84.424 | 29.387 | 1.00 | 12.60 | 6 |
| 4939 | CZ  | TYR | A | 637 | 20.521 | 84.221 | 28.728 | 1.00 | 11.69 | 6 |
| 4940 | OH  | TYR | A | 637 | 21.255 | 83.073 | 29.016 | 1.00 | 11.85 | 8 |
| 4941 | N   | VAL | A | 638 | 16.857 | 85.565 | 26.379 | 1.00 | 12.66 | 7 |
| 4942 | CA  | VAL | A | 638 | 16.033 | 84.508 | 25.827 | 1.00 | 10.90 | 6 |
| 4943 | C   | VAL | A | 638 | 15.492 | 83.693 | 27.023 | 1.00 | 11.04 | 6 |
| 4944 | O   | VAL | A | 638 | 16.202 | 83.367 | 27.980 | 1.00 | 13.35 | 8 |
| 4945 | CB  | VAL | A | 638 | 16.830 | 83.496 | 24.987 | 1.00 | 12.00 | 6 |
| 4946 | CG1 | VAL | A | 638 | 15.922 | 82.650 | 24.118 | 1.00 | 12.74 | 6 |
| 4947 | CG2 | VAL | A | 638 | 17.799 | 84.300 | 24.074 | 1.00 | 10.59 | 6 |
| 4948 | N   | PHE | A | 639 | 14.137 | 83.517 | 26.957 | 1.00 | 12.77 | 7 |
| 4949 | CA  | PHE | A | 639 | 13.441 | 82.960 | 28.082 | 1.00 | 9.34  | 6 |
| 4950 | C   | PHE | A | 639 | 12.466 | 81.877 | 27.665 | 1.00 | 11.56 | 6 |
| 4951 | O   | PHE | A | 639 | 11.814 | 81.982 | 26.632 | 1.00 | 12.26 | 8 |
| 4952 | CB  | PHE | A | 639 | 12.612 | 84.072 | 28.807 | 1.00 | 11.50 | 6 |
| 4953 | CG  | PHE | A | 639 | 13.498 | 85.209 | 29.322 | 1.00 | 12.29 | 6 |
| 4954 | CD1 | PHE | A | 639 | 14.294 | 85.042 | 30.446 | 1.00 | 11.38 | 6 |
| 4955 | CD2 | PHE | A | 639 | 13.567 | 86.380 | 28.563 | 1.00 | 13.67 | 6 |
| 4956 | CE1 | PHE | A | 639 | 15.176 | 86.094 | 30.829 | 1.00 | 12.05 | 6 |
| 4957 | CE2 | PHE | A | 639 | 14.416 | 87.425 | 28.965 | 1.00 | 13.84 | 6 |
| 4958 | CZ  | PHE | A | 639 | 15.196 | 87.301 | 30.113 | 1.00 | 13.28 | 6 |
| 4959 | N   | SER | A | 640 | 12.323 | 80.913 | 28.609 | 1.00 | 10.61 | 7 |
| 4960 | CA  | SER | A | 640 | 11.376 | 79.833 | 28.360 | 1.00 | 11.72 | 6 |
| 4961 | C   | SER | A | 640 | 10.005 | 80.223 | 28.872 | 1.00 | 11.19 | 6 |
| 4962 | O   | SER | A | 640 | 9.878  | 80.649 | 30.026 | 1.00 | 12.90 | 8 |
| 4963 | CB  | SER | A | 640 | 11.915 | 78.568 | 29.132 | 1.00 | 12.23 | 6 |
| 4964 | OG  | SER | A | 640 | 11.028 | 77.448 | 28.846 | 1.00 | 12.04 | 8 |
| 4965 | N   | VAL | A | 641 | 9.007  | 80.190 | 27.975 | 1.00 | 8.82  | 7 |
| 4966 | CA  | VAL | A | 641 | 7.635  | 80.609 | 28.374 | 1.00 | 11.37 | 6 |
| 4967 | C   | VAL | A | 641 | 6.697  | 79.601 | 27.775 | 1.00 | 11.35 | 6 |
| 4968 | O   | VAL | A | 641 | 7.075  | 78.840 | 26.864 | 1.00 | 10.31 | 8 |
| 4969 | CB  | VAL | A | 641 | 7.286  | 82.019 | 27.760 | 1.00 | 11.50 | 6 |
| 4970 | CG1 | VAL | A | 641 | 8.061  | 83.038 | 28.624 | 1.00 | 13.20 | 6 |
| 4971 | CG2 | VAL | A | 641 | 7.607  | 82.115 | 26.241 | 1.00 | 10.82 | 6 |
| 4972 | N   | PRO | A | 642 | 5.470  | 79.384 | 28.254 | 1.00 | 10.92 | 7 |
| 4973 | CA  | PRO | A | 642 | 4.582  | 78.438 | 27.626 | 1.00 | 11.56 | 6 |
| 4974 | C   | PRO | A | 642 | 4.256  | 78.780 | 26.166 | 1.00 | 10.87 | 6 |
| 4975 | O   | PRO | A | 642 | 4.048  | 79.994 | 25.888 | 1.00 | 12.26 | 8 |
| 4976 | CB  | PRO | A | 642 | 3.295  | 78.524 | 28.529 | 1.00 | 11.37 | 6 |
| 4977 | CG  | PRO | A | 642 | 3.352  | 79.948 | 29.064 | 1.00 | 11.52 | 6 |
| 4978 | CD  | PRO | A | 642 | 4.866  | 80.234 | 29.308 | 1.00 | 14.12 | 6 |
| 4979 | N   | ALA | A | 643 | 4.267  | 77.800 | 25.291 | 1.00 | 11.34 | 7 |
| 4980 | CA  | ALA | A | 643 | 4.033  | 77.992 | 23.839 | 1.00 | 12.12 | 6 |
| 4981 | C   | ALA | A | 643 | 2.531  | 78.215 | 23.567 | 1.00 | 13.78 | 6 |
| 4982 | O   | ALA | A | 643 | 1.681  | 77.650 | 24.236 | 1.00 | 15.31 | 8 |
| 4983 | CB  | ALA | A | 643 | 4.330  | 76.657 | 23.141 | 1.00 | 13.71 | 6 |

TABLE 1-continued

Atom Coordinates from the Crystal Structure of NOVAMYL

| 4984 | N   | GLY | A | 644 | 2.317  | 79.106 | 22.623 | 1.00 | 14.27 | 7 |
|------|-----|-----|---|-----|--------|--------|--------|------|-------|---|
| 4985 | CA  | GLY | A | 644 | 0.952  | 79.377 | 22.150 | 1.00 | 14.42 | 6 |
| 4986 | C   | GLY | A | 644 | 0.065  | 80.108 | 23.133 | 1.00 | 15.94 | 6 |
| 4987 | O   | GLY | A | 644 | −1.154 | 79.765 | 23.178 | 1.00 | 19.30 | 8 |
| 4988 | N   | LYS | A | 645 | 0.597  | 80.884 | 24.030 | 1.00 | 14.60 | 7 |
| 4989 | CA  | LYS | A | 645 | −0.171 | 81.519 | 25.092 | 1.00 | 14.20 | 6 |
| 4990 | C   | LYS | A | 645 | −0.060 | 83.017 | 24.926 | 1.00 | 17.57 | 6 |
| 4991 | O   | LYS | A | 645 | 1.002  | 83.579 | 24.623 | 1.00 | 17.47 | 8 |
| 4992 | CB  | LYS | A | 645 | 0.376  | 81.126 | 26.483 | 1.00 | 14.57 | 6 |
| 4993 | CG  | LYS | A | 645 | 0.313  | 79.611 | 26.725 | 1.00 | 17.45 | 6 |
| 4994 | CD  | LYS | A | 645 | −1.136 | 79.116 | 26.699 | 1.00 | 17.54 | 6 |
| 4995 | CE  | LYS | A | 645 | −1.184 | 77.572 | 26.837 | 1.00 | 21.69 | 6 |
| 4996 | NZ  | LYS | A | 645 | −0.587 | 77.121 | 28.112 | 1.00 | 31.91 | 7 |
| 4997 | N   | THR | A | 646 | −1.157 | 83.717 | 25.357 | 1.00 | 14.42 | 7 |
| 4998 | CA  | THR | A | 646 | −1.090 | 85.140 | 25.434 | 1.00 | 14.66 | 6 |
| 4999 | C   | THR | A | 646 | −0.662 | 85.594 | 26.824 | 1.00 | 13.55 | 6 |
| 5000 | O   | THR | A | 646 | −1.221 | 85.157 | 27.850 | 1.00 | 16.55 | 8 |
| 5001 | CB  | THR | A | 646 | −2.510 | 85.720 | 25.098 | 1.00 | 17.00 | 6 |
| 5002 | OG1 | THR | A | 646 | −2.824 | 85.361 | 23.738 | 1.00 | 16.76 | 8 |
| 5003 | CG2 | THR | A | 646 | −2.463 | 87.240 | 25.195 | 1.00 | 18.18 | 6 |
| 5004 | N   | ILE | A | 647 | 0.360  | 86.434 | 26.913 | 1.00 | 11.81 | 7 |
| 5005 | CA  | ILE | A | 647 | 1.001  | 86.816 | 28.152 | 1.00 | 11.47 | 6 |
| 5006 | C   | ILE | A | 647 | 1.047  | 88.357 | 28.250 | 1.00 | 13.84 | 6 |
| 5007 | O   | ILE | A | 647 | 0.991  | 89.054 | 27.201 | 1.00 | 14.89 | 8 |
| 5008 | CB  | ILE | A | 647 | 2.476  | 86.353 | 28.278 | 1.00 | 13.09 | 6 |
| 5009 | CG1 | ILE | A | 647 | 3.296  | 86.770 | 27.045 | 1.00 | 12.50 | 6 |
| 5010 | CG2 | ILE | A | 647 | 24.10  | 84.817 | 28.343 | 1.00 | 14.24 | 6 |
| 5011 | CD1 | ILE | A | 647 | 4.813  | 86.486 | 27.247 | 1.00 | 17.78 | 6 |
| 5012 | N   | GLN | A | 648 | 1.150  | 88.776 | 29.495 | 1.00 | 12.61 | 7 |
| 5013 | CA  | GLN | A | 648 | 1.402  | 90.212 | 29.726 | 1.00 | 11.91 | 6 |
| 5014 | C   | GLN | A | 648 | 2.687  | 90.407 | 30.490 | 1.00 | 15.15 | 6 |
| 5015 | O   | GLN | A | 648 | 3.041  | 89.586 | 31.338 | 1.00 | 15.89 | 8 |
| 5016 | CB  | GLN | A | 648 | 0.298  | 90.835 | 30.611 | 1.00 | 13.04 | 6 |
| 5017 | CG  | GLN | A | 648 | −1.032 | 90.704 | 29.820 | 1.00 | 20.15 | 6 |
| 5018 | CD  | GLN | A | 648 | −2.040 | 91.727 | 30.260 | 1.00 | 27.13 | 6 |
| 5019 | OE1 | GLN | A | 648 | −1.797 | 92.691 | 30.982 | 1.00 | 23.22 | 8 |
| 5020 | NE2 | GLN | A | 648 | −3.309 | 91.503 | 29.847 | 1.00 | 28.35 | 7 |
| 5021 | N   | PHE | A | 649 | 3.446  | 91.461 | 30.155 | 1.00 | 13.26 | 7 |
| 5022 | CA  | PHE | A | 649 | 4.767  | 91.622 | 30.746 | 1.00 | 12.72 | 6 |
| 5023 | C   | PHE | A | 649 | 5.219  | 93.094 | 30.663 | 1.00 | 14.64 | 6 |
| 5024 | O   | PHE | A | 649 | 4.697  | 93.903 | 29.862 | 1.00 | 14.50 | 8 |
| 5025 | CB  | PHE | A | 649 | 5.812  | 90.743 | 30.051 | 1.00 | 12.47 | 6 |
| 5026 | CG  | PHE | A | 649 | 5.875  | 90.962 | 28.544 | 1.00 | 13.33 | 6 |
| 5027 | CD1 | PHE | A | 649 | 4.996  | 90.400 | 27.682 | 1.00 | 14.84 | 6 |
| 5028 | CD2 | PHE | A | 649 | 6.861  | 91.790 | 28.013 | 1.00 | 13.41 | 6 |
| 5029 | CE1 | PHE | A | 649 | 5.031  | 90.678 | 26.303 | 1.00 | 15.17 | 6 |
| 5030 | CE2 | PHE | A | 649 | 6.977  | 92.043 | 26.666 | 1.00 | 16.16 | 6 |
| 5031 | CZ  | PHE | A | 649 | 6.057  | 91.493 | 25.807 | 1.00 | 13.88 | 6 |
| 5032 | N   | LYS | A | 650 | 6.135  | 93.413 | 31.538 | 1.00 | 13.99 | 7 |
| 5033 | CA  | LYS | A | 650 | 6.876  | 94.683 | 31.405 | 1.00 | 13.18 | 6 |
| 5034 | C   | LYS | A | 650 | 8.349  | 94.411 | 31.797 | 1.00 | 15.87 | 6 |
| 5035 | O   | LYS | A | 650 | 8.696  | 93.364 | 32.375 | 1.00 | 13.96 | 8 |
| 5036 | CB  | LYS | A | 650 | 6.358  | 95.735 | 32.410 | 1.00 | 14.62 | 6 |
| 5037 | CG  | LYS | A | 650 | 5.004  | 96.385 | 31.989 | 1.00 | 15.36 | 6 |
| 5038 | CD  | LYS | A | 650 | 4.922  | 97.604 | 32.979 | 1.00 | 19.44 | 6 |
| 5039 | CE  | LYS | A | 650 | 3.841  | 98.565 | 32.553 | 1.00 | 24.45 | 6 |
| 5040 | NZ  | LYS | A | 650 | 3.898  | 99.741 | 33.515 | 1.00 | 18.41 | 7 |
| 5041 | N   | PHE | A | 651 | 9.172  | 95.398 | 31.438 | 1.00 | 13.40 | 7 |
| 5042 | CA  | PHE | A | 651 | 10.571 | 95.420 | 31.850 | 1.00 | 14.23 | 6 |
| 5043 | C   | PHE | A | 651 | 10.800 | 96.474 | 32.926 | 1.00 | 16.48 | 6 |
| 5044 | O   | PHE | A | 651 | 9.990  | 97.396 | 33.132 | 1.00 | 17.07 | 8 |
| 5045 | CB  | PHE | A | 651 | 11.465 | 95.783 | 30.638 | 1.00 | 12.48 | 6 |
| 5046 | CG  | PHE | A | 651 | 11.280 | 94.796 | 29.512 | 1.00 | 15.91 | 6 |
| 5047 | CD1 | PHE | A | 651 | 10.277 | 94.943 | 28.564 | 1.00 | 13.76 | 6 |
| 5048 | CD2 | PHE | A | 651 | 12.127 | 93.681 | 29.453 | 1.00 | 14.89 | 6 |
| 5049 | CE1 | PHE | A | 651 | 10.114 | 94.016 | 27.568 | 1.00 | 12.48 | 6 |
| 5050 | CE2 | PHE | A | 651 | 11.957 | 92.759 | 28.426 | 1.00 | 13.50 | 6 |
| 5051 | CZ  | PHE | A | 651 | 10.944 | 92.884 | 27.461 | 1.00 | 16.56 | 6 |
| 5052 | N   | PHE | A | 652 | 11.849 | 96.240 | 33.723 | 1.00 | 15.18 | 7 |
| 5053 | CA  | PHE | A | 652 | 12.249 | 97.256 | 34.704 | 1.00 | 14.29 | 6 |
| 5054 | C   | PHE | A | 652 | 13.756 | 97.339 | 34.785 | 1.00 | 17.92 | 6 |
| 5055 | O   | PHE | A | 652 | 14.452 | 96.365 | 34.487 | 1.00 | 15.37 | 8 |
| 5056 | CB  | PHE | A | 652 | 11.634 | 96.950 | 36.084 | 1.00 | 15.14 | 6 |
| 5057 | CG  | PHE | A | 652 | 12.097 | 95.688 | 36.789 | 1.00 | 16.77 | 6 |
| 5058 | CD1 | PHE | A | 652 | 13.251 | 95.685 | 37.565 | 1.00 | 15.74 | 6 |
| 5059 | CD2 | PHE | A | 652 | 11.326 | 94.553 | 36.695 | 1.00 | 15.90 | 6 |
| 5060 | CE1 | PHE | A | 652 | 13.633 | 94.518 | 38.231 | 1.00 | 14.76 | 6 |

TABLE 1-continued

Atom Coordinates from the Crystal Structure of NOVAMYL

| 5061 | CE2 | PHE | A | 652 | 11.695 | 93.407 | 37.380 | 1.00 | 15.19 | 6 |
|---|---|---|---|---|---|---|---|---|---|---|
| 5062 | CZ | PHE | A | 652 | 12.866 | 93.343 | 38.139 | 1.00 | 14.25 | 6 |
| 5063 | N | ILE | A | 653 | 14.244 | 98.512 | 35.189 | 1.00 | 14.94 | 7 |
| 5064 | CA | ILE | A | 653 | 15.705 | 98.598 | 35.463 | 1.00 | 14.72 | 6 |
| 5065 | C | ILE | A | 653 | 15.906 | 98.394 | 36.962 | 1.00 | 18.67 | 6 |
| 5066 | O | ILE | A | 653 | 15.175 | 98.971 | 37.804 | 1.00 | 19.59 | 8 |
| 5067 | CB | ILE | A | 653 | 16.168 | 100.071 | 35.163 | 1.00 | 14.73 | 6 |
| 5068 | CG1 | ILE | A | 653 | 16.000 | 100.337 | 33.693 | 1.00 | 18.74 | 6 |
| 5069 | CG2 | ILE | A | 653 | 17.628 | 100.201 | 35.616 | 1.00 | 18.25 | 6 |
| 5070 | CD1 | ILE | A | 653 | 16.191 | 101.838 | 33.353 | 1.00 | 20.43 | 6 |
| 5071 | N | LYS | A | 654 | 16.847 | 97.524 | 37.282 | 1.00 | 17.58 | 7 |
| 5072 | CA | LYS | A | 654 | 17.273 | 97.382 | 38.690 | 1.00 | 18.28 | 6 |
| 5073 | C | LYS | A | 654 | 18.623 | 98.139 | 38.780 | 1.00 | 15.87 | 6 |
| 5074 | O | LYS | A | 654 | 19.571 | 97.760 | 38.135 | 1.00 | 18.77 | 8 |
| 5075 | CB | LYS | A | 654 | 17.469 | 95.933 | 39.131 | 1.00 | 16.77 | 6 |
| 5076 | CG | LYS | A | 654 | 17.774 | 95.976 | 40.661 | 1.00 | 20.67 | 6 |
| 5077 | CD | LYS | A | 654 | 17.709 | 94.558 | 41.225 | 1.00 | 24.12 | 6 |
| 5078 | CE | LYS | A | 654 | 18.152 | 94.544 | 42.680 | 1.00 | 30.47 | 6 |
| 5079 | NZ | LYS | A | 654 | 17.967 | 93.152 | 43.221 | 1.00 | 39.55 | 7 |
| 5080 | N | ARG | A | 655 | 18.538 | 99.361 | 39.337 | 1.00 | 19.37 | 7 |
| 5081 | CA | ARG | A | 655 | 19.776 | 100.164 | 39.391 | 1.00 | 21.00 | 6 |
| 5082 | C | ARG | A | 655 | 20.820 | 99.478 | 40.256 | 1.00 | 24.58 | 6 |
| 5083 | O | ARG | A | 655 | 20.486 | 98.604 | 41.057 | 1.00 | 22.97 | 8 |
| 5084 | CB | ARG | A | 655 | 19.445 | 101.531 | 40.003 | 1.00 | 18.71 | 6 |
| 5085 | CG | ARG | A | 655 | 18.411 | 102.323 | 39.192 | 1.00 | 19.26 | 6 |
| 5086 | CD | ARG | A | 655 | 19.036 | 102.699 | 37.864 | 1.00 | 24.72 | 6 |
| 5087 | NE | ARG | A | 655 | 18.169 | 103.597 | 37.102 | 1.00 | 23.26 | 7 |
| 5088 | CZ | ARG | A | 655 | 18.428 | 104.073 | 35.883 | 1.00 | 23.74 | 6 |
| 5089 | NH1 | ARG | A | 655 | 19.508 | 103.812 | 35.193 | 1.00 | 20.63 | 7 |
| 5090 | NH2 | ARG | A | 655 | 17.509 | 104.882 | 35.343 | 1.00 | 24.30 | 7 |
| 5091 | N | ALA | A | 656 | 22.090 | 99.900 | 40.135 | 1.00 | 24.51 | 7 |
| 5092 | CA | ALA | A | 656 | 23.170 | 99.305 | 40.898 | 1.00 | 28.24 | 6 |
| 5093 | C | ALA | A | 656 | 22.865 | 99.430 | 42.401 | 1.00 | 27.25 | 6 |
| 5094 | O | ALA | A | 656 | 23.305 | 98.533 | 43.117 | 1.00 | 32.90 | 8 |
| 5095 | CB | ALA | A | 656 | 24.518 | 100.009 | 40.656 | 1.00 | 29.09 | 6 |
| 5096 | N | ASP | A | 657 | 22.145 | 100.427 | 42.856 | 1.00 | 31.34 | 7 |
| 5097 | CA | ASP | A | 657 | 21.850 | 100.561 | 44.282 | 1.00 | 32.95 | 6 |
| 5098 | C | ASP | A | 657 | 20.617 | 99.783 | 44.694 | 1.00 | 33.22 | 6 |
| 5099 | O | ASP | A | 657 | 20.202 | 99.906 | 45.852 | 1.00 | 30.17 | 8 |
| 5100 | CB | ASP | A | 657 | 21.725 | 102.050 | 44.643 | 1.00 | 27.78 | 6 |
| 5101 | CG | ASP | A | 657 | 20.499 | 102.712 | 44.087 | 1.00 | 34.66 | 6 |
| 5102 | OD1 | ASP | A | 657 | 19.665 | 102.035 | 43.431 | 1.00 | 28.22 | 8 |
| 5103 | OD2 | ASP | A | 657 | 20.239 | 103.920 | 44.267 | 1.00 | 33.52 | 8 |
| 5104 | N | GLY | A | 658 | 20.019 | 98.958 | 43.803 | 1.00 | 29.54 | 7 |
| 5105 | CA | GLY | A | 658 | 18.874 | 98.181 | 44.227 | 1.00 | 29.70 | 6 |
| 5106 | C | GLY | A | 658 | 17.543 | 98.837 | 43.931 | 1.00 | 26.81 | 6 |
| 5107 | O | GLY | A | 658 | 16.531 | 98.126 | 43.935 | 1.00 | 30.39 | 8 |
| 5108 | N | THR | A | 659 | 17.502 | 100.106 | 43.566 | 1.00 | 23.52 | 7 |
| 5109 | CA | THR | A | 659 | 16.313 | 100.826 | 43.215 | 1.00 | 25.61 | 6 |
| 5110 | C | THR | A | 659 | 15.641 | 100.184 | 41.985 | 1.00 | 23.40 | 6 |
| 5111 | O | THR | A | 659 | 16.419 | 99.778 | 41.118 | 1.00 | 27.85 | 8 |
| 5112 | CB | THR | A | 659 | 16.614 | 102.279 | 42.717 | 1.00 | 19.42 | 6 |
| 5113 | OG1 | THR | A | 659 | 17.524 | 102.993 | 43.510 | 1.00 | 46.62 | 8 |
| 5114 | CG2 | THR | A | 659 | 15.276 | 103.016 | 42.706 | 1.00 | 37.02 | 6 |
| 5115 | N | ILE | A | 660 | 14.319 | 100.215 | 41.909 | 1.00 | 20.34 | 7 |
| 5116 | CA | ILE | A | 660 | 13.596 | 99.691 | 40.758 | 1.00 | 25.29 | 6 |
| 5117 | C | ILE | A | 660 | 12.933 | 100.761 | 39.919 | 1.00 | 25.57 | 6 |
| 5118 | O | ILE | A | 660 | 12.186 | 101.612 | 40.465 | 1.00 | 27.02 | 8 |
| 5119 | CB | ILE | A | 660 | 12.458 | 98.722 | 41.207 | 1.00 | 26.69 | 6 |
| 5120 | CG1 | ILE | A | 660 | 13.012 | 97.534 | 41.991 | 1.00 | 27.58 | 6 |
| 5121 | CG2 | ILE | A | 660 | 11.704 | 98.273 | 39.972 | 1.00 | 21.18 | 6 |
| 5122 | CD1 | ILE | A | 660 | 14.022 | 96.722 | 41.221 | 1.00 | 24.46 | 6 |
| 5123 | N | GLN | A | 661 | 13.169 | 100.849 | 38.624 | 1.00 | 20.86 | 7 |
| 5124 | CA | GLN | A | 661 | 12.479 | 101.793 | 37.743 | 1.00 | 19.49 | 6 |
| 5125 | C | GLN | A | 661 | 11.720 | 101.014 | 36.669 | 1.00 | 20.02 | 6 |
| 5126 | O | GLN | A | 661 | 12.266 | 100.405 | 35.730 | 1.00 | 19.24 | 8 |
| 5127 | CB | GLN | A | 661 | 13.410 | 102.775 | 37.023 | 1.00 | 20.06 | 6 |
| 5128 | CG | GLN | A | 661 | 12.611 | 103.688 | 36.077 | 1.00 | 21.00 | 6 |
| 5129 | CD | GLN | A | 661 | 13.541 | 104.665 | 35.350 | 1.00 | 21.47 | 6 |
| 5130 | OE1 | GLN | A | 661 | 13.279 | 104.997 | 34.195 | 1.00 | 28.51 | 8 |
| 5131 | NE2 | GLN | A | 661 | 14.578 | 105.095 | 36.040 | 1.00 | 22.67 | 7 |
| 5132 | N | TRP | A | 662 | 10.389 | 100.926 | 36.834 | 1.00 | 20.75 | 7 |
| 5133 | CA | TRP | A | 662 | 9.556 | 100.227 | 35.857 | 1.00 | 18.49 | 6 |
| 5134 | C | TRP | A | 662 | 9.441 | 100.967 | 34.536 | 1.00 | 21.67 | 6 |
| 5135 | O | TRP | A | 662 | 9.412 | 102.230 | 34.565 | 1.00 | 19.29 | 8 |
| 5136 | CB | TRP | A | 662 | 8.152 | 100.082 | 36.437 | 1.00 | 18.81 | 6 |
| 5137 | CG | TRP | A | 662 | 7.960 | 99.114 | 37.551 | 1.00 | 18.39 | 6 |

TABLE 1-continued

Atom Coordinates from the Crystal Structure of NOVAMYL

| 5138 | CD1 | TRP | A | 662 | 8.083 | 99.359 | 38.889 | 1.00 | 19.35 | 6 |
|---|---|---|---|---|---|---|---|---|---|---|
| 5139 | CD2 | TRP | A | 662 | 7.543 | 97.752 | 37.419 | 1.00 | 18.13 | 6 |
| 5140 | NE1 | TRP | A | 662 | 7.781 | 98.218 | 39.608 | 1.00 | 21.46 | 7 |
| 5141 | CE2 | TRP | A | 662 | 7.444 | 97.223 | 38.713 | 1.00 | 18.92 | 6 |
| 5142 | CE3 | TRP | A | 662 | 7.213 | 96.960 | 36.295 | 1.00 | 18.78 | 6 |
| 5143 | CZ2 | TRP | A | 662 | 6.994 | 95.923 | 38.966 | 1.00 | 16.39 | 6 |
| 5144 | CZ3 | TRP | A | 662 | 6.798 | 95.661 | 36.537 | 1.00 | 18.67 | 6 |
| 5145 | CH2 | TRP | A | 662 | 6.725 | 95.156 | 37.854 | 1.00 | 15.44 | 6 |
| 5146 | N | GLU | A | 663 | 9.170 | 100.250 | 33.453 | 1.00 | 18.24 | 7 |
| 5147 | CA | GLU | A | 663 | 8.551 | 100.857 | 32.292 | 1.00 | 17.79 | 6 |
| 5148 | C | GLU | A | 663 | 7.240 | 101.517 | 32.740 | 1.00 | 17.95 | 6 |
| 5149 | O | GLU | A | 663 | 6.519 | 100.973 | 33.574 | 1.00 | 18.49 | 8 |
| 5150 | CB | GLU | A | 663 | 8.001 | 99.880 | 31.232 | 1.00 | 22.54 | 6 |
| 5151 | CG | GLU | A | 663 | 9.065 | 99.526 | 30.195 | 1.00 | 23.03 | 6 |
| 5152 | CD | GLU | A | 663 | 8.380 | 98.560 | 29.223 | 1.00 | 19.52 | 6 |
| 5153 | OE1 | GLU | A | 663 | 8.159 | 97.397 | 29.619 | 1.00 | 17.12 | 8 |
| 5154 | OE2 | GLU | A | 663 | 8.063 | 98.990 | 28.102 | 1.00 | 18.01 | 8 |
| 5155 | N | ASN | A | 664 | 6.892 | 102.576 | 32.027 | 1.00 | 18.62 | 7 |
| 5156 | CA | ASN | A | 664 | 5.604 | 103.189 | 32.365 | 1.00 | 18.27 | 6 |
| 5157 | C | ASN | A | 664 | 4.522 | 102.581 | 31.484 | 1.00 | 20.85 | 6 |
| 5158 | O | ASN | A | 664 | 4.782 | 101.671 | 30.702 | 1.00 | 21.34 | 8 |
| 5159 | CB | ASN | A | 664 | 5.790 | 104.696 | 32.115 | 1.00 | 22.20 | 6 |
| 5160 | CG | ASN | A | 664 | 6.447 | 105.326 | 33.350 | 1.00 | 30.00 | 6 |
| 5161 | OD1 | ASN | A | 664 | 6.281 | 104.932 | 34.519 | 1.00 | 35.11 | 8 |
| 5162 | ND2 | ASN | A | 664 | 7.238 | 106.366 | 33.127 | 1.00 | 33.46 | 7 |
| 5163 | N | GLY | A | 665 | 3.295 | 103.085 | 31.667 | 1.00 | 22.07 | 7 |
| 5164 | CA | GLY | A | 665 | 2.187 | 102.708 | 30.786 | 1.00 | 23.10 | 6 |
| 5165 | C | GLY | A | 665 | 1.557 | 101.363 | 31.102 | 1.00 | 21.34 | 6 |
| 5166 | O | GLY | A | 665 | 1.827 | 100.710 | 32.119 | 1.00 | 22.70 | 8 |
| 5167 | N | SER | A | 666 | 0.832 | 100.839 | 30.093 | 1.00 | 18.43 | 7 |
| 5168 | CA | SER | A | 666 | 0.135 | 99.581 | 30.305 | 1.00 | 17.79 | 6 |
| 5169 | C | SER | A | 666 | 1.084 | 98.403 | 30.046 | 1.00 | 16.94 | 6 |
| 5170 | O | SER | A | 666 | 2.005 | 98.503 | 29.261 | 1.00 | 16.68 | 8 |
| 5171 | CB | SER | A | 666 | −1.037 | 99.440 | 29.297 | 1.00 | 24.19 | 6 |
| 5172 | OG | SER | A | 666 | −1.959 | 100.498 | 29.645 | 1.00 | 24.86 | 8 |
| 5173 | N | ASN | A | 667 | 0.642 | 97.227 | 30.470 | 1.00 | 14.27 | 7 |
| 5174 | CA | ASN | A | 667 | 1.491 | 96.058 | 30.168 | 1.00 | 16.75 | 6 |
| 5175 | C | ASN | A | 667 | 1.575 | 95.824 | 28.678 | 1.00 | 17.00 | 6 |
| 5176 | O | ASN | A | 667 | 0.616 | 96.050 | 27.899 | 1.00 | 15.91 | 8 |
| 5177 | CB | ASN | A | 667 | 0.795 | 94.804 | 30.736 | 1.00 | 16.66 | 6 |
| 5178 | CG | ASN | A | 667 | 0.703 | 94.817 | 32.248 | 1.00 | 19.33 | 6 |
| 5179 | OD1 | ASN | A | 667 | −0.178 | 94.105 | 32.855 | 1.00 | 20.96 | 8 |
| 5180 | ND2 | ASN | A | 667 | 1.594 | 95.513 | 32.887 | 1.00 | 16.21 | 7 |
| 5181 | N | HIS | A | 668 | 2.720 | 95.243 | 28.272 | 1.00 | 13.63 | 7 |
| 5182 | CA | HIS | A | 668 | 2.882 | 94.747 | 26.930 | 1.00 | 15.66 | 6 |
| 5183 | C | HIS | A | 668 | 2.137 | 93.408 | 26.856 | 1.00 | 16.10 | 6 |
| 5184 | O | HIS | A | 668 | 2.048 | 92.666 | 27.847 | 1.00 | 16.87 | 8 |
| 5185 | CB | HIS | A | 668 | 4.327 | 94.431 | 26.491 | 1.00 | 15.51 | 6 |
| 5186 | CG | HIS | A | 668 | 5.208 | 95.653 | 26.519 | 1.00 | 14.13 | 6 |
| 5187 | ND1 | HIS | A | 668 | 5.229 | 96.451 | 25.375 | 1.00 | 15.75 | 7 |
| 5188 | CD2 | HIS | A | 668 | 6.066 | 96.158 | 27.410 | 1.00 | 17.00 | 6 |
| 5189 | CE1 | HIS | A | 668 | 6.108 | 97.464 | 25.592 | 1.00 | 14.21 | 6 |
| 5190 | NE2 | HIS | A | 668 | 6.581 | 97.305 | 26.830 | 1.00 | 15.51 | 7 |
| 5191 | N | VAL | A | 669 | 1.434 | 93.208 | 25.734 | 1.00 | 15.02 | 7 |
| 5192 | CA | VAL | A | 669 | 0.684 | 91.987 | 25.490 | 1.00 | 16.94 | 6 |
| 5193 | C | VAL | A | 669 | 1.205 | 91.294 | 24.260 | 1.00 | 14.25 | 6 |
| 5194 | O | VAL | A | 669 | 1.414 | 91.936 | 23.206 | 1.00 | 17.08 | 8 |
| 5195 | CB | VAL | A | 669 | −0.852 | 92.295 | 25.322 | 1.00 | 17.60 | 6 |
| 5196 | CG1 | VAL | A | 669 | −1.624 | 90.970 | 25.253 | 1.00 | 20.63 | 6 |
| 5197 | CG2 | VAL | A | 669 | −1.341 | 93.078 | 26.547 | 1.00 | 17.53 | 6 |
| 5198 | N | ALA | A | 670 | 1.450 | 89.971 | 24.287 | 1.00 | 14.50 | 7 |
| 5199 | CA | ALA | A | 670 | 1.945 | 89.249 | 23.113 | 1.00 | 14.21 | 6 |
| 5200 | C | ALA | A | 670 | 1.437 | 87.798 | 23.234 | 1.00 | 15.38 | 6 |
| 5201 | O | ALA | A | 670 | 1.216 | 87.262 | 24.323 | 1.00 | 15.04 | 8 |
| 5202 | CB | ALA | A | 670 | 3.481 | 89.251 | 23.005 | 1.00 | 14.71 | 6 |
| 5203 | N | THR | A | 671 | 1.412 | 87.143 | 22.093 | 1.00 | 15.66 | 7 |
| 5204 | CA | THR | A | 671 | 1.145 | 85.704 | 22.056 | 1.00 | 15.06 | 6 |
| 5205 | C | THR | A | 671 | 2.463 | 85.017 | 21.737 | 1.00 | 15.13 | 6 |
| 5206 | O | THR | A | 671 | 3.141 | 85.293 | 20.734 | 1.00 | 16.78 | 8 |
| 5207 | CB | THR | A | 671 | 0.004 | 85.374 | 21.082 | 1.00 | 24.32 | 6 |
| 5208 | OG1 | THR | A | 671 | −1.181 | 86.041 | 21.584 | 1.00 | 19.33 | 8 |
| 5209 | CG2 | THR | A | 671 | −0.323 | 83.900 | 21.063 | 1.00 | 22.47 | 6 |
| 5210 | N | THR | A | 672 | 2.794 | 83.967 | 22.533 | 1.00 | 13.36 | 7 |
| 5211 | CA | THR | A | 672 | 4.035 | 83.264 | 22.249 | 1.00 | 14.54 | 6 |
| 5212 | C | THR | A | 672 | 3.911 | 82.312 | 21.096 | 1.00 | 14.80 | 6 |
| 5213 | O | THR | A | 672 | 2.831 | 81.798 | 20.772 | 1.00 | 13.92 | 8 |
| 5214 | CB | THR | A | 672 | 4.475 | 82.464 | 23.491 | 1.00 | 15.06 | 6 |

TABLE 1-continued

Atom Coordinates from the Crystal Structure of NOVAMYL

| 5215 | OG1 | THR | A | 672 | 3.485 | 81.497 | 23.805 | 1.00 | 13.92 | 8 |
|---|---|---|---|---|---|---|---|---|---|---|
| 5216 | CG2 | THR | A | 672 | 4.612 | 83.376 | 24.726 | 1.00 | 15.62 | 6 |
| 5217 | N | PRO | A | 673 | 5.068 | 81.983 | 20.499 | 1.00 | 16.20 | 7 |
| 5218 | CA | PRO | A | 673 | 5.116 | 81.063 | 19.381 | 1.00 | 21.02 | 6 |
| 5219 | C | PRO | A | 673 | 4.615 | 79.690 | 19.691 | 1.00 | 17.09 | 6 |
| 5220 | O | PRO | A | 673 | 4.691 | 79.290 | 20.893 | 1.00 | 16.99 | 8 |
| 5221 | CB | PRO | A | 673 | 6.606 | 80.975 | 18.937 | 1.00 | 22.47 | 6 |
| 5222 | CG | PRO | A | 673 | 7.309 | 81.859 | 19.872 | 1.00 | 22.50 | 6 |
| 5223 | CD | PRO | A | 673 | 6.355 | 82.558 | 20.857 | 1.00 | 20.76 | 6 |
| 5224 | N | THR | A | 674 | 4.164 | 78.885 | 18.724 | 1.00 | 16.36 | 7 |
| 5225 | CA | THR | A | 674 | 3.803 | 77.518 | 19.033 | 1.00 | 16.04 | 6 |
| 5226 | C | THR | A | 674 | 4.915 | 76.516 | 18.803 | 1.00 | 19.50 | 6 |
| 5227 | O | THR | A | 674 | 4.834 | 75.399 | 19.293 | 1.00 | 25.45 | 8 |
| 5228 | CB | THR | A | 674 | 2.613 | 77.053 | 18.117 | 1.00 | 26.38 | 6 |
| 5229 | OG1 | THR | A | 674 | 2.997 | 77.353 | 16.786 | 1.00 | 31.27 | 8 |
| 5230 | CG2 | THR | A | 674 | 1.409 | 77.936 | 18.521 | 1.00 | 27.63 | 6 |
| 5231 | N | GLY | A | 675 | 5.953 | 76.981 | 18.114 | 1.00 | 19.68 | 7 |
| 5232 | CA | GLY | A | 675 | 7.035 | 76.041 | 17.829 | 1.00 | 18.98 | 6 |
| 5233 | C | GLY | A | 675 | 8.164 | 76.145 | 18.885 | 1.00 | 21.20 | 6 |
| 5234 | O | GLY | A | 675 | 7.915 | 76.654 | 19.953 | 1.00 | 18.10 | 8 |
| 5235 | N | ALA | A | 676 | 9.349 | 75.612 | 18.560 | 1.00 | 14.92 | 7 |
| 5236 | CA | ALA | A | 676 | 10.419 | 75.562 | 19.578 | 1.00 | 12.67 | 6 |
| 5237 | C | ALA | A | 676 | 10.845 | 76.968 | 19.974 | 1.00 | 13.87 | 6 |
| 5238 | O | ALA | A | 676 | 11.505 | 77.096 | 21.031 | 1.00 | 12.93 | 8 |
| 5239 | CB | ALA | A | 676 | 11.611 | 74.771 | 19.006 | 1.00 | 12.85 | 6 |
| 5240 | N | THR | A | 677 | 10.860 | 77.884 | 19.014 | 1.00 | 13.69 | 7 |
| 5241 | CA | THR | A | 677 | 11.444 | 79.189 | 19.324 | 1.00 | 11.81 | 6 |
| 5242 | C | THR | A | 677 | 10.615 | 80.296 | 18.686 | 1.00 | 13.20 | 6 |
| 5243 | O | THR | A | 677 | 9.743 | 80.066 | 17.834 | 1.00 | 14.64 | 8 |
| 5244 | CB | THR | A | 677 | 12.847 | 79.366 | 18.681 | 1.00 | 14.32 | 6 |
| 5245 | OG1 | THR | A | 677 | 12.712 | 79.294 | 17.249 | 1.00 | 16.35 | 8 |
| 5246 | CG2 | THR | A | 677 | 13.851 | 78.287 | 19.079 | 1.00 | 14.03 | 6 |
| 5247 | N | GLY | A | 678 | 10.949 | 81.490 | 19.141 | 1.00 | 14.25 | 7 |
| 5248 | CA | GLY | A | 678 | 10.413 | 82.685 | 18.437 | 1.00 | 13.38 | 6 |
| 5249 | C | GLY | A | 678 | 10.969 | 83.958 | 19.066 | 1.00 | 13.68 | 6 |
| 5250 | O | GLY | A | 678 | 11.857 | 83.956 | 19.907 | 1.00 | 13.62 | 8 |
| 5251 | N | ASN | A | 679 | 10.374 | 85.094 | 18.654 | 1.00 | 13.18 | 7 |
| 5252 | CA | ASN | A | 679 | 10.858 | 86.398 | 19.082 | 1.00 | 11.86 | 6 |
| 5253 | C | ASN | A | 679 | 9.685 | 87.318 | 19.466 | 1.00 | 14.28 | 6 |
| 5254 | O | ASN | A | 679 | 8.718 | 87.315 | 18.699 | 1.00 | 15.54 | 8 |
| 5255 | CB | ASN | A | 679 | 11.485 | 87.180 | 17.892 | 1.00 | 16.45 | 6 |
| 5256 | CG | ASN | A | 679 | 12.952 | 86.818 | 17.758 | 1.00 | 25.76 | 6 |
| 5257 | OD1 | ASN | A | 679 | 13.201 | 85.708 | 17.294 | 1.00 | 24.19 | 8 |
| 5258 | ND2 | ASN | A | 679 | 13.881 | 87.684 | 18.146 | 1.00 | 26.44 | 7 |
| 5259 | N | ILE | A | 680 | 9.882 | 88.063 | 20.521 | 1.00 | 13.28 | 7 |
| 5260 | CA | ILE | A | 680 | 8.909 | 89.088 | 20.948 | 1.00 | 14.10 | 6 |
| 5261 | C | ILE | A | 680 | 9.758 | 90.331 | 21.083 | 1.00 | 16.54 | 6 |
| 5262 | O | ILE | A | 680 | 10.673 | 90.366 | 21.944 | 1.00 | 14.10 | 8 |
| 5263 | CB | ILE | A | 680 | 8.224 | 88.676 | 22.277 | 1.00 | 13.96 | 6 |
| 5264 | CG1 | ILE | A | 680 | 7.245 | 87.519 | 21.978 | 1.00 | 16.92 | 6 |
| 5265 | CG2 | ILE | A | 680 | 7.442 | 89.919 | 22.790 | 1.00 | 17.42 | 6 |
| 5266 | CD1 | ILE | A | 680 | 6.611 | 86.867 | 23.218 | 1.00 | 15.15 | 6 |
| 5267 | N | THR | A | 681 | 9.363 | 91.378 | 20.334 | 1.00 | 13.57 | 7 |
| 5268 | CA | THR | A | 681 | 10.236 | 92.583 | 20.392 | 1.00 | 12.91 | 6 |
| 5269 | C | THR | A | 681 | 9.280 | 93.751 | 20.616 | 1.00 | 13.01 | 6 |
| 5270 | O | THR | A | 681 | 8.253 | 93.845 | 19.929 | 1.00 | 18.59 | 8 |
| 5271 | CB | THR | A | 681 | 10.904 | 92.718 | 18.990 | 1.00 | 16.97 | 6 |
| 5272 | OG1 | THR | A | 681 | 11.807 | 91.633 | 18.765 | 1.00 | 17.30 | 8 |
| 5273 | CG2 | THR | A | 681 | 11.642 | 94.052 | 18.964 | 1.00 | 19.53 | 6 |
| 5274 | N | VAL | A | 682 | 9.639 | 94.595 | 21.608 | 1.00 | 15.51 | 7 |
| 5275 | CA | VAL | A | 682 | 8.758 | 95.732 | 21.946 | 1.00 | 15.78 | 6 |
| 5276 | C | VAL | A | 682 | 9.635 | 96.952 | 22.186 | 1.00 | 17.87 | 6 |
| 5277 | O | VAL | A | 682 | 10.838 | 96.797 | 22.256 | 1.00 | 15.49 | 8 |
| 5278 | CB | VAL | A | 682 | 7.874 | 95.472 | 23.195 | 1.00 | 16.15 | 6 |
| 5279 | CG1 | VAL | A | 682 | 6.968 | 94.243 | 23.002 | 1.00 | 16.76 | 6 |
| 5280 | CG2 | VAL | A | 682 | 8.730 | 95.365 | 24.469 | 1.00 | 16.17 | 6 |
| 5281 | N | THR | A | 683 | 9.082 | 98.162 | 22.306 | 1.00 | 15.89 | 7 |
| 5282 | CA | THR | A | 683 | 9.863 | 99.346 | 22.623 | 1.00 | 15.51 | 6 |
| 5283 | C | THR | A | 683 | 9.529 | 99.798 | 24.046 | 1.00 | 16.36 | 6 |
| 5284 | O | THR | A | 683 | 8.371 | 99.703 | 24.462 | 1.00 | 17.59 | 8 |
| 5285 | CB | THR | A | 683 | 9.481 | 100.473 | 21.614 | 1.00 | 22.31 | 6 |
| 5286 | OG1 | THR | A | 683 | 9.916 | 100.019 | 20.328 | 1.00 | 21.22 | 8 |
| 5287 | CG2 | THR | A | 683 | 10.245 | 101.759 | 21.921 | 1.00 | 19.31 | 6 |
| 5288 | N | TRP | A | 684 | 10.586 | 100.168 | 24.759 | 1.00 | 14.24 | 7 |
| 5289 | CA | TRP | A | 684 | 10.411 | 100.587 | 26.154 | 1.00 | 14.76 | 6 |
| 5290 | C | TRP | A | 684 | 9.369 | 101.706 | 26.222 | 1.00 | 17.75 | 6 |
| 5291 | O | TRP | A | 684 | 9.556 | 102.695 | 25.469 | 1.00 | 18.74 | 8 |

TABLE 1-continued

Atom Coordinates from the Crystal Structure of NOVAMYL

| 5292 | CB | TRP | A | 684 | 11.745 | 101.086 | 26.705 | 1.00 | 14.95 | 6 |
|---|---|---|---|---|---|---|---|---|---|---|
| 5293 | CG | TRP | A | 684 | 11.696 | 101.465 | 28.146 | 1.00 | 14.49 | 6 |
| 5294 | CD1 | TRP | A | 684 | 11.284 | 102.666 | 28.672 | 1.00 | 15.39 | 6 |
| 5295 | CD2 | TRP | A | 684 | 12.163 | 100.683 | 29.271 | 1.00 | 17.84 | 6 |
| 5296 | NE1 | TRP | A | 684 | 11.376 | 102.649 | 30.052 | 1.00 | 16.11 | 7 |
| 5297 | CE2 | TRP | A | 684 | 11.921 | 101.440 | 30.423 | 1.00 | 20.66 | 6 |
| 5298 | CE3 | TRP | A | 684 | 12.764 | 99.422 | 29.399 | 1.00 | 18.28 | 6 |
| 5299 | CZ2 | TRP | A | 684 | 12.245 | 101.024 | 31.726 | 1.00 | 22.23 | 6 |
| 5300 | CZ3 | TRP | A | 684 | 13.074 | 98.959 | 30.709 | 1.00 | 17.05 | 6 |
| 5301 | CH2 | TRP | A | 684 | 12.791 | 99.766 | 31.796 | 1.00 | 17.97 | 6 |
| 5302 | N | GLN | A | 685 | 8.396 | 101.650 | 27.102 | 1.00 | 17.70 | 7 |
| 5303 | CA | GLN | A | 685 | 7.399 | 102.716 | 27.315 | 1.00 | 18.97 | 6 |
| 5304 | C | GLN | A | 685 | 7.850 | 103.719 | 28.333 | 1.00 | 19.08 | 6 |
| 5305 | O | GLN | A | 685 | 8.067 | 103.430 | 29.512 | 1.00 | 19.01 | 8 |
| 5306 | CB | GLN | A | 685 | 6.071 | 102.025 | 27.745 | 1.00 | 15.69 | 6 |
| 5307 | CG | GLN | A | 685 | 5.536 | 101.157 | 26.596 | 1.00 | 17.89 | 6 |
| 5308 | CD | GLN | A | 685 | 4.352 | 100.283 | 26.995 | 1.00 | 18.78 | 6 |
| 5309 | OE1 | GLN | A | 685 | 3.797 | 99.604 | 26.110 | 1.00 | 20.58 | 8 |
| 5310 | NE2 | GLN | A | 685 | 3.960 | 100.246 | 28.267 | 1.00 | 17.75 | 7 |
| 5311 | N | ASN | A | 686 | 8.037 | 105.011 | 27.906 | 1.00 | 21.27 | 7 |
| 5312 | CA | ASN | A | 686 | 8.547 | 106.008 | 28.836 | 1.00 | 20.38 | 6 |
| 5313 | C | ASN | A | 686 | 7.489 | 106.854 | 29.654 | 1.00 | 22.87 | 6 |
| 5314 | O | ASN | A | 686 | 6.387 | 106.692 | 29.016 | 1.00 | 22.87 | 8 |
| 5315 | CB | ASN | A | 686 | 9.300 | 107.060 | 27.975 | 1.00 | 24.12 | 6 |
| 5316 | CG | ASN | A | 686 | 10.434 | 106.404 | 27.176 | 1.00 | 23.38 | 6 |
| 5317 | OD1 | ASN | A | 686 | 11.360 | 105.896 | 27.821 | 1.00 | 22.76 | 8 |
| 5318 | ND2 | ASN | A | 686 | 10.376 | 106.412 | 25.832 | 1.00 | 25.47 | 7 |
| 5319 | C11 | HEX | A | 690 | 38.644 | 78.012 | 38.228 | 1.00 | 27.46 | 6 |
| 5320 | O11 | HEX | A | 690 | 39.147 | 78.243 | 39.503 | 1.00 | 37.24 | 8 |
| 5321 | C12 | HEX | A | 690 | 37.596 | 79.172 | 38.058 | 1.00 | 23.95 | 6 |
| 5322 | O12 | HEX | A | 690 | 36.681 | 78.887 | 39.109 | 1.00 | 20.96 | 8 |
| 5323 | C13 | HEX | A | 690 | 36.915 | 78.887 | 36.685 | 1.00 | 17.64 | 6 |
| 5324 | O13 | HEX | A | 690 | 35.915 | 79.908 | 36.442 | 1.00 | 18.04 | 8 |
| 5325 | C14 | HEX | A | 690 | 38.048 | 79.023 | 35.670 | 1.00 | 17.74 | 6 |
| 5326 | C15 | HEX | A | 690 | 39.141 | 77.967 | 35.956 | 1.00 | 19.52 | 6 |
| 5327 | O15 | HEX | A | 690 | 39.679 | 78.312 | 37.276 | 1.00 | 26.20 | 8 |
| 5328 | C16 | HEX | A | 690 | 40.338 | 77.919 | 35.016 | 1.00 | 23.71 | 6 |
| 5329 | O16 | HEX | A | 690 | 40.867 | 79.240 | 34.817 | 1.00 | 28.38 | 8 |
| 5330 | C21 | HEX | A | 690 | 37.609 | 79.324 | 33.250 | 1.00 | 19.03 | 6 |
| 5331 | O21 | HEX | A | 690 | 37.414 | 78.562 | 34.414 | 1.00 | 18.39 | 8 |
| 5332 | C22 | HEX | A | 690 | 36.237 | 79.756 | 32.692 | 1.00 | 18.97 | 6 |
| 5333 | O22 | HEX | A | 690 | 35.419 | 80.404 | 33.669 | 1.00 | 17.96 | 8 |
| 5334 | C23 | HEX | A | 690 | 35.514 | 78.516 | 32.153 | 1.00 | 16.72 | 6 |
| 5335 | O23 | HEX | A | 690 | 34.355 | 79.014 | 31.406 | 1.00 | 16.31 | 8 |
| 5336 | C24 | HEX | A | 690 | 36.415 | 77.760 | 31.174 | 1.00 | 12.77 | 6 |
| 5337 | C25 | HEX | A | 690 | 37.690 | 77.301 | 31.955 | 1.00 | 17.32 | 6 |
| 5338 | O25 | HEX | A | 690 | 38.321 | 78.596 | 32.286 | 1.00 | 20.72 | 8 |
| 5339 | C26 | HEX | A | 690 | 38.704 | 76.681 | 30.979 | 1.00 | 18.94 | 6 |
| 5340 | O26 | HEX | A | 690 | 39.852 | 76.182 | 31.780 | 1.00 | 21.07 | 8 |
| 5341 | C31 | HEX | A | 690 | 35.507 | 76.403 | 29.409 | 1.00 | 11.28 | 6 |
| 5342 | O31 | HEX | A | 690 | 35.723 | 76.501 | 30.811 | 1.00 | 12.85 | 8 |
| 5343 | C32 | HEX | A | 690 | 34.026 | 76.118 | 29.118 | 1.00 | 13.04 | 6 |
| 5344 | O32 | HEX | A | 690 | 33.259 | 77.030 | 29.933 | 1.00 | 14.06 | 8 |
| 5345 | C33 | HEX | A | 690 | 33.654 | 74.698 | 29.626 | 1.00 | 13.59 | 6 |
| 5346 | O33 | HEX | A | 690 | 32.285 | 74.486 | 29.158 | 1.00 | 12.48 | 8 |
| 5347 | C34 | HEX | A | 690 | 34.578 | 73.670 | 28.936 | 1.00 | 11.83 | 6 |
| 5348 | C35 | HEX | A | 690 | 36.004 | 74.036 | 29.487 | 1.00 | 14.01 | 6 |
| 5349 | O35 | HEX | A | 690 | 36.301 | 75.341 | 28.930 | 1.00 | 12.70 | 8 |
| 5350 | C36 | HEX | A | 690 | 37.084 | 73.167 | 28.829 | 1.00 | 13.71 | 6 |
| 5351 | C41 | HEX | A | 690 | 33.322 | 71.601 | 28.292 | 1.00 | 9.18 | 6 |
| 5352 | N41 | HEX | A | 690 | 34.214 | 72.300 | 29.267 | 1.00 | 10.73 | 7 |
| 5353 | C42 | HEX | A | 690 | 33.682 | 70.074 | 28.156 | 1.00 | 11.48 | 6 |
| 5354 | O42 | HEX | A | 690 | 33.732 | 69.433 | 29.448 | 1.00 | 10.30 | 8 |
| 5355 | C43 | HEX | A | 690 | 35.023 | 69.963 | 27.455 | 1.00 | 10.39 | 6 |
| 5356 | O43 | HEX | A | 690 | 35.686 | 68.699 | 27.591 | 1.00 | 11.44 | 8 |
| 5357 | C44 | HEX | A | 690 | 34.791 | 70.257 | 25.986 | 1.00 | 11.02 | 6 |
| 5358 | C45 | HEX | A | 690 | 33.925 | 71.520 | 25.899 | 1.00 | 10.58 | 6 |
| 5359 | C40 | HEX | A | 690 | 33.262 | 72.097 | 26.944 | 1.00 | 9.08 | 6 |
| 5360 | C46 | HEX | A | 690 | 33.519 | 71.887 | 24.466 | 1.00 | 12.28 | 6 |
| 5361 | O46 | HEX | A | 690 | 32.492 | 71.022 | 24.020 | 1.00 | 12.58 | 8 |
| 5362 | C51 | HEX | A | 690 | 36.288 | 69.864 | 24.116 | 1.00 | 10.88 | 6 |
| 5363 | O51 | HEX | A | 690 | 36.061 | 70.541 | 25.327 | 1.00 | 12.10 | 8 |
| 5364 | C52 | HEX | A | 690 | 37.495 | 68.906 | 24.274 | 1.00 | 11.69 | 6 |
| 5365 | O52 | HEX | A | 690 | 37.227 | 67.917 | 25.285 | 1.00 | 12.57 | 8 |
| 5366 | C53 | HEX | A | 690 | 38.717 | 69.698 | 24.774 | 1.00 | 10.51 | 6 |
| 5367 | O53 | HEX | A | 690 | 39.832 | 68.756 | 24.609 | 1.00 | 11.97 | 8 |
| 5368 | C54 | HEX | A | 690 | 39.025 | 70.807 | 23.714 | 1.00 | 12.82 | 6 |

TABLE 1-continued

Atom Coordinates from the Crystal Structure of NOVAMYL

| | | | | | | | | | |
|---|---|---|---|---|---|---|---|---|---|
| 5369 | C55 | HEX | A | 690 | 37.748 | 71.660 | 23.566 | 1.00 | 12.56 | 6 |
| 5370 | O55 | HEX | A | 690 | 36.680 | 70.820 | 23.133 | 1.00 | 11.57 | 8 |
| 5371 | C56 | HEX | A | 690 | 37.890 | 72.687 | 22.436 | 1.00 | 12.61 | 6 |
| 5372 | O56 | HEX | A | 690 | 38.082 | 72.074 | 21.134 | 1.00 | 19.74 | 8 |
| 5373 | C61 | HEX | A | 690 | 40.720 | 72.590 | 24.188 | 1.00 | 22.95 | 6 |
| 5374 | O61 | HEX | A | 690 | 39.890 | 71.572 | 24.637 | 1.00 | 20.26 | 8 |
| 5375 | C62 | HEX | A | 690 | 42.050 | 72.500 | 24.991 | 1.00 | 23.13 | 6 |
| 5376 | O62 | HEX | A | 690 | 42.582 | 71.189 | 24.918 | 1.00 | 23.06 | 8 |
| 5377 | C63 | HEX | A | 690 | 41.937 | 73.006 | 26.411 | 1.00 | 24.03 | 6 |
| 5378 | O63 | HEX | A | 690 | 43.280 | 72.994 | 26.932 | 1.00 | 28.78 | 8 |
| 5379 | C64 | HEX | A | 690 | 41.310 | 74.405 | 26.428 | 1.00 | 25.79 | 6 |
| 5380 | O64 | HEX | A | 690 | 41.035 | 74.789 | 27.809 | 1.00 | 29.96 | 8 |
| 5381 | C65 | HEX | A | 690 | 39.918 | 74.255 | 25.759 | 1.00 | 22.19 | 6 |
| 5382 | O65 | HEX | A | 690 | 40.146 | 73.866 | 24.404 | 1.00 | 22.47 | 8 |
| 5383 | C66 | HEX | A | 690 | 39.177 | 75.555 | 25.611 | 1.00 | 26.12 | 6 |
| 5384 | O66 | HEX | A | 690 | 39.936 | 76.644 | 25.149 | 1.00 | 24.41 | 8 |
| 5385 | C11 | MAL | A | 691 | 38.534 | 71.299 | 69.464 | 1.00 | 19.75 | 6 |
| 5386 | O11 | MAL | A | 691 | 38.776 | 72.581 | 69.883 | 1.00 | 20.21 | 8 |
| 5387 | C12 | MAL | A | 691 | 37.973 | 71.384 | 68.024 | 1.00 | 17.66 | 6 |
| 5388 | O12 | MAL | A | 691 | 38.798 | 72.262 | 67.225 | 1.00 | 18.71 | 8 |
| 5389 | C13 | MAL | A | 691 | 36.555 | 71.949 | 68.006 | 1.00 | 16.03 | 6 |
| 5390 | O13 | MAL | A | 691 | 35.969 | 71.754 | 66.689 | 1.00 | 17.47 | 8 |
| 5391 | C14 | MAL | A | 691 | 35.642 | 71.104 | 68.925 | 1.00 | 15.64 | 6 |
| 5392 | C15 | MAL | A | 691 | 36.269 | 71.291 | 70.364 | 1.00 | 14.01 | 6 |
| 5393 | O15 | MAL | A | 691 | 37.561 | 70.667 | 70.312 | 1.00 | 16.48 | 8 |
| 5394 | C16 | MAL | A | 691 | 35.519 | 70.221 | 71.238 | 1.00 | 19.77 | 6 |
| 5395 | O16 | MAL | A | 691 | 36.004 | 70.431 | 72.581 | 1.00 | 18.54 | 8 |
| 5396 | C21 | MAL | A | 691 | 33.285 | 70.813 | 68.523 | 1.00 | 18.83 | 6 |
| 5397 | O21 | MAL | A | 691 | 34.336 | 71.683 | 68.968 | 1.00 | 17.92 | 8 |
| 5398 | C22 | MAL | A | 691 | 32.403 | 71.638 | 67.561 | 1.00 | 17.24 | 6 |
| 5399 | O22 | MAL | A | 691 | 33.177 | 72.083 | 66.433 | 1.00 | 17.89 | 8 |
| 5400 | C23 | MAL | A | 691 | 31.765 | 72.820 | 68.304 | 1.00 | 18.41 | 6 |
| 5401 | O23 | MAL | A | 691 | 30.812 | 73.419 | 67.431 | 1.00 | 18.30 | 8 |
| 5402 | C24 | MAL | A | 691 | 30.951 | 72.194 | 69.478 | 1.00 | 18.57 | 6 |
| 5403 | O24 | MAL | A | 691 | 30.444 | 73.291 | 70.263 | 1.00 | 19.15 | 8 |
| 5404 | C25 | MAL | A | 691 | 31.923 | 71.424 | 70.383 | 1.00 | 19.32 | 6 |
| 5405 | O25 | MAL | A | 691 | 32.521 | 70.374 | 69.608 | 1.00 | 18.98 | 8 |
| 5406 | C26 | MAL | A | 691 | 31.067 | 70.708 | 71.468 | 1.00 | 15.38 | 6 |
| 5407 | O26 | MAL | A | 691 | 31.944 | 70.075 | 72.412 | 1.00 | 18.74 | 8 |
| 5411 | S | SUL | A | 695 | 11.120 | 52.018 | 55.465 | 1.00 | 30.54 | 16 |
| 5412 | O1 | SUL | A | 695 | 11.470 | 52.936 | 56.533 | 1.00 | 30.07 | 8 |
| 5413 | O2 | SUL | A | 695 | 10.034 | 52.528 | 54.544 | 1.00 | 27.19 | 8 |
| 5414 | O3 | SUL | A | 695 | 12.310 | 51.631 | 54.662 | 1.00 | 34.25 | 8 |
| 5415 | O4 | SUL | A | 695 | 10.566 | 50.749 | 56.089 | 1.00 | 33.96 | 8 |
| 5451 | CA | WAT | A | 692 | 32.693 | 60.307 | 13.017 | 1.00 | 11.99 | 20 |
| 5452 | CA | WAT | A | 693 | 26.975 | 79.502 | 21.970 | 1.00 | 10.73 | 20 |
| 5453 | CA | WAT | A | 694 | 37.244 | 49.841 | 19.039 | 1.00 | 13.50 | 20 |
| 5454 | OW0 | WAT | V | 1 | 24.447 | 79.971 | 21.858 | 1.00 | 9.43 | 8 |
| 5455 | OW0 | WAT | V | 2 | 35.686 | 59.385 | 24.028 | 1.00 | 10.45 | 8 |
| 5456 | OW0 | WAT | V | 3 | 33.934 | 60.773 | 18.648 | 1.00 | 10.63 | 8 |
| 5457 | OW0 | WAT | V | 4 | 35.622 | 62.751 | 41.495 | 1.00 | 10.88 | 8 |
| 5458 | OW0 | WAT | V | 5 | 25.780 | 77.914 | 20.486 | 1.00 | 10.75 | 8 |
| 5459 | OW0 | WAT | V | 6 | 21.776 | 77.285 | 28.879 | 1.00 | 10.81 | 8 |
| 5460 | OW0 | WAT | V | 7 | 29.415 | 69.145 | 19.400 | 1.00 | 10.86 | 8 |
| 5461 | OW0 | WAT | V | 8 | 29.138 | 80.312 | 22.631 | 1.00 | 10.86 | 8 |
| 5462 | OW0 | WAT | V | 9 | 27.613 | 72.037 | 24.448 | 1.00 | 10.77 | 8 |
| 5463 | OW0 | WAT | V | 10 | 31.164 | 77.784 | 19.615 | 1.00 | 10.85 | 8 |
| 5464 | OW0 | WAT | V | 11 | 32.790 | 66.917 | 36.378 | 1.00 | 10.94 | 8 |
| 5465 | OW0 | WAT | V | 12 | 34.127 | 70.240 | 32.929 | 1.00 | 11.18 | 8 |
| 5466 | OW0 | WAT | V | 13 | 33.080 | 60.581 | 23.767 | 1.00 | 11.11 | 8 |
| 5467 | OW0 | WAT | V | 14 | 37.235 | 54.601 | 19.600 | 1.00 | 11.38 | 8 |
| 5468 | OW0 | WAT | V | 15 | 26.119 | 65.542 | 21.574 | 1.00 | 11.07 | 8 |
| 5469 | OW0 | WAT | V | 16 | 28.484 | 64.486 | 20.522 | 1.00 | 11.49 | 8 |
| 5470 | OW0 | WAT | V | 17 | 28.194 | 73.536 | 36.853 | 1.00 | 11.53 | 8 |
| 5471 | OW0 | WAT | V | 18 | 16.618 | 66.275 | 36.806 | 1.00 | 11.68 | 8 |
| 5472 | OW0 | WAT | V | 19 | 26.088 | 62.658 | 22.854 | 1.00 | 11.54 | 8 |
| 5473 | OW0 | WAT | V | 20 | 37.981 | 63.919 | 14.127 | 1.00 | 11.77 | 8 |
| 5474 | OW0 | WAT | V | 21 | 34.932 | 60.656 | 13.769 | 1.00 | 11.70 | 8 |
| 5475 | OW0 | WAT | V | 22 | 41.499 | 60.656 | 38.722 | 1.00 | 11.54 | 8 |
| 5476 | OW0 | WAT | V | 23 | 40.945 | 66.711 | 20.205 | 1.00 | 11.65 | 8 |
| 5477 | OW0 | WAT | V | 24 | 8.905 | 64.107 | 34.370 | 1.00 | 11.68 | 8 |
| 5478 | OW0 | WAT | V | 25 | 19.426 | 72.356 | 40.893 | 1.00 | 11.74 | 8 |
| 5479 | OW0 | WAT | V | 26 | 20.321 | 82.331 | 35.376 | 1.00 | 11.77 | 8 |
| 5480 | OW0 | WAT | V | 27 | 14.993 | 64.250 | 37.502 | 1.00 | 11.91 | 8 |
| 5481 | OW0 | WAT | V | 28 | 31.504 | 68.673 | 10.842 | 1.00 | 12.08 | 8 |
| 5482 | OW0 | WAT | V | 29 | 37.606 | 61.402 | 40.167 | 1.00 | 11.91 | 8 |
| 5483 | OW0 | WAT | V | 30 | 16.372 | 70.863 | 38.933 | 1.00 | 11.99 | 8 |

TABLE 1-continued

Atom Coordinates from the Crystal Structure of NOVAMYL

| 5484 | OW0 | WAT | V | 31 | 7.950 | 69.079 | 31.258 | 1.00 | 12.08 | 8 |
|---|---|---|---|---|---|---|---|---|---|---|
| 5485 | OW0 | WAT | V | 32 | 19.528 | 73.999 | 43.164 | 1.00 | 12.10 | 8 |
| 5486 | OW0 | WAT | V | 33 | 16.210 | 66.954 | 39.606 | 1.00 | 12.02 | 8 |
| 5487 | OW0 | WAT | V | 34 | 32.679 | 63.267 | 29.330 | 1.00 | 12.26 | 8 |
| 5488 | OW0 | WAT | V | 35 | 13.649 | 74.479 | 39.683 | 1.00 | 12.21 | 8 |
| 5489 | OW0 | WAT | V | 36 | 16.357 | 79.631 | 22.013 | 1.00 | 12.26 | 8 |
| 5490 | OW0 | WAT | V | 37 | 21.471 | 63.888 | 43.225 | 1.00 | 12.25 | 8 |
| 5491 | OW0 | WAT | V | 38 | 42.464 | 66.587 | 23.881 | 1.00 | 12.49 | 8 |
| 5492 | OW0 | WAT | V | 39 | 31.355 | 60.893 | 19.838 | 1.00 | 12.31 | 8 |
| 5493 | OW0 | WAT | V | 40 | 16.930 | 64.546 | 40.981 | 1.00 | 12.36 | 8 |
| 5494 | OW0 | WAT | V | 41 | 10.918 | 81.011 | 32.425 | 1.00 | 12.42 | 8 |
| 5495 | OW0 | WAT | V | 42 | 8.358 | 78.559 | 35.685 | 1.00 | 12.49 | 8 |
| 5496 | OW0 | WAT | V | 43 | 22.052 | 71.621 | 41.190 | 1.00 | 12.24 | 8 |
| 5497 | OW0 | WAT | V | 44 | 8.226 | 66.640 | 35.276 | 1.00 | 12.62 | 8 |
| 5498 | OW0 | WAT | V | 45 | 6.031 | 77.562 | 36.868 | 1.00 | 12.35 | 8 |
| 5499 | OW0 | WAT | V | 46 | 43.919 | 60.734 | 40.175 | 1.00 | 12.51 | 8 |
| 5500 | OW0 | WAT | V | 48 | 11.578 | 73.478 | 41.191 | 1.00 | 12.62 | 8 |
| 5501 | OW0 | WAT | V | 49 | 35.256 | 52.308 | 26.203 | 1.00 | 12.50 | 8 |
| 5502 | OW0 | WAT | V | 50 | 22.628 | 81.739 | 22.782 | 1.00 | 12.52 | 8 |
| 5503 | OW0 | WAT | V | 51 | 41.171 | 68.357 | 22.292 | 1.00 | 12.78 | 8 |
| 5504 | OW0 | WAT | V | 52 | 34.554 | 71.110 | 10.783 | 1.00 | 12.58 | 8 |
| 5505 | OW0 | WAT | V | 53 | 39.554 | 70.543 | 28.407 | 1.00 | 12.73 | 8 |
| 5506 | OW0 | WAT | V | 54 | 14.970 | 66.671 | 43.779 | 1.00 | 12.94 | 8 |
| 5507 | OW0 | WAT | V | 55 | 14.792 | 81.581 | 20.763 | 1.00 | 12.92 | 8 |
| 5508 | OW0 | WAT | V | 56 | 30.205 | 75.643 | 31.109 | 1.00 | 12.90 | 8 |
| 5509 | OW0 | WAT | V | 57 | 16.697 | 82.536 | 30.534 | 1.00 | 13.09 | 8 |
| 5510 | OW0 | WAT | V | 58 | 38.776 | 53.289 | 57.732 | 1.00 | 13.10 | 8 |
| 5511 | OW0 | WAT | V | 59 | 31.565 | 49.273 | 20.064 | 1.00 | 13.22 | 8 |
| 5512 | OW0 | WAT | V | 60 | 20.200 | 85.147 | 36.037 | 1.00 | 13.29 | 8 |
| 5513 | OW0 | WAT | V | 61 | 25.657 | 54.513 | 45.949 | 1.00 | 13.32 | 8 |
| 5514 | OW0 | WAT | V | 62 | 37.048 | 52.273 | 18.284 | 1.00 | 13.46 | 8 |
| 5515 | OW0 | WAT | V | 63 | 30.032 | 67.305 | 53.938 | 1.00 | 13.27 | 8 |
| 5516 | OW0 | WAT | V | 64 | 32.331 | 68.357 | 33.829 | 1.00 | 13.58 | 8 |
| 5517 | OW0 | WAT | V | 65 | 23.329 | 85.511 | 30.252 | 1.00 | 13.33 | 8 |
| 5518 | OW0 | WAT | V | 66 | 20.246 | 61.387 | 18.981 | 1.00 | 13.61 | 8 |
| 5519 | OW0 | WAT | V | 67 | 28.775 | 74.856 | 40.336 | 1.00 | 13.65 | 8 |
| 5520 | OW0 | WAT | V | 68 | 32.567 | 68.924 | 43.607 | 1.00 | 13.35 | 8 |
| 5521 | OW0 | WAT | V | 69 | 10.838 | 68.713 | 42.880 | 1.00 | 13.33 | 8 |
| 5522 | OW0 | WAT | V | 70 | 12.859 | 61.518 | 43.606 | 1.00 | 13.90 | 8 |
| 5523 | OW0 | WAT | V | 71 | 45.207 | 60.214 | 32.334 | 1.00 | 13.77 | 8 |
| 5524 | OW0 | WAT | V | 72 | 27.427 | 66.987 | 53.108 | 1.00 | 13.75 | 8 |
| 5525 | OW0 | WAT | V | 73 | 19.074 | 63.276 | 42.264 | 1.00 | 13.66 | 8 |
| 5526 | OW0 | WAT | V | 74 | 36.934 | 75.592 | 8.270 | 1.00 | 13.53 | 8 |
| 5527 | OW0 | WAT | V | 75 | 27.574 | 81.410 | 6.013 | 1.00 | 14.19 | 8 |
| 5528 | OW0 | WAT | V | 76 | 30.621 | 83.670 | 31.215 | 1.00 | 14.28 | 8 |
| 5529 | OW0 | WAT | V | 77 | 42.514 | 70.356 | 20.822 | 1.00 | 14.45 | 8 |
| 5530 | OW0 | WAT | V | 78 | 12.529 | 75.168 | 22.815 | 1.00 | 14.52 | 8 |
| 5531 | OW0 | WAT | V | 79 | 39.891 | 56.461 | 11.992 | 1.00 | 14.18 | 8 |
| 5532 | OW0 | WAT | V | 80 | 30.677 | 68.114 | 68.620 | 1.00 | 14.47 | 8 |
| 5533 | OW0 | WAT | V | 81 | 33.218 | 64.224 | 36.711 | 1.00 | 14.46 | 8 |
| 5534 | OW0 | WAT | V | 82 | 12.035 | 74.811 | 37.533 | 1.00 | 14.63 | 8 |
| 5535 | OW0 | WAT | V | 83 | 15.981 | 73.538 | 38.669 | 1.00 | 14.16 | 8 |
| 5536 | OW0 | WAT | V | 84 | 10.686 | 81.113 | 35.947 | 1.00 | 14.90 | 8 |
| 5537 | OW0 | WAT | V | 85 | 25.562 | 71.871 | 51.287 | 1.00 | 14.81 | 8 |
| 5538 | OW0 | WAT | V | 86 | 29.447 | 83.564 | 16.644 | 1.00 | 14.86 | 8 |
| 5539 | OW0 | WAT | V | 87 | 13.480 | 81.300 | 31.112 | 1.00 | 14.85 | 8 |
| 5540 | OW0 | WAT | V | 88 | 5.774 | 80.076 | 41.775 | 1.00 | 14.92 | 8 |
| 5541 | OW0 | WAT | V | 89 | 47.914 | 63.828 | 68.644 | 1.00 | 14.87 | 8 |
| 5542 | OW0 | WAT | V | 90 | 34.743 | 77.662 | 45.101 | 1.00 | 15.02 | 8 |
| 5543 | OW0 | WAT | V | 91 | 24.427 | 76.387 | 7.359 | 1.00 | 15.03 | 8 |
| 5544 | OW0 | WAT | V | 92 | −2.703 | 63.471 | 38.845 | 1.00 | 15.46 | 8 |
| 5545 | OW0 | WAT | V | 93 | 14.681 | 69.092 | 37.625 | 1.00 | 15.14 | 8 |
| 5546 | OW0 | WAT | V | 94 | 28.123 | 74.474 | 42.954 | 1.00 | 15.12 | 8 |
| 5547 | OW0 | WAT | V | 95 | 23.589 | 80.407 | 29.737 | 1.00 | 15.19 | 8 |
| 5548 | OW0 | WAT | V | 96 | 28.941 | 64.658 | 47.281 | 1.00 | 15.32 | 8 |
| 5549 | OW0 | WAT | V | 97 | 33.848 | 82.923 | 7.441 | 1.00 | 15.09 | 8 |
| 5550 | OW0 | WAT | V | 98 | 50.687 | 59.709 | 65.034 | 1.00 | 15.32 | 8 |
| 5551 | OW0 | WAT | V | 99 | 29.977 | 80.264 | 14.804 | 1.00 | 15.36 | 8 |
| 5552 | OW0 | WAT | V | 100 | 25.916 | 52.607 | 44.011 | 1.00 | 15.58 | 8 |
| 5553 | OW0 | WAT | V | 101 | 6.765 | 62.176 | 32.083 | 1.00 | 15.56 | 8 |
| 5554 | OW0 | WAT | V | 102 | 13.107 | 89.810 | 20.076 | 1.00 | 15.94 | 8 |
| 5555 | OW0 | WAT | V | 103 | 11.601 | 78.292 | 36.745 | 1.00 | 15.75 | 8 |
| 5556 | OW0 | WAT | V | 104 | 14.144 | 58.009 | 41.510 | 1.00 | 15.84 | 8 |
| 5557 | OW0 | WAT | V | 105 | 44.010 | 71.623 | 35.990 | 1.00 | 15.89 | 8 |
| 5558 | OW0 | WAT | V | 106 | 21.168 | 82.474 | 32.738 | 1.00 | 16.12 | 8 |
| 5559 | OW0 | WAT | V | 107 | 28.667 | 48.688 | 46.155 | 1.00 | 16.35 | 8 |
| 5560 | OW0 | WAT | V | 108 | 25.610 | 86.818 | 38.209 | 1.00 | 16.18 | 8 |

TABLE 1-continued

Atom Coordinates from the Crystal Structure of NOVAMYL

| | | | | | | | | | | |
|---|---|---|---|---|---|---|---|---|---|---|
| 5561 | OW0 | WAT | V | 109 | 29.070 | 89.992 | 31.492 | 1.00 | 16.47 | 8 |
| 5562 | OW0 | WAT | V | 110 | 1.291 | 75.000 | 41.091 | 1.00 | 16.32 | 8 |
| 5563 | OW0 | WAT | V | 111 | 34.624 | 56.600 | 71.328 | 1.00 | 16.34 | 8 |
| 5564 | OW0 | WAT | V | 112 | 28.281 | 69.481 | 68.152 | 1.00 | 16.52 | 8 |
| 5565 | OW0 | WAT | V | 113 | 26.135 | 87.038 | 35.304 | 1.00 | 16.58 | 8 |
| 5566 | OW0 | WAT | V | 114 | 35.168 | 78.123 | 51.153 | 1.00 | 16.64 | 8 |
| 5567 | OW0 | WAT | V | 115 | 19.827 | 81.281 | 46.203 | 1.00 | 16.48 | 8 |
| 5568 | OW0 | WAT | V | 116 | 30.082 | 84.087 | 8.323 | 1.00 | 16.75 | 8 |
| 5569 | OW0 | WAT | V | 117 | 45.164 | 71.238 | 15.992 | 1.00 | 16.58 | 8 |
| 5570 | OW0 | WAT | V | 118 | −2.555 | 86.829 | 29.585 | 1.00 | 16.73 | 8 |
| 5571 | OW0 | WAT | V | 119 | 1.879 | 75.860 | 26.297 | 1.00 | 16.96 | 8 |
| 5572 | OW0 | WAT | V | 120 | 20.960 | 94.415 | 22.713 | 1.00 | 16.87 | 8 |
| 5573 | OW0 | WAT | V | 121 | 12.300 | 72.626 | 21.951 | 1.00 | 16.94 | 8 |
| 5574 | OW0 | WAT | V | 122 | 21.720 | 86.954 | 37.648 | 1.00 | 17.08 | 8 |
| 5575 | OW0 | WAT | V | 123 | 17.342 | 46.052 | 29.967 | 1.00 | 16.89 | 8 |
| 5576 | OW0 | WAT | V | 124 | 15.847 | 84.337 | 34.562 | 1.00 | 16.74 | 8 |
| 5577 | OW0 | WAT | V | 125 | −3.241 | 60.294 | 45.682 | 1.00 | 16.67 | 8 |
| 5578 | OW0 | WAT | V | 126 | 11.587 | 104.148 | 24.323 | 1.00 | 17.24 | 8 |
| 5579 | OW0 | WAT | V | 127 | 28.501 | 56.852 | 51.441 | 1.00 | 17.40 | 8 |
| 5580 | OW0 | WAT | V | 128 | 14.206 | 82.937 | 18.392 | 1.00 | 17.21 | 8 |
| 5581 | OW0 | WAT | V | 129 | 41.516 | 56.407 | 63.525 | 1.00 | 17.22 | 8 |
| 5582 | OW0 | WAT | V | 130 | 36.936 | 73.986 | 40.016 | 1.00 | 17.65 | 8 |
| 5583 | OW0 | WAT | V | 131 | 20.790 | 40.115 | 27.752 | 1.00 | 17.53 | 8 |
| 5584 | OW0 | WAT | V | 132 | 45.240 | 52.146 | 20.212 | 1.00 | 17.55 | 8 |
| 5585 | OW0 | WAT | V | 133 | 41.799 | 49.726 | 28.892 | 1.00 | 17.29 | 8 |
| 5586 | OW0 | WAT | V | 134 | 23.108 | 66.755 | 60.083 | 1.00 | 17.41 | 8 |
| 5587 | OW0 | WAT | V | 135 | 26.863 | 48.805 | 41.435 | 1.00 | 17.67 | 8 |
| 5588 | OW0 | WAT | V | 136 | 27.488 | 90.699 | 28.339 | 1.00 | 17.76 | 8 |
| 5589 | OW0 | WAT | V | 137 | 0.191 | 69.111 | 49.096 | 1.00 | 17.78 | 8 |
| 5590 | OW0 | WAT | V | 138 | 34.447 | 43.232 | 33.946 | 1.00 | 17.85 | 8 |
| 5591 | OW0 | WAT | V | 139 | 22.589 | 64.044 | 49.415 | 1.00 | 18.18 | 8 |
| 5592 | OW0 | WAT | V | 140 | 17.697 | 81.339 | 35.462 | 1.00 | 17.98 | 8 |
| 5593 | OW0 | WAT | V | 141 | 2.444 | 96.838 | 37.934 | 1.00 | 18.09 | 8 |
| 5594 | OW0 | WAT | V | 142 | 35.347 | 81.251 | 39.545 | 1.00 | 17.94 | 8 |
| 5595 | OW0 | WAT | V | 143 | 14.511 | 56.297 | 49.652 | 1.00 | 18.35 | 8 |
| 5596 | OW0 | WAT | V | 144 | 10.014 | 71.654 | 20.618 | 1.00 | 18.11 | 8 |
| 5597 | OW0 | WAT | V | 145 | 47.629 | 63.815 | 18.991 | 1.00 | 18.25 | 8 |
| 5598 | OW0 | WAT | V | 146 | 15.832 | 79.962 | 31.635 | 1.00 | 18.52 | 8 |
| 5599 | OW0 | WAT | V | 147 | 35.482 | 76.428 | 39.594 | 1.00 | 18.64 | 8 |
| 5600 | OW0 | WAT | V | 149 | 16.532 | 67.334 | 48.159 | 1.00 | 18.61 | 8 |
| 5601 | OW0 | WAT | V | 150 | 32.280 | 83.173 | 33.550 | 1.00 | 18.44 | 8 |
| 5602 | OW0 | WAT | V | 151 | 35.037 | 62.885 | 71.628 | 1.00 | 18.62 | 8 |
| 5603 | OW0 | WAT | V | 152 | 14.756 | 56.448 | 28.743 | 1.00 | 18.87 | 8 |
| 5604 | OW0 | WAT | V | 153 | 51.007 | 64.138 | 32.515 | 1.00 | 18.45 | 8 |
| 5605 | OW0 | WAT | V | 154 | 44.683 | 55.406 | 52.749 | 1.00 | 18.86 | 8 |
| 5606 | OW0 | WAT | V | 155 | 30.803 | 47.286 | 18.413 | 1.00 | 19.00 | 8 |
| 5607 | OW0 | WAT | V | 156 | 21.419 | 87.008 | 31.586 | 1.00 | 18.86 | 8 |
| 5608 | OW0 | WAT | V | 157 | 27.471 | 54.562 | 13.822 | 1.00 | 18.93 | 8 |
| 5609 | OW0 | WAT | V | 158 | 19.938 | 85.031 | 32.888 | 1.00 | 18.77 | 8 |
| 5610 | OW0 | WAT | V | 160 | 23.159 | 58.927 | 72.012 | 1.00 | 19.01 | 8 |
| 5611 | OW0 | WAT | V | 161 | 20.470 | 84.773 | 18.243 | 1.00 | 19.09 | 8 |
| 5612 | OW0 | WAT | V | 162 | 15.077 | 66.831 | 13.792 | 1.00 | 18.88 | 8 |
| 5613 | OW0 | WAT | V | 164 | 34.016 | 76.548 | 58.886 | 1.00 | 19.18 | 8 |
| 5614 | OW0 | WAT | V | 165 | 1.791 | 96.077 | 35.490 | 1.00 | 19.39 | 8 |
| 5615 | OW0 | WAT | V | 168 | 16.921 | 65.681 | 50.173 | 1.00 | 19.74 | 8 |
| 5616 | OW0 | WAT | V | 169 | 36.015 | 49.508 | 63.823 | 1.00 | 19.75 | 8 |
| 5617 | OW0 | WAT | V | 170 | 19.146 | 93.639 | 20.716 | 1.00 | 19.72 | 8 |
| 5618 | OW0 | WAT | V | 171 | 41.081 | 74.262 | 43.114 | 1.00 | 19.99 | 8 |
| 5619 | OW0 | WAT | V | 172 | 27.356 | 86.834 | 41.150 | 1.00 | 19.86 | 8 |
| 5620 | OW0 | WAT | V | 173 | 32.541 | 61.241 | 6.239 | 1.00 | 19.49 | 8 |
| 5621 | OW0 | WAT | V | 174 | 51.971 | 65.011 | 17.317 | 1.00 | 20.07 | 8 |
| 5622 | OW0 | WAT | V | 175 | 36.754 | 79.161 | 49.332 | 1.00 | 19.96 | 8 |
| 5623 | OW0 | WAT | V | 176 | 21.529 | 68.516 | 52.600 | 1.00 | 19.88 | 8 |
| 5624 | OW0 | WAT | V | 177 | 52.175 | 64.476 | 48.627 | 1.00 | 19.48 | 8 |
| 5625 | OW0 | WAT | V | 178 | 47.687 | 55.894 | 28.556 | 1.00 | 19.85 | 8 |
| 5626 | OW0 | WAT | V | 180 | 28.309 | 57.733 | 12.302 | 1.00 | 19.86 | 8 |
| 5627 | OW0 | WAT | V | 181 | 19.852 | 88.585 | 39.017 | 1.00 | 20.03 | 8 |
| 5628 | OW0 | WAT | V | 182 | 48.116 | 65.053 | 11.253 | 1.00 | 19.75 | 8 |
| 5629 | OW0 | WAT | V | 183 | 45.728 | 49.401 | 46.755 | 1.00 | 20.07 | 8 |
| 5630 | OW0 | WAT | V | 184 | 23.090 | 51.403 | 56.173 | 1.00 | 19.76 | 8 |
| 5631 | OW0 | WAT | V | 185 | 23.972 | 69.604 | 53.226 | 1.00 | 20.10 | 8 |
| 5632 | OW0 | WAT | V | 186 | 49.679 | 65.500 | 55.245 | 1.00 | 19.98 | 8 |
| 5633 | OW0 | WAT | V | 187 | 50.720 | 57.388 | 48.688 | 1.00 | 20.39 | 8 |
| 5634 | OW0 | WAT | V | 188 | 34.857 | 63.152 | 38.228 | 1.00 | 20.23 | 8 |
| 5635 | OW0 | WAT | V | 189 | 37.511 | 43.029 | 19.233 | 1.00 | 20.32 | 8 |
| 5636 | OW0 | WAT | V | 190 | 50.567 | 67.974 | 10.449 | 1.00 | 20.64 | 8 |
| 5637 | OW0 | WAT | V | 191 | 29.875 | 92.014 | 24.922 | 1.00 | 20.34 | 8 |

TABLE 1-continued

Atom Coordinates from the Crystal Structure of NOVAMYL

| 5638 | OW0 | WAT | V | 192 | 4.055 | 100.811 | 36.567 | 1.00 | 20.35 | 8 |
|---|---|---|---|---|---|---|---|---|---|---|
| 5639 | OW0 | WAT | V | 194 | 23.592 | 87.859 | 32.780 | 1.00 | 20.02 | 8 |
| 5640 | OW0 | WAT | V | 195 | 43.898 | 69.204 | 9.296 | 1.00 | 20.35 | 8 |
| 5641 | OW0 | WAT | V | 196 | 17.503 | 91.553 | 19.944 | 1.00 | 20.36 | 8 |
| 5642 | OW0 | WAT | V | 197 | 22.079 | 71.014 | 56.203 | 1.00 | 20.50 | 8 |
| 5643 | OW0 | WAT | V | 198 | 24.611 | 90.278 | 32.659 | 1.00 | 20.71 | 8 |
| 5644 | OW0 | WAT | V | 199 | 15.822 | 79.667 | 34.285 | 1.00 | 20.71 | 8 |
| 5645 | OW0 | WAT | V | 200 | 41.507 | 64.519 | 35.769 | 1.00 | 20.47 | 8 |
| 5646 | OW0 | WAT | V | 201 | 50.582 | 63.510 | 21.444 | 1.00 | 20.44 | 8 |
| 5647 | OW0 | WAT | V | 202 | −4.254 | 88.781 | 28.481 | 1.00 | 20.69 | 8 |
| 5648 | OW0 | WAT | V | 203 | 41.289 | 48.120 | 25.349 | 1.00 | 20.50 | 8 |
| 5649 | OW0 | WAT | V | 204 | 33.838 | 47.522 | 55.491 | 1.00 | 20.42 | 8 |
| 5650 | OW0 | WAT | V | 205 | 28.696 | 42.611 | 30.481 | 1.00 | 21.10 | 8 |
| 5651 | OW0 | WAT | V | 206 | 29.680 | 89.479 | 34.207 | 1.00 | 20.71 | 8 |
| 5652 | OW0 | WAT | V | 207 | 13.375 | 82.989 | 38.528 | 1.00 | 20.79 | 8 |
| 5653 | OW0 | WAT | V | 208 | −0.381 | 94.652 | 35.925 | 1.00 | 20.71 | 8 |
| 5654 | OW0 | WAT | V | 209 | 32.894 | 53.249 | 7.401 | 1.00 | 20.79 | 8 |
| 5655 | OW0 | WAT | V | 210 | 47.202 | 71.009 | 63.961 | 1.00 | 20.83 | 8 |
| 5656 | OW0 | WAT | V | 211 | 16.432 | 73.589 | 49.935 | 1.00 | 20.64 | 8 |
| 5657 | OW0 | WAT | V | 212 | 34.761 | 42.123 | 23.718 | 1.00 | 20.49 | 8 |
| 5658 | OW0 | WAT | V | 213 | 1.326 | 98.176 | 25.977 | 1.00 | 21.14 | 8 |
| 5659 | OW0 | WAT | V | 215 | 32.369 | 84.143 | 13.694 | 1.00 | 21.27 | 8 |
| 5660 | OW0 | WAT | V | 216 | 1.000 | 72.006 | 27.168 | 1.00 | 21.23 | 8 |
| 5661 | OW0 | WAT | V | 217 | 21.907 | 50.669 | 62.000 | 1.00 | 21.19 | 8 |
| 5662 | OW0 | WAT | V | 218 | 30.956 | 41.738 | 21.314 | 1.00 | 21.03 | 8 |
| 5663 | OW0 | WAT | V | 219 | 36.121 | 71.463 | 4.684 | 1.00 | 21.46 | 8 |
| 5664 | OW0 | WAT | V | 220 | 13.404 | 81.016 | 34.970 | 1.00 | 21.65 | 8 |
| 5665 | OW0 | WAT | V | 221 | 22.957 | 65.844 | 62.604 | 1.00 | 21.35 | 8 |
| 5666 | OW0 | WAT | V | 222 | 4.260 | 99.337 | 39.649 | 1.00 | 21.63 | 8 |
| 5667 | OW0 | WAT | V | 223 | 17.535 | 84.263 | 32.555 | 1.00 | 20.98 | 8 |
| 5668 | OW0 | WAT | V | 224 | 16.496 | 59.065 | 45.746 | 1.00 | 21.66 | 8 |
| 5669 | OW0 | WAT | V | 225 | 16.576 | 52.574 | 34.164 | 1.00 | 21.65 | 8 |
| 5670 | OW0 | WAT | V | 226 | 30.825 | 51.406 | 13.432 | 1.00 | 21.28 | 8 |
| 5671 | OW0 | WAT | V | 227 | 39.177 | 82.848 | 23.121 | 1.00 | 21.63 | 8 |
| 5672 | OW0 | WAT | V | 229 | 19.109 | 58.790 | 36.143 | 1.00 | 21.40 | 8 |
| 5673 | OW0 | WAT | V | 230 | 19.087 | 75.378 | 50.063 | 1.00 | 21.22 | 8 |
| 5674 | OW0 | WAT | V | 231 | 47.413 | 69.881 | 16.583 | 1.00 | 21.29 | 8 |
| 5675 | OW0 | WAT | V | 232 | 26.686 | 91.040 | 31.058 | 1.00 | 21.61 | 8 |
| 5676 | OW0 | WAT | V | 233 | 29.036 | 52.089 | 61.852 | 1.00 | 21.25 | 8 |
| 5677 | OW0 | WAT | V | 234 | 36.187 | 79.293 | 46.671 | 1.00 | 21.45 | 8 |
| 5678 | OW0 | WAT | V | 235 | 37.289 | 74.835 | 65.582 | 1.00 | 21.65 | 8 |
| 5679 | OW0 | WAT | V | 236 | −0.428 | 68.770 | 30.109 | 1.00 | 21.94 | 8 |
| 5680 | OW0 | WAT | V | 237 | 50.762 | 57.829 | 44.061 | 1.00 | 22.15 | 8 |
| 5681 | OW0 | WAT | V | 238 | 45.167 | 70.565 | 24.893 | 1.00 | 22.00 | 8 |
| 5682 | OW0 | WAT | V | 239 | 28.609 | 48.609 | 51.930 | 1.00 | 22.03 | 8 |
| 5683 | OW0 | WAT | V | 241 | 2.366 | 94.552 | 38.603 | 1.00 | 21.97 | 8 |
| 5684 | OW0 | WAT | V | 242 | 9.365 | 68.970 | 20.742 | 1.00 | 22.04 | 8 |
| 5685 | OW0 | WAT | V | 243 | 38.583 | 85.642 | 29.447 | 1.00 | 21.90 | 8 |
| 5686 | OW0 | WAT | V | 244 | 24.639 | 49.542 | 55.081 | 1.00 | 22.42 | 8 |
| 5687 | OW0 | WAT | V | 245 | 18.177 | 95.474 | 18.838 | 1.00 | 22.69 | 8 |
| 5688 | OW0 | WAT | V | 246 | 37.307 | 43.276 | 33.862 | 1.00 | 22.90 | 8 |
| 5689 | OW0 | WAT | V | 247 | 23.478 | 86.290 | 16.425 | 1.00 | 21.85 | 8 |
| 5690 | OW0 | WAT | V | 248 | 43.569 | 60.466 | 72.156 | 1.00 | 23.10 | 8 |
| 5691 | OW0 | WAT | V | 249 | 23.281 | 40.658 | 26.691 | 1.00 | 22.77 | 8 |
| 5692 | OW0 | WAT | V | 250 | 8.761 | 65.837 | 24.376 | 1.00 | 23.00 | 8 |
| 5693 | OW0 | WAT | V | 251 | 27.215 | 72.803 | 60.509 | 1.00 | 22.60 | 8 |
| 5694 | OW0 | WAT | V | 252 | 16.174 | 91.014 | 44.772 | 1.00 | 22.53 | 8 |
| 5695 | OW0 | WAT | V | 253 | 3.297 | 98.395 | 35.969 | 1.00 | 23.15 | 8 |
| 5696 | OW0 | WAT | V | 254 | 10.918 | 68.974 | 53.447 | 1.00 | 23.22 | 8 |
| 5697 | OW0 | WAT | V | 255 | −5.802 | 66.167 | 37.375 | 1.00 | 23.15 | 8 |
| 5698 | OW0 | WAT | V | 256 | 8.490 | 91.603 | 44.099 | 1.00 | 22.65 | 8 |
| 5699 | OW0 | WAT | V | 257 | 9.234 | 73.507 | 16.552 | 1.00 | 22.92 | 8 |
| 5700 | OW0 | WAT | V | 258 | 15.730 | 56.257 | 16.556 | 1.00 | 23.08 | 8 |
| 5701 | OW0 | WAT | V | 259 | 19.989 | 82.268 | 13.713 | 1.00 | 22.90 | 8 |
| 5702 | OW0 | WAT | V | 260 | 27.613 | 49.792 | 60.562 | 1.00 | 23.09 | 8 |
| 5703 | OW0 | WAT | V | 261 | 26.408 | 61.061 | 10.006 | 1.00 | 23.11 | 8 |
| 5704 | OW0 | WAT | V | 262 | 14.277 | 70.834 | 12.781 | 1.00 | 23.32 | 8 |
| 5705 | OW0 | WAT | V | 263 | −3.969 | 72.948 | 34.601 | 1.00 | 22.98 | 8 |
| 5706 | OW0 | WAT | V | 264 | −1.028 | 93.829 | 38.475 | 1.00 | 23.17 | 8 |
| 5707 | OW0 | WAT | V | 265 | 19.230 | 101.476 | 27.805 | 1.00 | 22.95 | 8 |
| 5708 | OW0 | WAT | V | 266 | 17.914 | 54.281 | 55.523 | 1.00 | 23.31 | 8 |
| 5709 | OW0 | WAT | V | 267 | −1.163 | 64.024 | 50.895 | 1.00 | 23.41 | 8 |
| 5710 | OW0 | WAT | V | 268 | 16.209 | 48.607 | 29.481 | 1.00 | 23.45 | 8 |
| 5711 | OW0 | WAT | V | 269 | 35.070 | 63.595 | 75.008 | 1.00 | 23.90 | 8 |
| 5712 | OW0 | WAT | V | 270 | 38.343 | 43.626 | 21.918 | 1.00 | 23.33 | 8 |
| 5713 | OW0 | WAT | V | 271 | 32.197 | 85.153 | 37.181 | 1.00 | 23.49 | 8 |
| 5714 | OW0 | WAT | V | 272 | 28.789 | 71.419 | 66.331 | 1.00 | 22.79 | 8 |

TABLE 1-continued

Atom Coordinates from the Crystal Structure of NOVAMYL

| 5715 | OW0 | WAT | V | 273 | 41.806 | 79.697 | 18.591 | 1.00 | 23.39 | 8 |
|---|---|---|---|---|---|---|---|---|---|---|
| 5716 | OW0 | WAT | V | 274 | 38.127 | 43.105 | 36.443 | 1.00 | 23.39 | 8 |
| 5717 | OW0 | WAT | V | 275 | 16.104 | 65.021 | 59.364 | 1.00 | 23.44 | 8 |
| 5718 | OW0 | WAT | V | 276 | -6.314 | 69.710 | 39.367 | 1.00 | 24.17 | 8 |
| 5719 | OW0 | WAT | V | 277 | 25.476 | 86.458 | 13.742 | 1.00 | 23.04 | 8 |
| 5720 | OW0 | WAT | V | 278 | 0.680 | 86.883 | 37.755 | 1.00 | 23.27 | 8 |
| 5721 | OW0 | WAT | V | 279 | 33.015 | 81.157 | 29.976 | 1.00 | 23.30 | 8 |
| 5722 | OW0 | WAT | V | 280 | 1.763 | 88.744 | 19.524 | 1.00 | 23.68 | 8 |
| 5723 | OW0 | WAT | V | 281 | 13.574 | 55.293 | 46.773 | 1.00 | 23.63 | 8 |
| 5724 | OW0 | WAT | V | 282 | 13.480 | 62.142 | 18.325 | 1.00 | 23.48 | 8 |
| 5725 | OW0 | WAT | V | 283 | 19.332 | 56.925 | 43.429 | 1.00 | 23.84 | 8 |
| 5726 | OW0 | WAT | V | 284 | 7.117 | 53.127 | 42.902 | 1.00 | 23.57 | 8 |
| 5727 | OW0 | WAT | V | 285 | 27.829 | 78.220 | 46.852 | 1.00 | 24.20 | 8 |
| 5728 | OW0 | WAT | V | 286 | 49.295 | 57.105 | 51.124 | 1.00 | 23.77 | 8 |
| 5729 | OW0 | WAT | V | 287 | 13.680 | 105.356 | 27.022 | 1.00 | 24.03 | 8 |
| 5730 | OW0 | WAT | V | 288 | 17.824 | 106.639 | 32.939 | 1.00 | 24.44 | 8 |
| 5731 | OW0 | WAT | V | 289 | 15.542 | 66.715 | 53.507 | 1.00 | 24.42 | 8 |
| 5732 | OW0 | WAT | V | 290 | 27.050 | 47.324 | 23.573 | 1.00 | 24.19 | 8 |
| 5733 | OW0 | WAT | V | 291 | 39.482 | 73.577 | 31.816 | 1.00 | 24.19 | 8 |
| 5734 | OW0 | WAT | V | 292 | 10.356 | 77.638 | 16.052 | 1.00 | 23.96 | 8 |
| 5735 | OW0 | WAT | V | 293 | 24.405 | 50.730 | 63.252 | 1.00 | 24.31 | 8 |
| 5736 | OW0 | WAT | V | 294 | 15.639 | 54.776 | 31.091 | 1.00 | 24.31 | 8 |
| 5737 | OW0 | WAT | V | 295 | -5.196 | 74.449 | 41.013 | 1.00 | 24.22 | 8 |
| 5738 | OW0 | WAT | V | 296 | 40.985 | 72.335 | 29.872 | 1.00 | 24.55 | 8 |
| 5739 | OW0 | WAT | V | 297 | 48.449 | 77.051 | 18.858 | 1.00 | 24.18 | 8 |
| 5740 | OW0 | WAT | V | 298 | 25.992 | 92.521 | 26.784 | 1.00 | 24.84 | 8 |
| 5741 | OW0 | WAT | V | 299 | 45.814 | 49.306 | 39.112 | 1.00 | 24.65 | 8 |
| 5742 | OW0 | WAT | V | 300 | 44.725 | 55.968 | 11.440 | 1.00 | 24.94 | 8 |
| 5743 | OW0 | WAT | V | 301 | 20.058 | 84.809 | 46.357 | 1.00 | 24.73 | 8 |
| 5744 | OW0 | WAT | V | 302 | 18.079 | 50.984 | 17.334 | 1.00 | 24.58 | 8 |
| 5745 | OW0 | WAT | V | 303 | 17.020 | 65.666 | 56.879 | 1.00 | 24.81 | 8 |
| 5746 | OW0 | WAT | V | 304 | 44.682 | 72.661 | 22.319 | 1.00 | 24.66 | 8 |
| 5747 | OW0 | WAT | V | 305 | 0.091 | 75.457 | 45.401 | 1.00 | 24.37 | 8 |
| 5748 | OW0 | WAT | V | 306 | 50.222 | 58.393 | 53.380 | 1.00 | 24.90 | 8 |
| 5749 | OW0 | WAT | V | 307 | 44.639 | 52.674 | 53.486 | 1.00 | 25.29 | 8 |
| 5750 | OW0 | WAT | V | 308 | 49.725 | 64.827 | 52.493 | 1.00 | 24.60 | 8 |
| 5751 | OW0 | WAT | V | 309 | 39.542 | 61.118 | 7.698 | 1.00 | 24.82 | 8 |
| 5752 | OW0 | WAT | V | 310 | 41.190 | 79.148 | 23.073 | 1.00 | 25.15 | 8 |
| 5753 | OW0 | WAT | V | 311 | 1.598 | 80.899 | 39.623 | 1.00 | 24.95 | 8 |
| 5754 | OW0 | WAT | V | 312 | 25.053 | 45.139 | 19.817 | 1.00 | 24.92 | 8 |
| 5755 | OW0 | WAT | V | 313 | 16.135 | 84.191 | 47.663 | 1.00 | 25.20 | 8 |
| 5756 | OW0 | WAT | V | 314 | 11.381 | 71.857 | 49.110 | 1.00 | 25.29 | 8 |
| 5757 | OW0 | WAT | V | 315 | -4.512 | 57.278 | 42.326 | 1.00 | 25.43 | 8 |
| 5758 | OW0 | WAT | V | 316 | 3.805 | 93.061 | 22.790 | 1.00 | 25.09 | 8 |
| 5759 | OW0 | WAT | V | 317 | 34.832 | 82.782 | 37.221 | 1.00 | 25.16 | 8 |
| 5760 | OW0 | WAT | V | 318 | 3.711 | 95.706 | 23.179 | 1.00 | 25.31 | 8 |
| 5761 | OW0 | WAT | V | 319 | 20.209 | 70.499 | 54.469 | 1.00 | 25.69 | 8 |
| 5762 | OW0 | WAT | V | 320 | 11.697 | 68.339 | 56.789 | 1.00 | 25.01 | 8 |
| 5763 | OW0 | WAT | V | 321 | 7.254 | 91.019 | 18.448 | 1.00 | 25.40 | 8 |
| 5764 | OW0 | WAT | V | 322 | 42.661 | 49.979 | 21.111 | 1.00 | 25.81 | 8 |
| 5765 | OW0 | WAT | V | 323 | 17.078 | 70.892 | 50.293 | 1.00 | 25.51 | 8 |
| 5766 | OW0 | WAT | V | 324 | 49.200 | 60.915 | 31.600 | 1.00 | 25.53 | 8 |
| 5767 | OW0 | WAT | V | 325 | 31.661 | 71.214 | 4.552 | 1.00 | 25.64 | 8 |
| 5768 | OW0 | WAT | V | 326 | -2.062 | 96.310 | 27.990 | 1.00 | 25.87 | 8 |
| 5769 | OW0 | WAT | V | 327 | 39.125 | 80.230 | 56.164 | 1.00 | 26.25 | 8 |
| 5770 | OW0 | WAT | V | 328 | 48.433 | 70.294 | 57.525 | 1.00 | 25.87 | 8 |
| 5771 | OW0 | WAT | V | 329 | -2.772 | 64.990 | 34.941 | 1.00 | 25.71 | 8 |
| 5772 | OW0 | WAT | V | 330 | 35.352 | 40.001 | 22.353 | 1.00 | 25.96 | 8 |
| 5773 | OW0 | WAT | V | 331 | 34.557 | 81.627 | 46.792 | 1.00 | 26.23 | 8 |
| 5774 | OW0 | WAT | V | 332 | 23.250 | 92.581 | 31.676 | 1.00 | 26.20 | 8 |
| 5775 | OW0 | WAT | V | 333 | 23.167 | 53.251 | 13.715 | 1.00 | 25.74 | 8 |
| 5776 | OW0 | WAT | V | 334 | 20.707 | 52.356 | 39.202 | 1.00 | 25.65 | 8 |
| 5777 | OW0 | WAT | V | 335 | 4.870 | 93.727 | 41.264 | 1.00 | 26.54 | 8 |
| 5778 | OW0 | WAT | V | 336 | 0.053 | 71.401 | 29.885 | 1.00 | 25.67 | 8 |
| 5779 | OW0 | WAT | V | 337 | 20.015 | 56.517 | 72.324 | 1.00 | 25.86 | 8 |
| 5780 | OW0 | WAT | V | 338 | 13.826 | 74.132 | 49.507 | 1.00 | 26.36 | 8 |
| 5781 | OW0 | WAT | V | 339 | 44.958 | 71.632 | 28.685 | 1.00 | 26.80 | 8 |
| 5782 | OW0 | WAT | V | 340 | -0.093 | 73.784 | 33.119 | 1.00 | 26.07 | 8 |
| 5783 | OW0 | WAT | V | 341 | 49.630 | 56.579 | 40.106 | 1.00 | 26.64 | 8 |
| 5784 | OW0 | WAT | V | 342 | 15.628 | 79.186 | 45.524 | 1.00 | 26.42 | 8 |
| 5785 | OW0 | WAT | V | 343 | 31.176 | 91.867 | 30.769 | 1.00 | 26.10 | 8 |
| 5786 | OW0 | WAT | V | 344 | 15.626 | 67.643 | 55.543 | 1.00 | 26.46 | 8 |
| 5787 | OW0 | WAT | V | 345 | 21.398 | 95.678 | 38.839 | 1.00 | 26.79 | 8 |
| 5788 | OW0 | WAT | V | 346 | 41.099 | 41.982 | 39.915 | 1.00 | 26.66 | 8 |
| 5789 | OW0 | WAT | V | 347 | 22.442 | 79.888 | 2.661 | 1.00 | 26.18 | 8 |
| 5790 | OW0 | WAT | V | 348 | 44.448 | 72.532 | 39.099 | 1.00 | 27.08 | 8 |
| 5791 | OW0 | WAT | V | 349 | 40.265 | 82.719 | 10.175 | 1.00 | 26.27 | 8 |

TABLE 1-continued

Atom Coordinates from the Crystal Structure of NOVAMYL

| 5792 | OW0 | WAT | V | 350 | 40.934 | 43.657 | 30.662 | 1.00 | 27.04 | 8 |
|---|---|---|---|---|---|---|---|---|---|---|
| 5793 | OW0 | WAT | V | 351 | −1.666 | 97.213 | 32.163 | 1.00 | 27.31 | 8 |
| 5794 | OW0 | WAT | V | 352 | −8.111 | 67.221 | 45.293 | 1.00 | 27.12 | 8 |
| 5795 | OW0 | WAT | V | 353 | 16.355 | 56.614 | 42.471 | 1.00 | 27.10 | 8 |
| 5796 | OW0 | WAT | V | 354 | 11.346 | 65.531 | 19.934 | 1.00 | 27.40 | 8 |
| 5797 | OW0 | WAT | V | 355 | 11.189 | 105.275 | 21.949 | 1.00 | 27.29 | 8 |
| 5798 | OW0 | WAT | V | 356 | 23.545 | 83.502 | 8.615 | 1.00 | 27.06 | 8 |
| 5799 | OW0 | WAT | V | 357 | 22.122 | 49.913 | 14.384 | 1.00 | 27.06 | 8 |
| 5800 | OW0 | WAT | V | 358 | 6.833 | 52.668 | 34.000 | 1.00 | 27.79 | 8 |
| 5801 | OW0 | WAT | V | 359 | 30.479 | 47.598 | 56.666 | 1.00 | 27.66 | 8 |
| 5802 | OW0 | WAT | V | 360 | 33.166 | 42.826 | 19.802 | 1.00 | 27.33 | 8 |
| 5803 | OW0 | WAT | V | 361 | 24.029 | 55.851 | 13.947 | 1.00 | 28.08 | 8 |
| 5804 | OW0 | WAT | V | 362 | 39.488 | 85.709 | 20.632 | 1.00 | 27.01 | 8 |
| 5805 | OW0 | WAT | V | 363 | 2.130 | 49.916 | 43.049 | 1.00 | 27.26 | 8 |
| 5806 | OW0 | WAT | V | 364 | 35.616 | 41.373 | 27.626 | 1.00 | 27.13 | 8 |
| 5807 | OW0 | WAT | V | 365 | 50.664 | 58.560 | 41.450 | 1.00 | 26.59 | 8 |
| 5808 | OW0 | WAT | V | 366 | 30.943 | 49.068 | 15.778 | 1.00 | 26.98 | 8 |
| 5809 | OW0 | WAT | V | 367 | 43.193 | 44.166 | 34.878 | 1.00 | 26.97 | 8 |
| 5810 | OW0 | WAT | V | 368 | 6.994 | 74.430 | 21.876 | 1.00 | 27.26 | 8 |
| 5811 | OW0 | WAT | V | 369 | 34.427 | 88.111 | 38.939 | 1.00 | 27.30 | 8 |
| 5812 | OW0 | WAT | V | 370 | 1.636 | 93.582 | 40.791 | 1.00 | 27.54 | 8 |
| 5813 | OW0 | WAT | V | 371 | 5.971 | 98.241 | 21.504 | 1.00 | 27.42 | 8 |
| 5814 | OW0 | WAT | V | 372 | 29.223 | 75.038 | 60.445 | 1.00 | 26.93 | 8 |
| 5815 | OW0 | WAT | V | 373 | 31.316 | 53.650 | 9.481 | 1.00 | 27.85 | 8 |
| 5816 | OW0 | WAT | V | 374 | 43.939 | 56.548 | 55.050 | 1.00 | 27.63 | 8 |
| 5817 | OW0 | WAT | V | 375 | 46.559 | 74.427 | 54.610 | 1.00 | 27.46 | 8 |
| 5818 | OW0 | WAT | V | 376 | 26.961 | 70.400 | 70.205 | 1.00 | 28.10 | 8 |
| 5819 | OW0 | WAT | V | 377 | 48.989 | 57.080 | 35.445 | 1.00 | 28.37 | 8 |
| 5820 | OW0 | WAT | V | 378 | 14.950 | 47.050 | 27.899 | 1.00 | 27.90 | 8 |
| 5821 | OW0 | WAT | V | 379 | 46.760 | 46.713 | 39.616 | 1.00 | 27.67 | 8 |
| 5822 | OW0 | WAT | V | 380 | −1.380 | 79.896 | 38.771 | 1.00 | 28.02 | 8 |
| 5823 | OW0 | WAT | V | 381 | 12.690 | 81.625 | 15.826 | 1.00 | 28.03 | 8 |
| 5824 | OW0 | WAT | V | 382 | 10.617 | 104.039 | 32.646 | 1.00 | 28.19 | 8 |
| 5825 | OW0 | WAT | V | 383 | 13.859 | 80.594 | 13.625 | 1.00 | 27.99 | 8 |
| 5826 | OW0 | WAT | V | 384 | 7.322 | 72.231 | 20.822 | 1.00 | 28.35 | 8 |
| 5827 | OW0 | WAT | V | 385 | 29.284 | 46.632 | 44.658 | 1.00 | 28.26 | 8 |
| 5828 | OW0 | WAT | V | 386 | 18.064 | 50.559 | 24.862 | 1.00 | 28.35 | 8 |
| 5829 | OW0 | WAT | V | 387 | 35.054 | 45.412 | 46.835 | 1.00 | 28.58 | 8 |
| 5830 | OW0 | WAT | V | 388 | 22.478 | 83.558 | 13.277 | 1.00 | 28.32 | 8 |
| 5831 | OW0 | WAT | V | 389 | 10.928 | 67.510 | 14.236 | 1.00 | 28.65 | 8 |
| 5832 | OW0 | WAT | V | 390 | 33.397 | 82.246 | 49.220 | 1.00 | 27.37 | 8 |
| 5833 | OW0 | WAT | V | 391 | 23.434 | 88.556 | 18.508 | 1.00 | 28.95 | 8 |
| 5834 | OW0 | WAT | V | 392 | 29.832 | 42.212 | 39.251 | 1.00 | 28.21 | 8 |
| 5835 | OW0 | WAT | V | 393 | 15.076 | 70.102 | 51.758 | 1.00 | 27.91 | 8 |
| 5836 | OW0 | WAT | V | 394 | 35.566 | 48.453 | 66.263 | 1.00 | 28.16 | 8 |
| 5837 | OW0 | WAT | V | 395 | 34.691 | 46.594 | 49.301 | 1.00 | 28.85 | 8 |
| 5838 | OW0 | WAT | V | 396 | 39.702 | 74.440 | 36.238 | 1.00 | 28.77 | 8 |
| 5839 | OW0 | WAT | V | 397 | 50.176 | 56.086 | 14.851 | 1.00 | 28.75 | 8 |
| 5840 | OW0 | WAT | V | 398 | 14.115 | 57.834 | 59.211 | 1.00 | 27.83 | 8 |
| 5841 | OW0 | WAT | V | 399 | 38.189 | 49.702 | 11.383 | 1.00 | 29.29 | 8 |
| 5842 | OW0 | WAT | V | 400 | 3.241 | 100.941 | 39.033 | 1.00 | 28.47 | 8 |
| 5843 | OW0 | WAT | V | 401 | 44.298 | 73.510 | 63.099 | 1.00 | 28.91 | 8 |
| 5844 | OW0 | WAT | V | 402 | 7.061 | 75.135 | 47.544 | 1.00 | 28.59 | 8 |
| 5845 | OW0 | WAT | V | 403 | 5.477 | 86.910 | 42.452 | 1.00 | 29.56 | 8 |
| 5846 | OW0 | WAT | V | 404 | 25.564 | 72.515 | 56.246 | 1.00 | 29.09 | 8 |
| 5847 | OW0 | WAT | V | 405 | 25.075 | 41.160 | 32.189 | 1.00 | 29.20 | 8 |
| 5848 | OW0 | WAT | V | 406 | 2.074 | 56.387 | 58.854 | 1.00 | 28.86 | 8 |
| 5849 | OW0 | WAT | V | 407 | 47.163 | 58.038 | 33.355 | 1.00 | 28.76 | 8 |
| 5850 | OW0 | WAT | V | 408 | 27.438 | 44.407 | 21.116 | 1.00 | 28.21 | 8 |
| 5851 | OW0 | WAT | V | 409 | 32.690 | 89.765 | 34.445 | 1.00 | 29.13 | 8 |
| 5852 | OW0 | WAT | V | 410 | 8.726 | 56.984 | 33.875 | 1.00 | 28.81 | 8 |
| 5853 | OW0 | WAT | V | 411 | −2.765 | 74.847 | 45.763 | 1.00 | 28.58 | 8 |
| 5854 | OW0 | WAT | V | 412 | 9.880 | 76.028 | 48.593 | 1.00 | 29.43 | 8 |
| 5855 | OW0 | WAT | V | 413 | 18.587 | 55.405 | 41.191 | 1.00 | 28.66 | 8 |
| 5856 | OW0 | WAT | V | 414 | 0.831 | 95.595 | 23.928 | 1.00 | 28.90 | 8 |
| 5857 | OW0 | WAT | V | 415 | 18.167 | 58.042 | 65.360 | 1.00 | 28.57 | 8 |
| 5858 | OW0 | WAT | V | 416 | 42.814 | 47.661 | 27.620 | 1.00 | 29.34 | 8 |
| 5859 | OW0 | WAT | V | 417 | 19.226 | 89.316 | 19.020 | 1.00 | 29.13 | 8 |
| 5860 | OW0 | WAT | V | 418 | 17.933 | 82.283 | 11.952 | 1.00 | 28.48 | 8 |
| 5861 | OW0 | WAT | V | 419 | 44.723 | 79.313 | 13.493 | 1.00 | 30.12 | 8 |
| 5862 | OW0 | WAT | V | 420 | 34.399 | 78.316 | 0.819 | 1.00 | 29.81 | 8 |
| 5863 | OW0 | WAT | V | 421 | 28.282 | 72.460 | 57.888 | 1.00 | 29.12 | 8 |
| 5864 | OW0 | WAT | V | 422 | 50.448 | 63.547 | 18.793 | 1.00 | 29.31 | 8 |
| 5865 | OW0 | WAT | V | 423 | 43.033 | 55.323 | 65.913 | 1.00 | 29.32 | 8 |
| 5866 | OW0 | WAT | V | 424 | 45.865 | 51.168 | 51.498 | 1.00 | 29.29 | 8 |
| 5867 | OW0 | WAT | V | 425 | 12.844 | 59.751 | 19.386 | 1.00 | 29.45 | 8 |
| 5868 | OW0 | WAT | V | 426 | −3.707 | 82.697 | 22.959 | 1.00 | 29.58 | 8 |

TABLE 1-continued

Atom Coordinates from the Crystal Structure of NOVAMYL

| 5869 | OW0 | WAT | V | 427 | 28.989 | 45.171 | 18.941 | 1.00 | 29.97 | 8 |
|---|---|---|---|---|---|---|---|---|---|---|
| 5870 | OW0 | WAT | V | 428 | 14.689 | 65.149 | 11.472 | 1.00 | 29.76 | 8 |
| 5871 | OW0 | WAT | V | 429 | 49.962 | 74.061 | 53.225 | 1.00 | 29.59 | 8 |
| 5872 | OW0 | WAT | V | 430 | 26.674 | 46.428 | 17.647 | 1.00 | 29.59 | 8 |
| 5873 | OW0 | WAT | V | 431 | 32.017 | 64.281 | 73.846 | 1.00 | 29.67 | 8 |
| 5874 | OW0 | WAT | V | 432 | −1.685 | 89.735 | 36.396 | 1.00 | 29.42 | 8 |
| 5875 | OW0 | WAT | V | 433 | 35.326 | 90.671 | 32.858 | 1.00 | 30.08 | 8 |
| 5876 | OW0 | WAT | V | 434 | −5.217 | 86.519 | 22.737 | 1.00 | 30.64 | 8 |
| 5877 | OW0 | WAT | V | 435 | 22.655 | 40.619 | 31.468 | 1.00 | 30.18 | 8 |
| 5878 | OW0 | WAT | V | 436 | 9.970 | 66.686 | 21.940 | 1.00 | 30.16 | 8 |
| 5879 | OW0 | WAT | V | 437 | 22.156 | 103.267 | 41.579 | 1.00 | 28.97 | 8 |
| 5880 | OW0 | WAT | V | 438 | 40.919 | 45.553 | 23.996 | 1.00 | 30.13 | 8 |
| 5881 | OW0 | WAT | V | 439 | 24.378 | 42.994 | 18.498 | 1.00 | 30.29 | 8 |
| 5882 | OW0 | WAT | V | 440 | 27.456 | 90.485 | 38.760 | 1.00 | 29.87 | 8 |
| 5883 | OW0 | WAT | V | 441 | 41.628 | 78.372 | 57.406 | 1.00 | 30.24 | 8 |
| 5884 | OW0 | WAT | V | 442 | 10.162 | 67.365 | 58.879 | 1.00 | 30.51 | 8 |
| 5885 | OW0 | WAT | V | 443 | 7.899 | 70.258 | 55.642 | 1.00 | 29.98 | 8 |
| 5886 | OW0 | WAT | V | 444 | 7.439 | 62.721 | 58.664 | 1.00 | 30.04 | 8 |
| 5887 | OW0 | WAT | V | 445 | 30.182 | 60.296 | 5.170 | 1.00 | 30.62 | 8 |
| 5888 | OW0 | WAT | V | 446 | 36.835 | 87.065 | 16.010 | 1.00 | 30.22 | 8 |
| 5889 | OW0 | WAT | V | 447 | 48.154 | 58.076 | 55.789 | 1.00 | 30.39 | 8 |
| 5890 | OW0 | WAT | V | 448 | 9.079 | 102.838 | 38.708 | 1.00 | 30.45 | 8 |
| 5891 | OW0 | WAT | V | 449 | 31.488 | 67.009 | 5.903 | 1.00 | 30.35 | 8 |
| 5892 | OW0 | WAT | V | 450 | 8.486 | 84.645 | 16.251 | 1.00 | 30.46 | 8 |
| 5893 | OW0 | WAT | V | 451 | 17.712 | 70.200 | 52.856 | 1.00 | 31.30 | 8 |
| 5894 | OW0 | WAT | V | 452 | 45.187 | 54.640 | 9.218 | 1.00 | 30.47 | 8 |
| 5895 | OW0 | WAT | V | 453 | 23.220 | 65.098 | 2.001 | 1.00 | 30.15 | 8 |
| 5896 | OW0 | WAT | V | 454 | 43.353 | 48.993 | 23.792 | 1.00 | 30.21 | 8 |
| 5897 | OW0 | WAT | V | 455 | 0.241 | 76.716 | 42.809 | 1.00 | 30.43 | 8 |
| 5898 | OW0 | WAT | V | 456 | 38.954 | 90.362 | 25.885 | 1.00 | 31.19 | 8 |
| 5899 | OW0 | WAT | V | 457 | 8.998 | 51.618 | 42.193 | 1.00 | 30.65 | 8 |
| 5900 | OW0 | WAT | V | 458 | 47.484 | 70.509 | 20.484 | 1.00 | 30.75 | 8 |
| 5901 | OW0 | WAT | V | 459 | 26.632 | 83.732 | 7.006 | 1.00 | 30.86 | 8 |
| 5902 | OW0 | WAT | V | 460 | 27.887 | 84.031 | 46.702 | 1.00 | 31.16 | 8 |
| 5903 | OW0 | WAT | V | 461 | 10.456 | 52.659 | 39.931 | 1.00 | 31.37 | 8 |
| 5904 | OW0 | WAT | V | 462 | 25.474 | 53.247 | 11.551 | 1.00 | 31.54 | 8 |
| 5905 | OW0 | WAT | V | 463 | 21.666 | 48.674 | 41.178 | 1.00 | 31.71 | 8 |
| 5906 | OW0 | WAT | V | 464 | 51.799 | 63.643 | 37.234 | 1.00 | 30.69 | 8 |
| 5907 | OW0 | WAT | V | 465 | 17.686 | 48.668 | 36.134 | 1.00 | 31.38 | 8 |
| 5908 | OW0 | WAT | V | 466 | 47.081 | 52.951 | 49.717 | 1.00 | 30.51 | 8 |
| 5909 | OW0 | WAT | V | 467 | 15.593 | 93.203 | 42.768 | 1.00 | 30.90 | 8 |
| 5910 | OW0 | WAT | V | 468 | 36.480 | 80.071 | 53.771 | 1.00 | 30.56 | 8 |
| 5911 | OW0 | WAT | V | 469 | 42.137 | 47.781 | 14.882 | 1.00 | 31.85 | 8 |
| 5912 | OW0 | WAT | V | 470 | 22.333 | 61.351 | 70.096 | 1.00 | 31.36 | 8 |
| 5913 | OW0 | WAT | V | 471 | 40.228 | 72.527 | 72.095 | 1.00 | 31.17 | 8 |
| 5914 | OW0 | WAT | V | 472 | 1.666 | 74.527 | 48.132 | 1.00 | 31.28 | 8 |
| 5915 | OW0 | WAT | V | 473 | 14.531 | 66.936 | 59.718 | 1.00 | 31.26 | 8 |
| 5916 | OW0 | WAT | V | 474 | 21.000 | 68.421 | 1.879 | 1.00 | 31.59 | 8 |
| 5917 | OW0 | WAT | V | 475 | 37.163 | 82.170 | 41.385 | 1.00 | 31.32 | 8 |
| 5918 | OW0 | WAT | V | 476 | 26.307 | 62.094 | 4.445 | 1.00 | 31.75 | 8 |
| 5919 | OW0 | WAT | V | 477 | 51.579 | 61.409 | 40.641 | 1.00 | 31.25 | 8 |
| 5920 | OW0 | WAT | V | 478 | 41.761 | 64.533 | 7.578 | 1.00 | 31.59 | 8 |
| 5921 | OW0 | WAT | V | 479 | −7.353 | 65.632 | 35.219 | 1.00 | 31.13 | 8 |
| 5922 | OW0 | WAT | V | 480 | 16.514 | 82.720 | 36.237 | 1.00 | 31.25 | 8 |
| 5923 | OW0 | WAT | V | 481 | 23.770 | 75.891 | 54.586 | 1.00 | 31.53 | 8 |
| 5924 | OW0 | WAT | V | 482 | 50.377 | 68.458 | 56.245 | 1.00 | 31.72 | 8 |
| 5925 | OW0 | WAT | V | 483 | 15.979 | 105.053 | 38.501 | 1.00 | 30.98 | 8 |
| 5926 | OW0 | WAT | V | 484 | 27.194 | 93.867 | 31.829 | 1.00 | 31.85 | 8 |
| 5927 | OW0 | WAT | V | 485 | 39.487 | 68.664 | 5.438 | 1.00 | 31.02 | 8 |
| 5928 | OW0 | WAT | V | 486 | 30.446 | 58.438 | 75.573 | 1.00 | 31.49 | 8 |
| 5929 | OW0 | WAT | V | 487 | −2.258 | 85.349 | 34.418 | 1.00 | 31.74 | 8 |
| 5930 | OW0 | WAT | V | 488 | 46.873 | 56.769 | 65.770 | 1.00 | 31.57 | 8 |
| 5931 | OW0 | WAT | V | 489 | 18.407 | 47.617 | 19.229 | 1.00 | 31.61 | 8 |
| 5932 | OW0 | WAT | V | 490 | 2.500 | 78.686 | 43.392 | 1.00 | 31.62 | 8 |
| 5933 | OW0 | WAT | V | 491 | 7.727 | 97.913 | 42.497 | 1.00 | 32.36 | 8 |
| 5934 | OW0 | WAT | V | 492 | −5.430 | 71.658 | 30.991 | 1.00 | 32.45 | 8 |
| 5935 | OW0 | WAT | V | 493 | 47.547 | 72.958 | 21.222 | 1.00 | 31.57 | 8 |
| 5936 | OW0 | WAT | V | 494 | 9.955 | 91.961 | 24.393 | 1.00 | 32.43 | 8 |
| 5937 | OW0 | WAT | V | 495 | 12.996 | 52.420 | 46.232 | 1.00 | 31.76 | 8 |
| 5938 | OW0 | WAT | V | 496 | 7.952 | 65.594 | 58.841 | 1.00 | 32.02 | 8 |
| 5939 | OW0 | WAT | V | 497 | 37.204 | 88.789 | 33.415 | 1.00 | 31.57 | 8 |
| 5940 | OW0 | WAT | V | 498 | 36.857 | 41.938 | 29.865 | 1.00 | 32.38 | 8 |
| 5941 | OW0 | WAT | V | 499 | 7.220 | 51.844 | 54.727 | 1.00 | 32.32 | 8 |
| 5942 | OW0 | WAT | V | 500 | 16.110 | 76.377 | 49.777 | 1.00 | 32.31 | 8 |
| 5943 | OW0 | WAT | V | 501 | 24.511 | 47.736 | 42.135 | 1.00 | 32.37 | 8 |
| 5944 | OW0 | WAT | V | 502 | 22.783 | 46.357 | 48.051 | 1.00 | 32.64 | 8 |
| 5945 | OW0 | WAT | V | 503 | 27.138 | 60.897 | 7.569 | 1.00 | 32.20 | 8 |

TABLE 1-continued

Atom Coordinates from the Crystal Structure of NOVAMYL

| 5946 | OW0 | WAT | V | 504 | 47.227 | 50.290 | 36.850 | 1.00 | 32.13 | 8 |
|---|---|---|---|---|---|---|---|---|---|---|
| 5947 | OW0 | WAT | V | 505 | 6.733 | 67.493 | 23.991 | 1.00 | 32.68 | 8 |
| 5948 | OW0 | WAT | V | 506 | 16.514 | 70.176 | 56.941 | 1.00 | 32.03 | 8 |
| 5949 | OW0 | WAT | V | 507 | 43.175 | 79.662 | 8.514 | 1.00 | 31.76 | 8 |
| 5950 | OW0 | WAT | V | 508 | −3.757 | 80.394 | 22.899 | 1.00 | 32.62 | 8 |
| 5951 | OW0 | WAT | V | 509 | 10.932 | 85.936 | 45.262 | 1.00 | 32.65 | 8 |
| 5952 | OW0 | WAT | V | 510 | 3.455 | 97.650 | 41.755 | 1.00 | 32.31 | 8 |
| 5953 | OW0 | WAT | V | 511 | 33.419 | 50.551 | 69.455 | 1.00 | 32.14 | 8 |
| 5954 | OW0 | WAT | V | 512 | 4.069 | 99.962 | 23.550 | 1.00 | 33.21 | 8 |
| 5955 | OW0 | WAT | V | 513 | −7.206 | 65.717 | 41.690 | 1.00 | 33.20 | 8 |
| 5956 | OW0 | WAT | V | 514 | 53.785 | 60.262 | 61.406 | 1.00 | 33.37 | 8 |
| 5957 | OW0 | WAT | V | 515 | 16.599 | 87.045 | 17.346 | 1.00 | 32.99 | 8 |
| 5958 | OW0 | WAT | V | 516 | 47.349 | 54.074 | 30.752 | 1.00 | 32.14 | 8 |
| 5959 | OW0 | WAT | V | 517 | 7.038 | 85.163 | 42.409 | 1.00 | 32.78 | 8 |
| 5960 | OW0 | WAT | V | 518 | 16.879 | 50.503 | 27.538 | 1.00 | 32.69 | 8 |
| 5961 | OW0 | WAT | V | 519 | 30.838 | 91.776 | 22.385 | 1.00 | 33.06 | 8 |
| 5962 | OW0 | WAT | V | 520 | 33.882 | 41.296 | 32.218 | 1.00 | 34.59 | 8 |
| 5963 | OW0 | WAT | V | 521 | 53.502 | 60.512 | 23.358 | 1.00 | 32.27 | 8 |
| 5964 | OW0 | WAT | V | 522 | 41.841 | 73.003 | 34.316 | 1.00 | 33.63 | 8 |
| 5965 | OW0 | WAT | V | 523 | 18.807 | 69.394 | 5.371 | 1.00 | 32.65 | 8 |
| 5966 | OW0 | WAT | V | 524 | 0.567 | 102.365 | 27.670 | 1.00 | 32.87 | 8 |
| 5967 | OW0 | WAT | V | 525 | 28.899 | 48.822 | 64.451 | 1.00 | 32.62 | 8 |
| 5968 | OW0 | WAT | V | 526 | 42.766 | 46.627 | 21.339 | 1.00 | 33.04 | 8 |
| 5969 | OW0 | WAT | V | 527 | 18.159 | 66.472 | 60.034 | 1.00 | 33.02 | 8 |
| 5970 | OW0 | WAT | V | 528 | 22.385 | 49.518 | 59.427 | 1.00 | 33.48 | 8 |
| 5971 | OW0 | WAT | V | 529 | 14.542 | 53.899 | 35.438 | 1.00 | 32.40 | 8 |
| 5972 | OW0 | WAT | V | 530 | 0.923 | 81.260 | 18.821 | 1.00 | 33.19 | 8 |
| 5973 | OW0 | WAT | V | 531 | 35.980 | 91.602 | 25.073 | 1.00 | 32.89 | 8 |
| 5974 | OW0 | WAT | V | 532 | 40.667 | 67.024 | 71.313 | 1.00 | 32.79 | 8 |
| 5975 | OW0 | WAT | V | 533 | 8.626 | 61.294 | 60.713 | 1.00 | 32.69 | 8 |
| 5976 | OW0 | WAT | V | 534 | 35.615 | 48.266 | 53.410 | 1.00 | 33.74 | 8 |
| 5977 | OW0 | WAT | V | 535 | 50.581 | 54.379 | 41.752 | 1.00 | 32.75 | 8 |
| 5978 | OW0 | WAT | V | 536 | 34.738 | 50.213 | 7.372 | 1.00 | 33.68 | 8 |
| 5979 | OW0 | WAT | V | 537 | 42.324 | 79.266 | 54.340 | 1.00 | 32.72 | 8 |
| 5980 | OW0 | WAT | V | 538 | 16.132 | 78.441 | 8.864 | 1.00 | 33.64 | 8 |
| 5981 | OW0 | WAT | V | 539 | 20.256 | 45.911 | 20.702 | 1.00 | 33.89 | 8 |
| 5982 | OW0 | WAT | V | 540 | 37.253 | 43.882 | 46.170 | 1.00 | 33.73 | 8 |
| 5983 | OW0 | WAT | V | 541 | 31.158 | 88.960 | 12.651 | 1.00 | 34.15 | 8 |
| 5984 | OW0 | WAT | V | 542 | 2.885 | 65.252 | 30.182 | 1.00 | 33.66 | 8 |
| 5985 | OW0 | WAT | V | 543 | 24.093 | 72.008 | 54.068 | 1.00 | 33.53 | 8 |
| 5986 | OW0 | WAT | V | 544 | −4.660 | 58.902 | 52.534 | 1.00 | 34.13 | 8 |
| 5987 | OW0 | WAT | V | 545 | 20.523 | 52.571 | 71.335 | 1.00 | 34.29 | 8 |
| 5988 | OW0 | WAT | V | 546 | 50.389 | 70.373 | 43.120 | 1.00 | 34.05 | 8 |
| 5989 | OW0 | WAT | V | 547 | −1.784 | 74.917 | 34.717 | 1.00 | 34.27 | 8 |
| 5990 | OW0 | WAT | V | 548 | 25.051 | 100.468 | 31.517 | 1.00 | 33.73 | 8 |
| 5991 | OW0 | WAT | V | 549 | 21.989 | 83.148 | 46.194 | 1.00 | 34.71 | 8 |
| 5992 | OW0 | WAT | V | 550 | 47.521 | 62.364 | 11.718 | 1.00 | 34.05 | 8 |
| 5993 | OW0 | WAT | V | 551 | 52.236 | 59.305 | 62.786 | 1.00 | 33.21 | 8 |
| 5994 | OW0 | WAT | V | 552 | 40.232 | 80.510 | 16.448 | 1.00 | 34.62 | 8 |
| 5995 | OW0 | WAT | V | 553 | 46.253 | 56.949 | 70.930 | 1.00 | 33.53 | 8 |
| 5996 | OW0 | WAT | V | 554 | 47.895 | 53.053 | 37.454 | 1.00 | 33.41 | 8 |
| 5997 | OW0 | WAT | V | 555 | 13.358 | 71.030 | 49.662 | 1.00 | 34.43 | 8 |
| 5998 | OW0 | WAT | V | 556 | −0.137 | 73.990 | 26.087 | 1.00 | 34.05 | 8 |
| 5999 | OW0 | WAT | V | 557 | 43.973 | 74.382 | 6.399 | 1.00 | 34.44 | 8 |
| 6000 | OW0 | WAT | V | 558 | 35.593 | 60.367 | 77.022 | 1.00 | 33.63 | 8 |
| 6001 | OW0 | WAT | V | 559 | 6.112 | 83.592 | 41.192 | 1.00 | 34.97 | 8 |
| 6002 | OW0 | WAT | V | 560 | 38.614 | 41.425 | 25.492 | 1.00 | 34.42 | 8 |
| 6003 | OW0 | WAT | V | 561 | 34.074 | 88.144 | 12.960 | 1.00 | 34.41 | 8 |
| 6004 | OW0 | WAT | V | 562 | 40.114 | 63.213 | 5.786 | 1.00 | 34.56 | 8 |
| 6005 | OW0 | WAT | V | 563 | −0.202 | 64.215 | 60.019 | 1.00 | 34.60 | 8 |
| 6006 | OW0 | WAT | V | 564 | 4.614 | 92.264 | 20.329 | 1.00 | 33.82 | 8 |
| 6007 | OW0 | WAT | V | 565 | 15.212 | 50.738 | 32.687 | 1.00 | 34.54 | 8 |
| 6008 | OW0 | WAT | V | 566 | 13.018 | 70.753 | 53.378 | 1.00 | 35.00 | 8 |
| 6009 | OW0 | WAT | V | 567 | 37.836 | 57.700 | 75.968 | 1.00 | 33.91 | 8 |
| 6010 | OW0 | WAT | V | 568 | 18.054 | 71.354 | 7.047 | 1.00 | 34.28 | 8 |
| 6011 | OW0 | WAT | V | 569 | 20.435 | 57.091 | 12.782 | 1.00 | 34.06 | 8 |
| 6012 | OW0 | WAT | V | 570 | −1.113 | 72.836 | 30.802 | 1.00 | 34.18 | 8 |
| 6013 | OW0 | WAT | V | 571 | 45.394 | 47.985 | 15.576 | 1.00 | 34.25 | 8 |
| 6014 | OW0 | WAT | V | 572 | 18.083 | 105.524 | 25.739 | 1.00 | 35.26 | 8 |
| 6015 | OW0 | WAT | V | 573 | 42.363 | 51.035 | 61.868 | 1.00 | 34.64 | 8 |
| 6016 | OW0 | WAT | V | 574 | 3.332 | 65.717 | 27.045 | 1.00 | 35.54 | 8 |
| 6017 | OW0 | WAT | V | 575 | 0.099 | 70.672 | 51.291 | 1.00 | 34.72 | 8 |
| 6018 | OW0 | WAT | V | 576 | 0.045 | 61.496 | 31.457 | 1.00 | 35.51 | 8 |
| 6019 | OW0 | WAT | V | 577 | 46.395 | 53.881 | 61.040 | 1.00 | 34.53 | 8 |
| 6020 | OW0 | WAT | V | 578 | 52.136 | 68.150 | 59.956 | 1.00 | 35.10 | 8 |
| 6021 | OW0 | WAT | V | 579 | 19.009 | 41.546 | 26.130 | 1.00 | 33.65 | 8 |
| 6022 | OW0 | WAT | V | 580 | 34.720 | 74.712 | 71.942 | 1.00 | 34.54 | 8 |

TABLE 1-continued

Atom Coordinates from the Crystal Structure of NOVAMYL

| | | | | | | | | | | |
|---|---|---|---|---|---|---|---|---|---|---|
| 6023 | OW0 | WAT | V | 581 | 37.259 | 73.783 | 73.743 | 1.00 | 35.82 | 8 |
| 6024 | OW0 | WAT | V | 582 | 27.833 | 55.518 | 10.945 | 1.00 | 34.54 | 8 |
| 6025 | OW0 | WAT | V | 583 | 46.309 | 60.566 | 10.060 | 1.00 | 35.04 | 8 |
| 6026 | OW0 | WAT | V | 584 | 10.952 | 63.329 | 18.773 | 1.00 | 34.23 | 8 |
| 6027 | OW0 | WAT | V | 585 | −1.056 | 54.481 | 35.620 | 1.00 | 34.65 | 8 |
| 6028 | OW0 | WAT | V | 586 | −4.178 | 63.600 | 36.602 | 1.00 | 35.48 | 8 |
| 6029 | OW0 | WAT | V | 587 | 4.690 | 96.750 | 20.660 | 1.00 | 34.69 | 8 |
| 6030 | OW0 | WAT | V | 588 | 8.484 | 73.376 | 50.572 | 1.00 | 35.07 | 8 |
| 6031 | OW0 | WAT | V | 589 | 44.017 | 50.506 | 11.023 | 1.00 | 35.68 | 8 |
| 6032 | OW0 | WAT | V | 590 | 3.744 | 50.549 | 36.911 | 1.00 | 35.69 | 8 |
| 6033 | OW0 | WAT | V | 591 | 49.672 | 55.539 | 26.394 | 1.00 | 35.74 | 8 |
| 6034 | OW0 | WAT | V | 592 | 27.932 | 93.666 | 25.261 | 1.00 | 35.64 | 8 |
| 6035 | OW0 | WAT | V | 593 | 22.451 | 73.996 | 54.266 | 1.00 | 35.51 | 8 |
| 6036 | OW0 | WAT | V | 594 | 33.048 | 48.697 | 67.743 | 1.00 | 35.66 | 8 |
| 6037 | OW0 | WAT | V | 595 | 12.820 | 101.046 | 44.339 | 1.00 | 36.16 | 8 |
| 6038 | OW0 | WAT | V | 596 | 51.198 | 69.586 | 53.643 | 1.00 | 35.14 | 8 |
| 6039 | OW0 | WAT | V | 597 | 29.662 | 79.574 | 54.942 | 1.00 | 35.66 | 8 |
| 6040 | OW0 | WAT | V | 598 | 32.247 | 80.128 | 52.116 | 1.00 | 36.54 | 8 |
| 6041 | OW0 | WAT | V | 599 | 6.142 | 51.551 | 37.685 | 1.00 | 35.34 | 8 |
| 6042 | OW0 | WAT | V | 600 | 5.622 | 70.631 | 22.637 | 1.00 | 35.66 | 8 |
| 6043 | OW0 | WAT | V | 601 | 22.365 | 48.081 | 48.242 | 1.00 | 36.08 | 8 |
| 6044 | OW0 | WAT | V | 602 | 8.288 | 81.332 | 15.641 | 1.00 | 35.59 | 8 |
| 6045 | OW0 | WAT | V | 603 | 10.941 | 74.805 | 15.117 | 1.00 | 35.60 | 8 |
| 6046 | OW0 | WAT | V | 604 | 35.796 | 73.953 | 1.142 | 1.00 | 35.09 | 8 |
| 6047 | OW0 | WAT | V | 605 | 38.777 | 85.286 | 9.309 | 1.00 | 36.46 | 8 |
| 6048 | OW0 | WAT | V | 606 | 20.560 | 52.963 | 75.539 | 1.00 | 37.03 | 8 |
| 6049 | OW0 | WAT | V | 607 | −3.377 | 66.230 | 32.749 | 1.00 | 35.54 | 8 |
| 6050 | OW0 | WAT | V | 608 | 40.087 | 44.107 | 14.031 | 1.00 | 36.33 | 8 |
| 6051 | OW0 | WAT | V | 609 | −1.635 | 86.958 | 36.864 | 1.00 | 35.23 | 8 |
| 6052 | OW0 | WAT | V | 610 | 48.364 | 69.799 | 29.088 | 1.00 | 35.08 | 8 |
| 6053 | OW0 | WAT | V | 611 | 18.383 | 50.939 | 35.706 | 1.00 | 36.23 | 8 |
| 6054 | OW0 | WAT | V | 612 | 18.334 | 58.135 | 13.735 | 1.00 | 37.22 | 8 |
| 6055 | OW0 | WAT | V | 613 | 16.341 | 55.369 | 50.997 | 1.00 | 35.78 | 8 |
| 6056 | OW0 | WAT | V | 614 | 28.580 | 52.384 | 12.139 | 1.00 | 36.07 | 8 |
| 6057 | OW0 | WAT | V | 615 | 23.108 | 103.615 | 38.927 | 1.00 | 36.81 | 8 |
| 6058 | OW0 | WAT | V | 616 | 12.325 | 79.803 | 46.301 | 1.00 | 35.61 | 8 |
| 6059 | OW0 | WAT | V | 617 | 21.280 | 67.375 | 64.153 | 1.00 | 36.55 | 8 |
| 6060 | OW0 | WAT | V | 618 | 40.907 | 80.214 | 52.034 | 1.00 | 37.09 | 8 |
| 6061 | OW0 | WAT | V | 619 | 47.006 | 72.793 | 58.223 | 1.00 | 36.47 | 8 |
| 6062 | OW0 | WAT | V | 620 | 20.221 | 90.473 | 42.499 | 1.00 | 36.27 | 8 |
| 6063 | OW0 | WAT | V | 621 | 4.100 | 73.674 | 21.447 | 1.00 | 36.94 | 8 |
| 6064 | OW0 | WAT | V | 622 | 8.503 | 104.300 | 35.973 | 1.00 | 36.81 | 8 |
| 6065 | OW0 | WAT | V | 623 | 30.691 | 78.729 | 57.692 | 1.00 | 35.94 | 8 |
| 6066 | OW0 | WAT | V | 624 | −3.070 | 94.866 | 30.332 | 1.00 | 36.58 | 8 |
| 6067 | OW0 | WAT | V | 625 | 46.455 | 79.736 | 18.637 | 1.00 | 35.97 | 8 |
| 6068 | OW0 | WAT | V | 626 | 46.537 | 55.701 | 59.420 | 1.00 | 37.10 | 8 |
| 6069 | OW0 | WAT | V | 627 | 43.765 | 47.227 | 50.091 | 1.00 | 37.02 | 8 |
| 6070 | OW0 | WAT | V | 628 | −0.451 | 52.302 | 37.499 | 1.00 | 36.00 | 8 |
| 6071 | OW0 | WAT | V | 629 | 47.301 | 50.088 | 41.392 | 1.00 | 37.12 | 8 |
| 6072 | OW0 | WAT | V | 630 | 37.956 | 80.812 | 13.060 | 1.00 | 37.94 | 8 |
| 6073 | OW0 | WAT | V | 631 | 17.138 | 62.973 | 7.515 | 1.00 | 37.42 | 8 |
| 6074 | OW0 | WAT | V | 632 | 13.837 | 57.372 | 18.395 | 1.00 | 36.82 | 8 |
| 6075 | OW0 | WAT | V | 633 | 41.756 | 55.821 | 70.896 | 1.00 | 36.92 | 8 |
| 6076 | OW0 | WAT | V | 634 | 25.077 | 93.998 | 28.706 | 1.00 | 36.97 | 8 |
| 6077 | OW0 | WAT | V | 635 | 47.608 | 54.704 | 64.130 | 1.00 | 37.13 | 8 |
| 6078 | OW0 | WAT | V | 636 | 6.911 | 105.878 | 25.141 | 1.00 | 36.23 | 8 |
| 6079 | OW0 | WAT | V | 637 | 42.682 | 67.557 | 69.041 | 1.00 | 36.92 | 8 |
| 6080 | OW0 | WAT | V | 638 | 15.363 | 88.594 | 48.034 | 1.00 | 37.42 | 8 |
| 6081 | OW0 | WAT | V | 639 | 33.890 | 42.321 | 17.015 | 1.00 | 37.23 | 8 |
| 6082 | OW0 | WAT | V | 640 | 9.736 | 84.033 | 43.853 | 1.00 | 36.17 | 8 |
| 6083 | OW0 | WAT | V | 641 | 10.886 | 51.035 | 46.103 | 1.00 | 37.66 | 8 |
| 6084 | OW0 | WAT | V | 642 | 27.929 | 72.978 | 70.610 | 1.00 | 37.35 | 8 |
| 6085 | OW0 | WAT | V | 643 | 1.233 | 69.664 | 25.786 | 1.00 | 37.56 | 8 |
| 6086 | OW0 | WAT | V | 644 | 15.151 | 107.231 | 33.216 | 1.00 | 36.50 | 8 |
| 6087 | OW0 | WAT | V | 645 | 25.823 | 98.361 | 30.305 | 1.00 | 36.65 | 8 |
| 6088 | OW0 | WAT | V | 646 | 34.857 | 84.394 | 12.899 | 1.00 | 36.71 | 8 |
| 6089 | OW0 | WAT | V | 647 | 20.425 | 52.936 | 41.877 | 1.00 | 36.99 | 8 |
| 6090 | OW0 | WAT | V | 648 | 26.575 | 49.377 | 65.800 | 1.00 | 37.37 | 8 |
| 6091 | OW0 | WAT | V | 649 | 31.193 | 44.914 | 15.071 | 1.00 | 36.96 | 8 |
| 6092 | OW0 | WAT | V | 650 | 10.578 | 49.772 | 48.688 | 1.00 | 36.01 | 8 |
| 6093 | OW0 | WAT | V | 651 | 18.128 | 51.717 | 38.409 | 1.00 | 37.57 | 8 |
| 6094 | OW0 | WAT | V | 652 | 45.424 | 54.692 | 56.844 | 1.00 | 37.37 | 8 |
| 6095 | OW0 | WAT | V | 653 | 28.011 | 90.646 | 18.192 | 1.00 | 37.91 | 8 |
| 6096 | OW0 | WAT | V | 654 | 47.536 | 55.043 | 51.941 | 1.00 | 36.73 | 8 |
| 6097 | OW0 | WAT | V | 655 | 24.853 | 98.451 | 32.915 | 1.00 | 37.70 | 8 |
| 6098 | OW0 | WAT | V | 656 | 27.088 | 98.198 | 26.870 | 1.00 | 38.56 | 8 |
| 6099 | OW0 | WAT | V | 657 | 33.663 | 49.796 | 11.597 | 1.00 | 37.19 | 8 |

TABLE 1-continued

Atom Coordinates from the Crystal Structure of NOVAMYL

| | | | | | | | | | |
|---|---|---|---|---|---|---|---|---|---|
| 6100 | OW0 | WAT | V | 658 | 16.309 | 55.242 | 45.035 | 1.00 | 37.83 | 8 |
| 6101 | OW0 | WAT | V | 659 | 20.804 | 43.210 | 25.195 | 1.00 | 37.72 | 8 |
| 6102 | OW0 | WAT | V | 660 | 23.932 | 65.246 | 70.893 | 1.00 | 37.09 | 8 |
| 6103 | OW0 | WAT | V | 661 | 0.664 | 53.286 | 53.271 | 1.00 | 38.36 | 8 |
| 6104 | OW0 | WAT | V | 662 | 40.187 | 84.151 | 18.538 | 1.00 | 38.05 | 8 |
| 6105 | OW0 | WAT | V | 663 | 44.129 | 77.826 | 7.095 | 1.00 | 38.36 | 8 |
| 6106 | OW0 | WAT | V | 664 | 5.654 | 103.176 | 36.651 | 1.00 | 38.12 | 8 |
| 6107 | OW0 | WAT | V | 665 | -2.551 | 55.092 | 37.581 | 1.00 | 39.63 | 8 |
| 6108 | OW0 | WAT | V | 666 | 48.102 | 56.702 | 13.267 | 1.00 | 37.64 | 8 |
| 6109 | OW0 | WAT | V | 667 | 27.824 | 90.475 | 15.555 | 1.00 | 36.41 | 8 |
| 6110 | OW0 | WAT | V | 668 | 38.699 | 49.812 | 63.112 | 1.00 | 37.80 | 8 |
| 6111 | OW0 | WAT | V | 669 | -2.199 | 54.401 | 53.588 | 1.00 | 39.21 | 8 |
| 6112 | OW0 | WAT | V | 670 | 19.006 | 53.240 | 47.228 | 1.00 | 38.93 | 8 |
| 6113 | OW0 | WAT | V | 671 | 46.897 | 48.817 | 19.829 | 1.00 | 39.11 | 8 |
| 6114 | OW0 | WAT | V | 672 | 42.301 | 48.935 | 12.664 | 1.00 | 37.43 | 8 |
| 6115 | OW0 | WAT | V | 673 | 16.098 | 53.972 | 53.322 | 1.00 | 38.55 | 8 |
| 6116 | OW0 | WAT | V | 674 | 16.992 | 66.360 | 61.965 | 1.00 | 40.47 | 8 |
| 6117 | OW0 | WAT | V | 675 | 17.396 | 84.259 | 14.592 | 1.00 | 37.45 | 8 |
| 6118 | OW0 | WAT | V | 676 | 48.023 | 70.300 | 38.414 | 1.00 | 38.28 | 8 |
| 6119 | OW0 | WAT | V | 677 | 21.061 | 60.355 | 72.008 | 1.00 | 38.68 | 8 |
| 6120 | OW0 | WAT | V | 678 | 25.412 | 45.777 | 15.102 | 1.00 | 40.05 | 8 |
| 6121 | OW0 | WAT | V | 679 | 43.705 | 73.272 | 1.624 | 1.00 | 38.78 | 8 |
| 6122 | OW0 | WAT | V | 680 | 17.379 | 67.334 | 7.173 | 1.00 | 38.88 | 8 |
| 6123 | OW0 | WAT | V | 681 | 19.500 | 72.583 | 5.113 | 1.00 | 41.12 | 8 |
| 6124 | OW0 | WAT | V | 682 | 27.135 | 53.269 | 75.096 | 1.00 | 38.74 | 8 |
| 6125 | OW0 | WAT | V | 683 | 43.871 | 76.670 | 2.397 | 1.00 | 38.42 | 8 |
| 6126 | OW0 | WAT | V | 684 | 32.690 | 47.277 | 60.342 | 1.00 | 38.23 | 8 |
| 6127 | OW0 | WAT | V | 685 | 38.889 | 50.643 | 67.387 | 1.00 | 38.05 | 8 |
| 6128 | OW0 | WAT | V | 686 | 15.848 | 75.816 | 7.403 | 1.00 | 37.86 | 8 |
| 6129 | OW0 | WAT | V | 687 | 25.036 | 96.149 | 30.003 | 1.00 | 38.02 | 8 |
| 6130 | OW0 | WAT | V | 688 | 44.120 | 49.147 | 54.661 | 1.00 | 39.21 | 8 |
| 6131 | OW0 | WAT | V | 689 | 31.793 | 51.208 | 10.937 | 1.00 | 39.53 | 8 |
| 6132 | OW0 | WAT | V | 690 | 9.476 | 96.492 | 43.783 | 1.00 | 37.31 | 8 |
| 6133 | OW0 | WAT | V | 691 | 8.821 | 88.129 | 44.638 | 1.00 | 39.95 | 8 |
| 6134 | OW0 | WAT | V | 692 | 8.003 | 80.636 | 43.644 | 1.00 | 37.70 | 8 |
| 6135 | OW0 | WAT | V | 693 | 14.834 | 83.314 | 13.883 | 1.00 | 39.80 | 8 |
| 6136 | OW0 | WAT | V | 694 | 21.370 | 44.389 | 41.265 | 1.00 | 39.75 | 8 |
| 6137 | OW0 | WAT | V | 695 | 25.208 | 85.122 | 7.995 | 1.00 | 38.90 | 8 |
| 6138 | OW0 | WAT | V | 696 | 34.431 | 64.498 | 5.882 | 1.00 | 37.43 | 8 |
| 6139 | OW0 | WAT | V | 697 | 46.857 | 48.623 | 44.260 | 1.00 | 38.67 | 8 |
| 6140 | OW0 | WAT | V | 698 | 48.394 | 49.074 | 31.806 | 1.00 | 38.40 | 8 |
| 6141 | OW0 | WAT | V | 699 | 6.330 | 71.875 | 18.323 | 1.00 | 39.24 | 8 |
| 6142 | OW0 | WAT | V | 700 | 3.567 | 68.493 | 56.513 | 1.00 | 39.03 | 8 |
| 6143 | OW0 | WAT | V | 701 | 19.531 | 67.580 | 61.273 | 1.00 | 38.68 | 8 |
| 6144 | OW0 | WAT | V | 702 | 36.514 | 82.654 | 34.129 | 1.00 | 38.10 | 8 |
| 6145 | OW0 | WAT | V | 703 | 43.559 | 50.161 | 59.718 | 1.00 | 39.15 | 8 |
| 6146 | OW0 | WAT | V | 704 | 41.881 | 70.064 | 7.497 | 1.00 | 39.49 | 8 |
| 6147 | OW0 | WAT | V | 705 | 12.039 | 106.892 | 30.442 | 1.00 | 39.69 | 8 |
| 6148 | OW0 | WAT | V | 706 | 25.673 | 81.581 | 52.252 | 1.00 | 39.17 | 8 |
| 6149 | OW0 | WAT | V | 707 | 46.855 | 74.915 | 26.181 | 1.00 | 40.35 | 8 |
| 6150 | OW0 | WAT | V | 708 | 21.077 | 93.052 | 39.231 | 1.00 | 39.44 | 8 |
| 6151 | OW0 | WAT | V | 709 | 28.621 | 62.328 | 5.470 | 1.00 | 38.56 | 8 |
| 6152 | OW0 | WAT | V | 710 | -3.607 | 57.742 | 54.506 | 1.00 | 38.82 | 8 |
| 6153 | OW0 | WAT | V | 711 | 25.913 | 41.714 | 29.843 | 1.00 | 38.94 | 8 |
| 6154 | OW0 | WAT | V | 712 | 21.385 | 95.763 | 42.160 | 1.00 | 39.85 | 8 |
| 6155 | OW0 | WAT | V | 713 | 39.666 | 46.565 | 56.093 | 1.00 | 40.16 | 8 |
| 6156 | OW0 | WAT | V | 714 | 33.043 | 47.398 | 12.747 | 1.00 | 38.56 | 8 |
| 6157 | OW0 | WAT | V | 715 | 3.335 | 48.480 | 47.523 | 1.00 | 40.24 | 8 |
| 6158 | OW0 | WAT | V | 716 | -5.954 | 59.355 | 43.289 | 1.00 | 39.30 | 8 |
| 6159 | OW0 | WAT | V | 717 | -2.633 | 70.380 | 52.100 | 1.00 | 39.49 | 8 |
| 6160 | OW0 | WAT | V | 718 | 14.943 | 51.881 | 28.927 | 1.00 | 41.17 | 8 |
| 6161 | OW0 | WAT | V | 719 | 30.665 | 55.789 | 76.270 | 1.00 | 36.29 | 8 |
| 6162 | OW0 | WAT | V | 720 | 38.153 | 41.243 | 44.336 | 1.00 | 39.61 | 8 |
| 6163 | OW0 | WAT | V | 721 | 42.857 | 72.924 | 4.760 | 1.00 | 39.33 | 8 |
| 6164 | OW0 | WAT | V | 722 | 42.983 | 45.506 | 30.086 | 1.00 | 39.35 | 8 |
| 6165 | OW0 | WAT | V | 723 | 8.541 | 68.671 | 15.477 | 1.00 | 40.10 | 8 |
| 6166 | OW0 | WAT | V | 724 | 3.357 | 68.745 | 24.682 | 1.00 | 39.21 | 8 |
| 6167 | OW0 | WAT | V | 725 | 32.096 | 74.899 | 2.155 | 1.00 | 38.68 | 8 |
| 6168 | OW0 | WAT | V | 726 | -3.316 | 99.677 | 31.930 | 1.00 | 40.29 | 8 |
| 6169 | OW0 | WAT | V | 727 | 33.290 | 44.355 | 45.552 | 1.00 | 39.94 | 8 |
| 6170 | OW0 | WAT | V | 728 | 50.677 | 69.314 | 25.213 | 1.00 | 38.89 | 8 |
| 6171 | OW0 | WAT | V | 729 | 35.441 | 42.395 | 37.048 | 1.00 | 39.29 | 8 |
| 6172 | OW0 | WAT | V | 730 | 8.363 | 53.922 | 35.516 | 1.00 | 38.32 | 8 |
| 6173 | OW0 | WAT | V | 731 | -1.713 | 91.588 | 39.071 | 1.00 | 40.09 | 8 |
| 6174 | OW0 | WAT | V | 732 | 22.068 | 82.950 | 49.452 | 1.00 | 38.86 | 8 |
| 6175 | OW0 | WAT | V | 733 | -1.449 | 89.011 | 21.652 | 1.00 | 39.99 | 8 |
| 6176 | OW0 | WAT | V | 734 | 37.354 | 59.035 | 5.289 | 1.00 | 40.90 | 8 |

TABLE 1-continued

Atom Coordinates from the Crystal Structure of NOVAMYL

| 6177 | OW0 | WAT | V | 735 | 20.992 | 87.687 | 45.698 | 1.00 | 40.19 | 8 |
|---|---|---|---|---|---|---|---|---|---|---|
| 6178 | OW0 | WAT | V | 736 | 46.650 | 76.726 | 54.492 | 1.00 | 40.47 | 8 |
| 6179 | OW0 | WAT | V | 737 | 7.370 | 47.777 | 49.173 | 1.00 | 41.37 | 8 |
| 6180 | OW0 | WAT | V | 738 | 14.279 | 71.404 | 55.742 | 1.00 | 39.06 | 8 |
| 6181 | OW0 | WAT | V | 739 | 13.276 | 62.067 | 63.468 | 1.00 | 38.95 | 8 |
| 6182 | OW0 | WAT | V | 740 | 47.469 | 55.262 | 33.788 | 1.00 | 41.14 | 8 |
| 6183 | OW0 | WAT | V | 741 | 35.182 | 72.963 | 73.409 | 1.00 | 38.69 | 8 |
| 6184 | OW0 | WAT | V | 742 | 28.993 | 42.749 | 41.796 | 1.00 | 40.22 | 8 |
| 6185 | OW0 | WAT | V | 743 | 12.430 | 51.804 | 37.400 | 1.00 | 39.68 | 8 |
| 6186 | OW0 | WAT | V | 744 | 5.325 | 85.408 | 18.950 | 1.00 | 41.26 | 8 |
| 6187 | OW0 | WAT | V | 745 | 41.721 | 66.169 | 73.677 | 1.00 | 39.43 | 8 |
| 6188 | OW0 | WAT | V | 746 | 16.983 | 83.519 | 10.040 | 1.00 | 40.83 | 8 |
| 6189 | OW0 | WAT | V | 747 | −3.245 | 67.552 | 51.568 | 1.00 | 41.14 | 8 |
| 6190 | OW0 | WAT | V | 748 | 18.547 | 72.699 | 54.390 | 1.00 | 40.80 | 8 |
| 6191 | OW0 | WAT | V | 749 | 50.952 | 65.503 | 10.665 | 1.00 | 39.71 | 8 |
| 6192 | OW0 | WAT | V | 750 | 6.873 | 59.618 | 31.097 | 1.00 | 40.61 | 8 |
| 6193 | OW0 | WAT | V | 751 | 44.643 | 72.249 | 41.540 | 1.00 | 40.21 | 8 |
| 6194 | OW0 | WAT | V | 751 | 10.333 | 59.620 | 21.158 | 1.00 | 40.03 | 8 |
| 6195 | OW0 | WAT | V | 753 | 25.342 | 99.843 | 20.985 | 1.00 | 40.88 | 8 |
| 6196 | OW0 | WAT | V | 754 | 13.886 | 67.341 | 51.913 | 1.00 | 41.40 | 8 |
| 6197 | OW0 | WAT | V | 755 | 20.669 | 50.466 | 56.076 | 1.00 | 40.93 | 8 |
| 6198 | OW0 | WAT | V | 756 | 16.062 | 51.352 | 42.439 | 0.00 | 41.08 | 8 |
| 6199 | OW0 | WAT | V | 757 | −2.323 | 91.095 | 34.519 | 1.00 | 40.69 | 8 |
| 6200 | OW0 | WAT | V | 758 | 3.987 | 63.229 | 29.353 | 1.00 | 41.53 | 8 |
| 6201 | OW0 | WAT | V | 759 | 20.694 | 99.900 | 18.786 | 1.00 | 39.84 | 8 |
| 6202 | OW0 | WAT | V | 760 | 21.098 | 72.115 | 58.710 | 1.00 | 40.04 | 8 |
| 6203 | OW0 | WAT | V | 761 | 39.451 | 41.349 | 13.513 | 1.00 | 40.57 | 8 |
| 6204 | OW0 | WAT | V | 762 | 3.185 | 80.792 | 42.000 | 1.00 | 41.27 | 8 |
| 6205 | OW0 | WAT | V | 763 | 15.866 | 68.494 | 52.407 | 1.00 | 40.90 | 8 |
| 6206 | OW0 | WAT | V | 764 | 42.027 | 79.686 | 47.257 | 1.00 | 40.14 | 8 |
| 6207 | OW0 | WAT | V | 765 | 41.063 | 55.022 | 68.081 | 1.00 | 42.98 | 8 |
| 6208 | OW0 | WAT | V | 766 | 15.728 | 85.261 | 16.175 | 1.00 | 42.08 | 8 |
| 6209 | OW0 | WAT | V | 767 | −8.665 | 63.541 | 41.234 | 1.00 | 40.98 | 8 |
| 6210 | OW0 | WAT | V | 768 | 28.828 | 85.580 | 44.440 | 1.00 | 40.75 | 8 |
| 6211 | OW0 | WAT | V | 769 | 46.504 | 46.346 | 43.773 | 1.00 | 40.98 | 8 |
| 6212 | OW0 | WAT | V | 770 | 52.964 | 61.429 | 54.373 | 1.00 | 41.49 | 8 |
| 6213 | OW0 | WAT | V | 771 | 25.001 | 95.005 | 39.507 | 1.00 | 41.35 | 8 |
| 6214 | OW0 | WAT | V | 772 | 4.818 | 62.633 | 59.449 | 1.00 | 41.54 | 8 |
| 6215 | OW0 | WAT | V | 773 | 18.916 | 60.160 | 66.080 | 1.00 | 41.09 | 8 |
| 6216 | OW0 | WAT | V | 774 | 27.033 | 88.841 | 12.019 | 1.00 | 41.39 | 8 |
| 6217 | OW0 | WAT | V | 775 | 13.803 | 67.385 | 57.044 | 1.00 | 41.01 | 8 |
| 6218 | OW0 | WAT | V | 776 | 11.356 | 101.651 | 18.715 | 1.00 | 42.40 | 8 |
| 6219 | OW0 | WAT | V | 777 | 50.379 | 57.839 | 57.286 | 1.00 | 38.80 | 8 |
| 6220 | OW0 | WAT | V | 778 | 9.739 | 81.288 | 44.991 | 1.00 | 38.14 | 8 |
| 6221 | OW0 | WAT | V | 779 | 26.770 | 45.470 | 44.155 | 1.00 | 39.31 | 8 |
| 6222 | OW0 | WAT | V | 780 | 51.219 | 61.900 | 12.424 | 1.00 | 42.17 | 8 |
| 6223 | OW0 | WAT | V | 781 | 44.665 | 53.194 | 62.632 | 1.00 | 40.09 | 8 |
| 6224 | OW0 | WAT | V | 782 | −4.332 | 57.891 | 45.992 | 1.00 | 43.38 | 8 |
| 6225 | OW0 | WAT | V | 783 | 54.313 | 63.995 | 27.513 | 1.00 | 40.34 | 8 |
| 6226 | OW0 | WAT | V | 784 | 26.835 | 56.319 | 8.446 | 1.00 | 41.42 | 8 |
| 6227 | OW0 | WAT | V | 785 | 53.198 | 59.584 | 25.852 | 1.00 | 42.12 | 8 |
| 6228 | OW0 | WAT | V | 786 | 19.476 | 44.845 | 23.558 | 1.00 | 42.02 | 8 |
| 6229 | OW0 | WAT | V | 787 | 21.294 | 88.109 | 18.755 | 1.00 | 42.02 | 8 |
| 6230 | OW0 | WAT | V | 788 | 46.461 | 57.071 | 56.124 | 1.00 | 41.88 | 8 |
| 6231 | OW0 | WAT | V | 789 | 52.975 | 62.124 | 50.393 | 1.00 | 41.59 | 8 |
| 6232 | OW0 | WAT | V | 790 | 8.480 | 108.235 | 24.221 | 1.00 | 42.16 | 8 |
| 6233 | OW0 | WAT | V | 791 | 18.517 | 78.200 | 51.474 | 1.00 | 42.31 | 8 |
| 6234 | OW0 | WAT | V | 792 | −5.150 | 51.726 | 49.471 | 1.00 | 40.85 | 8 |
| 6235 | OW0 | WAT | V | 793 | 36.849 | 55.447 | 72.633 | 1.00 | 42.13 | 8 |
| 6236 | OW0 | WAT | V | 794 | 37.563 | 79.694 | 42.494 | 1.00 | 41.67 | 8 |
| 6237 | OW0 | WAT | V | 795 | 18.818 | 84.285 | 16.222 | 1.00 | 43.03 | 8 |
| 6238 | OW0 | WAT | V | 796 | 36.451 | 82.759 | 13.933 | 1.00 | 41.71 | 8 |
| 6239 | OW0 | WAT | V | 797 | 22.906 | 51.457 | 67.808 | 1.00 | 41.33 | 8 |
| 6240 | OW0 | WAT | V | 798 | 1.528 | 102.171 | 36.053 | 1.00 | 41.41 | 8 |
| 6241 | OW0 | WAT | V | 799 | 36.684 | 45.294 | 51.188 | 1.00 | 42.88 | 8 |
| 6242 | OW0 | WAT | V | 800 | 14.017 | 67.414 | 9.706 | 1.00 | 41.87 | 8 |
| 6243 | OW0 | WAT | V | 801 | 47.832 | 66.788 | 18.650 | 1.00 | 43.94 | 8 |
| 6244 | OW0 | WAT | V | 802 | 34.436 | 88.324 | 36.102 | 1.00 | 43.03 | 8 |
| 6245 | OW0 | WAT | V | 803 | 24.260 | 67.815 | 69.741 | 1.00 | 42.57 | 8 |
| 6246 | OW0 | WAT | V | 804 | 13.129 | 74.685 | 52.293 | 1.00 | 42.14 | 8 |
| 6247 | OW0 | WAT | V | 805 | 16.572 | 61.433 | 12.722 | 1.00 | 41.61 | 8 |
| 6248 | OW0 | WAT | V | 806 | 46.827 | 51.429 | 47.524 | 1.00 | 42.73 | 8 |
| 6249 | OW0 | WAT | V | 807 | 26.546 | 48.730 | 71.404 | 1.00 | 42.47 | 8 |
| 6250 | OW0 | WAT | V | 808 | 33.308 | 76.572 | 61.813 | 1.00 | 42.82 | 8 |
| 6251 | OW0 | WAT | V | 809 | 16.314 | 98.564 | 17.363 | 1.00 | 42.43 | 8 |
| 6252 | OW0 | WAT | V | 810 | 47.038 | 73.620 | 61.642 | 1.00 | 43.62 | 8 |
| 6253 | OW0 | WAT | V | 811 | 23.301 | 74.541 | 1.386 | 1.00 | 44.52 | 8 |

TABLE 1-continued

Atom Coordinates from the Crystal Structure of NOVAMYL

| 6254 | OW0 | WAT | V | 812 | 23.719 | 88.481 | 37.683 | 1.00 | 40.46 | 8 |
|---|---|---|---|---|---|---|---|---|---|---|
| 6255 | OW0 | WAT | V | 813 | 31.440 | 60.185 | 76.751 | 1.00 | 43.11 | 8 |
| 6256 | OW0 | WAT | V | 814 | 16.573 | 101.550 | 19.316 | 1.00 | 43.14 | 8 |
| 6257 | OW0 | WAT | V | 815 | 4.201 | 55.069 | 57.571 | 1.00 | 42.80 | 8 |
| 6258 | OW0 | WAT | V | 816 | −5.755 | 72.609 | 47.268 | 1.00 | 41.92 | 8 |
| 6259 | OW0 | WAT | V | 817 | 23.802 | 106.033 | 28.040 | 1.00 | 42.13 | 8 |
| 6260 | OW0 | WAT | V | 818 | 28.580 | 91.427 | 35.569 | 1.00 | 44.77 | 8 |
| 6261 | OW0 | WAT | V | 819 | −6.927 | 74.495 | 44.783 | 1.00 | 42.39 | 8 |
| 6262 | OW0 | WAT | V | 820 | 42.898 | 80.745 | 21.282 | 1.00 | 42.72 | 8 |
| 6263 | OW0 | WAT | V | 821 | 44.594 | 48.996 | 19.414 | 1.00 | 42.65 | 8 |
| 6264 | OW0 | WAT | V | 822 | 22.357 | 66.608 | 68.417 | 1.00 | 43.63 | 8 |
| 6265 | OW0 | WAT | V | 823 | 25.576 | 50.604 | 10.991 | 1.00 | 43.85 | 8 |
| 6266 | OW0 | WAT | V | 824 | 47.220 | 77.741 | 25.726 | 1.00 | 44.91 | 8 |
| 6267 | OW0 | WAT | V | 825 | 16.600 | 55.517 | 47.156 | 1.00 | 44.33 | 8 |
| 6268 | OW0 | WAT | V | 826 | 1.892 | 50.074 | 39.116 | 1.00 | 42.83 | 8 |
| 6269 | OW0 | WAT | V | 827 | 24.440 | 89.039 | 35.388 | 1.00 | 43.51 | 8 |
| 6270 | OW0 | WAT | V | 828 | 21.480 | 53.418 | 43.918 | 1.00 | 43.38 | 8 |
| 6271 | OW0 | WAT | V | 829 | 14.604 | 82.502 | 11.170 | 1.00 | 41.84 | 8 |
| 6272 | OW0 | WAT | V | 830 | 14.875 | 62.765 | 14.779 | 1.00 | 42.12 | 8 |
| 6273 | OW0 | WAT | V | 831 | 3.701 | 80.451 | 16.127 | 1.00 | 43.54 | 8 |
| 6274 | OW0 | WAT | V | 832 | 48.724 | 69.957 | 34.245 | 1.00 | 43.72 | 8 |
| 6275 | OW0 | WAT | V | 833 | 33.297 | 59.385 | 78.143 | 1.00 | 45.08 | 8 |
| 6276 | OW0 | WAT | V | 834 | 17.544 | 53.593 | 51.513 | 1.00 | 46.32 | 8 |
| 6277 | OW0 | WAT | V | 835 | 12.009 | 85.638 | 47.505 | 1.00 | 44.72 | 8 |
| 6278 | OW0 | WAT | V | 836 | 12.936 | 54.854 | 19.146 | 1.00 | 42.89 | 8 |
| 6279 | OW0 | WAT | V | 837 | 24.005 | 43.446 | 16.058 | 1.00 | 42.88 | 8 |
| 6280 | OW0 | WAT | V | 838 | 2.563 | 57.015 | 61.406 | 1.00 | 42.80 | 8 |
| 6281 | OW0 | WAT | V | 839 | 17.292 | 81.361 | 47.327 | 1.00 | 43.05 | 8 |
| 6282 | OW0 | WAT | V | 840 | 26.973 | 97.353 | 24.292 | 1.00 | 42.44 | 8 |
| 6283 | OW0 | WAT | V | 841 | 24.520 | 83.741 | 45.252 | 1.00 | 44.48 | 8 |
| 6284 | OW0 | WAT | V | 842 | 40.943 | 89.452 | 22.148 | 1.00 | 43.11 | 8 |
| 6285 | OW0 | WAT | V | 843 | 17.748 | 68.046 | 54.218 | 1.00 | 43.50 | 8 |
| 6286 | OW0 | WAT | V | 844 | 53.072 | 63.513 | 23.413 | 1.00 | 44.03 | 8 |
| 6287 | OW0 | WAT | V | 845 | −1.018 | 97.468 | 34.805 | 1.00 | 44.47 | 8 |
| 6288 | OW0 | WAT | V | 846 | 14.885 | 69.989 | 10.290 | 1.00 | 44.92 | 8 |
| 6289 | OW0 | WAT | V | 847 | 15.800 | 50.802 | 20.677 | 1.00 | 46.01 | 8 |
| 6290 | OW0 | WAT | V | 848 | 25.982 | 102.118 | 29.899 | 1.00 | 44.94 | 8 |
| 6291 | OW0 | WAT | V | 849 | 0.247 | 52.205 | 55.531 | 1.00 | 45.62 | 8 |
| 6292 | OW0 | WAT | V | 850 | 18.884 | 61.154 | 6.132 | 1.00 | 44.78 | 8 |
| 6293 | OW0 | WAT | V | 851 | 11.959 | 71.909 | 12.344 | 1.00 | 44.89 | 8 |
| 6294 | OW0 | WAT | V | 852 | −1.246 | 74.512 | 28.721 | 1.00 | 43.38 | 8 |
| 6295 | OW0 | WAT | V | 853 | 39.883 | 48.418 | 12.157 | 1.00 | 44.97 | 8 |
| 6296 | OW0 | WAT | V | 854 | 25.484 | 65.082 | 75.271 | 1.00 | 40.98 | 8 |
| 6297 | OW0 | WAT | V | 855 | 31.943 | 70.931 | 74.851 | 1.00 | 43.51 | 8 |
| 6298 | OW0 | WAT | V | 856 | 35.277 | 49.445 | 9.697 | 1.00 | 45.37 | 8 |
| 6299 | OW0 | WAT | V | 857 | 51.902 | 64.035 | 51.472 | 1.00 | 44.46 | 8 |
| 6300 | OW0 | WAT | V | 858 | 5.381 | 94.650 | 19.292 | 1.00 | 45.20 | 8 |
| 6301 | OW0 | WAT | V | 859 | 14.161 | 52.807 | 19.941 | 1.00 | 44.99 | 8 |
| 6302 | OW0 | WAT | V | 860 | 0.976 | 49.582 | 46.683 | 1.00 | 45.54 | 8 |
| 6303 | OW0 | WAT | V | 861 | 11.378 | 56.649 | 26.955 | 1.00 | 46.98 | 8 |
| 6304 | OW0 | WAT | V | 862 | 23.725 | 48.499 | 52.657 | 1.00 | 43.58 | 8 |
| 6305 | OW0 | WAT | V | 863 | 31.619 | 53.767 | 4.982 | 1.00 | 44.03 | 8 |
| 6306 | OW0 | WAT | V | 864 | 21.564 | 85.158 | 16.121 | 1.00 | 46.34 | 8 |
| 6307 | OW0 | WAT | V | 865 | 48.454 | 57.833 | 31.207 | 1.00 | 45.05 | 8 |
| 6308 | OW0 | WAT | V | 866 | 13.820 | 78.070 | 11.134 | 1.00 | 47.52 | 8 |
| 6309 | OW0 | WAT | V | 867 | 53.268 | 61.611 | 27.715 | 1.00 | 45.47 | 8 |
| 6310 | OW0 | WAT | V | 868 | 40.661 | 42.455 | 21.732 | 1.00 | 43.57 | 8 |
| 6311 | OW0 | WAT | V | 869 | 24.881 | 97.609 | 17.754 | 1.00 | 41.56 | 8 |
| 6312 | OW0 | WAT | V | 870 | 46.779 | 45.863 | 33.183 | 1.00 | 38.06 | 8 |
| 6313 | OW0 | WAT | V | 871 | 28.449 | 47.238 | 49.410 | 1.00 | 44.98 | 8 |
| 6314 | OW0 | WAT | V | 872 | 31.691 | 90.618 | 16.034 | 1.00 | 45.59 | 8 |
| 6315 | OW0 | WAT | V | 873 | 45.269 | 73.271 | 25.041 | 1.00 | 46.87 | 8 |
| 6316 | OW0 | WAT | V | 874 | 18.096 | 50.245 | 53.261 | 1.00 | 45.09 | 8 |
| 6317 | OW0 | WAT | V | 875 | −5.062 | 64.679 | 39.520 | 1.00 | 44.00 | 8 |
| 6318 | OW0 | WAT | V | 876 | 17.006 | 54.092 | 49.423 | 1.00 | 46.50 | 8 |
| 6319 | OW0 | WAT | V | 877 | 39.580 | 64.107 | 77.580 | 1.00 | 45.16 | 8 |
| 6320 | OW0 | WAT | V | 878 | 16.405 | 56.330 | 66.595 | 1.00 | 44.67 | 8 |
| 6321 | OW0 | WAT | V | 879 | 28.253 | 74.829 | 0.308 | 1.00 | 44.14 | 8 |
| 6322 | OW0 | WAT | V | 880 | 26.165 | 96.027 | 33.730 | 1.00 | 45.73 | 8 |
| 6323 | OW0 | WAT | V | 881 | 25.024 | 94.673 | 31.684 | 1.00 | 45.30 | 8 |
| 6324 | OW0 | WAT | V | 882 | 6.382 | 101.590 | 23.078 | 1.00 | 45.88 | 8 |
| 6325 | OW0 | WAT | V | 883 | 20.784 | 106.032 | 25.469 | 1.00 | 44.92 | 8 |
| 6326 | OW0 | WAT | V | 884 | 15.678 | 70.001 | 59.741 | 1.00 | 47.72 | 8 |
| 6327 | OW0 | WAT | V | 885 | 43.426 | 78.175 | 61.043 | 1.00 | 46.23 | 8 |
| 6328 | OW0 | WAT | V | 886 | 10.651 | 50.358 | 43.666 | 1.00 | 45.79 | 8 |
| 6329 | OW0 | WAT | V | 887 | 0.918 | 49.811 | 54.685 | 1.00 | 45.38 | 8 |
| 6330 | OW0 | WAT | V | 888 | 24.371 | 106.460 | 30.607 | 1.00 | 46.20 | 8 |

TABLE 1-continued

Atom Coordinates from the Crystal Structure of NOVAMYL

| | | | | | | | | | |
|---|---|---|---|---|---|---|---|---|---|
| 6331 | OW0 | WAT | V | 889 | 7.425 | 93.590 | 16.782 | 1.00 | 45.79 | 8 |
| 6332 | OW0 | WAT | V | 890 | 20.314 | 66.093 | 66.469 | 1.00 | 48.35 | 8 |
| 6333 | OW0 | WAT | V | 891 | 12.244 | 93.829 | 44.935 | 1.00 | 47.03 | 8 |
| 6334 | OW0 | WAT | V | 892 | 2.847 | 56.085 | 32.137 | 1.00 | 48.09 | 8 |
| 6335 | OW0 | WAT | V | 893 | 15.592 | 72.473 | 53.588 | 1.00 | 46.24 | 8 |
| 6336 | OW0 | WAT | V | 894 | 45.552 | 49.673 | 29.081 | 1.00 | 46.73 | 8 |
| 6337 | OW0 | WAT | V | 895 | 48.867 | 72.566 | 56.249 | 1.00 | 45.76 | 8 |
| 6338 | OW0 | WAT | V | 896 | 51.123 | 56.932 | 37.786 | 1.00 | 40.58 | 8 |
| 6339 | OW0 | WAT | V | 897 | 30.394 | 49.733 | 9.142 | 1.00 | 48.10 | 8 |
| 6340 | OW0 | WAT | V | 898 | 27.101 | 98.920 | 22.257 | 1.00 | 46.90 | 8 |
| 6341 | OW0 | WAT | V | 899 | 14.712 | 51.617 | 24.308 | 1.00 | 47.17 | 8 |
| 6342 | OW0 | WAT | V | 900 | 46.781 | 50.533 | 27.214 | 1.00 | 47.00 | 8 |
| 6343 | OW0 | WAT | W | 1 | −6.114 | 65.250 | 32.669 | 1.00 | 47.96 | 8 |
| 6344 | OW0 | WAT | W | 2 | 47.645 | 71.480 | 60.598 | 1.00 | 45.49 | 8 |
| 6345 | OW0 | WAT | W | 3 | 48.802 | 54.151 | 54.398 | 1.00 | 46.37 | 8 |
| 6346 | OW0 | WAT | W | 4 | 4.605 | 105.268 | 26.990 | 1.00 | 46.92 | 8 |
| 6347 | OW0 | WAT | W | 5 | 42.143 | 73.136 | 41.061 | 1.00 | 45.02 | 8 |
| 6348 | OW0 | WAT | W | 6 | 26.105 | 89.154 | 41.563 | 1.00 | 47.90 | 8 |
| 6349 | OW0 | WAT | W | 7 | 3.202 | 48.853 | 55.140 | 1.00 | 47.23 | 8 |
| 6350 | OW0 | WAT | W | 8 | −2.318 | 61.724 | 33.458 | 1.00 | 48.00 | 8 |
| 6351 | OW0 | WAT | W | 9 | 38.569 | 50.803 | 7.204 | 1.00 | 46.95 | 8 |
| 6352 | OW0 | WAT | W | 10 | 2.160 | 103.336 | 25.390 | 1.00 | 47.08 | 8 |
| 6353 | OW0 | WAT | W | 11 | 27.464 | 41.903 | 36.189 | 1.00 | 42.96 | 8 |
| 6354 | OW0 | WAT | W | 12 | 49.209 | 50.152 | 22.583 | 1.00 | 48.25 | 8 |
| 6355 | OW0 | WAT | W | 13 | 10.266 | 57.487 | 62.131 | 1.00 | 43.39 | 8 |
| 6356 | OW0 | WAT | W | 14 | 54.127 | 66.185 | 63.244 | 1.00 | 49.78 | 8 |
| 6357 | OW0 | WAT | W | 15 | 19.083 | 49.330 | 63.179 | 1.00 | 49.30 | 8 |
| 6358 | OW0 | WAT | W | 16 | 39.385 | 74.287 | 38.793 | 1.00 | 46.50 | 8 |
| 6359 | OW0 | WAT | W | 17 | −1.255 | 52.062 | 41.948 | 1.00 | 49.09 | 8 |
| 6360 | OW0 | WAT | W | 18 | 16.630 | 69.708 | 8.569 | 1.00 | 48.63 | 8 |
| 6361 | OW0 | WAT | W | 19 | 29.289 | 54.314 | 9.208 | 1.00 | 49.09 | 8 |
| 6362 | OW0 | WAT | W | 20 | 38.590 | 83.950 | 31.916 | 1.00 | 48.14 | 8 |
| 6363 | OW0 | WAT | W | 21 | 47.212 | 44.923 | 37.558 | 1.00 | 49.07 | 8 |
| 6364 | OW0 | WAT | W | 22 | 2.016 | 104.557 | 33.998 | 1.00 | 50.31 | 8 |
| 6365 | OW0 | WAT | W | 23 | 5.910 | 79.410 | 15.810 | 1.00 | 46.74 | 8 |
| 6366 | OW0 | WAT | W | 24 | 18.824 | 46.920 | 16.693 | 1.00 | 44.54 | 8 |
| 6367 | OW0 | WAT | W | 25 | 21.253 | 90.457 | 18.335 | 1.00 | 47.12 | 8 |
| 6368 | OW0 | WAT | W | 26 | 46.674 | 72.576 | 34.746 | 1.00 | 48.69 | 8 |
| 6369 | OW0 | WAT | W | 27 | 17.804 | 54.470 | 14.884 | 1.00 | 50.05 | 8 |
| 6370 | OW0 | WAT | W | 28 | −3.319 | 64.779 | 54.655 | 1.00 | 49.95 | 8 |
| 6371 | OW0 | WAT | W | 29 | 20.035 | 59.810 | 69.328 | 1.00 | 47.36 | 8 |
| 6372 | OW0 | WAT | W | 30 | 6.598 | 98.214 | 19.529 | 1.00 | 50.29 | 8 |
| 6373 | OW0 | WAT | W | 31 | 29.388 | 57.634 | 5.275 | 1.00 | 49.23 | 8 |
| 6374 | OW0 | WAT | W | 32 | 25.881 | 83.371 | 49.453 | 1.00 | 49.89 | 8 |
| 6375 | OW0 | WAT | W | 33 | 46.828 | 48.534 | 13.616 | 1.00 | 48.17 | 8 |
| 6376 | OW0 | WAT | W | 34 | 52.912 | 62.999 | 14.852 | 1.00 | 46.56 | 8 |
| 6377 | OW0 | WAT | W | 35 | 2.107 | 83.103 | 18.070 | 1.00 | 48.10 | 8 |
| 6378 | OW0 | WAT | W | 36 | 41.486 | 67.797 | 7.736 | 1.00 | 50.23 | 8 |
| 6379 | OW0 | WAT | W | 37 | 9.492 | 94.962 | 15.817 | 1.00 | 48.00 | 8 |
| 6380 | OW0 | WAT | W | 38 | 28.348 | 95.134 | 21.001 | 1.00 | 48.19 | 8 |
| 6381 | OW0 | WAT | W | 39 | 32.401 | 92.434 | 25.439 | 1.00 | 50.58 | 8 |
| 6382 | OW0 | WAT | W | 40 | 46.035 | 46.956 | 48.050 | 1.00 | 50.92 | 8 |
| 6383 | OW0 | WAT | W | 41 | 34.909 | 51.572 | 71.159 | 1.00 | 49.38 | 8 |
| 6384 | OW0 | WAT | W | 42 | 29.114 | 76.486 | 61.672 | 1.00 | 49.83 | 8 |
| 6385 | OW0 | WAT | W | 43 | −3.044 | 91.942 | 40.975 | 1.00 | 51.92 | 8 |
| 6386 | OW0 | WAT | W | 44 | −3.395 | 74.451 | 28.328 | 1.00 | 46.84 | 8 |
| 6387 | OW0 | WAT | W | 45 | 20.187 | 89.421 | 44.602 | 1.00 | 49.88 | 8 |
| 6388 | OW0 | WAT | W | 46 | −4.080 | 54.699 | 41.545 | 1.00 | 50.13 | 8 |
| 6389 | OW0 | WAT | W | 47 | 38.425 | 87.733 | 31.621 | 1.00 | 49.47 | 8 |
| 6390 | OW0 | WAT | W | 48 | 4.305 | 62.413 | 62.323 | 1.00 | 49.60 | 8 |
| 6391 | OW0 | WAT | W | 49 | 6.229 | 89.367 | 44.095 | 1.00 | 53.06 | 8 |
| 6392 | OW0 | WAT | W | 50 | 49.747 | 66.902 | 23.155 | 0.00 | 51.47 | 8 |
| 6393 | OW0 | WAT | W | 51 | 40.855 | 78.417 | 26.292 | 1.00 | 48.79 | 8 |
| 6394 | OW0 | WAT | W | 52 | 17.489 | 50.714 | 66.895 | 1.00 | 52.19 | 8 |
| 6395 | OW0 | WAT | W | 53 | 34.327 | 92.622 | 27.782 | 1.00 | 49.40 | 8 |
| 6396 | OW0 | WAT | W | 54 | 49.464 | 48.219 | 14.354 | 1.00 | 55.58 | 8 |
| 6397 | OW0 | WAT | W | 55 | −2.823 | 49.394 | 48.028 | 1.00 | 50.11 | 8 |
| 6398 | OW0 | WAT | W | 56 | 22.263 | 105.611 | 23.242 | 1.00 | 50.89 | 8 |
| 6399 | OW0 | WAT | W | 57 | 16.395 | 51.479 | 56.998 | 1.00 | 54.48 | 8 |
| 6400 | OW0 | WAT | W | 58 | 46.461 | 51.028 | 12.082 | 1.00 | 51.52 | 8 |
| 6401 | OW0 | WAT | W | 59 | 35.996 | 61.651 | 5.602 | 1.00 | 53.96 | 8 |
| 6402 | OW0 | WAT | W | 60 | 25.277 | 46.888 | 50.958 | 1.00 | 53.30 | 8 |
| 6403 | OW0 | WAT | W | 61 | 15.763 | 94.604 | 17.487 | 1.00 | 49.77 | 8 |
| 6404 | OW0 | WAT | W | 62 | 42.937 | 61.534 | 7.934 | 1.00 | 47.74 | 8 |
| 6405 | OW0 | WAT | W | 63 | 24.840 | 46.516 | 44.072 | 1.00 | 51.69 | 8 |
| 6406 | OW0 | WAT | W | 64 | 29.111 | 92.028 | 40.197 | 1.00 | 48.35 | 8 |
| 6407 | OW0 | WAT | W | 65 | 4.689 | 89.221 | 19.393 | 1.00 | 50.44 | 8 |

TABLE 1-continued

Atom Coordinates from the Crystal Structure of NOVAMYL

| 6408 | OW0 | WAT | W | 66 | 11.456 | 93.383 | 15.046 | 1.00 | 58.07 | 8 |
|---|---|---|---|---|---|---|---|---|---|---|
| 6409 | OW0 | WAT | W | 67 | 15.227 | 108.500 | 35.816 | 1.00 | 52.43 | 8 |
| 6410 | OW0 | WAT | W | 68 | 42.860 | 74.904 | 32.815 | 1.00 | 52.70 | 8 |
| 6411 | OW0 | WAT | W | 69 | 48.829 | 69.006 | 23.605 | 1.00 | 55.19 | 8 |
| 6412 | OW0 | WAT | W | 70 | 15.485 | 68.666 | 11.962 | 1.00 | 52.48 | 8 |
| 6413 | OW0 | WAT | W | 71 | −5.047 | 98.836 | 30.411 | 1.00 | 52.33 | 8 |
| 6414 | OW0 | WAT | W | 72 | 38.899 | 69.928 | 3.024 | 1.00 | 53.43 | 8 |
| 6415 | OW0 | WAT | W | 73 | 47.563 | 47.253 | 16.948 | 1.00 | 53.16 | 8 |
| 6416 | OW0 | WAT | W | 74 | 8.621 | 51.721 | 57.810 | 1.00 | 51.63 | 8 |
| 6417 | OW0 | WAT | W | 75 | 52.887 | 59.020 | 49.147 | 1.00 | 50.28 | 8 |
| 6418 | OW0 | WAT | W | 76 | 4.037 | 61.529 | 30.846 | 1.00 | 54.62 | 8 |
| 6419 | OW0 | WAT | W | 77 | 4.332 | 83.232 | 16.091 | 1.00 | 55.82 | 8 |
| 6420 | OW0 | WAT | W | 78 | 36.037 | 53.977 | 74.978 | 1.00 | 55.15 | 8 |
| 6421 | OW0 | WAT | W | 79 | 51.512 | 53.978 | 47.701 | 0.00 | 54.18 | 8 |
| 6422 | OW0 | WAT | W | 80 | 14.797 | 91.920 | 17.273 | 1.00 | 51.87 | 8 |
| 6423 | OW0 | WAT | W | 81 | 19.801 | 84.369 | 8.356 | 1.00 | 55.63 | 8 |
| 6424 | OW0 | WAT | W | 82 | 31.496 | 46.252 | 52.107 | 1.00 | 55.15 | 8 |
| 6425 | OW0 | WAT | W | 83 | −1.823 | 79.829 | 19.762 | 1.00 | 53.76 | 8 |
| 6426 | OW0 | WAT | W | 84 | 29.256 | 92.834 | 20.731 | 1.00 | 53.49 | 8 |
| 6427 | OW0 | WAT | W | 85 | −1.824 | 76.279 | 32.563 | 1.00 | 55.76 | 8 |
| 6428 | OW0 | WAT | W | 86 | 32.061 | 46.088 | 49.588 | 1.00 | 55.95 | 8 |
| 6429 | OW0 | WAT | W | 87 | 41.327 | 42.439 | 33.669 | 1.00 | 55.86 | 8 |
| 6430 | OW0 | WAT | W | 88 | 43.153 | 80.324 | 3.532 | 1.00 | 52.67 | 8 |
| 6431 | OW0 | WAT | W | 89 | 47.799 | 76.801 | 61.841 | 1.00 | 55.93 | 8 |
| 6432 | OW0 | WAT | W | 90 | 35.708 | 85.333 | 37.348 | 1.00 | 54.64 | 8 |
| 6433 | OW0 | WAT | W | 91 | 52.110 | 65.452 | 56.038 | 1.00 | 53.77 | 8 |
| 6434 | OW0 | WAT | W | 92 | 16.996 | 79.167 | 47.458 | 1.00 | 56.65 | 8 |
| 6435 | OW0 | WAT | W | 93 | 27.626 | 49.502 | 11.515 | 1.00 | 60.46 | 8 |
| 6436 | OW0 | WAT | W | 94 | 29.317 | 47.547 | 14.906 | 1.00 | 61.23 | 8 |
| 6437 | OW0 | WAT | W | 95 | 51.306 | 65.455 | 30.794 | 0.00 | 67.31 | 8 |
| 6438 | OW0 | WAT | W | 96 | 21.436 | 52.799 | 12.475 | 1.00 | 60.39 | 8 |
| 6439 | OW0 | WAT | W | 97 | 24.857 | 50.122 | 68.228 | 1.00 | 61.97 | 8 |
| 6440 | OW0 | WAT | W | 98 | 53.436 | 60.942 | 47.809 | 1.00 | 59.88 | 8 |
| 6441 | OW0 | WAT | W | 99 | 26.545 | 99.863 | 28.613 | 1.00 | 66.13 | 8 |
| 6442 | OW0 | WAT | W | 100 | 28.187 | 94.100 | 34.809 | 1.00 | 47.55 | 8 |
| 6443 | OW0 | WAT | W | 101 | 46.501 | 68.477 | 9.327 | 1.00 | 62.49 | 8 |
| 6444 | OW0 | WAT | W | 102 | 41.335 | 80.622 | 32.546 | 1.00 | 56.46 | 8 |
| 6445 | OW0 | WAT | W | 103 | 49.090 | 47.019 | 29.937 | 1.00 | 51.60 | 8 |
| 6446 | OW0 | WAT | W | 104 | 29.677 | 70.505 | 75.480 | 1.00 | 55.52 | 8 |
| 6447 | OW0 | WAT | W | 105 | 10.580 | 70.552 | 56.020 | 1.00 | 45.60 | 8 |
| 6448 | OW0 | WAT | W | 106 | −5.437 | 61.460 | 36.195 | 1.00 | 49.58 | 8 |
| 6449 | OW0 | WAT | W | 107 | 41.636 | 42.378 | 28.372 | 1.00 | 47.73 | 8 |
| 6450 | OW0 | WAT | W | 108 | 48.134 | 51.375 | 29.584 | 1.00 | 53.67 | 8 |
| 6451 | OW0 | WAT | W | 109 | 20.029 | 46.534 | 41.141 | 1.00 | 45.69 | 8 |
| 6452 | OW0 | WAT | W | 110 | 39.076 | 61.857 | 77.827 | 1.00 | 61.24 | 8 |
| 6453 | OW0 | WAT | W | 111 | 40.140 | 79.602 | 28.296 | 1.00 | 58.08 | 8 |
| 6454 | OW0 | WAT | W | 112 | 24.479 | 41.686 | 38.003 | 1.00 | 48.71 | 8 |
| 6455 | OW0 | WAT | W | 113 | 18.748 | 86.522 | 18.736 | 1.00 | 54.95 | 8 |
| 6456 | OW0 | WAT | W | 114 | 26.670 | 86.155 | 43.878 | 1.00 | 45.83 | 8 |
| 6457 | OW0 | WAT | W | 115 | 34.014 | 44.101 | 58.947 | 1.00 | 55.80 | 8 |
| 6458 | OW0 | WAT | W | 116 | 44.085 | 44.358 | 32.579 | 1.00 | 66.42 | 8 |
| 6459 | OW0 | WAT | W | 117 | 2.549 | 102.526 | 41.260 | 1.00 | 56.37 | 8 |
| 6460 | OW0 | WAT | W | 118 | 10.042 | 59.115 | 64.251 | 1.00 | 53.53 | 8 |
| 6461 | OW0 | WAT | W | 119 | 52.498 | 59.271 | 37.676 | 1.00 | 46.44 | 8 |
| 6462 | OW0 | WAT | W | 120 | 49.412 | 68.479 | 30.738 | 0.00 | 48.32 | 8 |
| 6463 | OW0 | WAT | W | 121 | 39.604 | 81.174 | 29.899 | 1.00 | 40.72 | 8 |
| 6464 | OW0 | WAT | W | 122 | 52.578 | 62.726 | 30.463 | 0.00 | 55.27 | 8 |
| 6465 | OW0 | WAT | W | 123 | 32.284 | 38.992 | 32.423 | 1.00 | 44.19 | 8 |
| 6466 | OW0 | WAT | W | 124 | 54.342 | 58.298 | 13.900 | 1.00 | 48.84 | 8 |
| 6467 | OW0 | WAT | W | 125 | 53.831 | 60.018 | 17.609 | 1.00 | 53.12 | 8 |
| 6468 | OW0 | WAT | W | 126 | 37.548 | 48.910 | 67.790 | 1.00 | 63.29 | 8 |
| 6469 | OW0 | WAT | W | 127 | 16.364 | 67.201 | 64.210 | 1.00 | 54.77 | 8 |
| 6470 | OW0 | WAT | W | 128 | 35.507 | 88.726 | 18.930 | 1.00 | 44.18 | 8 |
| 6471 | OW0 | WAT | W | 129 | 49.585 | 56.011 | 59.240 | 1.00 | 44.54 | 8 |
| 6472 | OW0 | WAT | W | 130 | 13.470 | 54.095 | 28.765 | 1.00 | 39.17 | 8 |
| 6473 | OW0 | WAT | W | 131 | 11.141 | 90.680 | 16.198 | 1.00 | 49.46 | 8 |
| 6474 | OW0 | WAT | W | 132 | −9.184 | 65.150 | 46.616 | 1.00 | 52.99 | 8 |
| 6475 | OW0 | WAT | W | 133 | 44.910 | 67.182 | 7.757 | 1.00 | 52.67 | 8 |
| 6476 | OW0 | WAT | W | 134 | 38.968 | 68.370 | 71.252 | 1.00 | 37.18 | 8 |
| 6477 | OW0 | WAT | W | 135 | 9.962 | 106.661 | 35.598 | 1.00 | 48.81 | 8 |
| 6478 | OW0 | WAT | W | 136 | −0.018 | 83.329 | 37.562 | 1.00 | 49.93 | 8 |
| 6479 | OW0 | WAT | W | 137 | 6.077 | 95.625 | 42.890 | 1.00 | 41.31 | 8 |
| 6480 | OW0 | WAT | W | 138 | 38.033 | 48.935 | 8.928 | 1.00 | 56.21 | 8 |
| 6481 | OW0 | WAT | W | 139 | 22.720 | 48.167 | 43.406 | 1.00 | 43.05 | 8 |
| 6482 | OW0 | WAT | W | 140 | 16.160 | 51.440 | 42.398 | 1.00 | 42.33 | 8 |
| 6483 | OW0 | WAT | W | 141 | 51.286 | 65.520 | 30.747 | 0.00 | 58.93 | 8 |
| 6484 | OW0 | WAT | W | 142 | 22.870 | 83.783 | −0.279 | 1.00 | 39.91 | 8 |

TABLE 1-continued

Atom Coordinates from the Crystal Structure of NOVAMYL

| 6485 | OW0 | WAT | W | 143 | 23.492 | 85.411 | 14.742 | 1.00 | 45.55 | 8 |
|---|---|---|---|---|---|---|---|---|---|---|
| 6486 | OW0 | WAT | W | 144 | 30.609 | 38.135 | 34.869 | 1.00 | 53.23 | 8 |
| 6487 | OW0 | WAT | W | 145 | 51.546 | 53.971 | 47.725 | 0.00 | 54.90 | 8 |
| 6488 | OW0 | WAT | W | 146 | 37.344 | 40.493 | 33.234 | 1.00 | 46.02 | 8 |
| 6489 | OW0 | WAT | W | 147 | 35.805 | 47.572 | 62.190 | 1.00 | 53.24 | 8 |
| 6490 | OW0 | WAT | W | 148 | 32.439 | 62.293 | 76.111 | 1.00 | 52.51 | 8 |
| 6491 | OW0 | WAT | W | 149 | 24.077 | 90.751 | 37.673 | 1.00 | 48.00 | 8 |
| 6492 | OW0 | WAT | W | 150 | 20.655 | 50.869 | 68.464 | 1.00 | 51.34 | 8 |
| 6493 | OW0 | WAT | W | 151 | 42.359 | 76.800 | 31.368 | 1.00 | 54.68 | 8 |
| 6494 | OW0 | WAT | W | 152 | 40.991 | 84.869 | 28.522 | 1.00 | 51.94 | 8 |
| 6495 | OW0 | WAT | W | 153 | −3.448 | 59.486 | 34.298 | 1.00 | 60.14 | 8 |
| 6496 | OW0 | WAT | W | 154 | 24.275 | 50.044 | 65.629 | 1.00 | 48.99 | 8 |
| 6497 | OW0 | WAT | W | 155 | 24.898 | 47.635 | 57.042 | 1.00 | 50.00 | 8 |
| 6498 | OW0 | WAT | W | 156 | 46.911 | 73.376 | 32.086 | 1.00 | 65.97 | 8 |
| 6499 | OW0 | WAT | W | 157 | 12.448 | 63.643 | 14.806 | 1.00 | 50.68 | 8 |
| 6500 | OW0 | WAT | W | 158 | 17.367 | 83.516 | 7.750 | 1.00 | 59.03 | 8 |
| 6501 | OW0 | WAT | W | 159 | 38.537 | 87.429 | 19.244 | 1.00 | 48.05 | 8 |
| 6502 | OW0 | WAT | W | 160 | 49.397 | 68.482 | 30.753 | 0.00 | 47.12 | 8 |
| 6503 | OW0 | WAT | W | 161 | 52.562 | 62.737 | 30.460 | 0.00 | 55.04 | 8 |
| 6504 | OW0 | WAT | W | 162 | 17.100 | 92.730 | 17.506 | 1.00 | 48.89 | 8 |
| 6505 | OW0 | WAT | W | 163 | 54.143 | 65.666 | 53.272 | 1.00 | 49.78 | 8 |
| 6506 | OW0 | WAT | W | 164 | 35.140 | 89.217 | 21.335 | 0.00 | 49.55 | 8 |
| 6507 | OW0 | WAT | W | 165 | 40.864 | 85.144 | 25.201 | 1.00 | 51.96 | 8 |
| 6508 | OW0 | WAT | W | 166 | 0.129 | 71.062 | 53.859 | 1.00 | 50.46 | 8 |
| 6509 | OW0 | WAT | W | 167 | 19.749 | 95.732 | 16.395 | 1.00 | 54.02 | 8 |
| 6510 | OW0 | WAT | W | 168 | 45.089 | 55.696 | 66.763 | 1.00 | 48.69 | 8 |
| 6511 | OW0 | WAT | W | 169 | 29.920 | 93.952 | 27.969 | 1.00 | 57.82 | 8 |
| 6512 | OW0 | WAT | W | 170 | −1.140 | 103.281 | 29.038 | 1.00 | 59.68 | 8 |
| 6513 | OW0 | WAT | W | 171 | 0.493 | 67.332 | 27.261 | 1.00 | 46.75 | 8 |
| 6514 | OW0 | WAT | W | 172 | 11.663 | 49.273 | 52.961 | 1.00 | 47.65 | 8 |
| 6515 | OW0 | WAT | W | 173 | 19.395 | 43.670 | 27.526 | 0.00 | 52.64 | 8 |
| 6516 | OW0 | WAT | W | 174 | 12.558 | 73.429 | 10.221 | 1.00 | 52.09 | 8 |
| 6517 | OW0 | WAT | W | 175 | 47.725 | 72.168 | 25.475 | 1.00 | 55.03 | 8 |
| 6518 | OW0 | WAT | W | 176 | 37.354 | 46.525 | 53.992 | 1.00 | 62.86 | 8 |
| 6519 | OW0 | WAT | W | 177 | 6.566 | 77.689 | 48.060 | 1.00 | 54.04 | 8 |
| 6520 | OW0 | WAT | W | 178 | 27.239 | 80.756 | 54.362 | 1.00 | 54.49 | 8 |
| 6521 | OW0 | WAT | W | 179 | 29.136 | 79.115 | 59.854 | 1.00 | 51.47 | 8 |
| 6522 | OW0 | WAT | W | 180 | 51.301 | 65.512 | 30.778 | 1.00 | 58.87 | 8 |
| 6523 | OW0 | WAT | W | 181 | 49.729 | 67.077 | 23.232 | 1.00 | 50.64 | 8 |
| 6524 | OW0 | WAT | W | 182 | 15.428 | 63.127 | 65.725 | 1.00 | 53.21 | 8 |
| 6525 | OW0 | WAT | W | 183 | 28.316 | 47.473 | 59.001 | 1.00 | 52.58 | 8 |
| 6526 | OW0 | WAT | W | 184 | 11.167 | 50.777 | 21.789 | 1.00 | 55.21 | 8 |
| 6527 | OW0 | WAT | W | 185 | 39.667 | 45.779 | 11.484 | 1.00 | 50.46 | 8 |
| 6528 | OW0 | WAT | W | 186 | 9.302 | 78.481 | 48.408 | 1.00 | 50.14 | 8 |
| 6529 | OW0 | WAT | W | 187 | −2.511 | 95.777 | 25.082 | 1.00 | 50.26 | 8 |
| 6530 | OW0 | WAT | W | 188 | 49.525 | 52.221 | 41.616 | 1.00 | 53.78 | 8 |
| 6531 | OW0 | WAT | W | 189 | 33.219 | 90.787 | 32.195 | 1.00 | 53.22 | 8 |
| 6532 | OW0 | WAT | W | 190 | 18.629 | 63.971 | 67.355 | 1.00 | 54.97 | 8 |
| 6533 | OW0 | WAT | W | 191 | 6.996 | 55.402 | 34.790 | 1.00 | 49.49 | 8 |
| 6534 | OW0 | WAT | W | 192 | 50.269 | 70.807 | 60.070 | 1.00 | 54.80 | 8 |
| 6535 | OW0 | WAT | W | 193 | −3.948 | 89.479 | 31.518 | 0.00 | 54.80 | 8 |
| 6536 | OW0 | WAT | W | 194 | 4.036 | 51.795 | 57.529 | 1.00 | 56.49 | 8 |
| 6537 | OW0 | WAT | W | 195 | 15.790 | 48.084 | 23.036 | 1.00 | 52.39 | 8 |
| 6538 | OW0 | WAT | W | 196 | 22.577 | 105.708 | 45.361 | 1.00 | 51.14 | 8 |
| 6539 | OW0 | WAT | W | 197 | 7.453 | 103.921 | 23.508 | 1.00 | 50.15 | 8 |
| 6540 | OW0 | WAT | W | 198 | 37.899 | 80.588 | 45.384 | 1.00 | 52.20 | 8 |
| 6541 | OW0 | WAT | W | 199 | 19.774 | 74.879 | 53.890 | 1.00 | 55.07 | 8 |
| 6542 | OW0 | WAT | W | 200 | 50.055 | 68.873 | 30.956 | 1.00 | 30.00 | 8 |
| 6543 | OW0 | WAT | W | 201 | 53.330 | 63.201 | 30.956 | 1.00 | 37.00 | 8 |
| 6544 | OW0 | WAT | W | 202 | 35.086 | 89.130 | 21.284 | 1.00 | 49.00 | 8 |
| 6545 | OW0 | WAT | W | 203 | 2.339 | 51.858 | 35.796 | 1.00 | 50.00 | 8 |
| 6546 | OW0 | WAT | W | 204 | 19.180 | 43.755 | 27.572 | 1.00 | 50.00 | 8 |
| 6547 | OW0 | WAT | W | 205 | 51.693 | 55.504 | 46.921 | 1.00 | 51.00 | 8 |
| 6548 | OW0 | WAT | W | 206 | 31.811 | 80.217 | 54.661 | 1.00 | 51.00 | 8 |
| 6549 | OW0 | WAT | W | 207 | 11.695 | 77.786 | 12.093 | 1.00 | 51.00 | 8 |
| 6550 | OW0 | WAT | W | 208 | 29.940 | 46.996 | 53.693 | 1.00 | 52.00 | 8 |
| 6551 | OW0 | WAT | W | 209 | 7.251 | 102.500 | 40.633 | 1.00 | 52.00 | 8 |
| 6552 | OW0 | WAT | W | 210 | 23.858 | 91.561 | 17.414 | 1.00 | 52.00 | 8 |
| 6553 | OW0 | WAT | W | 211 | 6.783 | 49.832 | 40.633 | 1.00 | 52.00 | 8 |
| 6554 | OW0 | WAT | W | 212 | 44.910 | 47.806 | 22.735 | 1.00 | 52.00 | 8 |
| 6555 | OW0 | WAT | W | 213 | 36.255 | 46.591 | 10.158 | 1.00 | 52.00 | 8 |
| 6556 | OW0 | WAT | W | 214 | 27.601 | 61.581 | 77.880 | 1.00 | 52.00 | 8 |
| 6557 | OW0 | WAT | W | 215 | 27.133 | 98.043 | 33.861 | 1.00 | 53.00 | 8 |
| 6558 | OW0 | WAT | W | 216 | 18.479 | 55.504 | 45.470 | 1.00 | 53.00 | 8 |

TABLE 1-continued

Atom Coordinates from the Crystal Structure of NOVAMYL

| 6559 | OW0 | WAT | W | 217 | 9.122  | 47.401 | 46.438 | 1.00 | 53.00 | 8 |
| 6560 | OW0 | WAT | W | 218 | 9.590  | 66.037 | 16.447 | 1.00 | 53.00 | 8 |
| 6561 | OW0 | WAT | W | 219 | 13.333 | 91.966 | 46.438 | 1.00 | 53.00 | 8 |

We claim:

1. A method of constructing a variant of a parent maltogenic alpha-amylase, wherein said parent maltogenic alpha-amylase has an amino acid sequence which is at least 70% identical to amino acid residues 1–686 of SEQ ID NO:2, and wherein said parent maltogenic alpha-amylase has an active site which comprises a cluster of three amino acid residues corresponding to positions D329, D228 and E256 in SEQ ID NO:2, which method comprises:
  a) modeling the parent alpha-amylase on the three-dimensional structure of amino acid residues 1–686 of SEQ ID NO:2 depicted in the Appendix to produce a three-dimensional structure of the parent alpha-amylase;
  b) identifying in said three-dimensional structure of the parent alpha-amylase an amino acid residue which (i) is within 15 Å of one of said three amino acid residues and (ii) is involved in electrostatic or hydrophobic interactions with an active site residue: and
  c) constructing the variant by substituting the amino acid residue identified in said b) with another amino add residue which changes the electrostatic and/or hydrophobic surroundings of said active site residue wherein the variant has maltogenic alpha-amylase activity.

2. The method of claim 1, wherein said b) comprises identifying in said three dimensional structure of the parent alpha-amylase an amino acid residue which (i) is within 10 Å of one of said three amino acid residues and (ii) is involved in electrostatic or hydrophobic interactions with an active site residue.

3. The method of claim 1, wherein the method further comprises
  d) testing the pH dependent activity of said variant constructed in said c); and
  e) selecting a variant having an altered pH dependent activity as compared to the parent amylase.

4. The method of claim 1, wherein said parent maltogenic alpha-amylase is at least 80% identical to amino acid residues 1–886 of SEQ ID NO:2.

5. The method of claim 1, wherein said parent maltogenic alpha amylase is at least 90% identical to amino acid residues 1–686 of SEQ ID NO:2.

6. The method of claim 1, wherein said parent maltogenic alpha-amylase is at least 95% identical to amino acid residues 1–686 of SEQ ID NO:2.

7. The method of claim 1, wherein said parent maltogenic alpha-amylase is at least 98% identical to amino add residues 1–686 of SEQ ID NO:2.

8. The method of claim 1, wherein said parent maltogenic alpha-amylase has the amino acid sequence of amino acid residues 1686 of SEQ ID NO:2.

9. The method of claim 1, wherein the method comprises repeating steps b) and c) at least once.

10. The method of claim 1, herein the method further comprises d) repeating steps b) and c);
  e) after the completion of step d, preparing the variant resulting from steps a)–d);
  f) testing the pH dependent activity of said variant; and
  g) selecting a variant having maltogenic alpha-amylase activity and having an altered pH dependent activity as compared to the parent amylase.

11. The method of claim 1, wherein the method further comprises
  d) repeating steps b) and c);
  e) making alterations each of which is an insertion, a deletion or a substitution of an amino acid residue at one or more positions other than c);
  f) after the completion of step e, preparing the variant resulting from steps a)–e);
  g) testing the pH dependent activity of said variant; and h) selecting a variant having maltogenic alpha-amylase activity and an altered pH dependent activity as compared to the parent amylase.

12. The method of claim 1, wherein the method further comprises:
   d) repeating steps b) and c);
   e) making alterations each of which is an insertion, a deletion or a substitution of an amino acid residue at one or more positions other than c);
   f) after the completion of step e, preparing the variant resulting from steps a)–e);
   g) testing the pH dependent activity of said variant;
   h) repeating steps a)–g); and
   i) selecting a variant having maltogenic alpha-amylase activity and an altered pH dependent activity as compared to the parent amylase.

13. The method of claim 2, wherein said parent maltogenic alpha-amylase is at least 80% identical to amino acid residues 1886 of SEQ ID NO:2.

14. The method of claim 2, wherein said parent maltogenic alpha amylase is at least 90% identical to amino acid residues 1486 of SEQ ID NO:2.

15. The method of claim 2, wherein said parent maltogenic alpha-amylase is at least 95% identical to amino acid residues 1–686 of SEQ ID NO:2.

16. The method of claim 2, wherein said parent maltogenic alpha-amylase is at least 98% identical to amino acid residues 1–686 of SEQ ID NO:2.

17. The method of claim 2, wherein said parent maltogenic alpha-amylase has the amino acid sequence of amino acid residues 1686 of SEQ ID NO:2.

* * * * *

UNITED STATES PATENT AND TRADEMARK OFFICE
CERTIFICATE OF CORRECTION

PATENT NO. : 6,876,932 B1
APPLICATION NO. : 09/607142
DATED : April 5, 2005
INVENTOR(S) : Cherry et al.

Page 1 of 1

It is certified that error appears in the above-identified patent and that said Letters Patent is hereby corrected as shown below:

Column 218, claim 4, line 35:
"residues 1-886 of SEQ ID NO:2" should read --residues 1-686 of SEQ ID NO:2--

Column 218, claim 8, line 47:
"residues 1686 of SEQ ID NO:2" should read --residues 1-686 of SEQ ID NO:2--

Column 220, claim 13, line 3:
"residues 1886 of SEQ ID NO:2" should read --residues 1-686 of SEQ ID NO:2--

Column 220, claim 14, line 6:
"residues 1486 of SEQ ID NO:2" should read --residues 1-686 of SEQ ID NO:2--

Column 220, claim 17, line 15:
"acid residues 1686 of SEQ ID NO:2" should read --acid residues 1-686 of SEQ ID NO:2--

Signed and Sealed this

Tenth Day of July, 2007

JON W. DUDAS
*Director of the United States Patent and Trademark Office*

SEQUENCE LISTING

<160> NUMBER OF SEQ ID NOS: 14

<210> SEQ ID NO 1
<211> LENGTH: 2160
<212> TYPE: DNA
<213> ORGANISM: Bacillus sp.
<220> FEATURE:
<221> NAME/KEY: CDS
<222> LOCATION: (1)..(2160)
<220> FEATURE:
<221> NAME/KEY: mat_peptide
<222> LOCATION: (100)..(2157)

<400> SEQUENCE: 1

```
atg aaa aag aaa acg ctt tct tta ttt gtg gga ctg atg ctc ctc atc        48
Met Lys Lys Lys Thr Leu Ser Leu Phe Val Gly Leu Met Leu Leu Ile
 -30                 -25                 -20 ggt ctc ctg ttc agc ggt tct ctt ccg tac aat cca aac gcc gct gaa        96
Gly Leu Leu Phe Ser Gly Ser Leu Pro Tyr Asn Pro Asn Ala Ala Glu
         -15                 -10                  -5 gcc agc agt tcc gca agc gtc aaa ggg gac gtg att tac cag att atc       144
Ala Ser Ser Ser Ala Ser Val Lys Gly Asp Val Ile Tyr Gln Ile Ile
 -1   1               5                  10                  15 att gac cgg ttt tac gat ggg gac acg acg aac aac aat cct gcc aaa       192
Ile Asp Arg Phe Tyr Asp Gly Asp Thr Thr Asn Asn Asn Pro Ala Lys
                 20                  25                  30 agt tat gga ctt tac gat ccg acc aaa tcg aag tgg aaa atg tat tgg       240
Ser Tyr Gly Leu Tyr Asp Pro Thr Lys Ser Lys Trp Lys Met Tyr Trp
             35                  40                  45 ggc ggg gat ctg gag ggg gtt cgt caa aaa ctt cct tat ctt aaa cag       288
Gly Gly Asp Leu Glu Gly Val Arg Gln Lys Leu Pro Tyr Leu Lys Gln
         50                  55                  60 ctg ggc gta acg aca atc tgg ttg tcc ccg gtt ttg gac aat ctg gat       336
Leu Gly Val Thr Thr Ile Trp Leu Ser Pro Val Leu Asp Asn Leu Asp
 65                  70                  75 aca ctg gcg ggc acc gat aac acg ggc tat cac gga tac tgg acg cgc       384
Thr Leu Ala Gly Thr Asp Asn Thr Gly Tyr His Gly Tyr Trp Thr Arg
 80                  85                  90                  95 gat ttt aaa cag att gag gaa cat ttc ggg aat tgg acc aca ttt gac       432
Asp Phe Lys Gln Ile Glu Glu His Phe Gly Asn Trp Thr Thr Phe Asp
                100                 105                 110 acg ttg gtc aat gat gct cac caa aac gga atc aag gtg att gtc gac       480
Thr Leu Val Asn Asp Ala His Gln Asn Gly Ile Lys Val Ile Val Asp
            115                 120                 125 ttt gtg ccc aat cat tcg act cct ttt aag gca aac gat tcc acc ttt       528
Phe Val Pro Asn His Ser Thr Pro Phe Lys Ala Asn Asp Ser Thr Phe
        130                 135                 140 gcg gaa ggc ggc gcc ctc tac aac aat gga acc tat atg ggc aat tat       576
Ala Glu Gly Gly Ala Leu Tyr Asn Asn Gly Thr Tyr Met Gly Asn Tyr
    145                 150                 155 ttt gat gac gca aca aaa ggg tac ttc cac cat aat ggg gac atc agc       624
Phe Asp Asp Ala Thr Lys Gly Tyr Phe His His Asn Gly Asp Ile Ser
```

-continued

| | | |
|---|---|---|
| aac tgg gac gac cgg tac gag gcg caa tgg aaa aac ttc acg gat cca<br>Asn Trp Asp Asp Arg Tyr Glu Ala Gln Trp Lys Asn Phe Thr Asp Pro<br>                     180                       185                  190 | 672 |
| gcc ggt ttc tcg ctt gcc gat ttg tcg cag gaa aat ggc acg att gct<br>Ala Gly Phe Ser Leu Ala Asp Leu Ser Gln Glu Asn Gly Thr Ile Ala<br>           195                      200                    205 | 720 |
| caa tac ctg acc gat gcg gcg gtt caa ttg gta gca cat gga gcg gat<br>Gln Tyr Leu Thr Asp Ala Ala Val Gln Leu Val Ala His Gly Ala Asp<br>      210                    215                 220 | 768 |
| ggt ttg cgg att gat gcg gtg aag cat ttt aat tcg ggg ttc tcc aaa<br>Gly Leu Arg Ile Asp Ala Val Lys His Phe Asn Ser Gly Phe Ser Lys<br>225                      230                 235 | 816 |
| tcg ttg gcc gat aaa ctg tac caa aag aaa gac att ttc ctg gtg ggg<br>Ser Leu Ala Asp Lys Leu Tyr Gln Lys Lys Asp Ile Phe Leu Val Gly<br>240                      245                 250                255 | 864 |
| gaa tgg tac gga gat gac ccc gga aca gcc aat cat ctg gaa aag gtc<br>Glu Trp Tyr Gly Asp Asp Pro Gly Thr Ala Asn His Leu Glu Lys Val<br>                     260                    265                 270 | 912 |
| cgg tac gcc aac aac agc ggt gtc aat gtg ctg gat ttt gat ctc aac<br>Arg Tyr Ala Asn Asn Ser Gly Val Asn Val Leu Asp Phe Asp Leu Asn<br>          275                     280                 285 | 960 |
| acg gtg att cga aat gtg ttc ggc aca ttt acg caa acg atg tac gat<br>Thr Val Ile Arg Asn Val Phe Gly Thr Phe Thr Gln Thr Met Tyr Asp<br>      290                    295                 300 | 1008 |
| ctt aac aat atg gtg aac caa acg ggg aac gag tac aaa tac aaa gaa<br>Leu Asn Asn Met Val Asn Gln Thr Gly Asn Glu Tyr Lys Tyr Lys Glu<br>305                      310                 315 | 1056 |
| aat cta atc aca ttt atc gat aac cat gat atg tca aga ttt ctt tcg<br>Asn Leu Ile Thr Phe Ile Asp Asn His Asp Met Ser Arg Phe Leu Ser<br>320                      325                 330                335 | 1104 |
| gta aat tcg aac aag gcg aat ttg cac cag gcg ctt gct ttc att ctc<br>Val Asn Ser Asn Lys Ala Asn Leu His Gln Ala Leu Ala Phe Ile Leu<br>                     340                    345                350 | 1152 |
| act tcg cgg ggt acg ccc tcc atc tat tat gga acc gaa caa tac atg<br>Thr Ser Arg Gly Thr Pro Ser Ile Tyr Tyr Gly Thr Glu Gln Tyr Met<br>          355                     360                 365 | 1200 |
| gca ggc ggc aat gac ccg tac aac cgg ggg atg atg ccg gcg ttt gat<br>Ala Gly Gly Asn Asp Pro Tyr Asn Arg Gly Met Met Pro Ala Phe Asp<br>      370                    375                 380 | 1248 |
| acg aca acc acc gcc ttt aaa gag gtg tca act ctg gcg ggg ttg cgc<br>Thr Thr Thr Thr Ala Phe Lys Glu Val Ser Thr Leu Ala Gly Leu Arg<br>385                      390                 395 | 1296 |
| agg aac aat gcg gcg atc cag tac ggc acc acc acc cag cgt tgg atc<br>Arg Asn Asn Ala Ala Ile Gln Tyr Gly Thr Thr Thr Gln Arg Trp Ile<br>400                      405                 410                415 | 1344 |
| aac aat gat gtt tac att tat gaa cgg aaa ttt ttc aac gat gtc gtg<br>Asn Asn Asp Val Tyr Ile Tyr Glu Arg Lys Phe Phe Asn Asp Val Val<br>                     420                    425                430 | 1392 |
| ttg gtg gcc atc aat cga aac acg caa tcc tcc tat tcg att tcc ggt<br>Leu Val Ala Ile Asn Arg Asn Thr Gln Ser Ser Tyr Ser Ile Ser Gly<br>                     435                    440                445 | 1440 |
| ttg cag acg gcc ttg cca aat ggc agc tat gcg gat tat ctg tca ggg<br>Leu Gln Thr Ala Leu Pro Asn Gly Ser Tyr Ala Asp Tyr Leu Ser Gly<br>      450                    455                 460 | 1488 |
| ctg ttg ggg ggg aac ggg att tcc gtt tcc aat gga agt gtc gct tcg<br>Leu Leu Gly Gly Asn Gly Ile Ser Val Ser Asn Gly Ser Val Ala Ser<br>465                      470                 475 | 1536 |
| ttc acg ctt gcg cct gga gcc gtg tct gtt tgg cag tac agc aca tcc | 1584 |

```
Phe Thr Leu Ala Pro Gly Ala Val Ser Val Trp Gln Tyr Ser Thr Ser
480             485                 490                 495 gct tca gcg ccg caa atc gga tcg gtt gct cca aat atg ggg att ccg     1632
Ala Ser Ala Pro Gln Ile Gly Ser Val Ala Pro Asn Met Gly Ile Pro
                500                 505                 510 ggt aat gtg gtc acg atc gac ggg aaa ggt ttt ggg acg acg cag gga     1680
Gly Asn Val Val Thr Ile Asp Gly Lys Gly Phe Gly Thr Thr Gln Gly
            515                 520                 525 acc gtg aca ttt ggc gga gtg aca gcg act gtg aaa tcc tgg aca tcc     1728
Thr Val Thr Phe Gly Gly Val Thr Ala Thr Val Lys Ser Trp Thr Ser
        530                 535                 540 aat cgg att gaa gtg tac gtt ccc aac atg gcc gcc ggg ctg acc gat     1776
Asn Arg Ile Glu Val Tyr Val Pro Asn Met Ala Ala Gly Leu Thr Asp
    545                 550                 555 gtg aaa gtc acc gcg ggt gga gtt tcc agc aat ctg tat tct tac aat     1824
Val Lys Val Thr Ala Gly Gly Val Ser Ser Asn Leu Tyr Ser Tyr Asn
560                 565                 570                 575 att ttg agt gga acg cag aca tcg gtt gtg ttt act gtg aaa agt gcg     1872
Ile Leu Ser Gly Thr Gln Thr Ser Val Val Phe Thr Val Lys Ser Ala
            580                 585                 590 cct ccg acc aac ctg ggg gat aag att tac ctg acg ggc aac ata ccg     1920
Pro Pro Thr Asn Leu Gly Asp Lys Ile Tyr Leu Thr Gly Asn Ile Pro
        595                 600                 605 gaa ttg ggg aat tgg agc acg gat acg agc gga gcc gtt aac aat gcg     1968
Glu Leu Gly Asn Trp Ser Thr Asp Thr Ser Gly Ala Val Asn Asn Ala
    610                 615                 620 caa ggg ccc ctg ctc gcg ccc aat tat ccg gat tgg ttt tat gta ttc     2016
Gln Gly Pro Leu Leu Ala Pro Asn Tyr Pro Asp Trp Phe Tyr Val Phe
625                 630                 635 agc gtt cca gca gga aag acg att caa ttc aag ttc ttc atc aag cgt     2064
Ser Val Pro Ala Gly Lys Thr Ile Gln Phe Lys Phe Phe Ile Lys Arg
640                 645                 650                 655 gcg gat gga acg att caa tgg gag aat ggt tcg aac cac gtg gcc aca     2112
Ala Asp Gly Thr Ile Gln Trp Glu Asn Gly Ser Asn His Val Ala Thr
            660                 665                 670 act ccc acg ggt gca acc ggt aac att act gtt acg tgg caa aac tag     2160
Thr Pro Thr Gly Ala Thr Gly Asn Ile Thr Val Thr Trp Gln Asn
        675                 680                 685

<210> SEQ ID NO 2
<211> LENGTH: 719
<212> TYPE: PRT
<213> ORGANISM: Bacillus sp.

<400> SEQUENCE: 2

Met Lys Lys Lys Thr Leu Ser Leu Phe Val Gly Leu Met Leu Leu Ile
1               5                   10                  15

Gly Leu Leu Phe Ser Gly Ser Leu Pro Tyr Asn Pro Asn Ala Ala Glu
            20                  25                  30

Ala Ser Ser Ser Ala Ser Val Lys Gly Asp Val Ile Tyr Gln Ile Ile
        35                  40                  45

Ile Asp Arg Phe Tyr Asp Gly Asp Thr Thr Asn Asn Pro Ala Lys
    50                  55                  60

Ser Tyr Gly Leu Tyr Asp Pro Thr Lys Ser Lys Trp Lys Met Tyr Trp
65                  70                  75                  80

Gly Gly Asp Leu Glu Gly Val Arg Gln Lys Leu Pro Tyr Leu Lys Gln
            85                  90                  95

Leu Gly Val Thr Thr Ile Trp Leu Ser Pro Val Leu Asp Asn Leu Asp
            100                 105                 110
```

-continued

```
Thr Leu Ala Gly Thr Asp Asn Thr Gly Tyr His Gly Tyr Trp Thr Arg
        115                 120                 125
Asp Phe Lys Gln Ile Glu Glu His Phe Gly Asn Trp Thr Thr Phe Asp
    130                 135                 140
Thr Leu Val Asn Asp Ala His Gln Asn Gly Ile Lys Val Ile Val Asp
145                 150                 155                 160
Phe Val Pro Asn His Ser Thr Pro Phe Lys Ala Asn Asp Ser Thr Phe
                165                 170                 175
Ala Glu Gly Gly Ala Leu Tyr Asn Asn Gly Thr Tyr Met Gly Asn Tyr
            180                 185                 190
Phe Asp Asp Ala Thr Lys Gly Tyr Phe His His Asn Gly Asp Ile Ser
        195                 200                 205
Asn Trp Asp Asp Arg Tyr Glu Ala Gln Trp Lys Asn Phe Thr Asp Pro
    210                 215                 220
Ala Gly Phe Ser Leu Ala Asp Leu Ser Gln Glu Asn Gly Thr Ile Ala
225                 230                 235                 240
Gln Tyr Leu Thr Asp Ala Ala Val Gln Leu Val Ala His Gly Ala Asp
                245                 250                 255
Gly Leu Arg Ile Asp Ala Val Lys His Phe Asn Ser Gly Phe Ser Lys
            260                 265                 270
Ser Leu Ala Asp Lys Leu Tyr Gln Lys Asp Ile Phe Leu Val Gly
        275                 280                 285
Glu Trp Tyr Gly Asp Asp Pro Gly Thr Ala Asn His Leu Glu Lys Val
    290                 295                 300
Arg Tyr Ala Asn Asn Ser Gly Val Asn Val Leu Asp Phe Asp Leu Asn
305                 310                 315                 320
Thr Val Ile Arg Asn Val Phe Gly Thr Phe Thr Gln Thr Met Tyr Asp
                325                 330                 335
Leu Asn Asn Met Val Asn Gln Thr Gly Asn Glu Tyr Lys Tyr Lys Glu
            340                 345                 350
Asn Leu Ile Thr Phe Ile Asp Asn His Asp Met Ser Arg Phe Leu Ser
        355                 360                 365
Val Asn Ser Asn Lys Ala Asn Leu His Gln Ala Leu Ala Phe Ile Leu
    370                 375                 380
Thr Ser Arg Gly Thr Pro Ser Ile Tyr Tyr Gly Thr Glu Gln Tyr Met
385                 390                 395                 400
Ala Gly Gly Asn Asp Pro Tyr Asn Arg Gly Met Met Pro Ala Phe Asp
                405                 410                 415
Thr Thr Thr Thr Ala Phe Lys Glu Val Ser Thr Leu Ala Gly Leu Arg
            420                 425                 430
Arg Asn Asn Ala Ala Ile Gln Tyr Gly Thr Thr Gln Arg Trp Ile
        435                 440                 445
Asn Asn Asp Val Tyr Ile Tyr Glu Arg Lys Phe Phe Asn Asp Val Val
    450                 455                 460
Leu Val Ala Ile Asn Arg Asn Thr Gln Ser Ser Tyr Ser Ile Ser Gly
465                 470                 475                 480
Leu Gln Thr Ala Leu Pro Asn Gly Ser Tyr Ala Asp Tyr Leu Ser Gly
                485                 490                 495
Leu Leu Gly Gly Asn Gly Ile Ser Val Ser Asn Gly Ser Val Ala Ser
            500                 505                 510
Phe Thr Leu Ala Pro Gly Ala Val Ser Val Trp Gln Tyr Ser Thr Ser
        515                 520                 525
```

-continued

```
Ala Ser Ala Pro Gln Ile Gly Ser Val Ala Pro Asn Met Gly Ile Pro
    530                 535                 540

Gly Asn Val Val Thr Ile Asp Gly Lys Gly Phe Gly Thr Thr Gln Gly
545                 550                 555                 560

Thr Val Thr Phe Gly Gly Val Thr Ala Thr Val Lys Ser Trp Thr Ser
                565                 570                 575

Asn Arg Ile Glu Val Tyr Val Pro Asn Met Ala Ala Gly Leu Thr Asp
            580                 585                 590

Val Lys Val Thr Ala Gly Gly Val Ser Ser Asn Leu Tyr Ser Tyr Asn
        595                 600                 605

Ile Leu Ser Gly Thr Gln Thr Ser Val Val Phe Thr Val Lys Ser Ala
    610                 615                 620

Pro Pro Thr Asn Leu Gly Asp Lys Ile Tyr Leu Thr Gly Asn Ile Pro
625                 630                 635                 640

Glu Leu Gly Asn Trp Ser Thr Asp Thr Ser Gly Ala Val Asn Asn Ala
                645                 650                 655

Gln Gly Pro Leu Leu Ala Pro Asn Tyr Pro Asp Trp Phe Tyr Val Phe
            660                 665                 670

Ser Val Pro Ala Gly Lys Thr Ile Gln Phe Lys Phe Ile Lys Arg
        675                 680                 685

Ala Asp Gly Thr Ile Gln Trp Glu Asn Gly Ser Asn His Val Ala Thr
    690                 695                 700

Thr Pro Thr Gly Ala Thr Gly Asn Ile Thr Val Thr Trp Gln Asn
705                 710                 715
```

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: F 188H
      Primer

<400> SEQUENCE: 3
gcaatggaaa aaccacacgg atccagccgg cttctcgc                              38

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: F188E
      Primer

<400> SEQUENCE: 4
gcaatggaaa aacgagacgg atccagccgg cttctcgc                              38

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: F 284E
      Primer

<400> SEQUENCE: 5
ggtgtcaatg tgctggatga agatctcaac acggtg                                36

<210> SEQ ID NO 6
<211> LENGTH: 36
<212> TYPE: DNA

```
<213> ORGANISM: Artificial Sequence
<220> FEATURE:
<223> OTHER INFORMATION: Description of Artificial Sequence: F 284D
      Primer

<400> SEQUENCE: 6
ggtgtcaatg ttctagatga tgatctcaac acggtg                              36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: F 284K
      Primer

<400> SEQUENCE: 7
ggtgtcaatg tgctggataa agatctcaac acggtg                              36

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: N 327D
      Primer

<400> SEQUENCE: 8
cacatttatc gatgatcatg atatgtcaag atttc                               35

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: T 288K
      Primer

<400> SEQUENCE: 9
cctaaaacta gagttgttcc actaggcctt acac                                34

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: T 288R
      Primer

<400> SEQUENCE: 10
cctaaaacta gagttgtccc actaggcctt acac                                34

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:A 189
      Primer

<400> SEQUENCE: 11
tgggcaatta ttttgatgac gc                                             22

<210> SEQ ID NO 12
<211> LENGTH: 20
<212> TYPE: DNA
<213> ORGANISM: Artificial Sequence
```

-continued

```
<220> FEATURE:
<223> OTHER INFORMATION: Description of Artificial Sequence: B 649
      Primer

<400> SEQUENCE: 12
tccgctcgta tccgtgctcc                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: A 82
      Primer

<400> SEQUENCE: 13
ggggatctgg aggggttcg                                               20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: B 346
      Primer

<400> SEQUENCE: 14
tttgtactcg ttccccgttt gg                                           22
```